US012213983B2

(12) United States Patent
Stern et al.

(10) Patent No.: US 12,213,983 B2
(45) Date of Patent: Feb. 4, 2025

(54) TREATMENT OF CANCERS USING PI3 KINASE ISOFORM MODULATORS

(71) Applicant: Infinity Pharmaceuticals, Inc., Cambridge, MA (US)

(72) Inventors: Howard M. Stern, Waban, MA (US); Jeffrey L. Kutok, Natick, MA (US)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 772 days.

(21) Appl. No.: 16/848,485

(22) Filed: Apr. 14, 2020

(65) Prior Publication Data

US 2021/0060022 A1 Mar. 4, 2021

Related U.S. Application Data

(63) Continuation of application No. 15/581,414, filed on Apr. 28, 2017, now abandoned, which is a continuation of application No. 14/439,965, filed as application No. PCT/US2013/067929 on Nov. 1, 2013, now abandoned, which is a continuation-in-part of application No. 13/840,822, filed on Mar. 15, 2013, now abandoned.

(60) Provisional application No. 61/888,454, filed on Oct. 8, 2013, provisional application No. 61/863,365, filed on Aug. 7, 2013, provisional application No. 61/836,088, filed on Jun. 17, 2013, provisional application No. 61/829,168, filed on May 30, 2013, provisional application No. 61/767,606, filed on Feb. 21, 2013, provisional application No. 61/733,852, filed on Dec. 5, 2012, provisional application No. 61/721,432, filed on Nov. 1, 2012.

(51) Int. Cl.
| | |
|---|---|
| *A61K 31/519* | (2006.01) |
| *A61K 31/505* | (2006.01) |
| *A61K 31/52* | (2006.01) |
| *A61K 31/704* | (2006.01) |
| *A61K 45/06* | (2006.01) |
| *C07D 401/12* | (2006.01) |
| *C07D 471/04* | (2006.01) |
| *C07D 473/00* | (2006.01) |
| *C07D 473/34* | (2006.01) |
| *G01N 33/50* | (2006.01) |
| *G01N 33/574* | (2006.01) |

(52) U.S. Cl.
CPC ............ *A61K 31/52* (2013.01); *A61K 31/505* (2013.01); *A61K 31/519* (2013.01); *A61K 31/704* (2013.01); *A61K 45/06* (2013.01); *C07D 401/12* (2013.01); *C07D 471/04* (2013.01); *C07D 473/00* (2013.01); *C07D 473/34* (2013.01); *G01N 33/5011* (2013.01); *G01N 33/574* (2013.01); *G01N 2333/521* (2013.01); *G01N 2333/525* (2013.01); *G01N 2333/53* (2013.01); *G01N 2333/5434* (2013.01); *G01N 2333/9121* (2013.01); *G01N 2333/96494* (2013.01)

(58) Field of Classification Search
CPC .................................................... A61K 31/519
See application file for complete search history.

(56) References Cited

U.S. PATENT DOCUMENTS

| | | | |
|---|---|---|---|
| 4,547,508 | A | 10/1985 | Konz et al. |
| 4,656,159 | A | 4/1987 | McPherson et al. |
| 4,704,381 | A | 11/1987 | Schaumann et al. |
| 4,795,627 | A | 1/1989 | Fisher et al. |
| 5,240,941 | A | 8/1993 | Bruneau |
| 5,294,612 | A | 3/1994 | Bacon et al. |
| 5,310,731 | A | 5/1994 | Olsson et al. |
| 5,364,862 | A | 11/1994 | Spada et al. |
| 5,409,930 | A | 4/1995 | Spada et al. |
| 5,420,419 | A | 5/1995 | Wood |
| 5,428,125 | A | 6/1995 | Hefner, Jr. et al. |
| 5,442,039 | A | 8/1995 | Hefner, Jr. et al. |
| 5,480,883 | A | 1/1996 | Spada et al. |
| 5,504,103 | A | 4/1996 | Bonjouklian et al. |
| 5,506,347 | A | 4/1996 | Erion et al. |
| 5,561,134 | A | 10/1996 | Spada et al. |
| 5,563,257 | A | 10/1996 | Zilch et al. |
| 5,593,997 | A | 1/1997 | Dow et al. |
| 5,624,679 | A | 4/1997 | Vournakis et al. |
| 5,646,128 | A | 7/1997 | Firestein et al. |
| 5,646,153 | A | 7/1997 | Spada et al. |
| 5,652,366 | A | 7/1997 | Spada et al. |
| 5,654,307 | A | 8/1997 | Bridges et al. |
| 5,656,643 | A | 8/1997 | Spada et al. |
| 5,665,721 | A | 9/1997 | Bhagwat et al. |
| 5,674,998 | A | 10/1997 | Boyer et al. |
| 5,686,455 | A | 11/1997 | Adams et al. |

(Continued)

FOREIGN PATENT DOCUMENTS

| | | |
|---|---|---|
| CA | 1338379 C | 6/1996 |
| CN | 101602768 A | 12/2009 |

(Continued)

OTHER PUBLICATIONS

Bryan, Jeffrey and Borthakur, Gautam. "Role of rituximab in first-line treatment of chronic lymphocytic leukemia." Therapeutics and Clinical Risk Management. (2011), vol. 7, pp. 1-11. (Year: 2011).*

(Continued)

*Primary Examiner* — John S Kenyon

(74) *Attorney, Agent, or Firm* — COOLEY LLP

(57) ABSTRACT

Provided herein are methods, kits, and pharmaceutical compositions that include a PI3 kinase inhibitor for treating cancers or hematologic disorders.

19 Claims, 39 Drawing Sheets

(56) References Cited

U.S. PATENT DOCUMENTS

| | | |
|---|---|---|
| 5,710,158 A | 1/1998 | Myers et al. |
| 5,714,493 A | 2/1998 | Myers et al. |
| 5,721,237 A | 2/1998 | Myers et al. |
| 5,736,554 A | 4/1998 | Spada et al. |
| 5,747,235 A | 5/1998 | Farid et al. |
| 5,756,711 A | 5/1998 | Zilch et al. |
| 5,763,596 A | 6/1998 | Boyer et al. |
| 5,763,597 A | 6/1998 | Ugarkar et al. |
| 5,763,885 A | 6/1998 | Murphy et al. |
| 5,795,977 A | 8/1998 | Ugarkar et al. |
| 5,811,454 A | 9/1998 | Springer |
| 5,824,492 A | 10/1998 | Hiles et al. |
| 5,858,753 A | 1/1999 | Chantry et al. |
| 5,914,488 A | 6/1999 | Sone |
| RE36,256 E | 7/1999 | Spada et al. |
| 5,919,808 A | 7/1999 | Petrie et al. |
| 5,922,753 A | 7/1999 | Petrie et al. |
| 5,948,776 A | 9/1999 | Petrie et al. |
| 5,962,457 A | 10/1999 | Chenard et al. |
| 5,965,573 A | 10/1999 | Petrie et al. |
| 5,977,061 A | 11/1999 | Holy et al. |
| 5,981,533 A | 11/1999 | Traxler et al. |
| 5,985,589 A | 11/1999 | Chantry et al. |
| 5,990,109 A | 11/1999 | Chen et al. |
| 5,990,169 A | 11/1999 | Petrie et al. |
| 5,994,358 A | 11/1999 | Petrie et al. |
| 6,001,839 A | 12/1999 | Calderwood et al. |
| 6,057,305 A | 5/2000 | Holy et al. |
| 6,057,320 A | 5/2000 | Spada et al. |
| 6,057,371 A | 5/2000 | Glennon |
| 6,084,095 A | 7/2000 | Bridges et al. |
| 6,093,737 A | 7/2000 | Anthony et al. |
| 6,127,121 A | 10/2000 | Meyer, Jr. et al. |
| 6,153,631 A | 11/2000 | Petrie et al. |
| 6,191,170 B1 | 2/2001 | Medina |
| 6,242,453 B1 | 6/2001 | Cirillo et al. |
| 6,251,901 B1 | 6/2001 | Petrie et al. |
| 6,265,410 B1 | 7/2001 | Bridges et al. |
| 6,268,370 B1 | 7/2001 | Adams et al. |
| 6,312,894 B1 | 11/2001 | Hedgpeth et al. |
| 6,323,201 B1 | 11/2001 | Carson et al. |
| 6,342,514 B1 | 1/2002 | Petrie et al. |
| 6,350,741 B1 | 2/2002 | Golec et al. |
| 6,358,945 B1 | 3/2002 | Breitfelder et al. |
| 6,362,216 B1 | 3/2002 | Burgess et al. |
| RE37,650 E | 4/2002 | Myers et al. |
| 6,383,790 B1 | 5/2002 | Shokat |
| 6,384,039 B1 | 5/2002 | Fossa |
| 6,387,894 B1 | 5/2002 | Fossa |
| 6,390,821 B1 | 5/2002 | Shokat |
| 6,455,534 B2 | 9/2002 | Bridges et al. |
| 6,472,153 B1 | 10/2002 | Dempcy et al. |
| 6,472,562 B1 | 10/2002 | Klingler et al. |
| 6,482,623 B1 | 11/2002 | Vanhaesebroeck et al. |
| 6,485,906 B2 | 11/2002 | Meyer, Jr. et al. |
| 6,492,346 B1 | 12/2002 | Hedgpeth et al. |
| 6,506,769 B2 | 1/2003 | Snow et al. |
| 6,518,277 B1 | 2/2003 | Sadhu et al. |
| 6,521,417 B1 | 2/2003 | Shokat |
| 6,521,620 B1 | 2/2003 | Bridges et al. |
| 6,531,491 B1 | 3/2003 | Kania et al. |
| 6,534,524 B1 | 3/2003 | Kania et al. |
| 6,545,005 B1 | 4/2003 | Baxter et al. |
| 6,552,192 B1 | 4/2003 | Hanus et al. |
| 6,562,819 B2 | 5/2003 | Carson et al. |
| 6,583,161 B1 | 6/2003 | Medina |
| 6,613,798 B1 | 9/2003 | Porter et al. |
| 6,630,495 B1 | 10/2003 | Cooke et al. |
| 6,632,789 B1 | 10/2003 | June |
| 6,645,969 B1 | 11/2003 | Myers et al. |
| 6,645,989 B2 | 11/2003 | Adams et al. |
| 6,649,631 B1 | 11/2003 | Orme et al. |
| 6,653,296 B1 | 11/2003 | Holy et al. |
| 6,653,306 B1 | 11/2003 | Alexander et al. |
| 6,660,744 B1 | 12/2003 | Hirst et al. |
| 6,660,845 B1 | 12/2003 | Gall et al. |
| 6,664,269 B2 | 12/2003 | Martin et al. |
| 6,664,393 B2 | 12/2003 | Klingler et al. |
| 6,667,300 B2 | 12/2003 | Sadhu et al. |
| 6,667,398 B2 | 12/2003 | Dunn et al. |
| 6,690,583 B1 | 2/2004 | Bergstedt et al. |
| 6,713,484 B2 | 3/2004 | Bridges et al. |
| 6,720,344 B2 | 4/2004 | Kerwin et al. |
| 6,734,187 B1 | 5/2004 | Tanaka et al. |
| 6,770,639 B2 | 8/2004 | Snow et al. |
| 6,777,425 B2 | 8/2004 | Burli et al. |
| 6,777,439 B2 | 8/2004 | Durden |
| 6,790,844 B2 | 9/2004 | Ueno et al. |
| 6,800,620 B2 | 10/2004 | Sadhu et al. |
| 6,825,219 B2 | 11/2004 | Cywin et al. |
| 6,849,420 B2 | 2/2005 | Vanhasebroeck et al. |
| 6,849,637 B2 | 2/2005 | Andrianjara et al. |
| 6,849,713 B2 | 2/2005 | Zhang et al. |
| 6,852,727 B2 | 2/2005 | Goulet et al. |
| 6,858,756 B2 | 2/2005 | Rampf et al. |
| 6,906,103 B2 | 6/2005 | Zhang et al. |
| 6,916,949 B2 | 7/2005 | Springer et al. |
| 6,919,332 B2 | 7/2005 | Noe et al. |
| 6,921,763 B2 | 7/2005 | Hirst et al. |
| 6,949,535 B2 | 9/2005 | Sadhu et al. |
| 7,005,520 B2 | 2/2006 | Dunn et al. |
| 7,026,461 B1 | 4/2006 | Shokat |
| 7,041,676 B2 | 5/2006 | McDonald et al. |
| 7,049,116 B2 | 5/2006 | Shokat |
| 7,049,312 B1 | 5/2006 | Rafferty et al. |
| 7,064,218 B2 | 6/2006 | Dyatkina et al. |
| 7,071,355 B2 | 7/2006 | Leban et al. |
| 7,087,597 B1 | 8/2006 | Miwa et al. |
| 7,102,046 B2 | 9/2006 | Rampf et al. |
| 7,115,627 B2 | 10/2006 | Pinto et al. |
| 7,115,653 B2 | 10/2006 | Baxter et al. |
| 7,144,903 B2 | 12/2006 | Collins et al. |
| 7,157,487 B2 | 1/2007 | Nakayama et al. |
| 7,166,293 B2 | 1/2007 | Teng et al. |
| 7,208,493 B2 | 4/2007 | Wrasidlo et al. |
| 7,208,601 B2 | 4/2007 | Mjalli et al. |
| 7,217,794 B2 | 5/2007 | Abdel-Meguid et al. |
| 7,223,780 B2 | 5/2007 | Nazare et al. |
| 7,235,585 B2 | 6/2007 | Springer et al. |
| 7,244,741 B2 | 7/2007 | Simon et al. |
| 7,247,736 B2 | 7/2007 | Leban et al. |
| 7,262,204 B2 | 8/2007 | Collins et al. |
| 7,265,111 B2 | 9/2007 | Bigot et al. |
| 7,265,131 B2 | 9/2007 | Johnson et al. |
| 7,317,027 B2 | 1/2008 | Nazare et al. |
| 7,329,765 B2 | 2/2008 | Burli et al. |
| 7,332,497 B2 | 2/2008 | Hirst et al. |
| 7,348,427 B2 | 3/2008 | Burli et al. |
| 7,365,088 B2 | 4/2008 | Nazare et al. |
| 7,365,094 B2 | 4/2008 | Leban et al. |
| 7,384,967 B2 | 6/2008 | Polisetti et al. |
| 7,396,836 B2 | 7/2008 | Harada et al. |
| 7,414,036 B2 | 8/2008 | Sevillano et al. |
| 7,429,596 B2 | 9/2008 | Tanaka et al. |
| 7,439,254 B2 | 10/2008 | Bergnes |
| 7,449,477 B2 | 11/2008 | Barda et al. |
| 7,459,462 B2 | 12/2008 | Simon et al. |
| 7,459,472 B2 | 12/2008 | Mjalli et al. |
| 7,465,806 B2 | 12/2008 | Bauer et al. |
| 7,470,721 B2 | 12/2008 | Durden |
| 7,501,538 B2 | 3/2009 | Mjalli et al. |
| 7,514,445 B2 | 4/2009 | Freyne et al. |
| 7,534,797 B2 | 5/2009 | Arnold et al. |
| 7,541,373 B2 | 6/2009 | Polisetti et al. |
| 7,569,571 B2 | 8/2009 | Dong et al. |
| 7,572,913 B2 | 8/2009 | McKerracher et al. |
| 7,579,348 B2 | 8/2009 | Wang et al. |
| 7,585,868 B2 | 9/2009 | Knight et al. |
| 7,608,594 B2 | 10/2009 | Blagg et al. |
| 7,615,552 B2 | 11/2009 | Ono et al. |
| 7,622,451 B2 | 11/2009 | Blagg et al. |
| 7,642,272 B2 | 1/2010 | Shankar et al. |
| 7,678,803 B2 | 3/2010 | Huang et al. |
| 7,700,552 B2 | 4/2010 | Wahling et al. |

(56) References Cited

U.S. PATENT DOCUMENTS

| | | |
|---|---|---|
| 7,700,607 B2 | 4/2010 | Hu et al. |
| 7,705,018 B2 | 4/2010 | Chen et al. |
| 7,745,485 B2 | 6/2010 | Durden |
| 7,829,590 B2 | 11/2010 | Brenchley et al. |
| 7,919,046 B2 | 4/2011 | Delapierre et al. |
| 7,932,260 B2 | 4/2011 | Fowler et al. |
| 8,053,445 B2 | 11/2011 | Yamamori et al. |
| 8,053,603 B2 | 11/2011 | Shao et al. |
| 8,088,385 B2 | 1/2012 | Chesney et al. |
| 8,101,637 B2 | 1/2012 | Bessis et al. |
| 8,106,146 B2 | 1/2012 | Benz et al. |
| 8,124,625 B2 | 2/2012 | Yamamori et al. |
| 8,188,134 B2 | 5/2012 | Brenchley et al. |
| 8,193,182 B2 | 6/2012 | Ren et al. |
| 8,399,483 B2 | 3/2013 | Allen et al. |
| 8,557,823 B2 | 10/2013 | Tapolsky et al. |
| 8,569,323 B2 | 10/2013 | Ren et al. |
| 8,703,777 B2 | 4/2014 | Ren et al. |
| 8,703,778 B2 | 4/2014 | Ren et al. |
| 8,785,456 B2 | 7/2014 | Ren et al. |
| 2001/0019829 A1 | 9/2001 | Nelson et al. |
| 2001/0027197 A1 | 10/2001 | Bridges et al. |
| 2002/0016460 A1 | 2/2002 | Snow et al. |
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0107245 A1 | 8/2002 | Wagle et al. |
| 2002/0127625 A1 | 9/2002 | Oxelius |
| 2002/0146690 A1 | 10/2002 | Meyer, Jr. et al. |
| 2002/0147160 A1 | 10/2002 | Bhat et al. |
| 2002/0156073 A1 | 10/2002 | Wagle et al. |
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2002/0193377 A1 | 12/2002 | Andrianjara et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 | 4/2003 | Shokat |
| 2003/0083268 A1 | 5/2003 | Burli et al. |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer, Jr. et al. |
| 2003/0166929 A1 | 9/2003 | Snow et al. |
| 2003/0180924 A1 | 9/2003 | DeSimone |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |
| 2003/0199516 A1 | 10/2003 | Moser et al. |
| 2003/0208800 A1 | 11/2003 | Eby et al. |
| 2003/0212113 A1 | 11/2003 | Dyatkina et al. |
| 2003/0232849 A1 | 12/2003 | Noe et al. |
| 2003/0235822 A1 | 12/2003 | Lokhov et al. |
| 2004/0029875 A1 | 2/2004 | Fauchere et al. |
| 2004/0039035 A1 | 2/2004 | Collins et al. |
| 2004/0043959 A1 | 3/2004 | Bloom et al. |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0072871 A1 | 4/2004 | Dublanchet et al. |
| 2004/0102423 A1 | 5/2004 | MacLaughlan et al. |
| 2004/0102437 A1 | 5/2004 | Takami et al. |
| 2004/0110717 A1 | 6/2004 | Carroll et al. |
| 2004/0110945 A1 | 6/2004 | Nakayama et al. |
| 2004/0116689 A1 | 6/2004 | Gall et al. |
| 2004/0122235 A1 | 6/2004 | Polisetti et al. |
| 2004/0127434 A1 | 7/2004 | Bigot et al. |
| 2004/0146941 A1 | 7/2004 | Zhang et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0235849 A1 | 11/2004 | Beyreuther et al. |
| 2004/0266780 A1 | 12/2004 | Sadhu et al. |
| 2005/0004149 A1 | 1/2005 | Harada et al. |
| 2005/0043239 A1 | 2/2005 | Douangpanya et al. |
| 2005/0043272 A1 | 2/2005 | Platt et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0153997 A1 | 7/2005 | Simon et al. |
| 2005/0171148 A1 | 8/2005 | Mjalli et al. |
| 2005/0182045 A1 | 8/2005 | Nagase et al. |
| 2005/0187418 A1 | 8/2005 | Small et al. |
| 2005/0197340 A1 | 9/2005 | Arora et al. |
| 2005/0214310 A1 | 9/2005 | Toki et al. |
| 2005/0215579 A1 | 9/2005 | Simon et al. |
| 2005/0239809 A1 | 10/2005 | Watts et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2005/0282814 A1 | 12/2005 | Wrasidlo et al. |
| 2006/0019967 A1 | 1/2006 | Wu et al. |
| 2006/0019988 A1 | 1/2006 | McDonald et al. |
| 2006/0069034 A1 | 3/2006 | Burli et al. |
| 2006/0079538 A1 | 4/2006 | Hallahan et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0183783 A1 | 8/2006 | Polisetti et al. |
| 2006/0199776 A1 | 9/2006 | Blagg et al. |
| 2006/0205694 A1 | 9/2006 | Alonso et al. |
| 2006/0235031 A1 | 10/2006 | Arnold et al. |
| 2006/0276470 A1 | 12/2006 | Jackson et al. |
| 2006/0287295 A1 | 12/2006 | Barlaam et al. |
| 2006/0293274 A1 | 12/2006 | Wu |
| 2007/0015773 A1 | 1/2007 | Bergeron et al. |
| 2007/0017915 A1 | 1/2007 | Weder et al. |
| 2007/0027193 A1 | 2/2007 | Leban et al. |
| 2007/0032640 A1 | 2/2007 | Varghese et al. |
| 2007/0054915 A1 | 3/2007 | Arora et al. |
| 2007/0072897 A1 | 3/2007 | Mahaney et al. |
| 2007/0099871 A1 | 5/2007 | Davis et al. |
| 2007/0142405 A1 | 6/2007 | Dong et al. |
| 2007/0179122 A1 | 8/2007 | Urmann et al. |
| 2007/0179151 A1 | 8/2007 | Chen et al. |
| 2007/0224672 A1 | 9/2007 | Leban et al. |
| 2007/0249598 A1 | 10/2007 | Wang et al. |
| 2007/0254318 A1 | 11/2007 | Sebti et al. |
| 2007/0270452 A1 | 11/2007 | Blagg et al. |
| 2008/0032960 A1 | 2/2008 | Knight et al. |
| 2008/0058521 A1 | 3/2008 | Krishnan et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0125432 A1 | 5/2008 | Blom et al. |
| 2008/0200461 A1 | 8/2008 | Anderson et al. |
| 2008/0200465 A1 | 8/2008 | Burli et al. |
| 2008/0249090 A1 | 10/2008 | Hu et al. |
| 2008/0261956 A1 | 10/2008 | Choi et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0306053 A1 | 12/2008 | Tachdjian et al. |
| 2008/0306093 A1 | 12/2008 | Servant et al. |
| 2008/0312180 A1 | 12/2008 | Liang et al. |
| 2008/0318942 A1 | 12/2008 | Simon et al. |
| 2009/0023729 A1 | 1/2009 | Nakamura et al. |
| 2009/0030023 A1 | 1/2009 | Harada et al. |
| 2009/0053192 A1 | 2/2009 | Millan et al. |
| 2009/0088452 A1 | 4/2009 | Coleman et al. |
| 2009/0099214 A1 | 4/2009 | Fairhurst et al. |

(56) References Cited

U.S. PATENT DOCUMENTS

| | | |
|---|---|---|
| 2009/0105233 A1 | 4/2009 | Chua et al. |
| 2009/0118283 A1 | 5/2009 | Defert et al. |
| 2009/0124638 A1 | 5/2009 | Shokat et al. |
| 2009/0124654 A1 | 5/2009 | Mjalli et al. |
| 2009/0137581 A1 | 5/2009 | Chen et al. |
| 2009/0163481 A1 | 6/2009 | Murphy et al. |
| 2009/0163709 A1 | 6/2009 | Blagg |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0232768 A1 | 9/2009 | Birkus et al. |
| 2009/0247513 A1 | 10/2009 | Burli et al. |
| 2009/0253694 A1 | 10/2009 | Ono et al. |
| 2009/0264409 A1 | 10/2009 | Dong et al. |
| 2009/0264423 A2 | 10/2009 | Chua et al. |
| 2009/0270426 A1 | 10/2009 | Knight et al. |
| 2009/0270567 A1 | 10/2009 | Small et al. |
| 2009/0312319 A1 | 12/2009 | Ren et al. |
| 2009/0312406 A1 | 12/2009 | Hsieh et al. |
| 2009/0318411 A1 | 12/2009 | Castanedo et al. |
| 2009/0318503 A1 | 12/2009 | Crooks et al. |
| 2009/0325967 A1 | 12/2009 | Fairhurst et al. |
| 2010/0009963 A1 | 1/2010 | Knight et al. |
| 2010/0022531 A1 | 1/2010 | Kincaid et al. |
| 2010/0022585 A1 | 1/2010 | Delong et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0063047 A1 | 3/2010 | Borchardt et al. |
| 2010/0105630 A1 | 4/2010 | Blagg |
| 2010/0168153 A1 | 7/2010 | Stowasser et al. |
| 2010/0179167 A1 | 7/2010 | Xu et al. |
| 2010/0190749 A1 | 7/2010 | Ren et al. |
| 2010/0216791 A1 | 8/2010 | Aquila et al. |
| 2010/0278811 A1 | 11/2010 | Wrasidlo et al. |
| 2010/0280067 A1 | 11/2010 | Sarma et al. |
| 2010/0280255 A1 | 11/2010 | Moniz et al. |
| 2010/0298290 A1 | 11/2010 | Anand et al. |
| 2011/0009378 A1 | 1/2011 | Lange et al. |
| 2011/0046165 A1 | 2/2011 | Ren et al. |
| 2011/0112137 A1 | 5/2011 | Eissenstat et al. |
| 2011/0124641 A1 | 5/2011 | Ren et al. |
| 2011/0135655 A1 | 6/2011 | Katsikis et al. |
| 2011/0144134 A1 | 6/2011 | Shokat et al. |
| 2011/0160463 A1 | 6/2011 | Moniz et al. |
| 2011/0172228 A1 | 7/2011 | Ren et al. |
| 2011/0172335 A1 | 7/2011 | Deshpande |
| 2011/0190157 A1 | 8/2011 | Kipps et al. |
| 2011/0212975 A1 | 9/2011 | Kao et al. |
| 2011/0224223 A1 | 9/2011 | Shokat et al. |
| 2011/0251182 A1 | 10/2011 | Sun et al. |
| 2011/0269779 A1 | 11/2011 | Wilson et al. |
| 2011/0275803 A1 | 11/2011 | Remenar et al. |
| 2011/0281866 A1 | 11/2011 | Ren et al. |
| 2011/0301144 A1 | 12/2011 | Knight et al. |
| 2011/0306622 A1 | 12/2011 | Lannutti et al. |
| 2012/0004198 A1 | 1/2012 | Liao et al. |
| 2012/0028925 A1 | 2/2012 | Tao et al. |
| 2012/0046307 A1 | 2/2012 | Engel et al. |
| 2012/0059000 A1 | 3/2012 | Ren et al. |
| 2012/0065154 A1 | 3/2012 | Tanaka et al. |
| 2012/0094997 A1 | 4/2012 | England et al. |
| 2012/0122838 A1 | 5/2012 | Ren et al. |
| 2012/0149701 A1 | 6/2012 | Ren et al. |
| 2012/0149715 A1 | 6/2012 | Kao et al. |
| 2012/0157696 A1 | 6/2012 | Chopra et al. |
| 2012/0177749 A1 | 7/2012 | Tapolsky et al. |
| 2012/0183535 A1 | 7/2012 | Buggy et al. |
| 2012/0184568 A1 | 7/2012 | Ren et al. |
| 2012/0196905 A1 | 8/2012 | Cashman |
| 2012/0202784 A1 | 8/2012 | Aronov et al. |
| 2012/0220575 A1 | 8/2012 | Chang et al. |
| 2012/0225851 A1 | 9/2012 | Cardone et al. |
| 2012/0238549 A1 | 9/2012 | Cusack et al. |
| 2012/0238559 A1 | 9/2012 | Baldwin et al. |
| 2012/0245169 A1 | 9/2012 | Ren et al. |
| 2012/0258953 A1 | 10/2012 | Aay et al. |
| 2012/0293063 A1 | 11/2012 | Kang et al. |
| 2012/0322769 A1 | 12/2012 | Yang et al. |
| 2012/0329776 A1 | 12/2012 | Ren et al. |
| 2013/0029982 A1 | 1/2013 | Castro et al. |
| 2013/0029984 A1 | 1/2013 | Castro et al. |
| 2013/0039945 A1 | 2/2013 | Iadonato et al. |
| 2013/0045229 A1 | 2/2013 | Iadonato et al. |
| 2013/0053362 A1 | 2/2013 | Castro et al. |
| 2013/0102608 A1 | 4/2013 | Hoelzemann et al. |
| 2013/0109713 A1 | 5/2013 | Lavoie et al. |
| 2013/0158003 A1 | 6/2013 | Campbell et al. |
| 2013/0172388 A1 | 7/2013 | Xie et al. |
| 2013/0344061 A1 | 12/2013 | Palombella et al. |
| 2013/0345216 A1 | 12/2013 | Ren et al. |
| 2014/0024637 A1 | 1/2014 | Rice |
| 2014/0031547 A1 | 1/2014 | Sheridan et al. |
| 2014/0037622 A1 | 2/2014 | Boshoff et al. |
| 2014/0046052 A1 | 2/2014 | Daniels |
| 2014/0080785 A1 | 3/2014 | Baker et al. |
| 2014/0120060 A1 | 5/2014 | Palombella et al. |
| 2014/0120083 A1 | 5/2014 | Stern et al. |
| 2014/0154203 A1 | 6/2014 | Castillo et al. |
| 2014/0206684 A1 | 7/2014 | Ren et al. |
| 2014/0371246 A1 | 12/2014 | Evarts et al. |
| 2014/0377258 A1 | 12/2014 | Stern et al. |
| 2015/0065431 A1 | 3/2015 | Xu et al. |
| 2015/0184249 A1 | 7/2015 | Chang et al. |
| 2015/0283142 A1 | 10/2015 | Stern et al. |
| 2016/0113932 A1 | 4/2016 | Stern et al. |
| 2017/0360795 A1 | 12/2017 | Stern et al. |
| 2018/0002335 A1 | 1/2018 | Stern et al. |
| 2018/0015093 A1 | 1/2018 | Stern et al. |

FOREIGN PATENT DOCUMENTS

| | | |
|---|---|---|
| CN | 102206172 A | 10/2011 |
| CN | 102448959 A | 5/2012 |
| CN | 102711767 A | 10/2012 |
| CN | 102731492 A | 10/2012 |
| DE | 2139107 A1 | 2/1973 |
| EP | 0773023 A1 | 5/1997 |
| EP | 1262176 A1 | 12/2002 |
| EP | 1020445 B1 | 8/2008 |
| EP | 2759299 A1 | 7/2014 |
| GB | 812366 A | 4/1959 |
| GB | 937725 A | 9/1963 |
| JP | S61109797 A | 5/1986 |
| JP | H04211063 A | 8/1992 |
| JP | H05256693 A | 10/1993 |
| JP | H08295667 A | 11/1996 |
| JP | H09143163 A | 6/1997 |
| JP | H10206995 A | 8/1998 |
| JP | 2000072773 A | 3/2000 |
| JP | 2002131859 A | 5/2002 |
| JP | 2003073357 A | 3/2003 |
| JP | 2004161716 A | 6/2004 |
| JP | 4834699 B2 | 12/2011 |
| JP | 4846769 B2 | 12/2011 |
| WO | WO-8301446 A1 | 4/1983 |
| WO | WO-9117161 A1 | 11/1991 |
| WO | WO-9214733 A1 | 9/1992 |
| WO | WO-9316091 A1 | 8/1993 |
| WO | WO-9316092 A1 | 8/1993 |
| WO | WO-9318035 A1 | 9/1993 |
| WO | WO-9319767 A1 | 10/1993 |
| WO | WO-9322443 A1 | 11/1993 |
| WO | WO-9413677 A1 | 6/1994 |
| WO | WO-9417803 A1 | 8/1994 |
| WO | WO-9429436 A1 | 12/1994 |
| WO | WO-9510628 A2 | 4/1995 |
| WO | WO-9512588 A1 | 5/1995 |
| WO | WO-9519744 A1 | 7/1995 |
| WO | WO-9519774 A1 | 7/1995 |

(56) References Cited

FOREIGN PATENT DOCUMENTS

| | | |
|---|---|---|
| WO | WO-9529673 A1 | 11/1995 |
| WO | WO-9532984 A1 | 12/1995 |
| WO | WO-9640706 A1 | 12/1996 |
| WO | WO-9728133 A1 | 8/1997 |
| WO | WO-9728161 A1 | 8/1997 |
| WO | WO-9841525 A1 | 9/1998 |
| WO | WO-9852611 A1 | 11/1998 |
| WO | WO-9857952 A1 | 12/1998 |
| WO | WO-0017202 A1 | 3/2000 |
| WO | WO-0102369 A2 | 1/2001 |
| WO | WO-0116114 A2 | 3/2001 |
| WO | WO-0119829 A2 | 3/2001 |
| WO | WO-0121160 A2 | 3/2001 |
| WO | WO-0125238 A2 | 4/2001 |
| WO | WO-0131063 A1 | 5/2001 |
| WO | WO-0138584 A2 | 5/2001 |
| WO | WO-0155140 A1 | 8/2001 |
| WO | WO-0156988 A1 | 8/2001 |
| WO | WO-0160824 A1 | 8/2001 |
| WO | WO-0181346 A2 | 11/2001 |
| WO | WO-0206192 A1 | 1/2002 |
| WO | WO-0228853 A1 | 4/2002 |
| WO | WO-0230944 A2 | 4/2002 |
| WO | WO-02057425 A2 | 7/2002 |
| WO | WO-02076986 A1 | 10/2002 |
| WO | WO-02080926 A1 | 10/2002 |
| WO | WO-02083143 A1 | 10/2002 |
| WO | WO-02088025 A1 | 11/2002 |
| WO | WO-02090334 A1 | 11/2002 |
| WO | WO-03000187 A2 | 1/2003 |
| WO | WO-03016275 A1 | 2/2003 |
| WO | WO-03020880 A2 | 3/2003 |
| WO | WO-03024969 A1 | 3/2003 |
| WO | WO-03028341 A2 | 4/2003 |
| WO | WO-03035075 A1 | 5/2003 |
| WO | WO-03059884 A1 | 7/2003 |
| WO | WO-03082341 A1 | 10/2003 |
| WO | WO-03106426 A1 | 12/2003 |
| WO | WO-2004006906 A2 | 1/2004 |
| WO | WO-2004018058 A2 | 3/2004 |
| WO | WO-2004031177 A1 | 4/2004 |
| WO | WO-2004039774 A2 | 5/2004 |
| WO | WO-2004046128 A1 | 6/2004 |
| WO | WO-2004058717 A1 | 7/2004 |
| WO | WO-2004075917 A1 | 9/2004 |
| WO | WO-2004087053 A2 | 10/2004 |
| WO | WO-2004087679 A1 | 10/2004 |
| WO | WO-2004089877 A1 | 10/2004 |
| WO | WO-2004111014 A1 | 12/2004 |
| WO | WO-2005002585 A1 | 1/2005 |
| WO | WO-2005007085 A2 | 1/2005 |
| WO | WO-2005012323 A2 | 2/2005 |
| WO | WO-2005016348 A1 | 2/2005 |
| WO | WO-2005016349 A1 | 2/2005 |
| WO | WO-2005016528 A2 | 2/2005 |
| WO | WO-2005021533 A1 | 3/2005 |
| WO | WO-2005044181 A2 | 5/2005 |
| WO | WO-2005047289 A1 | 5/2005 |
| WO | WO-2005061460 A1 | 7/2005 |
| WO | WO-2005063258 A1 | 7/2005 |
| WO | WO-2005067901 A2 | 7/2005 |
| WO | WO-2005074603 A2 | 8/2005 |
| WO | WO-2005097800 A1 | 10/2005 |
| WO | WO-2005105760 A1 | 11/2005 |
| WO | WO-2005112935 A1 | 12/2005 |
| WO | WO-2005113556 A1 | 12/2005 |
| WO | WO-2005117889 A1 | 12/2005 |
| WO | WO-2005120511 A1 | 12/2005 |
| WO | WO-2006015279 A1 | 2/2006 |
| WO | WO-2006030032 A1 | 3/2006 |
| WO | WO-2006038865 A1 | 4/2006 |
| WO | WO-2006050501 A2 | 5/2006 |
| WO | WO-2006050946 A1 | 5/2006 |
| WO | WO-2006068760 A2 | 6/2006 |
| WO | WO-2006089106 A2 | 8/2006 |
| WO | WO-2006108107 A1 | 10/2006 |
| WO | WO-2006112666 A1 | 10/2006 |
| WO | WO-2006114064 A2 | 11/2006 |
| WO | WO-2006114065 A2 | 11/2006 |
| WO | WO-2007002293 A2 | 1/2007 |
| WO | WO-2007006547 A1 | 1/2007 |
| WO | WO-2007020046 A1 | 2/2007 |
| WO | WO-2007025090 A2 | 3/2007 |
| WO | WO-2007029121 A2 | 3/2007 |
| WO | WO-2007061737 A2 | 5/2007 |
| WO | WO-2007075554 A2 | 7/2007 |
| WO | WO-2007079164 A2 | 7/2007 |
| WO | WO-2007103308 A2 | 9/2007 |
| WO | WO-2007112005 A2 | 10/2007 |
| WO | WO-2007114926 A2 | 10/2007 |
| WO | WO-2007121453 A2 | 10/2007 |
| WO | WO-2007121920 A2 | 11/2007 |
| WO | WO-2007121924 A2 | 11/2007 |
| WO | WO-2007124854 A1 | 11/2007 |
| WO | WO-2007125310 A2 | 11/2007 |
| WO | WO-2007125315 A2 | 11/2007 |
| WO | WO-2007126841 A2 | 11/2007 |
| WO | WO-2007134828 A1 | 11/2007 |
| WO | WO-2007135380 A2 | 11/2007 |
| WO | WO-2007135398 A2 | 11/2007 |
| WO | WO-2008001236 A2 | 1/2008 |
| WO | WO-2008012325 A2 | 1/2008 |
| WO | WO-2008012326 A1 | 1/2008 |
| WO | WO-2008025755 A1 | 3/2008 |
| WO | WO-2008047821 A1 | 4/2008 |
| WO | WO-2008063625 A2 | 5/2008 |
| WO | WO-2008064018 A1 | 5/2008 |
| WO | WO-2008070507 A2 | 6/2008 |
| WO | WO-2008079028 A1 | 7/2008 |
| WO | WO-2008082487 A2 | 7/2008 |
| WO | WO-2008094737 A2 | 8/2008 |
| WO | WO-2008112715 A2 | 9/2008 |
| WO | WO-2008117050 A1 | 10/2008 |
| WO | WO-2008118454 A2 | 10/2008 |
| WO | WO-2008118455 A1 | 10/2008 |
| WO | WO-2008118468 A1 | 10/2008 |
| WO | WO-2008125014 A1 | 10/2008 |
| WO | WO-2008125207 A1 | 10/2008 |
| WO | WO-2008127226 A2 | 10/2008 |
| WO | WO-2008136457 A1 | 11/2008 |
| WO | WO-2009000412 A1 | 12/2008 |
| WO | WO-2009004621 A1 | 1/2009 |
| WO | WO-2009010925 A2 | 1/2009 |
| WO | WO-2009019531 A2 | 2/2009 |
| WO | WO-2009023718 A2 | 2/2009 |
| WO | WO-2009029617 A1 | 3/2009 |
| WO | WO-2009044707 A1 | 4/2009 |
| WO | WO-2009050506 A2 | 4/2009 |
| WO | WO-2009064802 A2 | 5/2009 |
| WO | WO-2009088986 A1 | 7/2009 |
| WO | WO-2009088990 A1 | 7/2009 |
| WO | WO-2009100406 A2 | 8/2009 |
| WO | WO-2009103022 A1 | 8/2009 |
| WO | WO-2009117157 A1 | 9/2009 |
| WO | WO-2009118765 A2 | 10/2009 |
| WO | WO-2010006086 A2 | 1/2010 |
| WO | WO-2010009207 A1 | 1/2010 |
| WO | WO-2010019210 A2 | 2/2010 |
| WO | WO-2010036380 A1 | 4/2010 |
| WO | WO-2010039534 A2 | 4/2010 |
| WO | WO-2010053998 A1 | 5/2010 |
| WO | WO-2010057048 A1 | 5/2010 |
| WO | WO-2010065923 A2 | 6/2010 |
| WO | WO-2010070032 A1 | 6/2010 |
| WO | WO-2010092340 A1 | 8/2010 |
| WO | WO-2010133836 A1 | 11/2010 |
| WO | WO-2011008302 A1 | 1/2011 |
| WO | WO-2010138588 A9 | 5/2011 |
| WO | WO-2011058108 A1 | 5/2011 |
| WO | WO-2011058109 A1 | 5/2011 |
| WO | WO-2011058110 A1 | 5/2011 |
| WO | WO-2011075628 A1 | 6/2011 |
| WO | WO-2011094890 A1 | 8/2011 |
| WO | WO-2011111880 A1 | 9/2011 |

(56) References Cited

FOREIGN PATENT DOCUMENTS

| | | |
|---|---|---|
| WO | WO-2011146882 A1 | 11/2011 |
| WO | WO-2012009452 A1 | 1/2012 |
| WO | WO-2012032334 A1 | 3/2012 |
| WO | WO-2012037204 A1 | 3/2012 |
| WO | WO-2012052540 A1 | 4/2012 |
| WO | WO-2012061696 A1 | 5/2012 |
| WO | WO-2012064973 A2 | 5/2012 |
| WO | WO-2012068096 A2 | 5/2012 |
| WO | WO-2012068106 A2 | 5/2012 |
| WO | WO-2012071519 A1 | 5/2012 |
| WO | WO-2012097000 A1 * 7/2012 ......... A61K 31/4725 | |
| WO | WO-2012121953 A1 | 9/2012 |
| WO | WO-2012129562 A2 | 9/2012 |
| WO | WO-2013006532 A1 | 1/2013 |
| WO | WO-2013010868 A1 | 1/2013 |
| WO | WO-2013012915 A1 | 1/2013 |
| WO | WO-2013012918 A1 | 1/2013 |
| WO | WO-2013013504 A1 | 1/2013 |
| WO | WO-2013013505 A1 | 1/2013 |
| WO | WO-2013025498 A1 | 2/2013 |
| WO | WO-2013044169 A1 | 3/2013 |
| WO | WO-2013059738 A2 | 4/2013 |
| WO | WO-2013066483 A1 | 5/2013 |
| WO | WO-2013074583 A1 | 5/2013 |
| WO | WO-2013086131 A1 | 6/2013 |
| WO | WO-2013090725 A1 | 6/2013 |
| WO | WO-2013113838 A1 | 8/2013 |
| WO | WO-2013113841 A1 | 8/2013 |
| WO | WO-2013188763 A1 | 12/2013 |
| WO | WO-2014004470 A1 | 1/2014 |
| WO | WO-2014018567 A1 | 1/2014 |
| WO | WO-2014046617 A1 | 3/2014 |
| WO | WO-2014071105 A1 | 5/2014 |
| WO | WO-2014071109 A1 | 5/2014 |
| WO | WO-2014071125 A1 | 5/2014 |
| WO | WO-2014072937 A1 | 5/2014 |
| WO | WO-2014075393 A1 | 5/2014 |
| WO | WO-2014124458 A1 | 8/2014 |
| WO | WO-2014141165 A1 | 9/2014 |
| WO | WO-2014168975 A1 | 10/2014 |
| WO | WO-2014175267 A1 | 10/2014 |
| WO | WO-2014194254 A1 | 12/2014 |
| WO | WO-2014201409 A1 | 12/2014 |
| WO | WO-2014203959 A1 | 12/2014 |
| WO | WO-2015002729 A2 | 1/2015 |
| WO | WO-2015010641 A1 | 1/2015 |
| WO | WO-2015037005 A1 | 3/2015 |
| WO | WO-2015051252 A1 | 4/2015 |
| WO | WO-2015054099 A1 | 4/2015 |
| WO | WO-2015054355 A1 | 4/2015 |
| WO | WO-2015081127 A2 | 6/2015 |
| WO | WO-2015083008 A1 | 6/2015 |
| WO | WO-2015095807 A1 | 6/2015 |
| WO | WO-2015095819 A2 | 6/2015 |
| WO | WO-2015095825 A1 | 6/2015 |
| WO | WO-2015095829 A1 | 6/2015 |
| WO | WO-2015095831 A1 | 6/2015 |
| WO | WO-2015095834 A2 | 6/2015 |
| WO | WO-2015095840 A1 | 6/2015 |
| WO | WO-2015095842 A2 | 6/2015 |
| WO | WO-2015109286 A1 | 7/2015 |
| WO | WO-2015143382 A1 | 9/2015 |
| WO | WO-2015160975 A2 | 10/2015 |
| WO | WO-2015160986 A2 | 10/2015 |
| WO | WO-2015175966 A1 | 11/2015 |
| WO | WO-2015179772 A1 | 11/2015 |
| WO | WO-2015181053 A1 | 12/2015 |
| WO | WO-2015181055 A1 | 12/2015 |
| WO | WO-2015188119 A1 | 12/2015 |

OTHER PUBLICATIONS

Walter, Roland B., et al. "Pretargeted Radioimmunotherapy for Hematologic and Other Malignancies." Cancer Biotherapy and Radiopharmaceuticals. (2010), vol. 25, No. 2, pp. 125-142. (Year: 2010).*

Redondo-Munoz, Javier, et al. "Matrix metalloproteinase-9 is up-regulated by CCL21/CCR7 interaction via extracellular signal-regulated kinase-1/2 signaling and is involved in CCL21-driven B-cell chronic lymphocytic leukemia cell invasion and migration." Blood. (Jan. 1, 2008), vol. 111, No. 1. (Year: 2008).*

Burkle, Andrea, et al. "Overexpression of the CXCR5 chemokine receptor, and its ligand, CXCL13 in B-cell chronic lymphocytic leukemia." Blood. (Nov. 1, 2007), vol. 110, No. 9, pp. 3316-3325. (Year: 2007).*

Yan, Xiao-Jie, et al. "Identification of outcome-correlated cytokine clusters in chronic lymphocytic leukemia." Blood. (Nov. 10, 2011), vol. 118, No. 19, pp. 5201-5210. (Year: 2011).*

Davids, Matthew S. and Burger, Jan A. "Cell Trafficking in Chronic Lymphocytic Leukemia." Open J. Hematol. (2012), vol. 3(S1), pp .1-13. (Year: 2012).*

Roberts, Andrew W. "Substantial Susceptibility of Chronic Lymphocytic Leukemia to Bcl2 Inhibition: Results of a Phase I Study of Navitoclax in Patients with Relapsed or Refractory Disease." J. Clinical Oncology. (Feb. 10, 2012), vol. 30, No. 5, pp. 488-496. (Year: 2012).*

Hansen, Lea Ann. "Bruton's Tyrosine Kinase: An Exciting New Target for Treatment of B-Cell Malignancies." Cancer Therapy Advisor. (Jan. 2012). pp. 1 of 7 through 7 of 7. (Year: 2012).*

Lucas, DM. "The histone deacetylase inhibitor MS-275 induces caspase-dependent apoptosis in B-cell chronic lymphocytic leukemia cells." Leukemia. (2004), vol. 18, pp. 1207-1214. (Year: 2004).*

De Lartigue, Jane. "The MEK Junction: Protein Presents a Ripe Target for Inhibitors." OncologyLive. (Sep. 2012), vol. 13, Issue 9, pp. 1-6 of 6 (Year: 2012).*

Wu, Z., et al. "Polycomb protein EZH2 regulates cancer cell fate decision in response to DNA damage." Cell Death and Differentiation. (2011), vol. 18, pp. 1771-1779. (Year: 2011).*

Belov, Larissa, et al. "Immunophenotyping of Leukemias Using a Cluster of Differentiation Antibody Microarray." Cancer Research. (Jun. 1, 2001), vol. 61, pp. 4483-4489. (Year: 2001).*

Liu, Xiaoqi and Erikson, Raymond L. "Polo-like kinase (Plk)1 depletion induces apoptosis in cancer cells." PNAS. (May 13, 2003), vol. 100, No. 10, pp. 5789-5794. (Year: 2003).*

Abdel-Mohsen, "Synthesis, Reactions and Antimicrobial Activity of 2-Amino-4-(8-quinolinol-5-yl)-1-(p-tolyl)-pyrrole-3-carbonitrile," Bull. Korean Chem. Soc. 26(5):719-728 (2005).

Abe et al., "T Cell Receptor-mediated Recognition of Self-Ligand Induces Signaling in Immature Thymocytes before Negative Selection," J. Exp. Med. 176(2): 459-468 (1992).

Abraham, T., "Thermally induced intramolecular cycloaddition reaction of N-phenyl-2-phenylethynlbenzamide potential cure reaction for thermosetting polymers," J. Polym. Sci. Polym. Chem. Ed. 20(7): 1953-1957 (1982).

Abrahamian et al., "Immunological and Clinical Profile of Adult Patients with Selective immunoglobulin Subclass deficiency: response to intravenous immunoglobulin therapy," Clin. Exp. Immunol. 159(3): 344-350 (2010}.

American Cancer Society. Non-Hodgkin's Lymphoma. Last Revised Mar. 11, 2015, Retrieved online: http://www.cancer.org/cancer/nonhodgkinlymphoma/detailedguide/non-hodgkin-lymphoma-types-of-non-hodgkin-lymphoma, 79 pages.

Ameriks and Venable, "Small Molecule Inhibitors of Phosphoinositide 3-Kinase (PI3K) delta and gamma," Current Topics in Medicinal Chemistry 9: 738-753 (2009).

Ames et al., "Heterocyclic Syntheses from o-Halogeno-acids. Part II. Thienopyridinones and Thienopyranones from 3-Bromothiophen-2- and 4-Bromothiophen-3-carboxylic Acids," J. Chem. Soc., Perkin Trans. 1: 1390-1395 (1975).

Anderson et al., "Paradoxical inhibition of T-cell function in response to CTLA-4 blockade; heterogeneity within the human T-cell population," Nat. Med. 6(2): 211-214 (2000).

Andrews et al., "Effects of the 11 beta-hydroxysteroid dehydrogenase inhibitor carbenoxolone on insulin sensitivity in men with type 2 diabetes," J_ Clin. Endocrinol Metab. 88(1): 285-291 (2003).

(56) References Cited

OTHER PUBLICATIONS

Press Release: "Infinity Regains Worldwide Rights to PI3K, Faah and Early Discovery Programs", Infinity Pharmaceuticals, Jul. 18, 2012.
Arcaro et al., "Wortmannin is a potent phosphatidylinositol 3-kinase inhibitor: the role of phosphatidylinositol 3,4,5-triphosphate in neutrophil responses," Biochem J. 296(Pt 2): 297-301 (1993).
Arnold et al., "Pyrrolo[2,3-d]pyrimidines containing an extended 5-substituent as potent and selective inhibitors of Ick I," Bioorg. Med. Chem. Lett 10(19) 2167-2170 (2000).
Arteaga, C.L., "Clinical development of phosphatidylinositol-3 kinase pathway inhibitors," in Phosphoinositide 3-kinase in health and disease, Rommel, C. et al (eds), Springer, New York, 2010, vol. 2, pp. 189-208.
Ashizawa, Kazuhide, "Science of polymorphism and crystallization in pharmaceutical products", Maruzen Planet Co., Sep. 20, 2002, pp. 3-16.
Augustine et al., "Interleukin 2- and polyomavims middle T antigen-induced modification of phosphatidylinositol 3-kinase activity in activated T lymphocytes," Mol. Cell. Biol. 11(9):4431-4440 (1991).
Baggiolini et al., "Inhibition of the phagocytosis-induced respiratory burst by the fungal metabolite wortmannin and some analogues," Exp Cell Res 169(2): 408-418 (1987).
Ballell et al. "New Thiopyrazolo[3,4-d] pyrimidine derivatives as anti-mycobacterial agents," Bioorg. Med. Chem. Lett. 17(6):1736-1740 (2007).
Banker, G.S. et al, "Modern Pharmaceutics," 3ed., Marcel Dekker, New York, 1996, pp. 451 and 596.
Bansal et al., The Molecular Biology of Endometrial Cancers and the Implications for Pathogenesis, Classification. and Targeted Therapies, Cancer Control 16(1): 8-13 (2009).
Barber et al., "PI3Kgamma inhibition blocks glomemlonephritis and extends lifespan in a mouse model of systemic lupus," Nat. Med. 11(9):933-935 (2005).
Barf et al., "Arylsulfonamidolhiazoles as a new class of potential antidiabelic drugs. Discovery of potent and selective inhibitors of the 11 beta-hydroxysteroid dehydrogenase type 1," J. Med. Chem. 45(18): 3813-3815 (2002).
Barf et al., "Irreversible Protein Kinase Inhibitors: Balancing the Benefits and Risks", Journal of Medicinal Chemistry, vol. 55, No. 14, Jul. 26, 2012 (Jul. 26, 2012), pp. 6243-6262, XP055096173, ISSN: 0022-2623, DOI: 10.1021/jm3003203.
Barnes et al., "Efficacy and Safety of Inhaled Corticosteroids in Asthma. Report of a Workshop Held in Eze, France Oct. 1992," Am. Rev. Respir. Dis. 148: S1-S26 (1993).
Barnes et al., "Glucocortiod resistance in inflammatory diseases," The Lancet, 373:1905-1917 (2009).
Bartholomeusz et al., "Targeting the PI3K Signaling Pathway in Cancer Therapy," Expert Opin. Ther. Targets 16(1): 121-130 (2012).
BASOTEST®, Test Kit for the Quantitative Determination of the Degranulation of Basophilic Granulocytes in Heparinized Human Whole Blood, version Apr. 2002, pp. 1-10, [www.biocarta.com/TDS/10-0500.pdf], Retrieved from the Internet Nov. 29, 2011.
Beeram et al., "Aki-induced endocrine therapy resistance is reversed by inhibition of mTOR signaling," Ann. Oncol. 18 (8): 1323-1328 (2007).
Bell et al., "Glucokinase mutations insulin secretion, and diabetes mellitus", Annu. Rev. Physiol. 58:171-186 (1996).
Berndt et al., "The pl 108 crystal structure uncovers mechanisms for selectivity and potency of novel PI3K inhibitors," Nat. Chem. Biol. 6(2):117-124 (2010).
Bhat et al., "Pyrazolopyrimidine nucleosides. 12. Synthesis and biological activity of certain pyrazolo[3,4-d]pyrimidine nucleosides related to adenosine," J. Med. Chem. 24(10): 1165-1172 (1981).
Bhatt et al., "Dual inhibition of PI3K and mTOR inhibits autocrine and paracrine proliferative loops in PI3K/Akt/mTOR-addicted lymphomas," Blood I 15(22):4455-4463 (2010).
Bi et al., "Proliferative defect and embryonic lethality in mice homozygous for a deletion in the p110alpha subunit of phosphoinositide 3-kinase," J. Biol. Chem. 274(16): 10963-10968 (1999).

Billottet et al., A selective inhibitor of the p110delta isoform of PI 3-kinase inhibits AML cell proliferation and survival and increases the cytotoxic effects of VP16, Oncogene 25(50):6648-6659 {2006).
Billottet et al., "Inhibition of Class I Phosphoinositide 3-Kinase Activity Impairs Proliferation and Triggers Apoptosis in Acute Promyelocytic Leukemia without Affecting Atra-Induced Differentiation," Cancer Res. 69(3): 1027-1036 (2009).
Bishop et al., "Generation of monospecific nanomolar tyrosine kinase inhibitors via a chemical genetic approach," J. Am. Chem. Soc. 121(4):627-631 (1999).
Blunden et al., "Mycotoxins in food," Med. Lab_ Sci 48(4): 271-282 (1991j.
Bochner et a., "Immunological aspects of allergic asthma," Annu. Rev. Immunol. 12: 295-335 (1994).
Bohren et al., "Expression, crystallization and preliminary crystallographic analysis of human carbonyl reductase," J. Mol. Biol. 224:659-664 (1994).
Bojarczuk et al., "B-cell receptor pathway inhibitors affect CD20 levels and impair antitumor activity of anti-CD20 monoclonal antibodies," Leukemia 1-5 (2014).
Bone et al., "Phosphoinositide 3-kinase signalling regulates early development and developmental haemopoiesis," J. Cell. Sci. 120(Pt 10): 1752-1762 (2007).
Bouska et al., "Genome-wide copy-number analyses reveal genomic abnormalities involved in transformation of follicular lymphoma," Blood 123 (11): 1681-1690 (2014).
Bowers et al., "A platelet biomarker for assessing phosphoinositide 3-kinase inhibition during cancer chemotherapy," Mol Cancer Ther. 6(9): 2600-2607 (2007).
Boyle et al., "Efficacy of the Potent PI3K-delta,gamma Inhibitor IPI-145 in Rat Adjuvant Arthritis," Arthritis & Rheumatism 64(10): S879 (2012).
Brown et al., "Idelalisib, an inhibilor of phosphatidylinositol 3-kinase p110delta, for relapsed/refractory chronic lympocytic leukemia," Blood 123(22): 3390-3397 (2014).
Brown et al. "Phase I Trial of SAR245408 (S08), a Pan-Phosphatidylinositol 3 Kinase (PI3K) Inhibitor, in Patients with Chronic Lymphocytic Leukemia (CLL) and Lymphoma", Blood (ASH Annual Meeting Abstracts) 2011 118: Abstract 2683, Downloaded from the Internet.
Brown, "The treatment of Relapsed Refractory Chronic Lymphocytic Leukemia," Hematology 110-118 (2011).
Brzezianska et al., "A minireview: the role of MAPK/ERK and PI3K/Akt pathways in thyroid follicular cell-derived neoplasm," Front Biosci. 16: 422-439 (2011).
Buet et al., "Cotargeting signaling pathways driving survival and cell cycle circumvents resistance to Kil inhibitors in leukemia", Blood, vol. 119, No. 18, May 3, 2012, pp. 4228-4241.
Buitenhuis et al., "The role of the PI3K-PKB signaling module in regulation of hematopoiesis," Cell Cycle 8(4): 560-566 (2009.
Burger et al., "High-level expression of the T-cell chemokines CCL3 and CCL4 by chronic lymphocytic leukemia B cells in nurselike cell cocultures and after BCR stimulation," Blood 113(13) 3050-3058 (2009).
Burger, "Inhibiting B-Cell Receptor Signaling Pathways in Chronic Lymphocytic Leukemia," Curr. Memalol. Malig. Rep. 7(1): 26-33 (2012).
Byrd et al., "Translating PI3K-Delta Inhibitors to the Clinic in Chronic Lymphocytic Leukemia: The Story of CAL-101 (GS1101)," ASCO Program Proceedings, pp. 691-694 (2012).
Caira, "Crystalline polymorphism of organic compounds," Topics Curr Chem. Jan. 1, 1998;198:163-208.
Calin et al., "A MicroRNA Signature Associated with Prognosis and Progression in Chronic Lymphocytic Leukemia", N Engl J Med, 2005, vol. 353, pp. 1793-1801.
Campbell, et al., The Potent PI3K-delta Inhibitor, IPI-145, Exhibits Differential Activity in Diffuse Large B-cell Lymphoma (DLBCL) Cell Lines, Dec. 7, 2013, 55th ASH Annual Meeting and Exposition, New Orleans, LA, Poster 1832.
Campora et al., "Binuclear complexes of nickel bridged by hydrocarbon ligands. Isocyanide insertion chemistry and amide formation by intramolecular coupling of acyl and imidoyl functionalities," Organometallics 11(1):11-13 (1992).

(56) References Cited

OTHER PUBLICATIONS

Campora et al., "Isocyarnde insertion chemistry. Synthesis and structural characterization of bridging imidoyl complexes of nickel and amide formation by intramolecular coupling of acyl and imidoyl functionalities," Organometallics 12(10): 4025-4031 (1993).
Camps et al., "Blockade of PI3Kgamma suppresses joint inflammation and damage in mouse models of rheumatoid arthritis," Nat. Med. 11 (9): 936-943 (2005).
Cao et al., "The BCL2 antagonist ABT-199 triggers apoptosis, and augments ibrutinib and idelalisib mediated cytotoxicity in CXCR4 Wild-type and CXCR4 Whim mutated Waldenstrom macroglobulinaemia cells", British Journal of Haematology, vol. 170, online Jan. 12, 2015, pp. 134-138.
Castor et al, "PI3Kg controls leukocyte recruitment, tissue injury, and lethality in a model of graft-versus-host disease in mice," J. Leukocyte Biol. 89: 955-964 (2011) 2.
Chaisuparat et al, "Dual inhibition of PI3Kalpha and mTOR as an alternative treatment for Kaposi's Sarcoma," Cancer Res. 68: 8361-8368 (2008).
Chang et al., "Novel Synthesis and Reactions of 5, 7-Dialkyl-4,6-dioxo-4,5,6,7-tetrahydro-isothiazolo [3,4,-d]pyrimidine-3-carbonitriles and 6-Methyl-4-oxo-4H-I-aza-5-oxa-2-thiaindene-3-carbonitrile", Org. Lett. 5(4):507-510 (2003).
Chang et al., "PI3-Kinase Inhibitors in Chronic Lymphocytic Leukemia", Current Hematologic Malignancy Reports, 9(1):33-43 (2014).
Chang et al., "The Bruton tyrosine kinase inhibitor PCI-32765 ameliorates autoimmune arthritis by inhibition of multiple effector cells," Arthritis Research & Therapy 13(4): R115 (2011).
Chappelow, et al., "Neovascular Age-Related Macular Degeneration: Potential Therapies", Drugs, vol. 68, 2008, pp. 1029-1036.
Chapuis et al., "Dual Inhibition of PI3K and mTORC1/2 Signaling by NVP-BEZ235 as a New Therapeutic Strategy for Acute Myeloid Leukemia," Clin. Cancer Res. 16(22): 5425-5435 {2010}.
Chawla et al , "Challenges in Polymorphism of Pharmaceuticals," Current Research & Informabon on Pharmaceutical Science 5(1): 9-12 (2004).
Chen et al., "Characterization of Structurally Distinct, Isoform-Selective Phosphoinositide 3'-Kinase Inhibitors in Combination with Radiation in the Treatment of Glioblastoma," Mol. Cancer Ther. 7(4):841-850 (2008).
Cheson et al., "Bendamustine: Rebirth of an Old Drug," J. Clin. Oncol. 27(9): 1492-1501 (2009).
Cheson et al. "Novel Targeted Agents and the Need to Refine Clinical End Points in Chronic Lymphocytic Leukemia". Journal of Clinical Oncology, vol. 30, No. 23, pp. 2820-2822, Aug. 10, 2012.
Cheung et al., "Genome-wide profiling of follicular lymphoma by array comparative genomic hybridization reveals prognostically significant DNA copy number imbalances", Blood, Jan. 1, 2009, ,vol. 113, No. 1, pp. 137-148.
Cheung et al., "High Resolution Analysis of Follicular Lymphoma Genomes Reveals Somatic Recurrent Sites of Copy-Neutral Loss of Heterozygosity and Copy Number Alterations that Target Single Genes", Genes, Chromosomes & Cancer 49; 669-681 (2010), DOI 10.1002/gcc.
Chiarini et al., "Activity of the Novel Dual Phosphatidylinositol 3-Kinase/Mammalian Target of Rapamycin Inhibitor NVP-BEZ235 against T-Cell Acute Lymphoblastic Leukemia," Cancer Res. 70(20): 8097-8107 (2010).
Chiarini et al., "Dual Inhibition of Class IA Phosphatidylinositol 3-Kinase and Mammalian Target of Rapamycin as a New Therapeutic Option for T-Cell Acute Lymphoblastic Leukemia," Cancer Res. 69(8): 3250-3528 (2009).
Chiron et al., "791 Induction of Early G1-Arrest by CDK4/CDK6 Inhibition Sensitizes Mantle Cell Lymphoma Cells to Selective PI3K? Inhibition by GS-1101 Through Enhancing the Magnitude and Duration of p-AKT Inhibition", American Society of Hematology, Dec. 10, 2013, retrieved from the internet: https://ash.confex.com/ash/2012/webprogram/Paper52021.html.
Chiron et al., "Cell-Cycle Reprogramming for PI3K Inhibition Overrides a Relapse-Specific C48 I S BTK Mutation Revealed by Longitudinal Functional Genomics in Mantle Cell Lymphoma", Cancer Discovery, (Sep. 2014), vol. 4, pp. 1022-1035, Published Online First Jul. 31, 2014; DOI: 10.1158/2159-8290.CD-14-0098.
Cho et al., "A novel synthesis of benzo[c]phenanthridine skeleton and biological evaluation of isoquinoline derivatives," Chem. Pharm. Bull. (Tokyo) 47(6): 900-902 (1999).
Cho et al, "Targeting apoptosis in renal cell carcinoma (RCC): In vitro synergy between ABT-737 and inhibition of PI3-Kinase in RCC cell lines," AACR annual meeting, Apr. 2009 (2 pages).
Choi et al., Inhibitors of B-cell Receptor Signaling for patients with B-cell malignancies, Cancer J 18(5):404-410 (2012).
Choudhary et al., "MCL-1 and BCL-xL-dependent resistance to the BGL-2 inhibitor ABT-199 can be overcome by preventing PI3KJ AKT/mT4R activation in lymphoid malignancies", Cell Death & Disease 2015, vol. 6, 2015, online Jan. 15, 2015, p. e1593.
Clayton et al., "A crucial role for the P110 delta subunit of phosphatidylinositol 3-kinase in B cell development and activation," J. Exp. Med. 196(6): 753-763 (2002).
ClinicalTrials.gov, "Dose Escalation Study of CAL-101 in Select Relapsed or Refractory Hematologic Malignancies" [online] (2008) [Retrieved on Jul. 23, 2014] Retrieved from http://clinicaltrials.gov/ct2/show/NCT007I0528.
ClinicalTrials.gov NCT01476657 Study, "A Phase 1 Study of IPI-145 in Patients with Advanced Hematologic Malignancies", Nov. 17, 2011. D.
Closse et al., "2,3-dihydrobenzofuran-2-ones: a new class of highly potent antiinflammatory agents," J Med. Chem. 24(12):1465-1471 (1981).
Conte et a!., "Inhibition of PI3K Prevent the Proliferation and Differentiation of Human Lung Fibroblasts into Myofibroblasts: The Role of Class I Pi 10 Isoforms," Plos One 6(10) e24663: 1-10 (2011).
Courtney et al., "The PI3K Pathway as Drug Target in Human Cancer," J. Clin. Oncol. 28(6):1075-1083 (2010).
Cox et al., "Human colorectal cancer cells efficiently conjugate the cyclopentenone prostaglandin, prostaglandin J2, to glutathione," Biochem. Biophys. Acta. 1584(1): 37-45 (2002).
Cui et al., "MicroRNA -:155 influences B—cell receptor signaling and associates with aggressive disease m chronic lymphocytic leukemia", Blood. 2014, vol. 124{4), pp. 546.-554.
Cushing et al., "PI3Kdelta and PI3Kgamma as Targets for Autoimmune and Inflammatory Diseases," J. Med. Chem. 55 (20): 8559-8581 (2012).
Dai et al., "Distinct Roles of Phosphoinositide-3 Kinase and Phospholipase Cgamma2 in B-Cell Receptor-Mediated Signal Transduction," Mol. Cell. Biol. 26(1): 88-99 (2006).
D'Amore et al., "Clonal Evolution in t(I4;18)-Positive Follicular Lymphoma, Evidence for Multiple Common Pathways, and Frequent Parallel Clonal Evolution", Clin Cancer Res 2008;14(22) Nov. 15, 2008, pp. 7180-7187.
Davids et al., "Decreased mitochondrial apoptotic priming underlies stroma-mediated treatment resistance in chronic lymphocytic leukemia," Blood 120 (17): 3501-3509 (2012).
Davies et al., "The Human T3 y Chain is Phosphorylated at Serine 126 in Response to T Lymphocyte Activation," J. Biol. Chem. 262(23):10918-10921 (1987).
Davis et al., "Chronic active B-cell-receptor signaling in diffuse large B-cell lymphoma," Nature 463:88-92 (2010).
Davis et al., "The preparation of substituted 1(2H)-isoquinolinones from dilithiated 2-methyl- N-arylbenzamides, 2-methyl-N-(arylmethyl)-benzamides, or 2-methylbenzoic acid, 2, 2-dimethylhydrazide," Synthetic Commun. 27(17):2961-2969 (1997).
D'Cruz et al. "Novel Bruton's tyrosine kinase inhibitors currently in development," OncoTargets and Therapy, Mar. 5, 2013, vol. 6, pp. 161-176.
De Frias et al., "Akt inhibitors induce apoptosis in chronic lymphocytic leukemia cells," Haematologica 94: 1698-1707 2009).
De Vos et al., ".A Phase 1 Study of The Selective Phosphatidylinositol 3-Kinase-Delta (PI3K delta) Inhibitor, Cal-101 (GS-1101), in Combination with R1tuximab and/or Bendamustine in Patients with Previously Treated, Indolent Non-Hodgkin Lympr1oma (iNHL)", Blood (ASH) 118(21), p. 1160 (2011).

(56) References Cited

OTHER PUBLICATIONS

De Weers et al., "The Bruton's tyrosine kinase gene is expressed throughout B cell differentiation, from early precursor B cell stages preceding immunoglobulin gene rearrangement up to mature B cell stages," Eur. J. Immunol. 23:3109-3114 (1993).
Di Paolo et al: "Specific Btk inhibition suppresses B cell and myeloid cell-mediated arthritis", Nature Chemical Biology, vol. 7, No. 1, Nov. 28, 201 O (Nov. 28, 2010), pp. 41-50, XP055080245, GB ISSN: 1552-4450, DOI: 10.1038/nchembio.481.
Diederich et al., "In the search for specific inhibitors of human 11 beta-hydroxysteroid-dehydrogenases (11 beta-HSDs): chenodeoxycholic acid selectively inhibits 11beta-HSD-1," Eur. J. Endocrinol. 142(2): 200-207 (2000).
Dijksman et al., "271.1 : 2-dihydro-2-thianaphthalene derivatives. Part I. Preparation and reactions of 1 : 2-dihydro-I-keto-2-thianaphthalenes," J. Chem. Soc. 1213-1218 (1951).
Ding et al., "A combinatorial scaffold approach toward kinase-directed heterocycle libraries." J. Am. Chem. Soc. 124 (8): 1594-1596 (2002).
Ding et al, "A Concise and Traceless Linker Strategy toward Combinatorial Libraries of 2,6,9-Substituted Purines," J Org. Chem. 66(24): 8273-8276 (2001).
Ding et al., "Resin-capture and release strategy toward combinatorial libraries of 2,6,9-substituted purines," J. Comb. Chem. 4(2):183-186 (2002).
Donati, "Emerging therapies for neovascular age-related macular degeneration: state of the art," Ophthalmologica 221 (6): 366-377 (2007).
Douglas et al., "Serum Chemokines and Cytokines in CLL Patients Treated with Duvelisib, a PI3K-delia, gamma inhibitor", American Society of Clinical Oncology (ASCO) Annual Meeting, May 29-Jun. 2, 2015, Chicago, IL, 4 pages.
Engelman, J. "Targeting PI3K signalling in cancer: opportunities, challenges and limitations", Nature Reviews: Cancer. vol 9 (2009), pp. 550-562.
Equivalent Surface Area Dosage Conversion Factors (https://ncifrederick.cancer.gov/lasp/acuc/frederick/Media/Documents/ACUC42.pdf, Aug. 2007).
European Search Report and Search Opinion for EP Application No. 09700424.6 dated Oct. 26, 2011.
European Search Report for EP Application No. 05857011.0 dated Feb. 4, 2011.
European Search Report for EP Application No. 07754845.1 dated Sep. 20, 2011.
European Search Report for EP Application No. 07873406.8 dated Mar. 1, 2010.
European Search Report for EP Application No. 09700784.3 dated Oct. 28, 2011.
Extended European Search Report for EP Application No. 09816603.6 dated Mar. 19, 2012.
Faia et al., "High Throughput In vitro Combination Sensitivity Screen in Hematologic Malignancies with the Phosphoinositide-3 Kinase (PI3K)—delta gamma Inhibitor, Duvelisib," American Society of Clinical Oncology (ASCO) Annual Meeting, May 29-Jun. 2, 2015, Chicago, IL.
Fajans el al., "Maturity onset diabetes of the young (MODY)," Diabet. Med. 13(9 Suppl 6): S90-S95 (1996).
Feinstein et al., "Regulation of the action of hydrocortisone in airway epithelial cells by 11beta-hydroxysteroid dehydrogenase," Am. J. Respir. Cell. Mol. Biol. 21(3): 403-408 (1999).
Feldman, M.E. et al., "Active-Site Inhibitors of mTOR Target Rapamycin-Resistant Outputs of mTORC1 and mTORC2," PLoS Biol. 7(2):0371:0383 (2009).
Fingl et al, "Chapter 1—General Principles," The Pharmacological Basis of Therapeutics, 5th edition, Goodman and Gilman editors, MacMillan Publishings Co, Inc.. New York, pp. 1-46 (1975).
Flinn et al., "A Phase 1 Evaluation of Duvelisib (IPI-145), a PI3K-delta,gamma Inhibitor, in Patients with Relapsed/Refractory iNHL", American Society of Hematology Meeting, Dec. 6, 2014.

Flinn et al., "Clinical Safety and Activity in a Phase 1 Trial of IPI-145, a Potent Inhibitor of Phosphoinositide-3-Kinase-8, y, in Patients with advanced Hematologic Malignancies," Blood, vol. 120, No. 21, Nov. 16, 2012, p. 3663, XP008166549, & 54th ASH Annual Meeting (Dec. 10, 2012).
Flinn et al, poster presented at the ASH annual meeting and exposition, Dec. 10, 2012, Atlanta, Georgia (2 pages).
Flinn et al., "Preliminary Evidence of Clinical Activity in a Phase I Study of CAL-101, a Selective Inhibitor of the p110δ isoform of Phosphatidylinositol 3-Kinase (PI3K), in Patients with Select Hematologic Malignancies," J. Clin. Oncol. 15s) (Suppl: Abstr 3543) (2009).
Flinn et al., "Preliminary Safety and Efficacy of IPI-145, a Potent Inhibitor of Phosphoinositide-3-Kinase-δ,y in Patients With Chronic Lymphocytic Leukemia", Blood, vol. 122, No. 21, Nov. 2013, p. 677.
Flinn et al., Duvelisib, a novel oral dual inhibitor of PI3K-δ,y, is clinically active in advanced hematologic malignancies. Blood. Feb. 22, 2018;131(8):877-887. doi: 10.1182/blood-2017-05-86566. Epub Nov. 30, 2017. PMID: 29191916; PMCID: PMC6033052 ("Flinn").
Forrest et al., "Carbonyl Reductase," Chem. Biol. Interact. 129(1-2): 21-40 (2000).
Forrest et al., "Induction of a human carbonyl reductase gene localed on chromosome 21," Biochem. Biophys. Acta. 1048 (2-3): 149-155 (1990).
Franzen, "The Suzuki, the Heck, and the Stille reaction—three versatile methods for the introduction of new C-C bonds on solid support," Can. J. Chem. 78(7): 957-962 (2000).
Fruman, D.A., et al., "PI3Kδ Inhibitors in Cancer: Rationale and Serendipity Merge in the Clinic", Cancer Discovery, Dec. 2011, vol. 1(7), pp. 562-572.
Fulci et al., "Quantitative technologies establish a novel microRNA profile of chronic lymphocytic leukemia", Blood, 2007, vol. 109(11), pp. 4944-4951.
Funder et al., "Mineralocorticoid action: target tissue specificity is enzyme, not receptor, mediated," Science 242:583-585 (1998).
Fung-Leung, W. P., "Phosphoinositide 3-kinase delta (PI3Kdelta) in leukocyte signaling and function," Cell Signal. 23(4): 603-608 (2011).
Furman et al., "CAL-101, An Isoform-Selective Inhibitor of Phosphatidylinositol 3-Kinase P110 delta, Demonstrates Clinical Activity and Pharmacodynamic Effects In patients with Relapsed or Refractory Chronic Lymphocytic Leukemia", Blood, (Nov. 1, 2010), vol. 116(21), p. 31.
Furukawa. T., "Molecular Targeting Therapy for Pancreatic Cancer: Current Knowledge and Perspectives from Bench to Bedside," J Gastroenterol. 43(12): 905-911 (2008).
Garber et al., "Diversity of gene expression in adenocarcinoma of the lung," Proc. Natl. Acad. Sci. U.S.A. 98(24): 13784-13789 (2001).
Ghigo et al., "PI3K Inhibition in Inflammation: Toward tailored therapies for specific diseases," Bioessays 32 (2010), DD. 185-196.
Gillespie et al., "Antagonists of the human adenosine A2A receptor. Part 3: Design and synthesis of pyrazolo [3,4-d] pyrimidines, pyrrolo[2,3-d]pyrimidines and 6-arylpurines, " Bioorg. Med. Chem. Lett. 18(9): 2924-2929 (2008).
Gonzalez et al., "Protection against daunombicin cytotoxicity by expression of a cloned human carbonyl reductase cDNA in K562 leukemia cells," Cancer Res. 55(20):4646-4650 (1995).
Goodman, A., "Encouraging Early Results With Novel Agents in CLL", The ASCO Post, Mar. 1, 2014, Retrieved from the internet: URL: http://www.ascopost.com/issues/march-I,-2014/encouraging-early-results-with-novel-agents-in-cll.aspx.
Graber et al., "The protein tyrosine kinase inhibitor herbimycin A, but not genistein, specifically inhibits signal transduction by the T cell antigen receptor," Int. Immunol. 4(1):1201-1210 (1992).
Graham et al., "The TAM family: phosphatidylserine sensing receptor tyrosine kinases gone awry in cancer", Nature Rev Cancer, 2014, vol. 14, pp. 769-785.
Graupera et al., "Angiogenesis selectively requires the p110alpha isoform of PI3K to control endothelial cell migration," Nature 453 (7195): 662-666 (2008).

(56) References Cited

OTHER PUBLICATIONS

Gunther et al., "Acute pathological effects on rats of orally administered wortmannin-containing preparations and purified wortmannin from Fusarium oxyspomm," Food Chem. Toxicol. 27(3):173-179 (1989).

Gunther et al., "Immunosuppressive effects of dietary wortmannin on rats and mice," Immunopharmacol. Immunotoxicol. 11(4): 559-570 (1989).

Haase et al., "Detection of viral nucleic acids by in situ hybridization," Methods in Virology 7: 189-226 (1984).

Hall et al., "The dual PI3K/mTOR inhibitor NVP-BEZ235 enhances dexamethasone induced apoptosis in models of T-cell all with PTEN dysfunction and hyperactivated PI3K/Akt pathway.", Cancer Research: Apr. 15, 2013; vol. 73, Issue 8, Supplement 1, doi: 10. I158/1538-7445.AM2013-2757.

Haluska et al., "The RTK/RAS/BRAF/PI3K Pathways in Melanoma: Biology, Small Molecule Inhibitors, and Potential Applications," Semin. Oncol. 34 (6): 546-554 (2007).

Hanefeld et al., "One-pot synthesis of tetrasubstituted pyrazoles—proof of regiochemistry," J. Chem. Soc., Perkin Trans. 1: 1545-1552 (1996).

Harada et al., "Novel role of phosphatidylinositol 3-kinase in CD28-medialed costimulation," J. Biol. Chem. 276(12): 3003-9008 (2001).

Harb et al., "Combined Pharmacologic Inhibition of Bcl-XI/Bcl-2 and mTORC1/2 Survival Signals Trigger Apoptosis in -ABL1+ in Vitro Models of Blast Crisis Chronic Myelogenous leukemia (CMI-BC), and Primary CD34+/CD38- and CD34+ progenitor Cells From CML-BC Patients", Blood, 53rd Ash Annual Meeting and Exposition, San CA, Dec. 10-13, 2011, Retrieved Irom ttle internet URL:https:f/ash.conrex.com/ash/2011Jwebprogram/1.html.

Harding et al., "CD28-mediated signalling co-stimulates murine T cells and prevents induction of anergy in T-cell clones," Nature 356(6370): 607-609 (1992).

Harris et al., "PI3K isoforms as drug targets in inflammatory diseases: Lessons from pharmacological and genetic strategies", Curr. Opin. in Inv. Drugs, 2009, vol. 10(11), pp. 1151-1162.

Hasselblom et al., "High immunohistoct1ernical expression of p-AKT predicts inferior survival in patients witt1 diffuse large B-cell lympt1orna treated 'Nilh immunochemotherapy," Brit J Haematol. 149 (4): 560-568 (2010).

Haylock-Jacobs et al., "PI3Kdelta drives the pathogenesis of experimental autoimmune encephalomyelitis by inhibiting effector T cell apoptosis and promoting Th17 differentiation," J. Autoimmun. 36: 278-287 (2011).

Hellwinkel et al., "Heterocyclensynthesen mil MF/A1203-basensystemen; 2-arylbenzofurane and 2,3- diarylisochinolin-1 (2H)-one," Synthesis 1995(9): 1135-1141 (1995).

Henderson et al., "Delineation of a Minimal Region of Deletion at 6q16.3 in Follicular Lymphoma and Construction of a Bacterial Artificial Chromosome Config Spanning a 6-Megabase Region of 6q16-q21," Genes, Chromosomes & Cancer 40: 60-65 (2004).

Herishanu et al., "The lymph node microenvironment promotes B-cell receptor signaling, NF-κB activation, and tumor proliferation in chronic lymphocytic leukemia," Blood 117(2): 563-574 (2011).

Herman et al., "Molecular Pathways: Targeting the Phosphoinositide 3-Kinase (P13-Kinase) p110 delta in Chronic Lymphocytic Leukemia" Clin. Cancer Res., ePub Jun. 18, 2012, Aug. 2012, vol. 18, pp. 4013-4018.

Herman et al, "Phosphatidylinositol 3-kinase-delta inhibitor CAL-101 shows promising preclinical activity in chronic lymphocytic leukemia by antagonizing intrinsic and extrinsic cellular survival signals," Blood, 2010, vol. 116, No. 12, pp. 2078-2088.

Herman et al., "The role of phosphatidylinositol 3-kinase-8 in the immunomodulatory effects of lenalidomide in chronic lymphocytic leukemia," Blood II 7(16):4323-4327 (2011).

Herrera et al., "The dual PI3K/mTOR inhibitor BEZ235 is effective in lung cancer cell lines," Anticancer Res. 31(3): 849-854 (2011).

Hickey et al., "BCR-ABL Regulates Phosphatidylinositol 3-Kinase-p110 gamma Transcription and Activation and is Required for Proliferation and Drug Resistance," J. Biol. Chem. 281 (5): 2441-2450 (2006).

Higgs et al., "Patients with systemic lupus erythematosus, myositis, rheumatoid arthritis and scleroderma share activation of a common type I interferon pathway", Ann Rheum Dis, 2011, vol. 70 pp. 2029-2036.

Hirsch et al., "CALming Down T Cell Acute Leukemia," Cancer Cell 21(4): 449-450 (2012).

Hirsch et al., "Central Role for G Protein-Coupled Phosphoinositide 3-Kinase gamma in Inflammation," Science 287 5455): 1049-1053 (2000).

Hoe et al., "Drugging the p53 pathway: understanding the rout to clinical efficacy", Nature Reviews Drug Discovery, Mar. 2014, vol. 13, pp. 217-236.

Hoelienriegel et al., Phosphoinositide 3'-Kinase (PI3K) Delta Inhibition with CAL-101 Blocks B-Cell Receptor (BCR) Signaling and the Prosurvival Actions of Nurslike Cells (NLC), In Chronic Lymphocytic Leukemia, (ASH Annual Meeting 2010).

Hoelienriegel et al., The phosphoinositide 3'-kinase delta inhibitor, CAL-10.1, inhibits B-cell receptor signaling and chemokine networks in chronic lymphocytic leukemia. Blood 118(13): 3603-3612 (2011).

Hoellenriegel and Burger, "Phosphoinositide 3'-kinase delta: turning off BCR signaling in Chronic Lymphocytic leukemia," Oncotarget 2(10): 737-738 (2011).

Honigberg et al., "The Bruton tyrosine kinase inhibitor PCI-32765 blocks B-Cell activation and is efficacious in models of autoimmune disease and B-cell malignancy," PNAS 107(29): 13075-13080 (2010).

Horwitz et al., "Duvelisib (IPI-145), a Phosphoinositide-3-Kinase-delta, gamma Inhibitor, Shows Activity in Patients with Relapsed/Refractory T-Cell Lymphoma," American Society of Hematology Meeting, Dec. 6, 2014.

Ikeda et al., "PI3K/p110delta is a novel therapeutic target in multiple myeloma," Blood 116(9): 1460-1468 (2010).

Infinity Pharmaceuticals, Inc., "Infinity Reports Preclinical Data at ASH Annual Meeting in Diffuse Large B-cell Lymphoma and T-Cell Acute Lymphoblastic Leukemia Suggesting Broad Potential of IPI-145 in Blood Cancers", nttp://businesswire.com, Dec. 7, 2013, Downloaded from the internet: http://www.businesswire.com/news/nome/20131207005015/en/Infinity-Reports-Preclinical-Data-ASH-Annual-Meeting.

International Preliminary Report on Patentability and Written Opinion for PCT/US2005/042524 dated May 22, 2007.

International Preliminary Report on Patentability and Written Opinion for PCT/US2007/008395 dated Oct. 8, 2008.

International Preliminary Report on Patentability and Written Opinion for PCT/US2007i008355 dated Nov. 4, 2008.

International Preliminary Report on Patentability and Written Opinion for PCT/US2009/049969 dated Jan. 11, 2011.

International Preliminary Report on Patentability and Written Opinion for PCT/US2009/060985 dated Apr. 19, 2011.

International Preliminary Report on Patentability for PCT/US2009/000038 dated Jul. 6, 2010.

International Preliminary Report on Patentability for PCT/US2009/000042 dated Jul. 6, 2010.

International Preliminary Report on Patentability for PCT/US2009/005380 dated Apr. 7, 2011.

International Preliminary Report on Patentability for PCT/US2010/002020 dated Jan. 26. 2012.

International Search Report & Written Opinion for PCT/US2011/060212 dated Jun. 1, 2012.

International Search Report & Written Opinion issued after Submission of Request for Additional Search for PCT/ JS2011/060212 dated Jul. 6, 2012.

International Search Report and Written Opinion for PCT/US2009/005380 dated Nov. 20, 2009.

International Search Report and Written Opinion for PCT/US2009/049969 dated Mar. 15, 2010.

International Search Report and Written Opinion for PCT/US2010/033939 dated Nov. 5, 2010.

(56) References Cited

OTHER PUBLICATIONS

International Search Report and Written Opinion for PCT/US2012/020831 dated May 2, 2012.
International Search Report and Written Opinion for PCT/US2012/047190 dated Oct. 2, 2012.
International Search Report and Written Opinion for PCT/US2013/067929 mailed Mar. 31, 2014.
International search report and written opinion of PCT/US2016/046829 mailed Dec. 28, 2016 (10 pages).
International Search Report for PCT/US1995/005213 dated Aug. 21, 1995.
International Search Report for PCT/US2005/042524 (7 pages) dated Oct. 2, 2006.
International Search Report for PCT/US2007/008355 dated Sep. 25, 2008.
International Search Report for PCT/US2007/008395 (4 pages) dated Aug. 27, 2008.
International Search Report for PCT/US2009/000038 dated Mar. 11, 2009.
International Search Report for PCT/US2009/000042 dated Mar. 23, 2009.
International Search Report for PCT/US2009/060985 dated Jun. 28, 2010.
International Search Report for PCT/US2010/002020 dated Nov. 2, 2010.
International Search Report for PCT/US2011/037412 dated Aug. 22, 2011.
Ishiyama et al., "A stoichiometric aromatic C-H borylation catalyzed by iridium(I)/2,2'-bipyridine complexes at room temperature," Angew. Chem. Int. Ed. Engl. 41(16):3056-3058 (2002).
Ishiyama et al., "Mild iridium-catalyzed borylation of arenes. High turnover numbers room temperature reactions, and isolation of a potential intermediate," J. Am. Chem. Soc. 124(3):390-391 (2002).
Jackson et al., "PI3-kinase p110beta: a new target for antithrombotic therapy," Nat. Med. 11: 507-514 (2005).
Jimeno et al. "Phase I Trial of PX-866, a Novel Phosphoinositide-3-Kinase (PI-3K) Inhibitor," J. Clin. Oncol. 27: 15s (Suppl: Abstract 3542) (2009).
Johnson et al., "Accessory cell-derived signals required for T cell activation," Immunol. Res. 12 (1): 48-64 (1993).
Jou et al., "Essential, nonredundant role for the phosphoinositide 3-kinase p110delta in signaling by the B-cell receptor complex," Mol. Cell. Biol. 22 (24): 8580-8591 (2002).
June, C.H., "Signaling transduction in T cells," Curr. Opin. Immunol. 3(3): 287-293 {1991).
June et al., "Evidence for the involvement of three distinct signals in the induction of IL-2 gene expression in human T lymphocytes," J. Immunol. 143 (1): 153-161 (1989).
June et al., "Inhibition of tyrosine phosphorylation prevents T-cell receptor mediated signal transduction," Proc. Natl. Acad. Sci. U.S.A. 87:7722-7726 (1990).
June et al., "Role of CD28 receptor in T-ceil activation," Immunol. Today 11 (6): 211-216 (1990).
Kajila et al., "Nickel-Catalyzed Decarbonylative Addition of Phthalimides to Alkynes," J. Am. Chem. Soc. 130 (19): 6058-6059 (2008).
Kallberg et al., "Short-chain dehydrogenase/reductase (SDR) relationships: a large family with eight clusters conunon to human, animal, and plant genomes," Protein Sci. 11(3):636-641 (2002).
Kallberg et al., "Short-Chain Dehydrogenases/Reducatses (SDRs)—Coenzyme-Based Functional Assignments in Completed Genomes," Eur. J Biochem. 269 (18): 4409-4417 (2002).
Kang et al., "Oncogenic transformation induced by the p110beta, -gamma, and -delta isoforms of c:lass I phosphoinositide 3-kinase," PNAS 103 (5) 1289-1294 {2006).
Karpeiskii et aL, "Pyridoxal-5'-Derivatives of Nucleobases," Bioorganicheskaya Khirrnya 1·1 (8): 1097-1104 (1985).
Kassem, N., "Top Ten Bone Diseases," LiveStrong.com, Apr. 29, 2011. http://www.livestrong.com/article/ 119479-top-• ten--bone--d diseases/ _.

Kavanagh, et al., "Patient. Mylodysplastic syndromes. 2012," [online], Retrieved on Apr. 24, 2015, http://www.patient.co.uk/doctor/myelodysplastic-syndromes-pro.
Khwaja, A., "PI3K as a Target for Therapy in Haematological Malignancies," Curr. Top. Microbiol. Immunol. 347: 169-188 (2010).
Kiefer, "Lymphoma Prevention," Healthline. 2011, http://www.healthline.com/health/lymphoma/prevention.
Kim et al, "Activation and Function of the mTORC1 Pathway in Mast Cells," J. Immunol. 180 (7): 4586-4595 (2008).
Knight et al., "A Pharmacological Map of the PI3-K Family Defines a Role for p110alpha in Insulin Signaling," Cell 125 (4): 733-747 (2006).
Kong et al. "Advances in Development of Phosphatidylinositol 3-Kinase Inhibitors," Curr. Med. Chem. 16 (22): 2839-2854 (2009).
Kost et al., "Recyclization of 3-Alkyl- and 1,3-Dialkylisoquinolinium Salts to Naphthylamines," Chemistry of Heterocyclic Compounds 16 (9): 965-970 (1980).
Kraybill et al., "Inhibitor scaffolds as new allele specific kinase substrates," J. Am. Chem. Soc. 124 (41): 12118-12.128 (2002).
Kreutzberger et al. "5-Substituierte 4-Aminopyrimidine durch Aminomethinyliemng von Acetonitrilen," Liebigs Ann. Chem. 537-544 (1977).
Kridel et aL, "Pathogenesis of follicular lymphoma," J. of Clinical Investigation 122{10}: 3424-3431 {2012).
Kukulski et al., "The P2 receptor antagonist PPADS abrogates LPS-induced neutrophil migration in the murine air pouch via inhibition of MIP-2 and KC production, " Mol. Immun., 47(4):833-839 (2010).
Kulkami et al., "PI3Kbeta plays a critical role in neutrophil activation by immune complexes," Sci. Signal 4 (168): ra 23 (2011).
Kumar et aL, "Keten Dithioacetals. Part 11. Reaction of 3-Cyano-4-Methylthio-2(1H)-pyridones with Hydrazine and Guanicline: Synthesis of Novel Substituted and F-·used Pyrazolo[4,3c]pyridone and Pyrido [4,3-d]pyrimidine derivatives," J. Chem. Soc., Perkin Trans. 1, 8: 857-862 {1978).
Kundu et al., "Palladium-Catalysed Heteroannulation with Terminal Alkynes: a Highly Regio- and Stereoselective Synthesis of (Z)-3—Aryl(alkyl)idene isoindolin-1-ones," Tetrahedron 56 (27): 477T-4792 (2000).
Kurtova et al. "Diverse marrow stromal cells protect CLL cells from spontaneous and drug-induced apoptosis: development of a reliable and reproducible system to assess stromal cell adhesion-mediated drug resistance," Blood 14 (20): 4441-4450 (2009).
Kwok et al., "The anti-inflammatory natural product parthenolide from the medicinal herb Feverfew directly binds to and inhibits IκB kinase," Chem. Biol. 8 (8): 759-766 (2001).
Lannutti, B.J. et al. (Jan. 2011) "CAL-101, a p110 selective phosphatdylinositol-3-kinase inhibitor for the treatment of B-cell malignancies, inhibits PI3K signaling and cellular viability" Blood, 117(2):591-594.
Larabi et al., "Crystal Structure and Mechanism of Activation of TANK-Binding Kinase 1," Cell Reports 3 (3): 734-746 (2013).
Ledbetter et al., "CD28 Ligation in T-Cell Activation: Evidence for Two Signal Transduction Pathways," Blood 75 (7): 1531-1539 (1990).
Ledbetter et al., "Crosslinking of surface antigens causes mobilization of intracellular ionized calcium in T lymphocytes," Proc Natl. Acad. Sci. U.SA 84 (5}: 1384-1388 (1987).
Lee et al., "All roads lead to mTOR: integrating inflammation and tumor angiogenesis," Cell Cycle 6 (24): 3011-3014 2007).
Lee et al., "The CD28 signal transduction pathway in T cell activation", Advances in Cell Regulation of Cell Growth, vol. 2, pp. 141-160, New York: Raven Press, Ltd. (1991).
Letai et al., "Antiapoptotic BCL-2 is required for maintenance of a model leukemia", Cancer Cell, 6(3):241-249 (2004).
Ley et al., "The T cell receptor/CD3 complex and CD2 stimulate the tyrosine phosphorylation of indistinguishable patterns of polypeptides in the human T leukemic cell line Jurkat," Eur. J. Immunol. 21 (9): 2203-2209 (1991).
Li et al., "Roles of PLC-beta2 and -beta3 and PI3Kgamma in chemoattractant-mediated signal transduction," Science 287 (5455): 1046-1049 (2000).

(56) References Cited

OTHER PUBLICATIONS

Linhua et al., "Efficacy and Mechanisms of Apoptosis Induction by Simultaneous Inhibition of PI3K with GDC-0941 and Blockade of Bcl-2 (ABT-737) or FLT3 (Sorafenib) In AML Cells In the Hypoxic Bone Marrow Microenvironment", Blood, 116:777 (2010).

Liu et al, "BAY 80-6946, a highly selective and potent pan-class I PI3K inhibitor, induces tumor apoptosis in vitro and tumor regression in vivo in a subset of tumor models," AACR 101st Annual Meeting of the American Association for Cancer Research, Apr. 2010, Poster & Abstract 4476 (3 pages).

Liu et al., "Costimulation of T-cell growth," Curr. Opin. Immunol. 4 (3): 265-270 (1992).

Liu et al., "Improved syntheses of alpha-BOC-aminoketones from alpha-BOC-amino-Weinreb amides using a pre-deprotonation protocol", Tetrahedron Letters 43(46):8223-8226 (2002).

Lou et al: "Bruton's Tyrosine Kinase Inhibitors: Approaches to Potent and Selective Inhibition, Preclinical and Clinical Evaluation for Inflammatory Diseases and B Cell Malignancies", Journal of Medicinal Chemistry, vol. 55, No. 10, May 24, 2012 (May 24, 2012), pp. 4539-4550, XP055080230, ISSN: 0022-2623, DOI: 10.1021/jm300035p.

Lu et al., "CD28-induced T cell activation. Evidence for a protein-tyrosine kinase signal transduction pathway," J. Immunol. 149(1):24-29 (1992).

Macias-Perez et al: "B-Cell Receptor Pathobiology and Targeting in NHL", Current Oncology Reports, Current Science Inc, New York. val. 14, No. 5, Aug. 5, 2012 (Aug. 5, 2012), pp. 411-418, XP0351 06569, ISSN: 1534-6269, DOI: 10.1007/S11912-012-0254-8.

Macias-Perez I.M, et al., "B-cell Receptor Pathobiology and Targeting in NHL", Current Oncology Reports, Oct. 2012, vol. 14(5), pp. 411-418.

Majumder et al, "mTOR inhibition reverses Akt-dependent prostate intraepithelial neoplasia through regulation of apoptotic and HIF-1-dependent pathways," Nat Med. 10 (6): i94-601 (2004}.

Mansour et al., "Discovery of a Secreted Tumor Suppressor Provides a Promising Therapeutic Strategy for Follicular Lymphoma", Cancer Cell 20, Nov. 15, 2011, pp. 559-561.

Markman et al., "Status of PI3K inhibition and biomarker development in cancer therapeutics," Ann. Oncol. 21 (4): 683-691 (2010).

Martelli et al., "The emerging role of the phosphatidylinositol 3-kinase/Akt/mammalian target of rapamycin signaling network in normal myelopoiesis and leukemogenesis," Biochem. Biophys Acta. 1803 (9): 991-1002 (2010).

Martinez et al., The Molecular Signature of Mantle Cell Lymphoma f reveals Multiple Signals Favoring Cell Survival, Cancer Res 63: 8226-8232 (2003).

Martin-Sanchez et al., "Simultaneous inhibition of pan-phosphatidylinositol-3-kinases and MEK as a potential therapeutic strategy in peripheral T-cell lymphomas", Haematologica, vol. 98, No. 1, Jan. 2013, pp. 57-64.

Martin-Sanchez et al., "PI3K Inhibition as a Potential Therapeutic Strategy in Peripheral T-Cell Lymphomas," Blood (ASH Annual Meeting Abstracts) 118: Abstract 3493 (2011).

Mashkovskiy, Lekarstvennye sredstva, vol. 1, 2001, p. 11.

Mattes et al., "DNA sequence selectivity of guanine-N7 alkylation by nitrogen mustards," Nucleic Acids Res. 14 (7): 2971-2987 (1986).

Maxwell et al., "Attenuation of phosphoinositide 3-kinase 8 signaling restrains autoimmune disease," J. Autoimmun. 38:381-391 (2012).

Mayer et al., "Small molecule inhibitor of mitotic spindle bipolarity identified in a phenotype-based screen," Science 286(5441):971-974 (1999).

Mazzoletti and Broggini, "PI3K/AKT/mTOR inhibitors in ovarian cancer," Curr. Med. Chem. 17(36):4433-4447 (2010).

Meadows et al., "CAL-101, a Potent Selective Inhibitor of the p110delta isoform of Phosphatidylinositol 3-Kinase, Attenuates Pathway Signaling, Induces Apoptosis, and Overcomes Signals from the Microenvironment in Cellular Models of Hodgkin Lymphoma," Blood (ASH Annual Meeting Abstracts), 116: Abstract 3926 (2010)28 MedicineNel.com, Cancer Definition, http://www.medterms.com, 2004.

MedicineNet.com, Cancer Definition, http://ItNNv.rnedtenns.com, 2004.

Medline Plus, Autoimmune Diseases, NIH, 2014. http://www.nlm.nih.gov/medlineplus/autoimmunediseases.html.

Mellinghoff et al., "TORward AKTually useful mouse models," Nat. Med. 10 (6): 579-580 (2004).

Merida et al., "IL-2 binding activates a tyrosine-phosphorylated phosphatidylinositol-3-kinase," J. Immunol. 147(7): 2202-2207 (1991).

Milella et al., 566 Poster Anti-leukemic activity of the novel MEK inhibitor PD0325901, European Journal of Cancer Supplement, vol. 4, Iss 12, Nov. 1, 2006, p. 172.

Miyaura et al., "Palladium-Catalyzed Cross-Coupling Reactions of Organoboron Compounds," Chem. Rev. 95 (7): 2457-2483 (1995).

Modi et al., "Isoquinolones; part IV-synthesis of methyl, 3-formyl & other 3-substituted N-arylisoquinolones." Indian J. Chem. 18B:304-306 (1979).

Moon et al., "A Novel Microtubule Destabilizing Entity from Orthogonal Synthesis of Triazine Library and Zebrafish Embryo Screening," J. Am. Chem. Soc. 124 (39): 11608-11609 (2002).

Morrison, C., "First PI3k inhibitor launches info crowded hematology markets", Nature Biotechnology, vol. 32, No. 10, online Oct. 9, 2014, pp. 963-964.

Mosmann et al., "The expanding universe of T-cell subsets: Th1, Th2 and more," Immunology Today 17 (3): 138-146 (1996).

Mraz and Kipps, "MicroRNAs and B cell receptor signaling in chronic lymphocytic leukemia", Leukemia & Lymphoma, Aug. 2013, vol. 54(8), pp. 1836-1839.

Mraz et al., "MicroRNAs in chronic lymphocytic leukemia pathogenesis and disease subtypes", Leukemia & Lymphoma, 50(3):506-509 (2009).

Mraz et al., "miR-150 influences B-cell receptor signaling in chronic lymphocytic leukemia by regulating expression of GAB1 and FOXP1", Blood, 2014, vol. 124(1), pp. 84-95.

Muranen et al., "Inhibition of PI3K/mTOR Leads to Adaptive Resistance in Matrix-Attached Cancer Cells", Cancer Cell, 21(2):227-239 (2011).

Muranen et al., "Promising Rationally Derived Combination Therapy with PI3K and CDK4/6 Inhibitors", Cancer Cell, 26(1):7-9 (2014).

Musilova and Mraz, "MicroRNAs in B-cell lymphomas: how a complex biology gets more complex", Leukemia (2015), 1-14.

Nakai, Yoshinobu et al., New galenical pharmacy, NANZANDO Co., Ltd., Apr. 25, 1984, pp. 102-103, 232-233.

Nakanishi et al., "Cloning and sequence analysis of a cDNA encoding tetrameric carbonyl reductase of pig lung," Biochem. Biophys. Res. Commun. 194 (3}: 1311-1316 (1993).

National Cancer Institute, "AIDS-Related Lymphoma Treatment," 2015. http://www.cancer.gov/cancertopics/pdq/treatment/AIDS-related-lymphoma/Patient/page1.

NCBI, Nutritional and Metabolic Diseases, NCBI Bookshelf, 1998. http://www.ncbi.nlm.nih.gov/books/NBK22259/.

NCBI, The Nervous System, NCBI Bookshelf, 1998. http://www.ncbi.nlm.nih.gov/books/NBK22197/.

Nemazanyi et aL. "3-Amino-4-aryl-1{2H)-isoquinolones," Chemistry of Heterocyclic Compounds 27 (3): 307-308 {1991).

Newman et al., "Solid state analysis of the active pharmaceutical ingredient in drug products," Drug Discov. Today 8(19):898-905 (2003).

Nishigaki, Sadao, Dispensing pharmacy (Principle and application), NANZANDO Co., Ltd, Sep. 20, 1977, pp. 142-145.

Nisitani et al., "Posttranscriptional regulation of Bruton's tyrosine kinase expression in antigen receptor-stimulated Splenic B cells," PNAS 97 (6): 2737-2742 (2000).

Niswender et al., "Protein engineering of protein kinase A catalytic subunits results in the acquisition of novel inhibitor sensitivity," J, Biol Chem 277 (:12) 28916-28922 (2002).

Nobel et al., "Purification of full-length recombinant human and rat type l 11—hydroxysteroid dehydrogenases with retained oxidoreductase activities," Protein Expr. Purif. 26(3):349-356 (2002).

(56) References Cited

OTHER PUBLICATIONS

Norman, "Selective PI3K-delta Inhibitors, A Review of the Patent Literature," Expert Opinion on Therapeutic Patents 21 (11): 1773-1790 (2011).
Nunes et al, "Signalling through CD28 T-cell activation pathway involves an inositol phospholipid-specific phospholipase C activity," Biochem. J. 293 (pt 3): 835-842 (1993).
O'Connor, "Adult T-Cell Leukemia/Lymphoma (HTLV-1)", Lymphoma Research Foundation, 2008, 1-4.
Oda et al., "PIK3CA Cooperates with Other Phosphatidylinositol 3'-Kinase Pathway Mutations to Effect Oncogenic Transformation," Cancer Res. 68 (19): 8127-8136 {2008).
O'Shea et al., "Activation of human peripheral blood T lymphocytes by pharmacological induction of protein-tyrosine phosphorylation," Proc. Natl. Acad. Sci. U.S.A. 89 (21): 10306-10310 (1992).
Okada et al., "Blockage of chemotactic peptide-induced stimulation of neutrophils by wortmannin as a result of selective inhibition of phosphatidylinositol 3-kinase," J. Biol. Chem. 269 (5): 3563-3567 (1994).
Okada et al., "Essential role of phosphatidylinositol 3-kinase in insulin-induced glucose transport and antilipolysis in rat adipocytes. Studies with a selective inhibitor wortmannin," J. Biol. Chem. 269 (5): 3568-3573 (1994).
Okano, Teisuke, New general remarks of practical pharmacy, 3rd ed., Nankodo Co., Ltd, Apr. 10, 1987, pp. 111.
Okkenhaug, K., "Two Birds with One Stone: Dual p110? and p110? Inhibition", Chemistry and Biology, vol. 20, 10.11, Nov. 1, 2013,pp. 1309-1310.
Okosun et al., "Integrated genomic analysis identifies recurrent mutations and evolution patterns driving the initiation and progression of follicular lymphoma," Nature Genetics 46(2): 176-181 (2014).
Okosun et al., Supplementary Information "Integrated genomic analysis identifies recurrent mutations and evolution patterns driving the initiation and progression of follicular lymphoma", Nature Genetics (2014), doi:10.1038/ng.2856.
Oltersdorf et al., "An inhibitor of Bcl-2 family proteins induces regression of solid tumours", Nature, vol. 435, Jun. 2, 2005, pp. 677-681.
Oppermann et al., "Forms and functions of human SDR enzymes," Chem. Biol. Interact. 130-132(1-3):699-705 (2001).
Oricchio et al., "The Eph-Receptor A7 Is a Soluble Tumor Suppressor for Follicular Lymphoma," Cell 147: 554-564 (2011).
Ozaki et al., "Studies on 4(1 H)-Quinazolinones. IV. Convenient Syntheses of 12-Methyl-6H-isoquino [2, 1-a]10 1uinazolin-6—One and 6-Methyl-13H-quinazolino [3,4-a] quinazolin-13-one," Chem. Pharm. Bull. 32 (6): 2160-2164 1984).
Ozol et al., "Autoxidative transformations of 2-substituted 3-alkyl-4-hydroxy-1—0xo-1, 2-dihydroisoquinolines," Chemistry of Heterocyclic Compounds 14 (6): 644-648 (1978).
Patel et al., "Immunopathological aspects of age-related macular degeneration," Semin. Immunopathol. 30 (2): 97-110 (2008).
Patel, Manish R., "Early Clinical Activity and Pharmacodynamic Effects of Duvelisib, a PI3K-delta, gamma Inhibitor, in Patients with Treatment-Naive CLL", ASCO Annual Meeting, May 29-Jun. 2, 2015, Chicago, IL (poster).
Patten et al. Blood (2008), vol. 111 pp. 5173-5181. (Year: 2008).
Perez-Blas et al., "Impaired T cell signal transduction through CD28 in a patient witt1 idiopathic tt1rombocytopen1a," Clin. Exp Immunol. 85 (3) 424-428 {1991).
Persson, "Glucocorticoids for asthma—early contributions," Pulm. Pharmacol. 2 (3): 163-166 (1989).
Petrie et al., "A Novel biolinylaled adenylale analogue derived from pyrazolo[3,4-d]pyrimidine for labeling DNA probes," Bioconjug. Chem. 2 (6): 441-446 (1991).
Pharmacyclics Inc. Form 8-K Filing. May 16, 2013. Article retrieved from the Internet: http://www.sec.gov/Archives/edgar/data/949699/00009218951300 I I 15/0000921895-13-001115-index.htm on Dec. 11, 2014.

Pighi et al., "Phospho-proteomic analysis of mantle cell lymphoma cells suggests a pro-survival role of B-cell receptor signaling," Cell Oneal. (Dordr) 34 (2): 141-153 {2011).
Polak et al., "The PI3K/PKB signaling module as key regulator of hematopoiesis: implications for therapeutic strategies in leukemia," Blood 119 (4): 911-923 (2012).
Porta and Figlin, "Phosphalidylinositol-3-kinase/Akl signaling pathway and kidney cancer, and the therapeutic potential of phosphalidylinositol-3-kinase/Akl inhibitors," J Urol. 182 (6): 2569-2577 (2009).
Porter et al, "The Potent Phosphoinositide-3-Kinase-(delta,gamma) Inhibitor IPI-145 Is Active in Preclinical Models of Arthritis and Well Tolerated in Healthy Adult Subjects," ACR/ARHP annual meeting, Nov. 2012, Poster & Abstract 338.
Porter et al, Tt1e Potent Phosphoinositide-3-Kinase-{delta,garnma) Int1ibitor IPI-145 Is Active in Preclinical Models of Artt1ritis and Well Tolerated in Healtt1y Adult Subjects, Arthritis & Rheumatism 64(10): s147 (2012) (abstract only).
Prasad et al., "Phosphatidylinositol (PI) 3-kinase and PI 4-kinase binding to the CD4-p56lck complex: the p56lck SH3 domain binds to PI 3-kinase but not PI 4-kinase," Mol. Cell. Biol. 13(12): 7708-7717 (1993).
Prasad et al., "Src-homology 3 domain of protein kinase p59fyn mediates binding to phosphatidylinositol 3-kinase in T cells," Proc. Natl. Acad. Sci. U.S. A. 90(15): 7366-7370 (1993).
Prasad et al., "T-cell antigen CD28 interacts with the lipid kinase phosphalidylinositol 3-kinase by a cytoplasmic Tyr(P)-Met-Xaa-Mel motif," Proc. Nall. Acad. Sci. U.S.A. 91(7): 2832-2838 (1994).
PubChem CID49846579 [online] Retrieved from the internet, [Retrieved on Jun. 13, 2018] url: https://pubchem.ncbi.nlm.nih.gov/ compound/abt-199#section=Top (Year: 2011).
Pudlo et aL. "Synthesis, antiproliferative, and antiviral activity of certain 4-substituted and 4,5-disubstituted 7-[·1,3-dihydroxy-2-propoxy)methyl]pyrrolo[2,3-d]pyrimidines," J_ Med_ Chem 33 (7) 1984-1992 {1990).
Puri and Gold, "Selective inhibitors of phosphoinositide 3-•kinase delta: modulators of B-•cell function with potential for treating autoimmune inflammatory disease and B-cell malignancies," Front ImmunoL 3: 256 (2012).
Qian et al., "Synergy between phosphalidylinositol 3-kinase/Akt pathway and Bcl-xL in the control of apoptosis in Adenocarcinoma cells of the lung", Molecular Cancer Therapeutics, vol. 8, No. 1, Jan. 1, 2009, pp. 101-109.
Quiroga et al., -cell antigen receptor signaling enhances chronic lymphocytic leukemia cell migration and survival: specific targeting with a novel spleen tyrosine kinase inhibitor, R406, Blood 114 {5): 1029-1037 (2009).
Rahmani et al., "Dual Inhibition of Bcl-2 and Bcl-xL Strikingly Enhances PI3K Inhibition-Induced Apoptosis in Human Myeloid Leukemia Cells through a GSK3- and Bim-Dependent Mechanism," Cancer Research, vol. 73, No. 4, Feb. 013, pp. 1340-1351.
Reif et al., "Divergent regulation of phosphatidylinositol 3-kinase P85 alpha and P85 beta isoforms upon T cell activation," .J Biol. Chem. 268 {15): 10780-10788 (1993).
Report of the Expert Committee on the Diagnosis and Classification of Diabetes Mellitus, Diabetes Care 2(Suppl. 1 ): p5-S19 (1992).
Ringshausen et al, "Constitutively activated phosphatidylinositol-3 kinase (PI-3K) is involved in the defect of apoptosis in B-CLL: association with protein kinase C-delta," Blood, 2002, vol. 100, No. 10, pp. 3741-3748.
Rizzatti et al., "Gene expression profiling of mantle cell lymphoma cells reveals aberrant expression of genes from he PI3K-AKT, WNT and TGFbeta signalling pathways," Brit. J. Haematol. 130 (4): 516-526 (2005).
Roberts et al, "Substantial Susceptibility of Chronic Lymphocytic Leukemia to BCL2 Inhibition: Results of a Phase I Study of Navitoclax in Patients With Helapsed or Refractory Disease", Journal of Clinical Oncology, vol. 30, No , Feb. 10, 2012, pp. 488-496.
Robertson, "Eicosanoids and human disease", Harrison's Principles of Internal Medicine, Isselbacher K.J. et al. (eds.), vol. 1, pp. 431-435, McGraw-Hill, New York City (1994).

(56) References Cited

OTHER PUBLICATIONS

Roller et al., "Blockade of Phosphatidylinositol 3-Kinase (PI3K)delta or PI3Kgamma Reduces 11-17 and Ameliorates Imiquimod-Induced Psoriasis-like Dermatitis," J. Immunol. 189 (9): 4612-4620 {2012).

Romero et al., "Cloning and expression of the bovine 11β-hydroxysteroid dehydrogenase type-2," J. Steroid Biochem. Mol. Biol. 72(5):231-237 (2000).

Rommel et al., "PI3Kdelta and PI3Kgamma: partners in crime in inflammation in rheumatoid arthritis and beyond?" Nat. Rev. Immunol. 7 (3): 191-201 (2007).

Ross et al., "Comprehensive Analysis of Copy Number and Allele Status Identifies Multiple Chromosome Defects Underlying Follicular Lymphoma Pathogenesis," Clin. Cancer Res 2007 13(16): 4777-4785 (2007).

Rott et al., "Recent developments in the use of biologics in psoriasis and autoimmune disorders. The role of autoantibodies," BMJ 330 (7493): 716-720 (2005).

Rudelius et al., "Constitutive activation of Aki contributes to the pathogenesis and survival of mantle cell lymphoma," Blood 108 (5): 1668-1676 (2006).

Sail and Chu, "Biology of colorectal cancer," Cancer J. 16 (3): 196-201 (2010).

Salmena et al., "Tenets of PTEN Tumor Suppression," Cell 133 (3): 403-414 (2008).

Sarker et al, Targeting the PI3K/AKT pathway for the treatment of prostate cancer, Clin. Cancer Res. 15 (15): 4799-4805 (2009).

Sasaki et al., "Function of PI3Kγ in Thymocyte Development, T Cell Activation, and Neutrophil Migration," Science 287:1040-1046 (2000).

Schneider et al, "Molecular mechanisms by which BAY 80-6946 induces apoptosis in breast tumor cells as single agent or in combination," AACR 102nd Annual Meeting of the American Association for Cancer Research, Apr. 2011, Poster & Abstract 3833 (4 pages).

Schwaenen et al., "Microarray-Based Genomic Profiling Reveals Novel Genomic Aberrations in Follicular Lympt1orna Which Associate with Patient Survival and Gene Expression Status," Genes, Chromosomes & Cancer 48: 39-54 (2009).

Schwamb et al., "B-cell receptor triggers drug sensitivity of primary CLL cells by controlling glucosylation of ceramides", Blood, 120(19):3978-3985 (2012).

Schwartz, "A cell culture model for T lymphocyte clonal anergy," Science 248 (4961 ): 1349-1356 (1990).

Schwartz et al., "Quercelin inhibition of the induction and function of cytotoxic T lymphocytes," Immunopharmacology 4 (2): 125-138 ( 1982).

Seda and Mraz, "B-cell receptor signalling and its crosstalk with other pathways in normal and malignant cells", European Journal of Haematology, 2015, vol. 94 (3) p. 193-205.

Seymour et al., "Bcl-2 Inhibitor ABT-199 (GDC-0199) Monotherapy Shows Anti-Tumor Activity Including Complete Remissions in High-Risk Relapsed/Refractory (R/R) Chronic Lymphocytic Leukemia (CLL) and Small Lymphocytic lymphoma (SLL)", Blood, vol. 122, No. 21, Nov. 2013, p. 872.

Shapiro et al., "A Phase I Dose-Escalation Study of XL 147, A PI3K Inhibitor Administered Orally to Patients with Solid Tumors," J. Clin. Oncol. 27 (15s): 146x (suppl Abstr 3500) (2009).

Sharman et al, "A Phase 1 Study of the Selective Phosphatidylinositol 3-Kinase-Delta (PI3K delta) inhibitor, CAL-101 (GS-1·101), in Combination with Rituximab and/or Bendamustine in Patients with Relapsed or Refractory Chronic Lympt1ocytic leukemia (CLL)", Blood (ASH), 118(21), pp. 779-780 {2011).

Sheridan, "Companies in rapid pursuit of Btk immunokinase", Nature Biotechnology 30:199-200 (2012). Retrieved from the Internet: URL:http://www.nature.com/nbt/journal/v30/n3/pdf/nbt0312-199.pdf [retrieved on Apr. 8, 2016].

Shibasaki et al., "Different properties of monomer and heterodimer forms of phosphatidylinositol 3-kinases," Biochem. J. 289 (PI 1): 227-231 (1993).

Simioni et al., "Cytotoxic activity of the novel Aki inhibitor, MK-2206, in T-cell acute lymphoblastic leukemia", Leukemia, Vo. 26, No. 11, Nov. 2012, pp. 2336-2342.

Sinclair et al., "Phosphalidylinositol-3 Kinase Delta (PI3Kd) Inhibitor AMG 319 Is a Potent, Selective and Orally Bioavailable Small Molecule Inhibitor Thal Suppresses PI3K-Mediated Signaling and Viability in Neoplastic B Cells," Blood (ASH Annual Meeting Abstracts) 118: Abstract 4964 (2011).

Singer et al., "Optimization of in situ Hybridization Using Isotopic and Non-Isotopic Detection Methods," Biotechniques 4(3): 230-250 (1986).

Smith, C. I. E. et al., "Expression of Bruton's Agammaglobulinemia Tyrosine Kinase Gene, BTK, Is Selectively Down-Regulated in T Lymphocytes and Plasma Cells," J. Immunol., 152:557-565 (1994).

Smucker P. et al., "Intravenous Polyethylene Glycol Successfully Treats Severe Acceleration-Induced Brain Injury in Rats as Assessed by Magnetic Resonance Imaging," Neurosurgery (2009), vol. 64, Issue 5, 984-990.

Soldan et al., "Induction of daunombicin carbonyl reducing enzymes by daunombicin in sensitive and resistant pancreas carcinoma cells," Biochem. Pharmacol. 51(2):117-123 (1996).

Song et al., "The antagonistic effect of PI3K-gamma inhibitor AS605240 on cardiac hypertrophy and cardiac fibrosis induced by isoproterenol in rats," Sichuan Da Xue Xue Bao Yi Xue Ban 42(4):471-474 (2011) (abstract only).

Soond et al., "Pi3K p110delta regulates T-cell cytokine production during primary and secondary immune responses in mice and humans," Blood 115 (11 ): 2203-2213 (2010).

Srinivasan et al., "PB Kinase Signals BCR-Dependent Mature B Cell Survival," Cell 139:573-586 (2009).

Stanoeva et al., "Homophthalic anhydrides and their application to the synthesis of heterocyclic compounds (review)," Chemistry of Heterocyclic Compounds 20 (12): 1305-1315 (1984).

Stone, Richard. "Mast Cell Leukemia and Other Mast Cell Neoplasms." In: Kufe DW, Pollock RE, Weichselbaum RR, et al., editors. Holland-Frei Cancer Medicine. 6th Edition. Hamilton (ON): BC Decker, 2003. Available from: www.ncbi.nlm.nih.gov/books/NBK 13427/.

Subramaniam et al., "Targeting Nonclassical Oncogenes for Therapy in T-ALL," Cancer Cell 21 (4): 459-472 (2012).

Sujobert et al., "Essential role for the p110 delta isoform in phosphoinositide 3-kinase activation and cell proliferation in acute myeloid leukemia," Blood 106 (3): 1063-1066 (2005).

Supplementary EP Search Report for EP Application No. 16837600.2 mailed Jul. 10, 2019 (15 pages).

Supplementary European Examination Report EP Application No. 07754845.1 dated Sep. 20, 2011, 3 pages.

Supplementary European Search Report for EP Application No. 07754845 (4 pages) dated Feb. 24, 2010.

Supplementary European Search Report for EP Application No. 10800175.1 dated Nov. 7, 2012, 4 pages.

Suralkar et al., "In-Vivo Animal Models for Evaluation of Anti-Inflammatory Activity," Pharmainfo.net/reviews, vol. 6, Issue 2, Mar. 17, 2008.

Sykes et al., "Treatment of severe autoimmune disease by stem-cell transplantation," Nature 35 (7042): 620-627 (2005).

Sylvester Comprehensive Cancer Center, "Definition: Leukemia, Lymphoma and Myeloma," 2015. URL: http://sylvester.org/cancer/leukemia-lymphoma-and-myeloma/education/definition.

Takeuchi et al., "Synergistic Augmentation of Rapamycin-Induced Autophagy in Malignant Glioma Cells by Phosphatidylinositol 3-Kinase/Protein Kinase B Inhibitors," Cancer Res. 65(8):3336-3346 (2005).

Tanaka et al., "An unbiased cell morphology-based screen for new, biologically active small molecules," PLoS Biol. 3(5):0764-0776 (2005).

The Chemical Society of Japan ed., Jikken kagaku kouza (zoku), 2. Bunri to seisei (Experimental chemical lecture, second series, 2. Separation and purification), MARUZEN Co., Ltd., Jan. 25, 1967, pp. 159-178, 186-187.

Thompson et al., "Identification of distinct populations of PI-3 kinase activity following T-cell activation," Oncogene 7(4):719-725 (1992).

(56) References Cited

OTHER PUBLICATIONS

Tong et al., "Perifosine induces protective autophagy and upregulation of ATG5 in human chronic myeiogermus leukemia cells in vitro", Acta Pharmacologica Sinica, vol. 33, No. 4, pp. 542-550 (2012).
Torbett et al., "A chemical screen in diverse breast cancer cell lines reveals genetic enhancers and suppressors of sensitivity to PI3K isoform-selective inhibition," Biochem. J. 415(1):97-110 (2008).
Treon et al., "A Prospective Multicenter Study of the Bruton's Tyrosine Kinase Inhibitor Ibrutinib in Patients with Relapsed or Refractory Waldenstrom' s Macroglobulinemia," ASH Annual Meeting, Oral Presentation 251, Dec. 9, 2013.
Truitt et al., "Stimulation of CD28 triggers an association between CD28 and phosphatidylinositol 3-kinase in Jurkat T cells," J. Exp. Med. 179 (3): 1071-1076 (1994).
Tyukavkina et al., Bioorganicheskaya Khimiya, Moskva, DROFA, pp. 83-85 (2004).
Uddin et al., "Role of phosphatidylinositol 3'-kinase/AKT pathway in diffuse large B-cell lymphoma survival," Blood 08 (13): 4178-4186 (2006).
Ugarkar et al., "Adenosine kinase inhibitors. 2. Synthesis, enzyme inhibition, and antiseizure activity of diaryltubercidin analogues," J. Med. Chem. 43 (15): 2894-2905 (2000).
Vachhani et al., "Ratianal combination of dual PI3K/mTOR blockade and Bcl-2/-xl inhibition in AML", Physiological Genomics, 46(13):448-456 (2014).
Vandenberghe et al., "Antibody and B7/BB1-mediated ligation of the CD28 receptor induces tyrosine phosphorylation in human T cells," J. Exp. Med. 175(4):951-960 (1992).
Vanhaesebroeck et al., "PI3K: From the Bench to the Clinic and Back," Curr. Top. Microbiol. Immunol. 347: 1-19 (2010).
Vanhaesebroeck et al., "The emerging mechanisms of isoform—specific PI3K signalling," Nature Reviews Molecular Biology,, vol. 11, pp. 329-341 ( 2010).
Vara J.A.F., et al., "PI3K/Akt Signalling Pathway and Cancer," Cancer Treatment Reviews, 2004, vol. 30, pp. 193-204.
Vasilevsky et al., "Study of the Heterocyclization of vie-Substituted Hyrdazides of Acetylenylpyrazolecarboxylic Acids into N-Amino Pyrazolopyridinones," Journal of Heterocyclic Chemistry 39 (6): 1229-1233 (2002).
Vasilevsky et al., "Unexpected results in the heterocyclization of 5-acetylenylpyrazole-4-carboxylic acid hydrazides under the influence of CuCl: Formation of a diazepinone and dehydrodimerization into the corresponding bis(pyrazolo 4,3-d][1,2] diazepinone), " Tetrahedron Lett. 46 (26):4457-4459 (2005).
Veliz et al., "Treatment of relapsed or refractory chronic lymphocytic leukemia", Cancer Control, 19:37-53 (2012).
Venable et al., "Phosphoinositide 3-kinase gamma (PI3Kgamma) inhibitors for the treatment of inflammation and autoimmune disease", Recent Pat Inflamm Allergy Drug Discov (2010) 4: 1-15.
Viardot et al., "Clinicopathologic Correlations of Genomic GA1ns and Losses in Follicular Lymphoma", Journal of Clinical Oncology, vol. 20, No. 23 Dec. 1, 2002: pp. 4523-4530.
Vippagunta et al., "Crystalline Solids," Adv. Drug Deliv. Rev. 48(1):3-26 (2001).
Vitali et al., "Immunotherapy in rheumatoid arthritis: a review," Int. J. Artif. Organs 16 Suppl. 5: 196-200 (1993).
Vlahos et al., "A specific inhibitor of phosphatidylinositol 3-kinase, 2-(4-morpholinyl)-8-phenyl-4H-1-benzopyran-4-one (L Y294002)," J. Biol. Chem. 269 (7): 5241-5248 (1994).
Vogt et al., "Phosphatidylinositol 3-kinase: the oncoprotein," Curr. Top Microbiol. Immunol. 347: 79-104 (2010).
Vogt et al., "Phosphoinositide 3-kinase: from viral oncoprotein to drug target," Virology 344 (1): 131-138 (2006).
Vora et al., "CDK 4/6 Inhibitors Sensitize PIK3CA Mutant Breast Cancer to PI3K Inhibitors", Cancer Cell (Jul. 2014), vol. 26, pp. 136-149.

Wagner et al., "A First-in-Human Phase 1 Study to Evaluate the Pan-PI3K Inhibitor GDC-0941 Administered QD or BID in Patients with Advanced Solid Tumors," J. Clin. Oncol. 27: 146s (Suppl, Abstr 3501) (2009).
Wahlstrom et al., "Aberrant MAPK and PI3K Signaling Contribute to Chemotherapy Resistance in T Cell Acute Lymphoblastic Leukemia by Altering the Balance of Apoptosis Mediators," Blood (ASH Annual Meeting Abstracts) 118:Abstract 3490 (2011).
Ward et al., "Inhibition of CD28-mediated T cell costimulation by the phosphoinositide 3-kinase inhibitor wortmannin," Eur. J. Immunol. 25 (2): 526-532 (1995).
Ward et al., "Ligation of CD28 receptor by B7 induces formation of D-3 phosphoinositides in T lymphocytes independently of T cell receptor/CD3 activation," Eur. J. Immunol. 23 (10): 2572-2577 (1993).
Ward et al., "Regulation of D-3 phosphoinositides during T cell activation via the T cell antigen receptor/CD3 complex and CD2 antigens," Eur. J. Immunol. 22 (1): 45-49 (1992).
Ward et al., "Regulation of phosphoinositide kinases in T cells. Evidence that phosphatidylinositol 3-kinase is not a substrate for T cell antigen receptor-regulated tyrosine kinases," J. Biol. Chem. 267 (33) 23862-23869 (1992).
Ward et al., "Therapeutic potential of phosphoinositide 3-kinase inhibitors," Chem. Biol. 10(3):207-213 (2003).
WebMD. Chronic Myeloproliferative Disorders. 2014. webmd.com/cancer/lc/chronic--myeloproliferative-disorders-treatment-patient-information-nci-pdq-general-information.
WebMD, HIV & AIDS Health Center HTLV Type I and Type II. 2014. www.webmd.com/hiv-aids/htlv-type-i-and-type-ii.
WebMD, Leukemia-Prevention. Cancer Health Center. 2012. http://www.webmd.com/cancer/tc/leukemia-prevention.
WebMD, Lung Disease Overview. (2014). http://www.webmd.com/lung/lung-diseases-overview.
Wei et al.. "A phosphoinositide 3-kinase-gamma inhibitor, AS605240 prevents bleomycin-induced pulmonary fibrosis n rats," Biochem. Biophy. Res. Comm. 397: 311-317 (2010).
Wen et al., "Current Clinical Development of PI3K Pathway Inhibitors in Glioblastoma", Neuro-Oncology 14 (7):819-829, ePub May 22, 2012, 2012.
White et al., "11β-Hydroxysteroid Dehyrdogenase and the Syndrome of Apparent Mineralocorticoid Excess," Endocr. Rev. 18(1):135-156 (1997).
Widler et al., "7-alkyl- and 7-Cycloalkyl-5-aryl-pyrrolo[2,3-d]pyrimidines-potent inhibitors of the tyrosine kinase c-Src," Bioorg. Med. Chem. Lett. 11 (6): 849-852 (2001).
Wiesinger et al., "Antiinflammatory activity of the new mould metabolite 11-desacetoxy-wortmannin and of some of its derivates," Experientia 30 (2): 135-·136 (1974).
Wilson, W. H. et al., "686—The Bruton's Tyrosine Kinase (Btk) Inhibitor, Ibrutinib (PCI-32765), Has Preferential Activity in the ABC Subtype of Relapsed/Refractory De Novo Diffuse Large B-Cell Lymphoma (DLBCL): Interim Results of a Multicenter, Open-Label, Phase2 Study," Poster #686, 54th American Society of Hematology (ASH) annual meeting abstract (Dec. 10, 2012).
Winkler et al., "PI3K-d and PI3K-g Inhibition by IPI-145 Abrogates Immune Responses and Suppresses Activity in Autoimmune and Inflammatory Disease Models," Chemistry & Biology (2013),://dx.doi.org/10.1016/j.chembiol.2013.09.017.
Wolff, Manfred E. "Burger's Medicinal Chemistry, 5ed, Part I", John Wiley & Sons, 1995, pp. 975-977.
Wong et al., "Targeting the PI3K signaling pathway in cancer," Curr Opin Genet Dev. Feb. 2010 ; 20(1): 87, 7 pages.
Woscholski et al., "A comparison of demethoxyviridin and wortmannin as inhibitors of phosphatidylinositol 3- kinase," FEBS Lett. 342 (2): 109-114 (1994).
Woyach et al., "Resistance Mechanisms for the Bruton's Tyrosine Kinase Inhibitor Ibmtinib," N Engl J Med 2014; 370; p. 2286-2294.
Wu et al., "Decreased immunological responses by wortmannin-containing rice culture of Fusarium oxysporum and by purified wortmannin in avian species," Immunopharmacol. Immunotoxicol. 14 (4): 913-923 (1992).
Wu et al., "Wortmannin (a mycotoxin) inhibited immune responses in chickens," Poultry Sci. Vo. 71, Suppl 1, pp. 13 1992).

(56) References Cited

OTHER PUBLICATIONS

Wullschleger et al., "Quantitative MRI Establishes the Efficacy of PI3K Inhibitor (GDC-0941) Multi-Treatments in PTEN-deficient Mice Lymphoma", Anticancer Research, 32(2):415-420 (2012).

Wymann et al., "Phosphoinositide 3—kinase g: a key modulator in inflammation and allergy", 2003, Biochem Soc. Transactions. 31, Par I, pp. 275-280.

Yaguchi et al., "Antitumor activity of ZSTK474, a new phosphatidylinositol 3-kinase inhibitor," J. Nall. Cancer Inst. 98 8): 545-556 (2006).

Yang et al., "A novel activation pathway for mature thymocytes. Costimulation of CD2 (T,p50) and CD28 (T,p44) induces autocrine interleukin 2/interleukin 2 receptor-mediated cell proliferation," J. Exp. Med. 168 (4): 1457-1468 (1988).

Yano et al., "Inhibition of histamine secretion by wortmannin through the blockade of phosphatidylinositol 3-kinase in RBL-2H3 cells," J. Biol.. Chem. 268 (34): 25846-25856 {1993).

Yoshida et al., "Quercetin arrests human leukemic T—cells in late 81 phase of the cell cycle," Cancer Res. 52 (23): 6676-6681 (1992).

Yu et al., "Development of a Practical Synthesis of DPP IV Inhibitor LY2497282", Organic Process Research & Development, 2008, vol. 12, pp. 218-225.

Zhao and Vogt, "Class I PI3K in oncogenic cellular transformation," Oncogene 27(41):5486-5496 (2008).

Zhao et al, "TNF-a promotes LPA1- and LPA3-mediated recruitment of leukocytes in vivo through CXCR2 ligand chemokines," J. Lipid Res., 52(7):1307-1318 (2011).

Zhu et al., "PI3K inhibition potentiates Bcl-2-dependenl apoptosis in renal carcinoma cells", Journal of Cellular and 1olecular Medicine, vol. 17, No. 3, Mar. 2013, pp. 377-385.

Arcaro et al., "The Phosphoinositide 3-Kinase Pathway in Human Cancer: Genetic Alterations and Therapeutic Implications," Current Genomics, 2007, vol. 8, pp. 271-306.

Chang et al., "Use of Tumor Genomic Profiling to Reveal Mechanisms of Resistance to the BTK Inhibitor Ibrutinib in Chronic Lymphocytic Leukemia (CLL)," Journal of Clinical Oncology, May 20, 2013, vol. 31, No. 15, Suppl. 1, Abstract No. 7014, 4 pages.

Cheson et al., "Bendamustine: Mechanism of Action and Clinical Data," Clinical Advances in Hematology & Oncology 2011 .9(8:Suppl. 19): 1-11 ( 2011).

Herko et al., AMG 319, a Novel Inhibitor of Phosphoinositide-3 Kinase Delta (PI3Kd), Demonstrates Activity in Lymphoma Pre-Clinical Models, Blood 2012, vol. 120, No. 21, Abstract 3718, 2 pages.

Kakkola et al., "Anticancer compound ABT-263 accelerates apoptosis in vims-infected cells and imbalances cytokine production and lowers survival rates of infected mice", Cell Death & Disease (2013) 4, e742.

Kim et al., "The dual PI3K and mTOR inhibitor NVP-BEZ235 exhibits anti-proliferative activity and overcomes bortezomib resistance in mantle cell lymphoma cells," Leukemia Research 36:912-920 (2012).

Nakamaki et al., "Inhibition of Phosphatidylinositol 3-Kinase Is Effective to Suppress the Growth of CD20-Negative Refractory Diffuse Large B-Cell Lymphoma Cells," Blood, 2011, vol. 118, No. 21, Abstract 2421, 3 pages.

National Center for Biotechnology Information. PubChem Compound Summary for CID 58008990, Ipi-145;ink1197 (https://pubchem.ncbi.nlrn.nih.gov/cornpound/58008990. Accessed Jun. 7, 2022.) (Year: 2022), 11 pages.

NCT01882803 (Kelly, P Jun. 18, 2013, https://clinicaltrials.gov/ct2/history/NCT01882803?V_1=View#StudyPageTop ) (Year: 2013), 7 pages.

Robak & Robak, BCR Signaling in Chronic Lymphocytic Leukemia and Related Inhibitors Currently in Clinical Studies, International Reviews of Immunology, 32:4, 358-376 (2013).

Wagner-Johnston et al., "DYNAMO: A Phase 2 Trial of the PI3K-delta,y Inhibitor IPI-145 in Patients with Refractory Indolent non-Hodgkin Lymphoma", American Society of Clinical Oncology (ASCO), Annual Meeting, Jun. 2, 2014, Chicago, IL, 6 pages.

\* cited by examiner

SAD part, single dose QD

MAD part, multiple dose, BID (1, 2, 5 mg) or QD (10 mg)

AKT Phosphorylation in CLL Cells
(individual patients at 25 mg BID)

FIGURE 9A
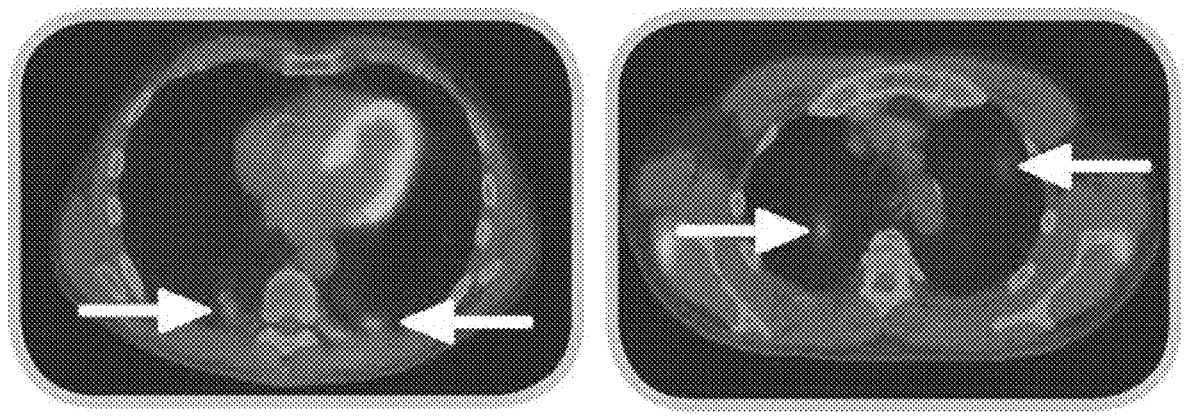
Pre Compound 292 Therapy PET/CT
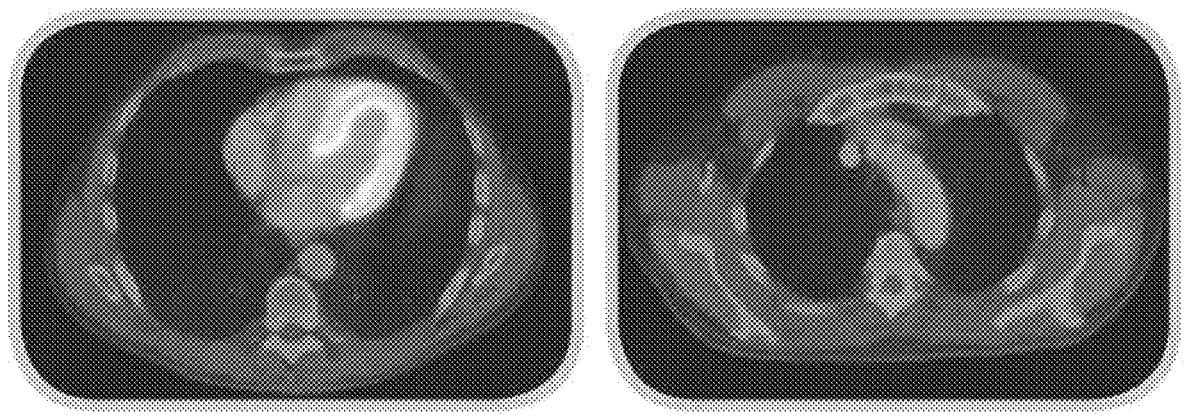
Post 2 Cycles of Compound 292 Therapy PET/CT
FIGURE 9B Serum CCL22

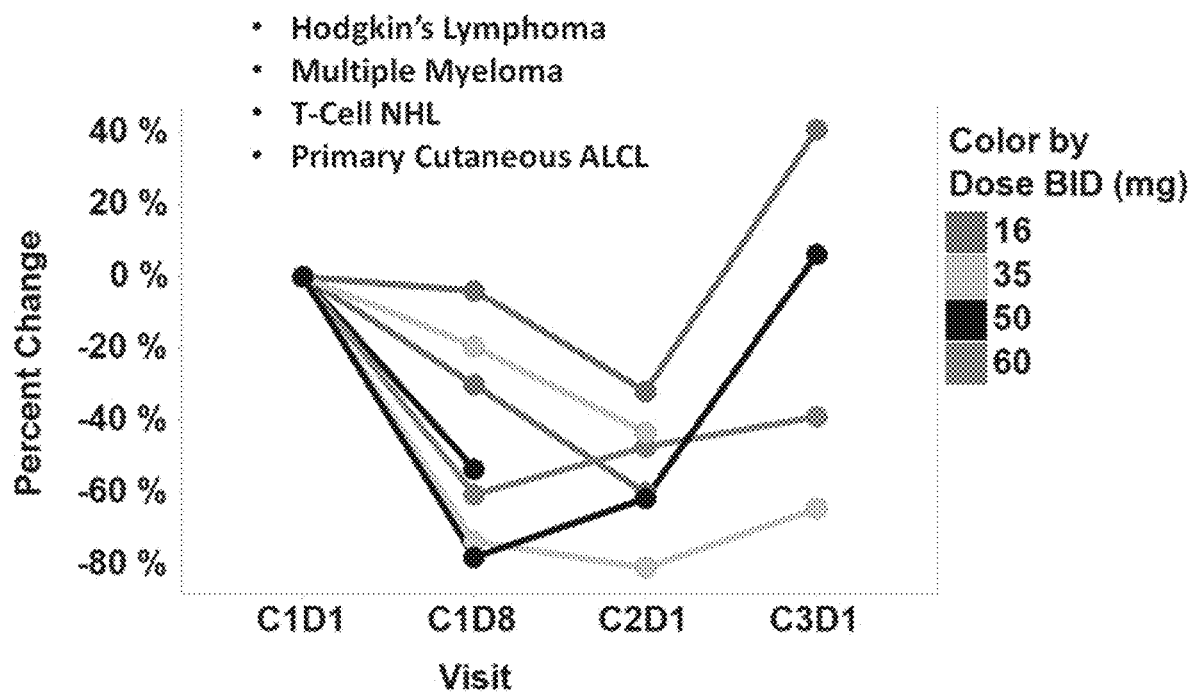

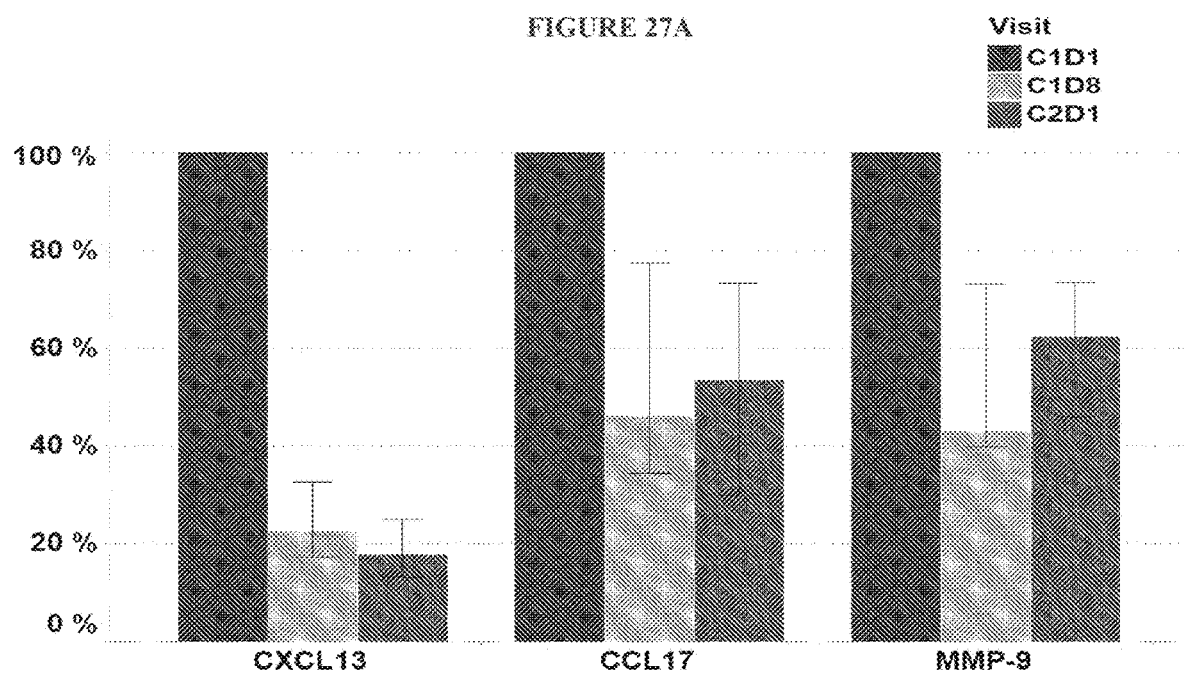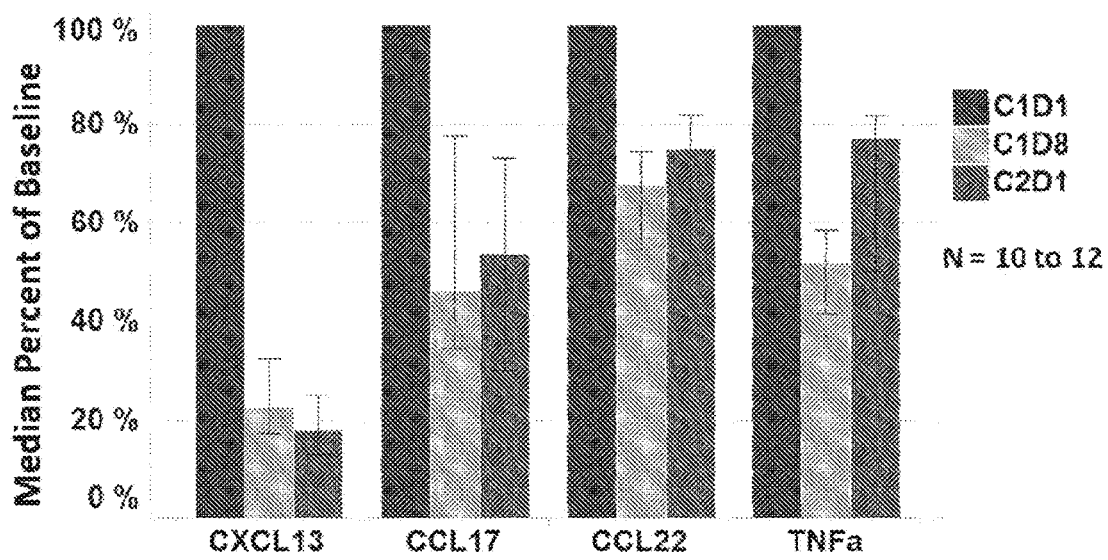

Sézary Cells per µL in Peripheral Blood

CT Response mSWAT Response

Done in 10% FBS
Loading controls not shown.

Absolute Lymphocyte Counts

%CD38 Positive Circulating CLL Cells

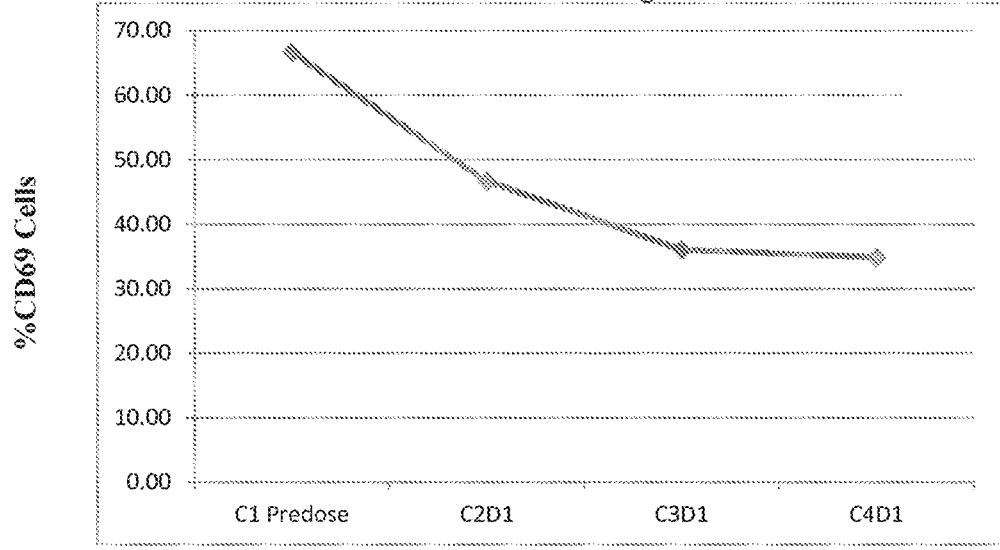
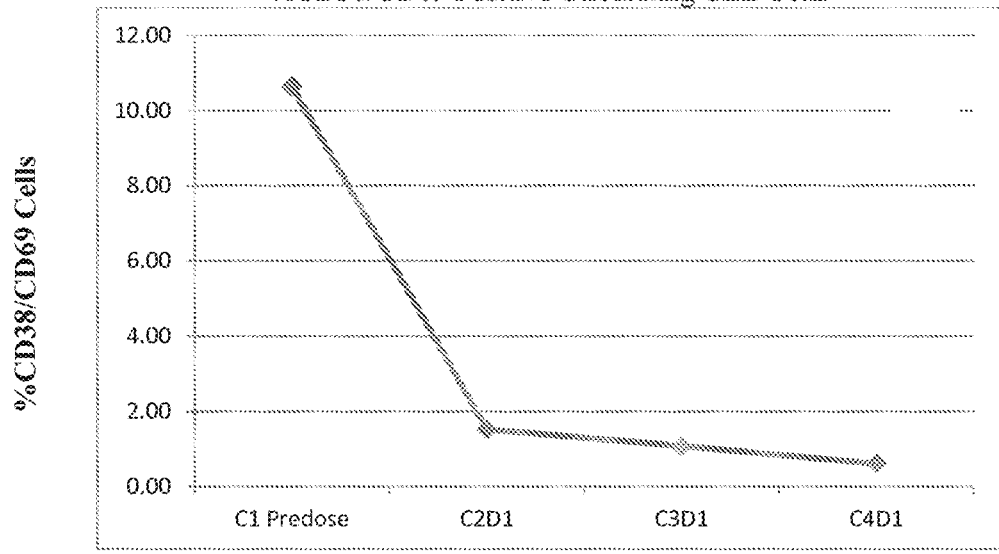

TREATMENT OF CANCERS USING PI3 KINASE ISOFORM MODULATORS

This application is a continuation of U.S. application Ser. No. 15/581,414 filed Apr. 28, 2017, which is a continuation of U.S. application Ser. No. 14/439,965, which is the U.S. National Phase Application of 35 U.S.C. § 371 of International Application No. PCT/US2013/067929, filed Nov. 1, 2013, which claims priority to U.S. Provisional Application Nos. 61/829,168, filed May 30, 2013, 61/836,088, filed Jun. 17, 2013, 61/863,365, filed Aug. 7, 2013, 61/888,454, filed Oct. 8, 2013, and is a continuation in part of U.S. application Ser. No. 13/840,822, filed Mar. 15, 2013, which claims priority to U.S. Provisional Application Nos. 61/721,432, filed Nov. 1, 2012, 61/733,852, filed Dec. 5, 2012, and 61/767,606, filed Feb. 21, 2013, the entireties of which are incorporated herein by reference.

BACKGROUND

The activity of cells can be regulated by external signals that stimulate or inhibit intracellular events. The process by which stimulatory or inhibitory signals are transmitted into and within a cell to elicit an intracellular response is referred to as signal transduction. Over the past decades, cascades of signal transduction events have been elucidated and found to play a central role in a variety of biological responses. Defects in various components of signal transduction pathways have been found to account for a vast number of diseases, including numerous forms of cancer, inflammatory disorders, metabolic disorders, vascular and neuronal diseases (Gaestel et al. Current Medicinal Chemistry (2007) 14:2214-2234).

Kinases represent a class of important signaling molecules. Kinases can generally be classified into protein kinases and lipid kinases, and certain kinases exhibit dual specificities. Protein kinases are enzymes that phosphorylate other proteins and/or themselves (i.e., autophosphorylation). Protein kinases can be generally classified into three major groups based upon their substrate utilization: tyrosine kinases which predominantly phosphorylate substrates on tyrosine residues (e.g., erb2, PDGF receptor, EGF receptor, VEGF receptor, src, abl), serine/threonine kinases which predominantly phosphorylate substrates on serine and/or threonine residues (e.g., mTorC1, mTorC2, ATM, ATR, DNA-PK, Akt), and dual-specificity kinases which phosphorylate substrates on tyrosine, serine and/or threonine residues.

Lipid kinases are enzymes that catalyze the phosphorylation of lipids. These enzymes, and the resulting phosphorylated lipids and lipid-derived biologically active organic molecules play a role in many different physiological processes, including cell proliferation, migration, adhesion, and differentiation. Certain lipid kinases are membrane associated and they catalyze the phosphorylation of lipids contained in or associated with cell membranes. Examples of such enzymes include phosphoinositide(s) kinases (e.g., PI3-kinases, PI4-kinases), diacylglycerol kinases, and sphingosine kinases.

The phosphoinositide 3-kinases (PI3Ks) signaling pathway is one of the most highly mutated systems in human cancers. PI3K signaling is also a key factor in many other diseases in humans. PI3K signaling is involved in many disease states including allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

PI3Ks are members of a unique and conserved family of intracellular lipid kinases that phosphorylate the 3'-OH group on phosphatidylinositols or phosphoinositides. The PI3K family comprises 15 kinases with distinct substrate specificities, expression patterns, and modes of regulation. The class I PI3Ks (p110α, p110β, p110δ, and p110γ) are typically activated by tyrosine kinases or G-protein coupled receptors to generate PIP3, which engages downstream effectors such as those in the Akt/PDK1 pathway, mTOR, the Tec family kinases, and the Rho family GTPases. The class II and III PI3Ks play a key role in intracellular trafficking through the synthesis of PI(3)P and PI(3,4)P2. The PI3Ks are protein kinases that control cell growth (mTORC1) or monitor genomic integrity (ATM, ATR, DNA-PK, and hSmg-1).

There are four mammalian isoforms of class I PI3Ks: PI3K-α, β, δ (class Ia PI3Ks) and PI3K-γ (a class Ib PI3K). These enzymes catalyze the production of phosphatidylinositol (3,4,5)-trisphosphate (PIP3), leading to activation of downstream effector pathways important for cellular survival, differentiation, and function. PI3K-α and PI3K-β are widely expressed and are important mediators of signaling from cell surface receptors. PI3K-α is the isoform most often found mutated in cancers and has a role in insulin signaling and glucose homeostasis (Knight et al. Cell (2006) 125(4):733-47; Vanhaesebroeck et al. Current Topic Microbiol. Immunol. (2010) 347:1-19). PI3K-β is activated in cancers where phosphatase and tensin homolog (PTEN) is deleted. Both isoforms are targets of small molecule therapeutics in development for cancer.

PI3K-δ and -γ are preferentially expressed in leukocytes and are important in leukocyte function. These isoforms also contribute to the development and maintenance of inflammatory and autoimmune diseases, and hematologic malignancies (Vanhaesebroeck et al. Current Topic Microbiol. Immunol. (2010) 347:1-19; Clayton et al. J Exp Med. (2002) 196(6):753-63; Fung-Leung Cell Signal. (2011) 23(4):603-8; Okkenhaug et al. Science (2002) 297(5583):1031-34). PI3K-δ is activated by cellular receptors (e.g., receptor tyrosine kinases) through interaction with the Sarc homology 2 (SH2) domains of the PI3K regulatory subunit (p85), or through direct interaction with RAS.

PI3K-γ is associated with G-protein coupled receptors (GPCRs), is responsible for the very rapid induction of PIP3 in response to GPCRs, and can also be activated by RAS downstream of other receptors. PIP3 produced by PI3K activates effector pathways downstream through interaction with pleckstrin homology (PH) domain containing enzymes (e.g., PDK-1 and AKT [PKB]).

Both PI3K-δ and -γ isoforms have been shown to be important in many aspects of leukocyte biology. Central regulatory roles for either or both enzymes have been demonstrated in B cells (Vanhaesebroeck et al. Current Topic Microbiol. Immunol. (2010) 347:1-19; Clayton et al. J Exp Med. (2002) 196(6):753-63; Fung-Leung Cell Signal. (2011) 23(4):603-8; Al-Alwan et al. J Immunol. (2007) 178(4):2328-35; Bilancio et al. Blood (2006) 107(2):642-50; Dil et al. Mol Immunol. (2009) 46(10):1970-78; Durand et al. J Immunol. (2009) 183(9):5673-84; Srinivasan et al. Cell (2009) 139(3):573-86; Zhang et al. J. Allergy & Clin. Immunol. (2008) 122(4):811-9.e2), T cells (Vanhaesebroeck et al. Current Topic Microbiol. Immunol. (2010) 347:1-19; Garcon et al. Blood (2008) 111(3):1464-71; Haylock-Jacobs et al. J Autoimmun. (2011) 36(3-4):278-87; Jarmin et al. J. Clin. Invest. (2008) 118(3):1154-64; Ji et al. Blood (2007)

110(8):2940-47; Liu et al. J Immunol. (2010) 184(6):3098-105; Okkenhaug et al. J. Immunol. (2006) 177(8):5122-28; Reif et al. J. Immunol. (2004) 173(4):2236-40; Soond et al. Blood (2010) 115(11):2203-13; Webb et al. J. Immunol. (2005) 175(5):2783-87), neutrophils (Schmid et al. Cancer Cell (2011) 19(6):715-27), macrophages/monocytes (Schmid et al. Cancer Cell (2011) 19(6):715-27; Konrad et al. J. Biol. Chem. (2008) 283(48):33296-303; Marwick et al. Am J Respir Crit Care Med. (2009) 179(7):542-48; Randis et al. Eur J Immunol. (2008) 38(5):1215-24), mast cells (Ali et al. Nature (2004) 431(7011):1007-11; Kim et al. Trends Immunol. (2008) 29(10):493-501; Lee et al. FASEB J. (2006) 20(3):455-65), and NK cells (Guo et al. J Exp Med. (2008) 205(10):2419-35; Kim et al. Blood (2007) 110(9):3202-08; Saudemont et al. Proc Natl Acad Sci USA. (2009) 106(14):5795-800; Tassi et al. Immunity. (2007) 27(2):214-27).

Both PI3K-δ and -γ are believed to be important for the development and persistence of autoimmune disease and hematologic malignancies.

There remains a significant need for improved therapy for cancers such as hematologic malignancies.

SUMMARY

Provided herein are methods, compositions, and kits for treating or preventing cancers or diseases, such as hematologic malignancies, which have a high expression level of one or more isoform(s) of PI3K (e.g., PI3K-δ and/or PI3K-γ). In one embodiment, the methods, compositions, and kits provided herein relate to administering an isoform-selective PI3K modulator (e.g., a compound provided herein, which selectively reduces or inhibits the activity of one or more PI3K isoform(s), e.g., PI3K-δ and/or PI3K-γ), alone or in combination with one or more other agents or therapeutic modalities, to a subject, e.g., a mammalian subject, e.g., a human, having a cancer or disease, such as a hematologic malignancy, which has a high expression level of the one or more PI3K isoform(s).

In one embodiment, provided herein are methods, compositions, and kits for treating or preventing a specific type of cancer or disease, such as, a specific type of hematologic malignancy, which has a high expression level of one or more isoform(s) of PI3K. In one embodiment, provided herein are methods, compositions, and kits for treating or preventing a specific sub-type of cancer or disease, such as, a specific sub-type of hematologic malignancy, which has a high expression level of one or more isoform(s) of PI3K. In one embodiment, the specific type or specific sub-type of cancer or hematologic malignancy has a high expression of PI3K isoform(s), including one or more of PI3K-δ or PI3K-γ, or a combination thereof. In one embodiment, the specific type or specific sub-type of cancer or hematologic malignancy has a high expression of PI3K-δ, or PI3K-γ, or both PI3K-δ and PI3K-γ.

In one embodiment, the methods, compositions, and kits comprise, or relate to, the step of selecting a specific type, or a specific sub-type, of cancer or disease, e.g., a specific type, or a specific sub-type, of hematologic malignancy, for treatment, using a biomarker provided herein (e.g., selecting a specific type or sub-type of cancer or hematologic malignancy that has a high expression level of one or more isoform(s) of PI3K as determined using a biomarker provided herein). In one embodiment, the methods, compositions, and kits comprise, or relate to, the step of administering to a subject having a specific type, or a specific sub-type, of cancer or disease, e.g., a specific type, or a specific sub-type, of hematologic malignancy, which has a high expression level of one or more isoform(s) of PI3K, a PI3K modulator that selectively modulates (e.g., selectively inhibits) the PI3K isoform(s) that is highly expressed in the specific type or subtype of disease.

In specific embodiments, provided herein are methods, compositions, and kits for treating or preventing a specific type, or a specific sub-type, of cancer or disease, e.g., a specific type, or a specific sub-type, of hematologic malignancy, which has a high expression level of PI3K-δ. In specific embodiments, provided herein are methods, compositions, and kits for treating or preventing a specific type, or a specific sub-type, of cancer or disease, e.g., a specific type, or a specific sub-type, of a hematologic malignancy, which has a high expression level of PI3K-γ. In specific embodiments, provided herein are methods, compositions, and kits for treating or preventing a specific type, or a specific sub-type, of cancer or disease, e.g., a specific type, or a specific sub-type, of a hematologic malignancy, which has a high expression level of PI3K-δ and PI3K-γ. In specific embodiments, provided herein are methods, compositions, and kits for treating or preventing a specific type, or a specific sub-type, of cancer or disease, e.g., a specific type, or a specific sub-type, of a hematologic malignancy, which has a high expression level of PI3K-γ and PI3K-α. In specific embodiments, provided herein are methods, compositions, and kits for treating or preventing a specific type, or a specific sub-type, of cancer or disease, e.g., a specific type, or a specific sub-type, of a hematologic malignancy, which has a high expression level of PI3K-γ and PI3K-β. In specific embodiments, provided herein are methods, compositions, and kits for treating or preventing a specific type, or a specific sub-type, of cancer or disease, e.g., a specific type, or a specific sub-type, of a hematologic malignancy, which has a high expression level of PI3K-δ and PI3K-α. In specific embodiments, provided herein are methods, compositions, and kits for treating or preventing a specific type, or a specific sub-type, of cancer or disease, e.g., a specific type, or a specific sub-type, of a hematologic malignancy, which has a high expression level of PI3K-δ and PI3K-β. In specific embodiments, provided herein are methods, compositions, and kits for treating or preventing a specific type, or a specific sub-type, of cancer or disease, e.g., a specific type, or a specific sub-type, of a hematologic malignancy, which has a high expression level of PI3K-δ, PI3K-γ, and PI3K-α. In specific embodiments, provided herein are methods, compositions, and kits for treating or preventing a specific type, or a specific sub-type, of cancer or disease, e.g., a specific type, or a specific sub-type, of a hematologic malignancy, which has a high expression level of PI3K-δ, PI3K-γ, and PI3K-β.

In one embodiment, provided herein are methods, compositions, and kits for treating or preventing a specific patient or group of patients, having a cancer or disease, such as, a hematologic malignancy, wherein the particular patient or group of patients has(ve) a high expression level of one or more isoform(s) of PI3K. In one embodiment, the PI3K isoform includes one or more of PI3K-δ or PI3K-γ, or a combination thereof. In one embodiment, the specific patient or group of patients, having a cancer or a hematologic malignancy, has(ve) a high expression of PI3K-δ or PI3K-γ, or both PI3K-δ and PI3K-γ.

In one embodiment, the methods, compositions, and kits comprise, or relate to, the step of selecting a patient or group of patients having a cancer or disease for treatment, using a biomarker provided herein (e.g., selecting a patient or group of patients that has(ve) a high expression level of one or more isoform(s) of PI3K as determined using a biomarker provided herein). In one embodiment, the methods, compositions, and kits comprise, or relate to, the step of administering to the patient or group of patients having a high expression level of one or more isoform(s) of PI3K, a PI3K modulator that selectively modulates (e.g., selectively inhibits) the PI3K isoform(s) that is/are highly expressed in the patient(s).

In specific embodiments, provided herein are methods, compositions, and kits for treating or preventing a specific patient or group of patients, having a cancer or disease, e.g., a hematologic malignancy, that has a high expression level of PI3K-δ. In specific embodiments, provided herein are methods, compositions, and kits for treating or preventing a specific patient or group of patients, having a cancer or disease, e.g., a hematologic malignancy, that has a high expression level of PI3K-γ. In specific embodiments, provided herein are methods, compositions, and kits for treating or preventing a specific patient or group of patients, having a cancer or disease, e.g., a hematologic malignancy, which has a high expression level of PI3K-δ and PI3K-γ. In specific embodiments, provided herein are methods, compositions, and kits for treating or preventing a specific patient or group of patients, having a cancer or disease, e.g., a hematologic malignancy, which has a high expression level of PI3K-γ and PI3K-α. In specific embodiments, provided herein are methods, compositions, and kits for treating or preventing a specific patient or group of patients, having a cancer or disease, e.g., a hematologic malignancy, which has a high expression level of PI3K-γ and PI3K-β. In specific embodiments, provided herein are methods, compositions, and kits for treating or preventing a specific patient or group of patients, having a cancer or disease, e.g., a hematologic malignancy, which has a high expression level of PI3K-δ and PI3K-α. In specific embodiments, provided herein are methods, compositions, and kits for treating or preventing a specific patient or group of patients, having a cancer or disease, e.g., a hematologic malignancy, which has a high expression level of PI3K-δ and PI3K-β. In specific embodiments, provided herein are methods, compositions, and kits for treating or preventing a specific patient or group of patients, having a cancer or disease, e.g., a hematologic malignancy, which has a high expression level PI3K-δ, PI3K-γ, and PI3K-α. In specific embodiments, provided herein are methods, compositions, and kits for treating or preventing a specific patient or group of patients, having a cancer or disease, e.g., a hematologic malignancy, which has a high expression level of PI3K-δ, PI3K-γ, and PI3K-β.

In certain embodiments, the expression level of one or more than one particular PI3K isoform in a cancer or a disease (e.g., a hematologic malignancy), or a patient or a group of patients, can be determined by detecting the expression level of protein of a particular PI3K isoform, or DNA of a particular PI3K isoform, or RNA of a particular PI3K isoform, for example, using a method provided herein or a method known in the art. In other embodiments, the expression level of one or more than one particular PI3K isoform in a cancer or a disease (e.g., a hematologic malignancy), or a patient or a group of patients, can be determined by measuring a biomarker provided herein (e.g., a signaling pathway biomarker, a protein mutation biomarker, a protein expression biomarker, a gene mutation biomarker, a gene expression biomarker, a cytokine biomarker, a chemokine biomarker, or a biomarker for particular cancer cells, among others). In yet another embodiment, the expression level of one or more than one particular PI3K isoform in a cancer or a disease (e.g., a hematologic malignancy), or a patient or a group of patients, can be determined based on information known in the art or based on prior studies on the cancer or disease (e.g., a hematologic malignancy), or prior testing of the patient or group of patients.

In one embodiment, the methods, compositions and kits provided herein relate to administering a PI3K modulator (e.g., a compound that selectively reduces the activity of one or more PI3K isoform(s)), alone or in combination with one or more other agents or therapeutic modalities, to a subject, e.g., a mammalian subject, e.g., a human. In one embodiment, the PI3K modulator is selective toward one or more isoform(s) of PI3K over the other isoform(s) of PI3K. In one embodiment, the PI3K modulator (e.g., a compound provided herein) is selective toward PI3K-δ; selective toward PI3K-γ; selective toward PI3K-δ and PI3K-γ; selective toward PI3K-γ and PI3K-α; selective toward PI3K-γ and PI3K-γ; selective toward PI3K-δ and PI3K-α; selective toward PI3K-δ and PI3K-β; selective toward PI3K-δ, PI3K-γ, and PI3K-α; or selective toward PI3K-δ, PI3K-γ, and PI3K-β; over other PI3K isoform(s). In one embodiment, the selectivity of the PI3K modulator (e.g., a compound provided herein) for one isoform of PI3K over another isoform of PI3K is about 2-fold, about 5-fold, about 10-fold, about 20-fold, about 30-fold, about 40-fold, about 50-fold, about 100-fold, about 200-fold, about 300-fold, about 400-fold, about 500-fold, about 1000-fold, about 2000-fold, about 5000-fold, about 10000-fold, or greater than about 10000-fold. In one embodiment, the selectivity of a compound provided herein for one isoform of PI3K over another isoform of PI3K is greater than about 2-fold, greater than about 5-fold, greater than about 10-fold, greater than about 20-fold, greater than about 30-fold, greater than about 40-fold, greater than about 50-fold, greater than about 100-fold, greater than about 200-fold, greater than about 300-fold, greater than about 400-fold, greater than about 500-fold, greater than about 1000-fold, greater than about 2000-fold, greater than about 5000-fold, or greater than about 10000-fold.

In certain embodiments, the selectivity of a PI3K modulator (e.g., a compound provided herein) for one or more PI3K isoform(s) over other PI3K isoform(s) can be determined by measuring the activity of the PI3K modulator toward PI3K isoforms (e.g., PI3K-α, PI3K-β, PI3K-δ, and/or PI3K-γ), for example, using a method provided herein or a method known in the art.

In one embodiment, provided herein is a method of treating or preventing a specific cancer or disease, such as, a hematologic malignancy (e.g., a specific type, or a specific sub-type, of hematologic malignancy), which has a high expression level of one or more isoform(s) of PI3K, wherein the method comprises: (1) determining the expression level of one or more PI3K isoform(s) in the cancer or disease; (2) selecting a treatment agent (e.g., a PI3K modulator having a particular selectivity profile for one or more PI3K isoform (s)), based on the expression levels of PI3K isoforms in the cancer or disease to be treated; and (3) administering the treatment agent to a patient having the cancer or disease, alone or in combination with one or more other agents or therapeutic modalities. In one embodiment, the expression level of one or more PI3K isoform(s) in the cancer or disease can be measured by determining the expression level of PI3K isoform protein, DNA, and/or RNA; or by measuring one or more biomarkers provided herein (e.g., a signaling pathway biomarker, a protein mutation biomarker, a protein expression biomarker, a gene mutation biomarker, a gene expression biomarker, a cytokine biomarker, a chemokine biomarker, or a biomarker for particular cancer cells, among others). In other embodiments, the expression level of one or more PI3K isoform(s) in the cancer or disease can be determined based on information known in the art or information obtained in prior studies on the cancer or disease.

Certain cancer or disorder, e.g., a hematologic malignancy (e.g., a specific type, or a specific sub-type, of hematologic malignancy), can exhibit heterogeneity in PI3K isoform expression among patient populations. In one embodiment, provided herein is a method of treating or preventing a specific patient or group of patients, having a cancer or disease, such as, a hematologic malignancy, wherein the method comprises: (1) determining the expression levels of one or more PI3K isoform(s) in the patient or group of patients having the cancer or disease; (2) selecting a treatment agent (e.g., a PI3K modulator having a particular selectivity profile for one or more PI3K isoform(s)) based on the expression levels of PI3K isoforms in the patient(s) to be treated; and (3) administering the treatment agent to the patient(s), alone or in combination with one or more other agents or therapeutic modalities. In one embodiment, the expression level of one or more PI3K isoform(s) in the patient or group of patients can be measured by determining the expression level of PI3K isoform protein, DNA, and/or RNA in the patient or group of patients; or by measuring one or more biomarkers provided herein in the patient or group of patients (e.g., a signaling pathway biomarker, a protein mutation biomarker, a protein expression biomarker, a gene mutation biomarker, a gene expression biomarker, a cytokine biomarker, a chemokine biomarker, or a biomarker for particular cancer cells, among others). In other embodiments, the expression level of one or more PI3K isoform(s) in the patient or group of patients can be determined based on information known in the art or information obtained in prior testing of the patient or group of patient(s).

In specific embodiments, the methods, compositions and kits provided herein relate to administering a PI3K modulator, alone or in combination with one or more other agents or therapeutic modalities, to a subject, e.g., a mammalian subject, e.g., a human; wherein the PI3K modulator is selective toward PI3K-δ over the other isoforms of PI3K. In specific embodiments, the methods, compositions and kits provided herein relate to administering a PI3K modulator, alone or in combination with one or more other agents or therapeutic modalities, to a subject, e.g., a mammalian subject, e.g., a human; wherein the PI3K modulator is selective toward PI3K-γ over the other isoforms of PI3K. In specific embodiments, the methods, compositions and kits provided herein relate to administering a PI3K modulator, alone or in combination with one or more other agents or therapeutic modalities, to a subject, e.g., a mammalian subject, e.g., a human; wherein the PI3K modulator is selective toward PI3K-δ and PI3K-γ over the other isoforms of PI3K. In specific embodiments, the methods, compositions and kits provided herein relate to administering a PI3K modulator, alone or in combination with one or more other agents or therapeutic modalities, to a subject, e.g., a mammalian subject, e.g., a human; wherein the PI3K modulator is selective toward PI3K-γ and PI3K-α over the other isoforms of PI3K. In specific embodiments, the methods, compositions and kits provided herein relate to administering a PI3K modulator, alone or in combination with one or more other agents or therapeutic modalities, to a subject, e.g., a mammalian subject, e.g., a human; wherein the PI3K modulator is selective toward PI3K-γ and PI3K-β over the other isoforms of PI3K. In specific embodiments, the methods, compositions and kits provided herein relate to administering a PI3K modulator, alone or in combination with one or more other agents or therapeutic modalities, to a subject, e.g., a mammalian subject, e.g., a human; wherein the PI3K modulator is selective toward PI3K-δ and PI3K-α over the other isoforms of PI3K. In specific embodiments, the methods, compositions and kits provided herein relate to administering a PI3K modulator, alone or in combination with one or more other agents or therapeutic modalities, to a subject, e.g., a mammalian subject, e.g., a human; wherein the PI3K modulator is selective toward PI3K-δ and PI3K-β over the other isoforms of PI3K. In specific embodiments, the methods, compositions and kits provided herein relate to administering a PI3K modulator, alone or in combination with one or more other agents or therapeutic modalities, to a subject, e.g., a mammalian subject, e.g., a human; wherein the PI3K modulator is selective toward PI3K-δ, PI3K-γ, and PI3K-α over other isoform of PI3K. In specific embodiments, the methods, compositions and kits provided herein relate to administering a PI3K modulator, alone or in combination with one or more other agents or therapeutic modalities, to a subject, e.g., a mammalian subject, e.g., a human; wherein the PI3K modulator is selective toward PI3K-δ, PI3K-γ, and PI3K-β over other isoform of PI3K.

In one embodiment, the methods, compositions, or kits provided herein relate to administering a PI3K modulator, alone or in combination with one or more other agents or therapeutic modalities, to a subject, e.g., a mammalian subject, e.g., a human; wherein the PI3K modulator is selective for one or more PI3K isoform(s) over other isoforms of PI3K (e.g., PI3K-δ selective, PI3K-γ selective, or PI3K-δ and PI3K-γ selective); and the subject being treated has a high expression level of the particular PI3K isoform(s) (e.g., high expression of PI3K-δ, high expression of PI3K-γ, or high expression of both PI3K-δ and PI3K-γ). Without being limited to a particular theory, the methods, compositions, or kits provided herein can provide reduced side effects and/or improved efficacy. Thus, in one embodiment, provided herein is a method of treating or preventing a cancer or disease, such as hematologic malignancy, or a specific type or sub-type of cancer or disease, such as a specific type or sub-type of hematologic malignancy, having a high expression level of one or more isoform(s) of PI3K, wherein the adverse effects associated with administration of PI3K inhibitors are reduced.

In one embodiment, provided herein is a method of treating or preventing a cancer or disease, such as hematologic malignancy, or a specific type or sub-type of cancer or disease, such as a specific type or sub-type of hematologic malignancy, with a PI3K-γ selective inhibitor, wherein the adverse effects associated with administration of inhibitors for other isoform(s) of PI3K (e.g., PI3K-α or PI3K-β) are reduced. In one embodiment, provided herein is a method of treating or preventing a cancer or disease, such as hematologic malignancy, or a specific type or sub-type of cancer or disease, such as a specific type or sub-type of hematologic malignancy, with a PI3K-γ selective inhibitor, at a lower (e.g., by about 10%, by about 20%, by about 30%, by about 40%, by about 50%, by about 60%, by about 70%, or by about 80%) dose as compared to treatment with a PI3K-γ non-selective or less selective inhibitor (e.g., a PI3K pan inhibitor (e.g., PI3K-α, β, γ, δ)).

In one embodiment, the methods, compositions, or kits provided herein relate to administering a PI3K modulator, in combination with one or more second active agent(s), e.g., one or more cancer therapeutic agent(s). In one embodiment, the second active agents that can be used in the methods, compositions, or kits provided herein include, but are not limited to, one or more of: an HDAC inhibitor, such as, e.g., belinostat, vorinostat, panobinostat, or romidepsin; an mTOR inhibitor, such as, e.g., everolimus (RAD 001); a proteasome inhibitor, such as, e.g., bortezomib or carfilzomib; a JAK inhibitor or a JAK/STAT inhibitor, such as, e.g., Tofacitinib, INCB16562, or AZD1480; a BCL-2 inhibitor, such as, e.g., ABT-737, ABT-263, or Navitoclax; a MEK inhibitor, such as, e.g., AZD8330 or ARRY-424704; an anti-folate, such as, e.g., pralatrexate; a farnesyl transferase inhibitor, such as, e.g., tipifarnib; an antibody or a biologic agent, such as, e.g., alemtuzumab, rituximab, ofatumumab, or brentuximab vedotin (SGN-035); an antibody-drug conjugate, such as, e.g., inotuzumab ozogamicin, or brentuximab vedotin; a cytotoxic agent, such as, e.g., bendamustine, gemcitabine, oxaliplatin, cyclophosphamide, vincristine, vinblastine, anthracycline (e.g., daunorubicin or daunomycin, doxorubicin, or actinomycin or dactinomycin), bleomycin, clofarabine, nelarabine, cladribine, asparaginase, methotrexate, or pralatrexate; or other anti-cancer agents or chemotherapeutic agents, such as, e.g., fludarabine, ibrutinib, fostamatinib, lenalidomide, thalidomide, rituximab, cyclophosphamide, doxorubicin, vincristine, prednisone, or R—CHOP (Rituximab, Cyclophosphamide, Doxorubicin or Hydroxydaunomycin, Vincristine or Oncovin, Prednisone). Additional embodiments of second active agents are provided herein elsewhere.

Without being limited by a particular theory, in one embodiment, the cancer or disease being treated or prevented, such as a blood disorder or hematologic malignancy, has a high expression level of one or more PI3K isoform(s) (e.g., PI3K-α, PI3K-β, PI3K-δ, or PI3K-γ, or a combination thereof). In one embodiment, the cancer or disease that can be treated or prevented by methods, compositions, or kits provided herein includes a blood disorder or a hematologic malignancy, including, but not limited to, myeloid disorder, lymphoid disorder, leukemia, lymphoma, myelodysplastic syndrome (MDS), myeloproliferative disease (MPD), mast cell disorder, and myeloma (e.g., multiple myeloma), among others. In one embodiment, the blood disorder or the hematologic malignancy includes, but is not limited to, acute lymphoblastic leukemia (ALL), T-cell ALL (T-ALL), B-cell ALL (B-ALL), acute myeloid leukemia (AML), chronic lymphocytic leukemia (CLL), chronic myelogenous leukemia (CML), blast phase CML, small lymphocytic lymphoma (SLL), CLL/SLL, Hodgkin lymphoma (HL), non-Hodgkin lymphoma (NHL), B-cell NHL, T-cell NHL, indolent NHL (iNHL), diffuse large B-cell lymphoma (DLBCL), mantle cell lymphoma (MCL), aggressive B-cell NHL, B-cell lymphoma (BCL), Richter's syndrome (RS), T-cell lymphoma (TCL), peripheral T-cell lymphoma (PTCL), cutaneous T-cell lymphoma (CTCL), transformed mycosis fungoides, Sézary syndrome, anaplastic large-cell lymphoma (ALCL), follicular lymphoma (FL), Waldenström macroglobulinemia (WM), lymphoplasmacytic lymphoma, Burkitt lymphoma, multiple myeloma (MM), amyloidosis, MPD, essential thrombocytosis (ET), myelofibrosis (MF), polycythemia vera (PV), chronic myelomonocytic leukemia (CMML), myelodysplastic syndrome (MDS), high-risk MDS, and low-risk MDS. In one embodiment, the hematologic malignancy is relapsed. In one embodiment, the hematologic malignancy is refractory. In one embodiment, the cancer or disease is in a pediatric patient (including an infantile patient). In one embodiment, the cancer or disease is in an adult patient. Additional embodiments of a cancer or disease being treated or prevented by methods, compositions, or kits provided herein are described herein elsewhere.

In one embodiment, the cancer or disease being treated or prevented, such as a blood disorder or hematologic malignancy, has a high expression level of PI3K-δ and/or PI3K-γ, which includes, but is not limited to, CLL, CLL/SLL, blast phase CLL, CML, DLBCL, MCL, B-ALL, T-ALL, multiple myeloma, B-cell lymphoma, CTCL (e.g., mycosis fungoides or Sézary syndrome), AML, Burkitt lymphoma, follicular lymphoma (FL), Hodgkin lymphoma, ALCL, or MDS.

In one embodiment, provided herein is a PI3K modulator, as a single agent or in combination with one or more additional therapies, for use in a method, composition, or kit provided herein, to ameliorate cancer or hematologic disease, such as a hematologic malignancy (e.g., by decreasing one or more symptoms associated with the cancer or hematologic disease) in a subject, e.g., a mammalian subject. Symptoms of cancer or hematologic disease that can be ameliorated include any one or combination of symptoms of cancer or hematologic disease, as known the art and/or as disclosed herein. Experimental conditions for evaluating the effects of a PI3K modulator in ameliorating cancer or hematologic disease in animal models of cancer or hematologic disease are provided herein or are known in the art.

In one embodiment, provided herein is a method of reducing a symptom associated with cancer or hematologic disease, such as a hematologic malignancy, in a biological sample, comprising contacting the biological sample with a PI3K modulator, e.g., a compound provided herein (e.g., a compound of Formula I, e.g., Compound 292) or a pharmaceutically acceptable form thereof (e.g., an enantiomer or a mixture of enantiomers thereof, or a pharmaceutically acceptable salt, solvate, hydrate, co-crystal, clathrate, or polymorph thereof), in an amount sufficient to reduce the symptom associated with cancer or hematologic disease.

In one embodiment, provided herein is a method of treating or preventing cancer or hematologic disease (e.g., a hematologic malignancy) in a subject, comprising administering an effective amount of a PI3K modulator, e.g., a compound provided herein (e.g., a compound of Formula I, e.g., Compound 292), or an enantiomer or a mixture of enantiomers thereof, or a pharmaceutically acceptable salt, solvate, hydrate, co-crystal, clathrate, or polymorph thereof.

In one embodiment, the compound is a compound of Formula I, or an enantiomer or a mixture of enantiomers thereof, or a pharmaceutically acceptable salt, solvate, hydrate, co-crystal, clathrate, or polymorph thereof:

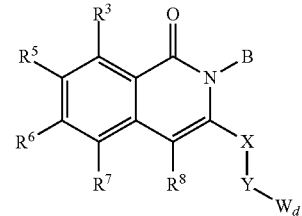

Formula I wherein
$W_d$ is heterocycloalkyl, aryl or heteroaryl;
B is alkyl or a moiety of Formula II;

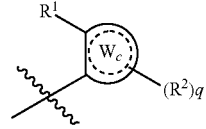

Formula II wherein $W_c$ is aryl, heteroaryl, heterocycloalkyl, or cycloalkyl, and q is an integer of 0, 1, 2, 3, or 4;

X is absent or —(CH($R^9$))$_z$—, and z is an integer of 1;

Y is absent, or —N($R^9$)—;

$R^1$ is hydrogen, alkyl, alkenyl, alkynyl, alkoxy, amido, alkoxycarbonyl, sulfonamido, halo, cyano, or nitro;

$R^2$ is alkyl, alkenyl, alkynyl, cycloalkyl, heterocycloalkyl, aryl, heteroaryl, heteroarylalkyl, alkoxy, amino, halo, cyano, hydroxy, or nitro;

$R^3$ is hydrogen, alkyl, alkenyl, alkynyl, cycloalkyl, heterocycloalkyl, alkoxy, amido, amino, alkoxycarbonyl sulfonamido, halo, cyano, hydroxy, or nitro;

$R^5$, $R^6$, $R^7$, and $R^8$ are each independently hydrogen, alkyl, alkenyl, alkynyl, cycloalkyl, heterocycloalkyl, alkoxy, amido, amino, acyl, acyloxy, sulfonamido, halo, cyano, hydroxy, or nitro; and each instance of $R^9$ is independently hydrogen, alkyl, cycloalkyl, or heterocycloalkyl.

In some embodiments, when both X and Y are present then Y is —NH—.

In some embodiments, X is absent or is —(CH($R^9$))$_z$—, and z is independently an integer of 1, 2, 3, or 4; and Y is absent, —O—, —S—, —S(=O)—, —S(=O)$_2$—, —N($R^9$)—, —C(=O)—(CHR$^9$)$_z$—, —C(=O)—, —N($R^9$)(C=O)—, —N($R^9$)(C=O)NH—, or —N($R^9$)C($R^9$)$_2$—.

In some embodiments, —X— is —CH$_2$—, —CH(CH$_2$CH$_3$)—, or —CH(CH$_3$)—.

In some embodiments, —X—Y— is —CH$_2$—N(CH$_3$)—, —CH$_2$—N(CH$_2$CH$_3$)—, —CH(CH$_2$CH$_3$)—NH—, or —CH(CH$_3$)—NH—.

In some embodiments, $W_d$ is a pyrazolopyrimidine of Formula III(a), or a purine of Formula III(b), Formula III(c) or Formula III(d):

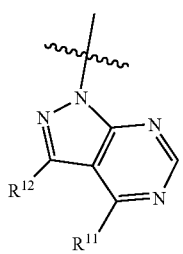

Formula III(a)

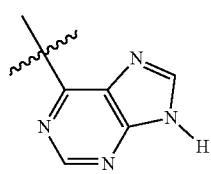

Formula III(b)

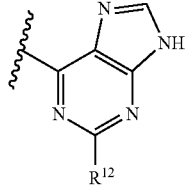

Formula III(c)

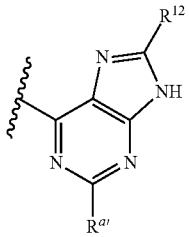

Formula III(d)

wherein $R^{a'}$ of Formula III(d) is hydrogen, halo, phosphate, urea, a carbonate, amino, alkyl, alkenyl, alkynyl, cycloalkyl, heteroalkyl, or heterocycloalkyl; $R^{11}$ of Formula III(a) is H, alkyl, halo, amino, amido, hydroxy, or alkoxy; and $R^{12}$ of Formula III(a), Formula III(c) or Formula III(d) is H, alkyl, alkynyl, alkenyl, halo, aryl, heteroaryl, heterocycloalkyl, or cycloalkyl. In some embodiments, $W_d$ is a pyrazolopyrimidine of Formula III(a), wherein $R^{11}$ is H, alkyl, halo, amino, amido, hydroxy, or alkoxy, and $R^{12}$ is cyano, amino, carboxylic acid, or amido.

In some embodiments, a compound of Formula I has the structure of Formula IV:

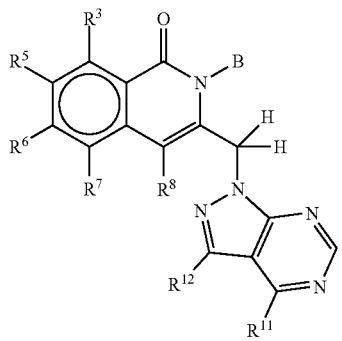

Formula IV wherein $R^{11}$ is H, alkyl, halo, amino, amido, hydroxy, or alkoxy, and $R^{12}$ is H, alkyl, alkynyl, alkenyl, halo, aryl, heteroaryl, heterocycloalkyl, or cycloalkyl. In some embodiments, the compound of Formula I has the structure of Formula IV wherein $R^{11}$ is H, alkyl, halo, amino, amido, hydroxy, or alkoxy, and $R^{12}$ is cyano, amino, carboxylic acid, or amido.

In some embodiments, $R^{11}$ is amino. In some embodiments, $R^{12}$ is alkyl, alkenyl, alkynyl, heteroaryl, aryl, or heterocycloalkyl. In some embodiments, $R^{12}$ is cyano, amino, carboxylic acid, amido, monocyclic heteroaryl, or bicyclic heteroaryl.

In some embodiments of a compound of Formula I, the compound has the structure of Formula V:

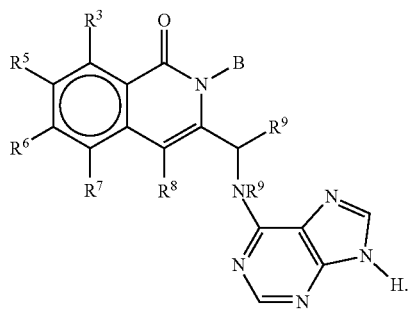

Formula V

In some embodiments, —NR$^9$— is —N(CH$_2$CH$_3$)CH$_2$— or —N(CH$_3$)CH$_2$—.

In some embodiments of a compound of Formula I, the compound has a structure of Formula VI:

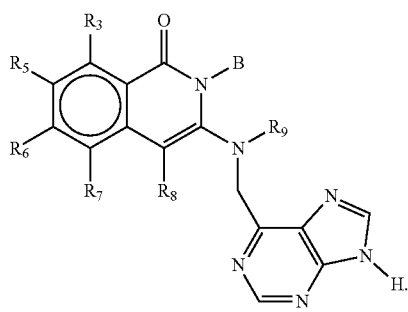

Formula VI

In some embodiments, R$^3$ is —H, —CH$_3$, —Cl, or —F, and R$^5$, R$^6$, R$^7$, and R$^8$ are independently hydrogen.

In some embodiments, B is a moiety of Formula II;

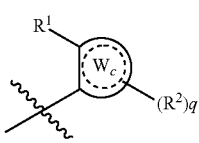

Formula II wherein W$_c$ is aryl, heteroaryl, heterocycloalkyl, or cycloalkyl, and q is an integer of 0, 1, 2, 3, or 4.

In one embodiment, the PI3 kinase modulator is a compound, or a pharmaceutically acceptable salt thereof, having the structure of Formula I-1:

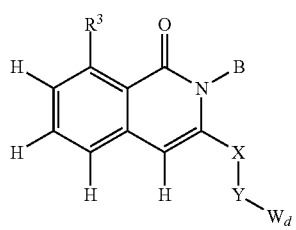

Formula I-1 wherein B is a moiety of Formula II;
wherein W$_c$ in B is aryl, heteroaryl, heterocycloalkyl, or cycloalkyl, and q is an integer of 0, 1, 2, 3, or 4;

X is absent or —(CH(R$^9$))$_z$—, and z is an integer of 1;
Y is absent, or —N(R$^9$)—;
when Y is absent, W$_d$ is:

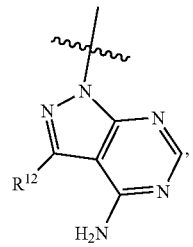

or when Y is present, W$_d$ is:

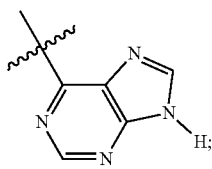

R$^1$ is hydrogen, alkyl, alkenyl, alkynyl, alkoxy, amido, alkoxycarbonyl, sulfonamido, halo, cyano, or nitro;

R$^2$ is alkyl, alkenyl, alkynyl, cycloalkyl, heterocycloalkyl, aryl, heteroaryl, heteroarylalkyl, alkoxy, amino, halo, cyano, hydroxy, or nitro;

R$^3$ is hydrogen, alkyl, alkenyl, alkynyl, cycloalkyl, heterocycloalkyl, alkoxy, amido, amino, alkoxycarbonyl sulfonamido, halo, cyano, hydroxy, or nitro;

each instance of R$^9$ is independently hydrogen, C$_1$-C$_{10}$ alkyl, cycloalkyl, or heterocycloalkyl; and R$^{12}$ is H, alkyl, alkynyl, alkenyl, halo, aryl, heteroaryl, heterocycloalkyl, or cycloalkyl.

In some embodiments, a compound of Formula I or Formula I-1 has the structure of Formula IV-A:

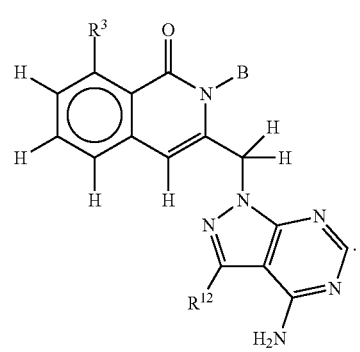

Formula IV-A

In some embodiments, R$^{12}$ is substituted benzoxazole.

In some embodiments, a compound of Formula I or Formula I-1 has the structure of Formula V-A:

Formula V-A

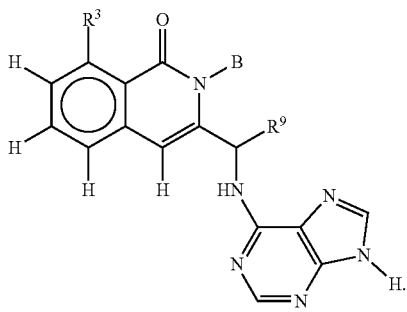

In some embodiments, a compound of Formula I or Formula I-1 has the structure of Formula IV-A or Formula V-A.

In some embodiments, a compound of Formula I or Formula I-1 has the structure of Formula V-B:

Formula V-B

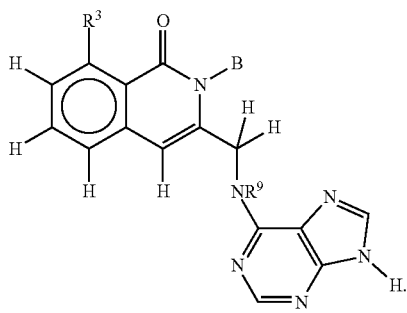

In some embodiments, a compound of Formula I or Formula I-1 has the structure of Formula VI-A:

Formula VI-A

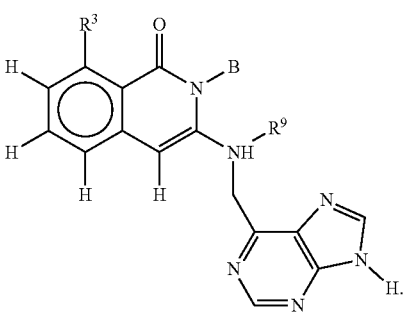

In some embodiments, a compound of Formula I or Formula I-1 is a compound wherein B is a moiety of Formula II:

Formula II

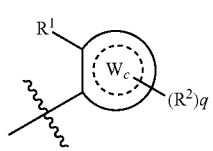

wherein $W_c$ is aryl, heteroaryl, heterocycloalkyl, or cycloalkyl; q is an integer of 0 or 1; $R^1$ is hydrogen, alkyl, or halo; $R^2$ is alkyl or halo; and $R^3$ is hydrogen, alkyl, or halo. In some embodiments, when both X and Y are present then Y is —NH—. In other embodiments, $R^3$ is —H, —CH$_3$, —CH$_2$CH$_3$, —CF$_3$, —Cl or —F. In other embodiments, $R^3$ is methyl or chloro.

In some embodiments, X is —(CH($R^9$))$_z$—, wherein $R^9$ is methyl and z is 1; and $W_d$ is

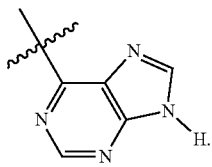

In some embodiments of a compound of Formula I or Formula I-1, the compound is predominately in an (S)-stereochemical configuration.

In some embodiments of a compound of Formula I or Formula I-1, the compound has a structure of Formula V-A2:

Formula V-A2

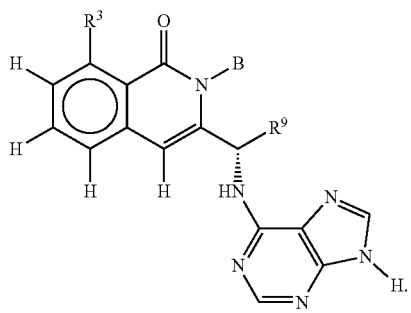

In some embodiments, $R^{12}$ is a monocyclic heteroaryl, bicyclic heteroaryl, or heterocycloalkyl.

In some embodiments, B is a moiety of Formula II:

Formula II

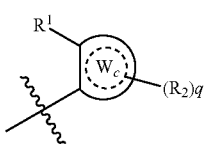

wherein $W_c$ is aryl or cycloalkyl.

In some embodiments, the compound of Formula I is a polymorph Form C of Compound 292 as disclosed herein.

In some embodiments, the compound inhibits or reduces the activity of a class I PI3K. In certain embodiments, the class I PI3K is p110 α, p110 β, p110 γ, or p110 δ.

In some embodiments, the compound inhibits one or more class I PI3K isoforms selected from the group consisting of PI3 kinase-α, PI3 kinase-β, PI3 kinase-γ, and PI3 kinase-δ.

In some embodiments, the compound selectively inhibits a class I PI3 kinase-δ isoform, as compared with other class I PI3 kinase isoforms. In some embodiments, the compound selectively inhibits a class I PI3 kinase-γ isoform, as compared with other class I PI3 kinase isoforms. In some embodiments, the compound selectively inhibits a class I PI3 kinase-δ and a PI3 kinase-γ isoform, as compared with other class I PI3 kinase isoforms.

In some embodiments, a pharmaceutical composition is used, wherein the composition comprises a pharmaceutically acceptable excipient and one or more compounds of any formulae provided herein, including but not limited to Formula I, I-1, and IV to XVIII (including IV-A, V, V-A, V-A2, V-B, VI, and VI-A, among others). In some embodiments, the composition is a liquid, solid, semi-solid, gel, or an aerosol form.

In some embodiments, two or more PI3K modulators (e.g., two or more PI3K modulators described herein) are administered in combination. In one embodiment, the PI3K modulators are administered concurrently. In another embodiment the modulators are administered sequentially. For example, a combination of e.g., Compound 292 and a second PI3K modulator, can be administered concurrently or sequentially. In one embodiment, the second PI3K modulator, is administered first, followed, with or without a period of overlap, by administration of Compound 292. In another embodiment, Compound 292 is administered first, followed, with or without a period of overlap, by administration of the second PI3K modulator.

In other embodiments, a PI3K modulator (e.g., one or more PI3K modulators described herein) are administered in combination with one or more than one additional therapeutic agent, such as a cancer therapeutic agent described herein. In one embodiment, the PI3K modulator and the second agent are administered concurrently. In another embodiment the PI3K modulator and the second agent are administered sequentially. For example, a combination of e.g., Compound 292 and a second agent, can be administered concurrently or sequentially. In one embodiment, the second agent, is administered first, followed, with or without a period of overlap, by administration of Compound 292. In another embodiment, Compound 292 is administered first, followed, with or without a period of overlap, by administration of the second agent.

In one embodiment, the subject treated is a mammal, e.g., a primate, typically a human (e.g., a patient having, or at risk of having, cancer or hematologic disorder, such as hematologic malignancy, as described herein). In some embodiments, the subject treated is in need of PI3 kinase inhibition (e.g., has been evaluated to show elevated PI3K levels or alterations in another component of the PI3K pathway). In one embodiment, the subject previously received other treatment (e.g., a treatment for cancer or a treatment for hematologic disorder).

In some embodiments, the PI3K modulator is administered as a pharmaceutical composition comprising the PI3K modulator, or a pharmaceutically acceptable salt thereof, and a pharmaceutically acceptable excipient.

In certain embodiments, the PI3K modulator is administered or is present in the composition, e.g., the pharmaceutical composition.

The PI3K modulators described herein can be administered to the subject systemically (e.g., orally, parenterally, subcutaneously, intravenously, rectally, intramuscularly, intraperitoneally, intranasally, transdermally, or by inhalation or intracavitary installation). Typically, the PI3K modulators are administered orally.

In one embodiment, the PI3K modulator is Compound 292, as disclosed in Table 4, or a pharmaceutically acceptable salt thereof. Compound 292, or a pharmaceutically acceptable salt thereof, can be administered orally. Other routes of administration are also provided herein.

The methods and compositions provided herein can, optionally, be used in combination with other therapies (e.g., one or more agents, surgical procedures, or radiation procedures). Any combination of one or more PI3K modulator (s) and one or more other agents or therapies can be used. The PI3K modulator(s) and other therapies can be administered before treatment, concurrently with treatment, post-treatment, or during remission of the disease. In one embodiment, a second agent is administered simultaneously or sequentially with the PI3K modulator.

In one embodiment, provided herein is a biomarker (e.g., a diagnostic biomarker, a predictive biomarker, or a prognostic biomarker), for use in treating or preventing a cancer or disease (e.g., a hematologic malignancy) described herein. In one embodiment, the biomarker provided herein include, but are not limited to: a target biomarker, a signaling pathway biomarker, a protein mutation biomarker, a protein expression biomarker, a gene mutation biomarker, a gene expression biomarker, a cytokine biomarker, a chemokine biomarker, or a biomarker for particular cancer cells. In one embodiment, the biomarker can be used to evaluate a particular type of cancer or disease, or a particular patient or group of patients. In one embodiment, the biomarker involves immunohistochemistry (IHC) of a particular protein target. In one embodiment, the biomarker involves the RNA (e.g., mRNA) (e.g., in situ hybridization (ISH) of mRNA) of a particular protein target. In one embodiment, the biomarker involves the DNA of a particular protein target, including genetic alteration such as somatic mutation, copy number alterations such as amplification or deletion, and chromosomal translocation as well as epigenetic alteration such as methylation and histone modification. In one embodiment, the biomarker involves micro-RNA (miRNA) which regulates expression of a particular protein target. In one embodiment, the biomarker involves measurement of a protein/protein modification. In one embodiment, the biomarker involves measurement of a non-protein marker, such as, e.g., metabolomics. In one embodiment, the biomarker is measured by ELISA, western blot, or mass spectroscopy. In one embodiment, the biomarker is a serum biomarker. In one embodiment, the biomarker is a blood biomarker. In one embodiment, the biomarker is a bone marrow biomarker. In one embodiment, the biomarker is a sputum biomarker. In one embodiment, the biomarker is a urine biomarker. In one embodiment, the biomarker involves bio-matrixes, including, but not limited to, serum, blood, bone marrow, sputum, or urine.

In exemplary embodiments, the biomarker provided herein is a target biomarker, such as, e.g., a biomarker to determine the protein and/or RNA expression of one or more particular PI3K isoform; e.g., a biomarker for PI3K-α expression, for PI3K-β expression, for PI3K-δ expression, or for PI3K-γ expression, or combinations thereof. In other embodiments, the biomarker could be DNA alteration of one or more particular PI3K isoforms (e.g., mutation, copy number variation, or epigenetic modification).

In exemplary embodiments, the biomarker provided herein is a signaling pathway biomarker, such as, e.g., a PTEN pathway biomarker and/or a biomarker of signaling pathway activation such as pAKT, pS6, and/or pPRAS40 (e.g., an IHC biomarker, a DNA alteration biomarker, a DNA deletion biomarker, or a DNA mutation biomarker). In exemplary embodiments, the biomarker provided herein is a mutation biomarker, such as, a protein mutation biomarker or a gene mutation biomarker, to assess the mutation of one or more targets, such as, e.g., IGH7, KRAS, NRAS, A20, CARD11, CD79B, TP53, CARD11, MYD88, GNA13, MEF2B, TNFRSF14, MLL2, BTG1, EZH2, NOTCH1, JAK1, JAK2, PTEN, FBW7, PHF6, IDH1, IDH2, TET2, FLT3, KIT, NPM1, CEBPA, DNMT3A, BAALC, RUNX1, ASXL1, IRF8, POU2F2, WIF1, ARID1A, MEF2B, TNFAIP3, PIK3R1, MTOR, PIK3CA, PI3Kδ, and/or PI3Kγ. In exemplary embodiments, the biomarker provided herein is an expression biomarker, such as, a protein expression biomarker, a gene expression biomarker, to assess the expression of one or more targets, or the upregulation or downregulation of a pathway, such as, e.g., pERK IHC biomarker or pERK expression biomarker, for example, to assess RAS or PI3K pathway activation.

In exemplary embodiments, the biomarker provided herein is a cytokine biomarker (e.g., serum cytokine biomarkers or other cytokine biomarkers provided herein). In exemplary embodiments, the biomarker provided herein is a chemokine biomarker (e.g., serum chemokine biomarkers or other chemokine biomarkers provided herein).

In exemplary embodiments, the biomarker provided herein is a biomarker for cancer cells (e.g., a particular cancer cell line, a particular cancer cell type, a particular cell cycle profile).

In exemplary embodiments, the biomarker provided herein relates to gene expression profiling of a patient or group of patients, e.g., as a predictive biomarker for PI3Kδ and/or PI3Kγ pathway activation, or as a predictive biomarker for response to a treatment described herein. In exemplary embodiments, the biomarker provided herein relates to a gene expression classifier, e.g., as a predictive biomarker for PI3Kδ and/or PI3Kγ expression or activation (e.g., differential expression or activation in the ABC, GCB, oxidative phosphorylation (Ox Phos), B-cell receptor/proliferation (BCR), or host response (HR) subtypes of DLBCL).

In one embodiment, the methods provided herein can further include the step of evaluating a subject, e.g., for one or more signs or symptoms or biological concomitants of cancer or hematologic disorder, as disclosed herein, e.g., evaluate a biomarker described herein in the subject. In some embodiments, one or more of these biological concomitants or biomarkers correlate with improved likelihood of response of a subject to a particular therapy. In some embodiments, one or more of these biological concomitants or biomarkers correlate with reduced side effect in a subject to a particular therapy.

In one embodiment, the methods provided herein can further include the step of monitoring the subject, e.g., for a change (e.g., an increase or decrease) in levels of one or more signs or symptoms or biological concomitants of cancer or hematologic disorder, as disclosed herein, e.g., a biomarker described herein. In some embodiments, one or more of these biological concomitants or biomarkers correlate with a decrease in one or more clinical symptoms associated with cancer or hematologic disorder. In some embodiments, one or more of these biological concomitants or biomarkers correlate with improved likelihood of response in a subject to a particular therapy. In some embodiments, one or more of these biological concomitants or biomarkers correlate with reduced side effect in a subject to a particular therapy.

In some embodiments, a normalization or change (e.g., a decrease in an elevated level or increase in a diminished level) of a biological concomitant or biomarker is indicative of treatment efficacy and/or is predictive of improvement in clinical symptoms. In some embodiments, the subject is monitored for a change in a biological concomitant or biomarker (e.g., a decrease or increase of a biological concomitant or biomarker, which can be indicative of treatment efficacy).

In one embodiment, the subject can be evaluated or monitored in one or more of the following periods: prior to beginning of treatment; during the treatment; or after one or more elements of the treatment have been administered. Evaluation and monitoring can be used to determine the need for further treatment with the same PI3K modulator, alone or in combination with, another agent, or for additional treatment with additional agents, or for adjusted dosing regimen of the same PI3K modulator.

In one embodiment, the methods provided herein can further include the step of analyzing a nucleic acid or protein from the subject, e.g., analyzing the genotype of the subject. In one embodiment, a PI3K protein, or a nucleic acid encoding a PI3K protein, and/or an upstream or downstream component(s) of a PI3K signaling pathway is analyzed. The nucleic acid or protein can be detected in any biological sample (e.g., blood, urine, circulating cells, a tissue biopsy or a bone marrow biopsy) using any method disclosed herein or known in the art. For example, the PI3K protein can be detected by systemic administration of a labeled form of an antibody to PI3K followed by imaging.

The analysis can be used, e.g., to evaluate the suitability of, or to choose between alternative treatments, e.g., a particular dosage, mode of delivery, time of delivery, inclusion of adjunctive therapy, e.g., administration in combination with a second agent, or generally to determine the subject's probable drug response phenotype or genotype. The nucleic acid or protein can be analyzed at any stage of treatment. In one embodiment, the nucleic acid or protein can be analyzed at least prior to administration of the PI3K modulator and/or agent, to thereby determine appropriate dosage(s) and treatment regimen(s) of the PI3K modulator (e.g., amount per treatment or frequency of treatments) for prophylactic or therapeutic treatment of the subject.

In certain embodiments, the methods provided herein further include the step of detecting an altered PI3K level in a patient, prior to, or after, administering a PI3K modulator to the patient. The PI3K level can be assessed in any biological sample, e.g., blood, urine, circulating cells, or a tissue biopsy. In some embodiments, the PI3K level is assessed by systemic administration of a labeled form of an antibody to PI3K followed by imaging.

In another embodiment, provided herein is a composition, e.g., a pharmaceutical composition, that includes one or more PI3K modulators, e.g., a PI3K modulator as described herein, and one or more agents (e.g., a second active agent as disclosed herein). The composition can further include a pharmaceutically-acceptable carrier or excipient.

In another embodiment, provided herein is a composition for use, or the use, of a PI3K modulator, alone or in combination with a second agent or a therapeutic modality described herein for the treatment of a cancer or disorder, such as a hematologic malignancy, as described herein.

In another embodiment, provided herein are therapeutic kits that include a PI3K modulator, alone or in combination with one or more additional agents, and instructions for use in the treatment of a cancer or disorder, such as a hematologic malignancy, as described herein.

INCORPORATION BY REFERENCE

All publications, patents, and patent applications mentioned in this specification are herein incorporated by reference in their entirety and to the same extent as if each

BRIEF DESCRIPTION OF THE DRAWINGS

FIG. 9A depicts PET/CT scans of a T-cell lymphoma patient before therapy with compound 292

FIG. 9B depicts PET/CT scans of a T-cell lymphoma patient after two cycles of Therapy with Compound 292.

FIG. 20 depicts the effects of Compound 292 treatment on serum concentration of MMP9 in some non-CLL/iNHL patients.

FIG. 27A depicts decrease in levels of lymphoma biomarkers in serum at various time points following 28 day cycles, 25 mg BID administration of Compound 292.

FIG. 27B depicts decrease in levels of iNHL biomarkers in serum at various time points following 28 day cycles, 25 mg BID administration of Compound 292.

FIG. 37C depicts reduction in CD69 positive circulating CLL cells in CLL patients treated by 25 mg BID Compound 292.

FIG. 37D depicts reduction in CD38/CD69 double positive circulating CLL cells in CLL patients treated by 25 mg BID Compound 292.

DETAILED DESCRIPTION

Figure 1:
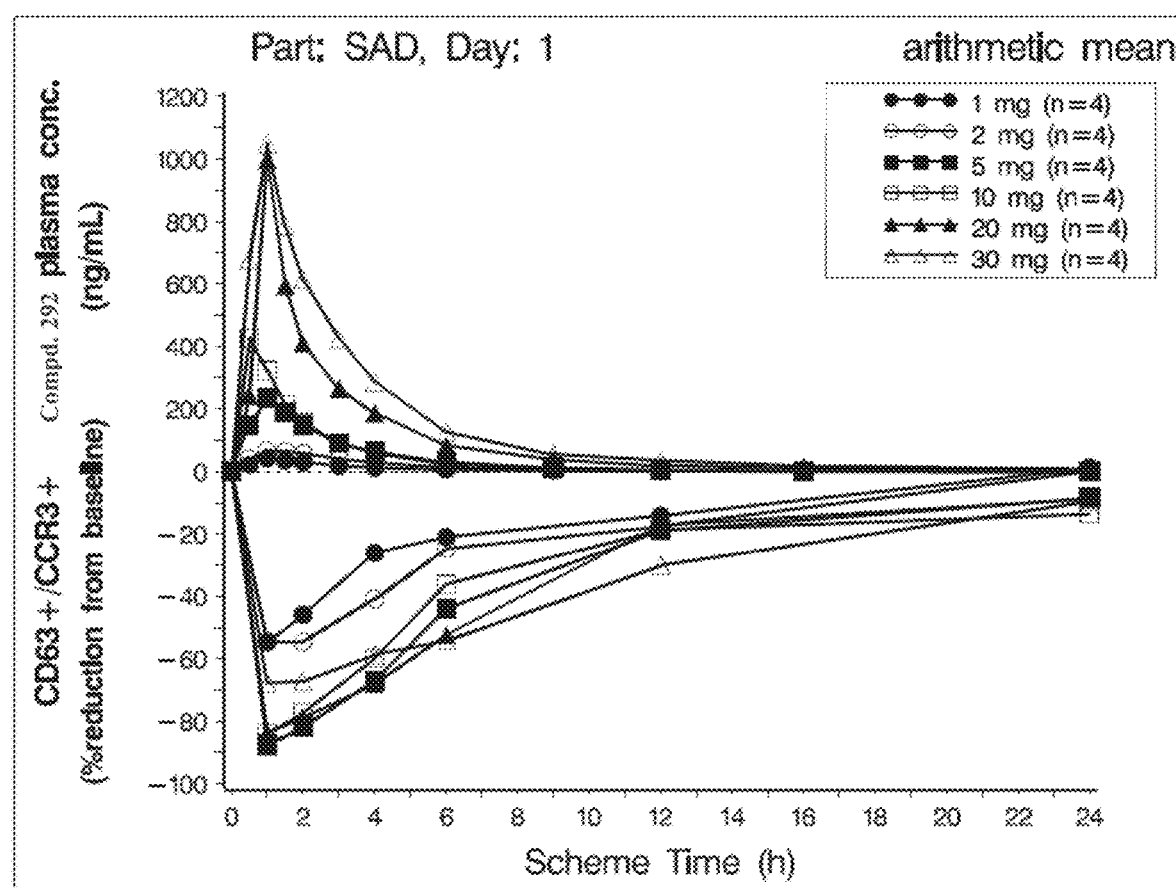
FIG. 1 depicts the PK/PD relationship of mean drug plasma concentration and mean % reduction from pre-dose for basophil activation over time, following single dose administration of Compound 292 in human.

While specific embodiments have been discussed, the specification is illustrative only and not restrictive. Many variations of this disclosure will become apparent to those skilled in the art upon review of this specification.

Unless defined otherwise, all technical and scientific terms used herein have the same meaning as is commonly understood by one of skill in the art. All patents and publications referred to herein are incorporated by reference.

As used in the specification and claims, the singular form "a", "an" and "the" includes plural references unless the context clearly dictates otherwise.

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

As used herein, the term "patient" or "subject" refers to an animal, typically a human (e.g., a male or female of any age group, e.g., a pediatric patient (e.g., infant, child, adolescent) or adult patient (e.g., young adult, middle-aged adult or senior adult) or other mammal, such as a primate (e.g., cynomolgus monkey, rhesus monkey); other mammals such as rodents (mice, rats), cattle, pigs, horses, sheep, goats, cats, dogs; and/or birds, that will be or has been the object of treatment, observation, and/or experiment. When the term is used in conjunction with administration of a compound or drug, then the patient has been the object of treatment, observation, and/or administration of the compound or drug.

A "therapeutic effect," as that term is used herein, encompasses a therapeutic benefit and/or a prophylactic benefit as described herein. A prophylactic effect includes delaying or eliminating the appearance of a disease or condition, delaying or eliminating the onset of symptoms of a disease or condition, slowing, halting, or reversing the progression of a disease or condition, or any combination thereof.

The term "effective amount" refers to that amount of a compound or pharmaceutical composition described herein that is sufficient to effect the intended application including, but not limited to, disease treatment, as illustrated below. An effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells. The specific dose will vary depending on, for example, the particular compounds chosen, the dosing regimen to be followed, whether it is administered in combination with other agents, timing of administration, the tissue to which it is administered, and the physical delivery system in which it is carried.

As used herein, the terms "treatment", "treating", "palliating" and "ameliorating" are used interchangeably herein. These terms refer to an approach for obtaining beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compositions can be administered to a patient at risk of developing a particular disease, or to a patient reporting one or more of the physiological symptoms of a disease, even though a diagnosis of this disease may not have been made. In one embodiment, these terms also refer to partially or completely inhibiting or reducing the condition from which the subject is suffering. In one embodiment, these terms refer to an action that occurs while a patient is suffering from, or is diagnosed with, the condition, which reduces the severity of the condition, or retards or slows the progression of the condition. Treatment need not result in a complete cure of the condition; partial inhibition or reduction of the condition is encompassed by this term. Treatment is intended to encompass prevention or prophylaxis.

"Therapeutically effective amount," as used herein, refers to a minimal amount or concentration of a compound, such as aPI3K modulator, that, when administered alone or in combination, is sufficient to provide a therapeutic benefit in the treatment of the condition, or to delay or minimize one or more symptoms associated with the condition. The term "therapeutically effective amount" can encompass an amount that improves overall therapy, reduces or avoids symptoms or causes of the condition, or enhances the therapeutic efficacy of another therapeutic agent. The therapeutic amount need not result in a complete cure of the condition; partial inhibition or reduction of the condition is encompassed by this term. The therapeutically effective amount can also encompass a prophylactically effective amount.

As used herein, unless otherwise specified, the terms "prevent," "preventing" and "prevention" refers to an action that occurs before the subject begins to suffer from the condition, or relapse of the condition. The prevention need not result in a complete prevention of the condition; partial prevention or reduction of the condition or a symptom of the condition, or reduction of the risk of developing the condition, is encompassed by this term.

As used herein, unless otherwise specified, a "prophylactically effective amount" of a compound, such as a PI3K modulator, that, when administered alone or in combination, prevents or reduces the risk of developing the condition, or one or more symptoms associated with the condition, or prevents its recurrence. The term "prophylactically effective amount" can encompass an amount that improves overall prophylaxis or enhances the prophylactic efficacy of another prophylactic agent. The prophylactic amount need not result in a complete prevention of the condition; partial prevention or reduction of the condition is encompassed by this term.

As used herein, to "decrease", "ameliorate," "reduce," "treat" (or the like) a condition or symptoms associated with the condition includes reducing the severity and/or frequency of symptoms of the condition, as well as preventing the condition and/or symptoms of the condition (e.g., by reducing the severity and/or frequency of flares of symptoms). In some embodiments, the symptom is reduced by at least 10%, at least 20%, at least 30%, at least 40%, at least 50%, at least 60%, at least 70%, at least 80%, at least 90%, or at least 95% relative to a control level. The control level includes any appropriate control as known in the art. For example, the control level can be the pre-treatment level in the sample or subject treated, or it can be the level in a control population (e.g., the level in subjects who do not have the condition or the level in samples derived from subjects who do not have the condition). In some embodiments, the decrease is statistically significant, for example, as assessed using an appropriate parametric or non-parametric statistical comparison.

As used herein, "agent" or "biologically active agent" or "second active agent" refers to a biological, pharmaceutical, or chemical compound or other moiety. Non-limiting examples include simple or complex organic or inorganic molecules, a peptide, a protein, an oligonucleotide, an antibody, an antibody derivative, an antibody fragment, a vitamin, a vitamin derivative, a carbohydrate, a toxin, or a chemotherapeutic compound, and metabolites thereof. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of this disclosure.

The term "agonist" as used herein refers to a compound or agent having the ability to initiate or enhance a biological function of a target protein or polypeptide, such as increasing the activity or expression of the target protein or polypeptide. Accordingly, the term "agonist" is defined in the context of the biological role of the target protein or polypeptide. While some agonists herein specifically interact with (e.g., bind to) the target, compounds and/or agents that initiate or enhance a biological activity of the target protein or polypeptide by interacting with other members of the signal transduction pathway of which the target polypeptide is a member are also specifically included within this definition.

The terms "antagonist" and "inhibitor" are used interchangeably, and they refer to a compound or agent having the ability to inhibit a biological function of a target protein or polypeptide, such as by inhibiting the activity or expression of the target protein or polypeptide. Accordingly, the terms "antagonist" and "inhibitor" are defined in the context of the biological role of the target protein or polypeptide. While some antagonists herein specifically interact with (e.g., bind to) the target, compounds that inhibit a biological activity of the target protein or polypeptide by interacting with other members of the signal transduction pathway of which the target protein or polypeptide are also specifically included within this definition. Non-limiting examples of biological activity inhibited by an antagonist include those associated with the development, growth, or spread of a tumor, or an undesired immune response as manifested in autoimmune disease.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, or buccal administration, or inhalation, or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

The term "co-administration," "administered in combination with," and their grammatical equivalents, as used herein, encompass administration of two or more agents to subject so that both agents and/or their metabolites are present in the subject at the same time. Co-administration includes simultaneous administration in separate compositions, administration at different times in separate compositions, or administration in a composition in which both agents are present.

As used herein, unless otherwise specified, a "phosphoinositide 3-kinase (PI3K) modulator" or "PI3K modulator" refers to a modulator of a PI3K, including an inhibitor of PI3K. PI3Ks are members of a unique and conserved family of intracellular lipid kinases that phosphorylate the 3'-OH group on phosphatidylinositols or phosphoinositides. The PI3K family includes kinases with distinct substrate specificities, expression patterns, and modes of regulation (see, e.g., Katso et al., 2001, *Annu. Rev. Cell Dev. Biol.* 17, 615-675; Foster, F. M. et al., 2003, *J Cell Sci* 116, 3037-3040). The class I PI3Ks (e.g., p110 α, p110 β, p110 γ, and p110 δ) are typically activated by tyrosine kinases or G-protein coupled receptors to generate PIP3, which engages downstream mediators such as those in the Akt/PDK1 pathway, mTOR, the Tec family kinases, and the Rho family GTPases. The class II PI3Ks (e.g., PI3K-C2α, PI3K-C2β, PI3K-C2γ) and III PI3Ks (e.g., Vps34) play a key role in intracellular trafficking through the synthesis of PI(3)P and PI(3,4)P2. Specific exemplary PI3K modulators and inhibitors are disclosed herein.

The class I PI3Ks comprise a p110 catalytic subunit and a regulatory adapter subunit. See, e.g., Cantrell, D. A. (2001) *Journal of Cell Science* 114: 1439-1445. Four isoforms of the p110 subunit (including PI3K-α (alpha), PI3K-β (beta), PI3K-γ (gamma), and PI3K-δ (delta) isoforms) have been implicated in various biological functions. Class I PI3Kα is involved, for example, in insulin signaling, and has been found to be mutated in solid tumors. Class I PI3K-β is involved, for example, in platelet activation and insulin signaling. Class I PI3K-γ plays a role in mast cell activation, innate immune function, and immune cell trafficking (chemokines). Class I PI3K-δ is involved, for example, in B-cell and T-cell activation and function and in Fc receptor signaling in mast cells. In some embodiments provided herein, the PI3K modulator is a class I PI3K modulator (e.g., an inhibitor). In some such embodiments, the PI3K modulator inhibits or reduces the activity of a PI3K-α (alpha), a PI3K-β (beta), a PI3K-γ (gamma), or a PI3K-δ (delta) isoform, or a combination thereof.

Downstream mediators of PI3K signal transduction include Akt and mammalian target of rapamycin (mTOR).

Akt possesses a pleckstrin homology (PH) domain that binds PIP3, leading to Akt kinase activation. Akt phosphorylates many substrates and is a central downstream effector of PI3K for diverse cellular responses. One function of Akt is to augment the activity of mTOR, through phosphorylation of TSC2 and other mechanisms. mTOR is a serine-threonine kinase related to the lipid kinases of the PI3K family.

"Signal transduction" is a process during which stimulatory or inhibitory signals are transmitted into and within a cell to elicit an intracellular response. A "modulator" of a signal transduction pathway refers to a compound which modulates the activity of one or more cellular proteins mapped to the same specific signal transduction pathway. A modulator can augment (agonist) or suppress (antagonist) the activity of a signaling molecule.

Unless otherwise specified, the term "selective inhibition" or "selectively inhibit" or "selective toward" as applied to a biologically active agent refers to the agent's ability to selectively reduce the target signaling activity as compared to off-target signaling activity, via direct or interact interaction with the target. For example, a compound that selectively inhibits one isoform of PI3K over another isoform of PI3K has an activity of at least 2× against a first isoform relative to the compound's activity against the second isoform (e.g., at least about 3×, 5×, 10×, 20×, 50×, 100×, 200×, 500×, or 1000×).

The term "in vivo" refers to an event that takes place in a subject's body.

The term "in vitro" refers to an event that takes places outside of a subject's body. For example, an in vitro assay encompasses any assay conducted outside of a subject. In vitro assays encompass cell-based assays in which cells, alive or dead, are employed. In vitro assays also encompass a cell-free assay in which no intact cells are employed "Radiation therapy" means exposing a patient, using routine methods and compositions known to the practitioner, to radiation emitters such as, but not limited to, alpha-particle emitting radionuclides (e.g., actinium and thorium radionuclides), low linear energy transfer (LET) radiation emitters (e.g., beta emitters), conversion electron emitters (e.g., strontium-89 and samarium-153-EDTMP), or high-energy radiation, including without limitation x-rays, gamma rays, and neutrons.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions as disclosed herein is contemplated. Supplementary active ingredients can also be incorporated into the pharmaceutical compositions.

As used herein, a "pharmaceutically acceptable form" of a disclosed compound includes, but is not limited to, pharmaceutically acceptable salts, hydrates, solvates, isomers, prodrugs, and isotopically labeled derivatives of disclosed compounds. In one embodiment, a "pharmaceutically acceptable form" includes, but is not limited to, pharmaceutically acceptable salts, isomers, prodrugs and isotopically labeled derivatives of disclosed compounds.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate. Organic bases from which salts can be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

In certain embodiments, the pharmaceutically acceptable form is a solvate (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or one to about 2, about 3 or about 4, solvent or water molecules. It will be understood that the term "compound" as used herein encompasses the compound and solvates of the compound, as well as mixtures thereof.

In certain embodiments, the pharmaceutically acceptable form is a prodrug. As used herein, the term "prodrug" refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs are typically designed to enhance pharmaceutically and/or pharmacokinetically based properties associated with the parent compound. The prodrug compound often offers advantages of solubility, tissue compatibility or delayed release in a mammalian organism (see, e.g., Bundgard, H., Design of Prodrugs (1985), pp. 7 9, 21 24 (Elsevier, Amsterdam). A discussion of prodrugs is provided in Higuchi, T., et al., "Pro drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. Exemplary advantages of a prodrug can include, but are not limited to, its physical properties, such as enhanced water solubility for parenteral administration at physiological pH compared to the parent compound, or it enhances absorption from the digestive tract, or it can enhance drug stability for long-term storage.

The term "prodrug" is also meant to include any covalently bonded carriers, which release the active compound in vivo when such prodrug is administered to a subject. Prodrugs of an active compound, as described herein, can be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. Other examples of prodrugs include compounds that comprise —NO, —NO$_2$, —ONO, or —ONO$_2$ moieties. Prodrugs can typically be prepared using well-known methods, such as those described in *Burger's Medicinal Chemistry and Drug Discovery*, 172-178, 949-982 (Manfred E. Wolff ed., 5th ed., 1995), and *Design of Prodrugs* (H. Bundgaard ed., Elsevier, New York, 1985).

For example, if a disclosed compound or a pharmaceutically acceptable form of the compound contains a carboxylic acid functional group, a prodrug can comprise a pharmaceutically acceptable ester formed by the replacement of the hydrogen atom of the acid group with a group such as (C$_1$-C$_8$)alkyl, (C$_2$-C$_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—(C$_1$-C$_2$)alkylamino(C$_2$-C$_3$)alkyl (such as β-dimethylaminoethyl), carbamoyl-(C$_1$-C$_2$)alkyl, N,N-di(C$_1$-C$_2$)alkylcarbamoyl-(C$_1$-C2)alkyl and piperidino-, pyrrolidino- or morpholino(C$_2$-C$_3$)alkyl.

Similarly, if a disclosed compound or a pharmaceutically acceptable form of the compound contains an alcohol functional group, a prodrug can be formed by the replacement of the hydrogen atom of the alcohol group with a group such as (C$_1$-C$_6$)alkanoyloxymethyl, 1-((C$_1$-C$_6$)alkanoyloxy) ethyl, 1-methyl-1-((C$_1$-C$_6$)alkanoyloxy)ethyl (C$_1$-C$_6$) alkoxycarbonyloxymethyl, N—(C$_1$-C$_6$)alkoxycarbonylaminomethyl, succinoyl, (C$_1$-C$_6$)alkanoyl, α-amino(C$_1$-C$_4$) alkanoyl, arylacyl and α-aminoacyl, or α-aminoacyl-α-aminoacyl, where each α-aminoacyl group is independently selected from naturally occurring L-amino acids, P(O)(OH)$_2$, —P(O)(O(C$_1$-C$_6$)alkyl)$_2$, and glycosyl (the radical resulting from the removal of a hydroxyl group of the hemiacetal form of a carbohydrate).

If a disclosed compound or a pharmaceutically acceptable form of the compound incorporates an amine functional group, a prodrug can be formed by the replacement of a hydrogen atom in the amine group with a group such as R-carbonyl, RO-carbonyl, NRR'-carbonyl where R and R' are each independently (C$_1$-C$_{10}$)alkyl, (C$_3$-C$_7$)cycloalkyl, benzyl, a natural α-aminoacyl or natural α-aminoacyl-natural α-aminoacyl, —C(OH)C(O)OY$^1$ wherein Y$^1$ is H, (C$_1$-C$_6$)alkyl or benzyl, —C(OY$^2$)Y$^2$ wherein Y$^2$ is (C$_1$-C$_4$) alkyl and Y$^3$ is (C$_1$-C$_6$)alkyl, carboxy(C$_1$-C$_6$)alkyl, amino(C$_1$-C$_4$) alkyl or mono-N— or di-N,N—(C$_1$-C$_6$)alkylaminoalkyl, —C(Y$^4$)Y$^5$ wherein Y$^4$ is H or methyl and Y$^5$ is mono-N— or di-N,N—(C$_1$-C$_6$)alkylamino, morpholino, piperidin-1-yl or pyrrolidin-1-yl.

In certain embodiments, the pharmaceutically acceptable form is an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this disclosure.

In one embodiment, provided herein are various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of the plane of the ring are designated "cis/trans."

"Enantiomers" are a pair of stereoisomers that are non-superimposable mirror images of each other. A mixture of a pair of enantiomers in any proportion can be known as a "racemic" mixture. The term "(±)" is used to designate a racemic mixture where appropriate. "Diastereoisomers" are stereoisomers that have at least two asymmetric atoms, but which are not mirror-images of each other. The absolute stereochemistry can be specified according to the Cahn-Ingold-Prelog R—S system. When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, optically substantially pure forms and intermediate mixtures. Optically active (R)- and (S)-isomers can be prepared, for example, using chiral synthons or chiral reagents, or resolved using conventional techniques.

The "enantiomeric excess" or "% enantiomeric excess" of a composition can be calculated using the equation shown below. In the example shown below, a composition contains 90% of one enantiomer, e.g., an S enantiomer, and 10% of the other enantiomer, e.g., an R enantiomer.

$$ee=(90-10)/100=80\%.$$

Thus, a composition containing 90% of one enantiomer and 10% of the other enantiomer is said to have an enantiomeric excess of 80%. Some compositions described herein contain an enantiomeric excess of at least about 1%, about 5%, about 10%, about 20%, about 30%, about 40%, about 50%, about 75%, about 90%, about 95%, or about 99% of the S enantiomer. In other words, the compositions contain an enantiomeric excess of the S enantiomer over the R enantiomer. In other embodiments, some compositions described herein contain an enantiomeric excess of at least about 1%, about 5%, about 10%, about 20%, about 30%, about 40%, about 50%, about 75%, about 90%, about 95%, or about 99% of the R enantiomer. In other words, the compositions contain an enantiomeric excess of the R enantiomer over the S enantiomer.

For instance, an isomer/enantiomer can, in some embodiments, be provided substantially free of the corresponding enantiomer, and can also be referred to as "optically enriched," "enantiomerically enriched," "enantiomerically pure" and "non-racemic," as used interchangeably herein. These terms refer to compositions in which the amount of one enantiomer is greater than the amount of that one enantiomer in a control mixture of the racemic composition (e.g., greater than 1:1 by weight). For example, an enantiomerically enriched preparation of the S enantiomer, means a preparation of the compound having greater than about 50% by weight of the S enantiomer relative to the total weight of the preparation (e.g., total weight of S and R isomers), such as at least about 75% by weight, further such as at least about 80% by weight. In some embodiments, the enrichment can be much greater than about 80% by weight, providing a "substantially enantiomerically enriched," "substantially enantiomerically pure" or a "substantially non-racemic" preparation, which refers to preparations of compositions which have at least about 85% by weight of one enantiomer relative to the total weight of the preparation, such as at least about 90% by weight, and further such as at least about 95% by weight. In certain embodiments, the compound provided herein is made up of at least about 90% by weight of one enantiomer. In other embodiments, the compound is made up of at least about 95%, about 98%, or about 99% by weight of one enantiomer In some embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, in some embodiments, the compound mixture has an (S)-enantiomeric excess of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, greater than about 96%, greater than about 97%, greater than about 98%, or greater than about 99%. In some embodiments, the compound mixture has an (S)-enantiomeric excess of about 55%, about 60%, about 65%, about 70%, about 75%, about 80%, about 85%, about 90%, about 95%, about 96%, about 9'7%, about 98%, about 99%, or about 99.5%, or more. In some embodiments, the compound mixture has an (S)-enantiomeric excess of about 55% to about 99.5%, about 60% to about 99.5%, about 65% to about 99.5%, about 70% to about 99.5%, about 75% to about 99.5%, about 80% to about 99.5%, about 85% to about 99.5%, about 90% to about 99.5%, about 95% to about 99.5%, about 96% to about 99.5%, about 97% to about 99.5%, about 98% to about 99.5%, or about 99% to about 99.5%, or more than about 99.5%.

In other embodiments, the compound mixture has an (R)-enantiomeric excess of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, greater than about 96%, greater than about 97%, greater than about 98%, or greater than about 99%. In some embodiments, the compound mixture has an (R)-enantiomeric excess of about 55%, about 60%, about 65%, about 70%, about 75%, about 80%, about 85%, about 90%, about 95%, about 96%, about 97%, about 98%, about 99%, or about 99.5%, or more. In some embodiments, the compound mixture has an (R)-enantiomeric excess of about 55% to about 99.5%, about 60% to about 99.5%, about 65% to about 99.5%, about 70% to about 99.5%, about 75% to about 99.5%, about 80% to about 99.5%, about 85% to about 99.5%, about 90% to about 99.5%, about 95% to about 99.5%, about 96% to about 99.5%, about 97% to about 99.5%, about 98% to about 99.5%, or about 99% to about 99.5%, or more than about 99.5%.

In other embodiments, the compound mixture contains identical chemical entities except for their stereochemical orientations, namely (S)- or (R)-isomers. For example, if a compound disclosed herein has —CH(R)— unit, and R is not hydrogen, then the —CH(R)— is in an (S)- or (R)-stereochemical orientation for each of the identical chemical entities (i.e., (S)- or (R)-stereoisomers). In some embodiments, the mixture of identical chemical entities (i.e., mixture of stereoisomers) is a racemic mixture of (S)- and (R)-isomers. In another embodiment, the mixture of the identical chemical entities (i.e., mixture of stereoisomers) contains predominately (S)-isomer or predominately (R)- isomer. For example, in some embodiments, the (S)-isomer in the mixture of identical chemical entities (i.e., mixture of stereoisomers) is present at about 55%, about 60%, about 65%, about 70%, about 75%, about 80%, about 85%, about 90%, about 95%, about 96%, about 97%, about 98%, about 99%, or about 99.5% by weight, or more, relative to the total weight of the mixture of (S)- and (R)-isomers. In some embodiments, the (S)-isomer in the mixture of identical chemical entities (i.e., mixture of stereoisomers) is present at an (S)-enantiomeric excess of about 10% to about 99.5%, about 20% to about 99.5%, about 30% to about 99.5%, about 40% to about 99.5%, about 50% to about 99.5%, about 55% to about 99.5%, about 60% to about 99.5%, about 65% to about 99.5%, about 70% to about 99.5%, about 75% to about 99.5%, about 80% to about 99.5%, about 85% to about 99.5%, about 90% to about 99.5%, about 95% to about 99.5%, about 96% to about 99.5%, about 97% to about 99.5%, about 98% to about 99.5%, or about 99% to about 99.5%, or more than about 99.5%.

In other embodiments, the (R)-isomer in the mixture of identical chemical entities (i.e., mixture of stereoisomers) is present at about 55%, about 60%, about 65%, about 70%, about 75%, about 80%, about 85%, about 90%, about 95%, about 96%, about 97%, about 98%, about 99%, or about 99.5% by weight, or more, relative to the total weight of the mixture of (S)- and (R)-isomers. In some embodiments, the (R)-isomers in the mixture of identical chemical entities (i.e., mixture of stereoisomers) is present at an (R)-enantiomeric excess of about 10% to about 99.5%, about 20% to about 99.5%, about 30% to about 99.5%, about 40% to about 99.5%, about 50% to about 99.5%, about 55% to about 99.5%, about 60% to about 99.5%, about 65% to about 99.5%, about 70% to about 99.5%, about 75% to about 99.5%, about 80% to about 99.5%, about 85% to about 99.5%, about 90% to about 99.5%, about 95% to about 99.5%, about 96% to about 99.5%, about 97% to about 99.5%, about 98% to about 99.5%, or about 99% to about 99.5%, or more than about 99.5%.

Enantiomers can be isolated from racemic mixtures by any method known to those skilled in the art, including chiral high pressure liquid chromatography (HPLC), the formation and crystallization of chiral salts, or prepared by asymmetric syntheses. See, for example, *Enantiomers, Racemates and Resolutions* (Jacques, Ed., Wiley Interscience, New York, 1981); Wilen et al., *Tetrahedron* 33:2725 (1977); *Stereochemistry of Carbon Compounds* (E. L. Eliel, Ed., McGraw-Hill, N.Y., 1962); and *Tables of Resolving Agents and Optical Resolutions* p. 268 (E. L. Eliel, Ed., Univ. of Notre Dame Press, Notre Dame, IN 1972).

In certain embodiments, the pharmaceutically acceptable form is a tautomer. As used herein, the term "tautomer" is a type of isomer that includes two or more interconvertible compounds resulting from at least one formal migration of a hydrogen atom and at least one change in valency (e.g., a single bond to a double bond, a triple bond to a double bond, or a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-enol; amide-imide; lactam-lactim; enamine-imine; and enamine-(a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

Unless otherwise stated, structures depicted herein are also meant to include compounds which differ only in the presence of one or more isotopically enriched atoms. For example, compounds having the present structures except for the replacement or enrichment of a hydrogen by deuterium or tritium, or the replacement or enrichment of a carbon by $^{13}C$ or $^{14}C$, are within the scope of this disclosure.

The disclosure also embraces isotopically labeled compounds which are identical to those recited herein, except that one or more atoms are replaced by an atom having an atomic mass or mass number different from the atomic mass or mass number usually found in nature. Examples of isotopes that can be incorporated into disclosed compounds include isotopes of hydrogen, carbon, nitrogen, oxygen, phosphorus, sulfur, fluorine, and chlorine, such as, e. $^{2}H$, $^{3}H$, $^{13}C$, $^{14}C$, $^{15}N$, $^{18}O$, $^{17}O$, $^{31}F$, $^{32}F$, $^{35}s$, $^{18}F$, and $^{36}Cl$, respectively. Certain isotopically-labeled disclosed compounds (e.g., those labeled with $^{3}H$ and/or $^{14}C$) are useful in compound and/or substrate tissue distribution assays. Tritiated (i.e., $^{3}H$) and carbon-14 (i.e., $^{14}C$) isotopes can allow for ease of preparation and detectability. Further, substitution with heavier isotopes such as deuterium (i.e., $^{2}H$) can afford certain therapeutic advantages resulting from greater metabolic stability (e.g., increased in vivo half-life or reduced dosage requirements). Isotopically labeled disclosed compounds can generally be prepared by substituting an isotopically labeled reagent for a non-isotopically labeled reagent. In some embodiments, provided herein are compounds that can also contain unnatural proportions of atomic isotopes at one or more of atoms that constitute such compounds. All isotopic variations of the compounds as disclosed herein, whether radioactive or not, are encompassed within the scope of the present disclosure.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range can vary from, for example, between 1% and 15% of the stated number or numerical range. When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

Definitions of specific functional groups and chemical terms are described in more detail below. The chemical elements are identified in accordance with the Periodic Table of the Elements, CAS version, Handbook of Chemistry and Physics, 75th ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's*

*Advanced Organic Chemistry,* 5th ed., John Wiley & Sons, Inc., New York, 2001; Larock, *Comprehensive Organic Transformations*, VCH Publishers, Inc., New York, 1989; and Carruthers, Some *Modern Methods of Organic Synthesis,* 3rd ed., Cambridge University Press, Cambridge, 1987.

Abbreviations used herein have their conventional meaning within the chemical and biological arts. The following abbreviations and terms have the indicated meanings throughout: PI3K=Phosphoinositide 3-kinase; PI=phosphatidylinositol; PDK=Phosphoinositide Dependent Kinase; DNA-PK=Deoxyribose Nucleic Acid Dependent Protein Kinase; PTEN=Phosphatase and Tensin homolog deleted on chromosome Ten; PIKK=Phosphoinositide Kinase Like Kinase; AIDS=Acquired Immuno Deficiency Syndrome; HIV=Human Immunodeficiency Virus; MeI=Methyl Iodide; $POCl_3$=Phosphorous Oxychloride; KCNS=Potassium Iso-Thiocyanate; TLC=Thin Layer Chromatography; MeOH=Methanol; and $CHCl_3$=Chloroform.

"Alkyl" refers to a straight or branched hydrocarbon chain radical consisting solely of carbon and hydrogen atoms, containing no unsaturation, having from one to ten carbon atoms (e.g., $C_1$-$C_{10}$ alkyl). Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a $C_1$-$C_4$ alkyl group. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$R^a$, $SR^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or $PO_3$($R^a$)$_2$ where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkylaryl" refers to an -(alkyl)aryl radical where aryl and alkyl are as disclosed herein and which are optionally substituted by one or more of the substituents described as suitable substituents for aryl and alkyl respectively.

"Alkylheteroaryl" refers to an -(alkyl)heteroaryl radical where hetaryl and alkyl are as disclosed herein and which are optionally substituted by one or more of the substituents described as suitable substituents for heteroaryl and alkyl respectively.

"Alkylheterocycloalkyl" refers to an -(alkyl)heterocycyl radical where alkyl and heterocycloalkyl are as disclosed herein and which are optionally substituted by one or more of the substituents described as suitable substituents for heterocycloalkyl and alkyl respectively.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, can be branched, straight chain, or cyclic.

"Alkenyl" refers to a straight or branched hydrocarbon chain radical group consisting solely of carbon and hydrogen atoms, containing at least one double bond, and having from two to ten carbon atoms (ie. $C_2$-$C_{10}$ alkenyl). Whenever it appears herein, a numerical range such as "2 to 10" refers to each integer in the given range; e.g., "2 to 10 carbon atoms" means that the alkenyl group can consist of 2 carbon atoms, 3 carbon atoms, etc., up to and including 10 carbon atoms. In certain embodiments, an alkenyl comprises two to eight carbon atoms. In other embodiments, an alkenyl comprises two to five carbon atoms (e.g., $C_2$-$C_5$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —N($R^a$)$_2$, —C(O)$R^a$, —C(O)O$R^a$, —OC(O)N($R^a$)$_2$, —C(O))N($R^a$)$_2$, —N($R^a$)C(O)O$R^a$, —N($R^a$)C(O)$R^a$, —N($R^a$)C(O)N($R^a$)$_2$, N($R^a$)C(N-$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or $PO_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to an -(alkenyl)cycloalkyl radical where alkenyl and cyclo alkyl are as disclosed herein and which are optionally substituted by one or more of the substituents described as suitable substituents for alkenyl and cycloalkyl respectively.

"Alkynyl" refers to a straight or branched hydrocarbon chain radical group consisting solely of carbon and hydrogen atoms, containing at least one triple bond, having from two to ten carbon atoms (ie. $C_2$-$C_{10}$ alkynyl). Whenever it appears herein, a numerical range such as "2 to 10" refers to each integer in the given range; e.g., "2 to 10 carbon atoms" means that the alkynyl group can consist of 2 carbon atoms, 3 carbon atoms, etc., up to and including 10 carbon atoms. In certain embodiments, an alkynyl comprises two to eight carbon atoms. In other embodiments, an alkynyl has two to five carbon atoms (e.g., $C_2$-$C_5$ alkynyl). The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N-$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or $PO_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkynyl-cycloalkyl" refers to an -(alkynyl)cycloalkyl radical where alkynyl and cyclo alkyl are as disclosed herein and which are optionally substituted by one or more of the substituents described as suitable substituents for alkynyl and cycloalkyl respectively.

"Carboxaldehyde" refers to a —(C=O)H radical.

"Carboxyl" refers to a —(C=O)OH radical.

"Cyano" refers to a —CN radical.

"Cycloalkyl" refers to a monocyclic or polycyclic radical that contains only carbon and hydrogen, and can be saturated, or partially unsaturated. Cycloalkyl groups include groups having from 3 to 10 ring atoms (ie. $C_2$-$C_{10}$ cycloalkyl). Whenever it appears herein, a numerical range such as "3 to 10" refers to each integer in the given range; e.g., "3 to 10 carbon atoms" means that the cycloalkyl group can consist of 3 carbon atoms, etc., up to and including 10 carbon atoms. In some embodiments, it is a $C_3$-$C_8$ cycloalkyl radical. In some embodiments, it is a $C_3$-$C_5$ cycloalkyl radical. Illustrative examples of cycloalkyl groups include, but are not limited to the following moieties: cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —SW, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_t$ $R^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl-alkenyl" refers to a -(cycloalkyl) alkenyl radical where cycloalkyl and heterocycloalkyl are as disclosed herein and which are optionally substituted by one or more of the substituents described as suitable substituents for heterocycloalkyl and cycloalkyl respectively.

"Cycloalkyl-heterocycloalkyl" refers to a -(cycloalkyl) heterocycyl radical where cycloalkyl and heterocycloalkyl are as disclosed herein and which are optionally substituted by one or more of the substituents described as suitable substituents for heterocycloalkyl and cycloalkyl respectively.

"Cycloalkyl-heteroaryl" refers to a -(cycloalkyl) heteroaryl radical where cycloalkyl and heterocycloalkyl are as disclosed herein and which are optionally substituted by one or more of the substituents described as suitable substituents for heterocycloalkyl and cycloalkyl respectively.

The term "alkoxy" refers to the group —O-alkyl, including from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. "Lower alkoxy" refers to alkoxy groups containing one to six carbons. In some embodiments, $C_1$-$C_4$ alkyl, is an alkyl group which encompasses both straight and branched chain alkyls of from 1 to 4 carbon atoms.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, $SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_t$ $R^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heteroarylalkyl, heteroaryl or heteroarylalkyl.

The term "alkoxycarbonyl" refers to a group of the formula (alkoxy)(C=O)— attached through the carbonyl carbon wherein the alkoxy group has the indicated number of carbon atoms. Thus a $C_1$-$C_6$ alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group. In some embodiments, $C_1$-$C_4$ alkoxy, is an alkoxy group which encompasses both straight and branched chain alkoxy groups of from 1 to 4 carbon atoms.

The term "substituted alkoxycarbonyl" refers to the group (substituted alkyl)-O—CO— wherein the group is attached to the parent structure through the carbonyl functionality. Unless stated otherwise specifically in the specification, the alkyl moiety of an alkoxycarbonyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, $SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)R^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyl" refers to the groups (alkyl)-C(O)—, (aryl)-C(O)—, (heteroaryl)-C(O)—, (heteroalkyl)-C(O)—, and (heterocycloalkyl)-C(O)—, wherein the group is attached to the parent structure through the carbonyl functionality. In some embodiments, it is a $C_1$-$C_{10}$ acyl radical which refers to the total number of chain or ring atoms of the alkyl, aryl, heteroaryl or heterocycloalkyl portion of the acyloxy group plus the carbonyl carbon of acyl, i.e three other ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, $SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)R^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyloxy" refers to a R(C=O)O— radical wherein "R" is alkyl, aryl, heteroaryl, heteroalkyl, or heterocycloalkyl, which are as described herein. In some embodiments, it is a $C_1$-$C_4$ acyloxy radical which refers to the total number of chain or ring atoms of the alkyl, aryl, heteroaryl or heterocycloalkyl portion of the acyloxy group plus the carbonyl carbon of acyl, i.e three other ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SW, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)R$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2-S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Amino" or "amine" refers to a —N(R$^a$)$_2$ radical group, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —N(R$^a$)$_2$ group has two Ra other than hydrogen they can be combined with the nitrogen atom to form a 4-, 5-, 6-, or 7-membered ring. For example, —N(R$^a$)$_2$ is meant to include, but not be limited to, 1-pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein.

The term "substituted amino" also refers to N-oxides of the groups —NHR$^d$, and NR$^d$R$^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Amide" or "amido" refers to a chemical moiety with formula —C(O)N(R)$_2$ or —NRC(O)R, where R is selected from the group consisting of hydrogen, alkyl, cycloalkyl, aryl, heteroaryl (bonded through a ring carbon) and heteroalicyclic (bonded through a ring carbon), each of which moiety can itself be optionally substituted. In some embodiments it is a $C_1$-$C_4$ amido or amide radical, which includes the amide carbonyl in the total number of carbons in the radical. The R$_2$ of —N(R)$_2$ of the amide can optionally be taken together with the nitrogen to which it is attached to form a 4-, 5-, 6-, or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide can be an amino acid or a peptide molecule attached to a compound of Formula (I), thereby forming a prodrug. Any amine, hydroxy, or carboxyl side chain on the compounds described herein can be amidified. The procedures and specific groups to make such amides are known to those of skill in the art and can readily be found in reference sources such as Greene and Wuts, Protective Groups in Organic Synthesis, 3.sup.rd Ed., John Wiley & Sons, New York, N.Y., 1999, which is incorporated herein by reference in its entirety.

"Aromatic" or "aryl" refers to an aromatic radical with six to up to fourteen ring atoms (e.g., $C_6$-$C_{10}$ aromatic or $C_6$-$C_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group can consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). Any amine, hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, 3.sup.rd Ed., John Wiley & Sons, New York, N.Y., 1999, which is incorporated herein by reference in its entirety. Unless stated otherwise specifically in the specification, an ester group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical can be optionally substituted as defined above for an alkyl group.

"Halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl" "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range can be given, e.g. $C_1$-$C_4$ heteroalkyl which refers to the chain length in total, which in this example is 4 atoms long. For example, a —CH$_2$OCH$_2$CH$_3$ radical is referred to as a "C$_4$" heteroalkyl, which includes the heteroatom center in the atom chain length description. Connection to the rest of the molecule can be through either a heteroatom or a carbon in the heteroalkyl chain. A heteroalkyl group can be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroalkylaryl" refers to an -(heteroalkyl)aryl radical where heteroalkyl and aryl are as disclosed herein and which are optionally substituted by one or more of the substituents described as suitable substituents for heteroalkyl and aryl respectively.

"Heteroalkylheteroaryl" refers to an -(heteroalkyl)heteroaryl radical where heteroalkyl and heteroaryl are as disclosed herein and which are optionally substituted by one or more of the substituents described as suitable substituents for heteroalkyl and heteroaryl respectively.

"Heteroalkylheterocycloalkyl" refers to an -(heteroalkyl) heterocycloalkyl radical where heteroalkyl and heteroaryl are as disclosed herein and which are optionally substituted by one or more of the substituents described as suitable substituents for heteroalkyl and heterocycloalkyl respectively "Heteroalkylcycloalkyl" refers to an -(heteroalkyl) cycloalkyl radical where heteroalkyl and cycloalkyl are as disclosed herein and which are optionally substituted by one or more of the substituents described as suitable substituents for heteroalkyl and cycloalkyl respectively.

"Heteroaryl" or, alternatively, "heteroaromatic" refers to a 5- to 18-membered aromatic radical (e.g., $C_5$-$C_{13}$ heteroaryl) that includes one or more ring heteroatoms selected from nitrogen, oxygen and sulfur, and which can be a monocyclic, bicyclic, tricyclic or tetracyclic ring system. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. An N-containing "heteroaromatic" or "heteroaryl" moiety refers to an aromatic group in which at least one of the skeletal atoms of the ring is a nitrogen atom. The polycyclic heteroaryl group can be fused or non-fused. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d] pyrimidinyl, 6,7-dihydro-5H-cyclopenta[4,5]thieno[2,3-d] pyrimidinyl, 5,6-dihydrobenzo[h]quinazolinyl, 5,6-dihydrobenzo[h]cinnolinyl, 6,7-dihydro-5H-benzo[6,7] cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7, 8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido [3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno [2,3-d]pyrimidinyl, 6,7,8,9-tetrahydro-5H-cyclohepta[4,5] thieno[2,3-d]pyrimidinyl, 5,6,7,8-tetrahydropyrido[4,5-c] pyridazinyl, thiazolyl, thiadiazolyl, thiapyranyl, triazolyl, tetrazolyl, triazinyl, thieno[2,3-d]pyrimidinyl, thieno[3,2-d] pyrimidinyl, thieno[2,3-c]pridinyl, and thiophenyl (i.e. thienyl). Unless stated otherwise specifically in the specification, a hetaryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

Substituted heteroaryl also includes ring systems substituted with one or more oxide (—O—) substituents, such as pyridinyl N-oxides.

"Heteroarylalkyl" refers to a moiety having an aryl moiety, as described herein, connected to an alkylene moiety, as described herein, wherein the connection to the remainder of the molecule is through the alkylene group.

"Heterocycloalkyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range; e.g., "3 to 18 ring atoms" means that the heterocycloalkyl group can consist of 3 ring atoms, 4 ring atoms, etc., up to and including 18 ring atoms. In some embodiments, it is a $C_5$-$C_{10}$ heterocycloalkyl. In some embodiments, it is a $C_4$-$C_{10}$ heterocycloalkyl. In some embodiments, it is a $C_3$-$C_{10}$ heterocycloalkyl. Unless stated otherwise specifically in the specification, the heterocycloalkyl radical is a monocyclic, bicyclic, tricyclic or tetracyclic ring system, which can include fused or bridged ring systems. The heteroatoms in the heterocycloalkyl radical can be optionally oxidized. One or more nitrogen atoms, if present, are optionally quaternized. The heterocycloalkyl radical is partially or fully saturated. The heterocycloalkyl can be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O))N(R$^a$)$_2$, —N(OC(O)R$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

"Moiety" refers to a specific segment or functional group of a molecule. Chemical moieties are often recognized chemical entities embedded in or appended to a molecule.

"Nitro" refers to the —NO$_2$ radical.

"Oxa" refers to the —O— radical.

"Oxo" refers to the =O radical.

A "leaving group or atom" is any group or atom that will, under the reaction conditions, leave from the starting material, thus promoting reaction at a specified site. Suitable examples of such groups unless otherwise specified are halogen atoms, mesyloxy, p-nitrobenzensulphonyloxy and tosyloxy groups.

"Protecting group" has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts, Protective Groups in Organic Synthesis, Third Edition, John Wiley & Sons, New York (1999). For example, a hydroxy protected form is where at least one of the hydroxy groups present in a compound is protected with a hydroxy protecting group. Likewise, amines and other reactive groups can similarly be protected.

"Solvate" refers to a compound (e.g., a compound selected from Formula I or a pharmaceutically acceptable salt thereof) in physical association with one or more molecules of a pharmaceutically acceptable solvent. It will be understood that "a compound of Formula I" encompass the compound of Formula I and solvates of the compound, as well as mixtures thereof.

"Substituted" means that the referenced group can be substituted with one or more additional group(s) individually and independently selected from acyl, alkyl, alkylaryl, cycloalkyl, aralkyl, aryl, carbohydrate, carbonate, heteroaryl, heterocycloalkyl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and the protected derivatives thereof. Di-substituted amino groups encompass those which form a ring together with the nitrogen of the amino group, such as for instance, morpholino. The substituents themselves can be substituted, for example, a cycloakyl substituent can have a halide substituted at one or more ring carbons, and the like. The protecting groups that can form the protective derivatives of the above substituents are known to those of skill in the art and can be found in references such as Greene and Wuts, above.

"Sulfanyl" refers to the groups: —S-(optionally substituted alkyl), —S-(optionally substituted aryl), —S-(optionally substituted heteroaryl), and —S-(optionally substituted heterocycloalkyl).

"Sulfinyl" refers to the groups: —S(O)—H, —S(O)-(optionally substituted alkyl), —S(O)-(optionally substituted amino), —S(O)-(optionally substituted aryl), —S(O)-(optionally substituted heteroaryl), and —S(O)-(optionally substituted heterocycloalkyl).

"Sulfonyl" refers to the groups: —S(O$_2$)—H, —S(O$_2$)-(optionally substituted alkyl), —S(O$_2$)-(optionally substituted amino), —S(O$_2$)-(optionally substituted aryl), —S(O$_2$)-(optionally substituted heteroaryl), and —S(O$_2$)-(optionally substituted heterocycloalkyl).

"Sulfonamidyl" or "sulfonamido" refers to a —S(═O)$_2$—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —S(═O)$_2$—NRR radical can be taken together with the nitrogen to which it is attached to form a 4-, 5-, 6-, or 7-membered ring. In some embodiments, it is a C$_1$-C$_{10}$ sulfonamido, wherein each R in sulfonamido contains 1 carbon, 2 carbons, 3 carbons, or 4 carbons total. A sulfonamido group is optionally substituted by one or more of the substituents described for alkyl, cycloalkyl, aryl, heteroaryl respectively "Sulfoxyl" refers to a —S(═O)$_2$OH radical.

"Sulfonate" refers to a —S(═O)$_2$—OR radical, where R is selected from the group consisting of alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, heteroaryl respectively.

Where substituent groups are specified by their conventional chemical formulae, written from left to right, they equally encompass the chemically identical substituents that would result from writing the structure from right to left, e.g., —CH$_2$O— is equivalent to —OCH$_2$—.

Compounds that can be used as described herein also include crystalline and amorphous forms of compounds, including, for example, polymorphs, pseudopolymorphs, solvates, hydrates, unsolvated polymorphs (including anhydrates), conformational polymorphs, and amorphous forms of the compounds, as well as mixtures thereof As used herein, and unless otherwise specified, "polymorph" can be used herein to describe a crystalline material, e.g., a crystalline form. In certain embodiments, "polymorph" as used herein are also meant to include all crystalline and amorphous forms of a compound or a salt thereof, including, for example, crystalline forms, polymorphs, pseudopolymorphs, solvates, hydrates, co-crystals, unsolvated polymorphs (including anhydrates), conformational polymorphs, tautomeric forms, disordered crystalline forms, and amorphous forms, as well as mixtures thereof, unless a particular crystalline or amorphous form is referred to. Compounds of the present disclosure include crystalline and amorphous forms of those compounds, including, for example, crystalline forms, polymorphs, pseudopolymorphs, solvates, hydrates, co-crystals, unsolvated polymorphs (including anhydrates), conformational polymorphs, tautomeric forms, disordered crystalline forms, and amorphous forms of the compounds or a salt thereof, as well as mixtures thereof.

Chemical entities include, but are not limited to, compounds of Formula I, I-1, IV, IV-A, V, V-A, V-A2, V-B, VI or VI-A, and all pharmaceutically acceptable forms thereof. Pharmaceutically acceptable forms of the compounds recited herein include pharmaceutically acceptable salts, chelates, non-covalent complexes, prodrugs, and mixtures thereof. In certain embodiments, the compounds described herein are in the form of pharmaceutically acceptable salts. Hence, the terms "chemical entity" and "chemical entities" also encompass pharmaceutically acceptable salts, chelates, non-covalent complexes, prodrugs, and mixtures.

In addition, if the compound of Formula I is obtained as an acid addition salt, the free base can be obtained by basifying a solution of the acid salt. Conversely, if the product is a free base, an addition salt, particularly a pharmaceutically acceptable addition salt, can be produced by dissolving the free base in a suitable organic solvent and treating the solution with an acid, in accordance with conventional procedures for preparing acid addition salts from base compounds. Those skilled in the art will recognize various synthetic methodologies that can be used to prepare non-toxic pharmaceutically acceptable addition salts.

Compounds

The compounds provided below are exemplary PI3K modulators that can be used in the pharmaceutical compositions, methods and kits disclosed herein.

In some aspects, the PI3K modulator is a compound of Formula I:

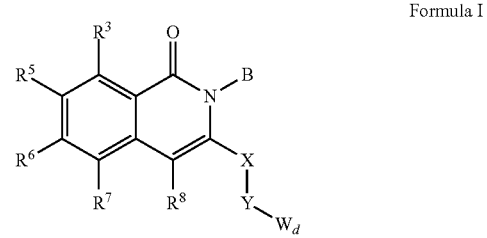

Formula I or its pharmaceutically acceptable salt thereof, wherein
W$_d$ is heterocycloalkyl, aryl or heteroaryl;
B is alkyl, amino, heteroalkyl, or a moiety of Formula II;

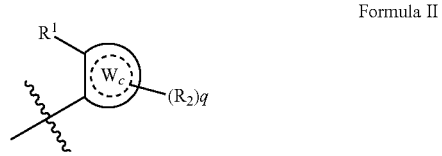

Formula II wherein W$_c$ is aryl, heteroaryl, heterocycloalkyl, or cycloalkyl, and q is an integer of 0, 1, 2, 3, or 4;

X is absent or is —(CH(R$^9$))$_z$— and z is an integer of 1, 2, 3, or 4;

Y is absent, —O—, —S—, —S(═O)—, —S(═O)$_2$—, —N(R$^9$)—, —C(═O)—(CHR$^9$)$_z$—, —C(═O)—, —N(R$^9$)—C(═O)—, or —N(R$^9$)—C(═O)NH—, —N(R$^9$)C(R$^9$)$_2$—, or —C(═O)—(CHR$^9$)$_z$—;

R$^1$ is hydrogen, alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, halo, cyano, hydroxy, nitro, phosphate, urea, or carbonate;

R$^2$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, halo, cyano, hydroxy, nitro, phosphate, urea, or carbonate;

R$^3$ is hydrogen, alkyl, alkenyl, alkynyl, cycloalkyl, heterocycloalkyl, alkoxy, amido, amino, acyl, acyloxy, alkoxycarbonyl, sulfonamido, halo, cyano, hydroxy, nitro, aryl, or heteroaryl;

R$^5$, R$^6$, R$^7$, and R$^8$ are independently hydrogen, C$_1$-C$_4$alkyl, C$_2$-C$_5$alkenyl, C$_2$-C$_5$alkynyl, C$_3$-C$_5$cycloalkyl, C$_1$-C$_4$heteroalkyl, C$_1$-C$_4$alkoxy, C$_1$-C$_4$amido, amino, acyl, C$_1$-C$_4$acyloxy, C$_1$-C$_4$sulfonamido, halo, cyano, hydroxy or nitro; and each instance of $R^9$ is independently hydrogen, $C_1$-$C_{10}$alkyl, $C_3$-$C_7$cycloalkyl, heterocycloalkyl, or $C_2$-$C_{10}$heteroalkyl.

In some embodiments, B is unsubstituted or substituted alkyl, including but not limited to —$(CH_2)_2$—$NR^aR^a$, wherein each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, or $NR^aR^a$ are combined together to form a cyclic moiety, which includes but is not limited to piperidinyl, piperazinyl, and morpholinyl. In some embodiments, B is unsubstituted or substituted amino. In some embodiments, B is unsubstituted or substituted heteroalkyl.

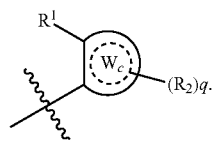

Formula II

In some embodiments, B is a moiety of Formula II and wherein $W_c$ is a member selected from the group consisting of unsubstituted or substituted aryl, substituted phenyl, unsubstituted or substituted heteroaryl including but not limited to pyridin-2-yl, pyridin-3-yl, pyridin-4-yl, pyrimidin-4-yl, pyrimidin-2-yl, pyrimidin-5-yl, or pyrazin-2-yl, unsubstituted or substituted monocyclic heteroaryl, unsubstituted or substituted bicyclic heteroaryl, a heteroaryl comprising two heteroatoms as ring atoms, unsubstituted or substituted heteroaryl comprising a nitrogen ring atom, heteroaryl comprising two nitrogen ring atoms, heteroaryl comprising a nitrogen and a sulfur as ring atoms, unsubstituted or substituted heterocycloalkyl including but not limited to morpholinyl, tetrahydropyranyl, piperazinyl, and piperidinyl, unsubstituted or substituted cycloalkyl including but not limited to cyclopentyl and cyclohexyl.

In some embodiments, B is one of the following moieties:

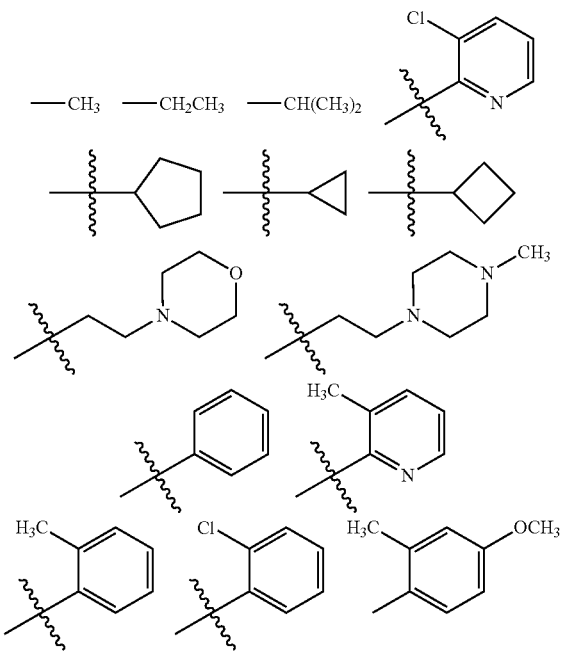

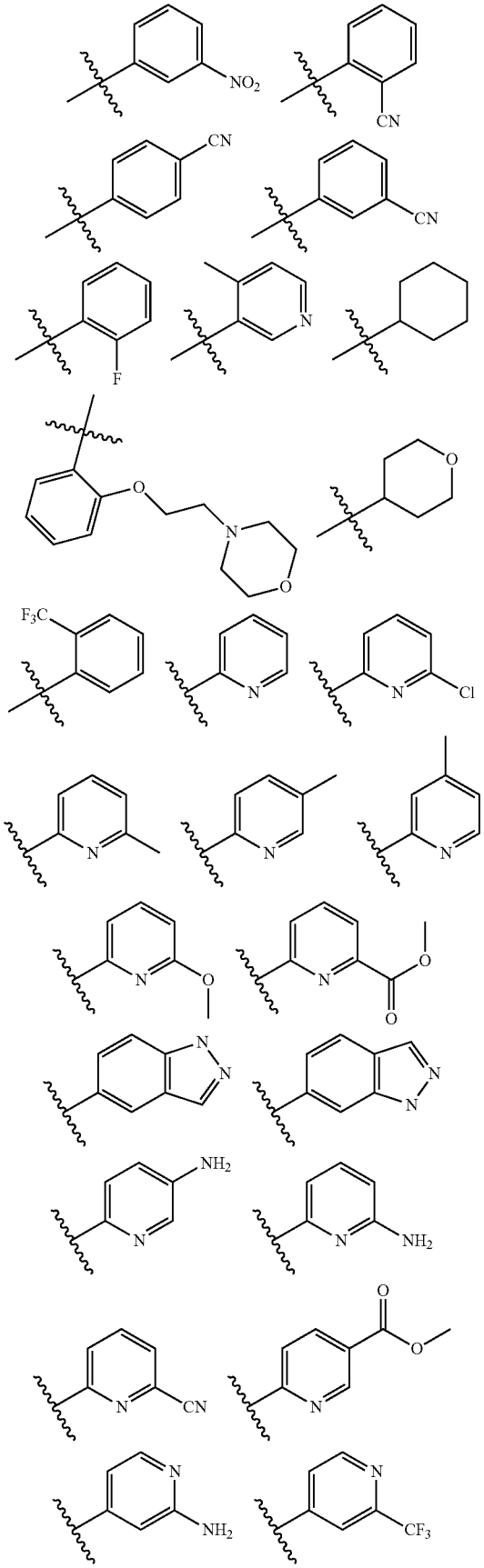

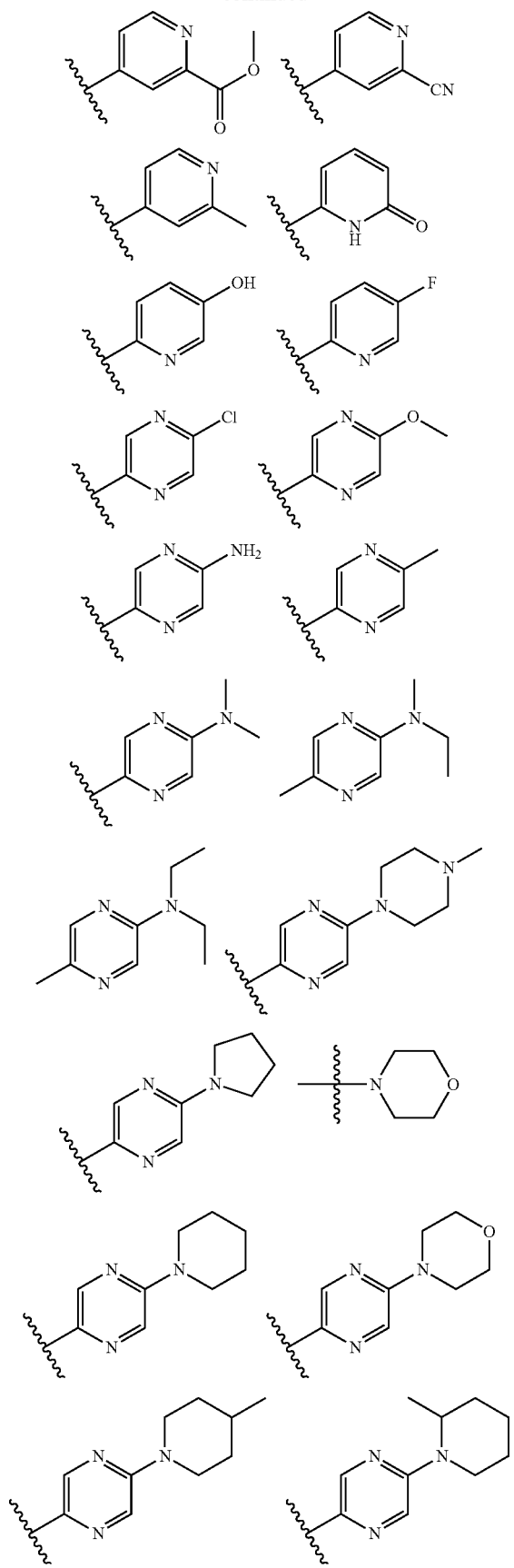
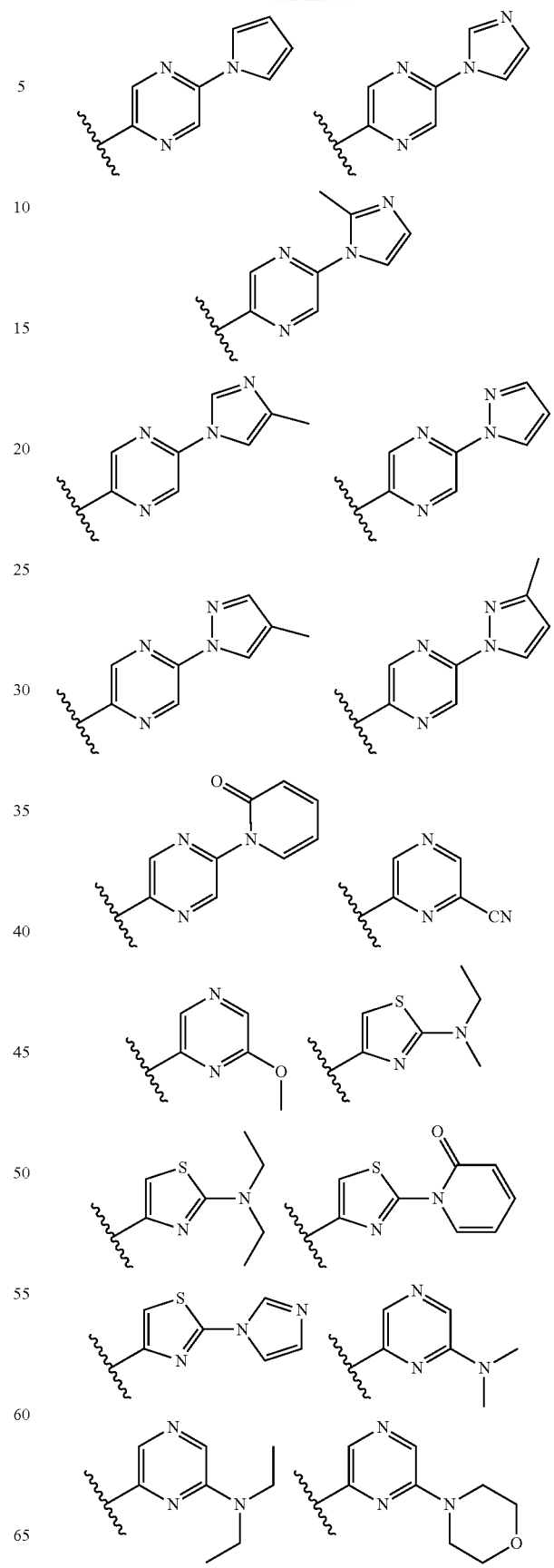

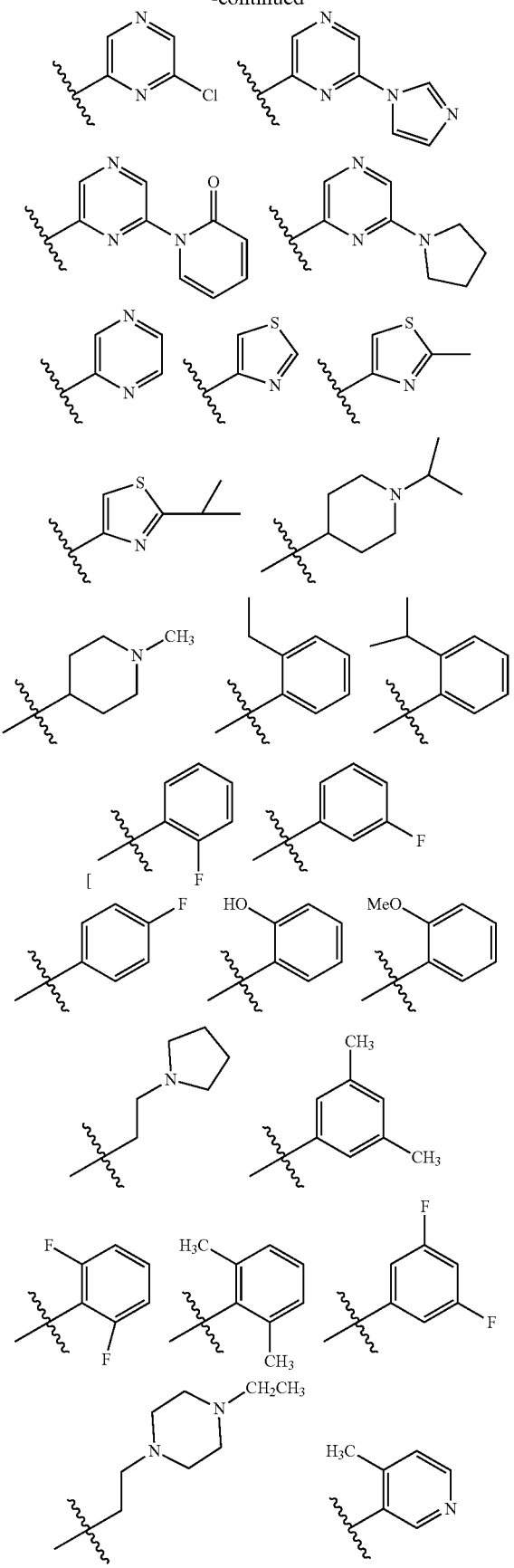
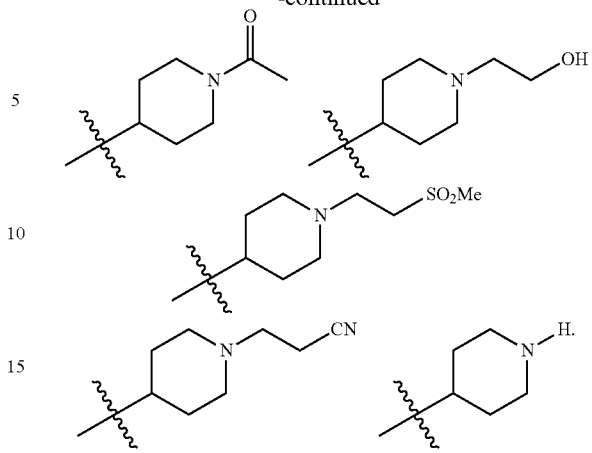

In some embodiments, B is substituted by one or more of alkyl, heteroalkyl, alkenyl, alkynyl, cycloalkyl, heterocycloalkyl, aryl, heteroaryl alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, or sulfonamido, can itself be substituted.

In some embodiments, $R^1$ is a member selected from the group consisting of hydrogen, unsubstituted or substituted alkyl, unsubstituted or substituted heteroalkyl, unsubstituted or substituted alkenyl, unsubstituted or substituted alkynyl, unsubstituted or substituted cycloalkyl, or unsubstituted or substituted heterocycloalkyl. In some embodiments, $R^1$ is unsubstituted or substituted aryl, unsubstituted or substituted arylalkyl, unsubstituted or substituted heteroaryl, or unsubstituted or substituted heteroarylalkyl. In some embodiments, $R^1$ is unsubstituted or substituted alkoxy, unsubstituted or substituted amido, unsubstituted or substituted amino. In some embodiments, $R^1$ is unsubstituted or substituted acyl, unsubstituted or substituted acyloxy, unsubstituted or substituted alkoxycarbonyl, or unsubstituted or substituted sulfonamido. In some embodiments, $R^1$ is halo which includes —Cl, —F, —I, and —Br. In some embodiments, $R^1$ is selected from the group consisting of cyano, hydroxy, nitro, unsubstituted or substituted phosphate, unsubstituted or substituted urea, and carbonate.

In some embodiments, when $R^1$ is alkyl, $R^1$ is methyl, ethyl, propyl, isopropyl, n-butyl, tert-butyl, sec-butyl, pentyl, hexyl or heptyl.

In some embodiments, when $R^1$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, or hydroxy, $R^1$ is substituted by phosphate, or unsubstituted urea, or substituted urea, or carbonic acid, or carbonate.

In some embodiments, when $R^1$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, or sulfonamido, $R^1$ is substituted by one or more of alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, or sulfonamido can itself be substituted.

In some embodiments, $R^2$ is a member selected from the group consisting of unsubstituted or substituted alkyl, unsubstituted or substituted heteroalkyl, unsubstituted or substituted alkenyl, unsubstituted or substituted alkynyl, unsubstituted or substituted cycloalkyl, and unsubstituted or substituted heterocycloalkyl. In some embodiments, $R^2$ is unsubstituted or substituted aryl, unsubstituted or substituted arylalkyl, unsubstituted or substituted heteroaryl, or unsubstituted or substituted heteroarylalkyl. In some embodiments, $R^2$ is unsubstituted or substituted alkoxy, unsubstituted or substituted amido, unsubstituted or substituted amino. In some embodiments, $R^2$ is unsubstituted or substituted acyl, unsubstituted or substituted acyloxy, unsubstituted or substituted alkoxycarbonyl, or unsubstituted or substituted sulfonamido. In some embodiments, $R^2$ is halo, which is —I, —F, —Cl, or —Br. In some embodiments, $R^2$ is selected from the group consisting of cyano, hydroxy, nitro, a carbonic acid, and a carbonate. In some embodiments, $R^2$ is unsubstituted or substituted phosphate. In some embodiments, $R^2$ is unsubstituted or substituted urea. In some embodiments, when $R^2$ is alkyl, $R^2$ is methyl, ethyl, propyl, isopropyl, n-butyl, tert-butyl, sec-butyl, pentyl, hexyl or heptyl.

In some embodiments, when $R^2$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, or hydroxy, it is substituted by phosphate, substituted by urea, or substituted by carbonate.

In some embodiments, when $R^2$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, or sulfonamido, it is substituted by one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido can itself be substituted.

In some embodiments, q is an integer of 0. In some embodiments, q is an integer of 1. In some embodiments, q is an integer of 2. In some embodiments, q is an integer of 3. In some embodiments, q is an integer of 4.

In some embodiments of the compound of Formula I, $R^3$ is a member selected from the group consisting of hydrogen, unsubstituted or substituted alkyl, unsubstituted or substituted alkenyl, and unsubstituted or substituted alkynyl. In some embodiments, $R^3$ is unsubstituted or substituted aryl, unsubstituted or substituted heteroaryl, unsubstituted or substituted cycloalkyl, or unsubstituted or substituted heterocycloalkyl. In some embodiments, $R^3$ is unsubstituted or substituted alkoxy, unsubstituted or substituted amido, unsubstituted or substituted amino. In some embodiments, $R^3$ is unsubstituted or substituted acyl, unsubstituted or substituted acyloxy, unsubstituted or substituted alkoxycarbonyl, or unsubstituted or substituted sulfonamido. In some embodiments, $R^3$ is halo, which is is —I, —F, —Cl, or —Br.

In some embodiments, $R^3$ is selected from the group consisting of cyano, hydroxy, and nitro. In some embodiments, when $R^3$ is alkyl, $R^3$ is methyl, ethyl, propyl, isopropyl, n-butyl, tert-butyl, sec-butyl, pentyl, hexyl or heptyl. In some embodiments, $R^3$ is —$CF_3$.

In some embodiments, when $R^3$ is alkyl, alkenyl, alkynyl, aryl, heteroaryl, cycloalkyl, heterocycloalkyl, alkoxy, amido, amino, acyl, acyloxy, alkoxycarbonyl, or sulfonamido, it is substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido can itself be substituted.

In some embodiments of the compound of Formula I, $R^5$ is hydrogen, unsubstituted or substituted alkyl (including but not limited to unsubstituted or substituted $C_1$-$C_4$alkyl). In some embodiments, $R^5$ is unsubstituted or substituted alkenyl including but not limited to unsubstituted or substituted $C_2$-$C_5$alkenyl. In some embodiments, $R^5$ is unsubstituted or substituted alkynyl including but not limited to unsubstituted or substituted $C_2$-$C_5$alkynyl. In some embodiments, $R^5$ is unsubstituted or substituted cycloalkyl including but not limited to unsubstituted or substituted $C_3$-$C_5$cycloalkyl. In some embodiments, $R^5$ is unsubstituted or substituted heterocycloalkyl. In some embodiments, $R^5$ is unsubstituted or substituted heteroalkyl including but not limited to unsubstituted or substituted $C_1$-$C_4$heteroalkyl. In some embodiments, $R^5$ is unsubstituted or substituted alkoxy including but not limited to unsubstituted or substituted $C_1$-$C_4$alkoxy. In some embodiments, $R^5$ is unsubstituted or substituted amido including but not limited to unsubstituted or substituted $C_1$-$C_4$amido. In some embodiments, $R^5$ is unsubstituted or substituted amino. In some embodiments, $R^5$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted sulfonamido, or unsubstituted or substituted $C_1$-$C_4$sulfonamido. In some embodiments, $R^5$ is halo, which is —I, —F, —Cl, or —Br. In some embodiments, $R^5$ is selected from the group consisting of cyano, hydroxy, and nitro. In some other embodiments, $R^5$ is —$CH_3$, —$CH_2CH_3$, n-propyl, isopropyl, —$OCH_3$, —$OCH_2CH_3$, or —$CF_3$.

In some embodiments, when $R^5$ is alkyl, alkenyl, alkynyl, cycloalkyl, heteroalkyl, acyl, alkoxy, amido, amino, acyloxy, alkoxycarbonyl, or sulfonamido, $R^5$ is optionally substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido can itself be substituted.

In some embodiments of the compound of Formula I, $R^6$ is hydrogen, unsubstituted or substituted alkyl (including but not limited to unsubstituted or substituted $C_1$-$C_4$alkyl). In some embodiments, $R^6$ is unsubstituted or substituted alkenyl including but not limited to unsubstituted or substituted $C_2$-$C_5$alkenyl. In some embodiments, $R^6$ is unsubstituted or substituted alkynyl including but not limited to unsubstituted or substituted $C_2$-$C_5$alkynyl. In some embodiments, $R^6$ is unsubstituted or substituted cycloalkyl including but not limited to unsubstituted or substituted $C_3$-$C_5$cycloalkyl. In some embodiments, $R^6$ is unsubstituted or substituted heterocycloalkyl. In some embodiments, $R^6$ is unsubstituted or substituted heteroalkyl including but not limited to unsubstituted or substituted $C_1$-$C_4$heteroalkyl. In some embodiments, $R^6$ is unsubstituted or substituted alkoxy including but not limited to unsubstituted or substituted $C_1$-$C_4$alkoxy. In some embodiments, $R^6$ is unsubstituted or substituted amido including but not limited to unsubstituted or substituted $C_1$-$C_4$amido. In some embodiments, $R^6$ is unsubstituted or substituted amino. In some embodiments, $R^6$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted sulfonamido, or unsubstituted or substituted $C_1$-$C_4$sulfonamido. In some embodiments, $R^6$ is halo, which is —I, —F, —Cl, or —Br. In some embodiments, $R^6$ is selected from the group consisting of cyano, hydroxy, and nitro. In some other embodiments, $R^6$ is —$CH_3$, —$CH_2CH_3$, n-propyl, isopropyl, —$OCH_3$, —$OCH_2CH_3$, or —$CF_3$.

In some embodiments, when $R^6$ is alkyl, alkenyl, alkynyl, cycloalkyl, heteroalkyl, acyl, alkoxy, amido, amino, acyloxy, alkoxycarbonyl, or sulfonamido, $R^6$ is optionally substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido can itself be substituted.

In some embodiments of the compound of Formula I, $R^7$ is hydrogen, unsubstituted or substituted alkyl (including but not limited to unsubstituted or substituted $C_1$-$C_4$alkyl). In some embodiments, $R^7$ is unsubstituted or substituted alkenyl including but not limited to unsubstituted or substituted $C_2$-$C_5$alkenyl. In some embodiments, $R^7$ is unsubstituted or substituted alkynyl including but not limited to unsubstituted or substituted $C_2$-$C_5$alkynyl. In some embodiments, $R^7$ is unsubstituted or substituted cycloalkyl including but not limited to unsubstituted or substituted $C_3$-$C_5$cycloalkyl. In some embodiments, $R^7$ is unsubstituted or substituted heterocycloalkyl. In some embodiments, $R^7$ is unsubstituted or substituted heteroalkyl including but not limited to unsubstituted or substituted $C_1$-$C_4$heteroalkyl. In some embodiments, $R^7$ is unsubstituted or substituted alkoxy including but not limited to unsubstituted or substituted $C_1$-$C_4$alkoxy. In some embodiments, $R^7$ is unsubstituted or substituted amido including but not limited to unsubstituted or substituted $C_1$-$C_4$amido. In some embodiments, $R^7$ is unsubstituted or substituted amino. In some embodiments, $R^7$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted sulfonamido, or unsubstituted or substituted $C_1$-$C_4$sulfonamido. In some embodiments, $R^7$ is halo, which is —I, —F, —Cl, or —Br. In some embodiments, $R^7$ is selected from the group consisting of cyano, hydroxy, and nitro. In some other embodiments, $R^7$ is —$CH_3$, —$CH_2CH_3$, n-propyl, isopropyl, —$OCH_3$, —$OCH_2CH_3$, or —$CF_3$.

In some embodiments, when $R^7$ is alkyl, alkenyl, alkynyl, cycloalkyl, heteroalkyl, acyl, alkoxy, amido, amino, acyloxy, alkoxycarbonyl, or sulfonamido, $R^7$ is optionally substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido can itself be substituted.

In some embodiments of the compound of Formula I, $R^8$ is hydrogen, unsubstituted or substituted alkyl (including but not limited to unsubstituted or substituted $C_1$-$C_4$alkyl). In some embodiments, $R^8$ is unsubstituted or substituted alkenyl including but not limited to unsubstituted or substituted $C_2$-$C_5$alkenyl. In some embodiments, $R^8$ is unsubstituted or substituted alkynyl including but not limited to unsubstituted or substituted $C_2$-$C_5$alkynyl. In some embodiments, $R^8$ is unsubstituted or substituted cycloalkyl including but not limited to unsubstituted or substituted $C_3$-$C_5$cycloalkyl. In some embodiments, $R^8$ is unsubstituted or substituted heterocycloalkyl. In some embodiments, $R^8$ is unsubstituted or substituted heteroalkyl including but not limited to unsubstituted or substituted $C_1$-$C_4$heteroalkyl. In some embodiments, $R^8$ is unsubstituted or substituted alkoxy including but not limited to unsubstituted or substituted $C_1$-$C_4$alkoxy. In some embodiments, $R^8$ is unsubstituted or substituted amido including but not limited to unsubstituted or substituted $C_1$-$C_4$amido. In some embodiments, $R^8$ is unsubstituted or substituted amino. In some embodiments, $R^8$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted sulfonamido, or unsubstituted or substituted $C_1$-$C_4$sulfonamido. In some embodiments, $R^8$ is halo, which is —I, —F, —Cl, or —Br. In some embodiments, $R^8$ is selected from the group consisting of cyano, hydroxy, and nitro. In some other embodiments, $R^8$ is —$CH_3$, —$CH_2CH_3$, n-propyl, isopropyl, —$OCH_3$, —$OCH_2CH_3$, or —$CF_3$.

In some embodiments, when $R^8$ is alkyl, alkenyl, alkynyl, cycloalkyl, heteroalkyl, acyl, alkoxy, amido, amino, acyloxy, alkoxycarbonyl, or sulfonamido, $R^8$ is optionally substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido can itself be substituted.

In some embodiments of the compound of Formula I, $R^5$, $R^6$, $R^7$, and $R^8$ are H and the compound has a structure of Formula I-1:

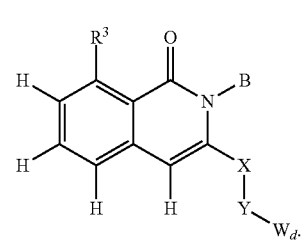

Formula I-1

In some embodiments of the compound of Formula I, X is absent. In some embodiments, X is —$(CH(R^9))_z$—, and z is an integer of 1, 2, 3 or 4.

In some embodiments, $R^9$ is unsubstituted or substituted alkyl including but not limited to unsubstituted or substituted $C_1$-$C_{10}$ alkyl. In some embodiments, $R^9$ is unsubstituted or substituted cycloalkyl including but not limited to unsubstituted or substituted $C_3$-$C_7$cycloalkyl. In some embodiments, $R^9$ is ethyl, methyl or hydrogen. In some embodiments, $R^9$ is unsubstituted or substituted heterocycloalkyl including but not limited to unsubstituted or substituted $C_2$-$C_{10}$ heteroalkyl. In some embodiments, $R^9$ is unsubstituted or substituted heteroalkyl including but not limited to unsubstituted or substituted $C_2$-$C_{10}$ heteroalkyl.

Also provided herein is a compound of Formula I wherein $R^9$ is hydrogen, and X is —$CH_2$—, —$CH_2CH_2$—, —$CH_2CH_2CH_2$—, —$CH(CH_3)$—, or —$CH(CH_2CH_3)$—. In other embodiments, X is —$(CH(R^9))_z$—, $R^9$ is not hydrogen, and z is an integer of 1. When X is —$CH(R^9)$— and $R^9$ is not hydrogen, then the compound can adopt either an (S)- or (R)-stereochemical configuration with respect to carbon X. In some embodiments, the compound is a racemic mixture of (S)- and (R) isomers with respect to carbon X. In other embodiments, provided herein is a mixture of compounds of Formula I wherein individual compounds of the mixture exist predominately in an (S)- or (R)-isomeric configuration. For example, the compound mixture has an (S)-enantiomeric purity of greater than about 55%, about 60%, about 65%, about 70%, about 75%, about 80%, about 85%, about 90%, about 95%, about 96%, about 97%, about 98%, about 99%, about 99.5%, or more at the X carbon. In other embodiments, the compound mixture has an (S)-enantiomeric purity of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5%, or more at the X carbon. In some other embodiments, the compound mixture has an (R)-enantiomeric purity of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In other embodiments, the compound mixture contains identical chemical entities except for their stereochemical orientations, namely (S)- or (R)-isomers. For instance, in the compounds of Formula I, when X is —CH($R^9$)—, and $R^9$ is not hydrogen, then the —CH($R^9$)— is in an (S)- or (R)-stereochemical orientation for each of the identical chemical entities. In some embodiments, the mixture of identical chemical entities of Formula I is a racemic mixture of (S)- and (R)-isomers at the carbon represented by X. In another embodiment, the mixture of the identical chemical entities (except for their stereochemical orientations), contain predominately (S)-isomers or predominately (R)-isomers. For example, the (S)-isomers in the mixture of identical chemical entities are present at about 55%, about 60%, about 65%, about 70%, about 75%, about 80%, about 85%, about 90%, about 95%, about 96%, about 97%, about 98%, about 99%, about 99.5%, or more, relative to the (R)-isomers. In some embodiments, the (S)-isomers in the mixture of identical chemical entities are present at an (S)-enantiomeric purity of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In another embodiment, the (R)-isomers in the mixture of identical chemical entities (except for their stereochemical orientations), are present at about 55%, about 60%, about 65%, about 70%, about 75%, about 80%, about 85%, about 90%, about 95%, about 96%, about 97%, about 98%, about 99%, about 99.5%, or more, relative to the (S)-isomers. In some embodiments, the (R)-isomers in the mixture of identical chemical entities (except for their stereochemical orientations), are present at a (R)-enantiomeric purity greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In some embodiments, the compound of Formula I, X is —CH($R^9$)—, $R^9$ is methyl or ethyl, and the compound is the (S)-isomer.

In some embodiments of the compound of Formula I, Y is absent. In some embodiments, Y is —O—, —S—, —S(=O)—, —S(=O)$_2$—, —C(=O)—, —N($R^9$)(C=O)—, —N($R^9$)(C=O)NH—, —N($R^9$)C($R^9$)$_2$— (such as —N($R^9$)CH$_2$—, specifically —N(CH$_3$)CH$_2$—, N(CH(CH$_3$)$_2$)CH$_2$— or N(CH$_2$CH$_3$)CH$_2$—), —N($R^9$)—, —N(CH$_3$)—, —N(CH$_2$CH$_3$)—, or —N(CH(CH$_3$)$_2$)—. In some embodiments, Y is —C(=O)—(CHR$^9$)$_z$— and z is an integer of 1, 2, 3, or 4.

In some embodiments, at least one of X and Y is present. In some embodiments of the compound of Formula I, —XY— is —CH$_2$—, —CH$_2$—N(CH$_3$), —CH$_2$—N(CH$_2$CH$_3$), —CH(CH$_3$)—NH—, (S)—CH(CH$_3$)—NH—, or (R)—CH(CH$_3$)—NH—. In other embodiments, X—Y is —N(CH$_3$)—CH$_2$—, N(CH$_2$CH$_3$) CH$_2$—, —N(CH(CH$_3$)$_2$) CH$_2$—, or —NHCH$_2$—. Provided herein are other compounds of Formula I wherein when X—Y is X is —(CH($R^9$))$_z$N($R^9$)—, z is an integer of 1, 2, 3 or 4, and —N($R^9$)— is not —NH—, then —XY— is not connected to purinyl.

In some embodiments, $W_d$ in a formula disclosed herein (including but not limited to I, I-1, IV, IV-A, V, V-A, V-A2, V-B, VI and VI-A), is a member selected from the group consisting of unsubstituted or substituted heterocycloalkyl, unsubstituted or substituted aryl, and unsubstituted or substituted heteroaryl.

In various embodiments, $W_d$ is unsubstituted or substituted monocyclic heteroaryl (including but not limited to pyrimidinyl, pyrrolyl, pyrazinyl, triazinyl, or pyridazinyl) or unsubstituted or substituted bicyclic heteroaryl.

In some embodiments, $W_d$ is a monocyclic heteroaryl of the following formula:

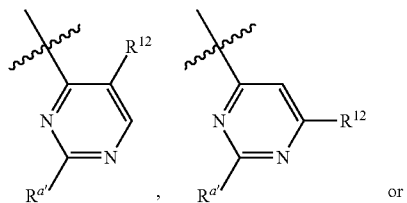

or

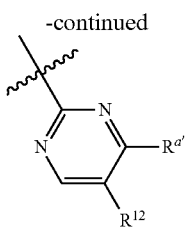

wherein $R^{a'}$ is hydrogen, halo, phosphate, urea, a carbonate, unsubstituted or substituted amino, unsubstituted or substituted alkyl, unsubstituted or substituted alkenyl, unsubstituted or substituted alkynyl, unsubstituted or substituted cycloalkyl, unsubstituted or substituted heteroalkyl, or unsubstituted or substituted heterocycloalkyl; and $R^{12}$ is H, unsubstituted or substituted alkyl, unsubstituted or substituted cyano, unsubstituted or substituted alkynyl, unsubstituted or substituted alkenyl, halo, unsubstituted or substituted aryl, unsubstituted or substituted heteroaryl, unsubstituted or substituted heterocycloalkyl, unsubstituted or substituted cycloalkyl, unsubstituted or substituted amino, carboxylic acid, unsubstituted or substituted alkoxycarbonyl, unsubstituted or substituted amido, unsubstituted or substituted acyl, or unsubstituted or substituted sulfonamido.

Also included herein are compounds having monocyclic heteroaryl $W_d$ including but not limited to one of the following formulae:

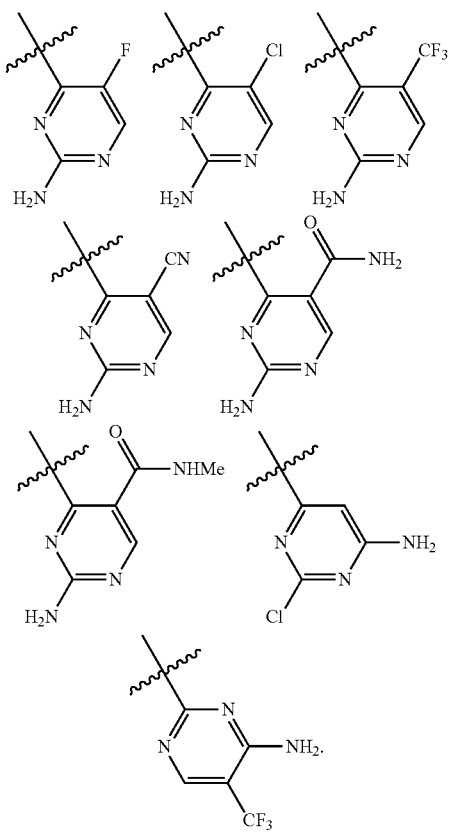

In some embodiments, $W_d$ in a formula disclosed herein (including but not limited to I, I-1, IV, IV-A, V, V-A, V-A2, V-B, VI and VI-A), is a bicyclic heteroaryl having at least one heteroatom, e.g., a bicyclic heteroaryl having at least one nitrogen ring atom. In some embodiments, $W_d$ is a bicyclic heteroaryl having at least two heteroatoms, e.g., a bicyclic heteroaryl having at least two nitrogen ring atoms. In some embodiments, $W_d$ is a bicyclic heteroaryl having two heteroatoms in the ring which is connected to XY. In some embodiments, $W_d$ is a bicyclic heteroaryl having two nitrogen ring atoms in the ring to which XY is connected. In some embodiments, $W_d$ is a bicyclic heteroaryl having four heteroatoms, e.g, a bicyclic heteroaryl having four nitrogen ring atoms. In some embodiments, $W_d$ is unsubstituted or substituted 4-amino-1H-pyrazolo[3,4-d]pyrimidin-1-yl, unsubstituted or substituted 7-amino-2-methyl-2H-pyrazolo[4,3-d]pyrimidin-3-yl, unsubstituted or substituted 6-methylenyl-9H-purin-6-yl, or unsubstituted or substituted 6-amino-9H-purin-9-yl.

In some embodiments $W_d$ is one of the following:

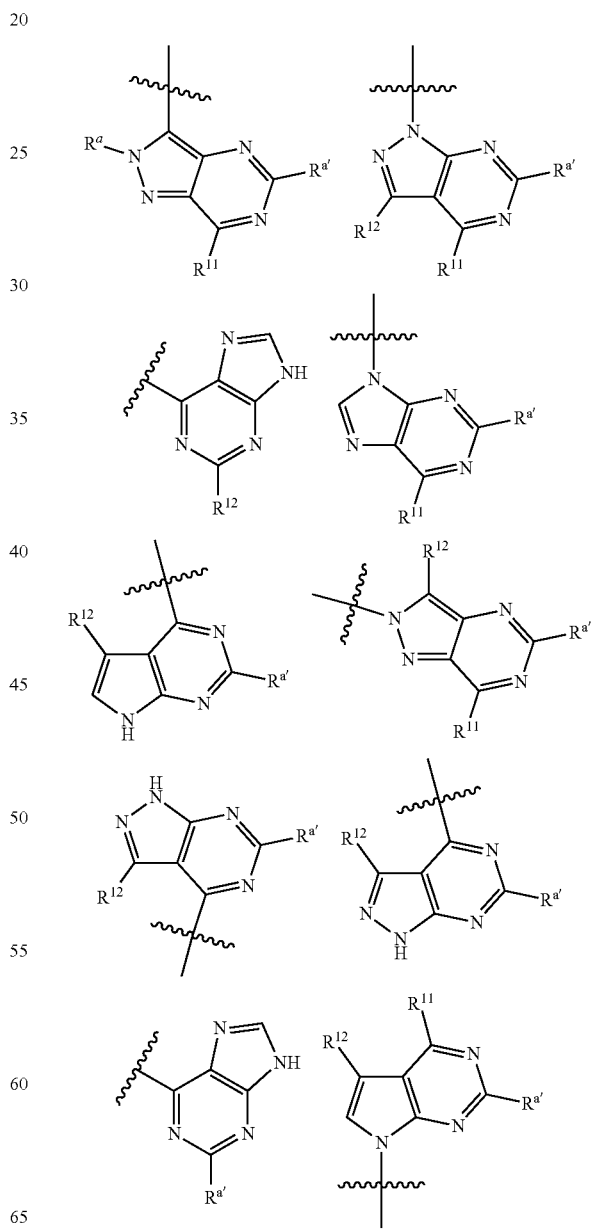

-continued

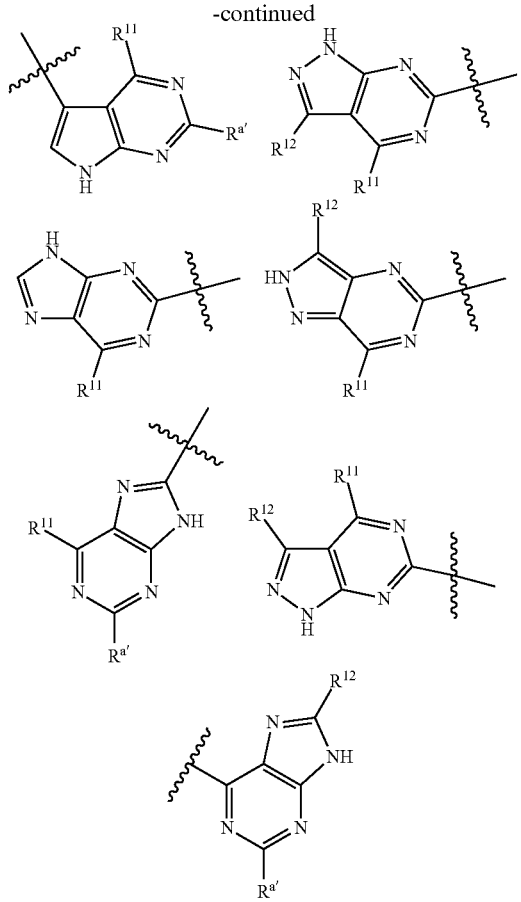

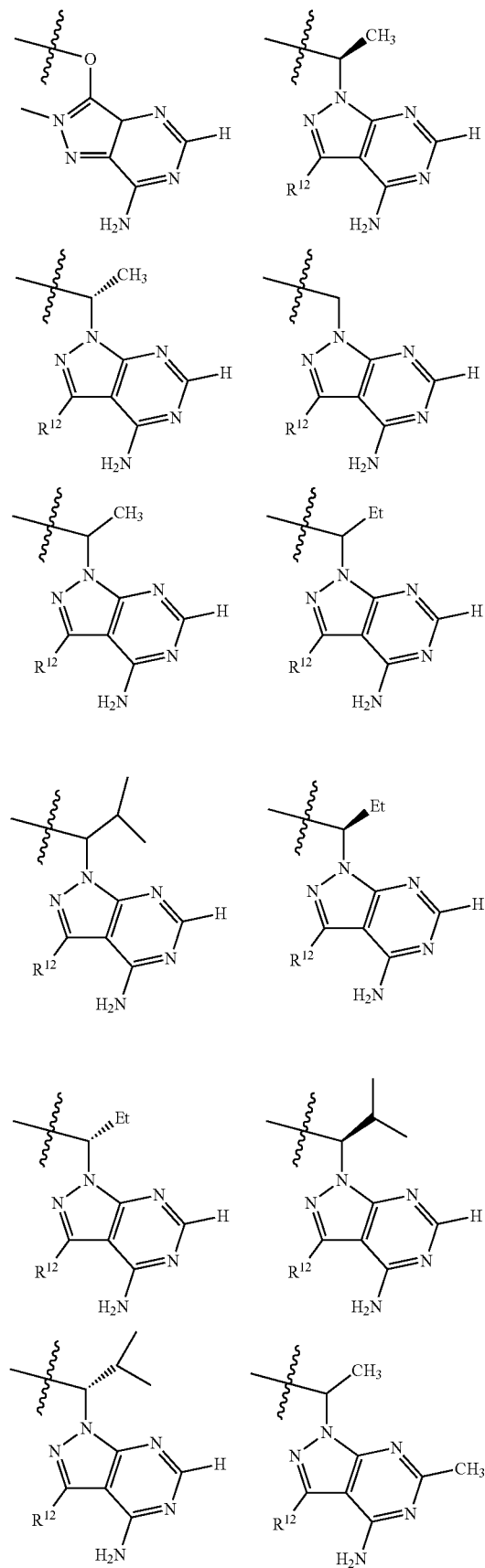

wherein $R^{a'}$ is hydrogen, halo, phosphate, urea, a carbonate, unsubstituted or substituted amino, unsubstituted or substituted alkyl, unsubstituted or substituted alkenyl, unsubstituted or substituted alkynyl, unsubstituted or substituted cycloalkyl, unsubstituted or substituted heteroalkyl, or unsubstituted or substituted heterocycloalkyl;

$R^{11}$ is hydrogen, unsubstituted or substituted alkyl, halo (which includes —I, —F, —Cl, or —Br), unsubstituted or substituted amino, unsubstituted or substituted amido, hydroxy, or unsubstituted or substituted alkoxy, phosphate, unsubstituted or substituted urea, or carbonate; and $R^{12}$ is H, unsubstituted or substituted alkyl, unsubstituted or substituted cyano, unsubstituted or substituted alkynyl, unsubstituted or substituted alkenyl, halo, unsubstituted or substituted aryl, unsubstituted or substituted heteroaryl, unsubstituted or substituted heterocycloalkyl, unsubstituted or substituted cycloalkyl, unsubstituted or substituted amino, carboxylic acid, unsubstituted or substituted alkoxycarbonyl, unsubstituted or substituted amido, unsubstituted or substituted acyl, or unsubstituted or substituted sulfonamido.

In some embodiments of $W_d$ of the compounds of Formula I, when $R^{a'}$ is alkyl, alkynyl, cycloalkyl, heteroalkyl, or heterocycloalkyl, it is substituted by phosphate, urea, or carbonate.

In some embodiments of $W_d$ of the compounds of Formula I, when $R^{11}$ is alkyl, amino, amido, hydroxy, or alkoxy, it is substituted by phosphate, urea, or carbonate.

In some embodiments of the compound of Formula I, —X—Y—$W_4$ is one of the following moieties:

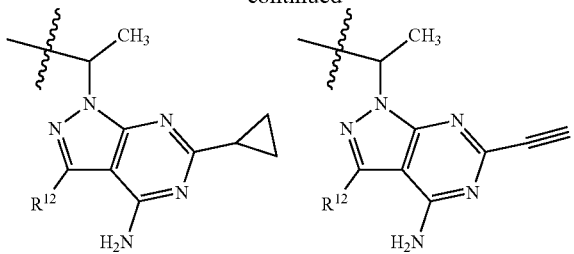
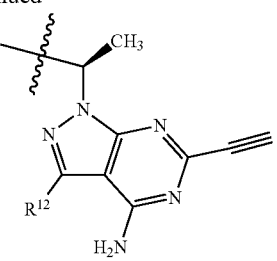
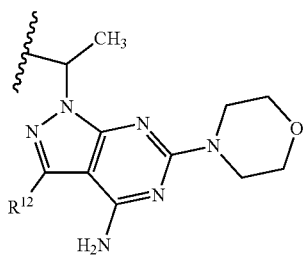
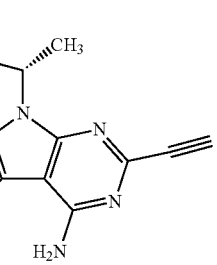
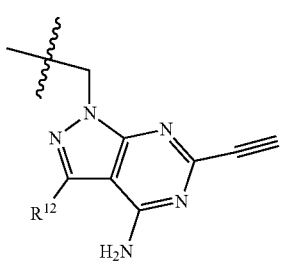
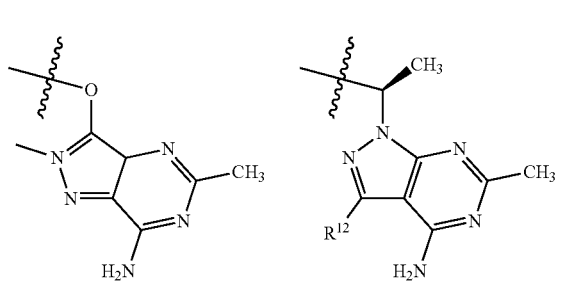
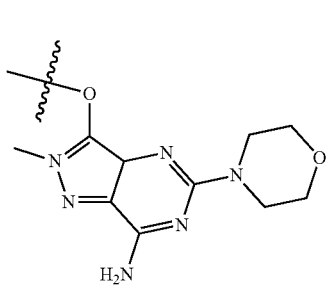
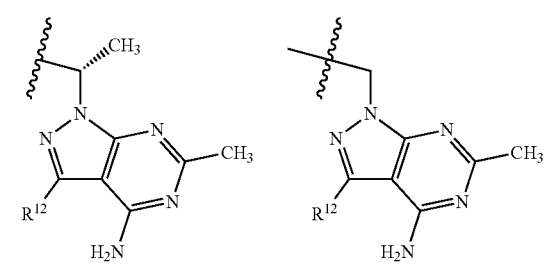
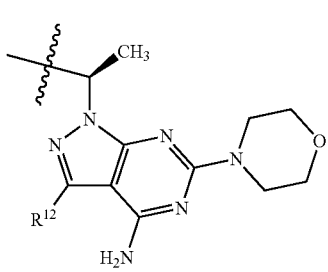
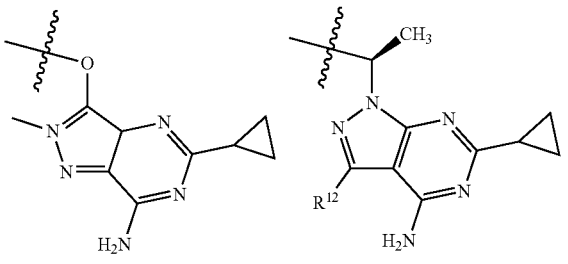
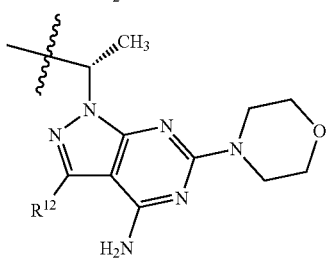
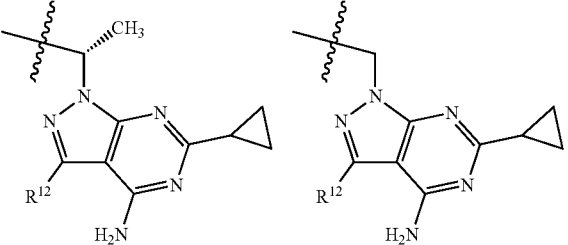
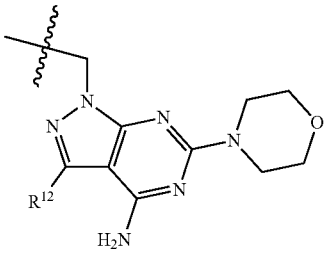
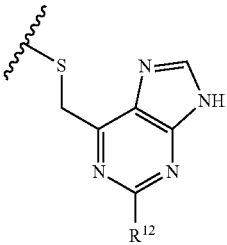

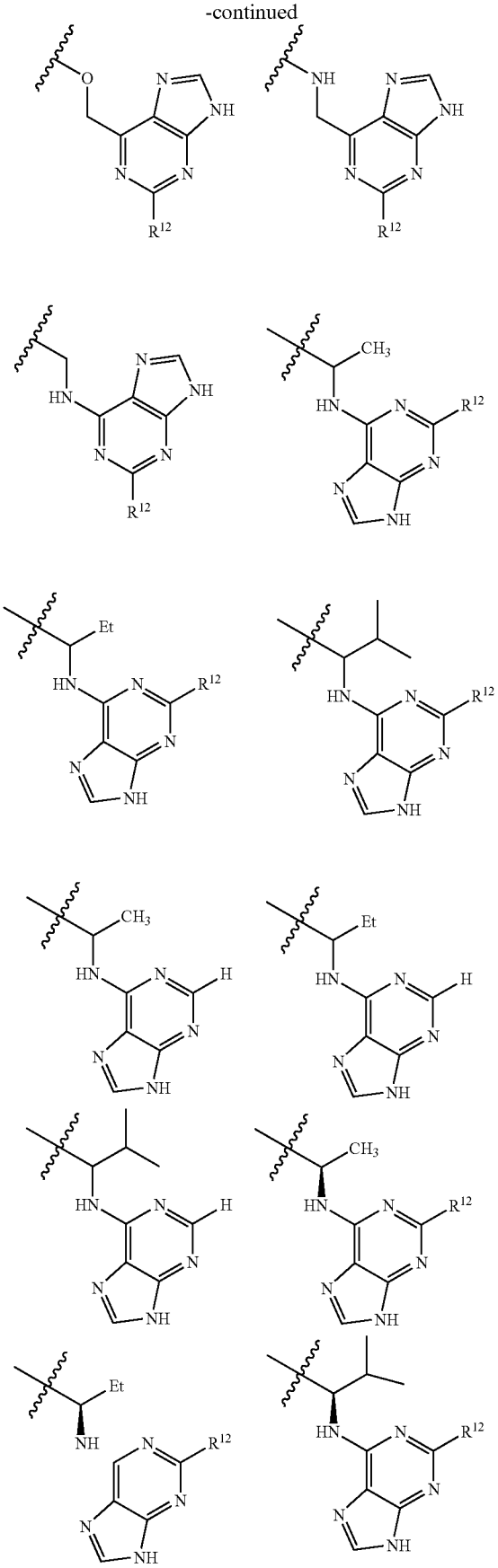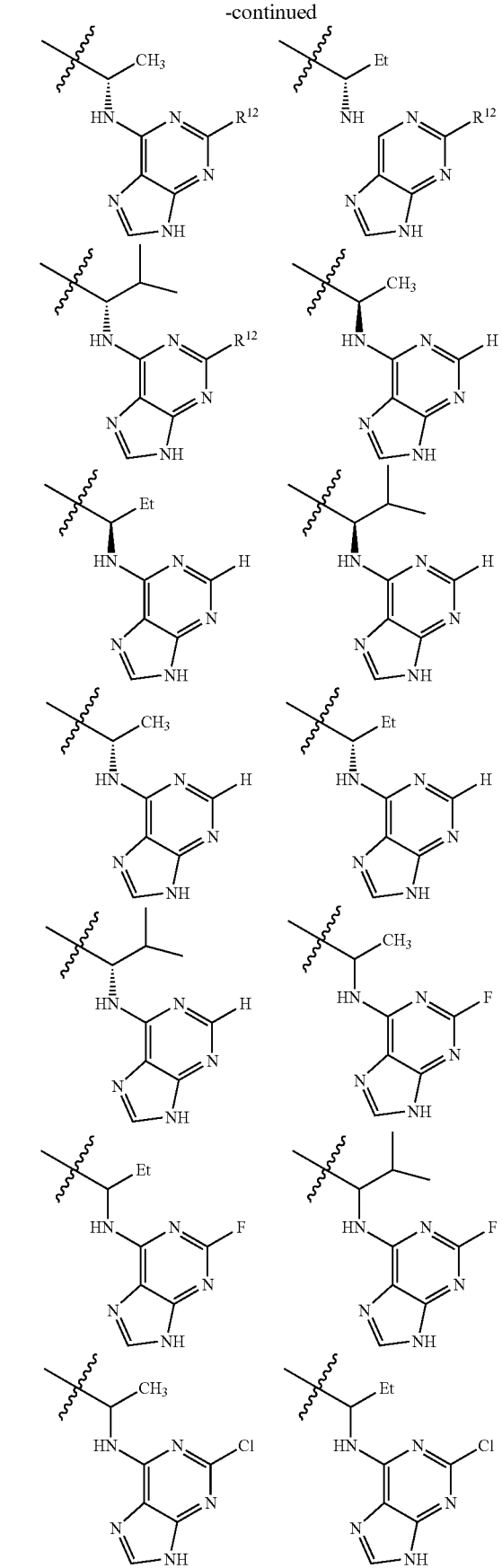

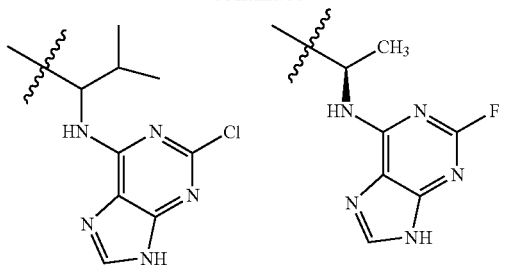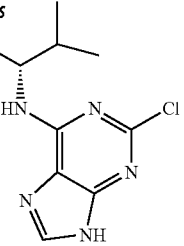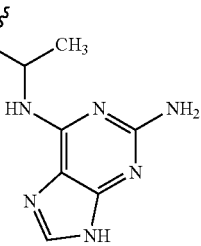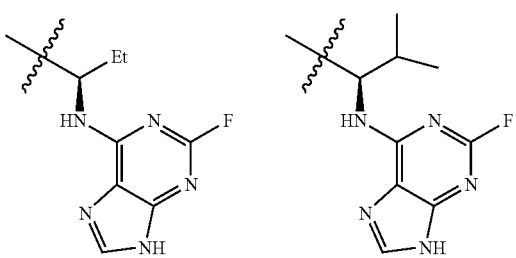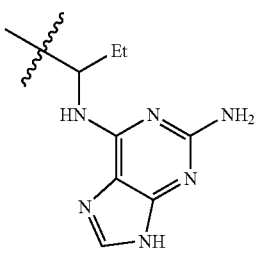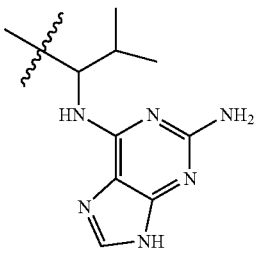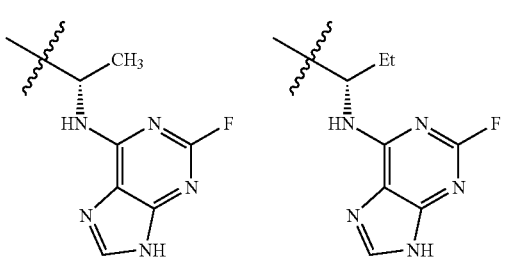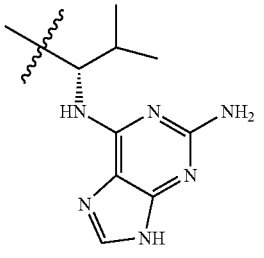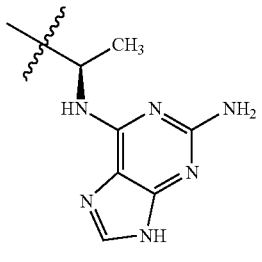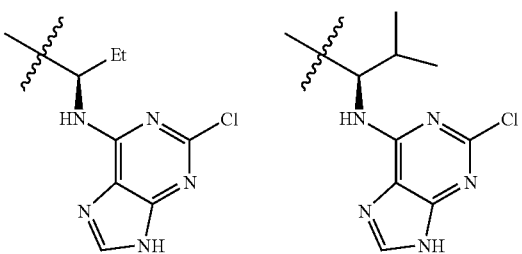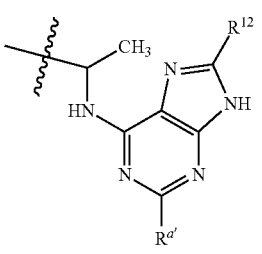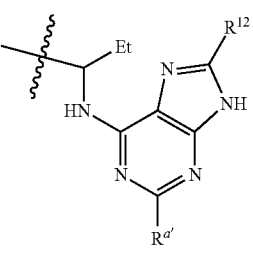

-continued
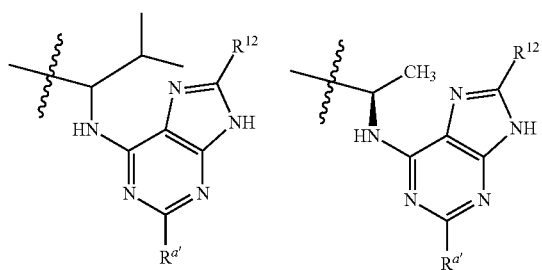
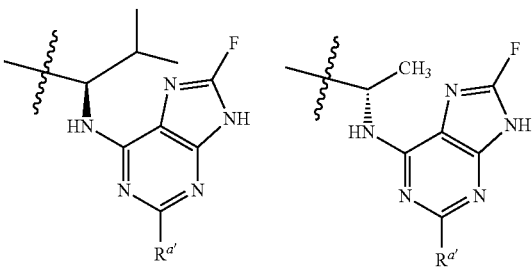
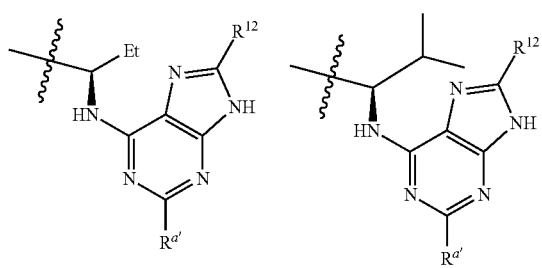
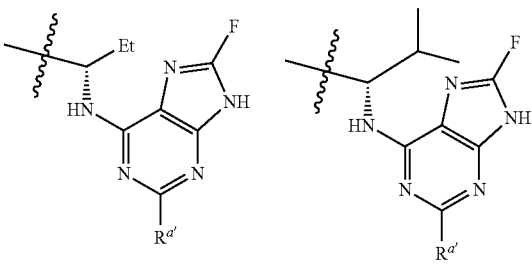
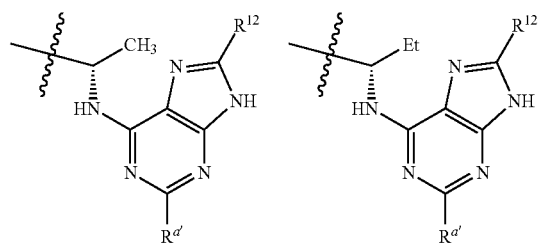
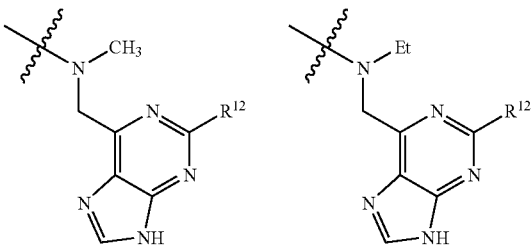
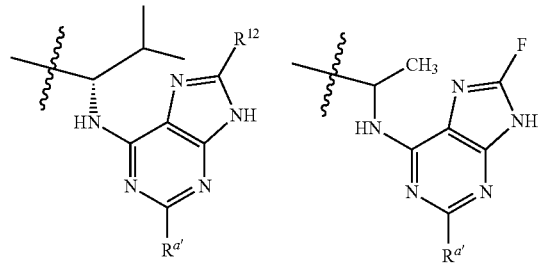
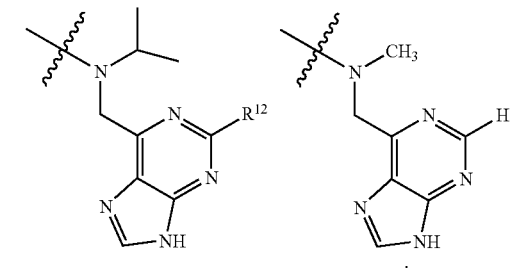
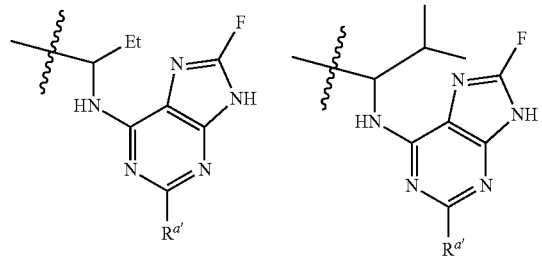
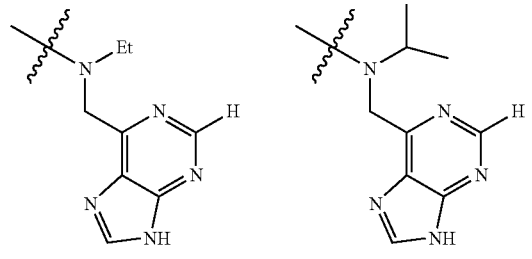
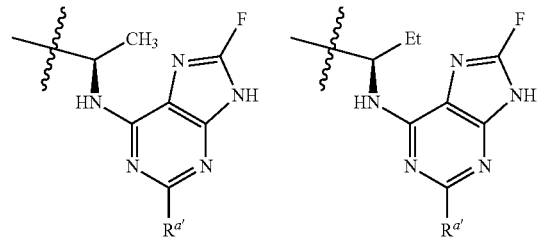
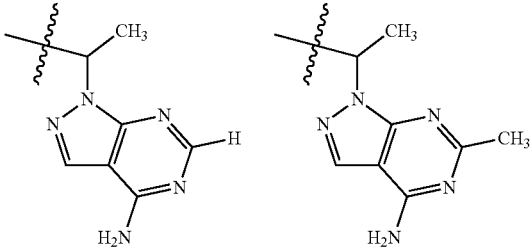

71 -continued
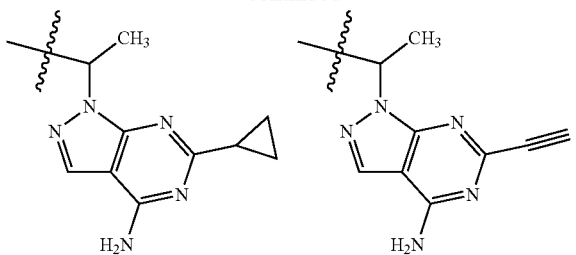
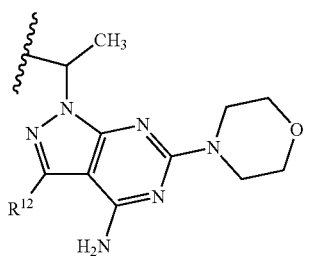
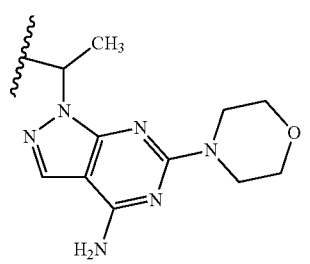
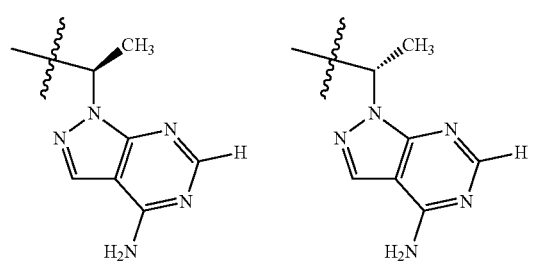
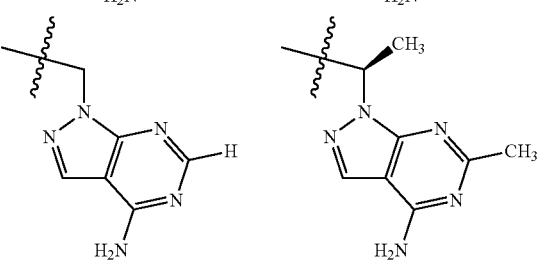
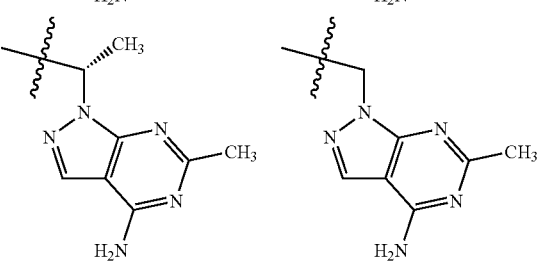
72 -continued
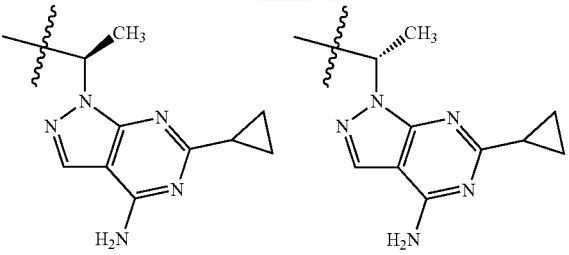
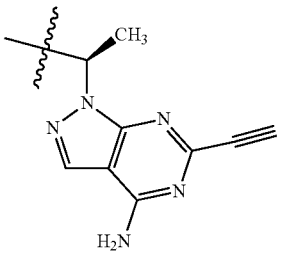
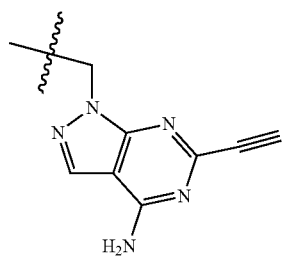
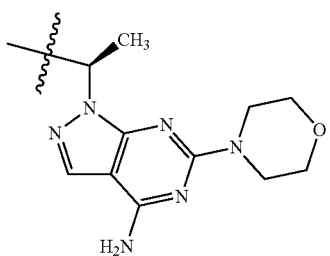
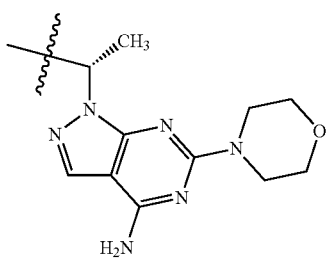
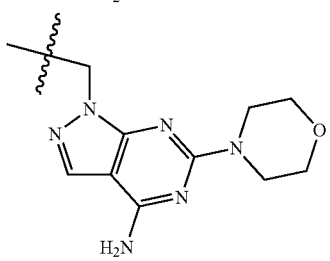

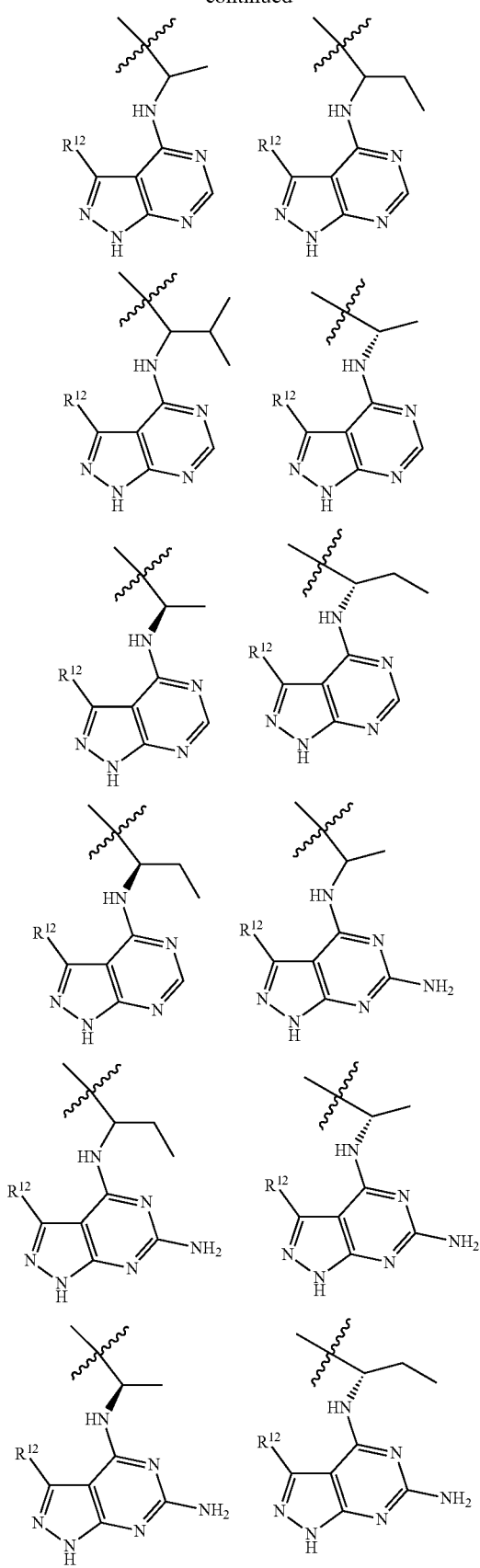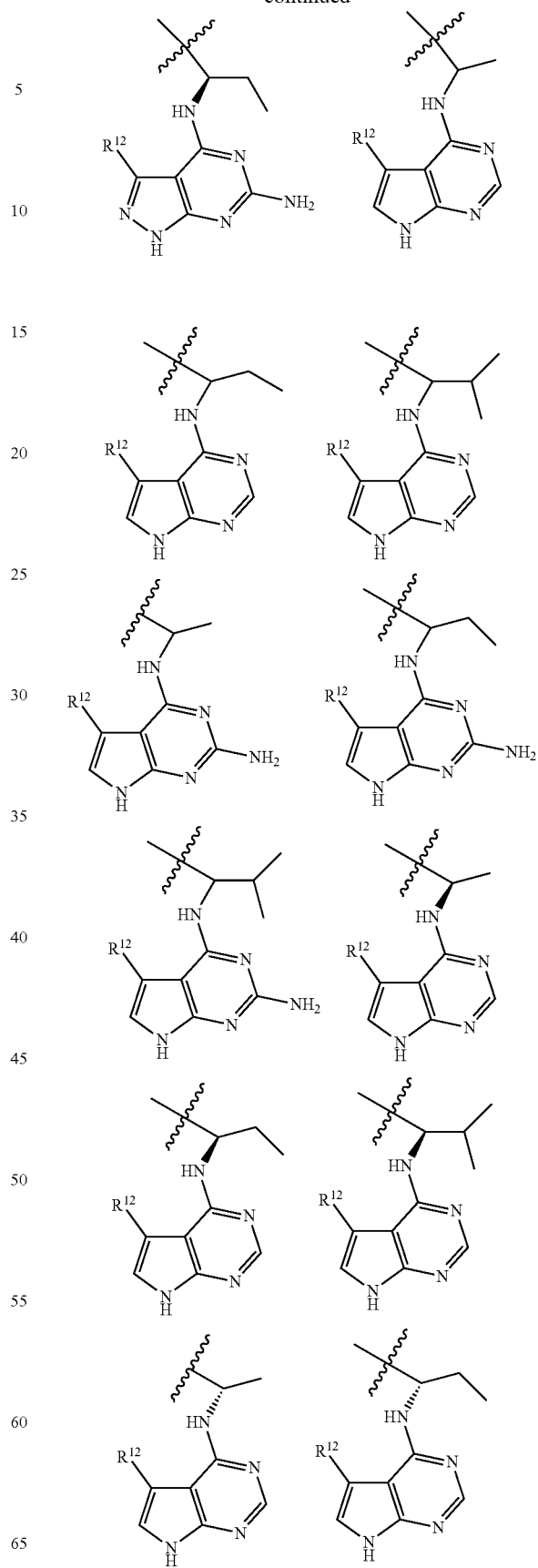

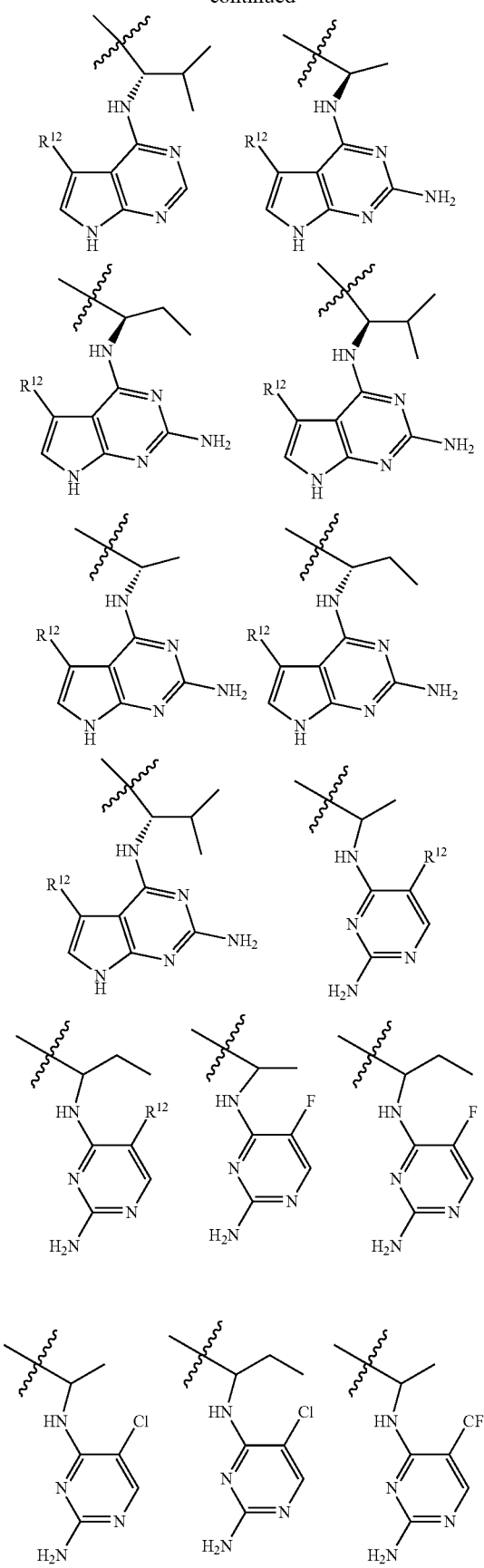
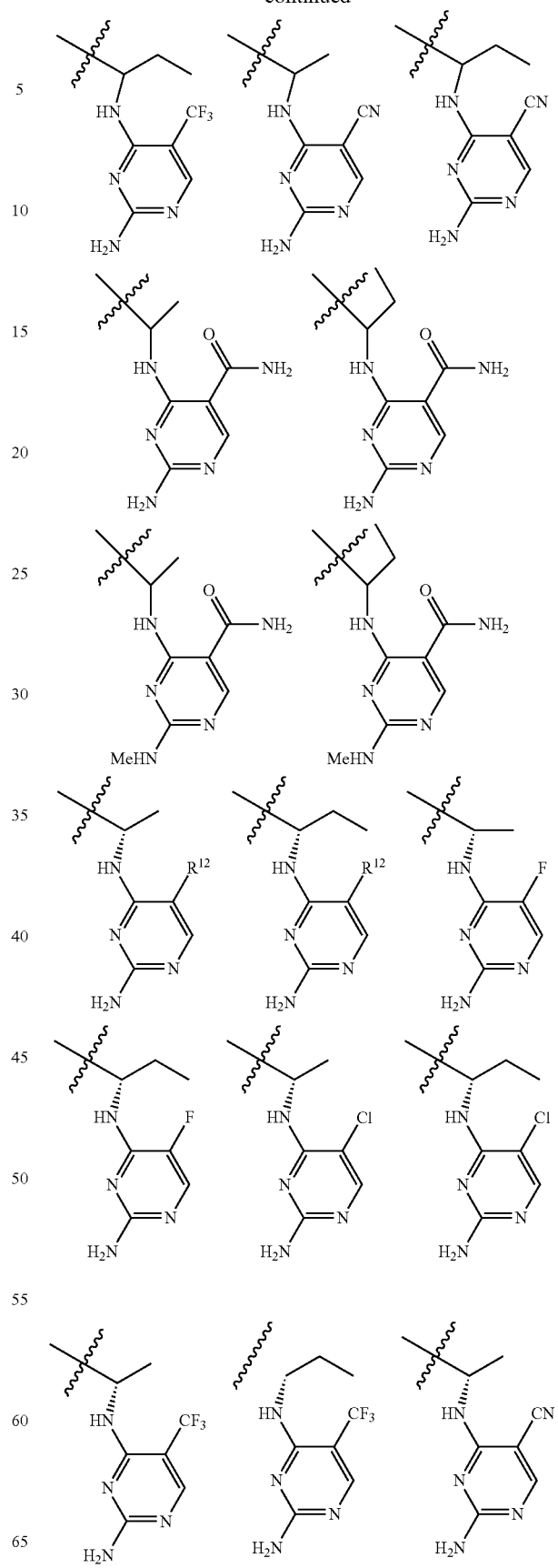

-continued
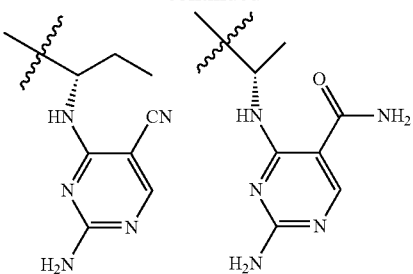
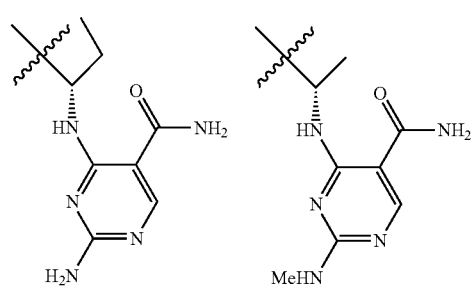
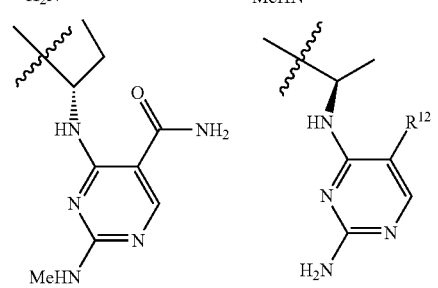
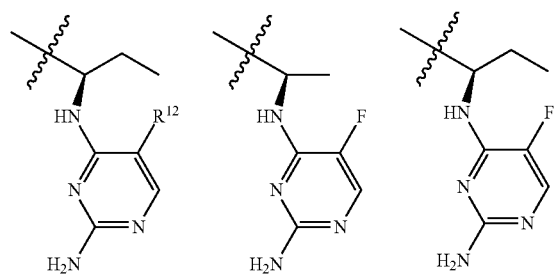
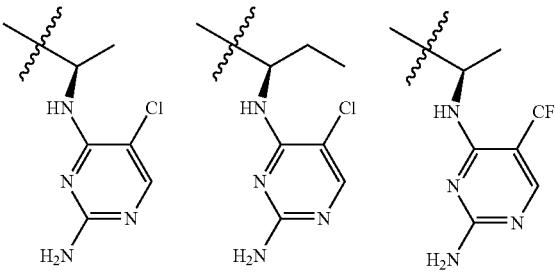
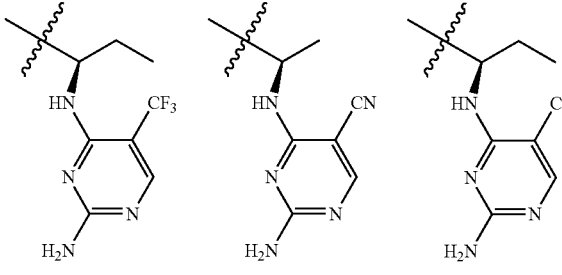
-continued
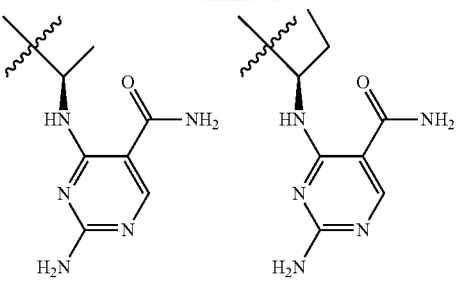
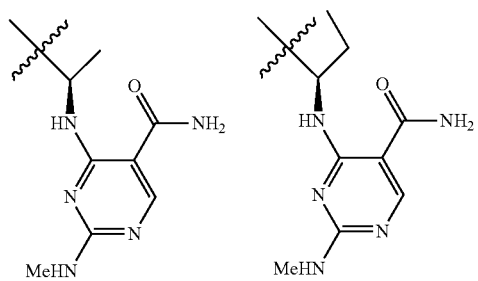
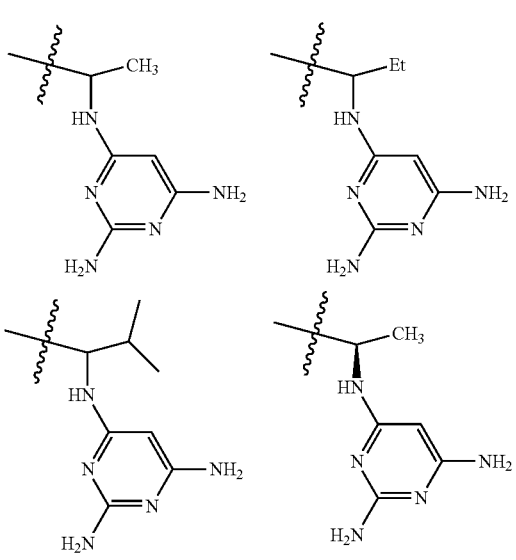
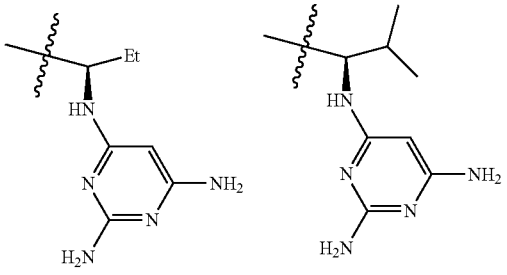
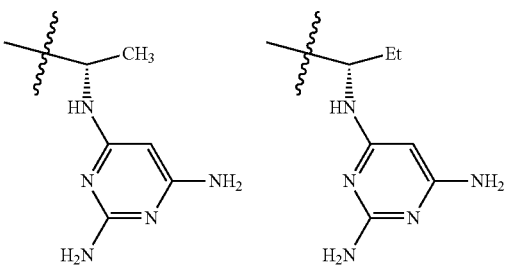

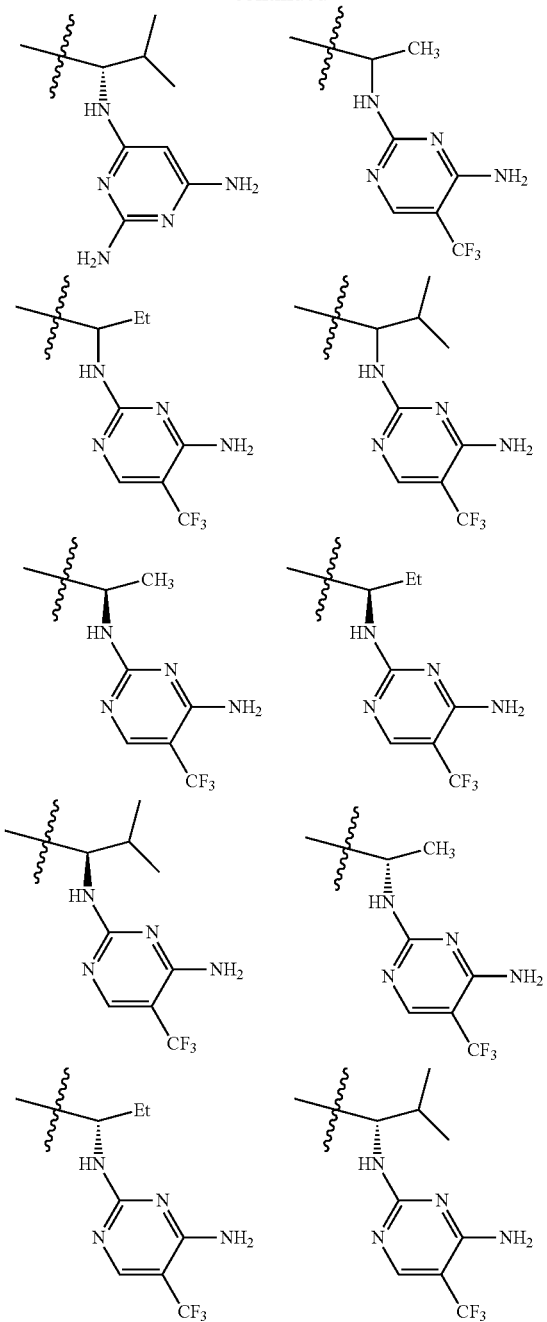

atom, $R^{12}$ is heterocycloalkyl with one sulfur ring atom, 5 membered heterocycloalkyl, 6 membered heterocycloalkyl, saturated heterocycloalkyl, unsaturated heterocycloalkyl, heterocycloalkyl having an unsaturated moiety connected to the heterocycloalkyl ring, heterocycloalkyl substituted by oxo, and heterocycloalkyl substituted by two oxo. In some embodiments, $R^{12}$ is unsubstituted or substituted cycloalkyl, including but not limited to cyclopropyl, cyclobutyl, cyclopentyl, cyclohexyl, cycloalkyl substituted by one oxo, cycloalkyl having an unsaturated moiety connected to the cycloalkyl ring. In some embodiments, $R^2$ is unsubstituted or substituted amido, carboxylic acid, unsubstituted or substituted acyloxy, unsubstituted or substituted alkoxycarbonyl, unsubstituted or substituted acyl, or unsubstituted or substituted sulfonamido.

In some embodiments, when $R^{12}$ is alkyl, alkynyl, alkenyl, aryl, heteroaryl, heterocycloalkyl, or cycloalkyl, it is substituted with phosphate. In some embodiments, when $R^{12}$ is alkyl, alkynyl, alkenyl, aryl, heteroaryl, heterocycloalkyl, or cycloalkyl, it is substituted with urea. In some embodiments, when $R^2$ is alkyl, alkynyl, alkenyl, aryl, heteroaryl, heterocycloalkyl, or cycloalkyl, it is substituted with carbonate.

In some embodiments, when $R^{12}$ is alkyl, alkynyl, alkenyl, aryl, heteroaryl, heterocycloalkyl, cycloalkyl, alkoxycarbonyl, amido, acyloxy, acyl, or sulfonamido, it is substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido can itself be substituted.

In some embodiments of the compound of Formula I, $R^{12}$ of $W_d$ is one of the following moieties:

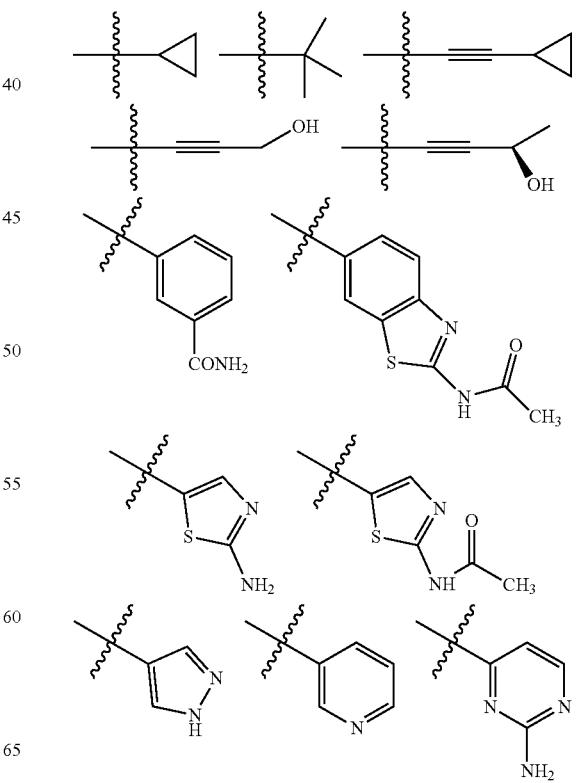

In some embodiments of the compound of Formula I, $R^{12}$ is a member of the group consisting of hydrogen, cyano, halo, unsubstituted or substituted alkyl, unsubstituted or substituted alkynyl, and unsubstituted or substituted alkenyl. In some embodiments, $R^{12}$ is unsubstituted or substituted aryl. In some embodiments, $R^{12}$ is unsubstituted or substituted heteroaryl, which includes but is not limited to heteroaryl having a 5 membered ring, heteroaryl having a six membered ring, heteroaryl with at least one nitrogen ring atom, heteroaryl with two nitrogen ring atoms, monocylic heteroaryl, and bicylic heteroaryl. In some embodiments, $R^{12}$ is unsubstituted or substituted heterocycloalkyl, which includes but is not limited to heterocycloalkyl with one nitrogen ring atom, heterocycloalkyl with one oxygen ring -continued
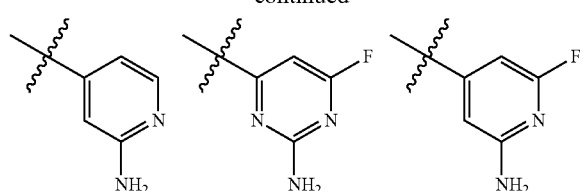
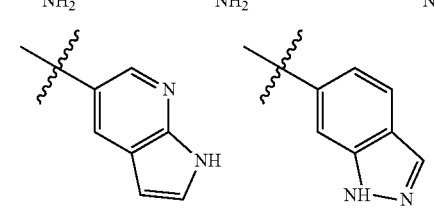
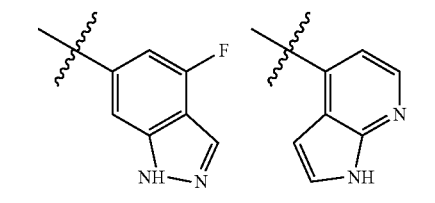
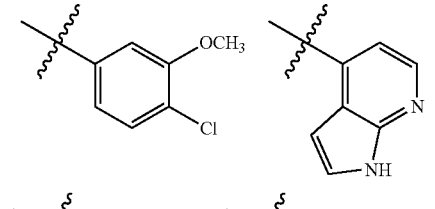
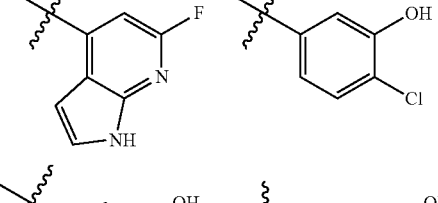
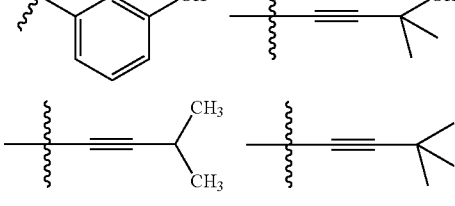
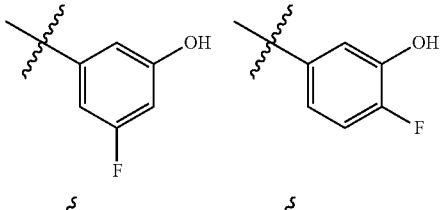

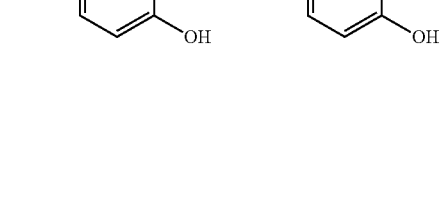
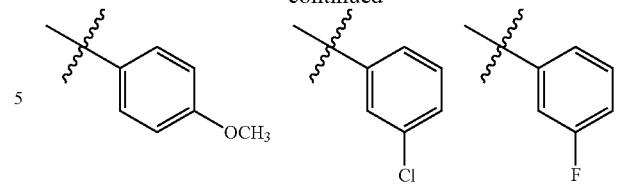
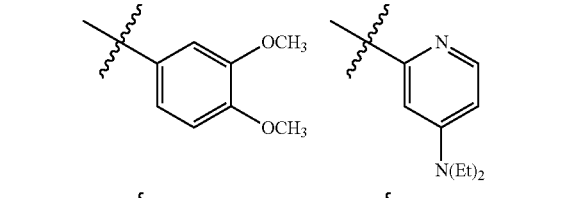
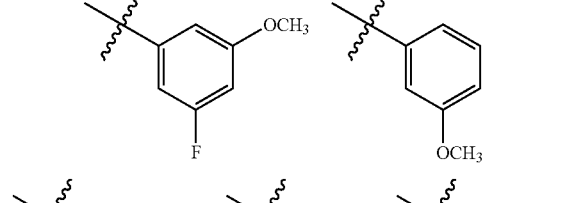
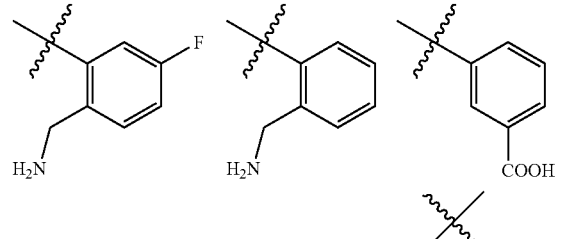
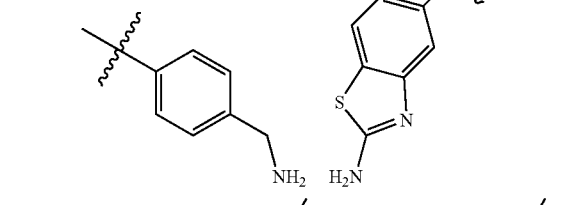

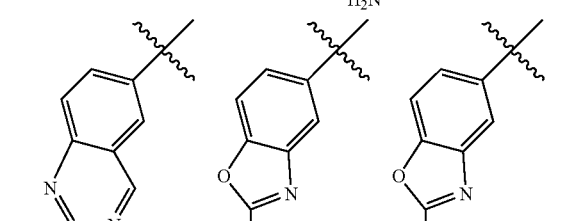
—CN, —Br, —Cl, —I, —H, —Me, —Et,
—i-Pr, 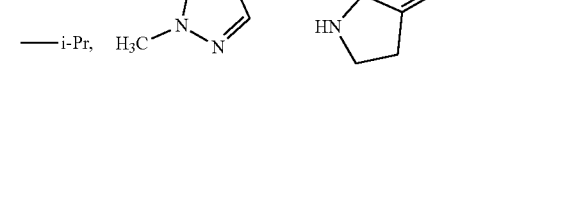

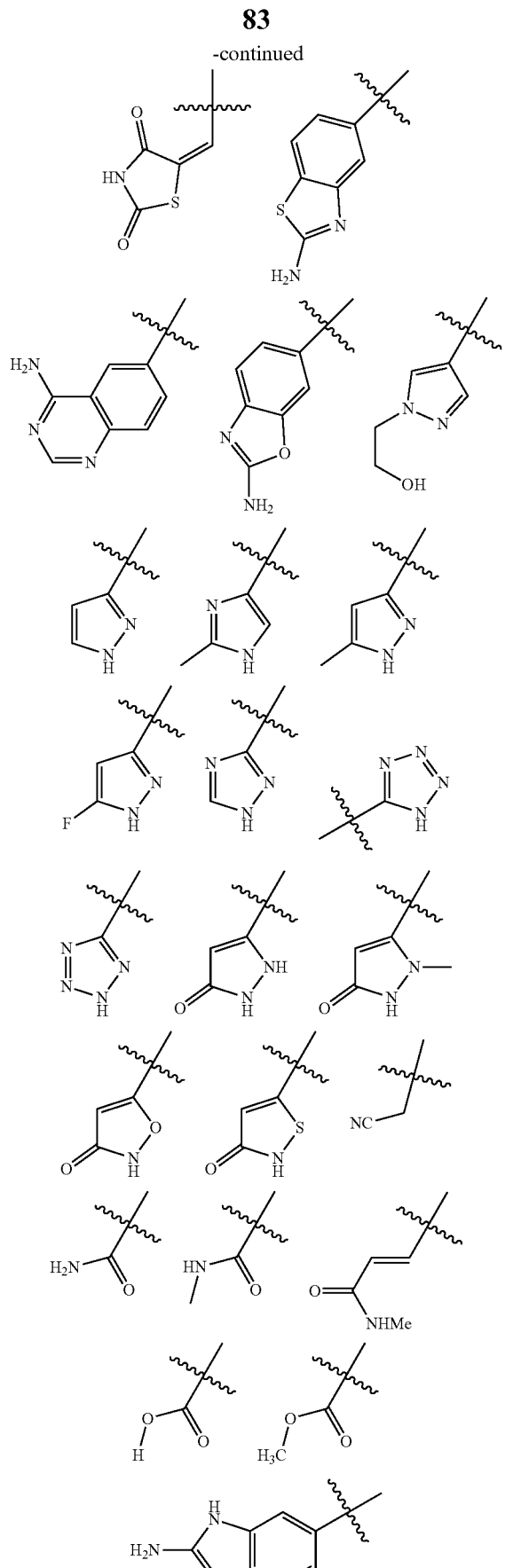

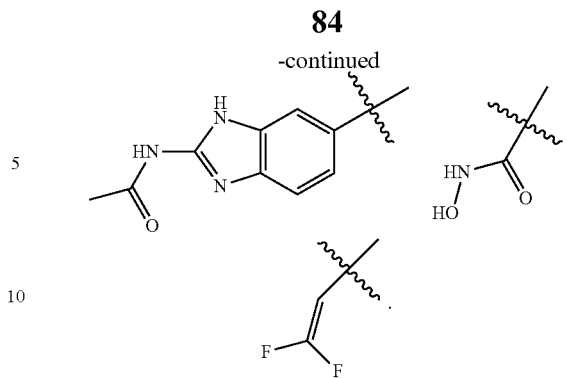

In some embodiments of the compound of Formula I, $W_d$ is a pyrazolopyrimidine of Formula III:

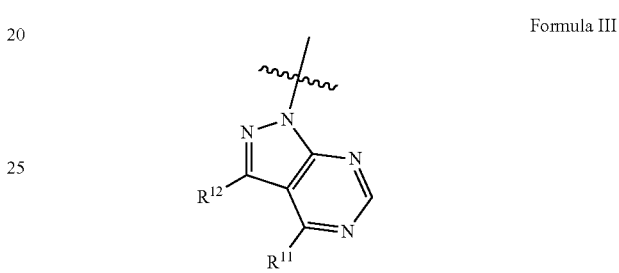

Formula III wherein $R^{11}$ is H, alkyl, halo, amino, amido, hydroxy, or alkoxy, and $R^{12}$ is H, alkyl, alkynyl, alkenyl, halo, aryl, heteroaryl, heterocycloalkyl, or cycloalkyl. In some embodiments, $R^{11}$ is amino and $R^{12}$ is H, alkyl, alkynyl, alkenyl, halo, aryl, heteroaryl, heterocycloalkyl, or cycloalkyl. In some embodiments, $R^{11}$ is amino and $R^{12}$ is alkyl, halo, aryl, heteroaryl, heterocycloalkyl, or cycloalkyl. In some embodiments, $R^{11}$ is amino and $R^{12}$ is monocyclic heteroaryl. In some embodiments, $R^{11}$ is amino and $R^{12}$ is bicyclic heteroaryl. In some embodiments, $R^{11}$ is amino and $R^{12}$ is cyano, amino, carboxylic acid, acyloxy, alkoxycarbonyl, or amido.

In some embodiments, the compound of Formula I is a compound having a structure of Formula IV:

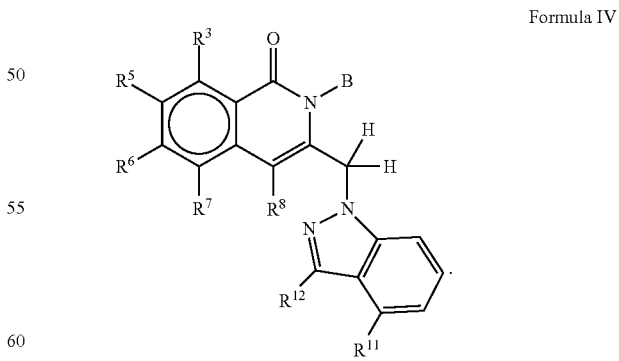

Formula IV

In some embodiments of the compound of Formula IV, $R^{11}$ is H, alkyl, halo, amino, amido, hydroxy, or alkoxy, and $R^{12}$ is H, alkyl, alkynyl, alkenyl, halo, aryl, heteroaryl, heterocycloalkyl, or cycloalkyl. In another embodiment, $R^{11}$ is amino and $R^{12}$ is alkyl, alkenyl, heteroaryl, aryl, or heterocycloalkyl. In some embodiments, $R^{11}$ is amino and $R^{12}$ is cyano, amino, carboxylic acid, alkoxycarbonyl, or amido.

In some embodiments, the compound of Formula IV is a compound of Formula IV-A:

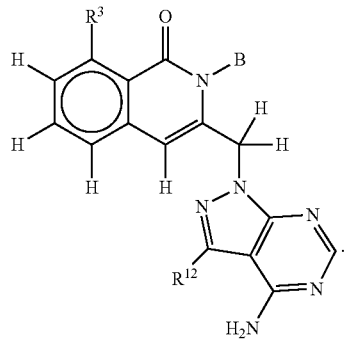

Formula IV-A

Also provided herein are compounds of Formula I having a structure of any of Formulae V, V-A1, V-A2, V-B, VI, VI-A, VII-A1, VII-A2, VIII-A1, VIII-A2, IX-A1, IX-A2, X-A1, X-A2, XI-A1, XI-A2, XII-A, XII-A1, XII-A2, XIII-A, XIII-A1, XIII-A2, XIV-A, XIV-A1, XIV-A2, XV-A, XV-A1, XV-A2, XVI-A, XVI-A1, XVI-A2, XVII-A, XVII-A1, XVII-A2, XVIII-A, XVIII-A1, or XVIII-A2:

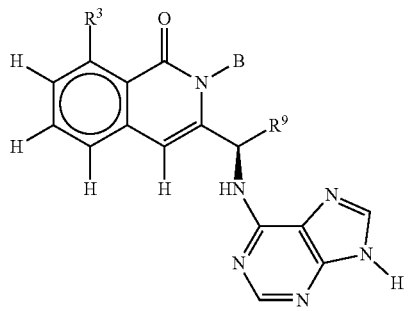

Formula V

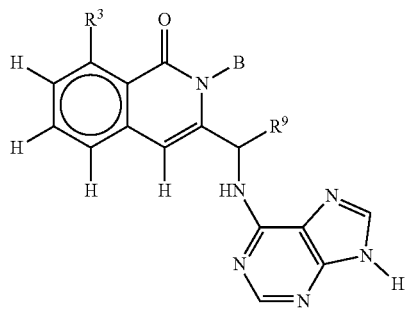

Formula V-A

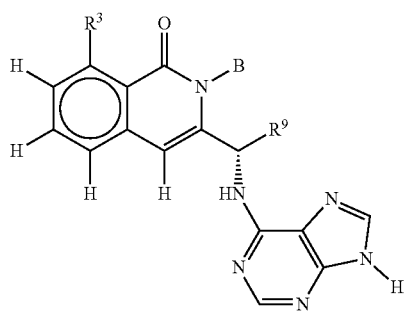

Formula V-A1

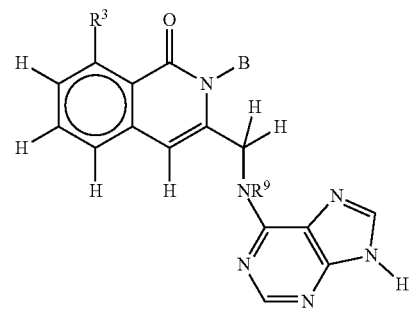

Formula V-A2

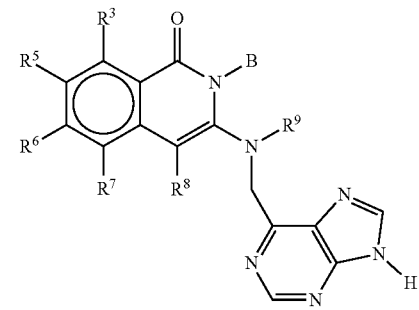

Formula V-B

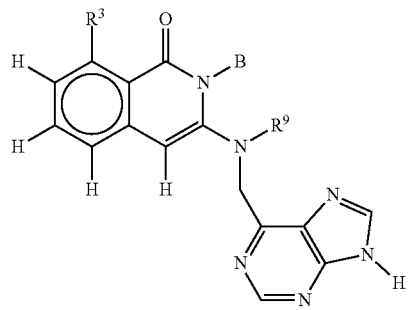

Formula VI

Formula VI-A

Formula VII-A
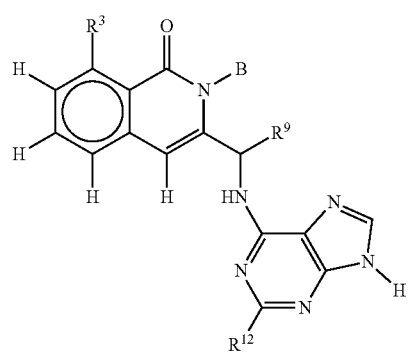
Formula VII-A1
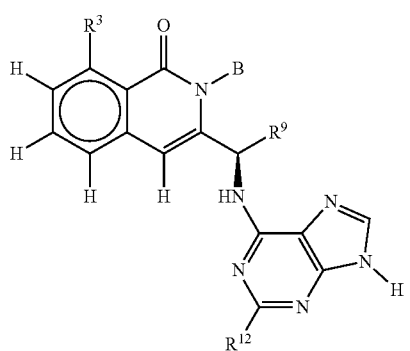
Formula VII-A2
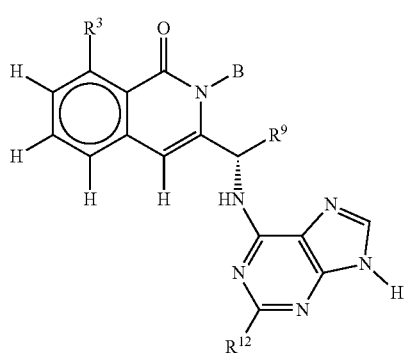
Formula VIII-A
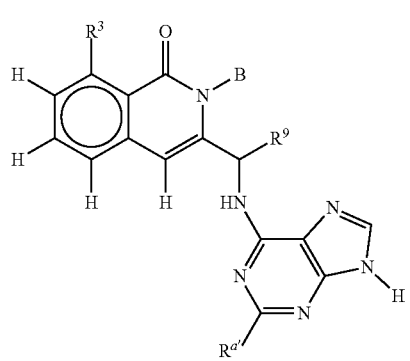
Formula VIII-A1
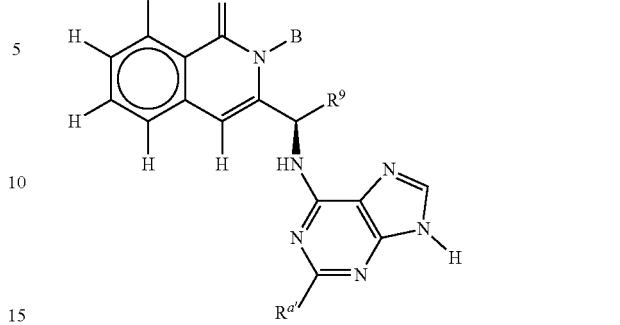
Formula VIII-A2
Formula IX-A
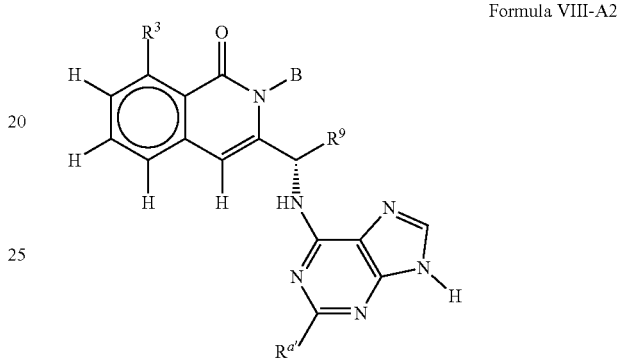
Formula IX-A1
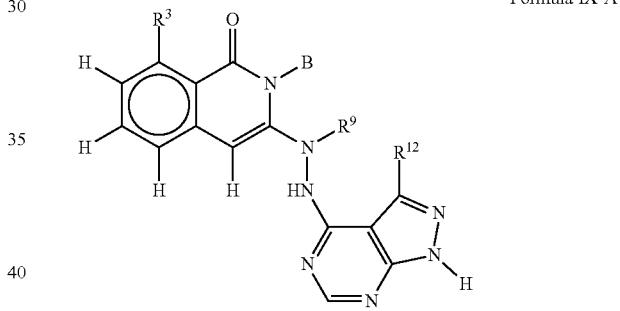
Formula IX-A2
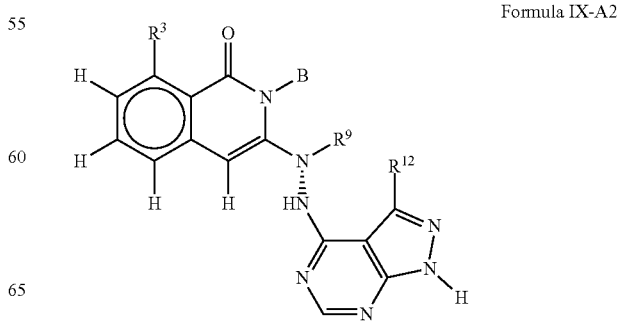

US 12,213,983 B2
-continued
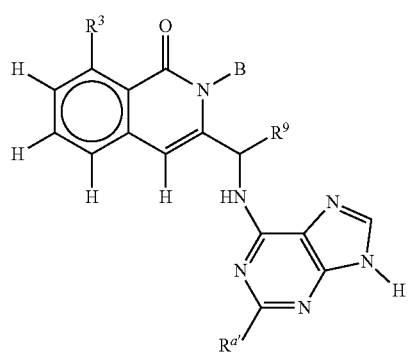
Formula X-A
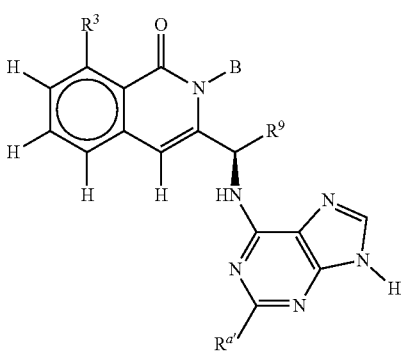
Formula X-A1
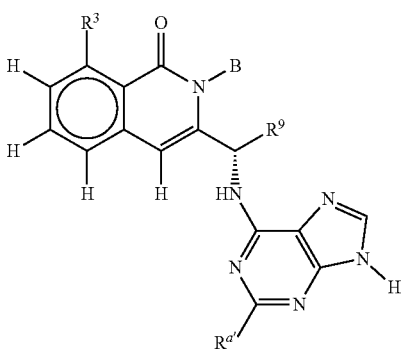
Formula X-A2
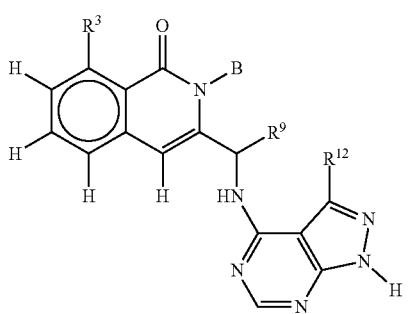
Formula XI-A
-continued
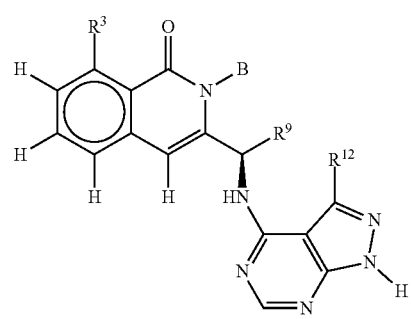
Formula XI-A1
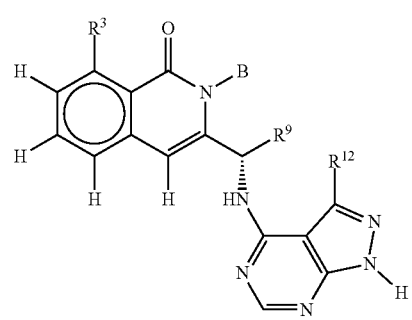
Formula XI-A2
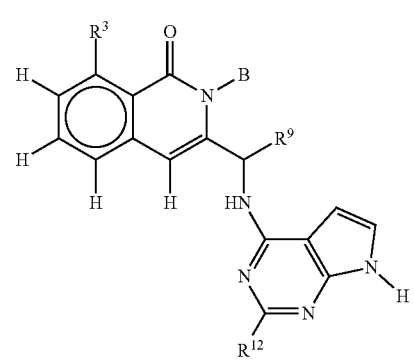
Formula XII-A
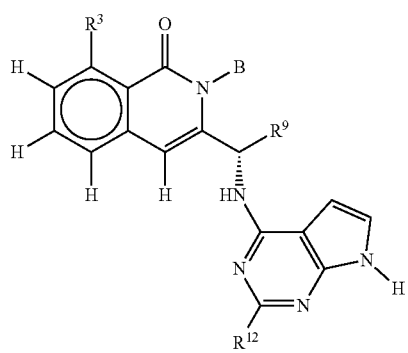
Formula XII-A1

Formula XII-A2
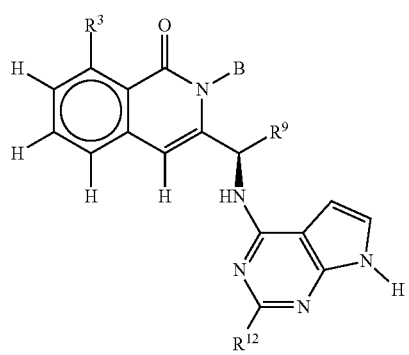
Formula XIV-A
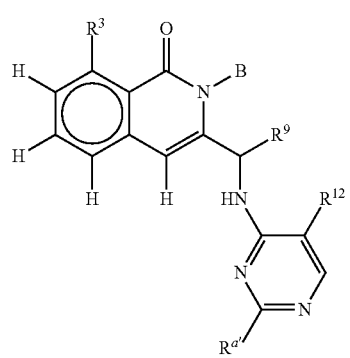
Formula XIII-A
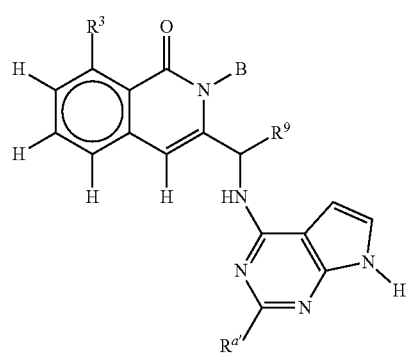
Formula XIV-A1
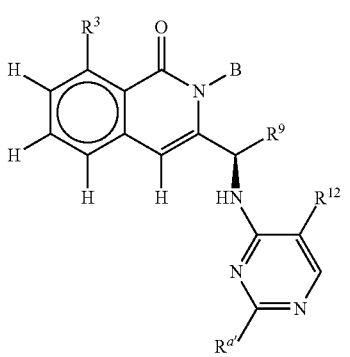
Formula XIII-A1
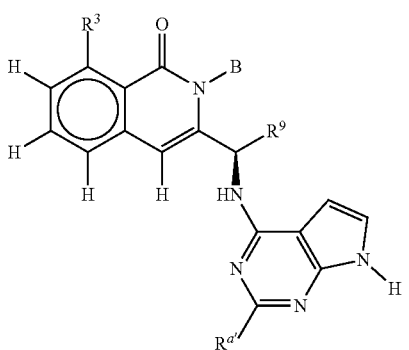
Formula XIV-A2
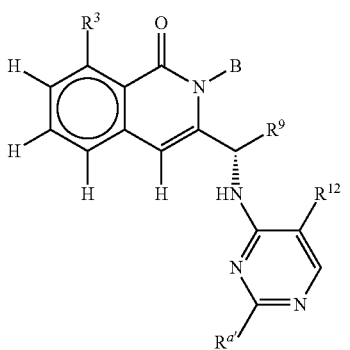
Formula XIII-A2
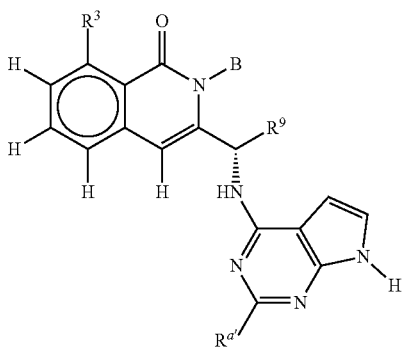
Formula XV-A
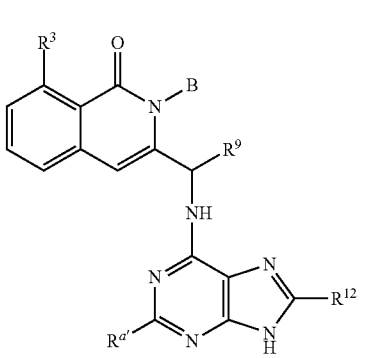

Formula XV-A1
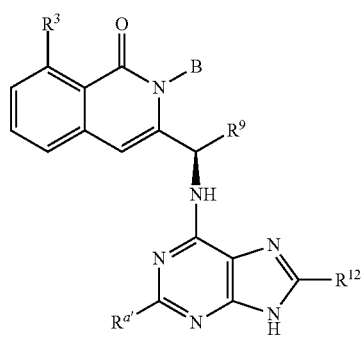
Formula XV-A2
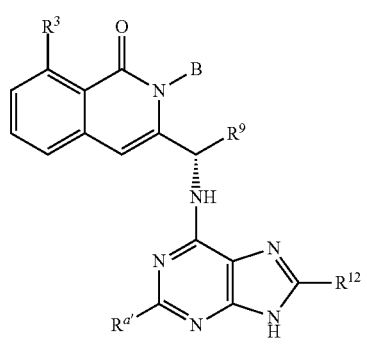
Formula XVI-A
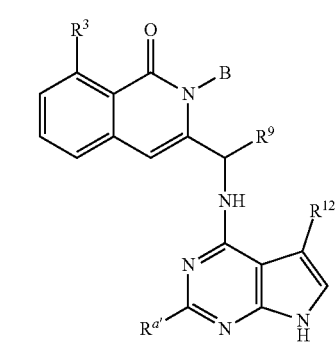
Formula XVI-A1
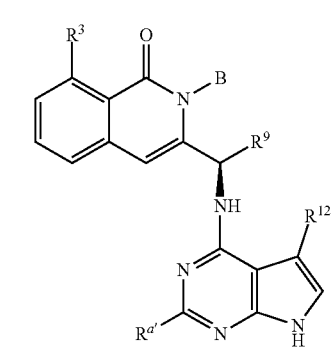
Formula XVI-A2
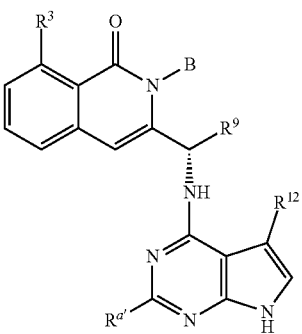
Formula XVII-A
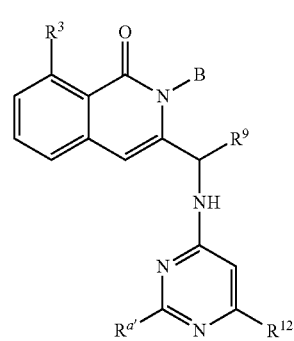
Formula XVII-A1
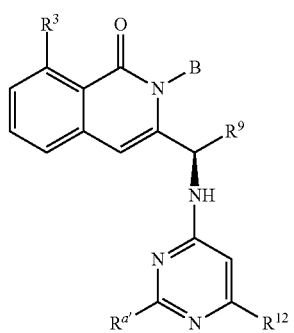
Formula XVII-A2
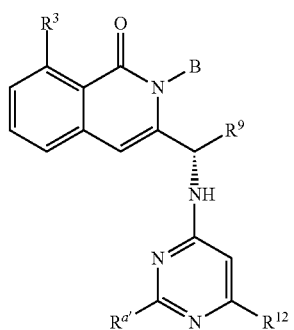

-continued

Formula XVIII-A

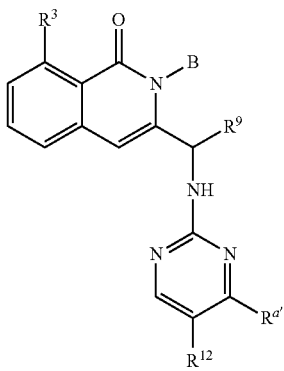

Formula XVIII-A1

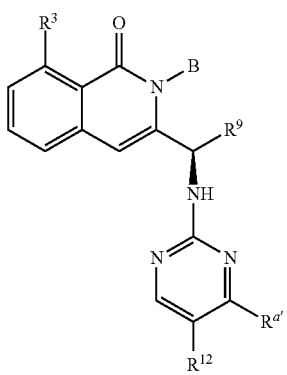

Formula XVIII-A2

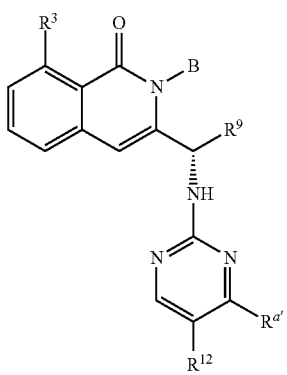

Any of the disclosed elements and their substituents for the compounds of Formula I can be used in any combination.

In one aspect, for the compounds of Formula I, $R_3$ is H, $CH_3$, $CF_3$, Cl, or F; and B is a moiety of Formula II:

Formula II

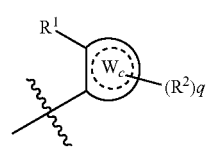

wherein $W_c$ is aryl, heteroaryl, heterocycloalkyl, or cycloalkyl; $R^1$ is H, —F, —CN, —CH$_3$, isopropyl, —CF$_3$, —OCH$_3$, nitro, or phosphate; $R^2$ is halo, hydroxy, cyano, or nitro; q is an integer of 0, 1, 2, 3, or 4; $R^5$, $R^6$, $R^7$, and $R^8$ are H; X is absent or $(CH_2)_z$; z is 1; Y is absent or —N(R$^9$)—; $R^9$ is hydrogen, $C_1$-$C_{10}$alkyl, $C_3$-$C_7$cycloalkyl, or $C_2$-$C_{10}$heteroalkyl; at least one of X and Y is present; and $W_d$ is pyrazolopyrimidine or purine. In some embodiments, when X and Y are present and $W_d$ is purine, then —N(R$^9$)— is —NH—.

In another aspect, for the compounds of Formula I, $R_3$ is H, CH$_3$, CF$_3$, Cl, or F; B is a moiety of Formula II which is aryl, heteroaryl, heterocycloalkyl, or cycloalkyl; $R^1$ is H, —F, —CN, —CH$_3$, isopropyl, —CF$_3$, —OCH$_3$, nitro, or phosphate; $R^2$ is halo, hydroxy, cyano, or nitro; q is 0, 1 or 2; $R^5$, $R^6$, $R^7$, and $R^8$ are H; X is absent or $(CH_2)_z$; z is 1; Y is absent or —N(R$^9$)—; $R^9$ is hydrogen, methyl, or ethyl; at least one of X and Y is present; $W_d$ is:

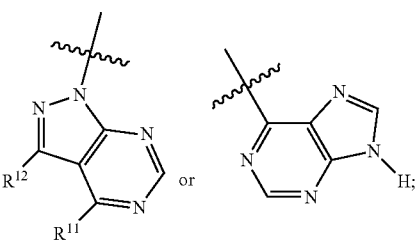

$R^{11}$ is amino; and $R^{12}$ is H, alkyl, alkynyl, alkenyl, halo, aryl, heteroaryl, heterocycloalkyl, or cycloalkyl. In some embodiments, when X and Y are present and $W_d$ is purine, then —N(R$^9$)— is —NH—.

In another aspect, for the compounds of Formula I, $R_3$ is H, CH$_3$, CF$_3$, Cl, or F; B is a moiety of Formula II, which is aryl, heteroaryl, heterocycloalkyl, or cycloalkyl, $R^1$ is H, —F, —Cl, —CN, —CH$_3$, isopropyl, —CF$_3$, —OCH$_3$, nitro, or phosphate; $R^2$ is halo, hydroxy, cyano, or nitro; q is 0, 1 or 2; X is $(CH_2)_z$; z is 1; $R^5$, $R^6$, $R^7$, and $R^8$ are H; Y is absent and $W_d$ is:

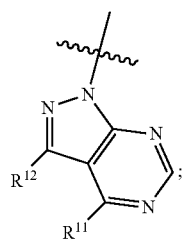

$R^{11}$ is amino; and $R^{12}$ is H, alkyl, alkynyl, alkenyl, halo, aryl, heteroaryl, heterocycloalkyl, or cycloalkyl.

In another aspect, $R_3$ is H, CH$_3$, CF$_3$, Cl, or F; B is aryl, heteroaryl, heterocycloalkyl, or cycloalkyl, $R^1$ is H, —F, —Cl, —CN, —CH$_3$, isopropyl, —CF$_3$, —OCH$_3$, nitro, or phosphate; $R^2$ is halo, hydroxy, cyano, or nitro; q is 0, 1 or 2; $R^5$, $R^6$, $R^7$, and $R^8$ are H; X is $(CH_2)_z$; z is 1; X is —$(CH_2)_z$; z is 1; Y is —N(R$^9$)—; $R^9$ is hydrogen, methyl, or ethyl; and $W_d$ is

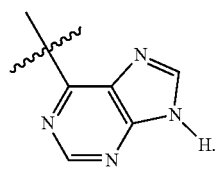

In some embodiments, Y is —NH—.

In another aspect, for the compounds of Formula I R$_3$ is aryl, heteroaryl, H, CH$_3$, CF$_3$, Cl, or F; B is alkyl or a moiety of Formula II;

wherein W$_c$ is aryl, heteroaryl, heterocycloalkyl, or cycloalkyl, and q is an integer of 0, 1, 2, 3, or 4; R$^1$ is H, —F, —Cl, —CN, —CH$_3$, isopropyl, —CF$_3$, —OCH$_3$, nitro, or phosphate; R$^2$ is halo, hydroxy, cyano, nitro, or phosphate; q is 0, 1 or 2; R$^5$, R$^6$, R$^7$, and R$^8$ are H; X is absent or (CH(R$^9$))$_z$; z is an integer of 1, 2, 3, or 4; Y is absent, —N(R$^9$)—, or —N(R$^9$) CH(R$^9$)—; R$^9$ is hydrogen, alkyl, cycloalkyl, or heteroalkyl; at least one of X and Y is present; and W$_d$ is pyrazolopyrimidine or purine. In some embodiments, when X is present, Y is —N(R$^9$)—, and W$_d$ is purine, then Y is —NH—.

In another aspect, for the compounds of Formula I, R$_3$ is aryl, heteroaryl, H, CH$_3$, CF$_3$, Cl, or F; B is alkyl or a moiety of Formula II which is aryl, heteroaryl, heterocycloalkyl, or cycloalkyl, R$^1$ is H, —F, —Cl, —CN, —CH$_3$, isopropyl, —CF$_3$, —OCH$_3$, nitro, or phosphate; R$^2$ is halo, hydroxy, cyano, nitro, or phosphate; q is 0, 1 or 2; R$^5$, R$^6$, R$^7$, and R$^8$ are H; X is absent or (CH(R$^9$))$_z$; z is an integer of 1, 2, 3, or 4; Y is absent, —N(R$^9$)—, or —N(R$^9$) CH(R$^9$)—; R$^9$ is hydrogen, methyl, or ethyl; at least one of X and Y is present; W$_d$ is:

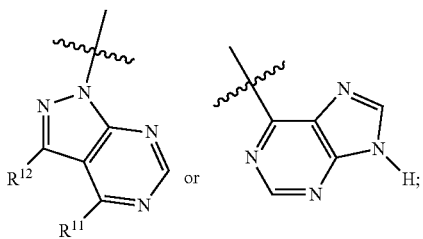

R$^{11}$ is amino; and R$^{12}$ is H, alkyl, alkynyl, alkenyl, halo, aryl, heteroaryl, heterocycloalkyl, cycloalkyl, cyano, amino, carboxylic acid, alkoxycarbonyl, or amido. In some embodiments, when X is present, Y is —N(R$^9$)—, and W$_d$ is purine, then Y is —NH—.

In another aspect, for the compounds of Formula I, R$_3$ is H, CH$_3$, CF$_3$, Cl, or F; B is alkyl or a moiety of Formula II which is aryl, heteroaryl, heterocycloalkyl, or cycloalkyl, R$^1$ is H, —F, —Cl, —CN, —CH$_3$, isopropyl, —CF$_3$, —OCH$_3$, nitro, or phosphate; R$^2$ is halo, hydroxy, cyano, nitro, or phosphate; q is 0, 1 or 2; R$^5$, R$^6$, R$^7$, and R$^8$ are H; X is (CH(R$^9$))$_z$; z is an integer of 1; Y is absent-; R$^9$ is hydrogen, methyl, or ethyl; W$_d$ is:

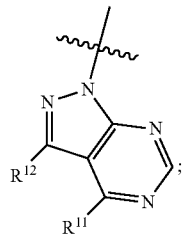

R$^{11}$ is amino; and R$^{12}$ is H, alkyl, alkynyl, alkenyl, halo, aryl, heteroaryl, heterocycloalkyl, cycloalkyl, cyano, amino, carboxylic acid, alkoxycarbonyl, or amido.

In another aspect, for the compounds of Formula I, R$_3$ is aryl, heteroaryl, H, CH$_3$, CF$_3$, Cl, or F; B is a moiety of Formula II which is aryl, heteroaryl, heterocycloalkyl, or cycloalkyl, R$^1$ is H, —F, —Cl, —CN, —CH$_3$, isopropyl, —CF$_3$, —OCH$_3$, nitro, or phosphate; R$^2$ is halo, hydroxy, cyano, nitro, or phosphate; q is 0, 1 or 2; R$^5$, R$^6$, R$^7$, and R$^8$ are H; X is absent or (CH(R$^9$))$_z$; z is an integer of 1; Y is absent, —N(R$^9$)—, or —N(R$^9$) CH(R$^9$)—; R$^9$ is hydrogen, methyl, or ethyl; at least one of X and Y is present, and W$_d$ is:

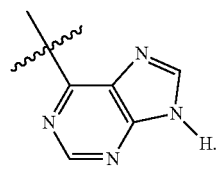

In some embodiments, when X is present, Y is —N(R$^9$)—, and W$_d$ is purine, then Y is —NH—.

In another aspect, for the compounds of Formula I, R$_3$ is aryl, heteroaryl, H, CH$_3$, CF$_3$, Cl, or F; B is a moiety of Formula II which is aryl, heteroaryl, heterocycloalkyl, or cycloalkyl, R$^1$ is H, —F, —Cl, —CN, —CH$_3$, isopropyl, —CF$_3$, —OCH$_3$, nitro, or phosphate; R$^2$ is halo, hydroxy, cyano, nitro, or phosphate; q is 0, 1 or 2; R$^5$, R$^6$, R$^7$, and R$^8$ are H; X is absent; Y is —N(R$^9$) CH(R$^9$)—; R$^9$ is hydrogen, methyl, or ethyl; and W$_d$ is

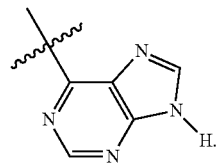

In another aspect, for the compounds of Formula I, R$_3$ is aryl, heteroaryl, H, CH$_3$, CF$_3$, Cl, or F; B is alkyl or a moiety of Formula II which is aryl, heteroaryl, heterocycloalkyl, or cycloalkyl, R$^1$ is H, —F, —Cl, —CN, —CH$_3$, isopropyl, —CF$_3$, —OCH$_3$, nitro, or phosphate; R$^2$ is halo, hydroxy, cyano, nitro, or phosphate; q is 0, 1 or 2; R$^5$, R$^6$, R$^7$, and R$^8$ are H; X is absent or (CH(R$^9$))$_z$; z is an integer of 1, 2, 3, or 4; Y is absent, —N(R$^9$)—, or —N(R$^9$) CH(R$^9$)—; R$^9$ is hydrogen, methyl, or ethyl; at least one of X and Y is present; W$_d$ is:

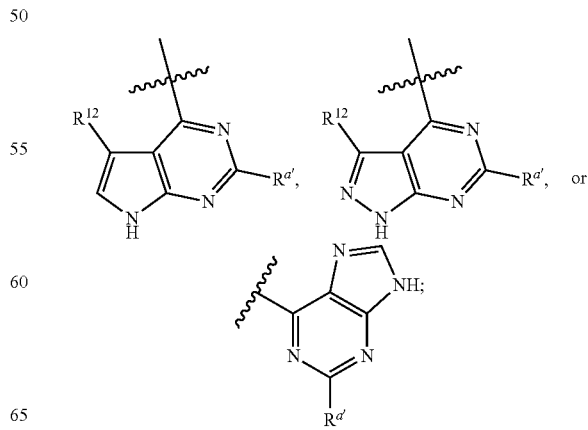

$R^{a'}$ is hydrogen, halo, or amino; and $R^{12}$ is H, alkyl, alkynyl, alkenyl, halo, aryl, heteroaryl, heterocycloalkyl, cycloalkyl, cyano, amino, carboxylic acid, alkoxycarbonyl, or amido. In some embodiments, when X is present, Y is —N($R^9$)—, and $W_d$ is purine, then Y is —NH—.

Additional exemplary compounds have a sub-structure of Formula IV-A.

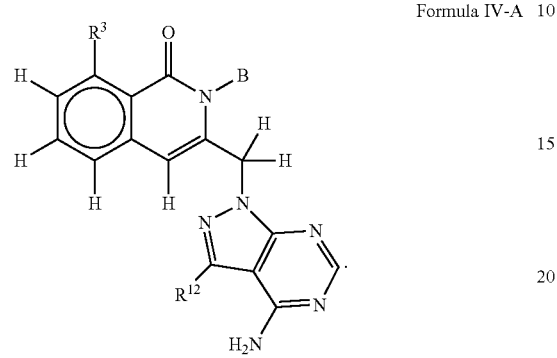

Formula IV-A

Some illustrative compounds of the present disclosure having a structure of Formula IV-A include those in which $R^3$ is —H, —Cl, —F, or —CH$_3$ in combination with any B moiety described in Table 1, and any $R^{12}$ as described in Table 2. A compound of Formula IV-A includes any combination of $R^3$, B, and $R^{12}$. Additional exemplary compounds of Formula IV-A are illustrated in Table 4.

TABLE 1

| Sub-class # | B |
| --- | --- |
| B-1 | cyclopentyl |
| B-2 | N-isopropyl piperidin-4-yl |
| B-3 | —CH(CH$_3$)2 |
| B-4 | 2-(CF$_3$)phenyl |
| B-5 | cyclopropyl |
| B-6 | 2-Cl-phenyl |

TABLE 1-continued

| Sub-class # | B |
| --- | --- |
| B-7 | 2-CH$_3$-phenyl |
| B-8 | 3-CH$_3$-pyridin-2-yl |
| B-9 | 2-ethyl-phenyl |
| B-10 | 2-F-phenyl |
| B-11 | N-methyl piperidin-4-yl |
| B-12 | 2-isopropyl-phenyl |
| B-13 | 2-MeO-phenyl |
| B-14 | 3-F-phenyl |
| B-15 | 2-HO-phenyl |

TABLE 1-continued
Illustrative B moieties of the compounds of Formula I.
| Sub-class # | B |
|---|---|
| B-16 | 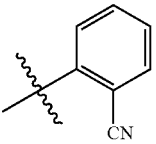 [SMILES: *c1ccccc1C#N] |
| B-17 | 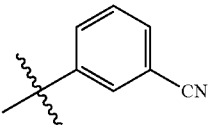 [SMILES: *c1cccc(C#N)c1] |
| B-18 | 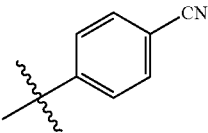 [SMILES: *c1ccc(C#N)cc1] |
| B-19 | 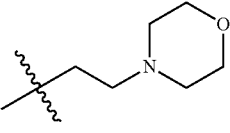 [SMILES: *CCN1CCOCC1] |
| B-20 | 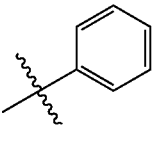 [SMILES: *c1ccccc1] |
| B-21 | 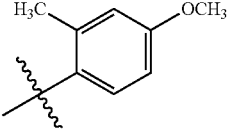 [SMILES: *c1ccc(OC)cc1C] |
| B-22 | 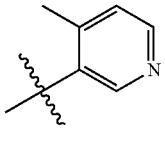 [SMILES: *c1cnccc1C] |
| B-23 | 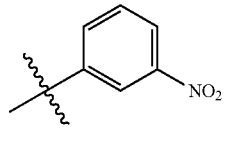 [SMILES: *c1cccc([N+](=O)[O-])c1] |
| B-24 | 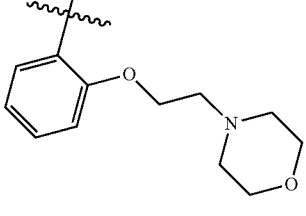 |
| B-25 | 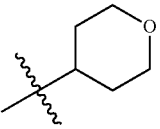 |
| B-26 | 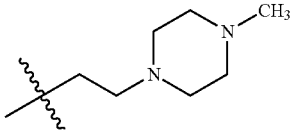 [SMILES: *CCN1CCN(C)CC1] |
| B-27 | 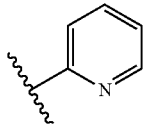 |
| B-28 | 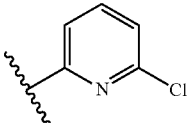 [SMILES: *c1cccc(Cl)n1] |
| B-29 | 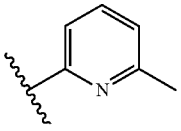 [SMILES: *c1cccc(C)n1] |
| B-30 | 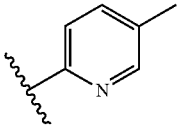 [SMILES: *c1ccc(C)cn1] |
| B-31 | 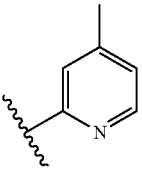 [SMILES: *c1cc(C)ccn1] |
| B-32 | 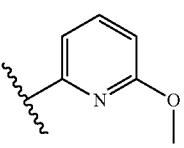 |
| B-33 | 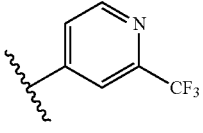 [SMILES: *c1ccnc(C(F)(F)F)c1] |
| B-34 | 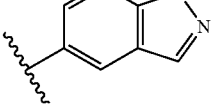 |

TABLE 1-continued
Illustrative B moieties of the compounds of Formula I.
| Sub-class # | B |
| --- | --- |
| B-35 | 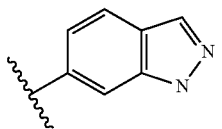 [SMILES: *c1ccc2cn[nH]c2c1] |
| B-36 | 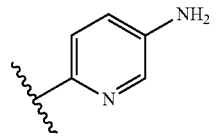 [SMILES: *c1ccc(N)cn1] |
| B-37 | 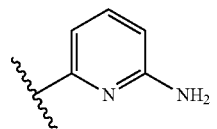 [SMILES: *c1cccc(N)n1] |
| B-38 | 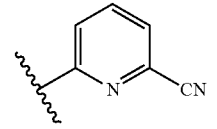 [SMILES: *c1cccc(C#N)n1] |
| B-39 | 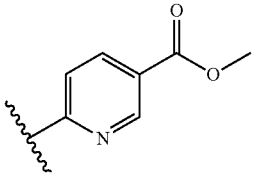 [SMILES: *c1ccc(C(=O)OC)cn1] |
| B-40 | 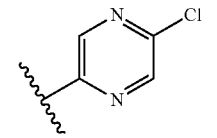 [SMILES: *c1cnc(Cl)cn1] |
| B-41 | 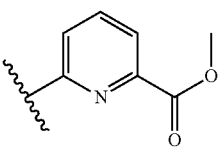 [SMILES: *c1cccc(C(=O)OC)n1] |
| B-42 | 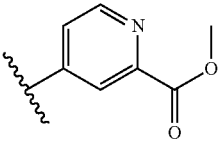 [SMILES: *c1ccnc(C(=O)OC)c1] |
| B-43 | 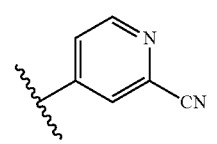 [SMILES: *c1ccnc(C#N)c1] |
| B-44 | 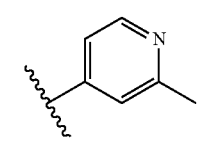 [SMILES: *c1ccnc(C)c1] |
TABLE 1-continued
Illustrative B moieties of the compounds of Formula I.
| Sub-class # | B |
| --- | --- |
| B-45 | 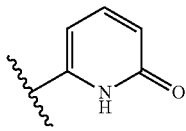 [SMILES: *c1cccc(=O)[nH]1] |
| B-46 | 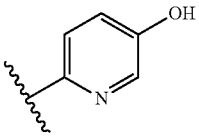 [SMILES: *c1ccc(O)cn1] |
| B-47 | 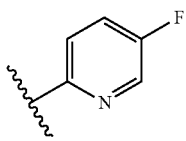 [SMILES: *c1ccc(F)cn1] |
| B-48 | 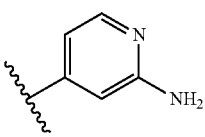 [SMILES: *c1ccnc(N)c1] |
| B-49 | 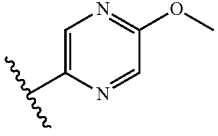 [SMILES: *c1cnc(OC)cn1] |
| B-50 | 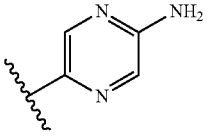 [SMILES: *c1cnc(N)cn1] |
| B-51 | 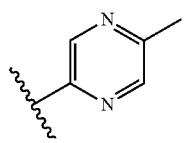 [SMILES: *c1cnc(C)cn1] |
| B-52 | 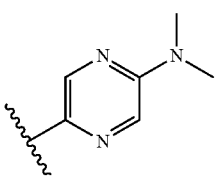 [SMILES: *c1cnc(N(C)C)cn1] |
| B-53 | 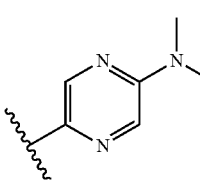 |

TABLE 1-continued
Illustrative B moieties of the compounds of Formula I.
| Sub-class # | B |
|---|---|
| B-54 | 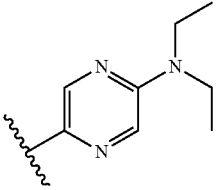 [SMILES: *c1cnc(N(CC)CC)cn1] |
| B-55 | 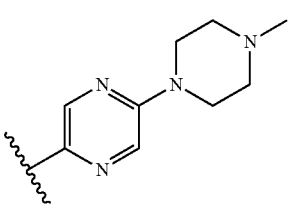 [SMILES: *c1cnc(N2CCN(C)CC2)cn1] |
| B-56 | 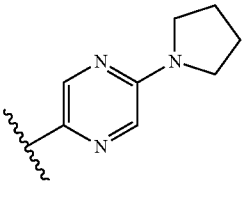 [SMILES: *c1cnc(N2CCCC2)cn1] |
| B-57 | 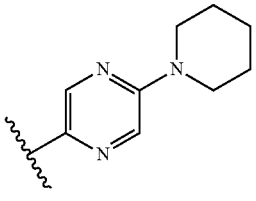 [SMILES: *c1cnc(N2CCCCC2)cn1] |
| B-58 | 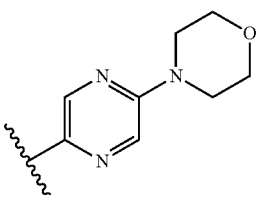 [SMILES: *c1cnc(N2CCOCC2)cn1] |
| B-59 | 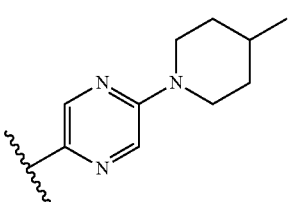 [SMILES: *c1cnc(N2CCC(C)CC2)cn1] |
| B-60 | 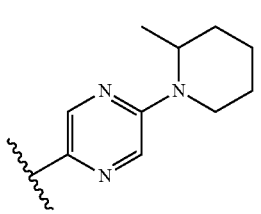 [SMILES: *c1cnc(N2CCCCC2C)cn1] |
| B-61 | 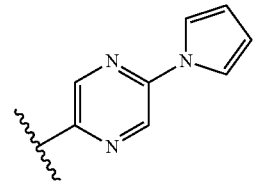 [SMILES: *c1cnc(-n2cccc2)cn1] |
| B-62 | 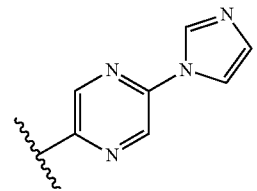 [SMILES: *c1cnc(-n2ccnc2)cn1] |
| B-63 | 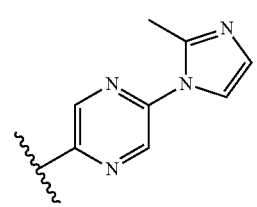 [SMILES: *c1cnc(-n2ccnc2C)cn1] |
| B-64 | 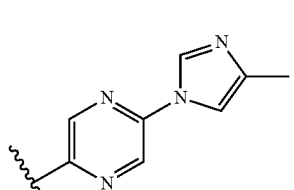 |
| B-65 | 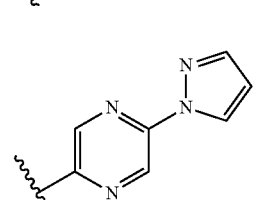 |
| B-66 | 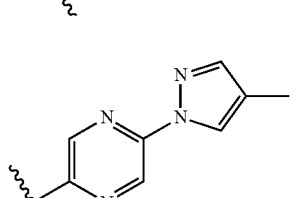 |
| B-67 | 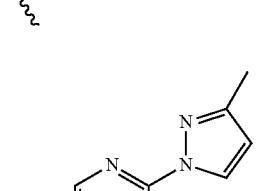 |

TABLE 1-continued
Illustrative B moieties of the compounds of Formula I.
| Sub-class # | B |
|---|---|
| B-68 | 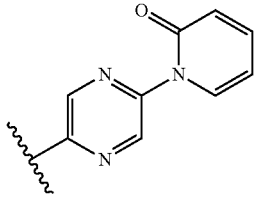 [SMILES: *c1cnc(-n2ccccc2=O)cn1] |
| B-69 | 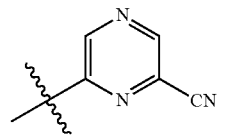 [SMILES: *c1cncc(C#N)n1] |
| B-70 | 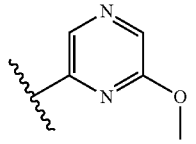 [SMILES: *c1cncc(OC)n1] |
| B-71 | 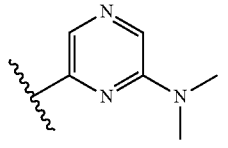 |
| B-72 | 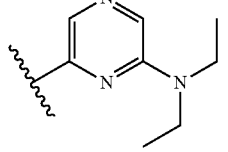 |
| B-73 | 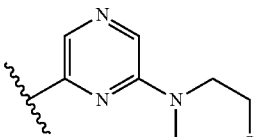 |
| B-74 | 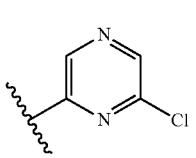 [SMILES: *c1cncc(Cl)n1] |
| B-75 | 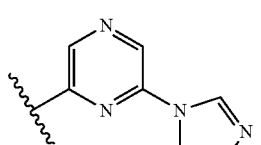 |
| B-76 | 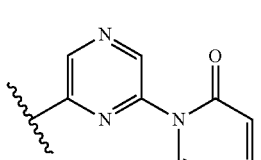 |
| B-77 | 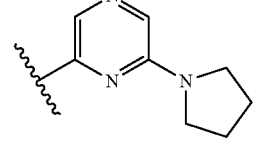 |
| B-78 | 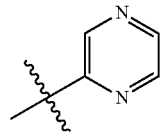 |
| B-79 | 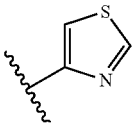 [SMILES: *c1cscn1] |
| B-80 | 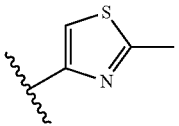 [SMILES: *c1csc(C)n1] |
| B-81 | 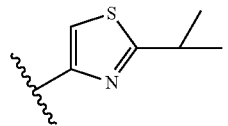 [SMILES: *c1csc(C(C)C)n1] |
| B-82 | 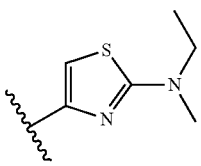 [SMILES: *c1csc(N(C)CC)n1] |
| B-83 | 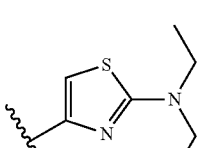 |
| B-84 | 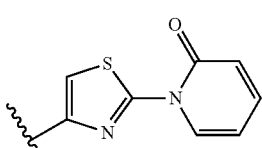 |
| B-85 | 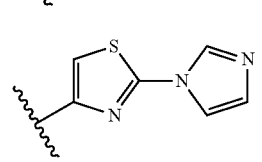 |
| B-86 | 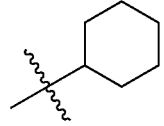 [SMILES: *C1CCCCC1] |

TABLE 1-continued

Illustrative B moieties of the compounds of Formula I.

| Sub-class # | B |
|---|---|
| B-87 | —CH₃ |
| B-88 | —CH₂CH₃ |
| B-89 | cyclobutyl |
| B-90 | 4-methylpyridin-3-yl |
| B-91 | 3-(pyrrolidin-1-yl)propyl |
| B-92 | 3,5-dimethylphenyl |
| B-93 | 2,6-difluorophenyl |
| B-94 | 2,6-dimethylphenyl |
| B-95 | 3,5-difluorophenyl |
| B-96 | 3-(4-ethylpiperazin-1-yl)propyl |
| B-97 | piperidin-4-yl (NH) |
| B-98 | 1-acetylpiperidin-4-yl |
| B-99 | 1-(2-hydroxyethyl)piperidin-4-yl |
| B-100 | 1-(2-(methylsulfonyl)ethyl)piperidin-4-yl |
| B-101 | 1-(2-cyanoethyl)piperidin-4-yl |
| B-102 | 4-fluorophenyl |

TABLE 2

Illustrative $R^{12}$ of compounds of Formula I.

| Sub-class # | $R^{12}$ |
|---|---|
| 12-1 | —CN |
| 12-2 | —Br |
| 12-3 | —Cl |
| 12-4 | —CH₂CH₃ |
| 12-5 | —CH₃ |
| 12-6 | —CH(CH₃)₂ |
| 12-7 | cyclopropyl |
| 12-8 | tert-butyl |

TABLE 2-continued
Illustrative R¹² of compounds of Formula I.
| Sub-class # | R¹² |
|---|---|
| 12-9 | 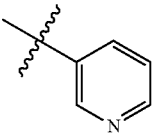 [SMILES: *c1cccnc1] |
| 12-10 | 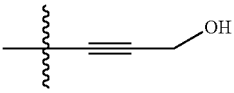 |
| 12-11 | 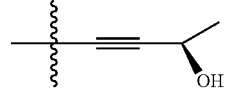 |
| 12-12 | 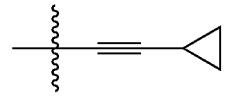 [SMILES: *C#CC1CC1] |
| 12-13 | 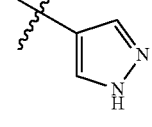 |
| 12-14 | 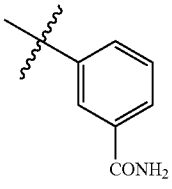 [SMILES: *c1cccc(C(N)=O)c1] |
| 12-15 | 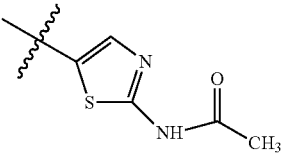 |
| 12-16 | 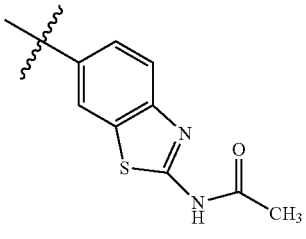 [SMILES: *c1ccc2nc(NC(C)=O)sc2c1] |
| 12-17 | 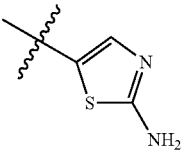 [SMILES: *c1cnc(N)s1] |
| 12-18 | 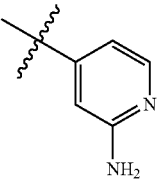 |
| 12-19 | 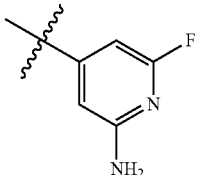 |
| 12-20 | 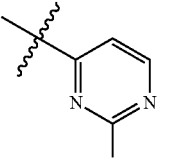 |
| 12-21 | 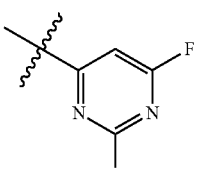 |
| 12-22 | 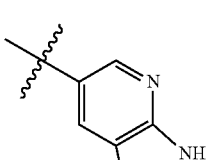 |
| 12-23 | 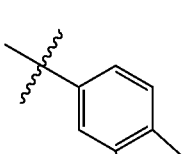 |
| 12-24 | 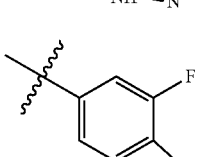 |
| 12-25 | 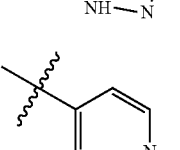 |

TABLE 2-continued

Illustrative R$^{12}$ of compounds of Formula I.

| Sub-class # | R$^{12}$ |
|---|---|
| 12-26 | 3-methoxyphenyl |
| 12-27 | 4-(6-fluoro-1H-pyrrolo[2,3-b]pyridin-4-yl) |
| 12-28 | -C≡C-C(CH$_3$)$_2$OH |
| 12-29 | -C≡C-C(CH$_3$)$_3$ |
| 12-30 | 4-ethylpyridin-2-yl |
| 12-31 | 4-chloro-3-methoxyphenyl |
| 12-32 | 4-chloro-3-hydroxyphenyl |
| 12-33 | 4-fluorophenyl |
| 12-34 | 3-fluoro-4-hydroxyphenyl |
| 12-35 | —H |
| 12-36 | 4-hydroxyphenyl |
| 12-37 | 4-fluorophenyl |
| 12-38 | 3-fluoro-4-hydroxyphenyl |
| 12-39 | 4-hydroxyphenyl |
| 12-40 | 3-chlorophenyl |
| 12-41 | 3-fluorophenyl |
| 12-42 | 3,4-dimethoxyphenyl |
| 12-43 | 4-methoxyphenyl |
| 12-44 | 2-(aminomethyl)-4-fluorophenyl |
| 12-45 | 2-(aminomethyl)phenyl |

TABLE 2-continued
Illustrative R¹² of compounds of Formula I.
| Sub-class # | R¹² |
|---|---|
| 12-46 | 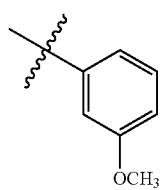 [SMILES: *c1cccc(OC)c1] |
| 12-47 | 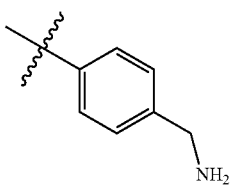 [SMILES: *c1ccc(CN)cc1] |
| 12-48 | 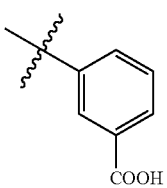 |
| 12-49 | 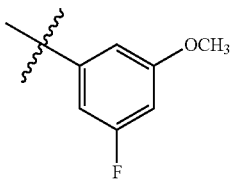 [SMILES: *c1cc(F)cc(OC)c1] |
| 12-50 | 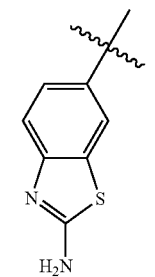 [SMILES: *c1ccc2nc(N)sc2c1] |
| 12-51 | 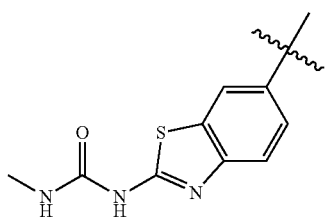 [SMILES: *c1ccc2nc(NC(=O)NC)sc2c1] |
| 12-52 | 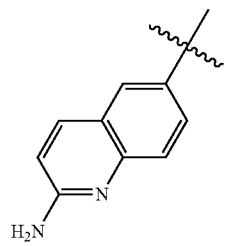 [SMILES: *c1ccc2nc(N)ccc2c1] |
| 12-53 | 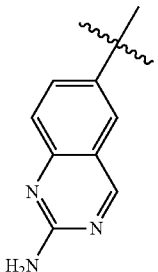 |
| 12-54 | 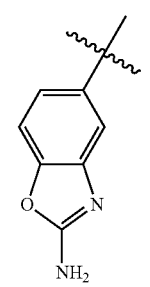 [SMILES: *c1ccc2oc(N)nc2c1] |
| 12-55 | 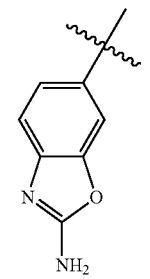 [SMILES: *c1ccc2nc(N)oc2c1] |
| 12-56 | 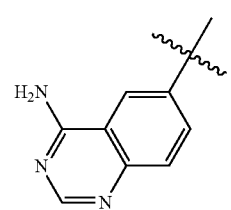 [SMILES: *c1ccc2ncnc(N)c2c1] |
| 12-57 | 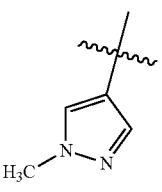 |
| 12-58 | 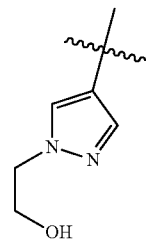 [SMILES: *c1cnn(CCO)c1] |

TABLE 2-continued
Illustrative $R^{12}$ of compounds of Formula I.
| Sub-class # | $R^{12}$ |
|---|---|
| 12-59 | 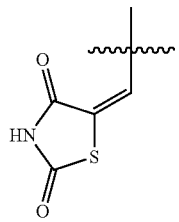 |
| 12-60 | 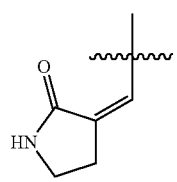 |
| 12-61 | —I |
| 12-62 | 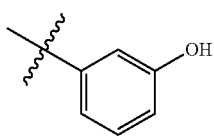 [SMILES: *c1cccc(O)c1] |
| 12-63 | 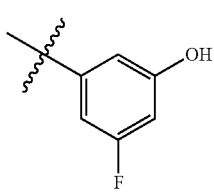 [SMILES: *c1cc(O)cc(F)c1] |
| 12-64 | 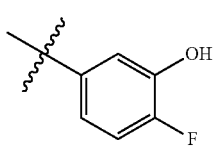 [SMILES: *c1ccc(F)c(O)c1] |
| 12-65 | 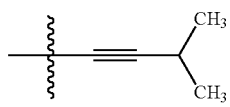 |
| 12-66 | 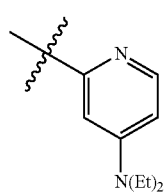 |
| 12-67 | 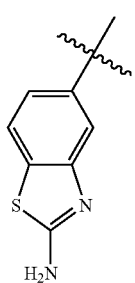 [SMILES: *c1ccc2sc(N)nc2c1] |
| 12-68 | 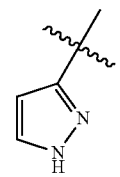 |
| 12-69 | 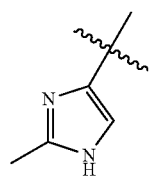 [SMILES: *c1c[nH]c(C)n1] |
| 12-70 | 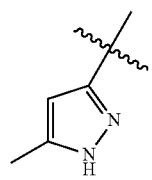 [SMILES: *c1cc(C)[nH]n1] |
| 12-71 | 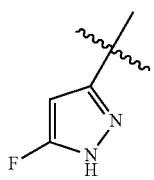 |
| 12-72 | 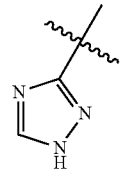 |
| 12-73 | 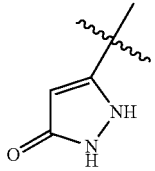 [SMILES: *c1cc(=O)[nH][nH]1] |
| 12-74 | 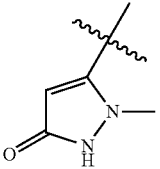 [SMILES: *c1cc(=O)[nH]n1C] |
| 12-75 | 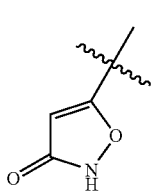 [SMILES: *c1cc(=O)[nH]o1] |

TABLE 2-continued
Illustrative R$^{12}$ of compounds of Formula I.
| Sub-class # | R$^{12}$ |
| --- | --- |
| 12-76 | 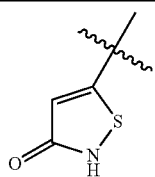 |
| 12-77 |  |
| 12-78 | 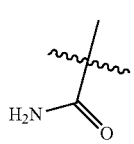 |
| 12-79 | 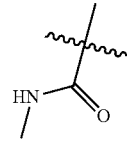 |
| 12-80 | 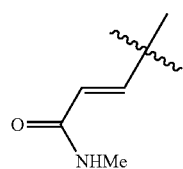 [SMILES: */C=C/C(=O)NC] |
| 12-81 | 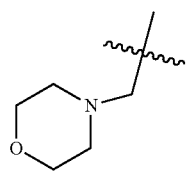 [SMILES: *CN1CCOCC1] |
| 12-82 | 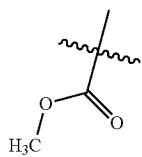 |
| 12-83 | 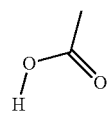 |
| 12-84 | 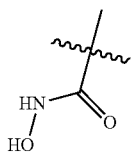 |
| 12-85 | 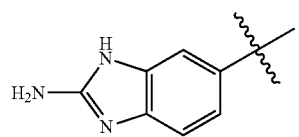 [SMILES: *c1ccc2nc(N)[nH]c2c1] |
| 12-86 | 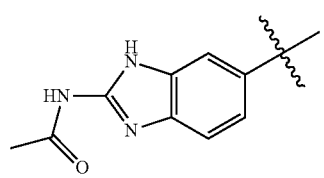 [SMILES: *c1ccc2nc(NC(C)=O)[nH]c2c1] |
| 12-87 | 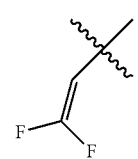 [SMILES: *C=C(F)F] |
| 12-88 | 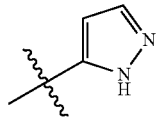 [SMILES: *c1ccn[nH]1] |
| 12-89 | 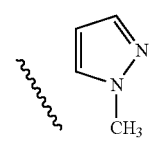 |
| 12-90 | 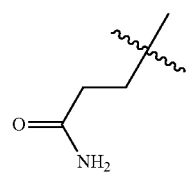 [SMILES: *CCC(N)=O] |
| 12-91 | 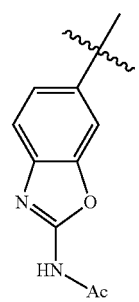 [SMILES: *c1ccc2nc(NC(C)=O)oc2c1] |
| 12-92 | 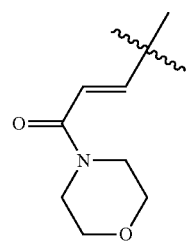 [SMILES: */C=C/C(=O)N1CCOCC1] |

TABLE 2-continued

Illustrative $R^{12}$ of compounds of Formula I.

| Sub-class # | $R^{12}$ |
| --- | --- |
| 12-93 | morpholine-N-C(=O)-CH2CH2- |
| 12-94 | H2N-C(=O)-CH=CH-CH2- |
| 12-95 | 1H-tetrazol-5-yl |
| 12-96 | 1H-tetrazol-5-ylmethyl |
| 12-97 | —F |
| 12-98 | —S(=O)2—NH2 |
| 12-99 | —S(=O)2—NHCH3 |
| 12-100 | —S(=O)2—N(CH3)2 |
| 12-101 | 2-(acetylamino)benzoxazol-5-yl |
| 12-102 | 2-(acetylamino)benzothiazol-5-yl |

Other illustrative compounds of the present disclosure have a structure of Formula V-A, V-A1, or V-A2, wherein B is a moiety described in Table 1, in combination with $R^3$, which is —H, —Cl, —F, or $CH_3$, and $R^9$, which is —H, —$CH_3$, or —$CH_2CH_3$. A compound of Formula V-A, V-A1, or V-A2 includes any combination of $R^3$, B, and $R^9$.

Formula V-A

Formula V-A1

Formula V-A2

Yet other illustrative compounds of the present disclosure have a structure of Formula V-B, wherein B is a moiety described in Table 1, in combination with $R^3$, which is —H, —Cl, —F, or $CH_3$, and $R^9$, which is —H, —$CH_3$, or —$CH_2CH_3$. A compound of Formula V-B includes any combination of $R^3$, B, and $R^9$.

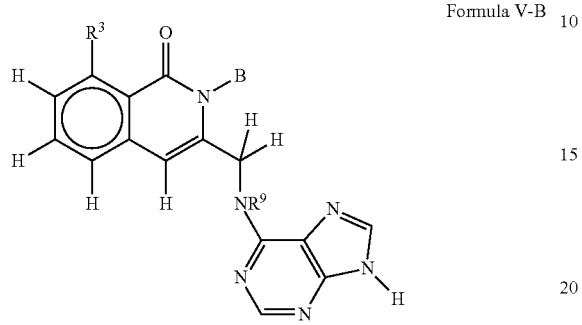

Formula V-B

Some other illustrative compounds of the present disclosure have a structure of Formula VI-A, wherein B is a moiety described in Table 1, in combination with $R^3$, which is —H, —Cl, —F, or $CH_3$, and $R^9$, which is —H, —$CH_3$, or —$CH_2CH_3$. A compound of Formula VI-A includes any combination of $R^3$, B, and $R^9$.

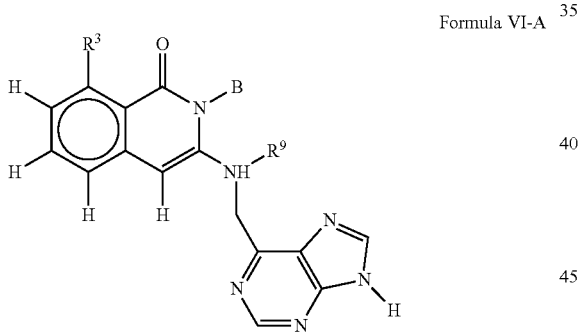

Formula VI-A

Further illustrative compounds that can be employed as described herein have a structure of one of Formulae VII-A1, VII-A2, VIII-A1, VIII-A2, IX-A1, IX-A2, X-A1, X-A2, XI-A1, XI-A2, XII-A, XII-A1, XII-A2, XIII-A, XIII-A1, XIII-A2, XIV-A, XIV-A1, or XIV-A2: wherein B is a moiety described in Table 1, any $R^{12}$ as described in Table 2, in combination with $R^3$, which is —H, —Cl, —F, or $CH_3$, $R^9$ which is —H, —$CH_3$, or —$CH_2CH_3$, and $R^{a'}$ which is —H, —Cl, —F, or —$NH_2$. A compound of Formulae VII-A1, VII-A2, VIII-A1, VIII-A2, IX-A1, IX-A2, X-A1, X-A2, XI-A1, XI-A2, XII-A, XII-A1, XII-A2, XIII-A, XIII-A1, XIII-A2, XIV-A, XIV-A1, or XIV-A2: includes any combination of $R^a$, $R^3$, B, $R^9$ and $R^{12}$.

Additional exemplary compounds include but are not limited to the following:

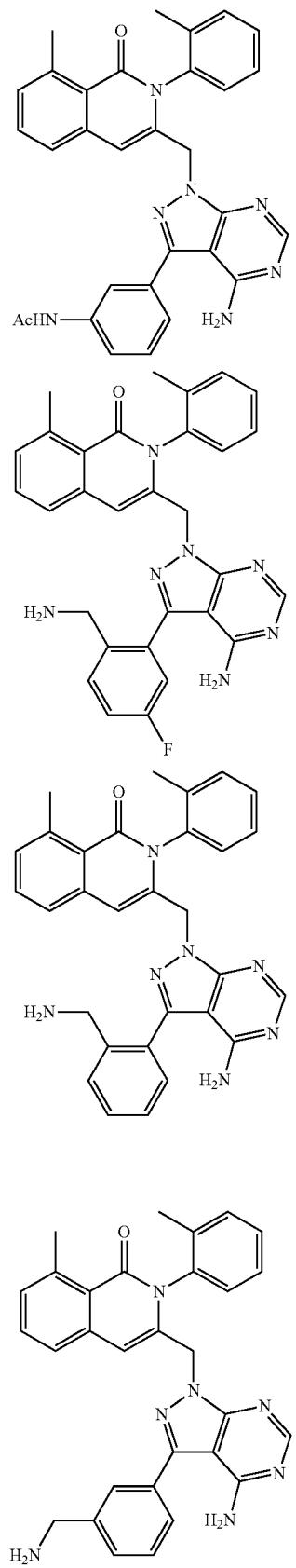

125
-continued
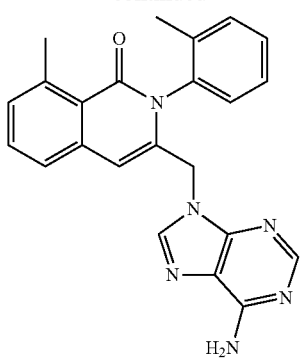
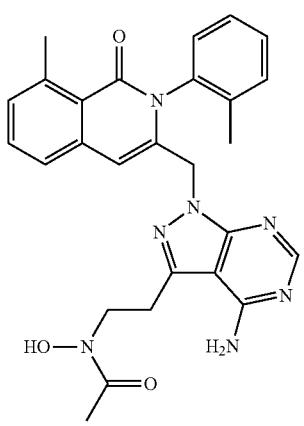
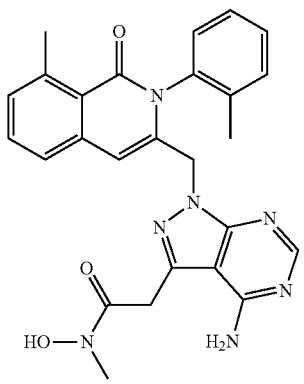
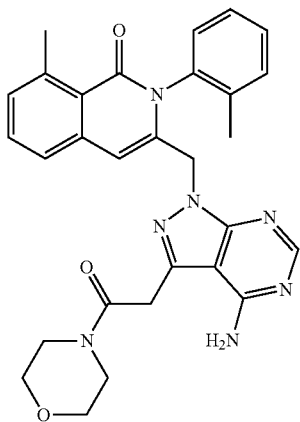
126
-continued
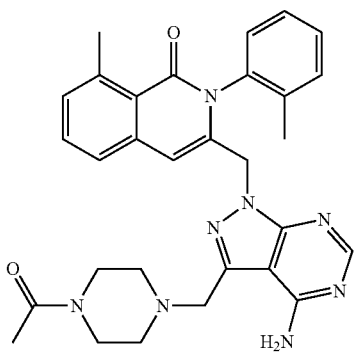
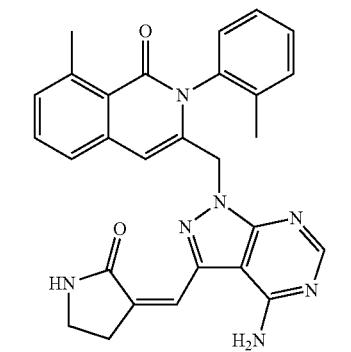
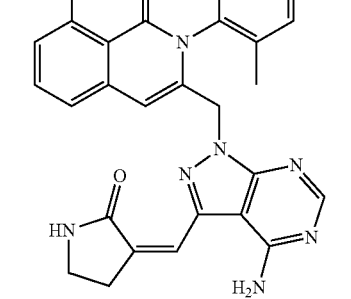
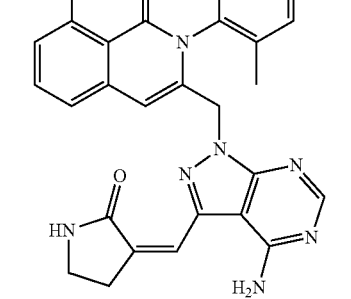

127
-continued
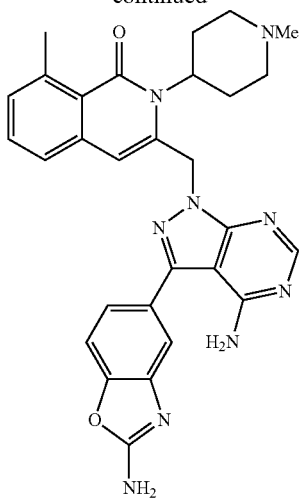
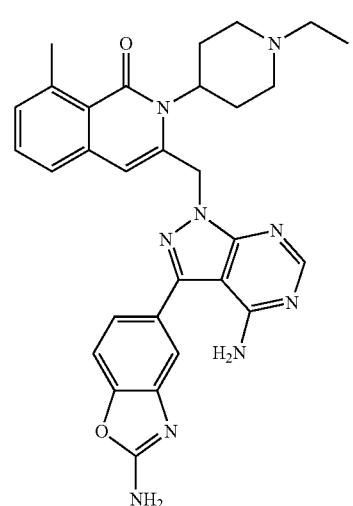
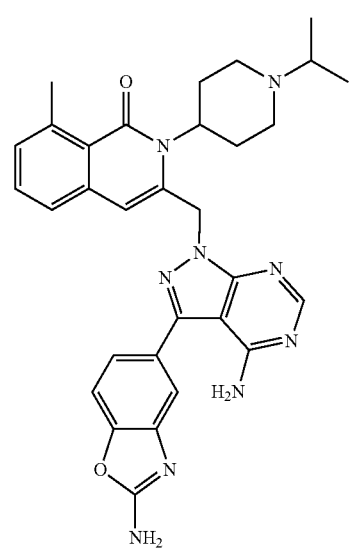
128
-continued
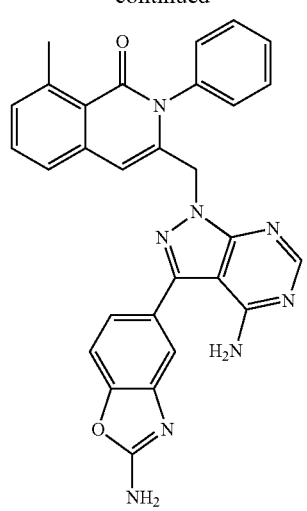
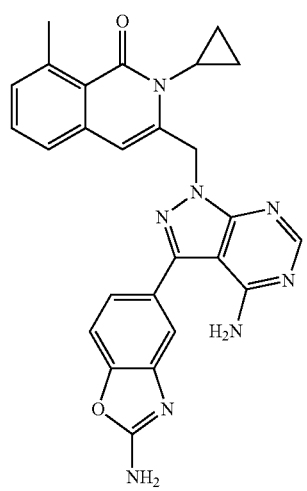
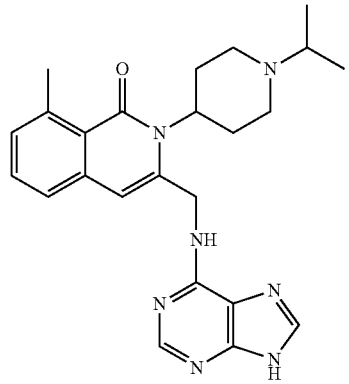

129
-continued
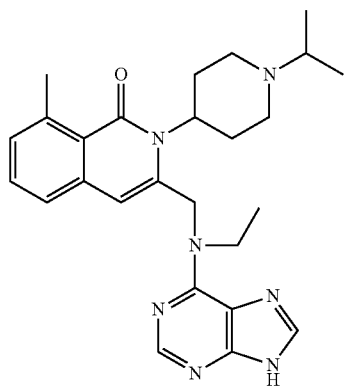
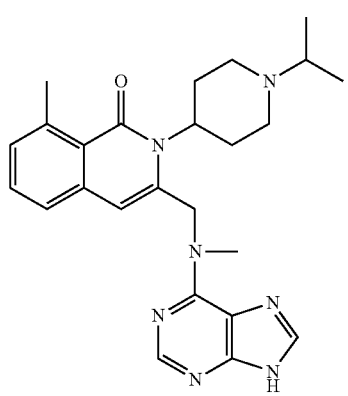
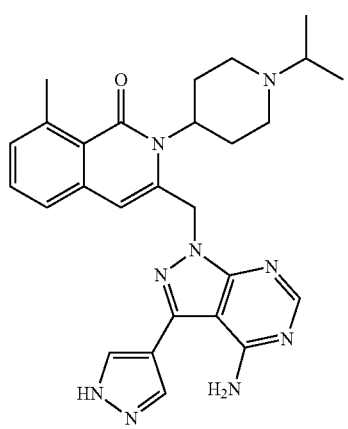
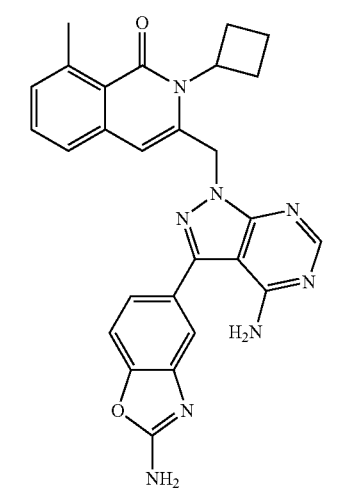
130
-continued
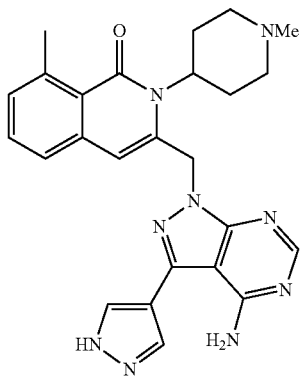
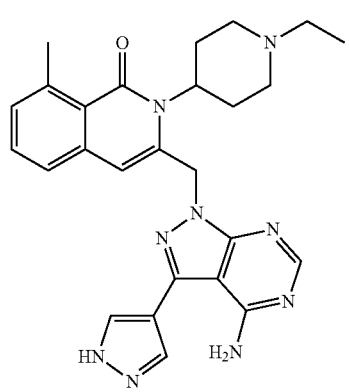
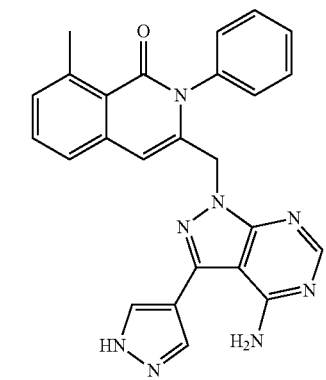
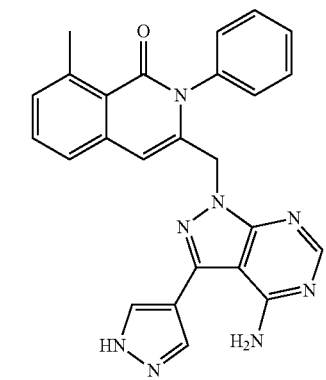

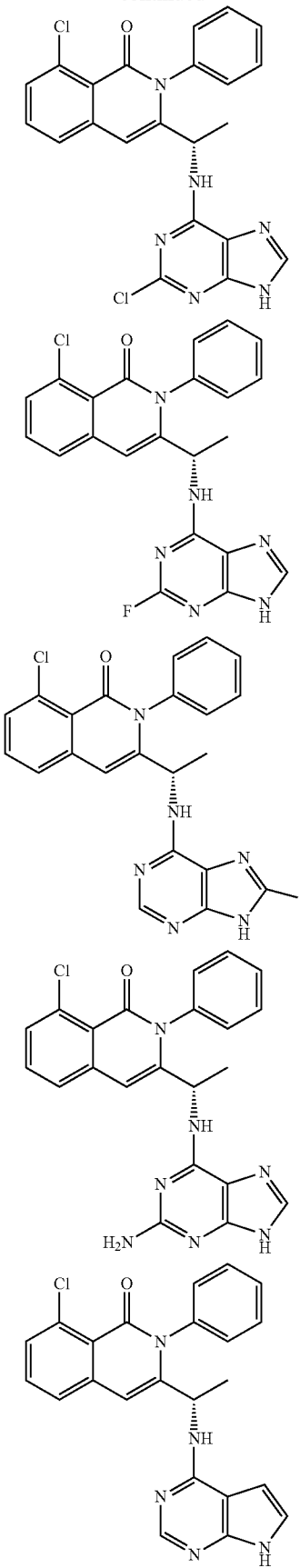
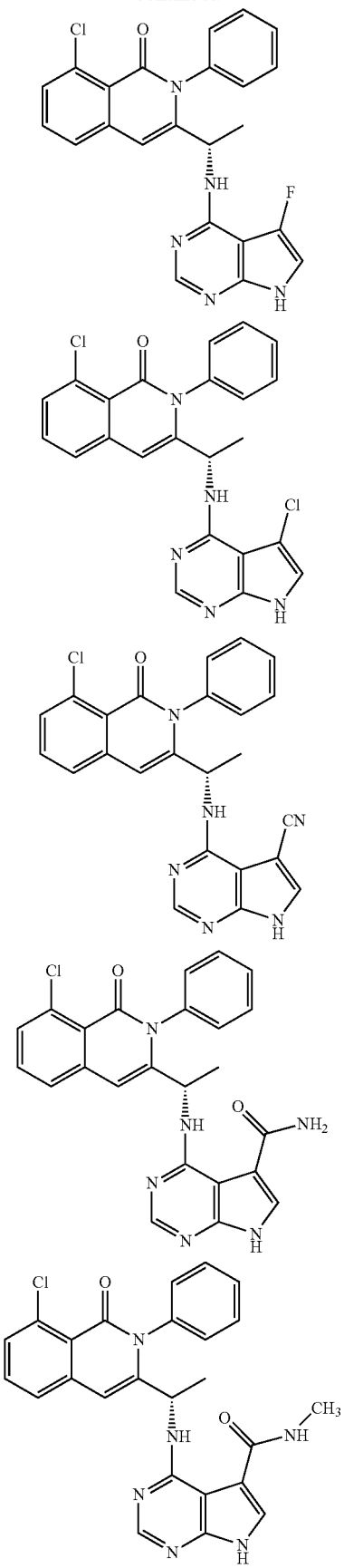

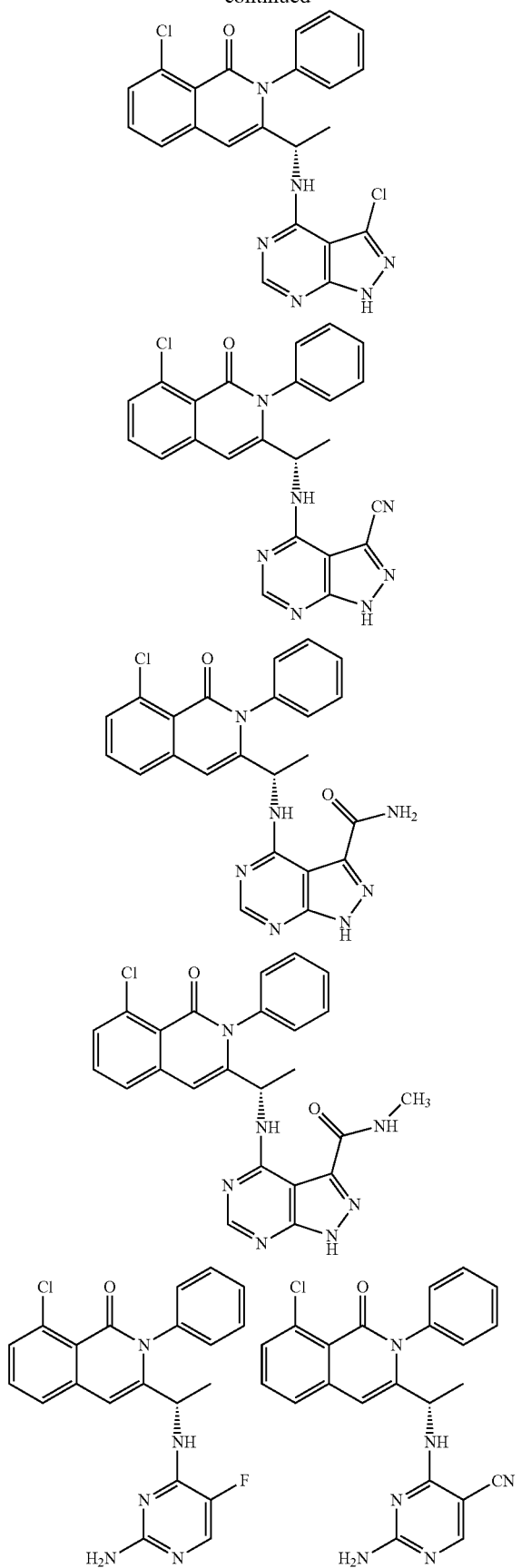
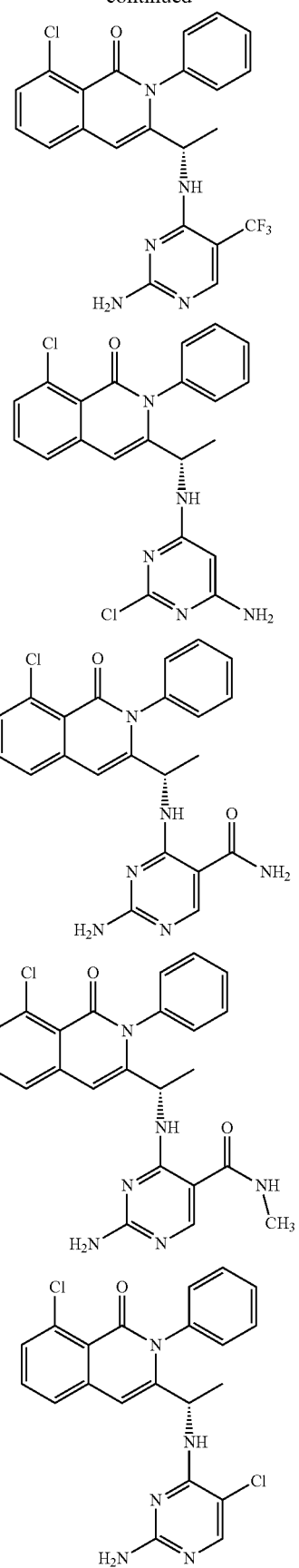

135
-continued
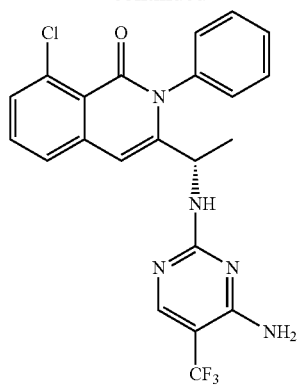
136
-continued
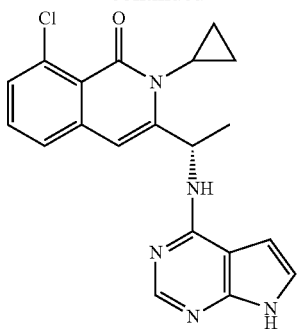
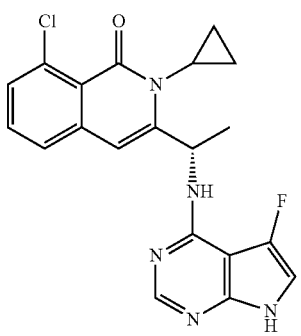
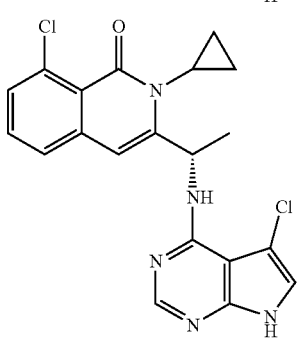
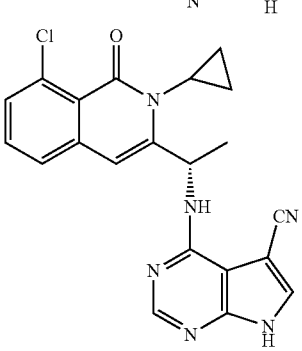
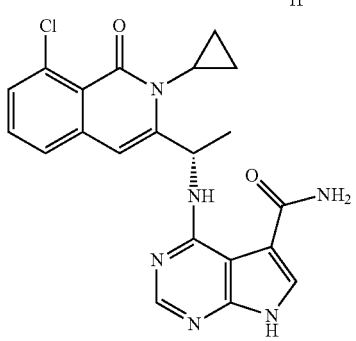

137
-continued
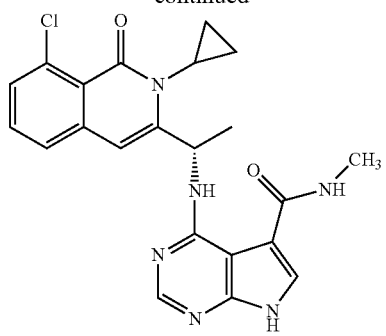
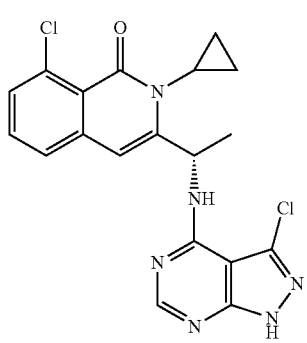
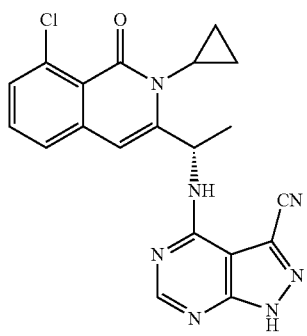
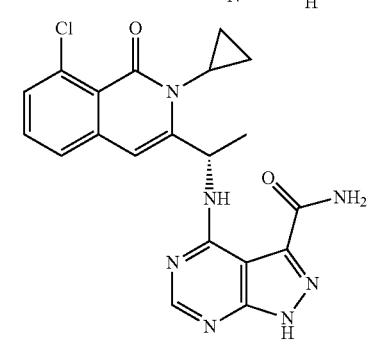
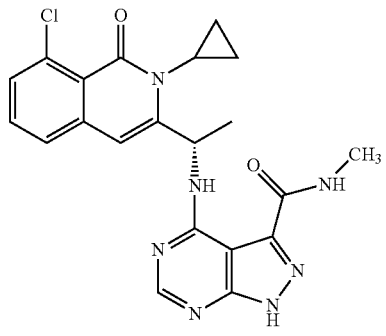
138
-continued
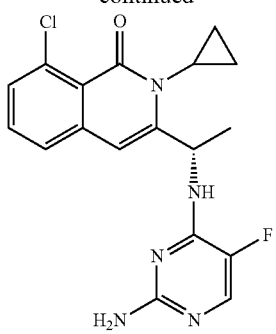
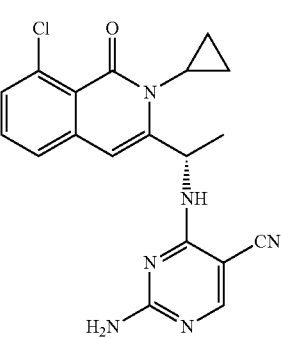
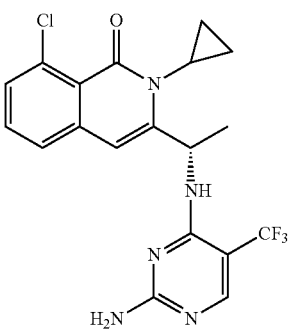
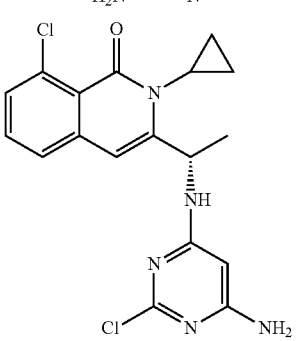
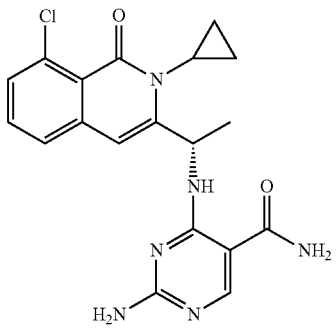

-continued

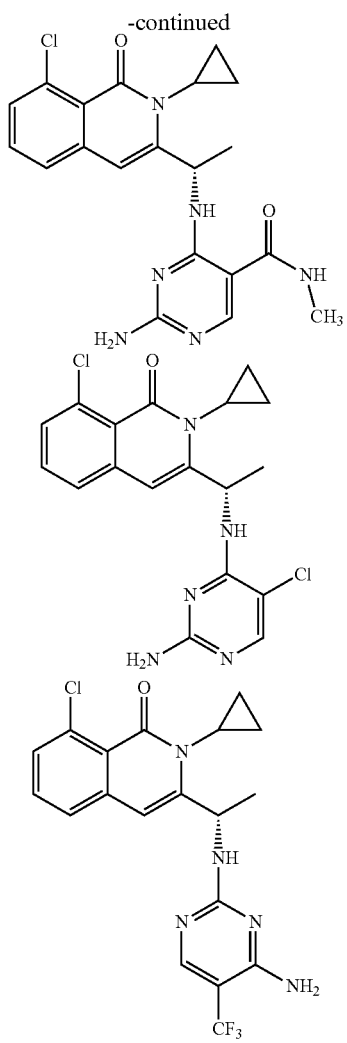

In some embodiments, the PI3K modulator is a compound of Formula I-1:

Formula I-1

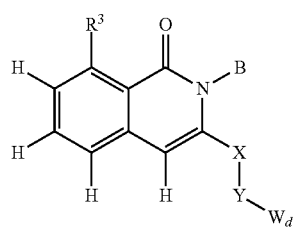

or its pharmaceutically acceptable salt thereof, wherein B is a moiety of Formula II:

Formula II

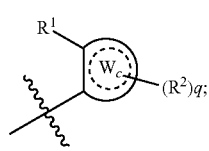

wherein $W_c$ is aryl, heteroaryl, heterocycloalkyl, or cycloalkyl, and q is an integer of 0, 1, 2, 3, or 4;

X is a bond or —$(CH(R^9))_z$—, and z is an integer of 1;

Y is —$N(R^9)$—;

$W_d$ is:

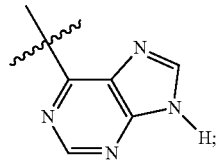

$R^1$ is hydrogen, alkyl, alkenyl, alkynyl, alkoxy, amido, alkoxycarbonyl, sulfonamido, halo, cyano, or nitro;

$R^2$ is alkyl, alkenyl, alkynyl, cycloalkyl, heterocycloalkyl, aryl, heteroaryl, heteroarylalkyl, alkoxy, amino, halo, cyano, hydroxy or nitro;

$R^3$ is hydrogen, alkyl, alkenyl, alkynyl, cycloalkyl, heterocycloalkyl, alkoxy, amido, amino, alkoxycarbonyl sulfonamido, halo, cyano, hydroxy or nitro; and each instance of $R^9$ is independently hydrogen, alkyl, or heterocycloalkyl.

In some embodiments, the compound is predominately in an (S)-stereochemical configuration In some embodiments, X is —$(CH(R^9))_z$—, and Y is —NH—.

In some embodiments, $R^3$ is —H, —$CH_3$, —$CH_2CH_3$, —$CF_3$, —Cl or —F.

In some embodiments, B is a moiety of Formula II:

Formula II

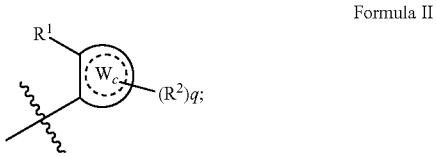

wherein $W_c$ is aryl, heteroaryl, heterocycloalkyl, or cycloalkyl;

q is an integer of 0 or 1;

$R^1$ is hydrogen, alkyl, or halo;

$R^2$ is alkyl or halo;

$R^3$ is hydrogen, alkyl, or halo; and, optionally wherein the compound has one or more of the following features:

(i) X is —$(CH(R^9))_z$—, wherein $R^9$ is methyl and z=1; and $W_d$ is

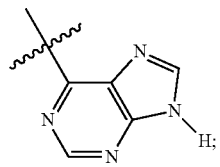

and/or (ii) $R^3$ is methyl or chloro.

In some embodiments, the compound has a structure of Formula V-A2:

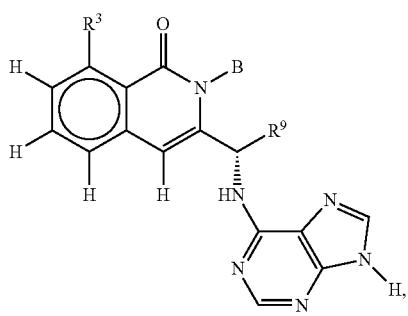

optionally wherein
(i) B is a moiety of Formula II:

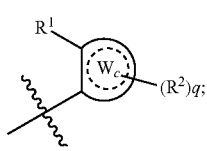

Formula II and $W_c$ is aryl or cycloalkyl, and/or (ii) $R^3$ is methyl or chloro and further, optionally wherein one or more of the following also applies: (a) $R^9$ is methyl or ethyl, (b) B is substituted or unsubstituted phenyl, (c) B is substituted or unsubstituted cycloalkyl. In some embodiments where B is substituted phenyl, B is substituted with fluoro. In some embodiments, B is phenyl that is substituted with one fluoro in the ortho or meta position of the phenyl ring.

In some embodiments, a compound used as described herein is selected from

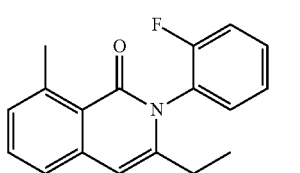

,

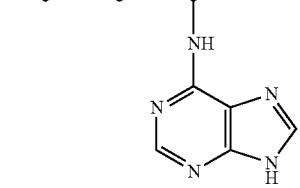

,

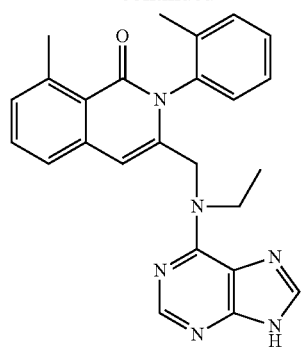

,

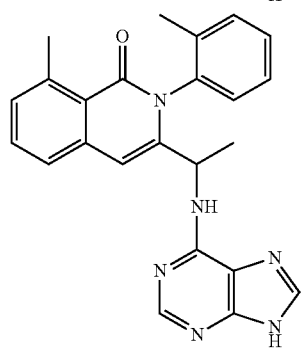

,

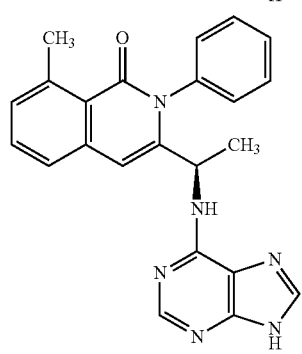

,

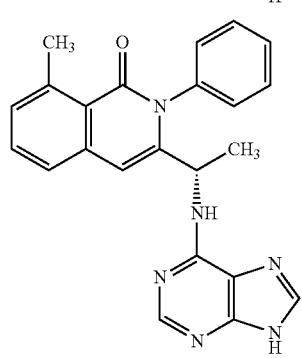

,

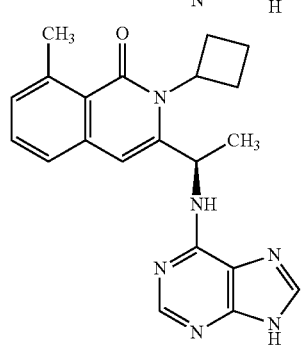

,

143
-continued
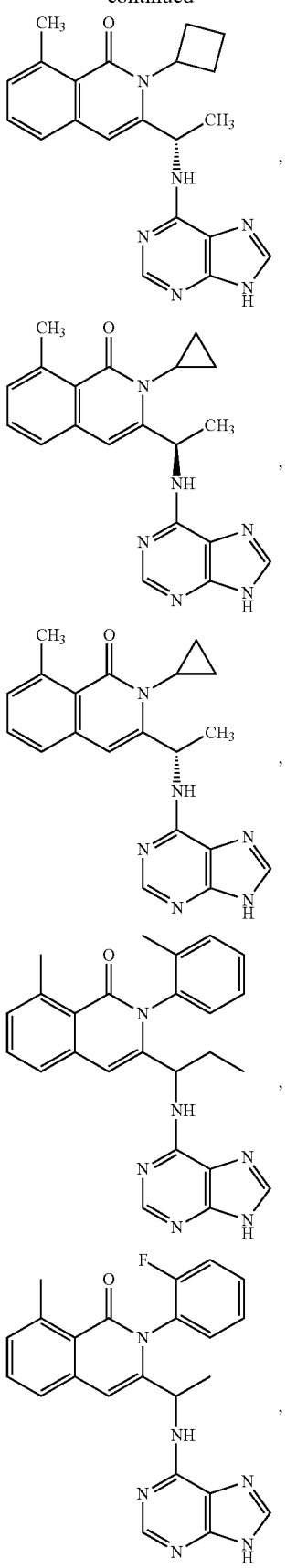
144
-continued
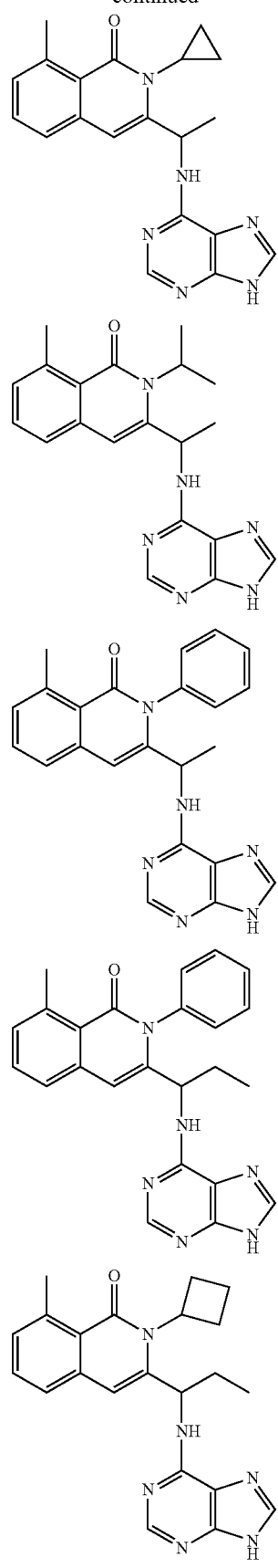

145
-continued
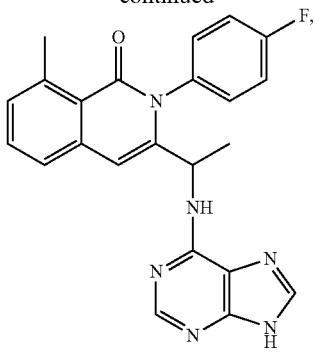
,
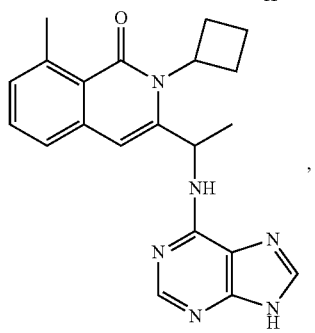
,
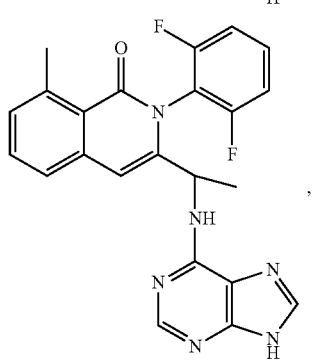
,
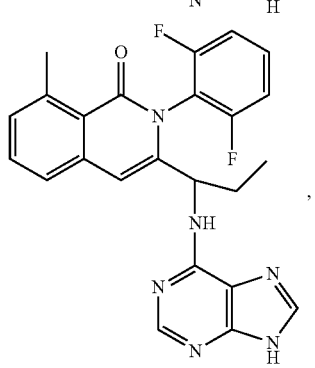
,
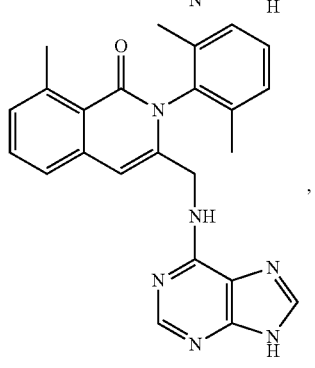
,
146
-continued
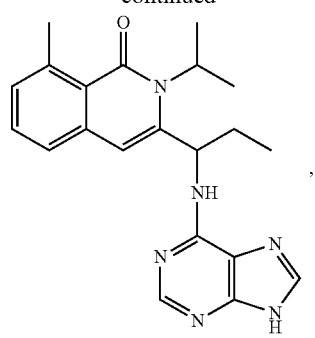
,
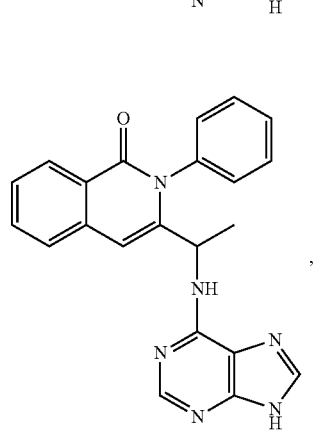
,
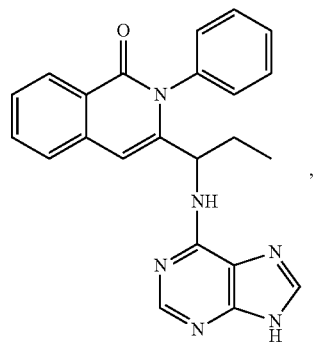
,
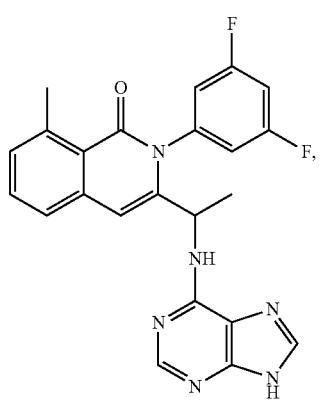
, -continued
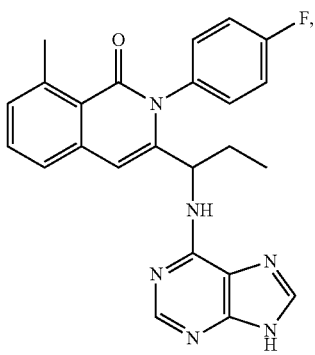
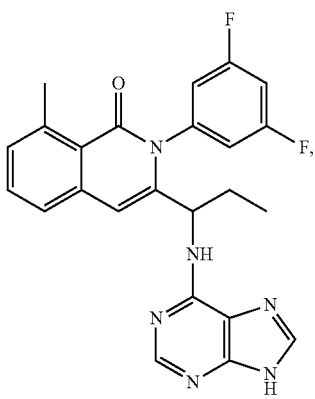
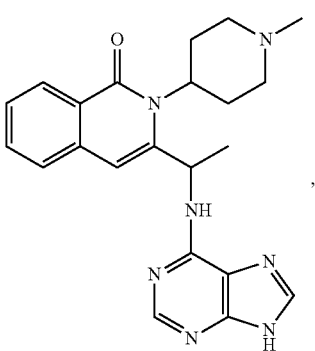
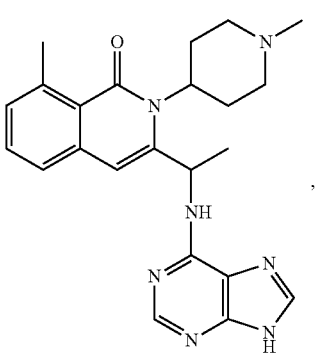
-continued
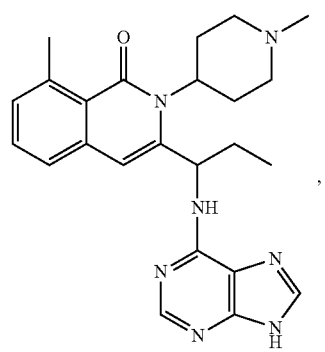
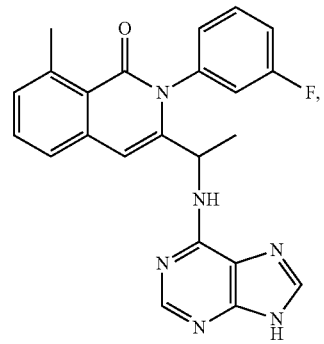
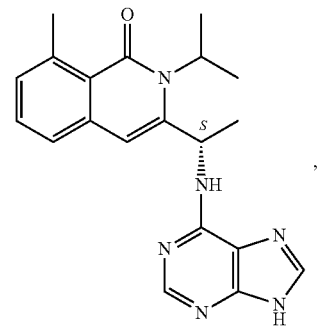
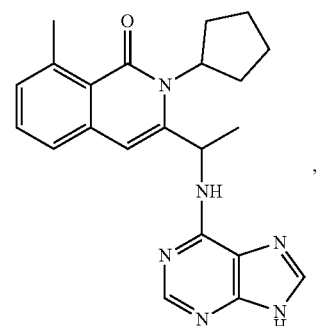
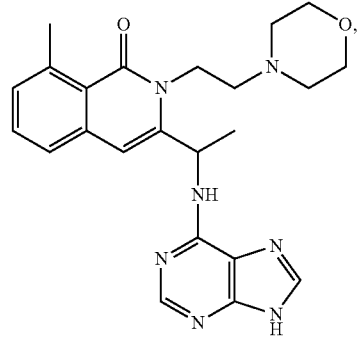

149
-continued
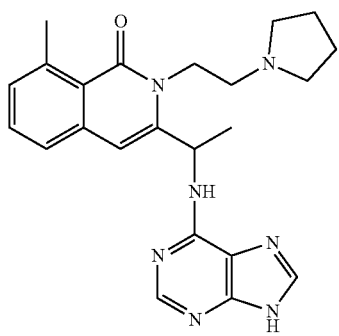
,
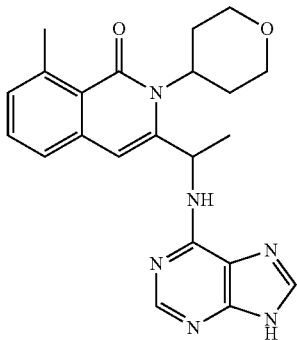
,
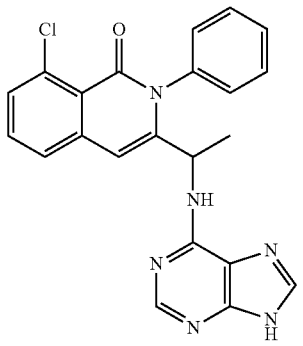
,
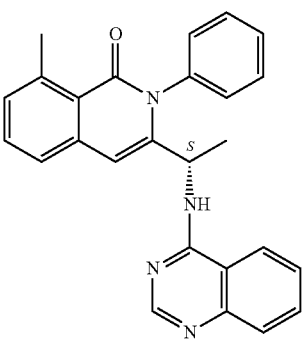
,
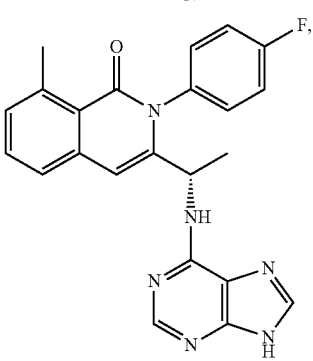
150
-continued
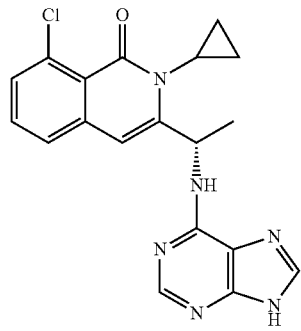
,
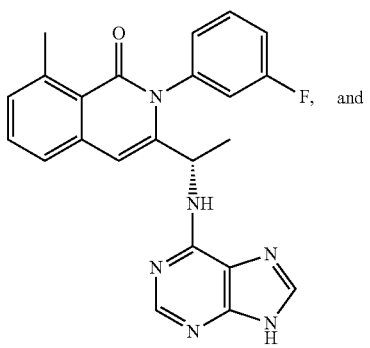 and
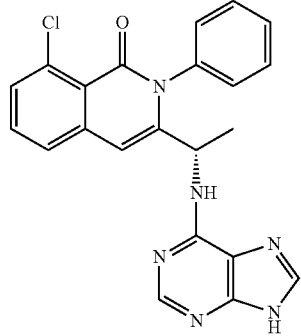
.
In some embodiments, the compound is selected from
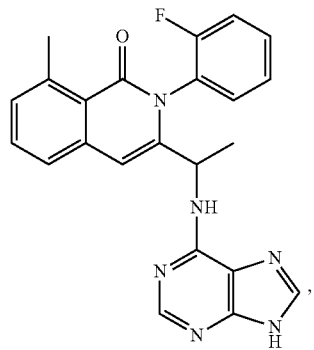
, 151
-continued
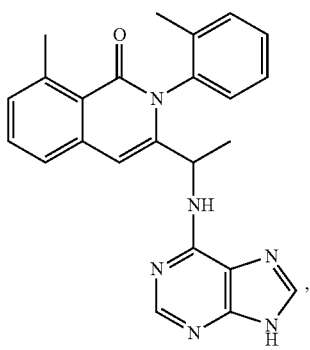
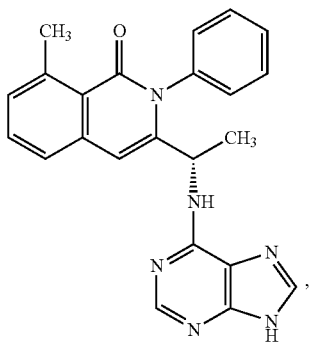
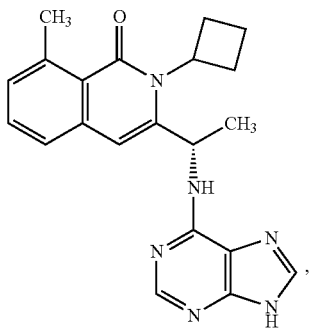
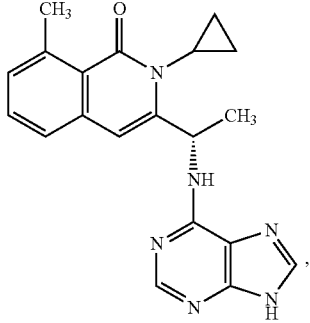
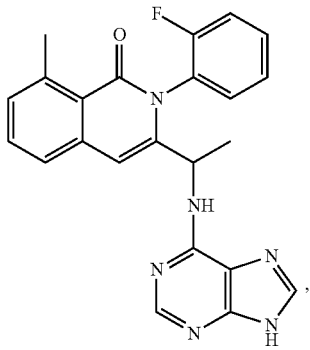
152
-continued
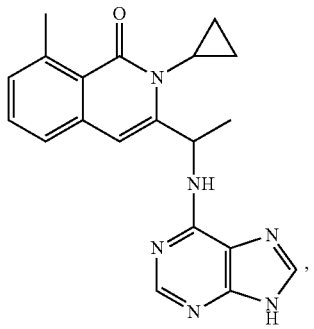
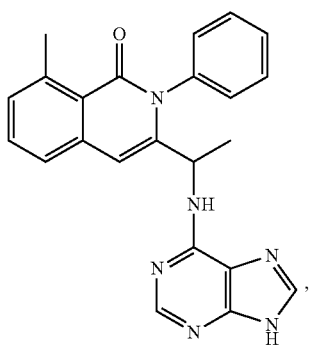
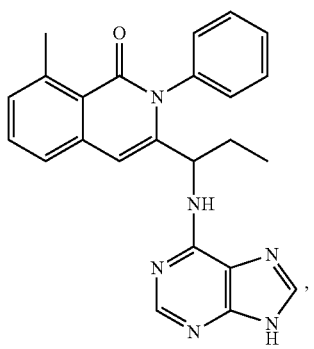
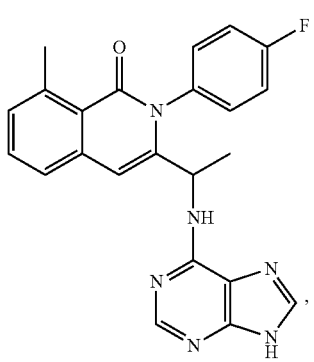
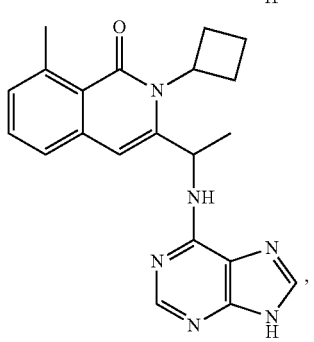

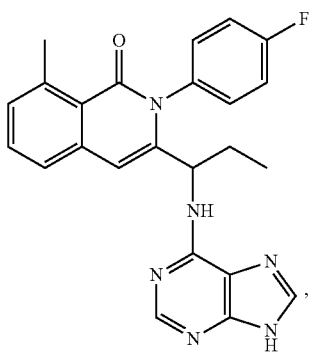
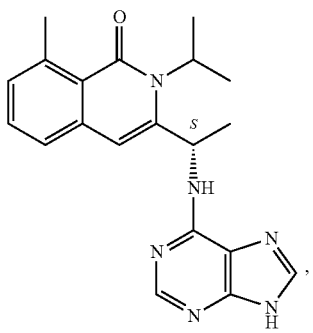
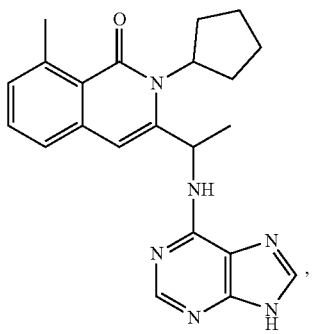
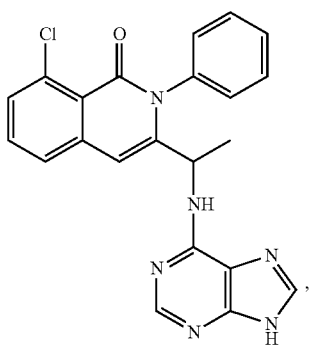
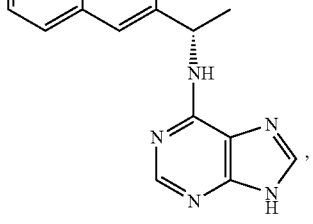
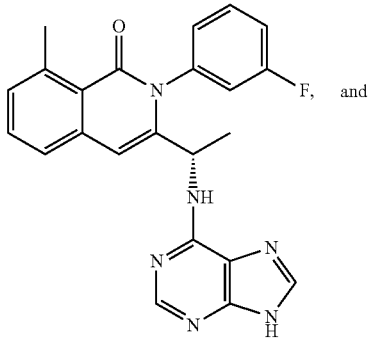
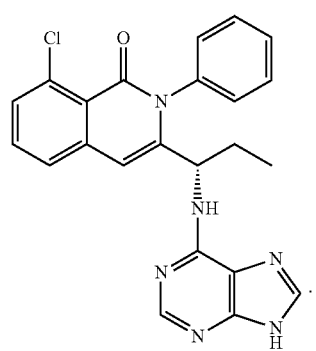
In some embodiments, the compound is selected from
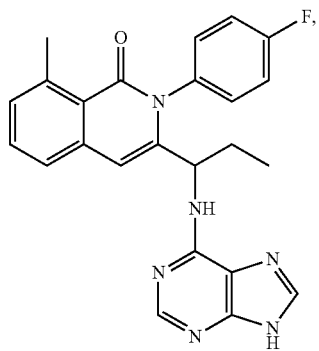
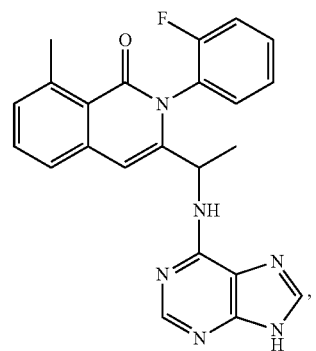

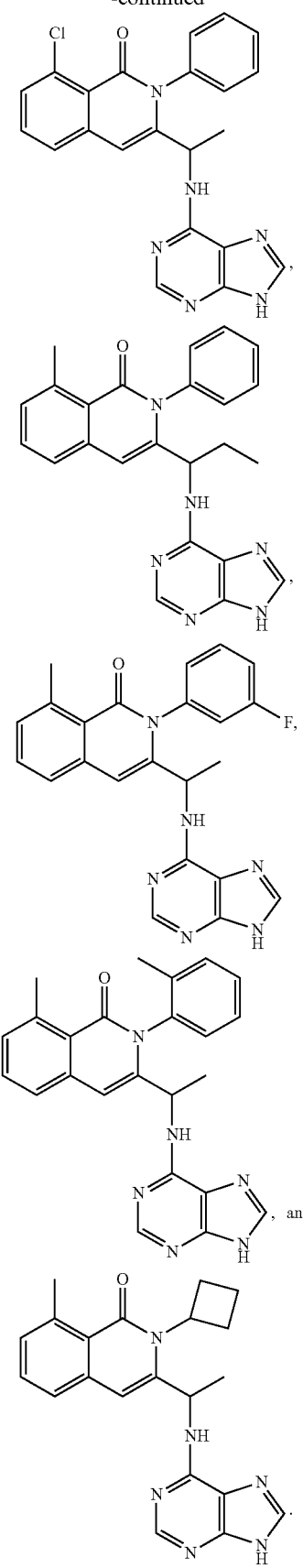
In some embodiments, the PI3K inhibitor has a formula selected from the group consisting of:
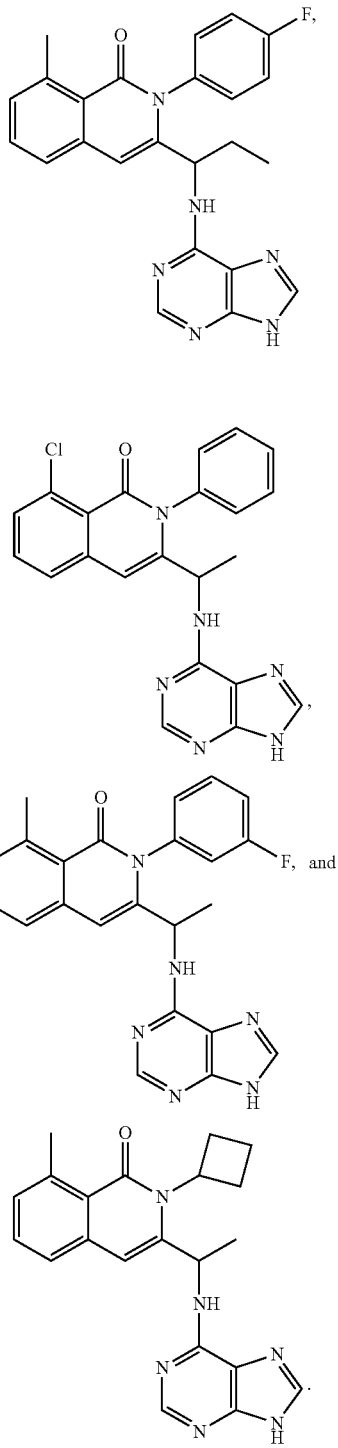
In some embodiments, the compound is the S-enantiomer having an enantiomeric purity selected from greater than about 55%, greater than about 80%, greater than about 90%, and greater than about 95%.
In some such embodiments, the compound is selected from:

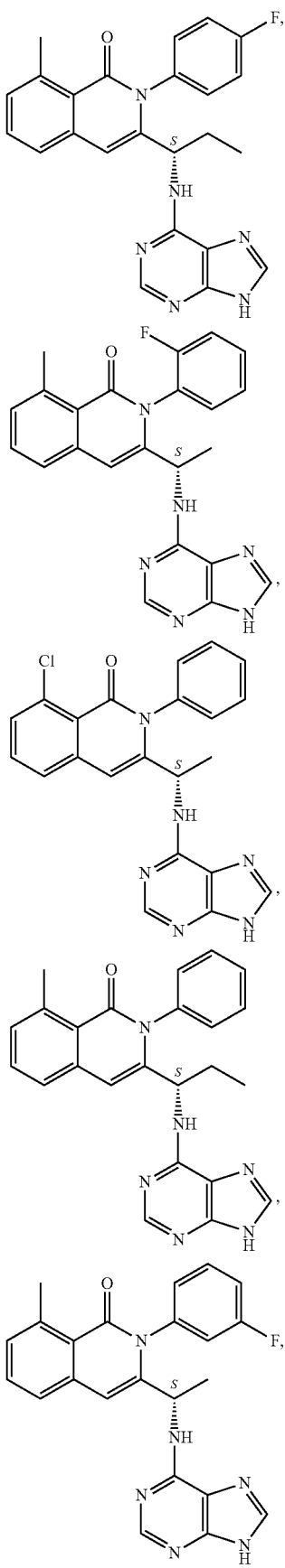
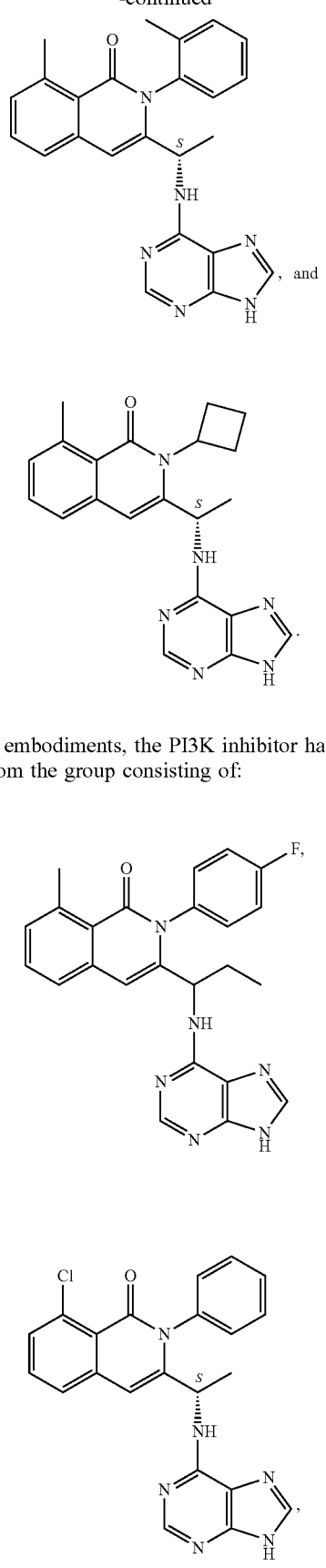
In some embodiments, the PI3K inhibitor has a formula selected from the group consisting of:

-continued

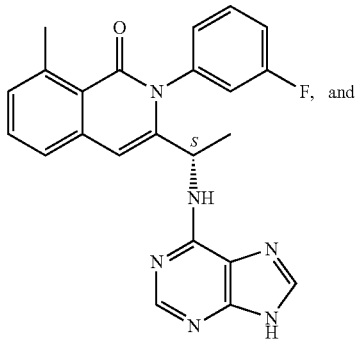

In certain such embodiments, the compound is

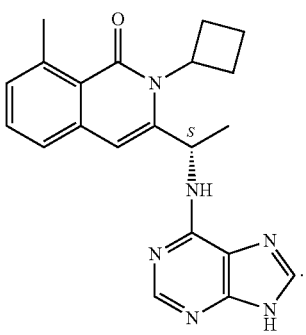

In other such embodiments, the compound is

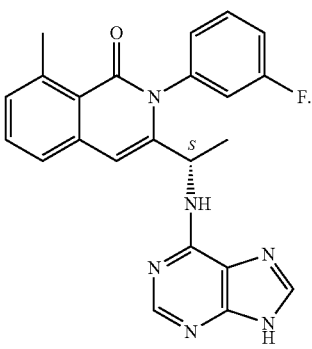

In yet other such embodiments, the compound is

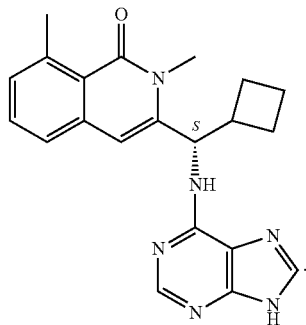

In some embodiments, the compound has the following structure:

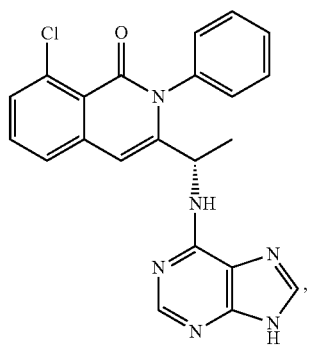 [SMILES: C[C@H](Nc1ncnc2[nH]cnc12)c1cc2cccc(Cl)c2c(=O)n1-c1ccccc1 ; ","]

which is also referred to herein as Compound 292.

In some embodiments, a polymorph of a compound disclosed herein is used. Exemplary polymorphs are disclosed in U.S. Patent Publication No. 2012-0184568 ("the '568 publication"), which is hereby incorporated by reference in its entirety.

In one embodiment, the compound is Form A of Compound 292, as described in the '568 publication. In another embodiment, the compound is Form B of Compound 292, as described in the '568 publication. In yet another embodiment, the compound is Form C of Compound 292, as described in the '568 publication. In yet another embodiment, the compound is Form D of Compound 292, as described in the '568 publication. In yet another embodiment, the compound is Form E of Compound 292, as described in the '568 publication. In yet another embodiment, the compound is Form F of Compound 292, as described in the '568 publication. In yet another embodiment, the compound is Form G of Compound 292, as described in the '568 publication. In yet another embodiment, the compound is Form H of Compound 292, as described in the '568 publication. In yet another embodiment, the compound is Form I of Compound 292, as described in the '568 publication. In yet another embodiment, the compound is Form J of Compound 292, as described in the '568 publication.

In specific embodiments, provided herein is a crystalline monohydrate of the free base of Compound 292, as described, for example, in the '568 application. In specific embodiments, provided herein is a pharmaceutically acceptable form of Compound 292, which is a crystalline monohydrate of the free base of Compound 292, as described, for example, in the '568 application.

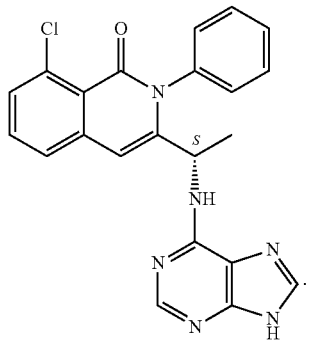

Any of the compounds (PI3K modulators) disclosed herein can be in the form of pharmaceutically acceptable salts, hydrates, solvates, chelates, non-covalent complexes, isomers, prodrugs, isotopically labeled derivatives, or mixtures thereof.

Chemical entities described herein can be synthesized according to exemplary methods disclosed in U.S. Patent Publication No. US 2009/0312319, International Patent Publication No. WO 2011/008302A1, and U.S. Patent Publication No. 2012-0184568, each of which is hereby incorporated by reference in its entirety, and/or according to methods known in the art.

Pharmaceutical Compositions

In some embodiments, provided herein are pharmaceutical compositions comprising a compound as disclosed herein, or an enantiomer, a mixture of enantiomers, or a mixture of two or more diastereomers thereof, or a pharmaceutically acceptable form thereof (e.g., pharmaceutically acceptable salts, hydrates, solvates, isomers, prodrugs, and isotopically labeled derivatives), and a pharmaceutically acceptable excipient, diluent, or carrier, including inert solid diluents and fillers, sterile aqueous solution and various organic solvents, permeation enhancers, solubilizers and adjuvants. In some embodiments, a pharmaceutical composition described herein includes a second active agent such as an additional therapeutic agent, (e.g., a chemotherapeutic agent).

1. Formulations

Pharmaceutical compositions can be specially formulated for administration in solid or liquid form, including those adapted for the following: oral administration, for example, drenches (aqueous or non-aqueous solutions or suspensions), tablets (e.g., those targeted for buccal, sublingual, and systemic absorption), capsules, boluses, powders, granules, pastes for application to the tongue, and intraduodenal routes; parenteral administration, including intravenous, intraarterial, subcutaneous, intramuscular, intravascular, intraperitoneal or infusion as, for example, a sterile solution or suspension, or sustained-release formulation; topical application, for example, as a cream, ointment, or a controlled-release patch or spray applied to the skin; intravaginally or intrarectally, for example, as a pessary, cream, stent or foam; sublingually; ocularly; pulmonarily; local delivery by catheter or stent; intrathecally, or nasally.

Examples of suitable aqueous and nonaqueous carriers which can be employed in pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents, dispersing agents, lubricants, and/or antioxidants. Prevention of the action of microorganisms upon the compounds described herein can be ensured by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

Methods of preparing these formulations or compositions include the step of bringing into association a compound described herein and/or the chemotherapeutic with the carrier and, optionally, one or more accessory ingredients. In general, the formulations are prepared by uniformly and intimately bringing into association a compound as disclosed herein with liquid carriers, or finely divided solid carriers, or both, and then, if necessary, shaping the product.

Preparations for such pharmaceutical compositions are well-known in the art. See, e.g., Anderson, Philip O.; Knoben, James E.; Troutman, William G, eds., *Handbook of Clinical Drug Data*, Tenth Edition, McGraw-Hill, 2002; Pratt and Taylor, eds., *Principles of Drug Action*, Third Edition, Churchill Livingston, New York, 1990; Katzung, ed., *Basic and Clinical Pharmacology*, Twelfth Edition, McGraw Hill, 2011; Goodman and Gilman, eds., *The Pharmacological Basis of Therapeutics*, Tenth Edition, McGraw Hill, 2001; *Remingtons Pharmaceutical Sciences*, 20th Ed., Lippincott Williams & Wilkins, 2000; Martindale, *The Extra Pharmacopoeia*, Thirty-Second Edition (The Pharmaceutical Press, London, 1999); all of which are incorporated by reference herein in their entirety. Except insofar as any conventional excipient medium is incompatible with the compounds provided herein, such as by producing any undesirable biological effect or otherwise interacting in a deleterious manner with any other component(s) of the pharmaceutically acceptable composition, the excipient's use is contemplated to be within the scope of this disclosure.

In some embodiments, the concentration of one or more of the compounds provided in the disclosed pharmaceutical compositions is equal to or less than about 100%, about 90%, about 80%, about 70%, about 60%, about 50%, about 40%, about 30%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about 0.0002%, or about 0.0001%, w/w, w/v or v/v.

In some embodiments, the concentration of one or more of the compounds as disclosed herein is greater than about 90%, about 80%, about 70%, about 60%, about 50%, about 40%, about 30%, about 20%, about 19.75%, about 19.50%, about 19.25%, about 19%, about 18.75%, about 18.50%, about 18.25%, about 18%, about 17.75%, about 17.50%, about 17.25%, about 17%, about 16.75%, about 16.50%, about 16.25%, about 16%, about 15.75%, about 15.50%, about 15.25%, about 15%, about 14.75%, about 14.50%, about 14.25%, about 14%, about 13.75%, about 13.50%, about 13.25%, about 13%, about 12.75%, about 12.50%, about 12.25%, about 12%, about 11.75%, about 11.50%, about 11.25%, about 11%, about 10.75%, about 10.50%, about 10.25%, about 10%, about 9.75%, about 9.50%, about 9.25%, about 9%, about 8.75%, about 8.50%, about 8.25%, about 8%, about 7.75%, about 7.50%, about 7.25%, about 7%, about 6.75%, about 6.50%, about 6.25%, about 6%, about 5.75%, about 5.50%, about 5.25%, about 5%, about 4.75%, about 4.50%, about 4.25%, about 4%, about 3.75%, about 3.50%, about 3.25%, about 3%, about 2.75%, about 2.50%, about 2.25%, about 2%, about 1.75%, about 1.50%, about 1.25%, about 1%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about 0.0002%, or about 0.0001%, w/w, w/v, or v/v.

In some embodiments, the concentration of one or more of the compounds as disclosed herein is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, or approximately 1% to approximately 10%, w/w, w/v or v/v.

In some embodiments, the concentration of one or more of the compounds as disclosed herein is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, or approximately 0.1% to approximately 0.9%, w/w, w/v or v/v.

In some embodiments, the amount of one or more of the compounds as disclosed herein is equal to or less than about 10 g, about 9.5 g, about 9.0 g, about 8.5 g, about 8.0 g, about 7.5 g, about 7.0 g, about 6.5 g, about 6.0 g, about 5.5 g, about 5.0 g, about 4.5 g, about 4.0 g, about 3.5 g, about 3.0 g, about 2.5 g, about 2.0 g, about 1.5 g, about 1.0 g, about 0.95 g, about 0.9 g, about 0.85 g, about 0.8 g, about 0.75 g, about 0.7 g, about 0.65 g, about 0.6 g, about 0.55 g, about 0.5 g, about 0.45 g, about 0.4 g, about 0.35 g, about 0.3 g, about 0.25 g, about 0.2 g, about 0.15 g, about 0.1 g, about 0.09 g, about 0.08 g, about 0.07 g, about 0.06 g, about 0.05 g, about 0.04 g, about 0.03 g, about 0.02 g, about 0.01 g, about 0.009 g, about 0.008 g, about 0.007 g, about 0.006 g, about 0.005 g, about 0.004 g, about 0.003 g, about 0.002 g, about 0.001 g, about 0.0009 g, about 0.0008 g, about 0.0007 g, about 0.0006 g, about 0.0005 g, about 0.0004 g, about 0.0003 g, about 0.0002 g, or about 0.0001 g.

In some embodiments, the amount of one or more of the compounds as disclosed herein is more than about 0.0001 g, about 0.0002 g, about 0.0003 g, about 0.0004 g, about 0.0005 g, about 0.0006 g, about 0.0007 g, about 0.0008 g, about 0.0009 g, about 0.001 g, about 0.0015 g, about 0.002 g, about 0.0025 g, about 0.003 g, about 0.0035 g, about 0.004 g, about 0.0045 g, about 0.005 g, about 0.0055 g, about 0.006 g, about 0.0065 g, about 0.007 g, about 0.0075 g, about 0.008 g, about 0.0085 g, about 0.009 g, about 0.0095 g, about 0.01 g, about 0.015 g, about 0.02 g, about 0.025 g, about 0.03 g, about 0.035 g, about 0.04 g, about 0.045 g, about 0.05 g, about 0.055 g, about 0.06 g, about 0.065 g, about 0.07 g, about 0.075 g, about 0.08 g, about 0.085 g, about 0.09 g, about 0.095 g, about 0.1 g, about 0.15 g, about 0.2 g, about 0.25 g, about 0.3 g, about 0.35 g, about 0.4 g, about 0.45 g, about 0.5 g, about 0.55 g, about 0.6 g, about 0.65 g, about 0.7 g, about 0.75 g, about 0.8 g, about 0.85 g, about 0.9 g, about 0.95 g, about 1 g, about 1.5 g, about 2 g, about 2.5 g, about 3 g, about 3.5 g, about 4 g, about 4.5 g, about 5 g, about 5.5 g, about 6 g, about 6.5 g, about 7 g, about 7.5 g, about 8 g, about 8.5 g, about 9 g, about 9.5 g, or about 10 g.

In some embodiments, the amount of one or more of the compounds as disclosed herein is in the range of about 0.0001 to about 10 g, about 0.0005 to about 5 g, about 0.001 to about 1 g, about 0.002 to about 0.5 g, 0.005 to about 0.5 g, about 0.01 to about 0.1 g, about 0.01 to about 0.05 g, or about 0.05 to about 0.1 g.

1A. Formulations for Oral Administration

In some embodiments, provided herein are pharmaceutical compositions for oral administration containing a compound as disclosed herein, and a pharmaceutical excipient suitable for oral administration. In some embodiments, provided herein are pharmaceutical compositions for oral administration containing: (i) an effective amount of a disclosed compound; optionally (ii) an effective amount of one or more second agents; and (iii) one or more pharmaceutical excipients suitable for oral administration. In some embodiments, the pharmaceutical composition further contains: (iv) an effective amount of a third agent.

In some embodiments, the pharmaceutical composition can be a liquid pharmaceutical composition suitable for oral consumption. Pharmaceutical compositions suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more ingredients. In general, the pharmaceutical compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The present disclosure further encompasses anhydrous pharmaceutical compositions and dosage forms comprising an active ingredient, since water can facilitate the degradation of some compounds. For example, water can be added (e.g., about 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. For example, pharmaceutical compositions and dosage forms which contain lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous pharmaceutical compositions can be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the pharmaceutical compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. In some embodiments, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants can be used in the pharmaceutical compositions as provided herein to provide tablets that disintegrate when exposed to an aqueous environment. Too much of a disintegrant can produce tablets which can disintegrate in the bottle. Too little can be insufficient for disintegration to occur and can thus alter the rate and extent of release of the active ingredient(s) from the dosage form. Thus, a sufficient amount of disintegrant that is neither too little nor too much to detrimentally alter the release of the active ingredient(s) can be used to form the dosage forms of the compounds disclosed herein. The amount of disintegrant used can vary based upon the type of formulation and mode of administration, and can be readily discernible to those of ordinary skill in the art. About 0.5 to about 15 weight percent of disintegrant, or about 1 to about 5 weight percent of disintegrant, can be used in the pharmaceutical composition. Disintegrants that can be used to form pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein can be combined with various sweetening or flavoring agents, coloring matter or dyes and, for example, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms include, but are not limited to, hydrophilic surfactants, lipophilic surfactants, and mixtures thereof. That is, a mixture of hydrophilic surfactants can be employed, a mixture of lipophilic surfactants can be employed, or a mixture of at least one hydrophilic surfactant and at least one lipophilic surfactant can be employed.

A suitable hydrophilic surfactant can generally have an HLB value of at least about 10, while suitable lipophilic surfactants can generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants can be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants can be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants can include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of triglycerides, vegetable oils, and hydrogenated vegetable oils. The polyol can be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of glycerides, vegetable oils, hydrogenated vegetable oils, fatty acids and sterols; oil-soluble vitamins/vitamin derivatives; and mixtures thereof. Within this group, non-limiting examples of lipophilic surfactants include glycerol fatty acid esters, propylene glycol fatty acid esters, and mixtures thereof, or are hydrophobic transesterification products of a polyol with at least one member of vegetable oils, hydrogenated vegetable oils, and triglycerides.

In one embodiment, the pharmaceutical composition can include a solubilizer to ensure good solubilization and/or dissolution of a compound as provided herein and to minimize precipitation of the compound. This can be especially important for pharmaceutical compositions for non-oral use, e.g., pharmaceutical compositions for injection. A solubilizer can also be added to increase the solubility of the hydrophilic drug and/or other components, such as surfactants, or to maintain the pharmaceutical composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers can also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. In some embodiments, solubilizers include sorbitol, glycerol, triacetin, ethyl alcohol, PEG-400, glycofurol and propylene glycol.

The amount of solubilizer that can be included is not particularly limited. The amount of a given solubilizer can be limited to a bioacceptable amount, which can be readily determined by one of skill in the art. In some circumstances, it can be advantageous to include amounts of solubilizers far in excess of bioacceptable amounts, for example to maximize the concentration of the drug, with excess solubilizer removed prior to providing the pharmaceutical composition to a subject using conventional techniques, such as distillation or evaporation. Thus, if present, the solubilizer can be in a weight ratio of about 10%, 25%, 50%, 100%, or up to about 200% by weight, based on the combined weight of the drug, and other excipients. If desired, very small amounts of solubilizer can also be used, such as about 5%, 2%, 1% or even less. Typically, the solubilizer can be present in an amount of about 1% to about 100%, more typically about 5% to about 25% by weight.

The pharmaceutical composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, oils, odorants, opacifiers, suspending agents, binders, fillers, plasticizers, lubricants, and mixtures thereof.

Exemplary preservatives can include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfate, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, German 115, Germaben II, Neolone, Kathon, and Euxyl. In certain embodiments, the preservative is an anti-oxidant. In other embodiments, the preservative is a chelating agent.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils also include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

In addition, an acid or a base can be incorporated into the pharmaceutical composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl)-aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Examples can include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

1B. Formulations for Parenteral Administration

In some embodiments, provided herein are pharmaceutical compositions for parenteral administration containing a compound as disclosed herein, and a pharmaceutical excipient suitable for parenteral administration. In some embodiments, provided herein are pharmaceutical compositions for parenteral administration containing: (i) an effective amount of a disclosed compound; optionally (ii) an effective amount of one or more second agents; and (iii) one or more pharmaceutical excipients suitable for parenteral administration. In some embodiments, the pharmaceutical composition further contains: (iv) an effective amount of a third agent.

The forms in which the disclosed pharmaceutical compositions can be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils can also be employed.

Aqueous solutions in saline are also conventionally used for injection. Ethanol, glycerol, propylene glycol, liquid polyethylene glycol, and the like (and suitable mixtures thereof), cyclodextrin derivatives, and vegetable oils can also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound as disclosed herein in the required amount in the appropriate solvent with various other ingredients as enumerated above, as appropriate, followed by filtered sterilization. Generally, dispersions are prepared by incorporating the various sterilized active ingredients into a sterile vehicle which contains the basic dispersion medium and the appropriate other ingredients from those enumerated above. In the case of sterile powders for the preparation of sterile injectable solutions, certain methods of preparation are vacuum-drying and freeze-drying techniques which yield a powder of the active ingredient plus any additional ingredient from a previously sterile-filtered solution thereof.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Injectable compositions can contain from about 0.1 to about 5% w/w of a compound as disclosed herein.

1C. Formulations for Topical Administration

In some embodiments, provided herein are pharmaceutical compositions for topical (e.g., transdermal) administration containing a compound as disclosed herein, and a pharmaceutical excipient suitable for topical administration. In some embodiments, provided herein are pharmaceutical compositions for topical administration containing: (i) an effective amount of a disclosed compound; optionally (ii) an effective amount of one or more second agents; and (iii) one or more pharmaceutical excipients suitable for topical administration. In some embodiments, the pharmaceutical composition further contains: (iv) an effective amount of a third agent.

Pharmaceutical compositions provided herein can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation can provide more immediate exposure of the active ingredient to the chosen area.

The pharmaceutical compositions also can comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the disclosed methods employs transdermal delivery devices ("patches"). Such transdermal patches can be used to provide continuous or discontinuous infusion of a compound as provided herein in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches can be constructed for continuous, pulsatile, or on demand delivery of pharmaceutical agents.

Suitable devices for use in delivering intradermal pharmaceutically acceptable compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Topically-administrable formulations can, for example, comprise from about 1% to about 10% (w/w) of a compound provided herein relative to the total weight of the formulation, although the concentration of the compound provided herein in the formulation can be as high as the solubility limit of the compound in the solvent. In some embodiments, topically-administrable formulations can, for example, comprise from about 1% to about 9% (w/w) of a compound provided herein, such as from about 1% to about 8% (w/w), further such as from about 1% to about 7% (w/w), further such as from about 1% to about 6% (w/w), further such as from about 1% to about 5% (w/w), further such as from about 1% to about 4% (w/w), further such as from about 1% to about 3% (w/w), and further such as from about 1% to about 2% (w/w) of a compound provided herein. Formulations for topical administration can further comprise one or more of the additional pharmaceutically acceptable excipients described herein.

1D. Formulations for Inhalation Administration

In some embodiments, provided herein are pharmaceutical compositions for inhalation administration containing a compound as disclosed herein, and a pharmaceutical excipient suitable for topical administration. In some embodiments, provided herein are pharmaceutical compositions for inhalation administration containing: (i) an effective amount of a disclosed compound; optionally (ii) an effective amount of one or more second agents; and (iii) one or more pharmaceutical excipients suitable for inhalation administration. In some embodiments, the pharmaceutical composition further contains: (iv) an effective amount of a third agent.

Pharmaceutical compositions for inhalation or insufflation include solutions and suspensions in pharmaceutically acceptable, aqueous or organic solvents, or mixtures thereof, and powders. The liquid or solid pharmaceutical compositions can contain suitable pharmaceutically acceptable excipients as described herein. In some embodiments, the pharmaceutical compositions are administered by the oral or nasal respiratory route for local or systemic effect. Pharmaceutical compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder pharmaceutical compositions can be administered, e.g., orally or nasally, from devices that deliver the formulation in an appropriate manner.

1E. Formulations for Ocular Administration

In some embodiments, the disclosure provides a pharmaceutical composition for treating ophthalmic disorders. The pharmaceutical composition can contain an effective amount of a compound as disclosed herein and a pharmaceutical excipient suitable for ocular administration. Pharmaceutical compositions suitable for ocular administration can be presented as discrete dosage forms, such as drops or sprays each containing a predetermined amount of an active ingredient a solution, or a suspension in an aqueous or non-aqueous liquid, an oil-in-water emulsion, or a water-in-oil liquid emulsion. Other administration forms include intraocular injection, intravitreal injection, topically, or through the use of a drug eluting device, microcapsule, implant, or microfluidic device. In some cases, the compounds as disclosed herein are administered with a carrier or excipient that increases the intraocular penetrance of the compound such as an oil and water emulsion with colloid particles having an oily core surrounded by an interfacial film. It is contemplated that all local routes to the eye can be used including topical, subconjunctival, periocular, retrobulbar, subtenon, intracameral, intravitreal, intraocular, subretinal, juxtascleral and suprachoroidal administration. Systemic or parenteral administration can be feasible including, but not limited to intravenous, subcutaneous, and oral delivery. An exemplary method of administration will be intravitreal or subtenon injection of solutions or suspensions, or intravitreal or subtenon placement of bioerodible or non-bioerodible devices, or by topical ocular administration of solutions or suspensions, or posterior juxtascleral administration of a gel or cream formulation.

Eye drops can be prepared by dissolving the active ingredient in a sterile aqueous solution such as physiological saline, buffering solution, etc., or by combining powder compositions to be dissolved before use. Other vehicles can be chosen, as is known in the art, including, but not limited to: balance salt solution, saline solution, water soluble polyethers such as polyethylene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. In some embodiments, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

In some cases, the colloid particles include at least one cationic agent and at least one non-ionic surfactant such as a poloxamer, tyloxapol, a polysorbate, a polyoxyethylene castor oil derivative, a sorbitan ester, or a polyoxyl stearate. In some cases, the cationic agent is an alkylamine, a tertiary alkyl amine, a quaternary ammonium compound, a cationic lipid, an amino alcohol, a biguanidine salt, a cationic compound or a mixture thereof. In some cases, the cationic agent is a biguanidine salt such as chlorhexidine, polyaminopropyl biguanidine, phenformin, alkylbiguanidine, or a mixture thereof. In some cases, the quaternary ammonium compound is a benzalkonium halide, lauralkonium halide, cetrimide, hexadecyltrimethylammonium halide, tetradecyltrimethylammonium halide, dodecyltrimethylammonium halide, cetrimonium halide, benzethonium halide, behenalkonium halide, cetalkonium halide, cetethyldimonium halide, cetylpyridinium halide, benzododecinium halide, chlorallyl methenamine halide, rnyristylalkonium halide, stearalkonium halide or a mixture of two or more thereof. In some cases, cationic agent is a benzalkonium chloride, lauralkonium chloride, benzododecinium bromide, benzethenium chloride, hexadecyltrimethylammonium bromide, tetradecyltrimethylammonium bromide, dodecyltrimethylammonium bromide or a mixture of two or more thereof. In some cases, the oil phase is mineral oil and light mineral oil, medium chain triglycerides (MCT), coconut oil; hydrogenated oils comprising hydrogenated cottonseed oil, hydrogenated palm oil, hydrogenate castor oil or hydrogenated soybean oil; polyoxyethylene hydrogenated castor oil derivatives comprising poluoxyl-40 hydrogenated castor oil, polyoxyl-60 hydrogenated castor oil or polyoxyl-100 hydrogenated castor oil.

1F. Formulations for Controlled Release Administration

In some embodiments, provided herein are pharmaceutical compositions for controlled release administration containing a compound as disclosed herein, and a pharmaceutical excipient suitable for controlled release administration. In some embodiments, provided herein are pharmaceutical compositions for controlled release administration containing: (i) an effective amount of a disclosed compound; optionally (ii) an effective amount of one or more second agents; and (iii) one or more pharmaceutical excipients suitable for controlled release administration. In some embodiments, the pharmaceutical composition further contains: (iv) an effective amount of a third agent.

Active agents such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 each of which is incorporated herein by reference. Such dosage forms can be used to provide slow or controlled release of one or more active agents using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active agents provided herein. Thus, the pharmaceutical compositions provided encompass single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. In some embodiments, the use of a controlled release preparation in medical treatment is characterized by a minimum of drug substance being employed to cure or control the disease, disorder, or condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

In some embodiments, controlled release formulations are designed to initially release an amount of a compound as disclosed herein that promptly produces the desired therapeutic effect, and gradually and continually release other amounts of the compound to maintain this level of therapeutic or prophylactic effect over an extended period of time. In order to maintain this constant level of the compound in the body, the compound should be released from the dosage form at a rate that will replace the amount of drug being metabolized and excreted from the body. Controlled release of an active agent can be stimulated by various conditions including, but not limited to, pH, temperature, enzymes, water, or other physiological conditions or compounds.

In certain embodiments, the pharmaceutical composition can be administered using intravenous infusion, an implantable osmotic pump, a transdermal patch, liposomes, or other modes of administration. In one embodiment, a pump can be used (see, Sefton, *CRC Crit. Ref. Biomed. Eng.* 14:201 (1987); Buchwald et al., *Surgery* 88:507 (1980); Saudek et al., *N Engl. J. Med.* 321:574 (1989)). In another embodiment, polymeric materials can be used. In yet another embodiment, a controlled release system can be placed in a subject at an appropriate site determined by a practitioner of skill, e.g., thus requiring only a fraction of the systemic dose (see, e.g., Goodson, *Medical Applications of Controlled Release*, 115-138 (vol. 2, 1984). Other controlled release systems are discussed in the review by Langer, *Science* 249:1527-1533 (1990). The one or more active agents can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The one or more active agents then diffuse through the outer polymeric membrane in a release rate controlling step. The percentage of active agent in such parenteral compositions is highly dependent on the specific nature thereof, as well as the needs of the subject.

2. Dosages

A compound described herein can be delivered in the form of pharmaceutically acceptable compositions which comprise a therapeutically effective amount of one or more compounds described herein and/or one or more additional therapeutic agents such as a chemotherapeutic, formulated together with one or more pharmaceutically acceptable excipients. In some instances, the compound described herein and the additional therapeutic agent are administered in separate pharmaceutical compositions and can (e.g., because of different physical and/or chemical characteristics) be administered by different routes (e.g., one therapeutic is administered orally, while the other is administered intravenously). In other instances, the compound described herein and the additional therapeutic agent can be administered separately, but via the same route (e.g., both orally or both intravenously). In still other instances, the compound described herein and the additional therapeutic agent can be administered in the same pharmaceutical composition.

The selected dosage level will depend upon a variety of factors including, for example, the activity of the particular compound employed, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

In general, a suitable daily dose of a compound described herein and/or a chemotherapeutic will be that amount of the compound which, in some embodiments, can be the lowest dose effective to produce a therapeutic effect. Such an effective dose will generally depend upon the factors described herein. Generally, doses of the compounds described herein for a patient, when used for the indicated effects, can range from about 1 mg to about 1000 mg, about 0.01 mg to about 500 mg per day, about 0.1 mg to about 500 mg per day, about 1 mg to about 500 mg per day, about 5 mg to about 500 mg per day, about 0.01 mg to about 200 mg per day, about 0.1 mg to about 200 mg per day, about 1 mg to about 200 mg per day, about 5 mg to about 200 mg per day, about 0.01 mg to about 100 mg per day, about 0.1 mg to about 100 mg per day, about 1 mg to about 100 mg per day, about 5 mg to about 100 mg per day, about 0.01 mg to about 50 mg per day, about 0.1 mg to about 50 mg per day, about 1 mg to about 50 mg per day, about 5 mg to about 50 mg per day, about 5 mg to about 40 mg, about 5 mg to about 30 mg, about 5 mg to about 25 mg, or about 5 mg to about 20 mg per day. An exemplary dosage is about 0.1 to 100 mg per day. Actual dosage levels of the active ingredients in the pharmaceutical compositions described herein can be varied so as to obtain an amount of the active ingredient which is effective to achieve the desired therapeutic response for a particular patient, composition, and mode of administration, without being toxic to the patient. In some instances, dosage levels below the lower limit of the aforesaid range can be more than adequate, while in other cases still larger doses can be employed without causing any harmful side effect, e.g., by dividing such larger doses into several small doses for administration throughout the day.

In some embodiments, the compounds can be administered daily, every other day, three times a week, twice a week, weekly, or bi-weekly. The dosing schedule can include a "drug holiday," e.g., the drug can be administered for two weeks on, one week off, or three weeks on, one week off, or four weeks on, one week off, etc., or continuously, without a drug holiday. The compounds can be administered orally, intravenously, intraperitoneally, topically, transdermally, intramuscularly, subcutaneously, intranasally, sublingually, or by any other route.

In some embodiments, a compound as provided herein is administered in multiple doses. Dosing can be about once, twice, three times, four times, five times, six times, or more than six times per day. Dosing can be about once a month, about once every two weeks, about once a week, or about once every other day. In another embodiment, a compound as disclosed herein and another agent are administered together from about once per day to about 6 times per day. In another embodiment, the administration of a compound as provided herein and an agent continues for less than about 7 days. In yet another embodiment, the administration continues for more than about 6 days, about 10 days, about 14 days, about 28 days, about two months, about six months, or about one year. In some cases, continuous dosing is achieved and maintained as long as necessary.

Administration of the pharmaceutical compositions as disclosed herein can continue as long as necessary. In some embodiments, an agent as disclosed herein is administered for more than about 1, about 2, about 3, about 4, about 5, about 6, about 7, about 14, about 21, or about 28 days. In some embodiments, an agent as disclosed herein is administered for less than about 28, about 21, about 14, about 7, about 6, about 5, about 4, about 3, about 2, or about 1 day. In some embodiments, an agent as disclosed herein is administered for about 1, about 2, about 3, about 4, about 5, about 6, about 7, about 14, about 21, or about 28 days. In some embodiments, an agent as disclosed herein is administered chronically on an ongoing basis, e.g., for the treatment of chronic effects.

Since the compounds described herein can be administered in combination with other treatments (such as additional chemotherapeutics, radiation or surgery), the doses of each agent or therapy can be lower than the corresponding dose for single-agent therapy. The dose for single-agent therapy can range from, for example, about 0.0001 to about 200 mg, or about 0.001 to about 100 mg, or about 0.01 to about 100 mg, or about 0.1 to about 100 mg, or about 1 to about 50 mg per day.

When a compound provided herein, is administered in a pharmaceutical composition that comprises one or more agents, and the agent has a shorter half-life than the compound provided herein unit dose forms of the agent and the compound provided herein can be adjusted accordingly.

In specific embodiments, provided herein is a pharmaceutical composition (e.g., a tablet or a capsule) comprising a PI3K modulator provided herein (e.g., Compound 292, or a pharmaceutically acceptable form thereof), wherein the PI3K modulator is in the amount of about 0.5 mg, about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 60 mg, about 75 mg, about 80 mg, or about 100 mg. In exemplary embodiments, a pharmaceutical composition (e.g., a tablet or a capsule) comprising a PI3K modulator provided herein (e.g., Compound 292, or a pharmaceutically acceptable form thereof) is administered once daily. In exemplary embodiments, a pharmaceutical composition (e.g., a tablet or a capsule) comprising a PI3K modulator provided herein (e.g., Compound 292, or a pharmaceutically acceptable form thereof) is administered twice daily. In exemplary embodiments, a pharmaceutical composition (e.g., a tablet or a capsule) comprising a PI3K modulator provided herein (e.g., Compound 292, or a pharmaceutically acceptable form thereof) is administered in a 28-day cycle.

In specific embodiments, provided herein is a pharmaceutical composition (e.g., a tablet or a capsule) comprising a PI3K modulator provided herein (e.g., Compound 292, or a pharmaceutically acceptable form thereof), which is prepared for oral delivery.

In specific embodiments, provided herein is a pharmaceutical composition (e.g., a tablet or a capsule) comprising a PI3K modulator provided herein (e.g., Compound 292, or a pharmaceutically acceptable form thereof), and a pharmaceutically acceptable excipient or carrier. In exemplary embodiments, the pharmaceutically acceptable excipient or carrier in the composition is one or more of microcrystalline cellulose (e.g., silicified microcrystalline cellulose), crospovidone, and/or magnesium stearate.

Methods of Treatment and Prevention

Without being limited to a particular theory, PI3Ks are regulators of signal transduction that mediate cell proliferation, differentiation, survival, and migration. PI3K-δ and PI3K-γ are expressed in hematopoietic cells and play roles in hematologic malignancies. For example, PI3K-δ and PI3K-γ have roles in the establishment and maintenance of the tumor microenvironment. PI3K-δ and PI3K-γ are highly expressed in the heme compartment, and can be useful in treating hematologic cancers. Class I PI3Ks, including PI3K-δ and PI3K-γ isoforms, are also associated with cancers (reviewed, e.g., in Vogt, P K et al. (2010) Curr Top Microbiol Immunol. 347:79-104; Fresno Vara, J A et al. (2004) Cancer Treat Rev. 30(2):193-204; Zhao, L and Vogt, P K. (2008) Oncogene 27(41):5486-96). Inhibitors of PI3K, e.g., PI3K-δ and/or PI3K-γ, have been shown to have anti-cancer activity (e.g., Courtney, K D et al. (2010) J Clin Oncol. 28(6):1075-1083); Markman, B et al. (2010) Ann Oncol. 21(4):683-91; Kong, D and Yamori, T (2009) Curr Med Chem. 16(22):2839-54; Jimeno, A et al. (2009) J Clin Oncol. 27:156s (suppl; abstr 3542); Flinn, I W et al. (2009) J Clin Oncol. 27:156s (suppl; abstr 3543); Shapiro, G et al. (2009) J Clin Oncol. 27:146s (suppl; abstr 3500); Wagner, A J et al. (2009) J Clin Oncol. 27:146s (suppl; abstr 3501); Vogt, P K et al. (2006) Virology 344(1):131-8; Ward, S et al. (2003) Chem Biol. 10(3):207-13; WO 2011/041399; US 2010/0029693; US 2010/0305096; US 2010/0305084; each incorporated herein by reference). PI3K-δ and PI3K-γ are expressed in some solid tumors, including prostate, breast, and glioblastomas (Chen J. S. et al. (2008) *Mol Cancer Ther.* 7(4):841-50; Ikeda H. et al. (2010) *Blood* 116(9):1460-8). Without being limited to a particular theory, inhibition of PI3K can have an effect on tumor inflammation and progression.

In one embodiment, provided herein is a method for treating or preventing a specific type of cancer or disease, such as, a specific type of hematologic malignancy, which has a high expression level of one or more isoform(s) of PI3K. The PI3K isoforms include one or more of PI3K-α, PI3K-β, PI3K-δ, or PI3K-γ, or a combination thereof. In one embodiment, the specific type of cancer or disease, such as, a specific type of hematologic malignancy, has a high expression level of PI3K-δ, or PI3K-γ, or both PI3K-δ and PI3K-γ.

In one embodiment, provided herein is a method for treating or preventing a specific sub-type of cancer or disease, such as, a specific sub-type of hematologic malignancy, which has a high expression level of one or more isoform(s) of PI3K. The PI3K isoforms include one or more of PI3K-α, PI3K-β, PI3K-δ, or PI3K-γ, or a combination thereof. In one embodiment, the specific sub-type of cancer or disease, such as, a specific sub-type of hematologic malignancy, has a high expression level of PI3K-δ, or PI3K-γ, or both PI3K-δ and PI3K-γ.

In one embodiment, provided herein is a method for treating or preventing a specific patient or group of patients, having a cancer or disease, such as, a hematologic malignancy, wherein the particular patient or group of patients has(ve) a high expression level of one or more isoform(s) of PI3K. The PI3K isoforms include one or more of PI3K-α, PI3K-β, PI3K-δ, or PI3K-γ, or a combination thereof. In one embodiment, the specific patient or group of patients has(v) a high expression level of PI3K-δ, or PI3K-γ, or both PI3K-δ and PI3K-γ.

In one embodiment, the methods provided herein comprise administering a PI3K modulator (e.g., a compound that selectively reduces the activity of one or more PI3K isoform (s)), alone or in combination with one or more other agents or therapeutic modalities, to a subject, e.g., a mammalian subject, e.g., a human. In one embodiment, the PI3K modulator is selective for one or more isoform(s) of PI3K over the other isoform(s) of PI3K (e.g., PI3K-δ selective, PI3K-γ selective, or PI3K-δ and PI3K-γ selective).

Exemplary PI3K-α selective inhibitors include, but are not limited to, GDC-0032 (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117/INK1117 ((2R)-1-Phenoxy-2-butanyl hydrogen (S)-methylphosphonate; or Methyl(oxo){[(2R)-1-phenoxy-2-butanyl]oxy}phosphonium), and BYL-719 ((2S)—N1-[4-Methyl-5-[2-(2,2,2-trifluoro-1,1-dimethylethyl)-4-pyridinyl]-2-thiazolyl]-1,2-pyrrolidinedicarboxamide).

Exemplary PI3K-α/m-TOR inhibitors include, but are not limited to, GSK2126458 (2,4-Difluoro-N-{2-(methyloxy)-5-[4-(4-pyridazinyl)-6-quinolinyl]-3-pyridinyl}benzenesulfonamide).

Exemplary PI3K-β selective inhibitors include, but are not limited to, TGX-221 ((±)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl) benzyl)-6-morpholino-1H-benzo[d]imidazole-4-carboxylic acid dihydrochloride), and KIN-193 ((R)-2-((1-(7-methyl-2-morpholino-4-oxo-4H-pyrido[1,2-a]pyrimidin-9-yl)ethyl) amino)benzoic acid).

Exemplary PI3K-δ selective inhibitors include, but are not limited to, TGR-1202/RP5264, GS-9820 ((S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one), GS-1101 (5-fluoro-3-phenyl-2-([S)]-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl) phenyl)-3-methoxy-4-methylbenzamide), and BAY80-6946 (2-amino-N-(7-methoxy-8-(3-morpholinopropoxy)-2,3-dihydroimidazo[1,2-c]quinazolin-5-yl)pyrimidine-5-carboxamide).

Exemplary PI3K-γ selective inhibitors include, but are not limited to, AS 252424 (5-[1-[5-(4-Fluoro-2-hydroxy-phenyl)-furan-2-yl]-meth-(Z)-ylidene]-thiazolidine-2,4-dione), and CZ 24832 (5-(2-amino-8-fluoro-[1,2,4]triazolo[1,5-a] pyridin-6-yl)-N-tert-butylpyridine-3-sulfonamide).

Exemplary pan-PI3K inhibitors include, but are not limited to, Buparlisib (5-[2,6-Di(4-morpholinyl)-4-pyrimidinyl]-4-(trifluoromethyl)-2-pyridinamine), SAR245409 (N-(4-(N-(3-((3,5-dimethoxyphenyl)amino)quinoxalin-2-yl) sulfamoyl)phenyl)-3-methoxy-4-methylbenzamide), and GDC-0941 (2-(1H-Indazol-4-yl)-6-[[4-(methylsulfonyl)-1-piperazinyl]methyl]-4-(4-morpholinyl)thieno[3,2-d]pyrimidine).

Exemplary pan-PI3K/mTOR inhibitors include, but are not limited to, GDC-0980 ((S)-1-(4-((2-(2-aminopyrimidin-5-yl)-7-methyl-4-morpholinothieno[3,2-d]pyrimidin-6-yl) methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12, 15-pentaoxo-1-(4-(4-oxo-8-phenyl-4H-chromen-2-yl)morpholino-4-ium)-2-oxa-7,10,13,16-tetraazaoctadecan-18-oate), PF-05212384 (N-[4-[[4-(Dimethylamino)-1-piperidinyl]carbonyl]phenyl]-N'-[4-(4,6-di-4-morpholinyl-1,3,5-triazin-2-yl)phenyl]urea), LY3023414, BEZ235 (2-Methyl-2-{4-[3-methyl-2-oxo-8-(quinolin-3-yl)-2,3-dihydro-1H-imidazo[4,5-c]quinolin-1-yl] phenyl}propanenitrile), XL-765 (N-(3-(N-(3-(3,5-dimethoxyphenylamino)quinoxalin-2-yl)sulfamoyl)phenyl)-3-methoxy-4-methylbenzamide), and GSK1059615 (5-[[4-(4-Pyridinyl)-6-quinolinyl]methylene]-2,4-thiazolidinedione).

Exemplary beta-sparing (PI3K-α/δ/γ) inhibitors include, but are not limited to, PX886 ([(3aR,6E,9 S,9aR,10R,11aS)-6-[[bis(prop-2-enyl)amino]methylidene]-5-hydroxy-9-

(methoxymethyl)-9a,11a-dimethyl-1,4,7-trioxo-2,3,3a,9,10,11-hexahydroindeno[4,5-h]isochromen-10-yl]acetate (also known as sonolisib)).

Without being limited to a particular theory, in one embodiment, as used herein, and unless otherwise indicated, high expression of a particular PI3K isoform can be an increased DNA copy number of the PI3K isoform or a receptor or target relating to the PI3K isoform, a high expression of RNA of the PI3K isoform or a receptor or target relating to the PI3K isoform, a high expression of the protein of the PI3K isoform or a receptor or target relating to the PI3K isoform, amplification of the PI3K isoform or a receptor or target relating to the PI3K isoform, deletion of a receptor or target relating to the PI3K isoform, downregulation of a receptor or target relating to the PI3K isoform, mutation of the PI3K isoform or a receptor or target relating to the PI3K isoform, and/or pathway activation of the PI3K isoform or a receptor or target relating to the PI3K isoform. Without being limited to a particular theory, in one embodiment, provided herein are biomarkers of pathway activation and methods of use thereof, which are predictive of response to treatment described herein (e.g., a biomarker relating to pAKT, pS6, pPRAS40, or other proteins or transcriptionally regulated genes downstream of PI3Kδ and/or PI3Kγ).

In certain embodiments, the expression level of one or more than one particular PI3K isoform in a cancer or a disease, or a patient or a group of patients, can be determined by detecting the expression level of a particular PI3K isoform protein, or RNA of a particular PI3K isoform, or the increased DNA copy number of a particular PI3K isoform, for example, using a method provided herein or a method known in the art. In other embodiments, the expression level of one or more than one particular PI3K isoform in a cancer or a disease, or a patient or a group of patients, can be determined by measuring a biomarker provided herein (e.g., a signaling pathway biomarker, a protein mutation biomarker, a protein expression biomarker, a gene mutation biomarker, a gene expression biomarker, a cytokine biomarker, a chemokine biomarker, a matrix metalloproteinase biomarker, or a biomarker for particular cancer cells, among others). In yet another embodiment, the expression level of one or more than one particular PI3K isoform in a cancer or a disease, or a patient or a group of patients, can be determined based on information known in the art or based on prior studies on the cancer or disease, or prior testing of the patient or group of patients.

In certain embodiments, the selectivity of a PI3K modulator (e.g., a compound provided herein) toward one or more PI3K isoform(s) over other PI3K isoform(s) can be determined by measuring the activity of the PI3K modulator toward PI3K isoforms (e.g., PI3K-α, PI3K-β, PI3K-δ, and/or PI3K-γ), for example, using a method provided herein or a method known in the art.

PI3K-γ is a Class 1B PI3K that associates with the p101 and p84 (p87PIKAP) adaptor proteins, and canonically signals through GPCRs. Non-cononical activation through tyrosine kinase receptors and RAS can occur. Activated PI3K-γ leads to production of PIP3, which serves as a docking site for downstream effector proteins including AKT and BTK, bringing these enzymes to the cell membrane where they may be activated. A scaffolding role for PI3k-γ has been proposed and may contribute to the activation of the RAS/MEK/ERK pathway. The interaction with the RAS pathway explains activities attributed to kinase dead PI3K-γ in cells or in animals. PI3K-γ is essential for function of a variety of immune cells and pathways. Production of chemokines that attract neutrophil or monocyte cell migration is mediated by PI3K-γ upon inflammatory stimulants (including IL8, fMLP, and C5a) (HIRSCH et al., "Central Role for G Protein-Coupled Phosphoinositide 3-Kinase γ in Inflammation," *Science* 287:1049-1053 (2000); SASAKI et al., "Function of PI3Kγ in Thymocyte Development, T Cell Activation, and Neutrophil Migration," *Science* 287:1040-1046 (2000); LI et al., "Roles of PLC-β2 and -β3 and PI3Kγ in Chemoattractant-Mediated Signal Transduction," *Science* 287:1046-1049 (2000)). The requirement for PI3K-γ-dependent neutrophil migration is demonstrated by failure of arthritis development in the K/BXN serum transfer arthritis model in PI3K-γ knockout mice (Randis et al., *Eur. I Immunol.*, 2008, 38(5), 1215-24). Similarly, the mice fail to develop cellular inflammation and airway hyper-responsiveness in the ovalbumin induced asthma model (Takeda et al., *J. Allergy Clin. Immunol.*, 2009; 123, 805-12). PI3K-γ deficient mice also have defects in T-helper cell function. T-cell cytokine production and proliferation in response to activation is reduced, and T helper dependent viral clearance is defective (Sasaki et al., *Science*, 2000, 287, 1040-46). T-cell dependent inflammatory disease models including EAE also do not develop in PI3K-γ deficient mice, and both the T-cell activation defect and cellular migration defects may contribute to efficacy in this model (Comerfold, *PLOS One*, 2012, 7, e45095). The imiquimod psoriasis model has also been used to demonstrate the importance of PI3K-γ in the inflammatory response. Using PI3K-γ deficient mice in this model, the accumulation of γδ T cells in the skin is blocked, as well as dendritic cell maturation and migration (ROLLER et al., "Blockade of Phosphatidylinositol 3-Kinase (PI3K)δ or PI3Kγ Reduces IL-17 and Ameliorates Imiquimod-Induced Psoriasis-like Dermatitis," *J. Immunol.* 189:4612-4620 (2012)). The role of PI3K-γ in cellular trafficking can also be demonstrated in oncology models where tumor inflammation is important for growth and metastasis of cancers. In the Lewis Lung Carcinoma model, monocyte activation, migration, and differentiation in tumors are defective. This defect results in a reduction in tumor growth and extended survival in PI3K-γ deficient mice (Schmid et al., *Cancer Cell*, 2011, 19, 715-27) or upon treatment with inhibitors that target PI3K-γ. In pancreatic cancer, PI3K-γ can be inappropriately expressed, and in this solid tumor cancer or others where PI3K-γ plays a functional role, inhibition of PI3K-γ can be beneficial. Inhibition of PI3K-γ shows promise for the treatment of hematologic malignancies. In a T-ALL model employing a T cell directed knockout of PTEN, PI3K-δ and PI3K-γ are both essential for the appropriate development of disease, as shown with genetic deletion of both genes (Subramaniam et al. *Cancer Cell* 21, 459-472, 2012). In addition, in this T-ALL model, treatment with a small molecule inhibitor of both kinases leads to extended survival of these mice. In CLL, chemokine networks support a pseudo-follicular microenvironment that includes nurse-like cells, stromal cells and T-helper cells. The roles of PI3K-γ in normal chemokine signaling and T cell biology suggest the value of inhibiting this target in CLL (BURGER, "Inhibiting B-Cell Receptor Signaling Pathways in Chronic Lymphocytic Leukemia," *Curr. Mematol. Malig. Rep.* 7:26-33 (2012)). Accordingly, PI3K-γ inhibitors are therapeutically interesting for diseases of the immune system where cell trafficking and T-cell or myeloid cell function is important. In oncology, solid tumors that are dependent on tumor inflammation, or tumors with high levels of PI3K-γ expression, may be targeted. For hematological cancers a special role for PI3K-γ and PI3K-δ isoforms in T-ALL and potentially in CLL suggests there could be benefit from targeting these PI3Ks in these diseases.

The role of PI3K-γ pathway in promoting myeloid cell trafficking to tumors and the role of blockade of p110γ in suppression of tumor inflammation and growth in breast cancer, pancreatic cancer, and lung cancer are reported in Schmid et al. (2011) *Cancer Cell* 19, 715-727, the entirety of which is incorporated herein by reference. In one embodiment, provided herein is a method of treating or preventing pancreatic cancer with a PI3K inhibitor. In another embodiment, provided herein is a method of treating or preventing breast cancer with a PI3K inhibitor. In yet another embodiment, provided herein is a method of treating or preventing lung cancer with a PI3K inhibitor. In one embodiment, the PI3K inhibitor is a PI3K-γ inhibitor, selective or non-selective over one or more other PI3K isoform(s). In one embodiment, the PI3K inhibitor is a PI3K-γ selective inhibitor.

PI3K-δ and PI3K-γ isoforms are preferentially expressed in leukocytes where they have distinct and non-overlapping roles in immune cell development and function. See, e.g., PURI and GOLD, "Selective inhibitors of phosphoinositide 3-kinase delta: modulators of B-cell function with potential for treating autoimmune inflammatory disease and B-cell malignancies," *Front. Immunol.* 3:256 (2012); BUITENHUIS et al., "The role of the PI3k-PKB signaling module in regulation of hematopoiesis," *Cell Cycle* 8(4):560-566 (2009); HOELLENRIEGEL and BURGER, "Phosphoinositide 3′-kinase delta: turning off BCR signaling in Chronic Lymphocytic Leukemia," *Oncotarget* 2(10):737-738 (2011); HIRSCH et al., "Central Role for G Protein-Coupled Phosphoinositide 3-Kinase γ in Inflammation," *Science* 287: 1049-1053 (2000); LI et al., "Roles of PLC-β2 and -β3 and PI3Kγ in Chemoattractant-Mediated Signal Transduction," *Science* 287:1046-1049 (2000); SASAKI et al., "Function of PI3Kγ in Thymocyte Development, T Cell Activation, and Neutrophil Migration," *Science* 287:1040-1046 (2000); CUSHING et al., "PI3Kδ and PI3Kγ as Targets for Autoimmune and Inflammatory Diseases," *J. Med. Chem.* 55:8559-8581 (2012); MAXWELL et al., "Attenuation of phosphoinositide 3-kinase δ signaling restrains autoimmune disease," *J. Autoimmun.* 38:381-391 (2012); HAYLOCK-JACOBS et al., "PI3Kδ drives the pathogenesis of experimental autoimmune encephalomyelitis by inhibiting effector T cell apoptosis and promoting Th17 differentiation," *J. Autoimmun.* 36:278-287 (2011); SOOND et al., "PI3K p110δ regulates T-cell cytokine production during primary and secondary immune responses in mice and humans," *Blood* 115(11): 2203-2213 (2010); ROLLER et al., "Blockade of Phosphatidylinositol 3-Kinase (PI3K)δ or PI3Kγ Reduces IL-17 and Ameliorates Imiquimod-Induced Psoriasis-like Dermatitis," *J. Immunol.* 189:4612-4620 (2012); CAMPS et al., "Blockade of PI3Kγ suppresses joint inflammation and damage in mouse models of rheumatoid arthritis," *Nat. Med.* 11(9): 936-943 (2005). As key enzymes in leukocyte signaling, PI3K-δ and PI3K-γ facilitate normal B-cell, T-cell and myeloid cell functions including differentiation, activation, and migration. See, e.g., HOELLENRIEGEL and BURGER, "Phosphoinositide 3′-kinase delta: turning off BCR signaling in Chronic Lymphocytic Leukemia," *Oncotarget* 2(10):737-738 (2011); CUSHING et al., "PI3Kδ and PI3Kγ as Targets for Autoimmune and Inflammatory Diseases," *J. Med. Chem.* 55:8559-8581 (2012). PI3K-δ or PI3K-γ activity is critical for preclinical models of autoimmune and inflammatory diseases. See, e.g., HIRSCH et al., "Central Role for G Protein-Coupled Phosphoinositide 3-Kinase γ in Inflammation," *Science* 287:1049-1053 (2000); LI et al., "Roles of PLC-β2 and β3 and PI3Kγ in Chemoattractant-Mediated Signal Transduction," *Science* 287:1046-1049 (2000); SASAKI et al., "Function of PI3Kγ in Thymocyte Development, T Cell Activation, and Neutrophil Migration," *Science* 287:1040-1046 (2000); CUSHING et al., "PI3Kδ and PI3Kγ as Targets for Autoimmune and Inflammatory Diseases," *J. Med. Chem.* 55:8559-8581 (2012); MAXWELL et al., "Attenuation of phosphoinositide 3-kinase δ signaling restrains autoimmune disease," *J. Autoimmun.* 38:381-391 (2012); HAYLOCK-JACOBS et al., "PI3Kδ drives the pathogenesis of experimental autoimmune encephalomyelitis by inhibiting effector T cell apoptosis and promoting Th17 differentiation," *J. Autoimmun.* 36:278-287 (2011); SOOND et al., "PI3K p110δ regulates T-cell cytokine production during primary and secondary immune responses in mice and humans," *Blood* 115(11): 2203-2213 (2010); ROLLER et al., "Blockade of Phosphatidylinositol 3-Kinase (PI3K)δ or PI3Kγ Reduces IL-17 and Ameliorates Imiquimod-Induced Psoriasis-like Dermatitis," *J. Immunol.* 189:4612-4620 (2012); CAMPS et al., "Blockade of PI3Kγ suppresses joint inflammation and damage in mouse models of rheumatoid arthritis," *Nat. Med.* 11(9): 936-943 (2005). Given the key role for PI3K-δ and PI3K-γ in immune function, inhibitors of the PI3K-δ and/or γ have therapeutic potential in immune-related inflammatory or neoplastic diseases.

PI3K-δ and PI3K-γ are central to the growth and survival of B- and T-cell malignancies and inhibition of these isoforms may effectively limit these diseases. See, e.g., SUBRAMANIAM et al., "Targeting Nonclassical Oncogenes for Therapy in T-ALL," *Cancer Cell* 21:459-472 (2012); LANNUTTI et al., "CAL-101 a p110δ selective phosphatidylinositol-3-kinase inhibitor for the treatment of B-cell malignancies, inhibits PI3K signaling and cellular viability," *Blood* 117(2):591-594 (2011). PI3K-δ and PI3K-γ support the growth and survival of certain B-cell malignancies by mediating intracellular BCR signaling and interactions between the tumor cells and their microenvironment. See, e.g., PURI and GOLD, "Selective inhibitors of phosphoinositide 3-kinase delta: modulators of B-cell function with potential for treating autoimmune inflammatory disease and B-cell malignancies," *Front. Immunol.* 3:256 (2012); HOELLENRIEGEL et al., "The phosphoinositide 3′-kinase delta inhibitor, CAL-101, inhibits B-cell receptor signaling and chemokine networks in chronic lymphocytic leukemia," Blood 118(13):3603-3612 (2011); BURGER, "Inhibiting B-Cell Receptor Signaling Pathways in Chronic Lymphocytic Leukemia," Curr. *Mematol. Malig. Rep.* 7:26-33 (2012). Increased BCR signaling is a central pathologic mechanism of B-cell malignancies and PI3K activation is a direct consequence of BCR pathway activation. See, e.g., BURGER, "Inhibiting B-Cell Receptor Signaling Pathways in Chronic Lymphocytic Leukemia," Curr. *Mematol. Malig. Rep.* 7:26-33 (2012); HERISHANU et al., "The lymph node microenvironment promotes B-cell receptor signaling, NF-κB activation, and tumor proliferation in chronic lymphocytic leukemia," *Blood* 117(2):563-574 (2011); DAVIS et al., "Chronic active B-cell-receptor signaling in diffuse large B-cell lymphoma," *Nature* 463:88-92 (2010); PIGHI et al., "Phospho-proteomic analysis of mantle cell lymphoma cells suggests a pro-survival role of B-cell receptor signaling," *Cell Oncol. (Dordr)* 34(2):141-153 (2011); RIZZATTI et al., "Gene expression profiling of mantle cell lymphoma cells reveals aberrant expression of genes from the PI3K-AKT, WNT and TGFβ signaling pathways," *Brit. J. Haematol.* 130:516-526 (2005); MARTINEZ et al., "The Molecular Signature of Mantle Cell Lymphoma Reveals Multiple Signals Favoring Cell Survival," *Cancer Res.* 63:8226-8232 (2003). Interactions between malignant B-cells and supporting cells (eg, stromal cells, nurse-like cells) in the tumor microenvironment are important for tumor cell survival, proliferation, homing, and tissue retention. See, e.g., BURGER, "Inhibiting B-Cell Receptor Signaling Pathways in Chronic Lymphocytic Leukemia," *Curr. Mematol. Malig. Rep.* 7:26-33 (2012); HERISHANU et al., "The lymph node microenvironment promotes B-cell receptor signaling, NF-κB activation, and tumor proliferation in chronic lymphocytic leukemia," *Blood* 117(2):563-574 (2011); KURTOVA et al., "Diverse marrow stromal cells protect CLL cells from spontaneous and drug-induced apoptosis: development of a reliable and reproducible system to assess stromal cell adhesion-mediated drug resistance," *Blood* 114(20): 4441-4450 (2009); BURGER et al., "High-level expression of the T-cell chemokines CCL3 and CCL4 by chronic lymphocytic leukemia B cells in nurse like cell cocultures and after BCR stimulation," *Blood* 113(13) 3050-3058 (2009); QUIROGA et al., "B-cell antigen receptor signaling enhances chronic lymphocytic leukemia cell migration and survival: specific targeting with a novel spleen tyrosine kinase inhibitor, R406," *Blood* 114(5):1029-1037 (2009). Inhibiting PI3K-δ, γ with an inhibitor in certain malignant B-cells can block the BCR-mediated intracellular survival and proliferation signals as well as key interactions with their microenvironment that are critical for their growth.

PI3K-δ and PI3K-γ also play a direct role in the survival and proliferation of certain T-cell malignancies. See, e.g., SUBRAMANIAM et al., "Targeting Nonclassical Oncogenes for Therapy in T-ALL," *Cancer Cell* 21:459-472 (2012). Aberrant PI3K-δ and PI3K-γ activity provides the signals necessary for the development and growth of certain T-cell malignancies. While BTK is expressed in B-cells, it is not expressed in T-cells, and therefore BTK is not a viable target for the treatment of T-cell malignancies. See, e.g., NISITANI et al., "Posttranscriptional regulation of Bruton's tyrosine kinase expression in antigen receptor-stimulated splenic B cells," *PNAS* 97(6):2737-2742 (2000); DE WEERS et al., "The Bruton's tyrosine kinase gene is expressed throughout B cell differentiation, from early precursor B cell stages preceding immunoglobulin gene rearrangement up to mature B cell stages," *Eur. J. Immunol.* 23:3109-3114 (1993); SMITH et al., "Expression of Bruton's Agammaglobulinemia Tyrosine Kinase Gene, BTK, Is Selectively Down-Regulated in T Lymphocytes and Plasma Cells," *J. Immunol.* 152:557-565 (1994). PI3K-δ and/or γ inhibitors can have unique therapeutic potential in T-cell malignancies.

In certain embodiments, provided herein is a method of treating cancer or hematologic malignancy comprising administering a PI3K δ/γ selective inhibitor. Without being limited by a particular theory, selectively inhibiting δ/γ isoform(s) can provide a treatment regimen where adverse effects associated with administration of a non-selective PI3K inhibitor are minimized or reduced. Without being limited by a particular theory, it is believed that the adverse effects can be reduced by avoiding the inhibition of other isoforms (e.g., α or β) of PI3K.

In one embodiment, the adverse effect is hyperglycemia. In another embodiment, the adverse effect is rash. In another embodiment, the adverse effect is impaired male fertility that may result from inhibition of β isoform of PI3K (see, e.g., Ciraolo et al., *Molecular Biology of the Cell,* 21: 704-711 (2010)). In another embodiment, the adverse effect is testicular toxicity that may result from inhibition of PI3K-β (see, e.g., Wisler et al., Amgen SOT, Abstract ID #2334 (2012)). In another embodiment, the adverse effect is embryonic lethality (see, e.g., Bi et al., *J Biol Chem,* 274: 10963-10968 (1999)). In another embodiment, the adverse effect is defective platelet aggregation (see, e.g., Kulkarni et al., *Science,* 287: 1049-1053 (2000)). In another embodiment, the adverse effect is functionally defective neutrophil (id.).

In one embodiment, provided herein is a method of treating or preventing a specific cancer or disease, such as, a hematologic malignancy, which has a high expression level of one or more isoform(s) of PI3K, wherein the method comprises: (1) determining the expression level of one or more PI3K isoform(s) in the cancer or disease; (2) selecting a treatment agent (e.g., a PI3K modulator having a particular selectivity profile for one or more PI3K isoform(s)) based on the expression levels of PI3K isoforms in the cancer or disease to be treated; and (3) administering the treatment agent to a patient having the cancer or disease, alone or in combination with one or more other agents or therapeutic modalities. In one embodiment, the expression level of one or more PI3K isoform(s) in the cancer or disease can be measured by determining the expression level of PI3K isoform protein, RNA; and/or DNA copy number, or by measuring one or more biomarkers provided herein (e.g., a signaling pathway biomarker, a protein mutation biomarker, a protein expression biomarker, a gene mutation biomarker, a gene expression biomarker, a cytokine biomarker, a chemokine biomarker, a matrix metalloproteinase biomarker, or a biomarker for particular cancer cells, among others). In other embodiments, the expression level of one or more PI3K isoform(s) in the cancer or disease can be determined based on information known in the art or information obtained in prior studies on the cancer or disease.

Certain cancer or disorder, e.g., a hematologic malignancy, can exhibit heterogeneity in PI3K isoform expression among patient populations. In one embodiment, provided herein is a method of treating or preventing a specific patient or group of patients, having a cancer or disease, such as, a hematologic malignancy, wherein the method comprises: (1) determining the expression levels of one or more PI3K isoform(s) in the patient or group of patients having the cancer or disease; (2) selecting a treatment agent (e.g., a PI3K modulator having a particular selectivity profile for one or more PI3K isoform(s)) based on the expression levels of PI3K isoforms in the patient(s) to be treated; and (3) administering the treatment agent to the patient(s), alone or in combination with one or more other agents or therapeutic modalities. In one embodiment, the expression level of one or more PI3K isoform(s) in the patient or group of patients can be measured by determining the expression level of PI3K isoform protein, RNA, and/or DNA copy number in the patient or group of patients; or by measuring one or more biomarkers provided herein in the patient or group of patients (e.g., a signaling pathway biomarker, a protein mutation biomarker, a protein expression biomarker, a gene mutation biomarker, a gene expression biomarker, a cytokine biomarker, a chemokine biomarker, a matrix metalloproteinase biomarker, or a biomarker for particular cancer cells, among others). In other embodiments, the expression level of one or more PI3K isoform(s) in the patient or group of patients can be determined based on information known in the art or information obtained in prior testing of the patient or group of patient(s).

In one embodiment, the methods provided herein comprise administering a PI3K modulator, alone or in combination with one or more other agents or therapeutic modalities, to a subject, e.g., a mammalian subject, e.g., a human;

wherein the PI3K modulator is selective for one or more PI3K isoform(s) over the other isoforms of PI3K (e.g., selective for PI3K-δ, selective for PI3K-γ, or selective for both PI3K-δ and PI3K-γ); and the subject being treated has a high expression level of the particular PI3K isoform(s) (e.g., high expression of PI3K-δ, high expression of PI3K-γ, or high expression of both PI3K-δ and PI3K-γ).

In one embodiment, provided herein is a method of determining whether a subject having a cancer or hematologic malignancy is more or less likely to respond to a treatment with a PI3K modulator that selectively reduces the activity of one or more isoform(s) of PI3K over other isoforms of PI3K, wherein the method comprises (1) administering the PI3K modulator to the subject; and (2) determining the response of the subject to treatment after about 7, 14, 21, 28, 35, 42, 49, 56, 63, or 70 days, or about 1, 2, 3, 4, or 5 months after first treatment with the PI3K modulator.

Without being limited by a particular theory, as provided herein, treating a specific cancer or hematologic malignancy, or a specific sub-type of cancer or hematologic malignancy, or a specific patient having a cancer or hematologic malignancy, that has a high expression of a particular PI3K isoform, with a PI3K inhibitor that selectively inhibits that particular PI3K isoform, allows the use of a lower dose of the therapeutic agent and/or reduced off-target effect (e.g., effects on other PI3K isoforms), thereby minimizing the potential for adverse effects. Without being limited by a particular theory, the methods provided herein can provide reduced side effects and/or improved efficacy. In one embodiment, provided herein is a method of treating or preventing a cancer or disease, such as a hematologic malignancy, having a high expression level of one or more isoform(s) of PI3K, wherein the adverse effects associated with administration of a PI3K inhibitor are reduced. In one embodiment, provided herein is a method of treating or preventing a cancer or disease, such as hematologic malignancy, or a specific type or sub-type of cancer or disease, such as a specific type or sub-type of hematologic malignancy, with a PI3K-γ selective inhibitor, wherein the adverse effects associated with administration of inhibitors for other isoform(s) of PI3K (e.g., PI3K-α or PI3K-β) are reduced. In one embodiment, provided herein is a method of treating or preventing a cancer or disease, such as hematologic malignancy, or a specific type or sub-type of cancer or disease, such as a specific type or sub-type of hematologic malignancy, with a PI3K-γ selective inhibitor, at a lower (e.g., by about 10%, by about 20%, by about 30%, by about 40%, by about 50%, by about 60%, by about 70%, or by about 80%) dose as compared to treatment with a PI3K-γ non-selective or less selective inhibitor (e.g., a PI3K pan inhibitor (e.g., PI3K-α, β, γ, δ)). Such adverse effects can include, but not be limited to, nausea, diarrhea, constipation, fatigue, pyrexia, chills, vomiting, decreased appetite, rash, elevated ASL, elevated ALT, increased blood urea, increased alanine aminotransferase, increased aspartate aminotransferase, increased blood alkaline phosphatase, neutropenia, thrombocytopenia, anaemia, hyperglycemia, hypercholesterolemia, hypertriglyceridemia, hyperphosphataemia, hypomagnesaemia, pain, back pain, muscle pain, cough, and dyspnoea. The term "reduction" of one or more adverse effects means a decrease of the occurrence and/or the severity of one or more of the adverse effects provided herein or known in the art that are typically associated with administration of a PI3K inhibitor, e.g., by about 10%, by about 20%, by about 30%, by about 40%, by about 50%, by about 60%, by about 70%, by about 80%, by about 90%, by about 95%, by about 100% as compared to treatment with another PI3K inhibitor (e.g., a non-selective or less selective inhibitor).

In one embodiment, described herein is a method of treating or preventing cancer, or a specific type or a specific sub-type of cancer provided herein. Examples of cancer that can be treated or prevented with a modulator of PI3K (e.g., PI3K-δ and/or PI3K-γ), e.g., a compound provided herein, include, e.g., leukemia, chronic lymphocytic leukemia, acute myeloid leukemia, chronic myeloid leukemia (e.g., Salmena, L et al. (2008) Cell 133:403-414; Chapuis, N et al. (2010) Clin Cancer Res. 16(22):5424-35; Khwaja, A (2010) Curr Top Microbiol Immunol. 347:169-88); lymphoma, e.g., non-Hodgkin lymphoma (e.g., Salmena, L et al. (2008) Cell 133:403-414); lung cancer, e.g., non-small cell lung cancer, small cell lung cancer (e.g., Herrera, V A et al. (2011) Anticancer Res. 31(3):849-54); melanoma (e.g., Haluska, F et al. (2007) Semin Oncol. 34(6):546-54); prostate cancer (e.g., Sarker, D et al. (2009) Clin Cancer Res. 15(15):4799-805); glioblastoma (e.g., Chen, J S et al. (2008) Mol Cancer Ther. 7:841-850); endometrial cancer (e.g., Bansal, N et al. (2009) Cancer Control. 16(1):8-13); pancreatic cancer (e.g., Furukawa, T (2008) J Gastroenterol. 43(12):905-11); renal cell carcinoma (e.g., Porta, C and Figlin, R A (2009) J Urol. 182(6):2569-77); colorectal cancer (e.g., Saif, M W and Chu, E (2010) Cancer J. 16(3):196-201); breast cancer (e.g., Torbett, N E et al. (2008) Biochem J. 415:97-100); thyroid cancer (e.g., Brzezianska, E and Pastuszak-Lewandoska, D (2011) Front Biosci. 16:422-39); and ovarian cancer (e.g., Mazzoletti, M and Broggini, M (2010) Curr Med Chem. 17(36):4433-47). In some embodiments, said method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g., lymphoma and Kaposi's sarcoma) or other viral-induced cancers. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

Patients that can be treated with a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, according to the methods as provided herein include, for example, but not limited to, patients that have been diagnosed as having breast cancer such as a ductal carcinoma, lobular carcinoma, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including or squamous cell carcinoma; prostate cancer, such as a prostate cancer selected from the following: an adenocarcinoma or an adenocarcinoma that has migrated to the bone; pancreatic cancer such as epitheloid carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphoblastic leukemia, chronic lymphocytic leukemia, chronic myeloid leukemia, hairy cell leukemia, myeloproliferative disorders, NK cell leukemia (e.g., blastic plasmacytoid dendritic cell neoplasm), acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer; kidney cancer; thyroid cancer such as papillary, follicular, medullary and anaplastic; lymphoma such as diffuse large B-cell lymphoma, B-cell immunoblastic lymphoma, NK cell lymphoma (e.g., blastic plasmacytoid dendritic cell neoplasm), and Burkitt lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), oligodendroglioma, ependymoma, meningioma, lymphoma, schwannoma, and medulloblastoma; peripheral nervous system (PNS) cancers such as acoustic neuromas and malignant peripheral nerve sheath tumor (MPNST) including neurofibromas and schwannomas, malignant fibrocytoma, malignant fibrous histiocytoma, malignant meningioma, malignant mesothelioma, and malignant mixed Mullerian tumor; oral cavity and oropharyngeal cancers such as, hypopharyngeal cancer, laryngeal cancer, nasopharyngeal cancer, and oropharyngeal cancer; stomach cancer such as lymphomas, gastric stromal tumors, and carcinoid tumors; testicular cancers such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin lymphoma, non-Hodgkin lymphomas, carcinoids or carcinoid tumors; rectal cancer; and colon cancer.

In one embodiment, described herein is a method of treating or preventing a hematologic malignancy (or a specific type or a specific subtype of the hematologic malignancy provided herein), including, but not limited to, myeloid disorder, lymphoid disorder, leukemia, lymphoma, myelodysplastic syndrome (MDS), myeloproliferative disease (MPD), mast cell disorder, and myeloma (e.g., multiple myeloma), among others. In one embodiment, the hematologic malignancy includes, but is not limited to, acute lymphoblastic leukemia (ALL), T-cell ALL (T-ALL), B-cell ALL (B-ALL), acute T-cell leukemia, acute B-cell leukemia, acute myeloid leukemia (AML), chronic lymphocytic leukemia (CLL), chronic myelogenous leukemia (CML), blast phase CML, small lymphocytic lymphoma (SLL), CLL/SLL, blast phase CLL, Hodgkin lymphoma (HL), non-Hodgkin lymphoma (NHL), B-cell NHL, T-cell NHL, indolent NHL (iNHL), diffuse large B-cell lymphoma (DLBCL), mantle cell lymphoma (MCL), aggressive B-cell NHL, B-cell lymphoma (BCL), Richter's syndrome (RS), T-cell lymphoma (TCL), peripheral T-cell lymphoma (PTCL), cutaneous T-cell lymphoma (CTCL), transformed mycosis fungoides, Sézary syndrome, anaplastic large-cell lymphoma (ALCL), follicular lymphoma, Waldenstrom macroglobulinemia (WM), lymphoplasmacytic lymphoma, Burkitt lymphoma, multiple myeloma (MM), amyloidosis, MPD, essential thrombocytosis (ET), myelofibrosis (MF), polycythemia vera (PV), chronic myelomonocytic leukemia (CMML), MDS, high-risk MDS, and low-risk MDS.

In exemplary embodiments, the cancer or hematologic malignancy is CLL. In exemplary embodiments, the cancer or hematologic malignancy is CLL/SLL. In exemplary embodiments, the cancer or hematologic malignancy is blast phase CLL. In exemplary embodiments, the cancer or hematologic malignancy is SLL.

In further embodiments, the cancer or hematologic malignancy is CLL, and a compound provided herein promotes apoptosis of CLL cells. Without being limited by a particular theory, it was found that the treatment by a compound provided herein (e.g., Compound 292) sensitizes CLL cells. In some instances, without being limited by a particular theory, the protective effects induced by anti-IgM crosslinking or stromal cells can be mitigated by a compound provided herein. Accordingly, provided herein is a method of promoting apoptosis of CLL cells comprising administering to a patient a therapeutically effective amount of a compound provided herein, or a pharmaceutically acceptable derivative (e.g., salt or solvate) thereof. In one embodiment, the compound is Compound 292. Also provided herein is a method of mitigating protective effects on CLL cells induced by anti-IgM crosslinking comprising administering to a patient a therapeutically effective amount of a compound provided herein, or a pharmaceutically acceptable derivative (e.g., salt or solvate) thereof. In one embodiment, the compound is Compound 292. In another embodiment, provided herein is a method of mitigating protective effects on CLL induced by stromal cells comprising administering to a patient a therapeutically effective amount of a compound provided herein, or a pharmaceutically acceptable derivative (e.g., salt or solvate) thereof. In one embodiment, the compound is Compound 292.

In another embodiment, provided herein is a method of inhibiting proliferation of CLL cells in the lymph nodes comprising administering to a patient a therapeutically effective amount of a compound provided herein, or a pharmaceutically acceptable derivative (e.g., salt or solvate) thereof. In one embodiment, the compound is Compound 292. In another embodiment, provided herein is a method of producing a rapid onset of response in CLL patients administering to a patient a therapeutically effective amount of a compound provided herein, or a pharmaceutically acceptable derivative (e.g., salt or solvate) thereof. In one embodiment, the compound is Compound 292.

In exemplary embodiments, the cancer or hematologic malignancy is iNHL. In exemplary embodiments, the cancer or hematologic malignancy is DLBCL. In exemplary embodiments, the cancer or hematologic malignancy is B-cell NHL (e.g., aggressive B-cell NHL). In exemplary embodiments, the cancer or hematologic malignancy is MCL. In exemplary embodiments, the cancer or hematologic malignancy is RS. In exemplary embodiments, the cancer or hematologic malignancy is AML. In exemplary embodiments, the cancer or hematologic malignancy is MM. In exemplary embodiments, the cancer or hematologic malignancy is ALL. In exemplary embodiments, the cancer or hematologic malignancy is T-ALL. In exemplary embodiments, the cancer or hematologic malignancy is B-ALL. In exemplary embodiments, the cancer or hematologic malignancy is TCL. In exemplary embodiments, the cancer or hematologic malignancy is ALCL. In exemplary embodiments, the cancer or hematologic malignancy is leukemia. In exemplary embodiments, the cancer or hematologic malignancy is lymphoma. In exemplary embodiments, the cancer or hematologic malignancy is T-cell lymphoma. In exemplary embodiments, the cancer or hematologic malignancy is MDS (e.g., low grade MDS). In exemplary embodiments, the cancer or hematologic malignancy is MPD. In exemplary embodiments, the cancer or hematologic malignancy is a mast cell disorder. In exemplary embodiments, the cancer or hematologic malignancy is Hodgkin lymphoma (HL). In exemplary embodiments, the cancer or hematologic malignancy is non-Hodgkin lymphoma. In exemplary embodiments, the cancer or hematologic malignancy is PTCL. In exemplary embodiments, the cancer or hematologic malignancy is CTCL (e.g., mycosis fungoides or Sézary syndrome). In exemplary embodiments, the cancer or hematologic malignancy is WM. In exemplary embodiments, the cancer or hematologic malignancy is CML. In exemplary embodiments, the cancer or hematologic malignancy is FL. In exemplary embodiments, the cancer or hematologic malignancy is transformed mycosis fungoides. In exemplary embodiments, the cancer or hematologic malignancy is Sézary syndrome. In exemplary embodiments, the cancer or hematologic malignancy is acute T-cell leukemia. In exemplary embodiments, the cancer or hematologic malignancy is acute B-cell leukemia. In exemplary embodiments, the cancer or hematologic malignancy is Burkitt lymphoma. In exemplary embodiments, the cancer or hematologic malignancy is myeloproliferative neoplasms. In exemplary embodiments, the cancer or hematologic malignancy is splenic marginal zone. In exemplary embodiments, the cancer or hematologic malignancy is nodal marginal zone. In exemplary embodiments, the cancer or hematologic malignancy is extranodal marginal zone.

In one embodiment, the cancer or hematologic malignancy is a B cell lymphoma. In a specific embodiment, provided herein is a method of treating or managing a B cell lymphoma comprising administering to a patient a therapeutically effective amount of a compound provided herein, or a pharmaceutically acceptable derivative (e.g., salt or solvate) thereof. In one embodiment, the compound is Compound 292. Also provided herein is a method of treating or lessening one or more of the symptoms associated with a B cell lymphoma comprising administering to a patient a therapeutically effective amount of a compound provided herein, or a pharmaceutically acceptable derivative (e.g., salt or solvate) thereof. In one embodiment, the B cell lymphoma is iNHL. In another embodiment, the B cell lymphoma is follicular lymphoma. In another embodiment, the B cell lymphoma is Waldenstrom macroglobulinemia (lymphoplasmacytic lymphoma). In another embodiment, the B cell lymphoma is marginal zone lymphoma (MZL). In another embodiment, the B cell lymphoma is MCL. In another embodiment, the B cell lymphoma is HL. In another embodiment, the B cell lymphoma is aNHL. In another embodiment, the B cell lymphoma is DLBCL. In another embodiment, the B cell lymphoma is Richters lymphoma.

In one embodiment, the cancer or hematologic malignancy is a T cell lymphoma. In a specific embodiment, provided herein is a method of treating or managing a T cell lymphoma comprising administering to a patient a therapeutically effective amount of a compound provided herein, or a pharmaceutically acceptable derivative (e.g., salt or solvate) thereof. In one embodiment, the compound is Compound 292. Also provided herein is a method of treating or lessening one or more of the symptoms associated with a T cell lymphoma comprising administering to a patient a therapeutically effective amount of a compound provided herein, or a pharmaceutically acceptable derivative (e.g., salt or solvate) thereof. In one embodiment, the T cell lymphoma is peripheral T cell lymphoma (PTCL). In another embodiment, the T cell lymphoma is cutaneous T cell lymphoma (CTCL).

In one embodiment, the cancer or hematologic malignancy is Sézary syndrome. In a specific embodiment, provided herein is a method of treating or managing Sézary syndrome comprising administering to a patient a therapeutically effective amount of a compound provided herein, or a pharmaceutically acceptable derivative (e.g., salt or solvate) thereof. In one embodiment, the compound is Compound 292. Also provided herein is a method of treating or lessening one or more of the symptoms associated with Sézary syndrome comprising administering to a patient a therapeutically effective amount of a compound provided herein, or a pharmaceutically acceptable derivative (e.g., salt or solvate) thereof. The symptoms associated with Sézary syndrome include, but are not limited to, epidermotropism by neoplastic CD4+ lymphocytes, Pautrier's microabscesses, erythroderma, lymphadenopathy, atypical T cells in the peripheral blood, and hepatosplenomegaly. In one embodiment, the compound is Compound 292. In one embodiment, the therapeutically effective amount for treating or managing Sézary syndrome is from about 25 mg to 75 mg, administered twice daily. In other embodiments, the therapeutically effective amount is from about 50 mg to about 75 mg, from about 30 mg to about 65 mg, from about 45 mg to about 60 mg, from about 30 mg to about 50 mg, or from about 55 mg to about 65 mg, each of which is administered twice daily. In one embodiment, the effective amount is about 60 mg, administered twice daily.

In one embodiment, the cancer or hematologic malignancy is relapsed. In one embodiment, the cancer or hematologic malignancy is refractory. In certain embodiments, the cancer being treated or prevented is a specific sub-type of cancer described herein. In certain embodiments, the hematologic malignancy being treated or prevented is a specific sub-type of hematologic malignancy described herein. Certain classifications of type or sub-type of a cancer or hematologic malignancy provided herein is known in the art. Without being limited by a particular theory, it is believed that many of the cancers that become relapsed or refractory develop resistance to the particular prior therapy administered to treat the cancers. Thus, without being limited by a particular theory, a compound provided herein can provide a second line therapy by providing an alternative mechanism to treat cancers different from those mechanisms utilized by certain prior therapies. Accordingly, in one embodiment, provided herein is a method of treating or managing cancer or hematologic malignancy comprising administering to a patient a therapeutically effective amount of a compound provided herein, or a pharmaceutically acceptable derivative (e.g., salt or solvate) thereof, wherein the cancer or hematologic malignancy is relapsed after, or refractory to, a prior therapy.

In exemplary embodiments, the cancer or hematologic malignancy is refractory iNHL. In exemplary embodiments, the cancer or hematologic malignancy is refractory CLL. In exemplary embodiments, the cancer or hematologic malignancy is refractory SLL. In exemplary embodiments, the cancer or hematologic malignancy is refractory to rituximab therapy. In exemplary embodiments, the cancer or hematologic malignancy is refractory to chemotherapy. In exemplary embodiments, the cancer or hematologic malignancy is refractory to radioimmunotherapy (RIT). In exemplary embodiments, the cancer or hematologic malignancy is iNHL, FL, splenic marginal zone, nodal marginal zone, extranodal marginal zone, or SLL, the cancer or hematologic malignancy is refractory to rituximab therapy, chemotherapy, and/or RIT.

In another exemplary embodiment, the cancer or hematologic malignancy is lymphoma, and the cancer is relapsed after, or refractory to, the treatment by a BTK inhibitor such as, but not limited to, ibrutinib. In another exemplary embodiment, the cancer or hematologic malignancy is CLL, and the cancer is relapsed after, or refractory to, the treatment by a BTK inhibitor such as, but not limited to, ibrutinib and AVL-292.

Without being limited by a particular theory, it was found that patients who develop resistance to a BTK inhibitor treatment often has a cysteine to serine mutation on residue 481 of BTK ($C_{481}S$) or a cysteine to phenylalanine mutation on residue 481 of BTK ($C_{481}F$). Accordingly, also provided herein is a method for treating or managing cancer or hematologic malignancy comprising administering to a patient having cysteine to serine or cysteine to phenylalanine mutation on residue 481 of BTK a therapeutically effective amount of a compound provided herein, or a pharmaceutically acceptable derivative (e.g., salt or solvate) thereof, wherein the cancer or hematologic malignancy is relapsed after, or refractory to, a prior therapy. In another embodiment, provided herein is a method of treating or managing cancer or hematologic malignancy comprising: (1) identifying a patient who has cysteine to serine or cysteine to phenylalanine mutation on residue 481 of BTK; and (2) administering to the patient a therapeutically effective amount of a compound provided herein, or a pharmaceutically acceptable derivative (e.g., salt or solvate) thereof. In one embodiment, the patient is a CLL patient. In another embodiment, the patient is an ibrutinib-resistant CLL patient.

Without being limited by a particular theory, it was found that patients who develop resistance to a BTK inhibitor treatment also can have a tyrosine to tryptophan mutation on residue 665 of PLCgamma2 gene (R665W). Accordingly, also provided herein is a method for treating or managing cancer or hematologic malignancy comprising administering to a patient having tyrosine to tryptophan mutation on residue 665 of PLCgamma2 gene a therapeutically effective amount of a compound provided herein, or a pharmaceutically acceptable derivative (e.g., salt or solvate) thereof, wherein the cancer or hematologic malignancy is relapsed after, or refractory to, a prior therapy. In another embodiment, provided herein is a method of treating or managing cancer or hematologic malignancy comprising: (1) identifying a patient who has tyrosine to tryptophan mutation on residue 665 of PLCgamma2 gene; and (2) administering to the patient a therapeutically effective amount of a compound provided herein, or a pharmaceutically acceptable derivative (e.g., salt or solvate) thereof. In one embodiment, the patient is a CLL patient. In another embodiment, the patient is an ibrutinib-resistant CLL patient.

In another embodiment, a method of treating or managing cancer or hematologic malignancy comprising: administering a therapeutically effective amount of a compound provided herein, or a pharmaceutically acceptable derivative (e.g., salt or solvate) and a therapeutically effective amount of a BTK inhibitor is disclosed. Exemplary BTK inhibitors include, but are not limited to, ibrutinib (1-[(3R)-3-[4-Amino-3-(4-phenoxyphenyl)pyrazolo[3,4-d]pyrimidin-1-yl]piperidin-1-yl]prop-2-en-1-one), GDC-0834 ([R—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide]), CGI-560 (4-(tert-butyl)-N-(3-(8-(phenylamino)imidazo[1,2-a]pyrazin-6-yl)phenyl)benzamide), CGI-1746 (4-tert-butyl-N-[2-methyl-3-[4-methyl-6-[4-(morpholine-4-carbonyl)anilino]5-oxopyrazin-2-yl]phenyl]benzamide), HM-71224, AVL-292 (CC-292) (N-(3-((5-fluoro-2-((4-(2-methoxyethoxy)phenyl)amino)pyrimidin-4-yl)amino)phenyl)acrylamide), ONO-4059, CNX-774 (4-(4-((4-((3-acrylamidophenyl)amino)-5-fluoropyrimidin-2-yl)amino)phenoxy)-N-methylpicolinamide), and LFM-A13 (2-Cyano-N-(2,5-dibromophenyl)-3-hydroxy-2-butenamide), and those BTK inhibitors disclosed in Akinleye et al., *Journal of Hematology & Oncology*, 2013, 6:59, the entirety of which is incorporated herein by reference. In one embodiment the compound is compound 292 and the BTK inhibitor is selected from ibrutinib and AVL-292. In some embodiments, the cancer is a lymphoma or leukemia. In one embodiment the lymphoma is non-Hodgkin lymphoma. In one embodiment, the leukemia is B-cell chronic lymphocytic leukemia.

In certain embodiments, without being limited by a particular theory, it was found that certain subtypes of a particular cancer are more susceptible to the treatment by a compound provided herein than the others. For example, while it was found that the sensitivity exists in both ABC and GCB subtypes of DLBCL, it was found that cells with BCR-dependent signaling have higher sensitivity to a compound provided herein than those without. Without being limited by a particular theory, additional factors, such as dependencies on other signaling pathways, anti-apoptotic characteristics (e.g., Bcl-2, HRK), and/or mutations status (e.g., IgH-BCL2, CD79b, MYD-88), can contribute to the differential sensitivities exhibited by various subtypes. Accordingly, in some embodiments, provided herein is a method of treating a particular subtype of a cancer by a compound provided herein, wherein the subtype comprises of cells having BCR-dependent signaling. In one embodiment, the subtype is Ri-1, WSU-DLCL2, Toledo, OCI-LY8, SU-DHL-4, or SU-DHL-6. In another embodiment, the subtype is Ri-1, SU-DHL-4 or SU-DHL-6.

In one embodiment, provided herein are methods of modulating a PI3K kinase activity (e.g., selectively modulating) by contacting the kinase with an effective amount of a compound as provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein. Modulation can be inhibition (e.g., reduction) or activation (e.g., enhancement) of kinase activity.

In one embodiment, provided herein are methods of inhibiting kinase activity by contacting the kinase with an effective amount of a compound as provided herein in solution. In some embodiments, provided herein are methods of inhibiting the kinase activity by contacting a cell, tissue, organ that express the kinase of interest, with a compound provided herein. In some embodiments, provided herein are methods of inhibiting kinase activity in a subject by administering into the subject an effective amount of a compound as provided herein, or a pharmaceutically acceptable form thereof. In some embodiments, the kinase activity is inhibited (e.g., reduced) by more than about 25%, 30%, 40%, 50%, 60%, 70%, 80%, or 90%, when contacted with a compound provided herein as compared to the kinase activity without such contact. In some embodiments, provided herein are methods of inhibiting PI3 kinase activity in a subject (including mammals such as humans) by contacting said subject with an amount of a compound as provided herein sufficient to inhibit or reduce the activity of the PI3 kinase in said subject. In some embodiments, the kinase is a lipid kinase or a protein kinase. In some embodiments, the kinase is selected from a PI3 kinase including different isoforms, such as PI3 kinase α, PI3 kinase β, PI3 kinase γ, PI3 kinase δ; DNA-PK; mTOR; Abl, VEGFR, Ephrin receptor B4 (EphB4); TEK receptor tyrosine kinase (TIE2); FMS-related tyrosine kinase 3 (FLT-3); Platelet derived growth factor receptor (PDGFR); RET; ATM; ATR; hSmg-1; Hck; Src; Epidermal growth factor receptor (EGFR); KIT; Insulin Receptor (IR); and IGFR.

In one embodiment, provided herein is a method of reducing a symptom associated with cancer or disorder such as a hematologic malignancy, in a biological sample, comprising contacting the biological sample with a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof), in an amount sufficient to reduce the symptom. In one embodiment, the method is carried out in vivo, for example, in a mammalian subject, e.g., an animal model or as part of therapeutic protocol. In one embodiment, the compound is used as a single agent or in combination with another agent or therapeutic modality.

As used herein, and unless otherwise specified, "contacting" can be direct (e.g., by direct application of the compound provided herein to a biological sample, e.g., in vitro) or indirect (e.g., by administering the compound provided herein to a subject (e.g., by any known administration route, e.g., orally), such that the compound provided herein reaches an affected biological sample within the body.

As used herein, and unless otherwise specified, a "biological sample" includes, for example, a cell or group of cells (e.g., PBMCs, or plasmacytoid dendritic cell(s)), a tissue, or a fluid (e.g., whole blood or serum) that comes into contact with a compound provided herein, e.g., a PI3K modulator, thereby resulting in a decrease or inhibition of cancer or hematologic malignancy, or associated symptoms. In some embodiments, the biological sample is present within or derived from a subject who has cancer or hematologic malignancy, or from a subject at risk for developing cancer or hematologic malignancy. In some embodiments, the biological sample can be contacted with the compound provided herein outside the body and then introduced into the body of a subject (e.g., into the body of the subject from whom the biological sample was derived or into the body of a different subject). In some embodiments, the biological sample includes cells that express one or more isoforms of PI3K.

In one embodiment, provided herein is a method of treating, preventing, and/or managing cancer or hematologic malignancy in a subject, comprising administering an effective amount of a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) to a subject in need thereof. In one embodiment, the compound is administered as a single agent. In another embodiment, the compound is administered in combination with another agent or therapeutic modality.

As used herein, and unless otherwise specified, hematologic malignancy or a symptom associated with hematologic malignancy encompasses all types of manifestation of hematologic malignancy as disclosed herein or as known in the art. As used herein, and unless otherwise specified, cancer or a symptom associated with cancer encompasses all types of manifestation of cancer as disclosed herein or as known in the art. Symptoms can be assessed using assays and scales disclosed and/or exemplified herein and/or as known in the art.

In some embodiments, the symptom is reduced by at least about 2%, at least about 5%, at least about 10%, at least about 15%, at least about 20%, at least about 25%, at least about 30%, at least about 40%, at least about 50%, at least about 60%, at least about 70%, at least about 80%, at least about 90%, or at least about 95% relative to a control level. The control level includes any appropriate control as known in the art. For example, the control level can be the pre-treatment level in the sample or subject treated, or it can be the level in a control population (e.g., the level in subjects who do not have cancer or hematologic malignancy or the level in samples derived from subjects who do not have cancer or hematologic malignancy). In some embodiments, the decrease is statistically significant, for example, as assessed using an appropriate parametric or non-parametric statistical comparison.

In some embodiments, the subject is a mammal. In some embodiments, the subject is a human.

In certain embodiments, the subject is an animal model of cancer or hematologic malignancy, a human with cancer or hematologic malignancy, or a subject (e.g., a human) at risk for developing cancer or hematologic malignancy. In some embodiments, the subject is a human who has a family history of cancer or hematologic malignancy, who carries a gene associated with cancer or hematologic malignancy, who is positive for a biomarker associated with cancer or hematologic malignancy (e.g., a biomarker provided herein), or a combination thereof. In some embodiments, the subject has been diagnosed with cancer or hematologic malignancy. In some embodiments, the subject has one or more signs or symptoms associated with cancer or hematologic malignancy. In some embodiments, the subject is at risk for developing cancer or hematologic malignancy (e.g., the subject carries a gene that, individually, or in combination with other genes or environmental factors, is associated with development of cancer or hematologic malignancy).

In some embodiments, the subject exhibits elevated level of one or more PI3K isoform(s) (e.g., PI3K-δ and/or PI3K-γ, which can be indicative of increased likelihood of responding to, or better efficacy of, a particular treatment or therapeutic agent, as compared to another subject with lower level of the PI3K isoform(s). The levels of PI3K isoforms can be assessed using methods known in the art.

In some embodiments, the subject exhibits one or more biomarkers provided herein, which can be indicative of increased likelihood of responding to, or better efficacy of, a particular treatment or therapeutic agent.

In some embodiments, the subject has a mutation (e.g., an SNP) in a gene associated with cancer or hematologic malignancy. In one embodiment, the gene is selected from CXCR4, IGH7, KRAS, NRAS, A20, CARD11, CD79B, TP53, CARD11, MYD88, GNA13, MEF2B, TNFRSF14, MLL2, BTG1, EZH2, NOTCH1, JAK1, JAK2, PTEN, FBW7, PHF6, IDH1, IDH2, TET2, FLT3, KIT, NPM1, CEBPA, DNMT3A, BAALC, RUNX1, ASXL1, IRF8, POU2F2, WIF1, ARID1A, MEF2B, TNFAIP3, PIK3R1, MTOR, PIK3CA, PI3Kδ, and/or PI3Kγ, or a combination thereof. In one embodiment, the disorder to be treated, prevented and/or managed is WM and the subject has a PTEN deficiency.

In some embodiments, the subject exhibits excessive PI3K activity or abnormal activity (e.g., excessive or reduced activity) of one or more components of the PI3K signaling pathway (e.g., Akt (PKB), mTOR, a Tec kinase (e.g., Btk, Itk, Tec), phospholipase C, PDK1, PKCs, NFκB, Rac GEF (e.g., Vav-1), or Rac).

In certain embodiments, provided herein is a method of treating or managing a hematologic malignancy comprising administering to a patient who has one or more mutations selected from MYD88 (L265P), CXCR4, ARID1A, MUC16, TRAF2, TRRAP, and MYBBP1A mutations a therapeutically effective amount of a compound provided herein (e.g., Compound 292), or a pharmaceutically acceptable derivative (e.g., salt or solvate) thereof. In one embodiment, the patient has MYD88 (L265P) and/or N-terminal domain of CXCR4 mutation. In one embodiment, the hematologic malignancy is Waldenström's macroglobulinemia (WM). In one embodiment, the hematologic malignancy is DLBCL. In one embodiment, the hematologic malignancy is CLL. In one embodiment, a compound provided herein (e.g., Compound 292), or a pharmaceutically acceptable derivative (e.g., salt or solvate) thereof, can be used in combination with one or more other therapeutic agents described herein below.

In certain embodiments, provided herein is a method of treating or managing WM comprising administering to a patient who has CXCR4 mutation a therapeutically effective amount of a compound provided herein (e.g., Compound 292), or a pharmaceutically acceptable derivative (e.g., salt or solvate) thereof. In one embodiment, the CXCR4 mutation occurs at the N-terminal domain of CXCR4. In other embodiments, a compound provided herein (e.g., Compound 292), or a pharmaceutically acceptable derivative (e.g., salt or solvate) thereof, can be used in combination with one or more other therapeutic agents described herein below.

In certain embodiments, provided herein is a method of treating or managing DLBCL comprising administering to a patient who has CXCR4 mutation a therapeutically effective amount of a compound provided herein (e.g., Compound 292), or a pharmaceutically acceptable derivative (e.g., salt or solvate) thereof. In one embodiment, the CXCR4 mutation occurs at the N-terminal domain of CXCR4. In other embodiments, a compound provided herein (e.g., Compound 292), or a pharmaceutically acceptable derivative (e.g., salt or solvate) thereof, can be used in combination with one or more other therapeutic agents described herein below.

In certain embodiments, provided herein is a method of treating or managing CLL comprising administering to a patient who has CXCR4 mutation a therapeutically effective amount of a compound provided herein (e.g., Compound 292), or a pharmaceutically acceptable derivative (e.g., salt or solvate) thereof. In one embodiment, the CXCR4 mutation occurs at the N-terminal domain of CXCR4. In other embodiments, a compound provided herein (e.g., Compound 292), or a pharmaceutically acceptable derivative (e.g., salt or solvate) thereof, can be used in combination with one or more other therapeutic agents described herein below.

In certain embodiments, provided herein is a method of treating or managing CLL comprising administering to a patient who has CD38 positive cancer cells a therapeutically effective amount of a compound provided herein (e.g., Compound 292), or a pharmaceutically acceptable derivative (e.g., salt or solvate) thereof. In other embodiments, a compound provided herein (e.g., Compound 292), or a pharmaceutically acceptable derivative (e.g., salt or solvate) thereof, can be used in combination with one or more other therapeutic agents described herein below.

In certain embodiments, provided herein is a method of treating or managing CLL comprising administering to a patient who has CD69 positive cancer cells a therapeutically effective amount of a compound provided herein (e.g., Compound 292), or a pharmaceutically acceptable derivative (e.g., salt or solvate) thereof. In other embodiments, a compound provided herein (e.g., Compound 292), or a pharmaceutically acceptable derivative (e.g., salt or solvate) thereof, can be used in combination with one or more other therapeutic agents described herein below.

In certain embodiments, provided herein is a method of treating or managing CLL comprising administering to a patient who has CD38/CD69 double positive cancer cells a therapeutically effective amount of a compound provided herein (e.g., Compound 292), or a pharmaceutically acceptable derivative (e.g., salt or solvate) thereof. In other embodiments, a compound provided herein (e.g., Compound 292), or a pharmaceutically acceptable derivative (e.g., salt or solvate) thereof, can be used in combination with one or more other therapeutic agents described herein below.

In certain embodiments, provided herein is a method of treating or managing CLL comprising administering to a patient who has Ki67 positive cancer cells a therapeutically effective amount of a compound provided herein (e.g., Compound 292), or a pharmaceutically acceptable derivative (e.g., salt or solvate) thereof. In other embodiments, a compound provided herein (e.g., Compound 292), or a pharmaceutically acceptable derivative (e.g., salt or solvate) thereof, can be used in combination with one or more other therapeutic agents described herein below.

In certain embodiments, provided herein is a method of treating or managing CLL comprising administering to a patient who has pAKT positive cancer cells a therapeutically effective amount of a compound provided herein (e.g., Compound 292), or a pharmaceutically acceptable derivative (e.g., salt or solvate) thereof. In other embodiments, a compound provided herein (e.g., Compound 292), or a pharmaceutically acceptable derivative (e.g., salt or solvate) thereof, can be used in combination with one or more other therapeutic agents described herein below.

In certain embodiments, provided herein is a method of treating or managing CLL comprising administering to a patient who has Ki67/pAKT double positive cancer cells a therapeutically effective amount of a compound provided herein (e.g., Compound 292), or a pharmaceutically acceptable derivative (e.g., salt or solvate) thereof. In other embodiments, a compound provided herein (e.g., Compound 292), or a pharmaceutically acceptable derivative (e.g., salt or solvate) thereof, can be used in combination with one or more other therapeutic agents described herein below.

In some embodiments, the subject has been previously treated for cancer or hematologic malignancy. In some embodiments, the subject has been previously treated for cancer or hematologic malignancy but are non-responsive to standard therapies. Thus, in one embodiment, provided herein is a method of treating, preventing, and/or managing cancer or hematologic malignancy in a subject, comprising administering an effective amount of a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) to a subject in need thereof, wherein the subject has been previously administered a therapy for cancer or hematologic malignancy.

In one embodiment, the subject has been previously administered a therapy for cancer or hematologic malignancy at least 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) is administered. In one embodiment, the subject has been previously administered a therapy for cancer or hematologic malignancy at least 1 week, 2 weeks, 1 month, 2 months, 3 months, or 4 months before a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) is administered.

In one embodiment, the subject has been administered a stable dose of a therapy for cancer or hematologic malignancy before a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) is administered. In one embodiment, the subject has been administered a stable dose of a therapy for cancer or hematologic malignancy for at least 24 hours, 48 hours, 72 hours, 96 hours, 1 week, 2 weeks, 3 weeks, 4 weeks, 5 weeks, 6 weeks, 8 weeks, 12 weeks, or 16 weeks before a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) is administered. In one embodiment, the subject has been administered a stable dose of a therapy for cancer or hematologic malignancy for at least 1 week, 2 weeks, 3 weeks, 4 weeks, 5 weeks, 6 weeks, 8 weeks, 12 weeks, or 16 weeks before a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) is administered.

In one embodiment, the subject has been previously administered a therapy for cancer or hematologic malignancy at least 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before, and the subject has been administered a stable dose of the same therapy for cancer or hematologic malignancy for at least 24 hours, 48 hours, 72 hours, 96 hours, 1 week, 2 weeks, 3 weeks, 4 weeks, 5 weeks, 6 weeks, 8 weeks, 12 weeks, or 16 weeks before, a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) is administered.

In one embodiment, the stable dose of the previously administered therapy is from about 0.005 to about 1,000 mg per week, from about 0.01 to about 500 mg per week, from about 0.1 to about 250 mg per week, from about 1 to about 100 mg per week, from about 2 to about 75 mg per week, from about 3 to about 50 mg per week, from about 5 to about 50 mg per week, from about 7.5 to about 25 mg per week, from about 10 to about 25 mg per week, from about 12.5 to about 25 mg per week, from about 15 to about 25 mg per week, or from about 15 to about 20 mg per week. The total dose per week can be administered once or administered among split doses.

In some embodiments, the subject has not been previously treated for cancer or hematologic malignancy.

In certain embodiments, a therapeutically or prophylactically effective amount of a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 2 to about 25 mg per day, or from about 5 to about 10 mg per day.

In certain embodiments, the therapeutically or prophylactically effective amount is about 0.1, about 0.2, about 0.5, about 1, about 2, about 5, about 10, about 15, about 20, about 25, about 30, about 35, about 40, about 45, about 50, about 60, about 70, about 80, about 90, about 100, or about 150 mg per day.

In one embodiment, the recommended daily dose range of a compound of Formula I (e.g., Compound 292), or an enantiomer or a mixture of enantiomers thereof, or a pharmaceutically acceptable salt, solvate, hydrate, co-crystal, clathrate, or polymorph thereof, for the conditions described herein lie within the range of from about 0.5 mg to about 100 mg per day, or from about 0.5 mg to about 50 mg per day, preferably given as a single once-a-day dose, or in divided doses throughout a day. In some embodiments, the dosage ranges from about 1 mg to about 50 mg per day. In other embodiments, the dosage ranges from about 0.5 to about 25 mg per day. Specific doses per day include 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or 100 mg per day.

In a specific embodiment, the recommended starting dosage can be 0.5, 1, 2, 3, 4, 5, 10, 15, 20, 25, 50, or 100 mg per day. In another embodiment, the recommended starting dosage can be 0.5, 1, 2, 3, 4, or 5 mg per day. The dose can be escalated to 15, 20, 25, 30, 35, 40, 45, 50, 75, or 100 mg/day.

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, or from about 0.01 to about 1 mg/kg/day.

The administered dose can also be expressed in units other than mg/kg/day. For example, doses for parenteral administration can be expressed as $mg/m^2/day$. One of ordinary skill in the art would readily know how to convert doses from mg/kg/day to $mg/m^2/day$ to given either the height or weight of a subject or both (see, www.fda.gov/ cder/cancer/animalframe.htm). For example, a dose of 1 mg/kg/day for a 65 kg human is approximately equal to 38 mg/m$^2$/day.

In one embodiment, the amount of the compound administered is sufficient to provide a plasma concentration of the compound at steady state, ranging from about 0.005 to about 100 µM, from about 0.005 to about 10 µM, from about 0.01 to about 10 µM, from about 0.01 to about 5 µM, from about 0.005 to about 1 µM, from about 0.005 to about 0.5 µM, from about 0.005 to about 0.5 µM, from about 0.01 to about 0.2 µM, or from about 0.01 to about 0.1 µM. In one embodiment, the amount of the compound administered is sufficient to provide a plasma concentration at steady state, of about 0.005 to about 100 µM. In another embodiment, the amount of the compound administered is sufficient to provide a plasma concentration at steady state, of about 0.005 to about 10 µM. In yet another embodiment, the amount of the compound administered is sufficient to provide a plasma concentration at steady state, of about 0.01 to about 10 µM. In yet another embodiment, the amount of the compound administered is sufficient to provide a plasma concentration at steady state, of about 0.01 to about 5 µM. In yet another embodiment, the amount of the compound administered is sufficient to provide a plasma concentration at steady state, of about 0.005 to about 1 µM. In yet another embodiment, the amount of the compound administered is sufficient to provide a plasma concentration at steady state, of about 0.005 to about 0.5 µM. In yet another embodiment, the amount of the compound administered is sufficient to provide a plasma concentration of the compound at steady state, of about 0.01 to about 0.2 µM. In still another embodiment, the amount of the compound administered is sufficient to provide a plasma concentration of the compound at steady state, of about 0.01 to about 0.1 µM.

As explained in more detail herein below, following 25 mg or 75 mg BID administration of Compound 292, it was found that the compound is rapidly absorbed, with maximal plasma concentrations typically observed around 1 hour following dosing. It was also found that AUC increases proportionally with doses through 75 mg BID, but elimination half-life (about 4-5 hours for both 25 mg and 75 mg BID) is independent of dose. The mean predose steady state plasma concentration following 25 mg BID was about 390 ng/ml, indicating complete suppression of PI3K-δ (IC$_{90}$=361 ng/ml) with inhibition of PI3K-γ (IC$_{50}$=429 ng/ml) throughout the dosing interval.

In another embodiment, the amount of the compound administered is sufficient to provide a plasma concentration of the compound at steady state at a level higher than IC$_{50}$ for a particular isoform of PI3K. In another embodiment, the amount of the compound administered is sufficient to provide a plasma concentration of the compound at steady state at a level higher than IC$_{90}$ for a particular isoform of PI3K. In one embodiment, the PI3K isoform is PI3K-δ for which IC$_{90}$ is about 361 mg/ml. In another embodiment, the PI3K isoform is PI3K-γ for which IC$_{50}$ is about 429 ng/ml.

In one embodiment, the compound is Compound 292, and the PI3K isoform is PI3K-δ. In another embodiment, the compound is Compound 292, and the PI3K isoform is PI3K-γ. In another embodiment wherein the compound is Compound 292, the amount of Compound 292 administered is sufficient to provide a plasma concentration of the compound at steady state of about 300 ng/ml to about 500 ng/ml, about 350 ng/ml to about 450 ng/ml, or from about 380 ng/ml to about 420 ng/ml. In another embodiment, wherein the compound is Compound 292, the amount of Compound 292 administered is sufficient to provide a plasma concentration of the compound at steady state of about 390 ng/ml. As used herein, the term "plasma concentration at steady state" is the concentration reached after a period of administration of a compound. Once steady state is reached, there are minor peaks and troughs on the time dependent curve of the plasma concentration of the compound.

In one embodiment, the amount administered is sufficient to provide a maximum plasma concentration (peak concentration) of the compound, ranging from about 0.005 to about 100 µM, from about 0.005 to about 10 µM, from about 0.01 to about 10 µM, from about 0.01 to about 5 µM, from about 0.005 to about 1 µM, from about 0.005 to about 0.5 µM, from about 0.01 to about 0.2 µM, or from about 0.01 to about 0.1 µM. In one embodiment, the amount of the compound administered is sufficient to provide a maximum plasma concentration of the compound of about 0.005 to about 100 µM. In another embodiment, the amount of the compound administered is sufficient to provide a maximum plasma concentration of the compound of about 0.005 to about 10 µM. In yet another embodiment, the amount of the compound administered is sufficient to provide a maximum plasma concentration of the compound of about 0.01 to about 10 µM. In yet another embodiment, the amount of the compound administered is sufficient to provide a maximum plasma concentration of the compound of about 0.01 to about 5 µM. In yet another embodiment, the amount of the compound administered is sufficient to provide a maximum plasma concentration of the compound of about 0.005 to about 1 µM. In yet another embodiment, the amount of the compound administered is sufficient to provide a maximum plasma concentration of the compound of about 0.005 to about 0.5 µM. In yet another embodiment, the amount of the compound administered is sufficient to provide a maximum plasma concentration of the compound of about 0.01 to about 0.2 µM. In still another embodiment, the amount of the compound administered is sufficient to provide a maximum plasma concentration of the compound of about 0.01 to about 0.1 µM.

In one embodiment, the amount administered is sufficient to provide a minimum plasma concentration (trough concentration) of the compound, ranging from about 0.005 to about 100 µM, from about 0.005 to about 10 µM, from about 0.01 to about 10 µM, from about 0.01 to about 5 µM, from about 0.005 to about 1 µM, about 0.005 to about 0.5 µM, from about 0.01 to about 0.2 µM, or from about 0.01 to about 0.1 µM, when more than one doses are administered. In one embodiment, the amount of the compound administered is sufficient to provide a minimum plasma concentration of the compound of about 0.005 to about 100 µM. In another embodiment, the amount of the compound administered is sufficient to provide a minimum plasma concentration of the compound of about 0.005 to about 10 µM. In yet another embodiment, the amount of the compound administered is sufficient to provide a minimum plasma concentration of the compound of about 0.01 to about 10 µM. In yet another embodiment, the amount of the compound administered is sufficient to provide a minimum plasma concentration of the compound of about 0.01 to about 5 µM. In yet another embodiment, the amount of the compound administered is sufficient to provide a minimum plasma concentration of the compound of about 0.005 to about 1 µM. In yet another embodiment, the amount of the compound administered is sufficient to provide a minimum plasma concentration of the compound of about 0.005 to about 0.5 µM. In yet another embodiment, the amount of the compound administered is sufficient to provide a minimum plasma concentration of the compound of about 0.01 to about 0.2 µM. In still another embodiment, the amount of the compound administered is sufficient to provide a minimum plasma concentration of the compound of about 0.01 to about 0.1 μM.

In one embodiment, the amount administered is sufficient to provide an area under the curve (AUC) of the compound, ranging from about 50 to about 10,000 ng*hr/mL, about 100 to about 50,000 ng*hr/mL, from about 100 to 25,000 ng*hr/mL, or from about 10,000 to 25,000 ng*hr/mL.

Without being limited by a particular theory, it was found that administration of a compound provided herein to a patient having cancer or hematologic malignancy results in rapid onset of response in patients. Accordingly, in one embodiment, provided herein is a method of achieving rapid onset of response in patients having cancer or hematologic malignancy comprising administering to the patient a compound provided herein, or a pharmaceutically acceptable derivative (e.g., salt or solvate) thereof. In some embodiments, the onset of response is achieved within about 4 months, 3 months, 2 months, or 1 month from the date of first administration of a compound provided herein. In one embodiment, the compound is Compound 292, or a pharmaceutically acceptable derivative thereof. In one embodiment where the compound is Compound 292, or a pharmaceutically acceptable derivative thereof, the cancer or hematologic malignancy is a T cell lymphoma and the onset of response is achieved within about 2 months of first administration of the compound. In another embodiment where the compound is Compound 292, or a pharmaceutically acceptable derivative thereof, the cancer or hematologic malignancy is a T cell lymphoma and the onset of response is achieved within about 1.9 months of first administration of the compound. In one embodiment where the compound is Compound 292, or a pharmaceutically acceptable derivative thereof, the cancer or hematologic malignancy is a B cell lymphoma and the onset of response is achieved within about 2 months of first administration of the compound. In another embodiment where the compound is Compound 292, or a pharmaceutically acceptable derivative thereof, the cancer or hematologic malignancy is a B cell lymphoma and the onset of response is achieved within about 1.8 months of first administration of the compound.

The compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) can be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. In one embodiment, the compound is administered orally. In another embodiment, the compound is administered parenterally. In yet another embodiment, the compound is administered intravenously.

A compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as a compound of Formula I, is administered once or more than once each day, for example, for a period of time. The term "continuous" is intended to mean that a therapeutic compound, such as a compound of Formula I, is administered daily for an uninterrupted period of at least 10 days to 52 weeks. The term "intermittent" or "intermittently" as used herein is intended to mean stopping and starting at either regular or irregular intervals. For example, intermittent administration of a compound of Formula I is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as a compound of Formula I, is administered daily or continuously but with a rest period (e.g., after dosing for 7, 14, 21, or 28 days).

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, the compound provided herein is administered once a day. In another embodiment, the compound provided herein is administered twice a day. In yet another embodiment, the compound provided herein is administered three times a day. In still another embodiment, the compound provided herein is administered four times a day.

In one embodiment, a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) is administered about 0.1, 0.2, 0.25, 0.5, 1, 2, 2.5, 5, 10, 15, 20, 25, 30, 35, 40, 45, 50 mg, or 75 mg BID. In one embodiment, a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) is administered about 0.5 mg BID. In another embodiment, a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) is administered about 1 mg BID. In another embodiment, a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) is administered about 5 mg BID. In another embodiment, a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) is administered about 8 mg BID. In another embodiment, a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) is administered about 15 mg BID. In another embodiment, a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) is administered about 25 mg BID. In another embodiment, a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) is administered about 35 mg BID. In another embodiment, a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) is administered about 50 mg BID. In another embodiment, a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) is administered about 75 mg BID.

In certain embodiments, the compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) is administered once per day from one day to six months, from one week to three months, from one week to four weeks, from one week to three weeks, or from one week to two weeks. In certain embodiments, the compound provided herein is administered once per day for one week, two weeks, three weeks, or four weeks. In one embodiment, the compound provided herein is administered once per day for one week. In another embodiment, the compound provided herein is administered once per day for two weeks. In yet another embodiment, the compound provided herein is administered once per day for three weeks. In still another embodiment, the compound provided herein is administered once per day for four weeks. In still another embodiment, the compound provided herein is administered once per day for more than four weeks.

In certain embodiments, the compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) is administered twice per day from one day to six months, from one week to three months, from one week to four weeks, from one week to three weeks, or from one week to two weeks. In certain embodiments, the compound provided herein is administered twice per day for one week, two weeks, three weeks, or four weeks. In one embodiment, the compound provided herein is administered twice per day for one week. In another embodiment, the compound provided herein is administered twice per day for two weeks. In yet another embodiment, the compound provided herein is administered twice per day for three weeks. In still another embodiment, the compound provided herein is administered twice per day for four weeks. In still another embodiment, the compound provided herein is administered twice per day for more than four weeks.

The compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) can be delivered as a single dose such as, e.g., a single bolus injection, or oral tablets or pills; or over time, such as, e.g., continuous infusion over time or divided bolus doses over time. The compound can be administered repeatedly if necessary, for example, until the patient experiences stable disease or regression, or until the patient experiences disease progression or unacceptable toxicity.

Combination Therapy

In some embodiments, the compound provided herein is administered in combination with one or more other therapies. In one embodiment, provided herein are methods for combination therapies in which an agent known to modulate other pathways, or other components of the same pathway, or even overlapping sets of target enzymes are used in combination with a compound provided herein, or a pharmaceutically acceptable form (e.g., pharmaceutically acceptable salts, hydrates, solvates, isomers, prodrugs, and isotopically labeled derivatives) thereof. In one aspect, such therapy includes, but is not limited to, the combination of the subject compound with chemotherapeutic agents, therapeutic antibodies, and/or radiation treatment, to provide a synergistic or additive therapeutic effect.

By "in combination with," it is not intended to imply that the other therapy and the PI3K modulator must be administered at the same time and/or formulated for delivery together, although these methods of delivery are within the scope of this disclosure. The compound provided herein can be administered concurrently with, prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before), or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after), one or more other therapies (e.g., one or more other additional agents). In general, each therapeutic agent will be administered at a dose and/or on a time schedule determined for that particular agent. The other therapeutic agent can be administered with the compound provided herein in a single composition or separately in a different composition. Triple therapy is also contemplated herein.

In general, it is expected that additional therapeutic agents employed in combination be utilized at levels that do not exceed the levels at which they are utilized individually. In some embodiments, the levels utilized in combination will be lower than those utilized individually.

In some embodiments, the compound provided herein is a first line treatment for cancer or hematologic malignancy, i.e., it is used in a subject who has not been previously administered another drug or therapy intended to treat cancer or hematologic malignancy or one or more symptoms thereof.

In other embodiments, the compound provided herein is a second line treatment for cancer or hematologic malignancy, i.e., it is used in a subject who has been previously administered another drug or therapy intended to treat cancer or hematologic malignancy or one or more symptoms thereof.

In other embodiments, the compound provided herein is a third or fourth line treatment for cancer or hematologic malignancy, i.e., it is used in a subject who has been previously administered two or three other drugs or therapies intended to treat cancer or hematologic malignancy or one or more symptoms thereof.

In embodiments where two agents are administered, the agents can be administered in any order. For example, the two agents can be administered concurrently (i.e., essentially at the same time, or within the same treatment) or sequentially (i.e., one immediately following the other, or alternatively, with a gap in between administration of the two). In some embodiments, the compound provided herein is administered sequentially (i.e., after the first therapeutic).

In one embodiment, provided herein is a combination therapy for inhibiting abnormal cell growth in a subject which comprises administering a compound provided herein, or a pharmaceutically acceptable form (e.g., pharmaceutically acceptable salts, hydrates, solvates, isomers, prodrugs, and isotopically labeled derivatives) thereof, in combination with an amount of an anti-cancer agent (e.g., a chemotherapeutic agent). Many chemotherapeutics are presently known in the art and can be used in combination with a compound provided herein.

In some embodiments, the chemotherapeutic is selected from mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec® (imatinib mesylate), Velcade® (bortezomib), Casodex™ (bicalutamide), Iressa® (gefitinib), Tarceva® (erlotinib), and Adriamycin® (doxorubicin) as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; BTK inhibitors such as ibrutinib (PCI-32765), AVL-292, Dasatinib, LFM-AI3, ONO-WG-307, and GDC-0834; HDAC inhibitors such as vorinostat, romidepsin, panobinostat, valproic acid, belinostat, mocetinostat, abrexinostat, entinostat, SB939, resminostat, givinostat, CUDC-101, AR-42, CHR-2845, CHR-3996, 4SC-202, CG200745, ACY-1215 and kevetrin; EZH2 inhibitors such as, but not limited to, EPZ-6438 (N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1, 1'-biphenyl]-3-carboxamide), GSK-126 ((S)-1-(sec-butyl)-N-((4,6-dimethyl-2-oxo-1,2-dihydropyridin-3-yl)methyl)-3-methyl-6-(6-(piperazin-1-yl)pyridin-3-yl)-1H-indole-4-carboxamide), GSK-343 (1-Isopropyl-N-((6-methyl-2-oxo-4-propyl-1,2-dihydropyridin-3-yl)methyl)-6-(2-(4-methylpiperazin-1-yl)pyridine-4-yl)-1H-indazole-4-carboxamide), E11, 3-deazaneplanocin A (DNNep, 5R-(4-amino-1H-imidazo[4,5-c]pyridin-1-yl)-3-(hydroxymethyl)-3-cyclopentene-1S,2R-diol), small interfering RNA (siRNA) duplexes targeted against EZH2 (S. M. Elbashir et al., Nature 411:494-498 (2001)), isoliquiritigenin, and those provided in, for example, U.S. Publication Nos. 2009/0012031, 2009/0203010, 2010/0222420, 2011/0251216, 2011/0286990, 2012/0014962, 2012/0071418, 2013/0040906, and 2013/0195843, all of which are incorporated herein by reference; JAK/STAT inhibitors such as lestaurtinib, tofacitinib, ruxolitinib, pacritinib, CYT387, baricitinib, GLPG0636, TG101348, INCB16562, CP-690550, and AZD1480; PKC-β inhibitor such as Enzastaurin; SYK inhibitors such as, but not limited to, GS-9973, R788 (fostamatinib), PRT 062607, R406, (S)-2-(2-((3,5-dimethylphenyl)amino)pyrimidin-4-yl)-N-(1-hydroxypropan-2-yl)-4-methylthiazole-5-carboxamide, R112, GSK143, BAY61-3606, PP2, PRT 060318, R348, and those provided in, for example, U.S. Publication Nos. 2003/0113828, 2003/0158195, 2003/0229090, 2005/0075306, 2005/0232969, 2005/0267059, 2006/0205731, 2006/0247262, 2007/0219152, 2007/0219195, 2008/0114024, 2009/0171089, 2009/0306214, 2010/0048567, 2010/0152159, 2010/0152182, 2010/0316649, 2011/0053897, 2011/0112098, 2011/0245205, 2011/0275655, 2012/0027834, 2012/0093913, 2012/0101275, 2012/0130073, 2012/0142671, 2012/0184526, 2012/0220582, 2012/0277192, 2012/0309735, 2013/0040984, 2013/0090309, 2013/0116260, and 2013/0165431, all of which are incorporated herein by reference; SYK/JAK dual inhibitor such as PRT2070; nitrogen mustards such as bendamustine, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomycins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pralatrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatrexate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™; razoxane; sizofiran; spirogermanium; tenuazonic acid; triaziquone; 2,2',2''-trichlorotriethyla-mine; urethan; vindesine; dacarbazine; mannomustine; mitobronitol; mitolactol; pipobroman; gacytosine; arabinoside (Ara-C); cyclophosphamide; thiotepa; taxanes, e.g., paclitaxel (e.g., TAXOL™) and docetaxel (e.g., TAXOTERE™) and ABRAXANE® (paclitaxel protein-bound particles); retinoic acid; esperamicins; capecitabine; and pharmaceutically acceptable forms (e.g., pharmaceutically acceptable salts, hydrates, solvates, isomers, prodrugs, and isotopically labeled derivatives) of any of the above. Also included as suitable chemotherapeutic cell conditioners are anti-hormonal agents that act to regulate or inhibit hormone action on tumors such as anti-estrogens including for example tamoxifen (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Where desired, the compounds or pharmaceutical composition as provided herein can be used in combination with commonly prescribed anti-cancer drugs such as Herceptin®, Avastin®, Erbitux®, Rituxan®, Taxol®, Arimidex®, Taxotere®, ABVD, AVICINE, abagovomab, acridine carboxamide, adecatumumab, 17-N-allylamino-17-demethoxygeldanamycin, alpharadin, alvocidib, 3-aminopyridine-2-carboxaldehyde thiosemicarbazone, amonafide, anthracenedione, anti-CD22 immunotoxins, antineoplastic, antitumorigenic herbs, apaziquone, atiprimod, azathioprine, belotecan, bendamustine, BIBW 2992, biricodar, brostallicin, bryostatin, buthionine sulfoximine, CBV (chemotherapy), calyculin, crizotinib, cell-cycle nonspecific antineoplastic agents, dichloroacetic acid, discodermolide, elsamitrucin, enocitabine, epothilone, eribulin, everolimus, exatecan, exisulind, ferruginol, forodesine, fosfestrol, ICE chemotherapy regimen, IT-101, imexon, imiquimod, indolocarbazole, irofulven, laniquidar, larotaxel, lenalidomide, lucanthone, lurtotecan, mafosfamide, mitozolomide, nafoxidine, nedaplatin, olaparib, ortataxel, PAC-1, pawpaw, pixantrone, proteasome inhibitor, rebeccamycin, resiquimod, rubitecan, SN-38, salinosporamide A, sapacitabine, Stanford V, swainsonine, talaporfin, tariquidar, tegafur-uracil, temodar, tesetaxel, triplatin tetranitrate, tris(2-chloroethyl)amine, troxacitabine, uramustine, vadimezan, vinflunine, ZD6126, and zosuquidar.

In some embodiments, the chemotherapeutic is selected from hedgehog inhibitors including, but not limited to IPI-926 (See U.S. Pat. No. 7,812,164). Other suitable hedgehog inhibitors include, for example, those described and disclosed in U.S. Pat. No. 7,230,004, U.S. Patent Application Publication No. 2008/0293754, U.S. Patent Application Publication No. 2008/0287420, and U.S. Patent Application Publication No. 2008/0293755, the entire disclosures of which are incorporated by reference herein. Examples of other suitable hedgehog inhibitors include those described in U.S. Patent Application Publication Nos. US 2002/0006931, US 2007/0021493 and US 2007/0060546, and International Application Publication Nos. WO 2001/19800, WO 2001/26644, WO 2001/27135, WO 2001/49279, WO 2001/74344, WO 2003/011219, WO 2003/088970, WO 2004/020599, WO 2005/013800, WO 2005/033288, WO 2005/032343, WO 2005/042700, WO 2006/028958, WO 2006/050351, WO 2006/078283, WO 2007/054623, WO 2007/059157, WO 2007/120827, WO 2007/131201, WO 2008/070357, WO 2008/110611, WO 2008/112913, and WO 2008/131354, each incorporated herein by reference. Additional examples of hedgehog inhibitors include, but are not limited to, GDC-0449 (also known as RG3616 or vismodegib) described in, e.g., Von Hoff D. et al., *N Engl. J. Med.* 2009; 361(12):1164-72; Robarge K. D. et al., *Bioorg Med Chem Lett.* 2009; 19(19):5576-81; Yauch, R. L. et al. (2009) *Science* 326: 572-574; Sciencexpress: 1-3 (10.1126/science.1179386); Rudin, C. et al. (2009) *New England J of Medicine* 361-366 (10.1056/nejma0902903); BMS-833923 (also known as XL139) described in, e.g., in Siu L. et al., *J. Clin. Oncol.* 2010; 28:15s (suppl; abstr 2501); and National Institute of Health Clinical Trial Identifier No. NCT006701891; LDE-225 described, e.g., in Pan S. et al., *ACS Med. Chem. Lett.,* 2010; 1(3): 130-134; LEQ-506 described, e.g., in National Institute of Health Clinical Trial Identifier No. NCT01106508; PF-04449913 described, e.g., in National Institute of Health Clinical Trial Identifier No. NCT00953758; Hedgehog pathway antagonists disclosed in U.S. Patent Application Publication No. 2010/0286114; SMOi2-17 described, e.g., U.S. Patent Application Publication No. 2010/0093625; SANT-1 and SANT-2 described, e.g., in Rominger C. M. et al., *J. Pharmacol. Exp. Ther.* 2009; 329(3):995-1005; 1-piperazinyl-4-arylphthalazines or analogues thereof, described in Lucas B. S. et al., *Bioorg. Med. Chem. Lett.* 2010; 20(12):3618-22.

Other hormonal therapy and chemotherapeutic agents include, but are not limited to, anti-estrogens (e.g. tamoxifen, raloxifene, and megestrol acetate), LHRH agonists (e.g. goserelin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids or taxanes (e.g. paclitaxel or a paclitaxel equivalent such as nanoparticle albumin-bound paclitaxel (Abraxane), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, raltitrexed, tegafur-uracil, capecitabine), cytosine analogs (e.g. cytarabine (ara C, cytosine arabinoside), and fludarabine), purine analogs (e.g. mercaptopurine and thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracyclines (e.g. daunorubicin, doxorubicin, pegylated liposomal doxorubicin, idarubicin, epirubicin, pirarubicin, zorubicin, mitoxantrone), MDR inhibitors (e.g. verapamil), Ca2+ ATPase inhibitors (e.g. thapsigargin), thalidomide, lenalidomide (REVLIMID®), tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD- 001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbazine, prednisolone, dexamethasone, camptothecin, plicamycin, asparaginase, aminopterin, methopterin, porfiromycin, melphalan, leurosidine, leurosine, chlorambucil, trabectedin, procarbazine, discodermolide, carminomycin-aminopterin, and hexamethyl melamine.

Exemplary biotherapeutic agents include, but are not limited to, interferons, cytokines (e.g., tumor necrosis factor, interferon α, interferon γ), vaccines, hematopoietic growth factors, monoclonal serotherapy, immuno-stimulants and/or immuno-modulatory agents (e.g., IL-1, 2, 4, 6, or 12), immune cell growth factors (e.g., GM-CSF) and antibodies (e.g. Herceptin (trastuzumab), T-DM1, AVASTIN (bevacizumab), ERBITUX (cetuximab), Vectibix (panitumumab), Rituxan (rituximab), Bexxar (tositumomab), or Perjeta (pertuzumab)).

In one embodiment, the biotherapeutic agent is an anti-CD37 antibody such as, but not limited to, IMGN529, K7153A and TRU-016. In another embodiment, the biotherapeutic agent is an anti-CD20 antibody such as, but not limited to, $^{131}$I tositumomab, $^{90}$Y ibritumomab, $^{111}$I ibritumomab, obinutuzumab and ofatumumab. In another embodiment, the biotherapeutic agent is an anti-CD52 antibody such as, but not limited to, alemtuzumab.

In some embodiments, the chemotherapeutic is selected from HSP90 inhibitors. The HSP90 inhibitor can be a geldanamycin derivative, e.g., a benzoquinone or hydroquinone ansamycin HSP90 inhibitor (e.g., IPI-493 and/or IPI-504). Non-limiting examples of HSP90 inhibitors include IPI-493, IPI-504, 17-AAG (also known as tanespimycin or CNF-1010), BIIB-021 (CNF-2024), BIIB-028, AUY-922 (also known as VER-49009), SNX-5422, STA-9090, AT-13387, XL-888, MPC-3100, CU-0305, 17-DMAG, CNF-1010, Macbecin (e.g., Macbecin I, Macbecin II), CCT-018159, CCT-129397, PU—H71, or PF-04928473 (SNX-2112).

In some embodiments, the chemotherapeutic is selected from PI3K inhibitors (e.g., including those PI3K inhibitors provided herein and those PI3K inhibitors not provided herein). In some embodiment, the PI3K inhibitor is an inhibitor of delta and gamma isoforms of PI3K. In some embodiment, the PI3K inhibitor is an inhibitor of delta isoform of PI3K. In some embodiment, the PI3K inhibitor is an inhibitor of gamma isoform of PI3K. In some embodiments, the PI3K inhibitor is an inhibitor of alpha isoform of PI3K. In other embodiments, the PI3K inhibitor is an inhibitor of one or more alpha, beta, delta and gamma isoforms of PI3K. Exemplary PI3K inhibitors that can be used in combination are described in, e.g., WO 09/088990, WO 09/088086, WO 2011/008302, WO 2010/036380, WO 2010/006086, WO 09/114870, WO 05/113556; US 2009/0312310, and US 2011/0046165, each incorporated herein by reference. Additional PI3K inhibitors that can be used in combination with the pharmaceutical compositions, include but are not limited to, AMG-319, GSK 2126458, GDC-0980, GDC-0941, Sanofi XL147, XL499, XL756, XL147, PF-4691502, BKM 120, GA-101 (obinutuzumab), CAL-101 (GS-1101), CAL 263, SF1126, PX-886, and a dual PI3K inhibitor (e.g., Novartis BEZ235). In one embodiment, the PI3K inhibitor is an isoquinolinone.

In some embodiments, the chemotherapeutic is selected from polo-like kinase 1 (PLK1) inhibitors such as, but not limited to, volasertib (BI6727; N-4[S,4S)-4-(4-(cyclopropylmethyl)piperazin-1-yl)cyclohexyl)-4-(((R)-7-ethyl-8-isopropyl-5-methyl-6-oxo-5,6,7,8-tetrahydropteridin-2-yl)amino)-3-methoxybenzamide), BI2536 ((R)-4-[(8-Cyclopentyl-7-ethyl-5,6,7,8-tetrahydro-5-methyl-6-oxo-2-pteridinyl)amino]-3-methoxy-N-(1-methyl-4-piperidinyl)benzamide), ZK-Thiazolidone ((2-imidazol-1-yl-1-oxidanyl-1-phosphono-ethyl)phosphonic acid), TAK-960 (4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxy-N-(1-methylpiperidin-4-yl)benzamide), MLN0905 (2-((5-(3-(dimethylamino)propyl)-2-methylpyridin-3-yl)amino)-9-(trifluoromethyl)-5H-benzo[b]pyrimido[4,5-d]azepine-6(7H)-thione), GSK461364 ((R)-5-(6-((4-methylpiperazin-1-yl)methyl)-1H-benzo[d]imidazol-1-yl)-3-(1-(2-(trifluoromethyl)phenyl)ethoxy)thiophene-2-carboxamide), rigosertib (ON-01910; sodium (E)-2-((2-methoxy-5-(((2,4,6-trimethoxystyryl)sulfonyl)methyl)phenyl)amino)acetate) and HMN-214 ((E)-4-(2-(N-((4-methoxyphenyl)sulfonyl)acetamido)styryl)pyridine 1-oxide).

In some embodiments, the chemotherapeutic is selected from IRAK inhibitors. Inhibitors of the IRAK protein kinase family refer to compounds which inhibit the function of IRAK protein kinases and more preferably compounds which inhibit the function of IRAK-4 and/or IRAK-1. Exemplary IRAK inhibitors include, but are not limited to, IRAK4 inhibitors such as ND-2110 and ND-2158; the IRAK inhibitors disclosed in WO2003/030902, WO2004/041285, WO2008/030579, and Buckley et al. (IRAK-4 inhibitors. Part 1: a series of amides. In Bioorganic & medicinal chemistry letters 2008, 18(11):3211-3214; IRAK-4 inhibitors. Part II: a structure-based assessment of imidazo[1,2-a]pyridine binding. In Bioorganic & medicinal chemistry letters 2008, 18(11):3291-3295; IRAK-4 inhibitors. Part III: a series of imidazo[1,2-a]pyridines. In Bioorganic & medicinal chemistry letters 2008, 18(11):3656-3660), the entireties of which are incorporated herein by reference; RO6245, RO0884, N-acyl 2-aminobenzimidazoles 1-(2-(4-Morpholinyl)ethyl)-2-(3-nitrobenzoylamino)benzimidazole, and/or N-(2-Morpholinylethyl)-2-(3-nitrobenzoylamido)-benzimidazole.

In some embodiments, provided herein is a method for using the a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, in combination with radiation therapy in inhibiting abnormal cell growth or treating the hyperproliferative disorder in the subject. Techniques for administering radiation therapy are known in the art, and these techniques can be used in the combination therapy described herein. The administration of a compound provided herein in this combination therapy can be determined as described herein.

Radiation therapy can be administered through one of several methods, or a combination of methods, including without limitation, external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner as provided herein include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, can render abnormal cells more sensitive to treatment with radiation for purposes of killing and/or inhibiting the growth of such cells. Accordingly, provided herein is a method for sensitizing abnormal cells in a subject to treatment with radiation which comprises administering to the subject an amount of a compound provided herein, or a pharmaceutically acceptable form (e.g., pharmaceutically acceptable salts, hydrates, solvates, isomers, prodrugs, and isotopically labeled derivatives) thereof, which amount is effective in sensitizing abnormal cells to treatment with radiation. The amount of the compound used in this method can be determined according to the means for ascertaining effective amounts of such compounds described herein.

In some embodiments, provided herein is a method for using the a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, in combination with hormonal therapy in inhibiting abnormal cell growth or treating hyperproliferative disorder in the subject.

In some embodiments, provided herein is a method for using the a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, in combination with surgery in inhibiting abnormal cell growth or treating hyperproliferative disorder in the subject.

In one embodiment, a compound as provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, can be used in combination with an amount of one or more substances selected from anti-angiogenesis agents, signal transduction inhibitors, and antiproliferative agents, glycolysis inhibitors, or autophagy inhibitors.

Other therapeutic agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a compound provided herein, or a pharmaceutically acceptable form thereof, or a pharmaceutical composition described herein. Such therapeutic agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. In some embodiments, MMP-2 and MMP-9 inhibitors are those that have little or no activity inhibiting MMP-1. Other embodiments include those that selectively inhibit MMP-2 and/or AMP-9 relative to the other matrix-metalloproteinases (e.g., MAP-1, MMP-3, MMP-4, MMP-5, MMP-6, MMP-7, MMP-8, MMP-10, MMP-11, MMP-12, and MMP-13). Some non-limiting examples of MMP inhibitors are AG-3340, RO 32-3555, and RS 13-0830.

Autophagy inhibitors include, but are not limited to, chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNAs that inhibit expression of proteins including, but not limited to ATG5 (which are implicated in autophagy), can also be used.

Other exemplary therapeutic agents useful for a combination therapy include, but are not limited to, agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, 0-adrenergic agonists, ipratropium, glucocorticoids, methylxanthines, sodium channel blockers, opioid receptor agonists, calcium channel blockers, membrane stabilizers and leukotriene inhibitors.

Examples of therapeutic antibodies that can be combined with a compound provided herein include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immuno-modulation, such as immuno-modulators, immuno-suppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and anti-platelet drugs are also contemplated by the methods herein.

In exemplary embodiments, for treating renal carcinoma, one can combine a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, with sorafenib and/or avastin. For treating an endometrial disorder, one can combine a compound provided herein with doxorubicin, taxotere (taxol), and/or cisplatin (carboplatin). For treating ovarian cancer, one can combine a compound provided herein with cisplatin, carboplatin, docetaxel, doxorubicin, topotecan, and/or tamoxifen. For treating breast cancer, one can combine a compound provided herein with paclitaxel or docetaxel, gemcitabine, capecitabine, tamoxifen, letrozole, erlotinib, lapatinib, PD0325901, bevacizumab, trastuzumab, OSI-906, and/or OSI-930. For treating lung cancer, one can combine a compound as provided herein with paclitaxel, docetaxel, gemcitabine, cisplatin, pemetrexed, erlotinib, PD0325901, and/or bevacizumab.

In some embodiments, the disorder to be treated, prevented and/or managed is a hematological cancer, e.g., lymphoma (e.g., T-cell lymphoma; NHL), myeloma (e.g., multiple myeloma), and leukemia (e.g., CLL), and a compound provided herein (e.g., Compound 292) is used in combination with: HDAC inhibitors such as vorinostat, romidepsin and ACY-1215; mTOR inhibitors such as everolimus; anti-folates such as pralatrexate; nitrogen mustard such as bendamustine; gemcitabine, optionally in further combination with oxaliplatin; rituximab-cyclophosphamide combination; PI3K inhibitors such as GS-1101, XL 499, GDC-0941, and AMG-319; angiogenesis inhibitors such as pomalidomide or BTK inhibitors such as ibrutinib, AVL-292, Dasatinib, LFM-AI3, ONO-WG-307, and GDC-0834.

In some embodiments, the disorder to be treated, prevented and/or managed is DLBCL, and a compound provided herein (e.g., Compound 292), or a pharmaceutically acceptable derivative (e.g., salt or solvate) thereof, is used in combination with HDAC inhibitors provided herein. In one particular embodiment, the HDAC inhibitor is ACY-1215.

In some embodiments, the disorder to be treated, prevented and/or managed is DLBCL, and a compound provided herein (e.g., Compound 292), or a pharmaceutically acceptable derivative (e.g., salt or solvate) thereof, is used in combination with BTK inhibitors provided herein. In one particular embodiment, the BTK inhibitor is ibrutinib. In one embodiment, the BTK inhibitor is AVL-292.

In some embodiments, the disorder to be treated, prevented and/or managed is DLBCL, and a compound provided herein (e.g., Compound 292), or a pharmaceutically acceptable derivative (e.g., salt or solvate) thereof, is used in combination with IRAK inhibitors provided herein. In one particular embodiment, the IRAK4 inhibitor is ND-2110 or ND-2158.

In some embodiments, the disorder to be treated, prevented and/or managed is WM, and a compound provided herein (e.g., Compound 292), or a pharmaceutically acceptable derivative (e.g., salt or solvate) thereof, is used in combination with BTK inhibitors provided herein. In one particular embodiment, the BTK inhibitor is ibrutinib. In one embodiment, the BTK inhibitor is AVL-292.

In some embodiments, the disorder to be treated, prevented and/or managed is WM, and a compound provided herein (e.g., Compound 292), or a pharmaceutically acceptable derivative (e.g., salt or solvate) thereof, is used in combination with IRAK4 inhibitors provided herein. In one particular embodiment, the IRAK4 inhibitor is ND-2110 or ND-2158.

In some embodiments, the disorder to be treated, prevented and/or managed is T-ALL, the subject/patient has a PTEN deficiency, and a compound provided herein (e.g., Compound 292), or a pharmaceutically acceptable derivative (e.g., salt or solvate) thereof, is used in combination with doxorubicin and/or vincristine.

Further therapeutic agents that can be combined with a compound provided herein can be found in Goodman and Gilman's "*The Pharmacological Basis of Therapeutics*" Tenth Edition edited by Hardman, Limbird and Gilman or the Physician's Desk Reference, both of which are incorporated herein by reference in their entirety.

In one embodiment, the compounds described herein can be used in combination with the agents provided herein or other suitable agents, depending on the condition being treated. Hence, in some embodiments, a compound provided herein, or a pharmaceutically acceptable form thereof, will be co-administered with other agents as described above. When used in combination therapy, a compound described herein, or a pharmaceutically acceptable form thereof, can be administered with a second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound provided herein and any of the agents described above can be simultaneously administered, wherein both agents are present in separate formulations. In another alternative, a compound provided herein can be administered just followed by any of the agents described above, or vice versa. In the separate administration protocol, a compound provided herein and any of the agents described above can be administered a few minutes apart, or a few hours apart, or a few days apart.

Administration of a compound provided herein, or a pharmaceutically acceptable form thereof, can be effected by any method that enables delivery of the compound to the site of action. An effective amount of a compound provided herein, or a pharmaceutically acceptable form thereof, can be administered in either single or multiple doses by any of the accepted modes of administration of agents having similar utilities, including rectal, buccal, intranasal, and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

When a compound provided herein, or a pharmaceutically acceptable form thereof, is administered in a pharmaceutical composition that comprises one or more agents, and the agent has a shorter half-life than the compound provided herein, unit dose forms of the agent and the compound as provided herein can be adjusted accordingly.

In some embodiments, the compound provided herein and the second agent are administered as separate compositions, e.g., pharmaceutical compositions. In some embodiments, the PI3K modulator and the agent are administered separately, but via the same route (e.g., both orally or both intravenously). In other embodiments, the PI3K modulator and the agent are administered in the same composition, e.g., pharmaceutical composition.

In some embodiments, a compound provided herein (e.g., Compound 292), or a pharmaceutically acceptable derivative (e.g., salt or solvate) thereof, is used in combination with an HDAC inhibitor, such as, e.g., belinostat, vorinostat, panobinostat, ACY-1215, or romidepsin.

In some embodiments, a compound provided herein (e.g., Compound 292), or a pharmaceutically acceptable derivative (e.g., salt or solvate) thereof, is used in combination with an mTOR inhibitor, such as, e.g., everolimus (RAD 001).

In some embodiments, a compound provided herein (e.g., Compound 292), or a pharmaceutically acceptable derivative (e.g., salt or solvate) thereof, is used in combination with a proteasome inhibitor, such as, e.g., bortezomib or carfilzomib.

In some embodiments, a compound provided herein (e.g., Compound 292), or a pharmaceutically acceptable derivative (e.g., salt or solvate) thereof, is used in combination with a PKC-β inhibitor, such as, e.g., Enzastaurin (LY317615).

In some embodiments, a compound provided herein (e.g., Compound 292), or a pharmaceutically acceptable derivative (e.g., salt or solvate) thereof, is used in combination with a JAK/STAT inhibitor, such as, e.g., INCB16562 or AZD1480.

In some embodiments, a compound provided herein (e.g., Compound 292), or a pharmaceutically acceptable derivative (e.g., salt or solvate) thereof, is used in combination with an anti-folate, such as, e.g., pralatrexate.

In some embodiments, a compound provided herein (e.g., Compound 292), or a pharmaceutically acceptable derivative (e.g., salt or solvate) thereof, is used in combination with a farnesyl transferase inhibitor, such as, e.g., tipifarnib.

In some embodiments, a compound provided herein (e.g., Compound 292), or a pharmaceutically acceptable derivative (e.g., salt or solvate) thereof, is used in combination bendamustine and one additional active agent. In one embodiment, the cancer or hematological malignancy is iNHL.

In some embodiments, a compound provided herein (e.g., Compound 292), or a pharmaceutically acceptable derivative (e.g., salt or solvate) thereof, is used in combination rituximab and one additional active agent. In one embodiment, the cancer or hematological malignancy is iNHL.

In some embodiments, a compound provided herein (e.g., Compound 292), or a pharmaceutically acceptable derivative (e.g., salt or solvate) thereof, is used in combination bendamustine and rituximab. In one embodiment, the cancer or hematological malignancy is iNHL.

In some embodiments, a compound provided herein (e.g., Compound 292), or a pharmaceutically acceptable derivative (e.g., salt or solvate) thereof, is used in combination fludarabine, cyclophosphamide, and rituximab. In one embodiment, the cancer or hematological malignancy is CLL.

In some embodiments, a compound provided herein (e.g., Compound 292), or a pharmaceutically acceptable derivative (e.g., salt or solvate) thereof, is used in combination with an antibody or a biologic agent, such as, e.g., alemtuzumab, rituximab, ofatumumab, or brentuximab vedotin (SGN-035). In one embodiment, the second agent is rituximab. In one embodiment, the second agent is rituximab and the combination therapy is for treating, preventing, and/or managing iNHL, FL, splenic marginal zone, nodal marginal zone, extranodal marginal zone, and/or SLL.

In some embodiments, a compound provided herein (e.g., Compound 292), or a pharmaceutically acceptable derivative (e.g., salt or solvate) thereof, is used in combination with an antibody-drug conjugate, such as, e.g., inotuzumab ozogamicin, or brentuximab vedotin.

In some embodiments, a compound provided herein (e.g., Compound 292), or a pharmaceutically acceptable derivative (e.g., salt or solvate) thereof, is used in combination with a cytotoxic agent, such as, e.g., bendamustine, gemcitabine, oxaliplatin, cyclophosphamide, vincristine, vinblastine, anthracycline (e.g., daunorubicin or daunomycin, doxorubicin), actinomycin, dactinomycin, bleomycin, clofarabine, nelarabine, cladribine, asparaginase, methotrexate, or pralatrexate.

In some embodiments, a compound provided herein (e.g., Compound 292), or a pharmaceutically acceptable derivative (e.g., salt or solvate) thereof, is used in combination with one or more other anti-cancer agents or chemotherapeutic agents, such as, e.g., fludarabine, ibrutinib, fostamatinib, lenalidomide, thalidomide, rituximab, cyclophosphamide, doxorubicin, vincristine, prednisone, or R—CHOP (Rituximab, Cyclophosphamide, Doxorubicin or Hydroxydaunomycin, Vincristine or Oncovin, Prednisone).

In some embodiments, a compound provided herein (e.g., Compound 292), or a pharmaceutically acceptable derivative (e.g., salt or solvate) thereof, is used in combination with an antibody for a cytokine (e.g., an IL-15 antibody, an IL-21 antibody, an IL-4 antibody, an IL-7 antibody, an IL-2 antibody, an IL-9 antibody). In some embodiments, the second agent is a JAK1 inhibitor, a JAK3 inhibitor, a pan-JAK inhibitor, a BTK inhibitor, an SYK inhibitor, or a PI3K delta inhibitor. In some embodiments, the second agent is an antibody for a chemokine.

Without being limited to a particular theory, a targeted combination therapy described herein has reduced side effect and/or enhanced efficacy. For example, in one embodiment, provided herein is a combination therapy for treating CLL with a compound described herein (e.g., Compound 292), or a pharmaceutically acceptable derivative (e.g., salt or solvate) thereof, and a second active agent (e.g., IL-15 antibodies, IL-21 antibodies, IL-4 antibodies, IL-7 antibodies, IL-2 antibodies, IL-9 antibodies, JAK1 inhibitors, JAK3 inhibitors, pan-JAK inhibitors, BTK inhibitors, SYK inhibitors, and/or PI3K delta inhibitors).

Further without being limited by a particular theory, it was found that a compound provided herein (e.g., Compound 292) does not affect BTK or MEK pathway. Accordingly, in some embodiments, provided herein is a method of treating or managing cancer or hematological malignancy comprising administering to a patient a therapeutically effective amount of a compound provided herein (e.g., Compound 292), or a pharmaceutically acceptable derivative (e.g., salt or solvate) thereof, in combination with a BTK inhibitor. In one embodiment, the BTK inhibitor is ibrutinib. In one embodiment, the BTK inhibitor is AVL-292. In one embodiment, the cancer or hematological malignancy is DLBCL. In another embodiment, the cancer or hematological malignancy is iNHL. In another embodiment, the cancer or hematological malignancy is CLL.

In other embodiments, provided herein is a method of treating or managing cancer or hematological malignancy comprising administering to a patient a therapeutically effective amount of a compound provided herein (e.g., Compound 292), or a pharmaceutically acceptable derivative (e.g., salt or solvate) thereof, in combination with a MEK inhibitor. In one embodiment, the MEK inhibitor is trametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H)-yl}phenyl)acetamide), selumetinob (6-(4-bromo-2-chloroanilino)-7-fluoro-N-(2-hydroxyethoxy)-3-methylbenzimidazole-5-carboxamide), pimasertib/AS703026/MSC1935369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEA119 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3-d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6-carboxamide), RO5126766 (3-[[3-Fluoro-2-(methylsulfamoylamino)-4-pyridyl]methyl]-4-methyl-7-pyrimidin-2-yloxychromen-2-one), WX-554, RO4987655/CH4987655 (3,4-difluoro-2-((2-fluoro-4-iodophenyl)amino)-N-(2-hydroxyethoxy)-5-((3-oxo-1,2-oxazinan-2-yl)methyl)benzamide), or AZD8330 (2-((2-fluoro-4-iodophenyl)amino)-N-(2-hydroxyethoxy)-1,5-dimethyl-6-oxo-1,6-dihydropyridine-3-carboxamide). In one embodiment, the cancer or hematological malignancy is DLBCL. In another embodiment, the cancer or hematological malignancy is ALL. In another embodiment, the cancer or hematological malignancy is CTCL.

In other embodiments, provided herein is a method of treating or managing cancer or hematological malignancy comprising administering to a patient a therapeutically effective amount of a compound provided herein (e.g., Compound 292), or a pharmaceutically acceptable derivative (e.g., salt or solvate) thereof, in combination with an EZH2 inhibitor. In one embodiment, the EZH2 inhibitor is EPZ-6438, GSK-126, GSK-343, E11, or 3-deazaneplanocin A (DNNep). In one embodiment, the cancer or hematological malignancy is DLBCL. In another embodiment, the cancer or hematological malignancy is iNHL. In another embodiment, the cancer or hematological malignancy is ALL. In another embodiment, the cancer or hematological malignancy is CTCL.

In other embodiments, provided herein is a method of treating or managing cancer or hematological malignancy comprising administering to a patient a therapeutically effective amount of a compound provided herein (e.g., Compound 292), or a pharmaceutically acceptable derivative (e.g., salt or solvate) thereof, in combination with a bcl-2 inhibitor. In one embodiment, the BCL2 inhibitor is ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[[(2R)-4-(dimethylamino)-1-phenylsulfanylbutan-2-yl]amino]-3-nitrophenyl]sulfonylbenzamide), ABT-263 ((R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), or G3139 (Oblimersen). In one embodiment, the cancer or hematological malignancy is DLBCL. In another embodiment, the cancer or hematological malignancy is iNHL. In another embodiment, the cancer or hematological malignancy is CLL. In another embodiment, the cancer or hematological malignancy is ALL. In another embodiment, the cancer or hematological malignancy is CTCL.

In other embodiments, provided herein is a method of treating or managing iNHL comprising administering to a patient a therapeutically effective amount of a compound provided herein (e.g., Compound 292), or a pharmaceutically acceptable derivative (e.g., salt or solvate) thereof, in combination with rituximab. In one embodiment, the patient is an elderly patient. In another embodiment, iNHL is relapsed or refractory.

In other embodiments, provided herein is a method of treating or managing iNHL comprising administering to a patient a therapeutically effective amount of a compound provided herein (e.g., Compound 292), or a pharmaceutically acceptable derivative (e.g., salt or solvate) thereof, in combination with bendamustine. In one embodiment, iNHL is relapsed or refractory.

In other embodiments, provided herein is a method of treating or managing iNHL comprising administering to a patient a therapeutically effective amount of a compound provided herein (e.g., Compound 292), or a pharmaceutically acceptable derivative (e.g., salt or solvate) thereof, in combination with rituximab, and in further combination with bendamustine. In one embodiment, iNHL is relapsed or refractory.

In other embodiments, provided herein is a method of treating or managing iNHL comprising administering to a patient a therapeutically effective amount of a compound provided herein (e.g., Compound 292), or a pharmaceutically acceptable derivative (e.g., salt or solvate) thereof, in combination with lenalidomide. In one embodiment, iNHL is relapsed or refractory.

In other embodiments, provided herein is a method of treating or managing CLL comprising administering to a patient a therapeutically effective amount of a compound provided herein (e.g., Compound 292), or a pharmaceutically acceptable derivative (e.g., salt or solvate) thereof, in combination with rituximab. In one embodiment, the patient is an elderly patient. In another embodiment, CLL is relapsed or refractory.

In other embodiments, provided herein is a method of treating or managing CLL comprising administering to a patient a therapeutically effective amount of a compound provided herein (e.g., Compound 292), or a pharmaceutically acceptable derivative (e.g., salt or solvate) thereof, in combination with bendamustine. In one embodiment, CLL is relapsed or refractory.

In other embodiments, provided herein is a method of treating or managing CLL comprising administering to a patient a therapeutically effective amount of a compound provided herein (e.g., Compound 292), or a pharmaceutically acceptable derivative (e.g., salt or solvate) thereof, in combination with rituximab, and in further combination with bendamustine. In one embodiment, CLL is relapsed or refractory.

In other embodiments, provided herein is a method of treating or managing CLL comprising administering to a patient a therapeutically effective amount of a compound provided herein (e.g., Compound 292), or a pharmaceutically acceptable derivative (e.g., salt or solvate) thereof, in combination with lenalidomide. In one embodiment, CLL is relapsed or refractory.

In other embodiments, provided herein is a method of treating or managing DLBCL comprising administering to a patient a therapeutically effective amount of a compound provided herein (e.g., Compound 292), or a pharmaceutically acceptable derivative (e.g., salt or solvate) thereof, in combination with rituximab. In one embodiment, the patient is an elderly patient. In another embodiment, DLBCL is relapsed or refractory.

In other embodiments, provided herein is a method of treating or managing DLBCL comprising administering to a patient a therapeutically effective amount of a compound provided herein (e.g., Compound 292), or a pharmaceutically acceptable derivative (e.g., salt or solvate) thereof, in combination with bendamustine. In one embodiment, DLBCL is relapsed or refractory.

In other embodiments, provided herein is a method of treating or managing DLBCL comprising administering to a patient a therapeutically effective amount of a compound provided herein (e.g., Compound 292), or a pharmaceutically acceptable derivative (e.g., salt or solvate) thereof, in combination with rituximab, and in further combination with bendamustine. In one embodiment, DLBCL is relapsed or refractory.

In other embodiments, provided herein is a method of treating or managing DLBCL comprising administering to a patient a therapeutically effective amount of a compound provided herein (e.g., Compound 292), or a pharmaceutically acceptable derivative (e.g., salt or solvate) thereof, in combination with R-GDP (rituximab, cyclophosphamide, vincristine and prednisone). In one embodiment, DLBCL is relapsed or refractory. In another embodiment, the treatment is done subsequent to treatment by R—CHOP.

In other embodiments, provided herein is a method of treating or managing DLBCL comprising administering to a patient a therapeutically effective amount of a compound provided herein (e.g., Compound 292), or a pharmaceutically acceptable derivative (e.g., salt or solvate) thereof, in combination with ibrutinib. In one embodiment, DLBCL is relapsed or refractory.

In other embodiments, provided herein is a method of treating or managing T-cell lymphoma (PTCL or CTCL) comprising administering to a patient a therapeutically effective amount of a compound provided herein (e.g., Compound 292), or a pharmaceutically acceptable derivative (e.g., salt or solvate) thereof, in combination with rituximab. In one embodiment, T-cell lymphoma is relapsed or refractory.

In other embodiments, provided herein is a method of treating or managing T-cell lymphoma (PTCL or CTCL) comprising administering to a patient a therapeutically effective amount of a compound provided herein (e.g., Compound 292), or a pharmaceutically acceptable derivative (e.g., salt or solvate) thereof, in combination with bendamustine. In one embodiment, T-cell lymphoma is relapsed or refractory.

In other embodiments, provided herein is a method of treating or managing T-cell lymphoma (PTCL or CTCL) comprising administering to a patient a therapeutically effective amount of a compound provided herein (e.g., Compound 292), or a pharmaceutically acceptable derivative (e.g., salt or solvate) thereof, in combination with rituximab, and in further combination with bendamustine. In one embodiment, T-cell lymphoma is relapsed or refractory.

In other embodiments, provided herein is a method of treating or managing T-cell lymphoma (PTCL or CTCL) comprising administering to a patient a therapeutically effective amount of a compound provided herein (e.g., Compound 292), or a pharmaceutically acceptable derivative (e.g., salt or solvate) thereof, in combination with romidepsin. In one embodiment, T-cell lymphoma is relapsed or refractory.

In other embodiments, provided herein is a method of treating or managing mantle cell lymphoma comprising administering to a patient a therapeutically effective amount of a compound provided herein (e.g., Compound 292), or a pharmaceutically acceptable derivative (e.g., salt or solvate) thereof, in combination with rituximab. In one embodiment, mantle cell lymphoma is relapsed or refractory.

In other embodiments, provided herein is a method of treating or managing mantle cell lymphoma comprising administering to a patient a therapeutically effective amount of a compound provided herein (e.g., Compound 292), or a pharmaceutically acceptable derivative (e.g., salt or solvate) thereof, in combination with bendamustine. In one embodiment, mantle cell lymphoma is relapsed or refractory.

In other embodiments, provided herein is a method of treating or managing mantle cell lymphoma comprising administering to a patient a therapeutically effective amount of a compound provided herein (e.g., Compound 292), or a pharmaceutically acceptable derivative (e.g., salt or solvate) thereof, in combination with rituximab, an din further combination with bendamustine. In one embodiment, mantle cell lymphoma is relapsed or refractory.

In other embodiments, provided herein is a method of treating or managing mantle cell lymphoma comprising administering to a patient a therapeutically effective amount of a compound provided herein (e.g., Compound 292), or a pharmaceutically acceptable derivative (e.g., salt or solvate) thereof, in combination with ibrutinib. In one embodiment, mantle cell lymphoma is relapsed or refractory.

Further, without being limited by a particular theory, it was found that cancer cells exhibit differential sensitivity profiles to doxorubicin and compounds provided herein. Thus, provided herein is a method of treating or managing cancer or hematological malignancy comprising administering to a patient a therapeutically effective amount of a compound provided herein (e.g., Compound 292), or a pharmaceutically acceptable derivative (e.g., salt or solvate) thereof, in combination with a doxorubicin. In one embodiment, the cancer or hematological malignancy is ALL.

In some embodiments, provided herein is a method of treating or managing cancer or hematological malignancy comprising administering to a patient a therapeutically effective amount of a compound provided herein (e.g., Compound 292), or a pharmaceutically acceptable derivative (e.g., salt or solvate) thereof, in combination with a AraC. In one embodiment, the cancer or hematological malignancy is AML.

In specific embodiments, Compound 292 or a pharmaceutically acceptable form thereof, is used in combination with one or more second agent or second therapy provided herein.

Biomarkers and Screening Methods

In one embodiment, provided herein is a biomarker (e.g., a diagnostic biomarker, a predictive biomarker, or a prognostic biomarker), for use in a method provided herein, or for use in treating or preventing a cancer or disease provided herein (e.g., a hematologic malignancy). In one embodiment, the biomarker provided herein include, but are not limited to: a target biomarker, a signaling pathway biomarker, a protein mutation biomarker, a protein expression biomarker, a gene mutation biomarker, a DNA copy number biomarker, a gene expression biomarker, a cytokine biomarker, a chemokine biomarker, a matrix metalloproteinase biomarker, or a biomarker for particular cancer cells. In one embodiment, the biomarker can be used to evaluate the prognosis, and/or sensitivity to a treatment agent, of a particular type of cancer or disease, or of a particular patient or group of patients.

In one embodiment, the biomarker provided herein is a target biomarker, such as, e.g., a biomarker to determine the protein and/or RNA expression of one or more particular PI3K isoform; e.g., a biomarker for PI3K-α expression, for PI3K-β expression, for PI3K-δ expression, or for PI3K-γ expression, or combinations thereof. In other embodiments, the target biomarker is DNA alteration of one or more particular PI3K isoforms (e.g., mutation, copy number variation, or epigenetic modification). In one embodiment, the biomarker involves IHC of a particular protein target. In one embodiment, the biomarker involves the RNA (e.g., mRNA) (e.g., ISH of mRNA) of a particular protein target. In one embodiment, the biomarker involves the DNA of a particular protein target including genetic alteration such as somatic mutation, copy number alterations such as amplification or deletion, and chromosomal translocation as well as epigenetic alteration such as methylation and histone modification. In one embodiment, the biomarker involves miRNA which regulates expression of a particular protein target.

In one embodiment, the biomarker provided herein is a signaling pathway biomarker, such as, e.g., a PTEN pathway biomarker and/or a biomarker of signaling pathway activation such as pAKT, pS6, and/or pPRAS40 (e.g., an IHC biomarker, a DNA alteration biomarker, a DNA deletion biomarker, a DNA copy number biomarker, or a DNA mutation biomarker). In one embodiment, the biomarker provided herein is a mutation biomarker, such as, a protein mutation biomarker or a gene mutation biomarker, to assess the mutation of one or more targets, such as, e.g., CXCR4, IGH7, KRAS, NRAS, A20, CARD11, CD79B, TP53, CARD11, MYD88, GNA13, MEF2B, TNFRSF14, MLL2, BTG1, EZH2, NOTCH1, JAK1, JAK2, PTEN, FBW7, PHF6, IDH1, IDH2, TET2, FLT3, KIT, NPM1, CEBPA, DNMT3A, BAALC, RUNX1, ASXL1, IRF8, POU2F2, WIF1, ARID1A, MEF2B, TNFAIP3, PIK3R1, MTOR, PIK3CA, PI3Kδ, and/or PI3Kγ. In one embodiment, the biomarker provided herein is an expression biomarker, such as, a protein expression biomarker, a gene expression biomarker, to assess the expression of one or more targets, or the upregulation or downregulation of a pathway, such as, e.g., pERK IHC biomarker or pERK expression biomarker, for example, to assess RAS or PI3K pathway activation.

In one embodiment, the biomarker provided herein is a cytokine biomarker, including, but not limited to, IL-2, IL-4, IL-7, IL-9, IL-10, IL-12 (p40), IL-15, IL-16, IL-21, TNFα and TGFα. In one embodiment, the biomarker provided herein is a chemokine biomarker, including, but not limited to, CCL1, CXCL10, CXCL12, CXCL13, CCL2, and CCL3. In one embodiment, the biomarker provided herein is a serum cytokine biomarker. In one embodiment, the biomarker provided herein is a serum chemokine biomarker. In one embodiment, the biomarker provided herein relates to gene expression patterns of one or more cytokines, cytokine receptors, chemokines, and/or chemokine receptors. In one embodiment, the biomarker provided herein is CXCL13, CCL4, CCL17, CCL22, GM-CSF or TNF-α, or a combination thereof. In another embodiment, the biomarker provided herein is a matrix metalloproteinases. In one embodiment, the matrix metalloproteinase is MMP-9. In another embodiment, the matrix metalloproteinase is MMP-12.

In one embodiment, the biomarkers provided herein can be used to identify, diagnose, predict efficacy, predict long term clinical outcome, predict prognosis, and/or select patients for a treatment described herein. In one embodiment, the biomarkers provided herein can be used for subsets of patients with different prognostic factors, such as, e.g., Rai stages, β2-microglobulin, diverse cytogenetics including trisomy 12, del 13q, 17p, PTEN, and 11q mutations or deletions, ZAP-70 status, CD38 status, CD49d status, and/or IgHV gene mutations. In one embodiment, the biomarker is 11q deletion. In another embodiment, the biomarker is PTEN deletion and/or decreased PTEN expression. In another embodiment, the biomarker is 17p deletion. In some embodiments, a method of determining a subject's susceptibility to treatment comprising detecting the presence of a biomarker in a sample from the subject is disclosed. In some embodiments, the presence of one or more of Rai stages, β2-microglobulin, diverse cytogenetics including trisomy 12, del 13q, 17p, PTEN, and 11q mutations or deletions, ZAP-70 status, CD38 status, CD49d status, and/or IgHV gene mutations indicates that the subject has an increased susceptibility to treatment with a PI3K inhibitor. In some embodiments, the presence of 11 q deletion indicates that the subject has an increased susceptibility to treatment with a PI3K inhibitor. In some embodiments, the presence of 17p deletion indicates that the subject has an increased susceptibility to treatment with a PI3K inhibitor. In some embodiments, the presence of PTEN deletion and/or decreased PTEN expression indicates that the subject has an increased susceptibility to treatment with a PI3K inhibitor. In some embodiments, the presence of pS6 indicates that the subject has a decreased susceptibility to treatment with a PI3K inhibitor. In some embodiments, the method further comprises administering a PI3K inhibitor to a subject identified as having an increased susceptibility to treatment. In some embodiments, the PI3K inhibitor is compound 292. In some embodiments, the method further comprises using the information to stratify subjects have increased likelihood of response to a treatment from those with a decreased likelihood of response to a treatment.

In one embodiment, a method for predicting the likelihood that a subject will respond therapeutically to a method of treating cancer is disclosed comprising administering a PI3K inhibitor (e.g., compound 292), said method comprises: (a) measuring the expression level of a biomarker in a biological cancer sample of said subject; (b) determining the presence of or level of said biomarker in said cancer sample relative to a predetermined level of said biomarker, (c) classifying said subject as having an increased or decreased likelihood of responding therapeutically to said method of treating cancer if said patient has a biomarker, and (d) administering a PI3K inhibitor to said patient classified as having an increased likelihood of responding. For example, detection of one of more of Rai stages, β2-microglobulin, diverse cytogenetics including trisomy 12, del 13q, 17p, PTEN, and 11q mutations or deletions, ZAP-70 status, CD38 status, CD49d status, and/or IgHV gene mutations can be classified as having an increased likelihood of response. For example, detection of one of more of pS6 can be classified as having a decreased likelihood of response. In one embodiment, detection of 11q deletion can be classified as having an increased likelihood of response. In another embodiment, detection of 17p deletion can be classified as having an increased likelihood of response. In another embodiment, detection of PTEN deletion and/or decreased PTEN expression can be classified as having an increased likelihood of response.

In some embodiments, once the treatment begins with patients with an increased likelihood of response (e.g., patients identified based on the detection of), the actual efficacy of the treatment can also be monitored by assessing the modulation of a second set of biomarkers such as pAKT, c-MYC, NOTCH1, CXCL13, CCL3, CCL4, IL-10, TNFα, IL-12p40, IL-16, MMP-9, CCL17, CCL22, CCL1, CXCL10, MMP-12, and combinations thereof.

In one specific embodiment, provided herein is a method of monitoring the efficacy of a compound provided herein (e.g., Compound 292) in a cancer patient having 11q deletion comprising: (a) obtaining a first biological sample from the patient; (b) determining the level of a biomarker in the first biological sample, wherein the biomarker is pAKT, c-MYC, NOTCH1, CXCL13, CCL3, CCL4, IL-10, TNFα, IL-12p40, IL-16, MMP-9, CCL17, CCL22, CCL1, CXCL10, MMP-12, or a combination thereof; (c) administering the treatment compound to the patient; (d) thereafter obtaining a second biological sample from the patient; (e) determining the level of the biomarker in the second biological sample; and (f) comparing the levels of the biomarker in the first and second biological samples; wherein the patient is responsive to the treatment if the level of the biomarker in the second biological sample of the patient is decreased as compared to the level of the biomarker in the first biological sample of the patient. In one embodiment, the cancer is a hematological cancer. In one embodiment, the cancer is a lymphoma or a leukemia. In another embodiment, the cancer is T cell lymphoma. In another embodiment, the cancer is NHL. In another embodiment, the cancer is iNHL. In another embodiment, the cancer is CTCL. In another embodiment, the cancer is CLL. In another embodiment, the cancer is SLL.

In another specific embodiment, provided herein is a method of monitoring the efficacy of a compound provided herein (e.g., Compound 292) in a cancer patient having 17p deletion comprising: (a) obtaining a first biological sample from the patient; (b) determining the level of a biomarker in the first biological sample, wherein the biomarker is pAKT, c-MYC, NOTCH1, CXCL13, CCL3, CCL4, IL-10, TNFα, IL-12p40, IL-16, MMP-9, CCL17, CCL22, CCL1, CXCL10, MMP-12, or a combination thereof; (c) administering the treatment compound to the patient; (d) thereafter obtaining a second biological sample from the patient; (e) determining the level of the biomarker in the second biological sample; and (f) comparing the levels of the biomarker in the first and second biological samples; wherein the patient is responsive to the treatment if the level of the biomarker in the second biological sample of the patient is decreased as compared to the level of the biomarker in the first biological sample of the patient. In one embodiment, the cancer is a hematological cancer. In one embodiment, the cancer is a lymphoma or a leukemia. In another embodiment, the cancer is T cell lymphoma. In another embodiment, the cancer is NHL. In another embodiment, the cancer is iNHL. In another embodiment, the cancer is CTCL. In another embodiment, the cancer is CLL. In another embodiment, the cancer is SLL.

In another specific embodiment, provided herein is a method of monitoring the efficacy of a compound provided herein (e.g., Compound 292) in a cancer patient having PTEN deletion and/or decreased PTEN expression comprising: (a) obtaining a first biological sample from the patient; (b) determining the level of a biomarker in the first biological sample, wherein the biomarker is pAKT, c-MYC, NOTCH1, CXCL13, CCL3, CCL4, IL-10, TNFα, IL-12p40, IL-16, MMP-9, CCL17, CCL22, CCL1, CXCL10, MMP-12, or a combination thereof; (c) administering the treatment compound to the patient; (d) thereafter obtaining a second biological sample from the patient; (e) determining the level of the biomarker in the second biological sample; and (f) comparing the levels of the biomarker in the first and second biological samples; wherein the patient is responsive to the treatment if the level of the biomarker in the second biological sample of the patient is decreased as compared to the level of the biomarker in the first biological sample of the patient. In one embodiment, the cancer is a hematological cancer. In one embodiment, the cancer is a lymphoma or a leukemia. In another embodiment, the cancer is T cell lymphoma. In another embodiment, the cancer is NHL. In another embodiment, the cancer is iNHL. In another embodiment, the cancer is CTCL. In another embodiment, the cancer is CLL. In another embodiment, the cancer is SLL.

In another specific embodiment, provided herein is a method of monitoring the efficacy of a compound provided herein (e.g., Compound 292) in a cancer patient having 13q deletion comprising: (a) obtaining a first biological sample from the patient; (b) determining the level of a biomarker in the first biological sample, wherein the biomarker is pAKT, c-MYC, NOTCH1, CXCL13, CCL3, CCL4, IL-10, TNFα, IL-12p40, IL-16, MMP-9, CCL17, CCL22, CCL1, CXCL10, MMP-12, or a combination thereof; (c) administering the treatment compound to the patient; (d) thereafter obtaining a second biological sample from the patient; (e) determining the level of the biomarker in the second biological sample; and (f) comparing the levels of the biomarker in the first and second biological samples; wherein the patient is responsive to the treatment if the level of the biomarker in the second biological sample of the patient is decreased as compared to the level of the biomarker in the first biological sample of the patient. In one embodiment, the cancer is a hematological cancer. In one embodiment, the cancer is a lymphoma or a leukemia. In another embodiment, the cancer is T cell lymphoma. In another embodiment, the cancer is NHL. In another embodiment, the cancer is iNHL. In another embodiment, the cancer is CTCL. In another embodiment, the cancer is CLL. In another embodiment, the cancer is SLL.

In another specific embodiment, provided herein is a method of monitoring the efficacy of a compound provided herein (e.g., Compound 292) in a cancer patient having trisomy 12 deletion comprising: (a) obtaining a first biological sample from the patient; (b) determining the level of a biomarker in the first biological sample, wherein the biomarker is pAKT, c-MYC, NOTCH1, CXCL13, CCL3, CCL4, IL-10, TNFα, IL-12p40, IL-16, MMP-9, CCL17, CCL22, CCL1, CXCL10, MMP-12, or a combination thereof; (c) administering the treatment compound to the patient; (d) thereafter obtaining a second biological sample from the patient; (e) determining the level of the biomarker in the second biological sample; and (f) comparing the levels of the biomarker in the first and second biological samples; wherein the patient is responsive to the treatment if the level of the biomarker in the second biological sample of the patient is decreased as compared to the level of the biomarker in the first biological sample of the patient. In one embodiment, the cancer is a hematological cancer. In one embodiment, the cancer is a lymphoma or a leukemia. In another embodiment, the cancer is T cell lymphoma. In another embodiment, the cancer is NHL. In another embodiment, the cancer is iNHL. In another embodiment, the cancer is CTCL. In another embodiment, the cancer is CLL. In another embodiment, the cancer is SLL.

In another specific embodiment, provided herein is a method of monitoring the efficacy of a compound provided herein (e.g., Compound 292) in a cancer patient having IgHV gene mutation comprising: (a) obtaining a first biological sample from the patient; (b) determining the level of a biomarker in the first biological sample, wherein the biomarker is pAKT, c-MYC, NOTCH1, CXCL13, CCL3, CCL4, IL-10, TNFα, IL-12p40, IL-16, MMP-9, CCL17, CCL22, CCL1, CXCL10, MMP-12, or a combination thereof; (c) administering the treatment compound to the patient; (d) thereafter obtaining a second biological sample from the patient; (e) determining the level of the biomarker in the second biological sample; and (f) comparing the levels of the biomarker in the first and second biological samples; wherein the patient is responsive to the treatment if the level of the biomarker in the second biological sample of the patient is decreased as compared to the level of the biomarker in the first biological sample of the patient. In one embodiment, the cancer is a hematological cancer. In one embodiment, the cancer is a lymphoma or a leukemia. In another embodiment, the cancer is T cell lymphoma. In another embodiment, the cancer is NHL. In another embodiment, the cancer is iNHL. In another embodiment, the cancer is CTCL. In another embodiment, the cancer is CLL. In another embodiment, the cancer is SLL.

In one embodiment, the biomarker provided herein is a biomarker for cancer cells (e.g., a particular cancer cell line, a particular cancer cell type, a particular cell cycle profile).

In exemplary embodiments, the biomarker provided herein relates to gene expression profiling of a patient or group of patients, e.g., as a predictive biomarker for PI3Kδ and/or PI3Kγ pathway activation, or as a predictive biomarker for response to a treatment described herein. In exemplary embodiments, the biomarker provided herein relates to a gene expression classifier, e.g., as a predictive biomarker for PI3Kδ and/or PI3Kγ expression or activation (e.g., differential expression or activation in the ABC, GCB, oxidative phosphorylation (Ox Phos), B-cell receptor/proliferation (BCR), or host response (HR) subtypes of DLBCL).

In one embodiment, provided herein are methods relating to the use of mRNAs or proteins as biomarkers to ascertain the effectiveness of a therapy provided herein. In one embodiment, mRNA or protein levels can be used to determine whether a particular agent is likely to be successful in the treatment of a particular cancer or hematologic malignancy.

As used herein, and unless otherwise specified, a biological marker or biomarker is a substance whose detection indicates a particular biological state, such as, for example, the presence of cancer or hematologic malignancy. In some embodiments, biomarkers can either be determined individually, or several biomarkers can be measured simultaneously.

In some embodiments, a biomarker indicates a change in the level of mRNA expression that can correlate with the risk or progression of a disease, or with the susceptibility of the disease to a given treatment. In some embodiments, the biomarker is a nucleic acid, such as a mRNA, miRNA or cDNA.

In additional embodiments, a biomarker indicates a change in the level of polypeptide or protein expression that can correlate with the risk, susceptibility to treatment, or progression of a disease. In some embodiments, the biomarker can be a polypeptide or protein, or a fragment thereof. The relative level of specific proteins can be determined by methods known in the art. For example, antibody based methods, such as an immunoblot, enzyme-linked immunosorbent assay (ELISA), or other methods can be used.

In one embodiment, the methods provided herein encompass methods for screening or identifying patients having a cancer or hematologic malignancy, for treatment with a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof). In one embodiment, the method comprises obtaining a biological sample from a subject, and measuring the level of a biomarker in the biological sample, where an abnormal baseline level (e.g., higher or lower than the level in a control group) of the biomarker indicates a higher likelihood that the subject has a cancer or hematologic malignancy that can be treated with a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof). In one embodiment, the method optionally comprises isolating or purifying mRNA from the biological sample, amplifying the mRNA transcripts (e.g., by RT-PCR). In one embodiment, the level of a biomarker is the level of an mRNA or a protein.

In some embodiments, provided herein are methods of predicting the sensitivity to treatment with a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) in a patient having a cancer or hematologic malignancy. The method comprises obtaining a biological sample from the patient, and measuring the level of a biomarker in the biological sample, where an abnormal baseline level (e.g., higher or lower than the level in a control group) of the biomarker indicates a higher likelihood that the patient will be sensitive to treatment with a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof). In one embodiment, the method optionally comprises isolating or purifying mRNA from the biological sample, amplifying the mRNA transcripts (e.g., by RT-PCR). In one embodiment, the level of a biomarker is the level of an mRNA or a protein.

In one embodiment, provided herein is a method for treating or managing cancer or hematologic malignancy in a patient, comprising: (i) obtaining a biological sample from the patient and measuring the level of a biomarker in the biological sample; and (ii) administering to the patient with an abnormal baseline level of at least one biomarker (e.g., higher or lower than the level in a control group) a therapeutically effective amount of a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof). In one embodiment, step (i) optionally comprises isolating or purifying mRNA from the biological sample, amplifying the mRNA transcripts (e.g., by RT-PCR). In one embodiment, the level of a biomarker is the level of an mRNA or a protein.

In another embodiment, provided herein is a method of monitoring response to treatment with a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) in a patient having a cancer or hematologic malignancy. In one embodiment, the method comprises obtaining a biological sample from the patient, measuring the level of a biomarker in the biological sample, administering a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) to the patient, thereafter obtaining a second biological sample from the patient, measuring the level of the biomarker in the second biological sample, and comparing the two levels of the biomarker, where an altered (e.g., increased or decreased) level of the biomarker after treatment indicates the likelihood of an effective tumor response. In one embodiment, a decreased level of biomarker after treatment indicates the likelihood of effective tumor response. In another embodiment, an increased level of biomarker after treatment indicates the likelihood of effective tumor response. The level of biomarker can be, for example, the level of an mRNA or a protein. The expression in the treated sample can increase, for example, by about 1.5×, 2.0×, 3×, 5×, or more.

In yet another embodiment, a method for monitoring patient compliance with a drug treatment protocol is provided. In one embodiment, the method comprises obtaining a biological sample from the patient, measuring the level of at least one biomarker in the sample, and determining if the level is increased or decreased in the patient sample compared to the level in a control untreated sample, wherein an increased or decreased level indicates patient compliance with the drug treatment protocol. In one embodiment, the level of at least one biomarker is increased. The biomarker level monitored can be, for example, mRNA level or protein level. The expression in the treated sample can increase, for example, by about 1.5×, 2.0×, 3×, 5×, or more.

A gene expression signature characteristic of a particular type of cancer or hematologic malignancy can also be evaluated. The gene expression signature can include analysis of the level (e.g., expression) of one or more genes involved in the cancer or hematologic malignancy.

A gene methylation signature characteristic of a particular type of cancer or hematologic malignancy can also be evaluated. The gene methylation signature can include analysis of the level (e.g., expression) of one or more genes involved in the cancer or hematologic malignancy.

Any combination of the biomarkers provided herein can be used to evaluate a subject.

In one embodiment, the biomarker used in the methods provided herein is the expression level of PI3K-δ. In one embodiment, the biomarker used in the methods provided herein is the expression level of PI3K-γ. In one embodiment, the biomarker used in the methods provided herein is the expression level of PI3K-β. In one embodiment, the biomarker used in the methods provided herein is the expression level of PI3K-α.

In one embodiment, the biomarker used in the methods provided herein is the expression level of mRNA of PI3K-δ. In one embodiment, the biomarker used in the methods provided herein is the expression level of mRNA of PI3K-γ. In one embodiment, the biomarker used in the methods provided herein is the expression level of mRNA of PI3K-β. In one embodiment, the biomarker used in the methods provided herein is the expression level of mRNA of PI3K-α. In some embodiments, the expression level of mRNA for a PI3K isoform is determined from a whole blood sample from the subject. In one embodiment, the expression level of mRNA for a PI3K isoform is determined by techniques known in the art (e.g., RNA expression).

In one embodiment, the biomarker used in the methods provided herein is the expression level of PI3K-δ protein. In one embodiment, the biomarker used in the methods provided herein is the expression level of PI3K-γ protein. In one embodiment, the biomarker used in the methods provided herein is the expression level of PI3K-β protein. In one embodiment, the biomarker used in the methods provided herein is the expression level of PI3K-α protein.

In one embodiment, the biomarker used in the methods provided herein is high level of expression, increased DNA amplification, and/or detection of gene mutation of PI3K-δ. In one embodiment, the biomarker used in the methods provided herein is high level of expression, increased DNA amplification, and/or detection of gene mutation of PI3K-γ. In one embodiment, the biomarker used in the methods provided herein is high level of expression, increased DNA amplification, and/or detection of gene mutation of PI3K-β. In one embodiment, the biomarker used in the methods provided herein is high level of expression, increased DNA amplification, and/or detection of gene mutation of PI3K-α.

In certain embodiments, the biomarker used in the methods provided herein is the detection of the normal level of expression of a PI3K isoform in certain cell types. In one embodiment, the biomarker used in the methods provided herein is the detection of the normal level of expression of PI3K-γ and/or PI3K-δ in normal immune cells.

In one embodiment, the biomarker used in the methods provided herein is a germline SNP that has been previously linked to susceptibility to cancer or hematologic malignancy.

In one embodiment, the biomarker used in the methods provided herein is a germline SNP that has been previously linked to pathways of drug metabolism or transport (e.g., CYP3A family and/or other drug metabolizing enzymes that have been associated with metabolism of a compound provided herein).

In specific embodiments, provided herein is a method of identifying a subject who is likely to be responsive to a treatment of a cancer or disease, e.g., a hematologic malignancy, with a treatment compound (e.g., a compound provided herein), comprising: (a) determining the level of a biomarker in a biological sample from the subject, wherein the biomarker is described herein (e.g., a biomarker for an isoform of PI3K (e.g., PI3K-δ, PI3K-γ, PI3K-α, or PI3K-β, or a combination thereof)); and (b) comparing the level of the biomarker in the biological sample to a reference level of the biomarker; wherein the subject is likely to be responsive to the treatment if the level of the biomarker in the biological sample from the subject is altered (e.g., high or low) as compared to the reference level of the biomarker.

In some embodiments, provided herein is a method for predicting the likelihood that a subject will respond therapeutically to a method of treating cancer comprising administering a PI3K inhibitor (e.g., compound 292), said method comprises: (a) administering the PI3K inhibitor, (b) measuring the expression level of a biomarker in a biological cancer sample of said subject 8 days following administering of said PI3K inhibitor; (c) determining the level of said biomarker in said cancer sample relative to a predetermined level of said biomarker, (d) classifying said subject as having an increased likelihood of responding therapeutically to said method of treating cancer if said patient has a decreased level of said biomarker following administration of said PI3K inhibitor, and (e) administering a PI3K inhibitor to said patient classified as having an increased likelihood of responding. For example, detection of decrease in one of more of CXCL13, CCL3, CCL4, IL-10, TNFα, IL-12p40, MMP-9, CCL17, CCL22, and CCL1 following treatment can be classified as having an increased likelihood of response to treatment in a subject with CLL. For example, detection of decrease in one of more of CXCL13, MMP-9, TNF□, CCL22, CCL1, CCL17, and MMP-12 following treatment can be classified as having an increased likelihood of response to treatment in a subject with iNHL.

In specific embodiments, provided herein is a method of identifying a subject who is likely to be responsive to a treatment of a cancer or disease, e.g., a hematologic malignancy, with a treatment compound (e.g., a compound provided herein), comprising: (a) determining the level of a biomarker in a biological sample from the subject, wherein the biomarker is described herein (e.g., a biomarker for an isoform of PI3K (e.g., PI3K-δ, PI3K-γ, PI3K-α, or PI3K-β, or a combination thereof)); (b) determining the level of the biomarker in a control sample; and (c) comparing the level of the biomarker in the biological sample from the subject to the level of the biomarker in the control sample; wherein the subject is likely to be responsive to the treatment if the level of the biomarker in the biological sample from the subject is altered (e.g., high or low) as compared to the level of the biomarker in the control sample.

In specific embodiments, provided herein is a method of identifying a subject who is likely to be responsive to a treatment of a cancer or disease, e.g., a hematologic malignancy, with a treatment compound (e.g., a compound provided herein), comprising: (a) obtaining a biological sample from the subject; (b) determining the level of a biomarker in the biological sample, wherein the biomarker is described herein (e.g., a biomarker for an isoform of PI3K (e.g., PI3K-δ, PI3K-γ, PI3K-α, or PI3K-β, or a combination thereof)); and (c) comparing the level of the biomarker in the biological sample to a reference level of the biomarker; wherein the subject is likely to be responsive to the treatment if the level of the biomarker in the biological sample from the subject is altered (e.g., high or low) as compared to the reference level of the biomarker.

In specific embodiments, provided herein is a method of identifying a subject who is likely to be responsive to a treatment of a cancer or disease, e.g., a hematologic malignancy, with a treatment compound (e.g., a compound provided herein), comprising: (a) obtaining a biological sample from the subject; (b) determining the level of a biomarker in the biological sample, wherein the biomarker is described herein (e.g., a biomarker for an isoform of PI3K (e.g., PI3K-δ, PI3K-γ, PI3K-α, or PI3K-β, or a combination thereof)); (c) determining the level of the biomarker in a control sample; and (d) comparing the level of the biomarker in the biological sample from the subject to the level of the biomarker in the control sample; wherein the subject is likely to be responsive to the treatment if the level of the biomarker in the biological sample from the subject is altered (e.g., high or low) as compared to the level of the biomarker in the control sample.

In specific embodiments, provided herein is a method of predicting the responsiveness of a subject to a treatment of a cancer or disease, e.g., a hematologic malignancy, with a treatment compound (e.g., a compound provided herein), comprising: (a) determining the level of a biomarker in a biological sample from the subject, wherein the biomarker is described herein (e.g., a biomarker for an isoform of PI3K (e.g., PI3K-δ, PI3K-γ, PI3K-α, or PI3K-β, or a combination thereof)); and (b) comparing the level of the biomarker in the biological sample to a reference level of the biomarker; wherein the difference between the level of the biomarker in the biological sample from the subject and the reference level of the biomarker (e.g., higher or lower) correlates with the responsiveness of the subject to the treatment.

In specific embodiments, provided herein is a method of predicting the responsiveness of a subject to a treatment of a cancer or disease, e.g., a hematologic malignancy, with a treatment compound (e.g., a compound provided herein), comprising: (a) determining the level of a biomarker in a biological sample from the subject, wherein the biomarker is described herein (e.g., a biomarker for an isoform of PI3K (e.g., PI3K-δ, PI3K-γ, PI3K-α, or PI3K-β, or a combination thereof)); (b) determining the level of the biomarker in a control sample; and (c) comparing the level of the biomarker in the biological sample from the subject to the level of the biomarker in the control sample; wherein the difference between the level of the biomarker in the biological sample from the subject and the level of the biomarker in the control sample (e.g., higher or lower) correlates with the responsiveness of the subject to the treatment.

In specific embodiments, provided herein is a method of predicting the responsiveness of a subject to a treatment of a cancer or disease, e.g., a hematologic malignancy, with a treatment compound (e.g., a compound provided herein), comprising: (a) obtaining a biological sample from the subject; (b) determining the level of a biomarker in the biological sample, wherein the biomarker is described herein (e.g., a biomarker for an isoform of PI3K (e.g., PI3K-δ, PI3K-γ, PI3K-α, or PI3K-β, or a combination thereof)); and (c) comparing the level of the biomarker in the biological sample to a reference level of the biomarker; wherein the difference between the level of the biomarker in the biological sample from the subject and the reference level of the biomarker (e.g., higher or lower) correlates with the responsiveness of the subject to the treatment.

In specific embodiments, provided herein is a method of predicting the responsiveness of a subject to a treatment of a cancer or disease, e.g., a hematologic malignancy, with a treatment compound (e.g., a compound provided herein), comprising: (a) obtaining a biological sample from the subject; (b) determining the level of a biomarker in the biological sample, wherein the biomarker is described herein (e.g., a biomarker for an isoform of PI3K (e.g., PI3K-δ, PI3K-γ, PI3K-α, or PI3K-β, or a combination thereof)); (c) determining the level of the biomarker in a control sample; and (d) comparing the level of the biomarker in the biological sample from the subject to the level of the biomarker in the control sample; wherein the difference between the level of the biomarker in the biological sample from the subject and the level of the biomarker in the control sample (e.g., higher or lower) correlates with the responsiveness of the subject to the treatment.

In specific embodiments, provided herein is a method of monitoring the efficacy of a treatment of a cancer or disease, e.g., a hematologic malignancy, in a subject treated with a treatment compound (e.g., a compound provided herein), comprising: (a) obtaining a first biological sample from the subject; (b) determining the level of a biomarker in the first biological sample, wherein the biomarker is described herein (e.g., a biomarker for an isoform of PI3K (e.g., PI3K-δ, PI3K-γ, PI3K-α, or PI3K-β, or a combination thereof)); (c) administering the treatment compound to the subject; (d) thereafter obtaining a second biological sample from the subject; (e) determining the level of the biomarker in the second biological sample; and (f) comparing the levels of the biomarker in the first and second biological samples; wherein the subject is responsive to the treatment if the level of the biomarker in the second biological sample of the subject is altered (e.g., high or low) as compared to the level of the biomarker in the first biological sample of the subject.

In specific embodiments, provided herein is a method of monitoring the compliance of a subject with a treatment of a cancer or disease, e.g., a hematologic malignancy, with a treatment compound (e.g., a compound provided herein), comprising: (a) obtaining a biological sample from the subject; (b) determining the level of a biomarker in the biological sample, wherein the biomarker is described herein (e.g., a biomarker for an isoform of PI3K (e.g., PI3K-δ, PI3K-γ, PI3K-α, or PI3K-β, or a combination thereof)); and (c) comparing the level of the biomarker with the level of the biomarker in a control sample from the subject; wherein the change in the level of the biomarker in the biological sample in comparison with the level of the biomarker in the control sample (e.g., high or low) indicates the compliance of the subject with the treatment.

In one embodiment, for the methods provided herein, a change in the level of a biomarker provided herein over a period of time is indicative of a targeted effect, such as, but not limited to, the likelihood of a subject to be responsive to a treatment, the responsiveness of a subject to a treatment, the efficacy of a treatment, and the compliance of a subject with a treatment, of a cancer or disease, e.g., a hematologic malignancy. In one embodiment, the change in the level of a biomarker is a decrease in the level of the biomarker. In one embodiment, the change in the level of a biomarker is a decrease in the serum concentration of the biomarker. In one embodiment, the change in the level of a biomarker is a decrease in the serum concentration of a cytokine/chemokine biomarker. In one embodiment, the cytokine/chemokine biomarker is CXCL13, CCL4, CCL17, CCL22, or TNF-α, or a combination thereof. In one embodiment, the change in the level of a biomarker is a decrease in the serum concentration of a matrix metalloproteinases. In one embodiment, the matrix metalloproteinase is MMP-9.

In one embodiment, the period of time is 180 days, 90 days, 50 days, 40 days, 35 days, 30 days, 28 days, 24 days, 20 days, 16 days, 14 days, 12 days, 8 days, 4 days, 3 days, 2 days, 1 day, 18 hours, 12 hours, 6 hours, 3 hours, or 1 hour, after a starting time point (e.g., administration of a compound provided herein to a subject). In one embodiment, the period of time is 28 days after administration of a compound provided herein (e.g., Compound 292) to a subject. In another embodiment, the period of time is 14 days after administration of a compound provided herein (e.g., Compound 292) to a subject. In yet another embodiment, the period of time is 8 days after administration of a compound provided herein (e.g., Compound 292) to a subject.

In one embodiment, for the methods provided herein, a decrease in the serum concentration of CXCL13, CCL4, CCL17, CCL22, TNF-α, or MMP-9, or a combination thereof, over 28 days after the administration of a compound provided herein (e.g., Compound 292) to a subject is indicative of a targeted effect, such as, but not limited to, the likelihood of a subject to be responsive to a treatment, the responsiveness of a subject to a treatment, the efficacy of a treatment, and the compliance of a subject with a treatment, of a cancer or disease, e.g., a hematologic malignancy. In another embodiment, for the methods provided herein, a decrease in the serum concentration of CXCL13, CCL4, CCL17, CCL22, TNF-α, or MMP-9, or a combination thereof, over 8 days after the administration of a compound provided herein (e.g., Compound 292) to a subject is indicative of a targeted effect, such as, but not limited to, the likelihood of a subject to be responsive to a treatment, the responsiveness of a subject to a treatment, the efficacy of a treatment, and the compliance of a subject with a treatment, of a cancer or disease, e.g., a hematologic malignancy.

In one embodiments, the cancer or disease is a leukemia or lymphoma. In another embodiment, the cancer or disease is a B-cell lymphoma or T-cell lymphoma. In another embodiment, the cancer or disease is a B-cell malignancy including, but not limited to, precursor B cell neoplasm (e.g., precursor B-lymphoblastic leukemia/lymphoma, and precursor B-cell acute lymphoblastic leukemia), and mature (peripheral) B-cell neoplasms (e.g., B-cell chronic lymphocytic leukemia/small lymphocytic lymphoma (SLL/CLL), B-cell prolymphocytic leukemia, Lymphoplasmacytic lymphoma (LPL), splenic marginal zone B-cell lymphoma (with/without villous lymphocytes), hairy cell leukemia, plasma cell myeloma/plasmacytoma, extranodal marginal zone B-cell lymphoma of MALT type (MALT), nodal marginal zone B-cell lymphoma (with/without monocytoid B-cells) (MZL), follicular lymphoma (FL), mantle cell lymphoma (MCL), diffuse large B-cell lymphoma (DLBCL), or Burkitt lymphoma/Burkitt cell leukemia (BL)). In another embodiment, the cancer or disease is a T-cell/NK-cell neoplasms including, but not limited to, precursor T-cell neoplasm (e.g., precursor T-lymphoblastic lymphoma/leukemia, and precursor T-cell acute lymphoblastic leukemia), and mature (peripheral) T-cell neoplasms (e.g., T-cell prolymphocytic leukemia, T-cell large granular lymphocytic leukemia, NK-cell lymphoma/leukemia (NKL), adult T-cell lymphoma/leukemia (HTLV-1 positive), extranodal NK/T-cell lymphoma nasal type, enteropathy-type T-cell lymphoma, hepatosplenic gamma-delta T-cell lymphoma, subcutaneous panniculitis-like T-cell lymphoma, mycosis fungoides/Sezary syndrome, anaplastic large-cell lymphoma T/null cell primary cutaneous type, peripheral T-cell lymphoma not otherwise characterized (PTL), angioimmunoblastic T-cell lymphoma, or anaplastic large-cell lymphoma T/null cell primary systemic type)). In another embodiment, the cancer or disease is non-Hodgkin lymphoma (NHL) including, but not limited to, B-cell NHL (e.g., Burkitt lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma, or mantle cell lymphoma) and T-cell NHL (e.g., mycosis fungoides, anaplastic large cell lymphoma, or precursor T-lymphoblastic lymphoma). An NHL can also be divided into aggressive (fast-growing) and indolent (slow-growing) (iNHL) types.

In one embodiment, the cancer or disease is iNHL, MCL, or FL. In another embodiment, the cancer or disease is a T-cell lymphoma. In yet another embodiment, the cancer or disease is CLL or SLL.

In one embodiment, the cancer or disease is CLL or SLL, and the biomarker is CCL1, IL-10, CXCL13, CCL3, CCL4, CCL17, CCL22, TNFα, IL-12 (p40), CXCL10, MMP-9, or a combination thereof. In one embodiment, the cancer or disease is CLL or SLL, and the biomarker is CCL1, IL-10, CXCL13, CCL3, CCL4, CCL17, CCL22, TNFα, IL-12 (p40), CXCL10, MMP-9, or a combination thereof, further in combination with other known biomarkers for CLL such as pAKT and Ki-67.

In specific embodiments, provided herein is a method of identifying a subject who is likely to be responsive to a treatment of CLL or SLL, with a treatment compound (e.g., a compound provided herein), comprising: (a) determining the level of a biomarker in a biological sample from the subject, wherein the biomarker is CCL1, IL-10, CXCL13, CCL3, CCL4, CCL17, CCL22, TNFα, IL-12 (p40), CXCL10, MMP-9, or a combination thereof; and (b) comparing the level of the biomarker in the biological sample to a reference or control level of the biomarker; wherein the subject is likely to be responsive to the treatment if the level of the biomarker in the biological sample from the subject is decreased as compared to the reference or control level of the biomarker.

In specific embodiments, provided herein is a method of predicting the responsiveness of a subject to a treatment of CLL or SLL with a treatment compound comprising: (a) determining the level of a biomarker in a biological sample from the subject, wherein the biomarker is CCL1, IL-10, CXCL13, CCL3, CCL4, CCL17, CCL22, TNFα, IL-12 (p40), CXCL10, MMP-9, or a combination thereof; and (b) comparing the level of the biomarker in the biological sample to a reference or control level of the biomarker; wherein the difference between the level of the biomarker in the biological sample from the subject and the reference or control level of the biomarker correlates with the responsiveness of the subject to the treatment.

In specific embodiments, provided herein is a method of monitoring the efficacy of a treatment of CLL or SLL in a subject treated with a treatment compound (e.g., a compound provided herein), comprising: (a) obtaining a first biological sample from the subject; (b) determining the level of a biomarker in the first biological sample, wherein the biomarker is CCL1, IL-10, CXCL13, CCL3, CCL4, CCL17, CCL22, TNFα, IL-12 (p40), CXCL10, MMP-9, or a combination thereof; (c) administering the treatment compound to the subject; (d) thereafter obtaining a second biological sample from the subject; (e) determining the level of the biomarker in the second biological sample; and (f) comparing the levels of the biomarker in the first and second biological samples; wherein the subject is responsive to the treatment if the level of the biomarker in the second biological sample of the subject is decreased as compared to the level of the biomarker in the first biological sample of the subject.

In specific embodiments, provided herein is a method of monitoring the compliance of a subject with a treatment of CLL or SLL with a treatment compound (e.g., a compound provided herein), comprising: (a) obtaining a biological sample from the subject; (b) determining the level of a biomarker in the biological sample, wherein the biomarker is CCL1, IL-10, CXCL13, CCL3, CCL4, CCL17, CCL22, TNFα, IL-12 (p40), CXCL10, MMP-9, or a combination thereof, and (c) comparing the level of the biomarker with the level of the biomarker in a control sample from the subject; wherein the decrease in the level of the biomarker in the biological sample in comparison with the level of the biomarker in the control sample indicates the compliance of the subject with the treatment.

In another embodiment, the cancer or disease is lymphoma, and the biomarker is CXCL13, CCL17, MMP-9, or a combination thereof.

In specific embodiments, provided herein is a method of identifying a subject who is likely to be responsive to a treatment of lymphoma, with a treatment compound (e.g., a compound provided herein), comprising: (a) determining the level of a biomarker in a biological sample from the subject, wherein the biomarker is CXCL13, CCL17, MMP-9, or a combination thereof; and (b) comparing the level of the biomarker in the biological sample to a reference or control level of the biomarker; wherein the subject is likely to be responsive to the treatment if the level of the biomarker in the biological sample from the subject is decreased as compared to the reference or control level of the biomarker.

In specific embodiments, provided herein is a method of predicting the responsiveness of a subject to a treatment of lymphoma with a treatment compound comprising: (a) determining the level of a biomarker in a biological sample from the subject, wherein the biomarker is CXCL13, CCL17, MMP-9, or a combination thereof; and (b) comparing the level of the biomarker in the biological sample to a reference or control level of the biomarker; wherein the difference between the level of the biomarker in the biological sample from the subject and the reference or control level of the biomarker correlates with the responsiveness of the subject to the treatment.

In specific embodiments, provided herein is a method of monitoring the efficacy of a treatment of lymphoma in a subject treated with a treatment compound (e.g., a compound provided herein), comprising: (a) obtaining a first biological sample from the subject; (b) determining the level of a biomarker in the first biological sample, wherein the biomarker is CXCL13, CCL17, MMP-9, or a combination thereof; (c) administering the treatment compound to the subject; (d) thereafter obtaining a second biological sample from the subject; (e) determining the level of the biomarker in the second biological sample; and (f) comparing the levels of the biomarker in the first and second biological samples; wherein the subject is responsive to the treatment if the level of the biomarker in the second biological sample of the subject is decreased as compared to the level of the biomarker in the first biological sample of the subject.

In specific embodiments, provided herein is a method of monitoring the compliance of a subject with a treatment of lymphoma with a treatment compound (e.g., a compound provided herein), comprising: (a) obtaining a biological sample from the subject; (b) determining the level of a biomarker in the biological sample, wherein the biomarker is CXCL13, CCL17, MMP-9, or a combination thereof; and (c) comparing the level of the biomarker with the level of the biomarker in a control sample from the subject; wherein the decrease in the level of the biomarker in the biological sample in comparison with the level of the biomarker in the control sample indicates the compliance of the subject with the treatment.

In another embodiment, the cancer or disease is iNHL, and the biomarker is CCL1, CCL17, CCL22, CXCL13, IL-12 (p40), MMP-12, MMP-9, TNFα, IL-16, or a combination thereof.

In specific embodiments, provided herein is a method of identifying a subject who is likely to be responsive to a treatment of iNHL, with a treatment compound (e.g., a compound provided herein), comprising: (a) determining the level of a biomarker in a biological sample from the subject, wherein the biomarker is CCL1, CCL17, CCL22, CXCL13, IL-12 (p40), MMP-12, MMP-9, TNFα, IL-16, or a combination thereof; and (b) comparing the level of the biomarker in the biological sample to a reference or control level of the biomarker; wherein the subject is likely to be responsive to the treatment if the level of the biomarker in the biological sample from the subject is decreased as compared to the reference or control level of the biomarker.

In specific embodiments, provided herein is a method of predicting the responsiveness of a subject to a treatment of iNHL with a treatment compound comprising: (a) determining the level of a biomarker in a biological sample from the subject, wherein the biomarker is CCL1, CCL17, CCL22, CXCL13, IL-12 (p40), MMP-12, MMP-9, TNFα, IL-16, or a combination thereof; and (b) comparing the level of the biomarker in the biological sample to a reference or control level of the biomarker; wherein the difference between the level of the biomarker in the biological sample from the subject and the reference or control level of the biomarker correlates with the responsiveness of the subject to the treatment.

In specific embodiments, provided herein is a method of monitoring the efficacy of a treatment of iNHL in a subject treated with a treatment compound (e.g., a compound provided herein), comprising: (a) obtaining a first biological sample from the subject; (b) determining the level of a biomarker in the first biological sample, wherein the biomarker is CCL1, CCL17, CCL22, CXCL13, IL-12 (p40), MMP-12, MMP-9, TNFα, IL-16 or a combination thereof; (c) administering the treatment compound to the subject; (d) thereafter obtaining a second biological sample from the subject; (e) determining the level of the biomarker in the second biological sample; and (f) comparing the levels of the biomarker in the first and second biological samples; wherein the subject is responsive to the treatment if the level of the biomarker in the second biological sample of the subject is decreased as compared to the level of the biomarker in the first biological sample of the subject.

In specific embodiments, provided herein is a method of monitoring the compliance of a subject with a treatment of iNHL with a treatment compound (e.g., a compound provided herein), comprising: (a) obtaining a biological sample from the subject; (b) determining the level of a biomarker in the biological sample, wherein the biomarker is CCL1, CCL17, CCL22, CXCL13, IL-12 (p40), MMP-12, MMP-9, TNFα, IL-16, or a combination thereof; and (c) comparing the level of the biomarker with the level of the biomarker in a control sample from the subject; wherein the decrease in the level of the biomarker in the biological sample in comparison with the level of the biomarker in the control sample indicates the compliance of the subject with the treatment.

In one embodiment, the cancer or disease is MCL, and the biomarker is CCL17, CCL22, CXCL10, CXCL13, MMP-9, or a combination thereof.

In specific embodiments, provided herein is a method of identifying a subject who is likely to be responsive to a treatment of MCL, with a treatment compound (e.g., a compound provided herein), comprising: (a) determining the level of a biomarker in a biological sample from the subject, wherein the biomarker is CCL17, CCL22, CXCL10, CXCL13, MMP-9, or a combination thereof; and (b) comparing the level of the biomarker in the biological sample to a reference or control level of the biomarker; wherein the subject is likely to be responsive to the treatment if the level of the biomarker in the biological sample from the subject is decreased as compared to the reference or control level of the biomarker.

In specific embodiments, provided herein is a method of predicting the responsiveness of a subject to a treatment of MCL with a treatment compound comprising: (a) determining the level of a biomarker in a biological sample from the subject, wherein the biomarker is CCL17, CCL22, CXCL10, CXCL13, MMP-9, or a combination thereof; and (b) comparing the level of the biomarker in the biological sample to a reference or control level of the biomarker; wherein the difference between the level of the biomarker in the biological sample from the subject and the reference or control level of the biomarker correlates with the responsiveness of the subject to the treatment.

In specific embodiments, provided herein is a method of monitoring the efficacy of a treatment of MCL in a subject treated with a treatment compound (e.g., a compound provided herein), comprising: (a) obtaining a first biological sample from the subject; (b) determining the level of a biomarker in the first biological sample, wherein the biomarker is CCL17, CCL22, CXCL10, CXCL13, MMP-9, or a combination thereof; (c) administering the treatment compound to the subject; (d) thereafter obtaining a second biological sample from the subject; (e) determining the level of the biomarker in the second biological sample; and (f) comparing the levels of the biomarker in the first and second biological samples; wherein the subject is responsive to the treatment if the level of the biomarker in the second biological sample of the subject is decreased as compared to the level of the biomarker in the first biological sample of the subject.

In specific embodiments, provided herein is a method of monitoring the compliance of a subject with a treatment of MCL with a treatment compound (e.g., a compound provided herein), comprising: (a) obtaining a biological sample from the subject; (b) determining the level of a biomarker in the biological sample, wherein the biomarker is CCL17, CCL22, CXCL10, CXCL13, MMP-9, or a combination thereof, and (c) comparing the level of the biomarker with the level of the biomarker in a control sample from the subject; wherein the decrease in the level of the biomarker in the biological sample in comparison with the level of the biomarker in the control sample indicates the compliance of the subject with the treatment.

In another embodiment, the cancer or disease is T-cell lymphoma (e.g., CTCL), and the biomarker is CCL17, CCL22, CXCL10, CXCL13, MMP-9, GM-CSF, IL-12 (p40), TNFα, TGFα, an ERK (extracellular signal regulated kinase), PRAS40, pS6, or a combination thereof.

In specific embodiments, provided herein is a method of identifying a subject who is likely to be responsive to a treatment of T-cell lymphoma, with a treatment compound (e.g., a compound provided herein), comprising: (a) determining the level of a biomarker in a biological sample from the subject, wherein the biomarker is CCL17, CCL22, CXCL10, CXCL13, MMP-9, GM-CSF, IL-12 (p40), TNFα, TGFα, an ERK, PRAS40, pS6, or a combination thereof; and (b) comparing the level of the biomarker in the biological sample to a reference or control level of the biomarker; wherein the subject is likely to be responsive to the treatment if the level of the biomarker in the biological sample from the subject is decreased as compared to the reference or control level of the biomarker.

In specific embodiments, provided herein is a method of predicting the responsiveness of a subject to a treatment of T-cell lymphoma with a treatment compound comprising: (a) determining the level of a biomarker in a biological sample from the subject, wherein the biomarker is CCL17, CCL22, CXCL10, CXCL13, MMP-9, GM-CSF, IL-12 (p40), TNFα, TGFα, an ERK, PRAS40, pS6, or a combination thereof; and (b) comparing the level of the biomarker in the biological sample to a reference or control level of the biomarker; wherein the difference between the level of the biomarker in the biological sample from the subject and the reference or control level of the biomarker correlates with the responsiveness of the subject to the treatment.

In specific embodiments, provided herein is a method of monitoring the efficacy of a treatment of T-cell lymphoma in a subject treated with a treatment compound (e.g., a compound provided herein), comprising: (a) obtaining a first biological sample from the subject; (b) determining the level of a biomarker in the first biological sample, wherein the biomarker is CCL17, CCL22, CXCL10, CXCL13, MMP-9, GM-CSF, IL-12 (p40), TNFα, TGFα, an ERK, PRAS40, pS6, or a combination thereof; (c) administering the treatment compound to the subject; (d) thereafter obtaining a second biological sample from the subject; (e) determining the level of the biomarker in the second biological sample; and (f) comparing the levels of the biomarker in the first and second biological samples; wherein the subject is responsive to the treatment if the level of the biomarker in the second biological sample of the subject is decreased as compared to the level of the biomarker in the first biological sample of the subject.

In specific embodiments, provided herein is a method of monitoring the compliance of a subject with a treatment of T-cell lymphoma with a treatment compound (e.g., a compound provided herein), comprising: (a) obtaining a biological sample from the subject; (b) determining the level of a biomarker in the biological sample, wherein the biomarker is CCL17, CCL22, CXCL10, CXCL13, MMP-9, GM-CSF, IL-12 (p40), TNFα, TGFα, an ERK, PRAS40, pS6, or a combination thereof; and (c) comparing the level of the biomarker with the level of the biomarker in a control sample from the subject; wherein the decrease in the level of the biomarker in the biological sample in comparison with the level of the biomarker in the control sample indicates the compliance of the subject with the treatment.

In one embodiment, the change in the level of a biomarker over a period of time is determined by comparing the levels of the biomarker at the beginning of the period of time and the end of the period of time. In one embodiment, the change in the level of a biomarker over a period of time is determined by comparing the levels of the biomarker at multiple time points within the period of time (inclusive). In another embodiment, the change in the level of a biomarker over a period of time includes one or more change of level of biomarker within the period of time. In yet another embodiment, the change in the level of a biomarker over a period of time is determined by comparing the level of the biomarker to reference standard level(s).

In one embodiment, the methods provided herein further comprising a step of adjusting the dose of the treatment (e.g., Compound 292 treatment) based on the change in the level of a biomarker over a period of time.

In one embodiment, provided herein is a probe for determining the level of a biomarker in a sample by hybridizing with a polynucleotide of the biomarker, wherein the biomarker is described herein (e.g., a biomarker for an isoform of PI3K (e.g., PI3K-δ, PI3K-γ, PI3K-α, or PI3K-β, or a combination thereof)). In certain embodiments, the level of the biomarker is used to select a subject for a treatment with a treatment compound (e.g., a compound provided herein); to predict or monitor the responsiveness of a subject to the treatment; or monitoring the compliance of a subject with the treatment. In certain embodiments, the probe is one that hybridizes with a splice junction of a polynucleotide of the biomarker. In specific embodiments, the probe is specific for detecting or quantitating an isoform of PI3K (e.g., PI3K-δ, PI3K-γ, PI3K-α, or PI3K-β, or a combination thereof).

In one embodiment, provided herein is a probe for determining the level of a biomarker in a sample by hybridizing with an mRNA of the biomarker, wherein the biomarker is described herein (e.g., a biomarker for an isoform of PI3K (e.g., PI3K-δ, PI3K-γ, PI3K-α, or PI3K-β, or a combination thereof)). In certain embodiments, the level of the biomarker is used to select a subject for a treatment with a treatment compound (e.g., a compound provided herein); to predict or monitor the responsiveness of a subject to the treatment; or monitoring the compliance of a subject with the treatment. In certain embodiments, the probe is one that hybridizes with a splice junction of an mRNA of the biomarker. In specific embodiments, the probe is specific for detecting or quantitating an isoform of PI3K (e.g., PI3K-δ, PI3K-γ, PI3K-α, or PI3K-β, or a combination thereof).

In one embodiment, provided herein is an antibody for determining the level of a biomarker in a sample, wherein the biomarker is described herein (e.g., a biomarker for an isoform of PI3K (e.g., PI3K-δ, PI3K-γ, PI3K-α, or PI3K-β, or a combination thereof)). In certain embodiments, the level of the biomarker is used to select a subject for a treatment with a treatment compound (e.g., a compound provided herein); to predict or monitor the responsiveness of a subject to the treatment; or monitoring the compliance of a subject with the treatment. In certain embodiments, the antibody is one that binds to a splice junction of the biomarker (e.g., a biomarker for an isoform of PI3K (e.g., PI3K-δ, PI3K-γ, PI3K-α, or PI3K-β, or a combination thereof)). In specific embodiments, the antibody is specific for detecting or quantitating an isoform of PI3K (e.g., PI3K-δ, PI3K-γ, PI3K-α, or PI3K-β, or a combination thereof).

In one embodiment, the levels of mRNAs of the biomarkers can be detected or quantitated by a method known in the art. Exemplary detecting or quantitating methods include, but are not limited to, northern blots, ribonuclease protection assays, and PCR-based methods. When the biomarker is an mRNA molecule, the mRNA sequence or a fragment thereof can be used to prepare a probe that is at least partially complementary. The probe can then be used to detect the mRNA sequence in a sample, using a method known in the art, including, not limited to PCR-based methods, Northern blotting, or a dipstick assay.

In certain embodiments, the detecting or quantitating method is a northern blot, ribonuclease protection assay, or a PCR-based method. In certain embodiments, the detecting or quantitating method is a northern blot. In certain embodiments, the detecting or quantitating method is a ribonuclease protection assay. In certain embodiments, the detecting or quantitating method is a PCR-based method. In certain embodiments, the detecting or quantitating method is qRT-PCR.

In one embodiment, any suitable assay platform can be used to determine the presence of the mRNA in a sample. For example, an assay can be in the form of a dipstick, a membrane, a chip, a disk, a test strip, a filter, a microsphere, a slide, a multiwell plate, or an optical fiber. An assay system can have a solid support on which a nucleic acid corresponding to the mRNA is attached. The solid support can comprise, for example, a plastic, silicon, a metal, a resin, glass, a membrane, a particle, a precipitate, a gel, a polymer, a sheet, a sphere, a polysaccharide, a capillary, a film a plate, or a slide. The assay components can be prepared and packaged together as a kit for detecting an mRNA.

The mRNAs can be labeled, if desired, to make a population of labeled mRNAs. In general, a sample can be labeled using methods that are known in the art (e.g., using an RNA ligase or terminal transferase, or by labeling the RNA backbone). See e.g., Ausubel et al., *Short Protocols in Molecular Biology*, 3rd ed., Wiley & Sons 1995 and Sambrook et al., *Molecular Cloning: A Laboratory Manual*, Third Edition, 2001 Cold Spring Harbor, N.Y. In certain embodiments, the sample is labeled with a fluorescent label. Exemplary fluorescent dyes include, but are not limited to, xanthene dyes, fluorescein dyes, rhodamine dyes, fluorescein isothiocyanate (FITC), 6-carboxyfluorescein (FAM), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine 6G (R6G5 or G5), 6-carboxyrhodamine 6G (R6G6 or G6), rhodamine 110, cyanine dyes (e.g., Cy3, Cy5, and Cy7 dyes), Alexa dyes (e.g., Alexa-fluor-555), coumarin, diethylaminocoumarin, umbelliferone; benzamide dyes (e.g., Hoechst 33258), phenanthridine dyes (e.g., Texas red), ethidium dyes, acridine dyes, carbazole dyes, phenoxazine dyes, porphyrin dyes, polymethine dyes, BODIPY dyes, quinoline dyes, pyrene, fluorescein chlorotriazinyl, R110, Eosin, JOE, R6G, tetramethylrhodamine, lissamine, ROX, and naphthofluorescein.

In certain embodiments, nucleic acid probes can be present in specific, addressable locations on a solid support; each corresponding to at least a portion of mRNA sequences of a biomarker.

In certain embodiments, an mRNA assay comprises the steps of 1) obtaining surface-bound probes for one or more biomarkers; 2) hybridizing a population of mRNAs to the surface-bound probes under conditions sufficient to provide for specific binding; 3) removing unbound nucleic acids in the hybridization step; and 4) detecting the hybridized mRNAs.

Hybridization can be carried out under suitable hybridization conditions, which may vary in stringency as desired. Typical conditions are sufficient to produce probe/target complexes on a solid surface between complementary binding members, i.e., between surface-bound probes and complementary mRNAs in a sample.

In certain embodiments, stringent hybridization conditions are used. Standard hybridization techniques (e.g., under conditions sufficient to provide for specific binding of target mRNAs in the sample to the probes) are described in Kallioniemi et al., *Science* 258:818-821 (1992) and WO 93/18186, the disclosure of each which is incorporated herein by reference in its entirety. Several guides to general techniques are available, e.g., Tijssen, *Hybridization with Nucleic Acid Probes*, Parts I and II (Elsevier, Amsterdam 1993). For descriptions of techniques suitable for in situ hybridizations, see Gall et al. *Meth. Enzymol.*, 21:470-480 (1981); and Angerer et al. in *Genetic Engineering: Principles and Methods* (Setlow and Hollaender, Eds.) Vol. 7, pages 43-65 (Plenum Press, New York 1985). Selection of appropriate conditions, including temperature, salt concentration, polynucleotide concentration, hybridization time, and stringency of washing conditions, depends on experimental design, including the source of a sample, the identity of capture agents, the degree of complementarity expected, etc.

After the mRNA hybridization procedure, the surface bound polynucleotides are washed to remove unbound nucleic acids. Washing may be performed using any convenient washing protocol. In certain embodiments, the washing conditions are stringent. The hybridization of the target mRNAs to the probes is then detected using standard techniques.

In certain embodiments, the mRNA level of a biomarker is determined using a PCR-based method. Examples of PCR assays can be found in U.S. Pat. No. 6,927,024, the disclosure of which is incorporated by reference herein in its entirety. Examples of RT-PCR methods can be found in U.S. Pat. No. 7,122,799, the disclosure of which is incorporated by reference herein in its entirety. Examples of fluorescent in situ PCR methods can be found in U.S. Pat. No. 7,186,507, the disclosure of which is incorporated by reference herein in its entirety.

In certain embodiments, real-time reverse transcription-PCR (qRT-PCR) is used for both the detection and quantification of mRNAs (Bustin et al., Clin. Sci., 2005, 109, 365-379). Quantitative results obtained by qRT-PCR are generally more informative than qualitative data. Examples of qRT-PCR-based methods can be found in U.S. Pat. No. 7,101,663, the disclosure of which is incorporated by reference herein in its entirety.

In contrast to regular reverse transcriptase-PCR and analysis by agarose gels, real-time PCR gives quantitative results. An additional advantage of real-time PCR is the relative ease and convenience of use. Instruments for real-time PCR, such as Applied Biosystems 7500, are available commercially. The reagents for real-time PCR, such as TaqMan Sequence Detection chemistry, are also commercially available.

To determine the cycle number at which the fluorescence signal associated with a particular amplicon accumulation crosses the threshold (referred to as CT), the data can be analyzed, for example, using a 7500 Real-Time PCR System Sequence Detection software v1.3, using the comparative CT relative quantification calculation method. Using this method, the output is expressed as a fold-change in expression levels. In some embodiments, the threshold level can be selected to be automatically determined by the software. In some embodiments, the threshold level is set to be above the baseline, but sufficiently low to be within the exponential growth region of an amplification curve.

The levels of the protein biomarkers provided herein can be detected or quantitated by any methods known in the art. In certain embodiments, antibody-based methods are used. In certain embodiments, the detecting or quantitating method is immunoblotting (western blot), an enzyme-linked immunosorbent assay (ELISA), immunohistochemistry, flow cytometry, a cytometric bead array, or mass spectroscopy.

In certain embodiments, the detecting or quantitating method is immunoblotting (western blot). In certain embodiments, the detecting or quantitating method is an enzyme-linked immunosorbent assay (ELISA). In certain embodiments, the detecting or quantitating method is a direct ELISA. In certain embodiments, the detecting or quantitating method is an indirect ELISA. In certain embodiments, the detecting or quantitating method is an sandwich ELISA. In certain embodiments, the detecting or quantitating method is immunohistochemistry. In certain embodiments, the detecting or quantitating method is flow cytometry. In certain embodiments, the detecting or quantitating method is a cytometric bead array. In certain embodiments, the detecting or quantitating method is mass spectroscopy.

Without being limited by a particular theory, it was found that patients having a baseline Absolute Lymphocyte Count (ALC) of greater than about $10 \times 10^3/\mu l$ showed a trend in post-baseline ALC over time than those patients having less than $10 \times 103/\mu l$ ALC. For example, the trend showed that the patients with a higher baseline ALC exhibited rapid onset of clinical activity in CLL following the administration of Compound 292 25 mg BID, and thus are more likely to be responsive to the treatment.

Accordingly, in another embodiment, provided herein is a method of predicting the responsiveness of a subject to a treatment of cancer with a treatment compound comprising: (1) obtaining a blood sample from the patient; and (2) determining Absolute Lymphocyte Count (ALC) in the sample prior to the administration of the treatment compound, wherein the patient is likely to be responsive if the ALC is greater than about $10 \times 10^3/\mu l$. In one embodiment, the cancer is CLL or SLL. In another embodiment, the compound is Compound 292. In other embodiments, also provided herein is a method of treating cancer comprising administering a compound provided herein to a patient who has been identified as a likely responder, determined based on the method described above.

Without being limited by a particular theory, it was found that a cytokine cocktail consisting of CD40L, IL-2 and IL-10 can mimic microenvironmental proliferative signals and induce PI3K signaling and proliferation in CLL cells. Accordingly, such a cocktail can provide a valuable in vitro tool in studying cancer behavior and screening for anticancer compounds.

In some embodiments, provided herein is a method of inducing PI3K signaling in a cancer cell in vitro comprising contacting the cancer cell with a cytokine cocktail consisting of CD40L, IL-2 and IL-10. In other embodiments, provided herein is a method of inducing proliferation of a cancer cell in vitro comprising contacting the cancer cell with a cytokine cocktail consisting of CD40L, IL-2 and IL-10.

In some embodiments, provided herein is a method for determining anti-cancer activity of a test compound comprising: (a) contacting a cancer cell with a cytokine cocktail consisting of CD40L, IL-2, and IL-10; (b) determining the extent of PI3K signaling and/or cell proliferation; (c) contacting the cytokine cocktail treated cancer cell with the test compound; and (d) determining the PI3K signaling and/or cell proliferation, wherein the reduction in PI3K signaling and/or cell proliferation determined in step (d) as compared to the same determined in step (b) is indicative of the anti-cancer activity of the test compound.

Kits

Also provided herein are kits useful for predicting the likelihood of an effective cancer or hematologic malignancy treatment or for monitoring the effectiveness of a treatment with a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof).

In one embodiment, the kit comprises a solid support, and a means for detecting the protein expression of at least one biomarker in a biological sample. Such a kit can employ, for example, a dipstick, a membrane, a chip, a disk, a test strip, a filter, a microsphere, a slide, a multiwell plate, or an optical fiber. The solid support of the kit can be, for example, a plastic, silicon, a metal, a resin, glass, a membrane, a particle, a precipitate, a gel, a polymer, a sheet, a sphere, a polysaccharide, a capillary, a film, a plate, or a slide. The biological sample can be, for example, a cell culture, a cell line, a tissue, an oral tissue, gastrointestinal tissue, an organ, an organelle, a biological fluid, a blood sample, a urine sample, or a skin sample. The biological sample can be, for example, a lymph node biopsy, a bone marrow biopsy, or a sample of peripheral blood tumor cells.

In one embodiment, the kit comprises a solid support, at least one nucleic acid contacting the support, where the nucleic acids are complementary to at least 20, 50, 100, 200, 350, or more bases of mRNA of the biomarker, and a means for detecting the expression of the mRNA in a biological sample.

In certain embodiments, the kits provided herein employ means for detecting the expression of a biomarker by quantitative real-time PCR (QRT-PCR), microarray, flow cytometry or immunofluorescence. In other embodiments, the expression of the biomarker is measured by ELISA-based methodologies or other similar methods known in the art.

In certain embodiments, provided herein is a kit for detecting the mRNA levels of one or more biomarkers. In certain embodiments, the kit comprises one or more probes that bind specifically to the mRNAs of the one or more biomarkers. In certain embodiments, the kit further comprises a washing solution. In certain embodiments, the kit further comprises reagents for performing a hybridization assay, mRNA isolation or purification means, detection means, as well as positive and negative controls. In certain embodiments, the kit further comprises an instruction for using the kit. The kit can be tailored for in-home use, clinical use, or research use.

In certain embodiments, provided herein is a kit for detecting the protein level of one or more biomarkers. In certain embodiments, the kits comprises a dipstick coated with an antibody that recognizes the protein biomarker, washing solutions, reagents for performing the assay, protein isolation or purification means, detection means, as well as positive and negative controls. In certain embodiments, the kit further comprises an instruction for using the kit. The kit can be tailored for in-home use, clinical use, or research use.

Such a kit can employ, for example, a dipstick, a membrane, a chip, a disk, a test strip, a filter, a microsphere, a slide, a multiwell plate, or an optical fiber. The solid support of the kit can be, for example, a plastic, silicon, a metal, a resin, glass, a membrane, a particle, a precipitate, a gel, a polymer, a sheet, a sphere, a polysaccharide, a capillary, a film, a plate, or a slide. The biological sample can be, for example, a cell culture, a cell line, a tissue, an oral tissue, gastrointestinal tissue, an organ, an organelle, a biological fluid, a blood sample, a urine sample, or a skin sample.

Dosing kits are also provided herein. The kits include a compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof), or a composition thereof, in suitable packaging, and written material. The written material can include any of the following information: instructions for use, discussion of clinical studies, listing of side effects, scientific literature references, package insert materials, clinical trial results, and/or summaries of these and the like. The written material can indicate or establish the activities and/or advantages of the composition, and/or describe dosing, administration, side effects, drug interactions, or other information useful to the health care provider. Such information can be based on the results of various studies, for example, studies using experimental animals involving in vivo models and/or studies based on human clinical trials. The kit can further contain another therapy (e.g., another agent) and/or written material such as that described above that serves to provide information regarding the other therapy (e.g., the other agent). In some embodiments, the compound provided herein (e.g., a compound of Formula I (e.g., Compound 292), or an enantiomer or a mixture of enantiomers thereof, or a pharmaceutically acceptable salt, solvate, hydrate, co-crystal, clathrate, or polymorph thereof) and the agent are provided as separate compositions in separate containers within the kit. In some embodiments, the compound provided herein and the agent are provided as a single composition within a container in the kit. Suitable packaging and additional articles for use (e.g., measuring cup for liquid preparations, foil wrapping to minimize exposure to air, and the like) are known in the art and can be included in the kit. Kits described herein can be provided, marketed and/or promoted to health providers, including physicians, nurses, pharmacists, formulary officials, and the like. Kits can also, in some embodiments, be marketed directly to the consumer.

EXAMPLES

Example 1

IC50 Values for Selected PI3K Modulators

The $IC_{50}$ values for selected compounds were determined and are provided in Table 3. These data demonstrate that these compounds can serve as PI3K-δ and/or PI3K-γ inhibitors.

TABLE 3

In Vitro $IC_{50}$ data for selected compounds.

| IC50 (nM) | + (greater than 10 microMolar) | ++ (less than 10 microMolar) | +++ (less than 1 microMolar | ++++ (less than 100 nM) |
|---|---|---|---|---|
| PI3K δ | Compound No. | Compound No. | Compound No. | Compound No. |
| | 197, 199, 241, 259, 261, 263, 280, 282, 283, 314, 315, 318, 321, 322 | 1, 5, 22, 27, 38, 39, 40, 41, 46, 92, 117, 118, 120, 129, 132, 164, 165, 172, 188, 186, 193, 194, 195, 217, 242, 246, 281, 284, 305, 317, 325 | 4, 14, 15, 17, 18, 21, 26, 29, 31, 32, 34, 35, 36, 42, 43, 44, 45, 47, 49, 57, 69, 71, 85, 87, 94, 106, 107, 143, 175, 179, 181, 182, 183, 187, 189, 192, 225, 226, 228, 235, 236, 239, 248, 250, 258, 269, 274, 275, 285, 286, 297, 298, 299, 300, 307, 309, 313, 319, | 2, 3, 6, 7, 8, 9, 10, 11, 12, 13, 16, 19, 20, 23, 24, 25, 28, 30, 33, 37, 48, 50, 51, 52, 53, 54, 55, 56, 58, 59, 60, 61, 62, 63, 64, 65, 66, 67, 68, 70, 72, 73, 74, 75, 76, 77, 78, 79, 80, 81, 82, 83, 84, 86, 88, 89, 90, 91, 93, 95, 96, 97, 98, 99, 100, 101, 102, 103, 104, 105, 108, 109, 110, 111, 112, 113, 114, 115, 119, 123, 124, 125, 126, 128, 134, 135, 136, 137, 138, 139, 141, 142, 144, 145, 146, 147, 148, 149, 150, 151.152, 153, 154, 155, 156, 157, 158, 159, 160, 161, 162, 166, 167, 168, 169, 170, 171, 173, 174, 176, 177, 178, 180, 185, 188, 190, 191, 196, 198, 200, 201, 202, 203, 204, 205, 206, 207, 208, 209, 210, 211, 212, 213, 214, 215, 216, 218, 219, 220, 221, 222, 223, 224, 227, 229, 230, 231, 232, 233, 234, 237, 238, 240, 243, 244, 245, 247, 249, 251, 252, 253, 254, 255, 256, 257, 260, 262, 264, 265, 266, 267, 268, 270, 271, 272, 273, 276, 277, 278, 279, 287, 288, 289, 290, 291, 292, 293, 294, 295, 296, 301, 302, 303, 306, 308, 310, 311, 312, 316, 320, 323, 324 |

TABLE 3-continued

In Vitro IC$_{50}$ data for selected compounds.

| IC50 (nM) | + (greater than 10 microMolar) | ++ (less than 10 microMolar) | +++ (less than 1 microMolar) | ++++ (less than 100 nM) |
|---|---|---|---|---|
| PI3K γ | Compound No. | Compound No. | Compound No. | Compound No. |
| | 1, 4, 5, 18, 38, 43, 60, 69, 169, 172, 192, 193, 194, 199, 227, 228, 233, 259, 263, 280, 281, 282, 283, 314, 315, 317, 318, 321, 322, 325 | 17, 34, 35, 37, 38, 40, 42, 57, 61, 65, 91, 92, 94, 105, 107, 164, 170, 175, 179, 181, 183, 184, 186, 187, 189, 195, 197, 219, 221, 224, 232, 239, 241, 242, 246, 248, 258, 261, 274, 284, 285, 294, 299, 303, 305, 307, 309, 312, 313, 319 | 2, 8, 9, 10, 11, 14, 15, 20, 22, 27, 28, 39, 41, 46, 47, 49, 51, 55, 58, 66, 70, 71, 73, 76, 78, 80, 93, 98, 99, 100, 103, 104, 106, 108, 109, 161, 162, 163, 165, 166, 180, 188, 202, 206, 209, 212, 214, 216, 218, 220, 222, 229, 234, 236, 238, 250, 267, 268, 269, 271, 275, 279, 286, 293, 298, 300, 301, 308, 316 | 3, 6, 7, 12, 13, 16, 19, 21, 23, 24, 25, 26, 29, 30, 31, 33, 36, 44, 45, 48, 50, 52, 53, 54, 56, 59, 62, 63, 64, 67, 68, 72, 74, 75, 77, 79, 81, 82, 83, 84, 86, 87, 88, 89, 90, 95, 96, 97, 101, 102, 142, 145, 146, 147, 148, 149, 150, 151, 152, 160, 167, 168, 171, 173, 174, 176, 177, 178, 182, 185, 190, 191, 196, 198, 200, 201, 203, 204, 205, 207, 208, 210, 211, 213, 215, 223, 230, 231, 235, 237, 240, 243, 244, 245, 247, 249, 251, 252, 253, 254, 255, 256, 257, 260, 262, 264, 265, 266, 270, 272, 273, 276, 277, 278, 287, 288, 289, 290, 291, 292, 295, 296, 302, 304, 306, 310, 311, 320, 323, 324 |
| PI3K α | Compound No. | Compound No. | Compound No. | Compound No. |
| | 6, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 54, 55, 56, 57, 58, 59, 60, 61, 62, 64, 65, 67, 68, 69, 70, 71, 72, 73, 74, 79, 80, 81, 82, 83, 85, 87, 88, 91, 93, 96, 98, 99, 100, 103, 104, 105, 106, 107, 109, 110, 111, 112, 114, 146, 160, 161, 162, 163, 164, 165, 166, 167, 169, 170, 172, 174, 175, 179, 180, 181, 182, 183, 184, 186, 187, 188, 189, 191, 192, 193, 194, 197, 202, 211, 212, 214, 215, 216, 218, 219, 220, 221, 222, 224, 227, 228, 238, 239, 241, 242, 246, 247, 248, 249, 250, 258, 259, 261, 263, 265, 266, 267, 268, 271, 274, 275, 280, 281, 282, 283, 284, 285, 286, 290, 293, 294, 298, 299, 300, 304, 308, 309, 313, 314, 315, 316, 317, 318, 319, 321, 322, 324, 325 | 3, 7, 63, 66, 84, 86, 89, 90, 97, 108, 113, 115, 152, 168, 171, 173, 185, 190, 198, 203, 204, 205, 206, 207, 209, 210, 213, 223, 235, 237, 240, 243, 244, 245, 251, 253, 254, 255, 256, 269, 273, 279, 291, 292, 295, 296 | 53, 95, 101, 102, 145, 147, 149, 151, 177, 208, 257, 260, 262, 264, 270, 272, 276, 277, 278, 287, 288, 289, 320, 323 | 142, 148, 150, 153, 154, 155, 156, 157, 158, 159, 176, 201, 252 |

TABLE 3-continued

In Vitro IC$_{50}$ data for selected compounds.

| IC50 (nM) | + (greater than 10 microMolar) | ++ (less than 10 microMolar) | +++ (less than 1 microMolar) | ++++ (less than 100 nM) |
|---|---|---|---|---|
| PI3K β | Compound No. | Compound No. | Compound No. | Compound No. |
| | 8, 9, 10, 11, 14, 21, 22, 24, 26, 27, 28, 29, 34, 35, 36, 37, 38, 39, 40, 41, 42, 43, 44, 46, 52, 54, 56, 57, 59, 60, 64, 68, 69, 70, 73, 76, 78, 79, 80, 87, 88, 91, 93, 98, 103, 104, 105, 107, 109, 112, 146, 152, 162, 163, 164, 165, 166, 169, 170, 172, 175, 179, 180, 181, 182, 183, 184, 186, 187, 188, 189, 192, 193, 194, 197, 216, 217, 218, 221, 222, 224, 238, 248, 259, 261, 263, 266, 271, 275, 280, 282, 283, 284, 285, 286, 294, 299, 304, 310, 311, 312, 315, 317, 321, 322, 325 | 3, 12, 13, 23, 25, 53, 55, 58, 61, 63, 65, 67, 71, 72, 74, 75, 77, 81, 82, 83, 84, 85, 86, 96, 99, 106, 108, 110, 111, 113, 114, 115, 145, 147, 149, 151, 154, 158, 160, 161, 167, 168, 171, 173, 174, 177, 178, 190, 191, 198, 202, 203, 205, 206, 207, 209, 210, 211, 212, 214, 215, 219, 220, 223, 228, 235, 240, 243, 244, 247, 249, 265, 269, 274, 281, 295, 296, 298, 300, 308, 316, 324 | 7, 62, 66, 82, 89, 90, 95, 97, 100, 102, 150, 153, 159, 176, 185, 201, 204, 208, 213, 227, 237, 251, 252, 267, 276, 277, 290, 292, 293 | 101, 142, 155, 156, 157, 200, 253, 254, 255, 256, 257, 260, 262, 264, 268, 270, 272, 273, 278, 279, 287, 288, 289, 291, 320, 323, |
| B cell proliferation EC$_{50}$ (nM) | Compound No. | Compound No. | Compound No. | Compound No. |
| | 38, 162, 199 | 1, 2, 5, 22, 26, 27, 39, 40, 43, 49, 57, 71, 87, 112, 197, 207, 235 | 4, 8, 9, 10, 11, 14, 15, 18, 19, 20, 21, 24, 25, 28, 29, 30, 31, 32, 34, 35, 36, 41, 42, 45, 46, 47, 50, 51, 61, 69, 70, 76, 77, 78, 79, 80, 85, 86, 91, 98, 100, 103, 104, 105, 106, 107, 110, 111, 114, 119, 124, 133, 135, 145, 152, 161, 162, 163, 169, 195, 212, 243, 294, 312 | 3, 6, 7, 12, 13, 16, 17, 23, 33, 37, 44, 48, 53, 54, 55, 62, 63, 66, 67, 68, 72, 73, 74, 75, 81, 82, 83, 84, 88, 89, 90, 93, 95, 96, 97, 99, 101, 102, 108, 109, 113, 115, 123, 125, 126, 128, 134, 136, 137, 138, 139, 141, 142, 144, 146, 147, 148, 149, 150, 151, 153, 154, 155, 156, 157, 158, 159, 160, 166, 167, 168, 170, 171, 173, 174, 176, 177, 178, 180, 187, 185, 188, 190, 191. 196, 198, 200, 201, 202, 203, 204, 205, 206, 208, 209, 210, 211, 213, 214, 215, 216, 219, 220, 221, 222, 223, 224, 227, 228, 229, 230, 231, 232, 233, 234, 237, 244, 245, 247, 248, 249, 251, 252, 253, 254, 255, 256, 257, 270, 276, 277, 278, 289, 290, 292, 295, 296, 298, 300, 301, 302, 303, 306, 308, 310, 311 |

TABLE 4
Structures of the Compounds for the IC50 results described in Table 3.
Structure
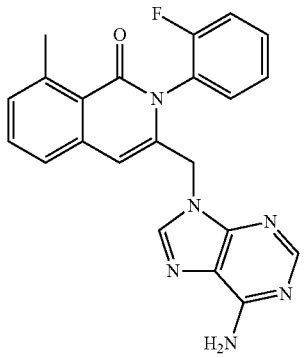 [SMILES: Cc1cccc2cc(Cn3cnc4c(N)ncnc43)n(-c3ccccc3F)c(=O)c12]
Compound 1
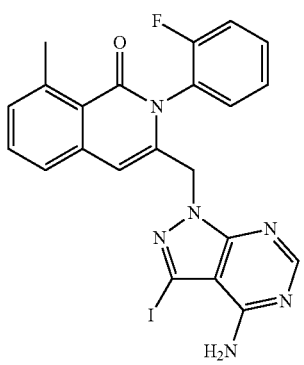
Compound 2
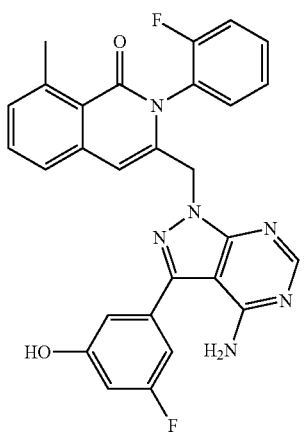 [SMILES: Cc1cccc2cc(Cn3nc(-c4cc(O)cc(F)c4)c4c(N)ncnc43)n(-c3ccccc3F)c(=O)c12]
Compound 3
TABLE 4-continued
Structures of the Compounds for the IC50 results described in Table 3.
Structure
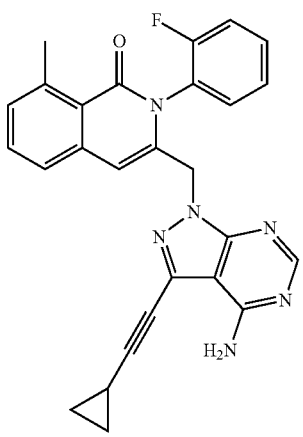 [SMILES: Cc1cccc2cc(Cn3nc(C#CC4CC4)c4c(N)ncnc43)n(-c3ccccc3F)c(=O)c12]
Compound 4
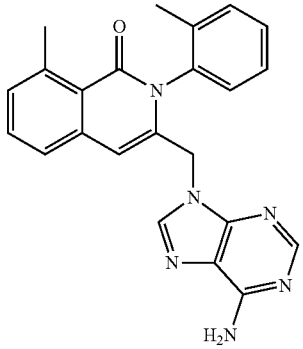 [SMILES: Cc1ccccc1-n1c(Cn2cnc3c(N)ncnc32)cc2cccc(C)c2c1=O]
Compound 5
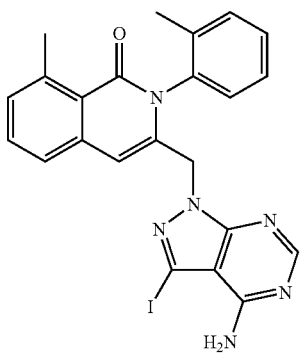
Compound 6

TABLE 4-continued
Structures of the Compounds for the IC50 results described in Table 3.
Structure
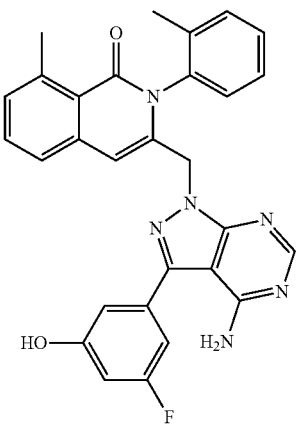 [SMILES: Cc1ccccc1-n1c(Cn2nc(-c3cc(O)cc(F)c3)c3c(N)ncnc32)cc2cccc(C)c2c1=O]
Compound 7
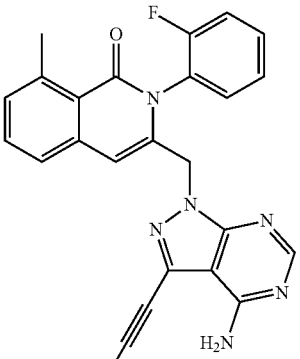
Compound 8
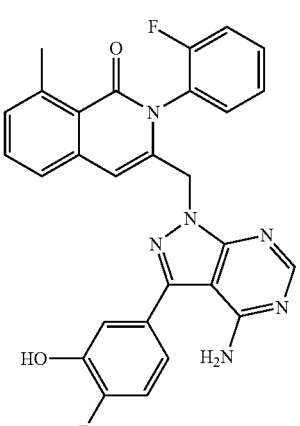
Compound 9
TABLE 4-continued
Structures of the Compounds for the IC50 results described in Table 3.
Structure
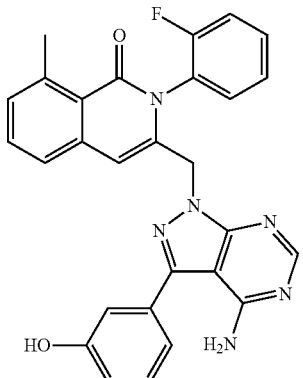
Compound 10
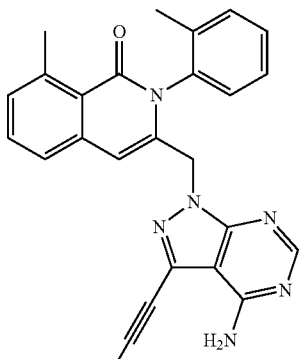
Compound 11
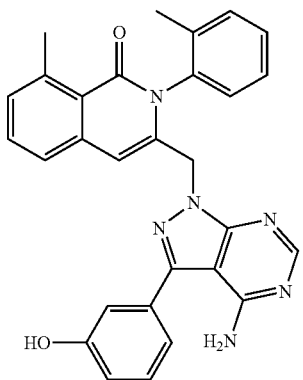 [SMILES: Cc1ccccc1-n1c(Cn2nc(-c3cccc(O)c3)c3c(N)ncnc32)cc2cccc(C)c2c1=O]
Compound 12

TABLE 4-continued
Structures of the Compounds for the IC50 results described in Table 3.
Structure
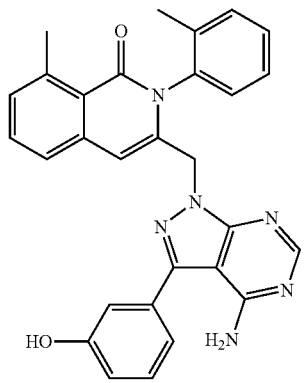
Compound 13
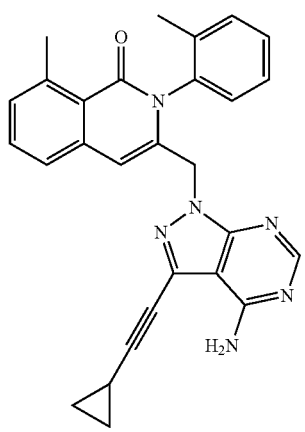 [SMILES: Cc1ccccc1-n1c(Cn2nc(C#CC3CC3)c3c(N)ncnc32)cc2cccc(C)c2c1=O]
Compound 14
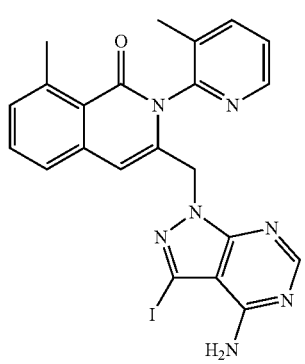 [SMILES: Cc1cccnc1-n1c(Cn2nc(I)c3c(N)ncnc32)cc2cccc(C)c2c1=O]
Compound 15
TABLE 4-continued
Structures of the Compounds for the IC50 results described in Table 3.
Structure
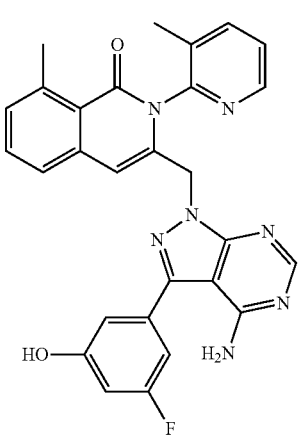 [SMILES: Cc1cccnc1-n1c(Cn2nc(-c3cc(O)cc(F)c3)c3c(N)ncnc32)cc2cccc(C)c2c1=O]
Compound 16
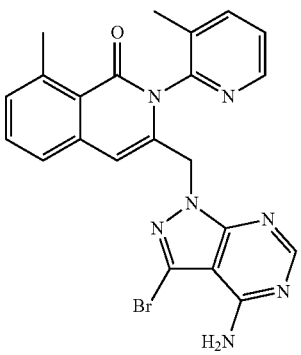 [SMILES: Cc1cccnc1-n1c(Cn2nc(Br)c3c(N)ncnc32)cc2cccc(C)c2c1=O]
Compound 17
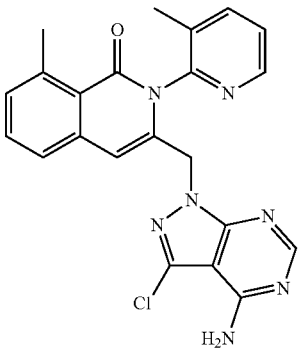
Compound 18

TABLE 4-continued
Structures of the Compounds for the IC50 results described in Table 3.
Structure
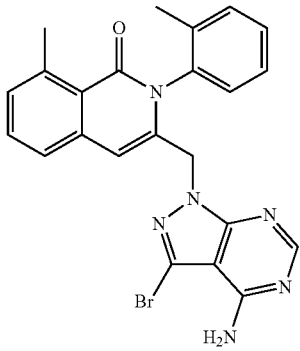 [SMILES: Cc1ccccc1-n1c(Cn2nc(Cl)c3c(N)ncnc32)cc2cccc(C)c2c1=O]
Compound 19
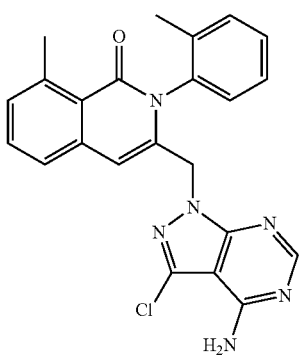
Compound 20
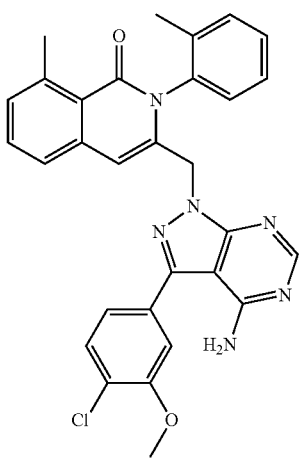 [SMILES: COc1cc(-c2nn(Cc3cc4cccc(C)c4c(=O)n3-c3ccccc3C)c3ncnc(N)c23)ccc1Cl]
Compound 21
TABLE 4-continued
Structures of the Compounds for the IC50 results described in Table 3.
Structure
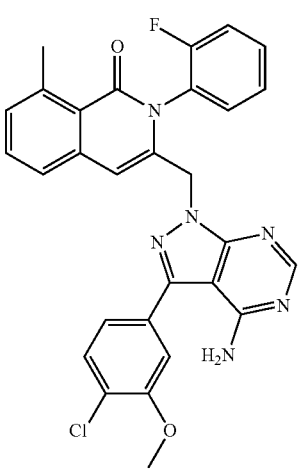 [SMILES: COc1cc(-c2nn(Cc3cc4cccc(C)c4c(=O)n3-c3ccccc3F)c3ncnc(N)c23)ccc1Cl]
Compound 22
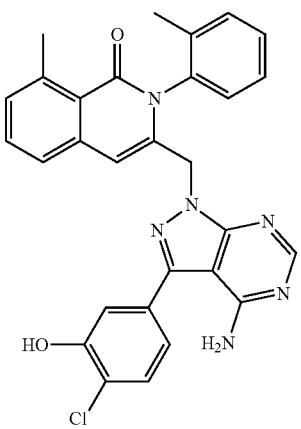 [SMILES: Cc1ccccc1-n1c(Cn2nc(-c3ccc(Cl)c(O)c3)c3c(N)ncnc32)cc2cccc(C)c2c1=O]
Compound 23
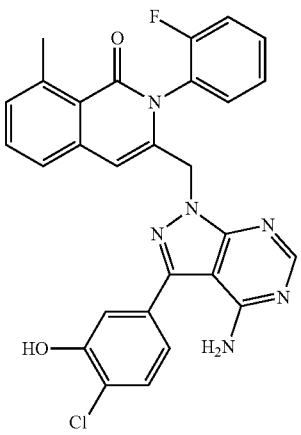 [SMILES: Cc1cccc2cc(Cn3nc(-c4ccc(Cl)c(O)c4)c4c(N)ncnc43)n(-c3ccccc3F)c(=O)c12]
Compound 24

TABLE 4-continued
Structures of the Compounds for the IC50 results described in Table 3.
Structure
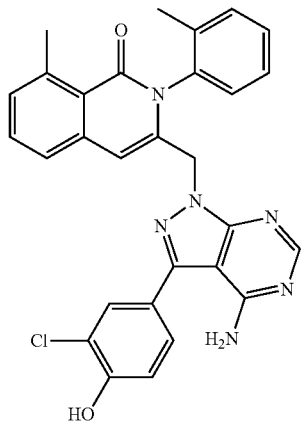 [SMILES: Cc1ccccc1-n1c(Cn2nc(-c3ccc(O)c(Cl)c3)c3c(N)ncnc32)cc2cccc(C)c2c1=O]
Compound 25
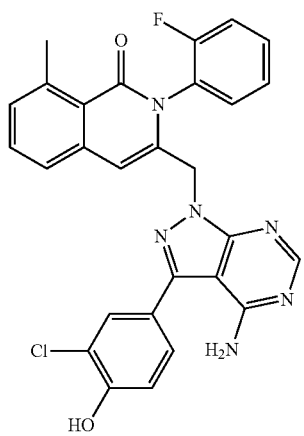 [SMILES: Cc1cccc2cc(Cn3nc(-c4ccc(O)c(Cl)c4)c4c(N)ncnc43)n(-c3ccccc3F)c(=O)c12]
Compound 26
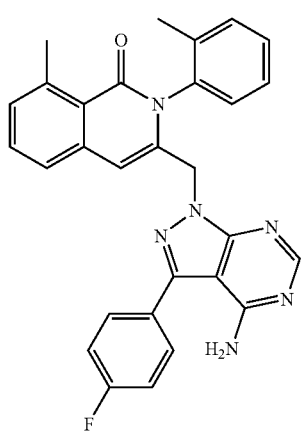 [SMILES: Cc1ccccc1-n1c(Cn2nc(-c3ccc(F)cc3)c3c(N)ncnc32)cc2cccc(C)c2c1=O]
Compound 27
TABLE 4-continued
Structures of the Compounds for the IC50 results described in Table 3.
Structure
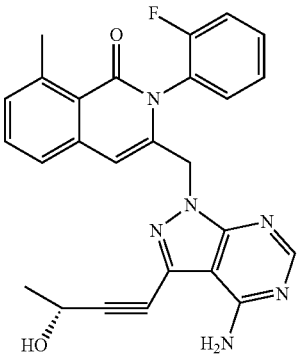 [SMILES: Cc1cccc2cc(Cn3nc(C#C[C@@H](C)O)c4c(N)ncnc43)n(-c3ccccc3F)c(=O)c12]
Compound 28
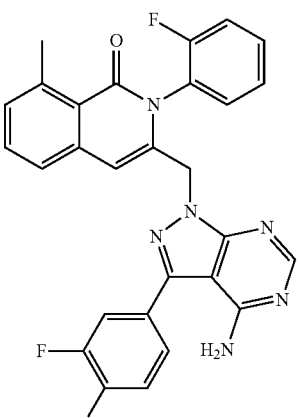
Compound 29
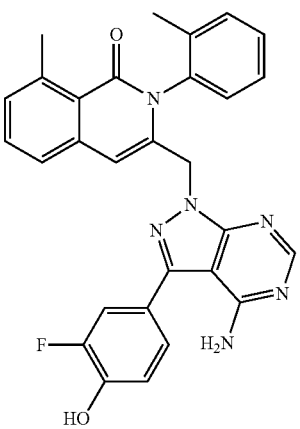 [SMILES: Cc1ccccc1-n1c(Cn2nc(-c3ccc(O)c(F)c3)c3c(N)ncnc32)cc2cccc(C)c2c1=O]
Compound 30

TABLE 4-continued
Structures of the Compounds for the IC50 results described in Table 3.
Structure
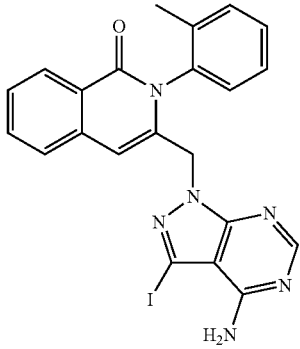
Compound 31
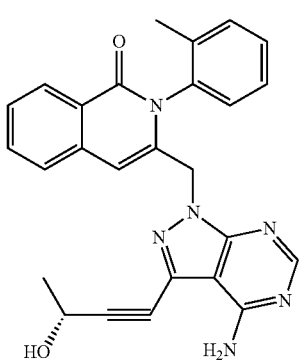 [SMILES: Cc1ccccc1-n1c(Cn2nc(C#C[C@@H](C)O)c3c(N)ncnc32)cc2ccccc2c1=O]
Compound 32
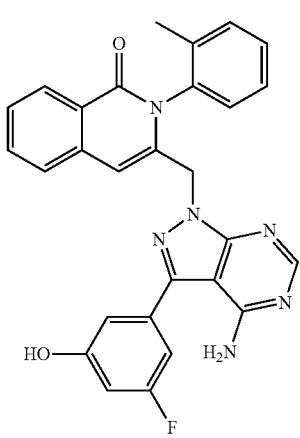 [SMILES: Cc1ccccc1-n1c(Cn2nc(-c3cc(O)cc(F)c3)c3c(N)ncnc32)cc2ccccc2c1=O]
Compound 33
TABLE 4-continued
Structures of the Compounds for the IC50 results described in Table 3.
Structure
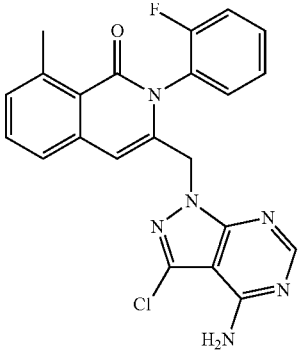
Compound 34
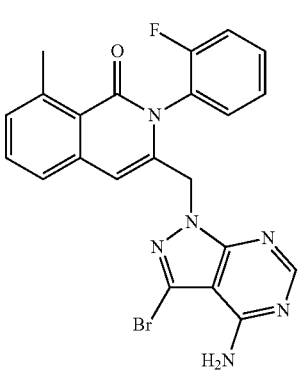 [SMILES: Cc1cccc2cc(Cn3nc(Cl)c4c(N)ncnc43)n(-c3ccccc3F)c(=O)c12]
Compound 35
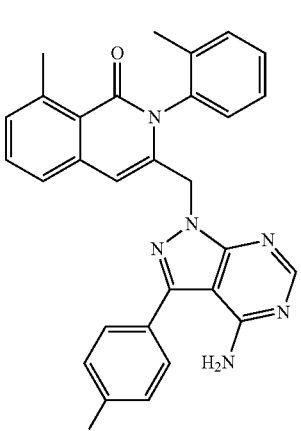
Compound 36

TABLE 4-continued
Structures of the Compounds for the IC50 results described in Table 3.
Structure
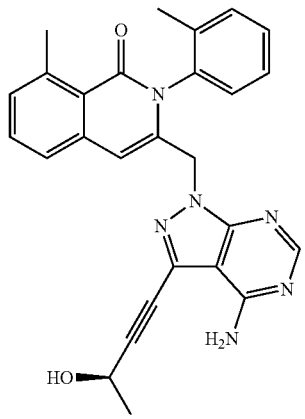 [SMILES: Cc1ccccc1-n1c(Cn2nc(C#C[C@@H](C)O)c3c(N)ncnc32)cc2cccc(C)c2c1=O]
Compound 37
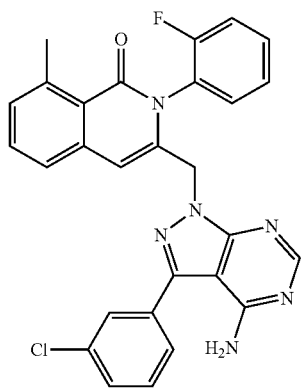 [SMILES: Cc1cccc2cc(Cn3nc(-c4cccc(Cl)c4)c4c(N)ncnc43)n(-c3ccccc3F)c(=O)c12]
Compound 38
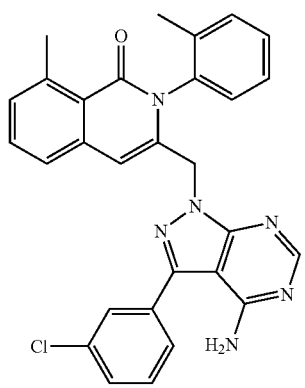 [SMILES: Cc1ccccc1-n1c(Cn2nc(-c3cccc(Cl)c3)c3c(N)ncnc32)cc2cccc(C)c2c1=O]
Compound 39
TABLE 4-continued
Structures of the Compounds for the IC50 results described in Table 3.
Structure
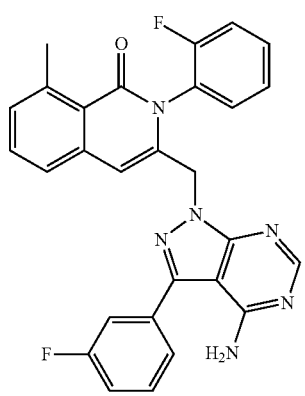 [SMILES: Cc1cccc2cc(Cn3nc(-c4cccc(F)c4)c4c(N)ncnc43)n(-c3ccccc3F)c(=O)c12]
Compound 40
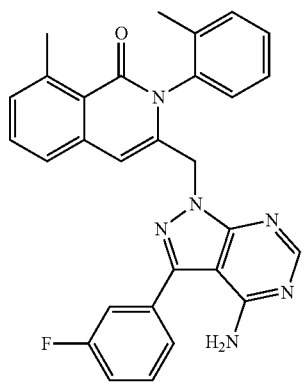 [SMILES: Cc1ccccc1-n1c(Cn2nc(-c3cccc(F)c3)c3c(N)ncnc32)cc2cccc(C)c2c1=O]
Compound 41
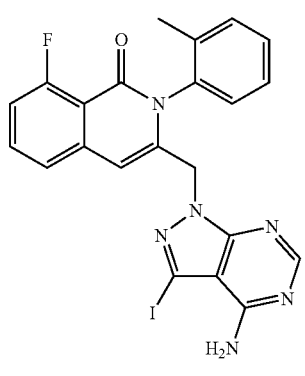 [SMILES: Cc1ccccc1-n1c(Cn2nc(I)c3c(N)ncnc32)cc2cccc(F)c2c1=O]
Compound 42

TABLE 4-continued
Structures of the Compounds for the IC50 results described in Table 3.
Structure
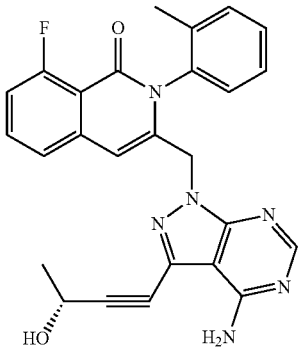 [SMILES: Cc1ccccc1-n1c(Cn2nc(C#C[C@@H](C)O)c3c(N)ncnc32)cc2cccc(F)c2c1=O]
Compound 43
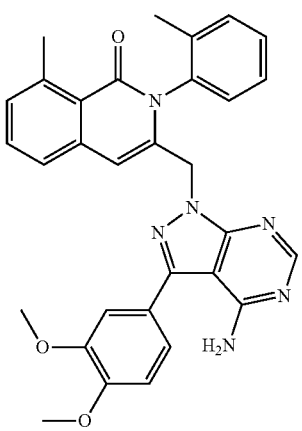 [SMILES: COc1ccc(-c2nn(Cc3cc4cccc(C)c4c(=O)n3-c3ccccc3C)c3ncnc(N)c23)cc1OC]
Compound 44
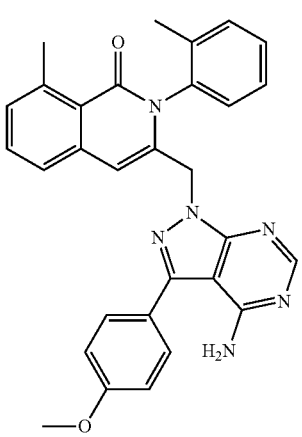 [SMILES: COc1ccc(-c2nn(Cc3cc4cccc(C)c4c(=O)n3-c3ccccc3C)c3ncnc(N)c23)cc1]
Compound 45
TABLE 4-continued
Structures of the Compounds for the IC50 results described in Table 3.
Structure
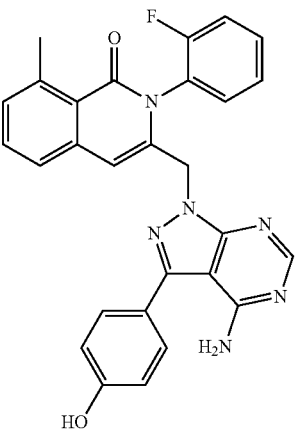 [SMILES: Cc1cccc2cc(Cn3nc(-c4ccc(O)cc4)c4c(N)ncnc43)n(-c3ccccc3F)c(=O)c12]
Compound 46
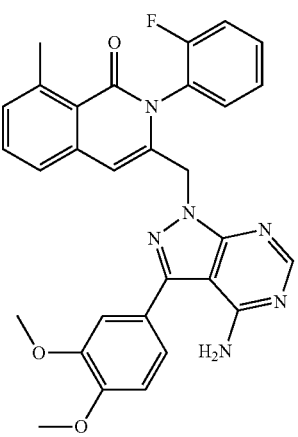 [SMILES: COc1ccc(-c2nn(Cc3cc4cccc(C)c4c(=O)n3-c3ccccc3F)c3ncnc(N)c23)cc1OC]
Compound 47
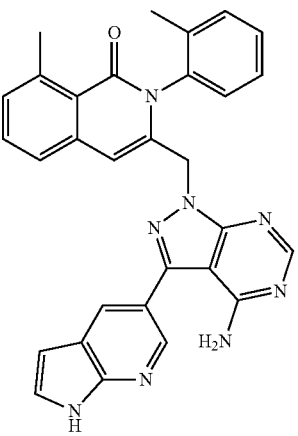 [SMILES: Cc1ccccc1-n1c(Cn2nc(-c3cnc4[nH]ccc4c3)c3c(N)ncnc32)cc2cccc(C)c2c1=O]
Compound 48

TABLE 4-continued
Structures of the Compounds for the IC50 results described in Table 3.
Structure
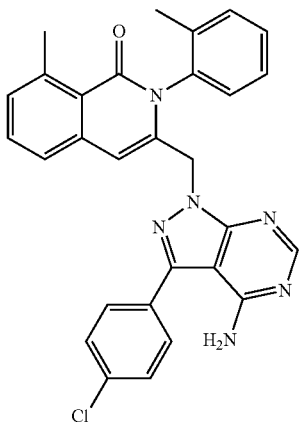 [SMILES: Cc1ccccc1-n1c(Cn2nc(-c3ccc(Cl)cc3)c3c(N)ncnc32)cc2cccc(C)c2c1=O]
Compound 49
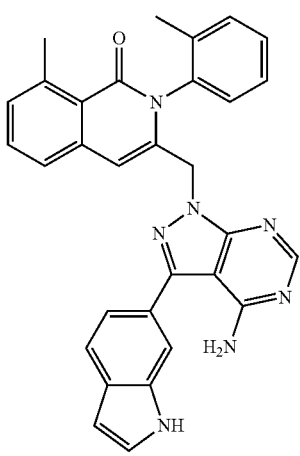 [SMILES: Cc1ccccc1-n1c(Cn2nc(-c3ccc4cc[nH]c4c3)c3c(N)ncnc32)cc2cccc(C)c2c1=O]
Compound 50
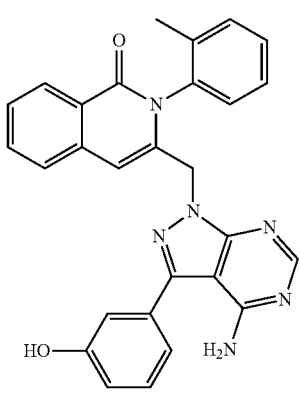 [SMILES: Cc1ccccc1-n1c(Cn2nc(-c3cccc(O)c3)c3c(N)ncnc32)cc2ccccc2c1=O]
Compound 51
TABLE 4-continued
Structures of the Compounds for the IC50 results described in Table 3.
Structure
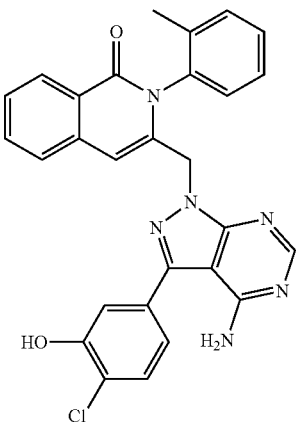 [SMILES: Cc1ccccc1-n1c(Cn2nc(-c3ccc(Cl)c(O)c3)c3c(N)ncnc32)cc2ccccc2c1=O]
Compound 52
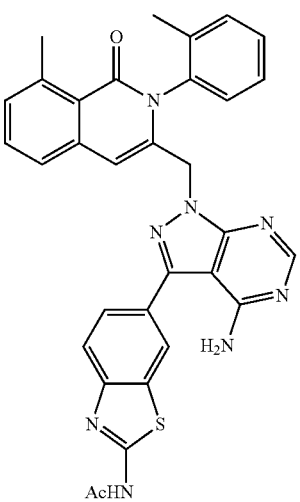 [SMILES: CC(=O)Nc1nc2ccc(-c3nn(Cc4cc5cccc(C)c5c(=O)n4-c4ccccc4C)c4ncnc(N)c34)cc2s1]
Compound 53
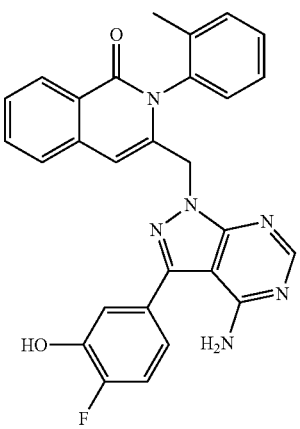 [SMILES: Cc1ccccc1-n1c(Cn2nc(-c3ccc(F)c(O)c3)c3c(N)ncnc32)cc2ccccc2c1=O]
Compound 54

TABLE 4-continued
Structures of the Compounds for the IC50 results described in Table 3.
Structure
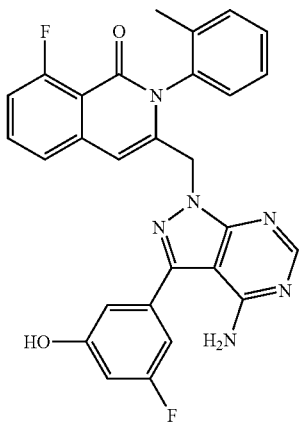 [SMILES: Cc1ccccc1-n1c(Cn2nc(-c3cc(O)cc(F)c3)c3c(N)ncnc32)cc2cccc(F)c2c1=O]
Compound 55
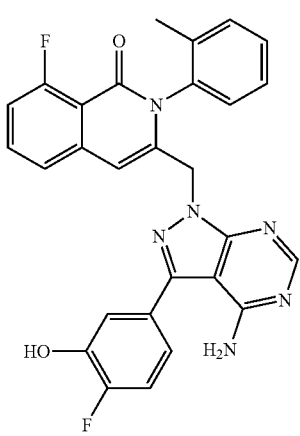 [SMILES: Cc1ccccc1-n1c(Cn2nc(-c3ccc(F)c(O)c3)c3c(N)ncnc32)cc2cccc(F)c2c1=O]
Compound 56
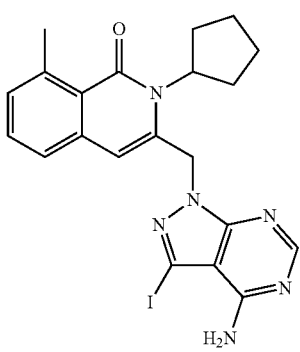 [SMILES: Cc1cccc2cc(Cn3nc(I)c4c(N)ncnc43)n(C3CCCC3)c(=O)c12]
Compound 57
TABLE 4-continued
Structures of the Compounds for the IC50 results described in Table 3.
Structure
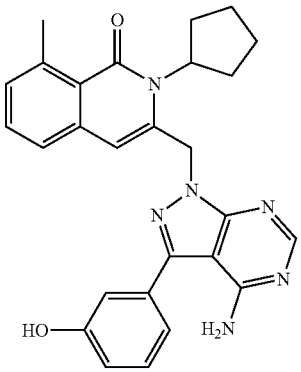 [SMILES: Cc1cccc2cc(Cn3nc(-c4cccc(O)c4)c4c(N)ncnc43)n(C3CCCC3)c(=O)c12]
Compound 58
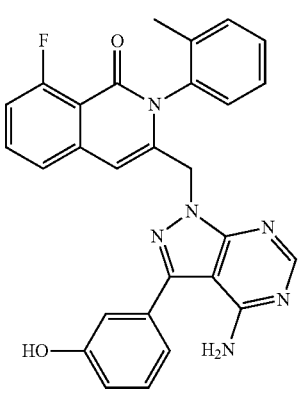
Compound 59
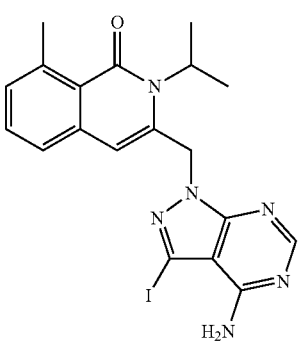
Compound 60

TABLE 4-continued
Structures of the Compounds for the IC50 results described in Table 3.
Structure
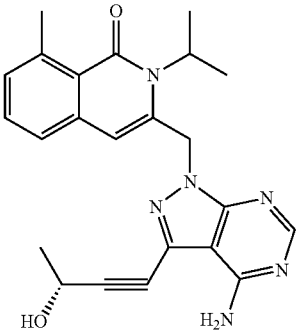 [SMILES: Cc1cccc2cc(Cn3nc(C#C[C@@H](C)O)c4c(N)ncnc43)n(C(C)C)c(=O)c12]
Compound 61
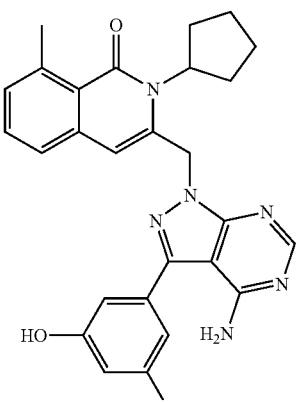
Compound 62
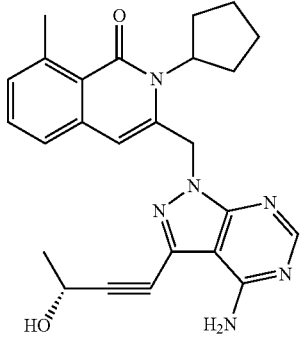
Compound 63
TABLE 4-continued
Structures of the Compounds for the IC50 results described in Table 3.
Structure
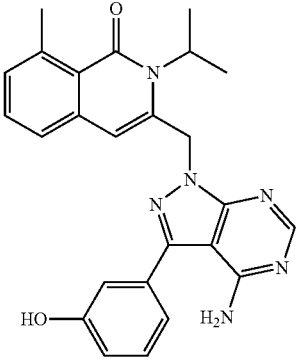 [SMILES: Cc1cccc2cc(Cn3nc(-c4cccc(O)c4)c4c(N)ncnc43)n(C(C)C)c(=O)c12]
Compound 64
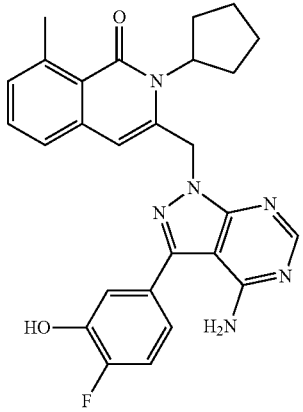 [SMILES: Cc1cccc2cc(Cn3nc(-c4ccc(F)c(O)c4)c4c(N)ncnc43)n(C3CCCC3)c(=O)c12]
Compound 65
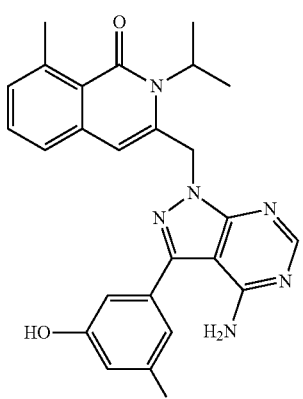
Compound 66

TABLE 4-continued
Structures of the Compounds for the IC50 results described in Table 3.
Structure
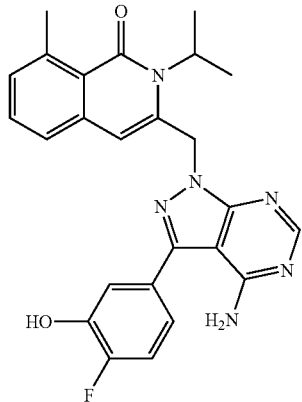 [SMILES: Cc1cccc2cc(Cn3nc(-c4ccc(F)c(O)c4)c4c(N)ncnc43)n(C(C)C)c(=O)c12]
Compound 67
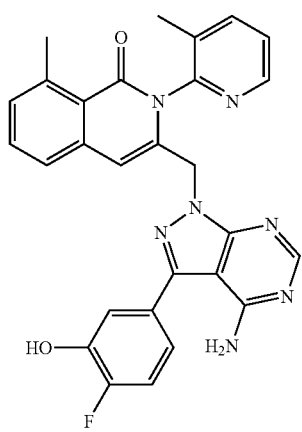
Compound 68
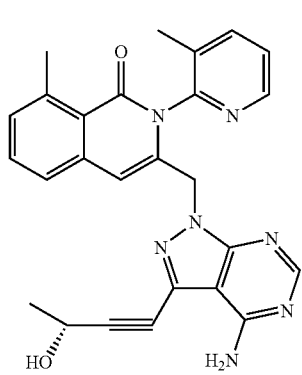 [SMILES: Cc1cccnc1-n1c(Cn2nc(C#C[C@@H](C)O)c3c(N)ncnc32)cc2cccc(C)c2c1=O]
Compound 69
TABLE 4-continued
Structures of the Compounds for the IC50 results described in Table 3.
Structure
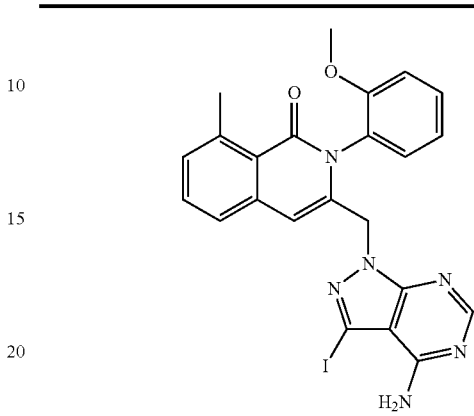
Compound 70
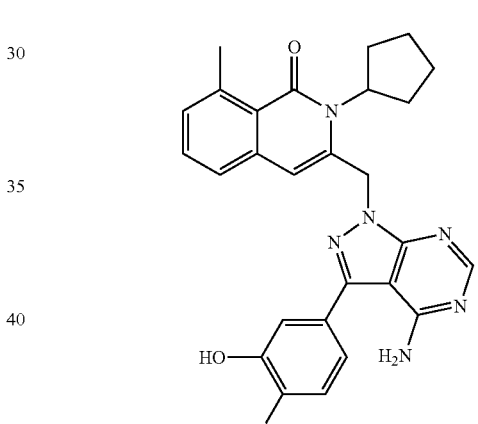
Compound 71
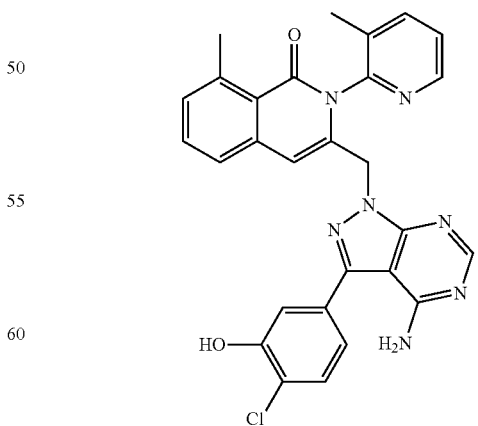
Compound 72

TABLE 4-continued
Structures of the Compounds for the IC50 results described in Table 3.
Structure
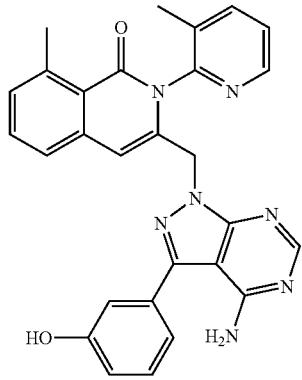 [SMILES: Cc1cccnc1-n1c(Cn2nc(-c3cccc(O)c3)c3c(N)ncnc32)cc2cccc(C)c2c1=O]
Compound 73
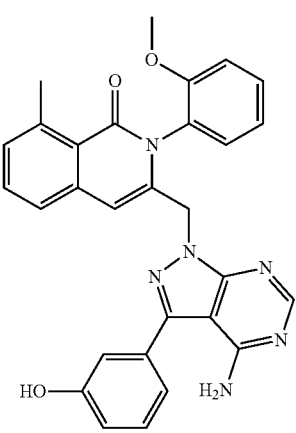 [SMILES: COc1ccccc1-n1c(Cn2nc(-c3cccc(O)c3)c3c(N)ncnc32)cc2cccc(C)c2c1=O]
Compound 74
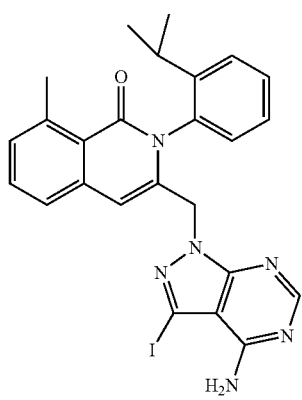 [SMILES: Cc1cccc2cc(Cn3nc(I)c4c(N)ncnc43)n(-c3ccccc3C(C)C)c(=O)c12]
Compound 75
TABLE 4-continued
Structures of the Compounds for the IC50 results described in Table 3.
Structure
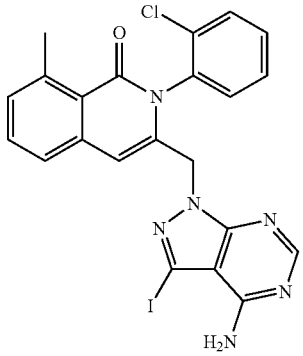
Compound 76
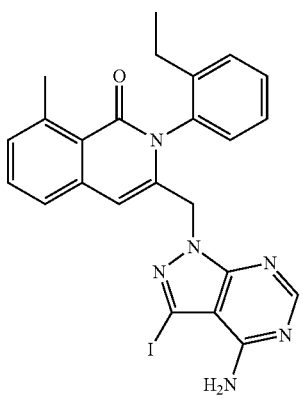 [SMILES: CCc1ccccc1-n1c(Cn2nc(I)c3c(N)ncnc32)cc2cccc(C)c2c1=O]
Compound 77
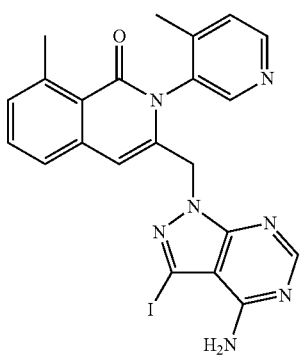
Compound 78

TABLE 4-continued

Structures of the Compounds for the IC50 results described in Table 3.

Structure

Compound 79

Compound 80

Compound 81

TABLE 4-continued

Structures of the Compounds for the IC50 results described in Table 3.

Structure

Compound 82

Compound 83

Compound 84

TABLE 4-continued
Structures of the Compounds for the IC50 results described in Table 3.
Structure
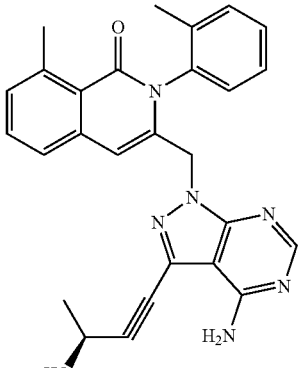
Compound 85
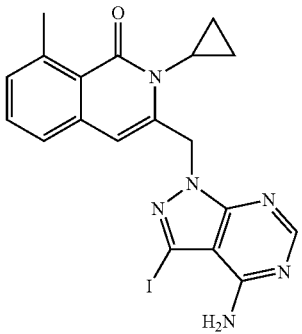
Compound 86
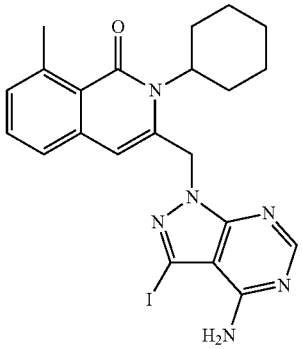
Compound 87
TABLE 4-continued
Structures of the Compounds for the IC50 results described in Table 3.
Structure
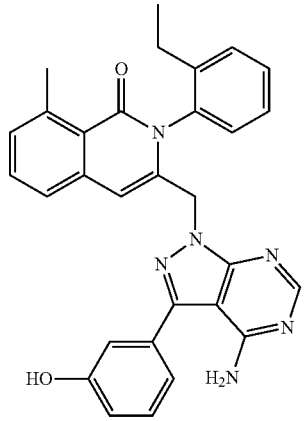 [SMILES: CCc1ccccc1-n1c(Cn2nc(-c3cccc(O)c3)c3c(N)ncnc32)cc2cccc(C)c2c1=O]
Compound 88
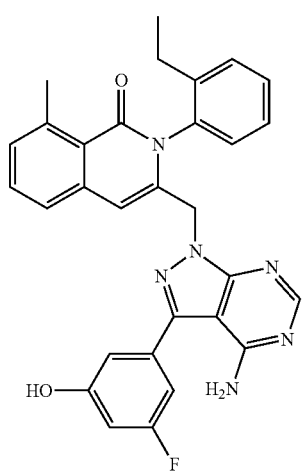 [SMILES: CCc1ccccc1-n1c(Cn2nc(-c3cc(O)cc(F)c3)c3c(N)ncnc32)cc2cccc(C)c2c1=O]
Compound 89
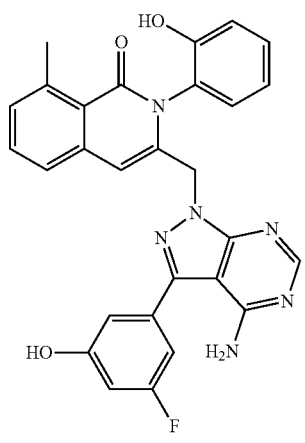 [SMILES: Cc1cccc2cc(Cn3nc(-c4cc(O)cc(F)c4)c4c(N)ncnc43)n(-c3ccccc3O)c(=O)c12]
Compound 90

TABLE 4-continued
Structures of the Compounds for the IC50 results described in Table 3.
Structure
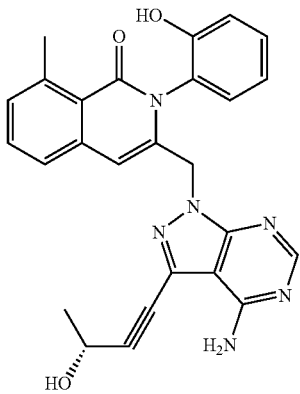 [SMILES: Cc1cccc2cc(Cn3nc(C#C[C@@H](C)O)c4c(N)ncnc43)n(-c3ccccc3O)c(=O)c12]
Compound 91
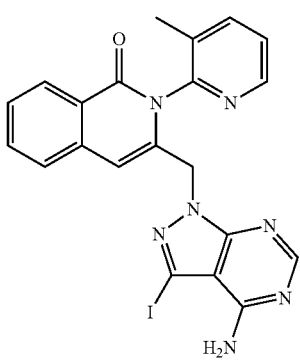 [SMILES: Cc1cccnc1-n1c(Cn2nc(I)c3c(N)ncnc32)cc2ccccc2c1=O]
Compound 92
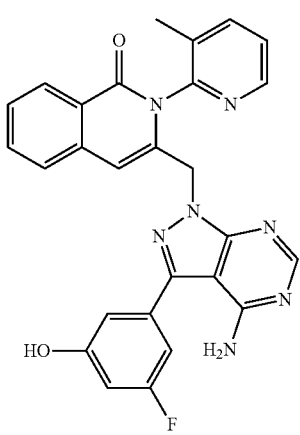 [SMILES: Cc1cccnc1-n1c(Cn2nc(-c3cc(O)cc(F)c3)c3c(N)ncnc32)cc2ccccc2c1=O]
Compound 93
TABLE 4-continued
Structures of the Compounds for the IC50 results described in Table 3.
Structure
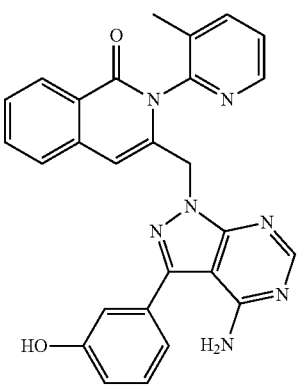 [SMILES: Cc1cccnc1-n1c(Cn2nc(-c3cccc(O)c3)c3c(N)ncnc32)cc2ccccc2c1=O]
Compound 94
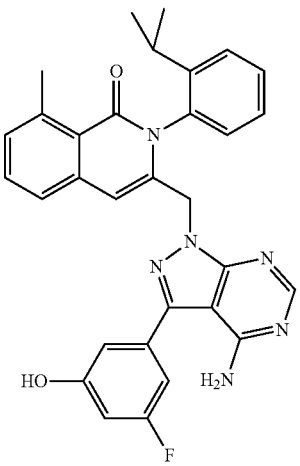 [SMILES: Cc1cccc2cc(Cn3nc(-c4cc(O)cc(F)c4)c4c(N)ncnc43)n(-c3ccccc3C(C)C)c(=O)c12]
Compound 95
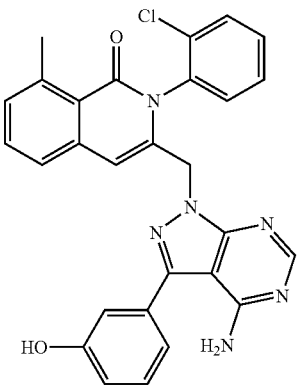 [SMILES: Cc1cccc2cc(Cn3nc(-c4cccc(O)c4)c4c(N)ncnc43)n(-c3ccccc3Cl)c(=O)c12]
Compound 96

283
TABLE 4-continued
Structures of the Compounds for the IC50 results described in Table 3.
Structure
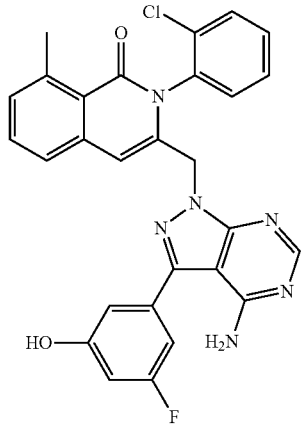 [SMILES: Cc1cccc2cc(Cn3nc(-c4cc(O)cc(F)c4)c4c(N)ncnc43)n(-c3ccccc3Cl)c(=O)c12]
Compound 97
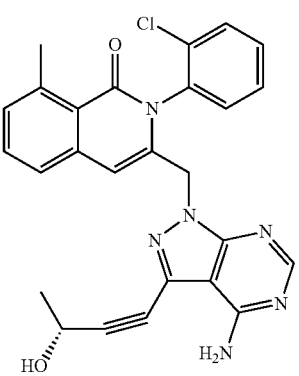 [SMILES: Cc1cccc2cc(Cn3nc(C#C[C@@H](C)O)c4c(N)ncnc43)n(-c3ccccc3Cl)c(=O)c12]
Compound 98
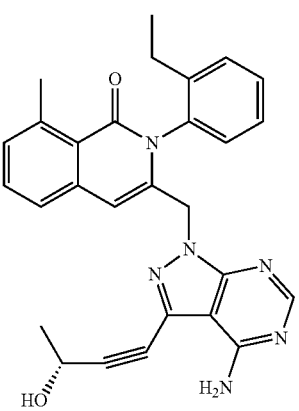 [SMILES: CCc1ccccc1-n1c(Cn2nc(C#C[C@@H](C)O)c3c(N)ncnc32)cc2cccc(C)c2c1=O]
Compound 99
284
TABLE 4-continued
Structures of the Compounds for the IC50 results described in Table 3.
Structure
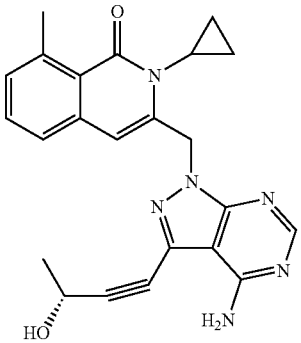 [SMILES: Cc1cccc2cc(Cn3nc(C#C[C@@H](C)O)c4c(N)ncnc43)n(C3CC3)c(=O)c12]
Compound 100
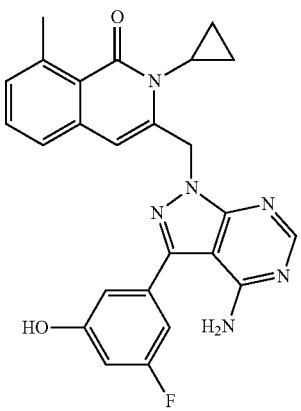
Compound 101
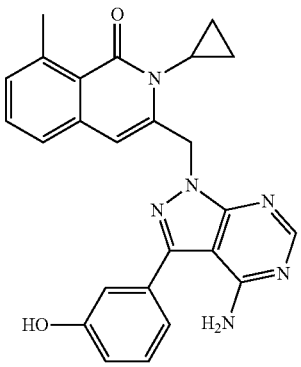 [SMILES: Cc1cccc2cc(Cn3nc(-c4cccc(O)c4)c4c(N)ncnc43)n(C3CC3)c(=O)c12]
Compound 102

285
TABLE 4-continued
Structures of the Compounds for the IC50 results described in Table 3.
Structure
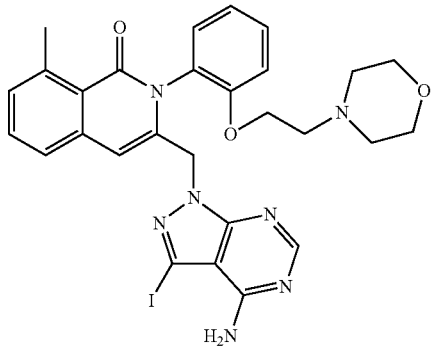 [SMILES: Cc1cccc2cc(Cn3nc(I)c4c(N)ncnc43)n(-c3ccccc3OCCN3CCOCC3)c(=O)c12]
Compound 103
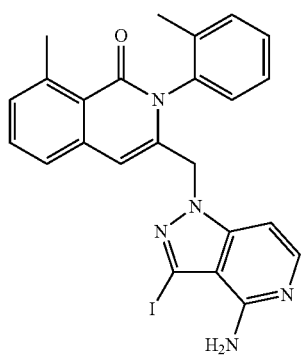 [SMILES: Cc1ccccc1-n1c(Cn2nc(I)c3c(N)nccc32)cc2cccc(C)c2c1=O]
Compound 104
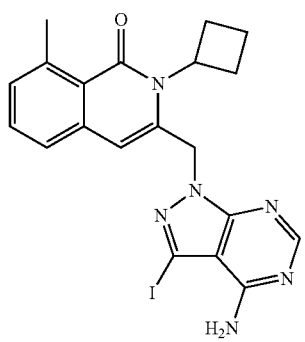 [SMILES: Cc1cccc2cc(Cn3nc(I)c4c(N)ncnc43)n(C3CCC3)c(=O)c12]
Compound 105
286
TABLE 4-continued
Structures of the Compounds for the IC50 results described in Table 3.
Structure
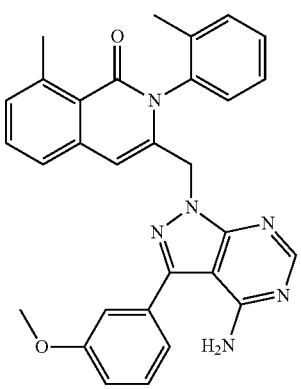 [SMILES: COc1cccc(-c2nn(Cc3cc4cccc(C)c4c(=O)n3-c3ccccc3C)c3ncnc(N)c23)c1]
Compound 106
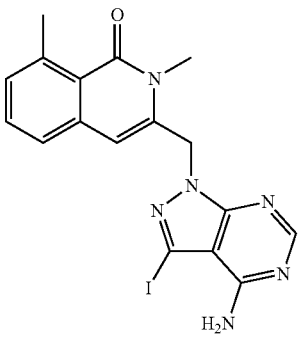 [SMILES: Cc1cccc2cc(Cn3nc(I)c4c(N)ncnc43)n(C)c(=O)c12]
Compound 107
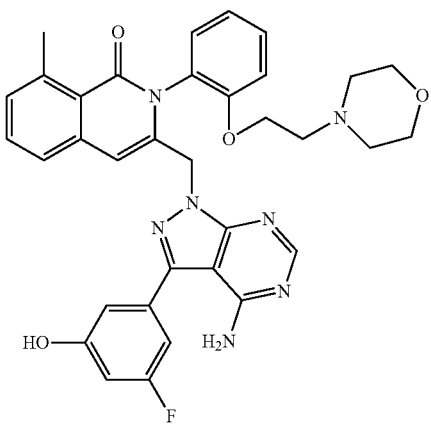 [SMILES: Cc1cccc2cc(Cn3nc(-c4cc(O)cc(F)c4)c4c(N)ncnc43)n(-c3ccccc3OCCN3CCOCC3)c(=O)c12]
Compound 108

TABLE 4-continued
Structures of the Compounds for the IC50 results described in Table 3.
Structure
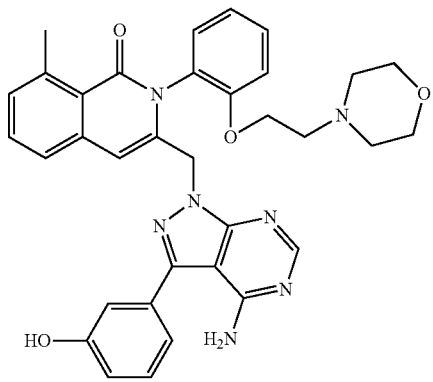 [SMILES: Cc1cccc2cc(Cn3nc(-c4cccc(O)c4)c4c(N)ncnc43)n(-c3ccccc3OCCN3CCOCC3)c(=O)c12]
Compound 109
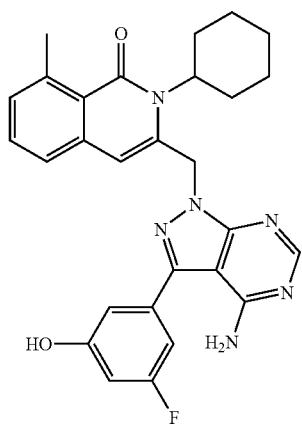 [SMILES: Cc1cccc2cc(Cn3nc(-c4cc(O)cc(F)c4)c4c(N)ncnc43)n(C3CCCCC3)c(=O)c12]
Compound 110
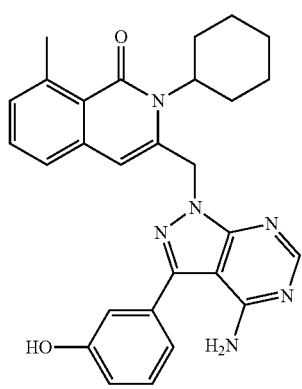 [SMILES: Cc1cccc2cc(Cn3nc(-c4cccc(O)c4)c4c(N)ncnc43)n(C3CCCCC3)c(=O)c12]
Compound 111
TABLE 4-continued
Structures of the Compounds for the IC50 results described in Table 3.
Structure
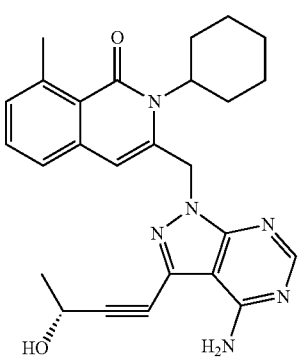 [SMILES: Cc1cccc2cc(Cn3nc(C#C[C@@H](C)O)c4c(N)ncnc43)n(C3CCCCC3)c(=O)c12]
Compound 112
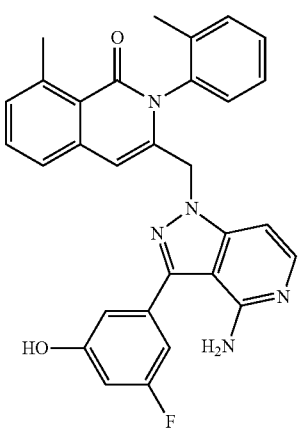 [SMILES: Cc1ccccc1-n1c(Cn2nc(-c3cc(O)cc(F)c3)c3c(N)nccc32)cc2cccc(C)c2c1=O]
Compound 113
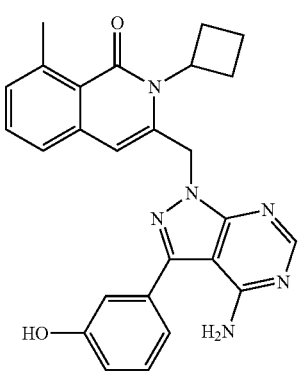 [SMILES: Cc1cccc2cc(Cn3nc(-c4cccc(O)c4)c4c(N)ncnc43)n(C3CCC3)c(=O)c12]
Compound 114

TABLE 4-continued
Structures of the Compounds for the IC50 results described in Table 3.
Structure
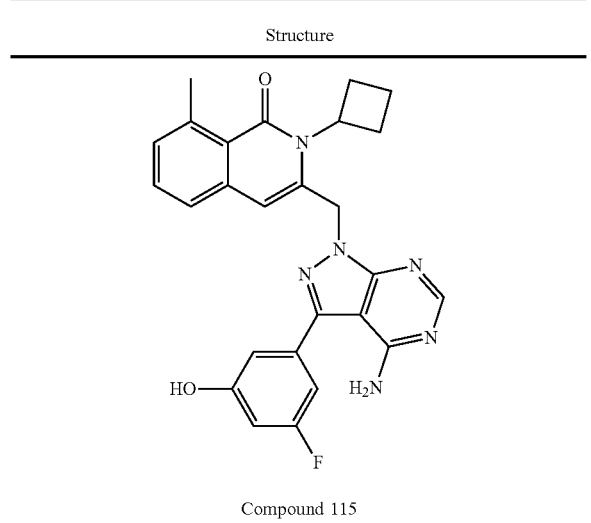
Compound 115
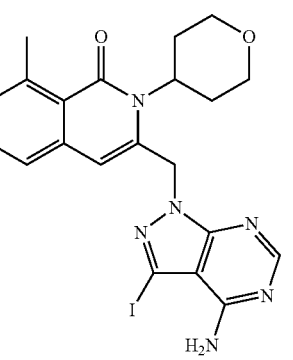
Compound 116
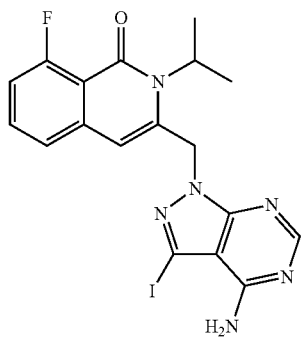 [SMILES: CC(C)n1c(Cn2nc(I)c3c(N)ncnc32)cc2cccc(F)c2c1=O]
Compound 117
TABLE 4-continued
Structures of the Compounds for the IC50 results described in Table 3.
Structure
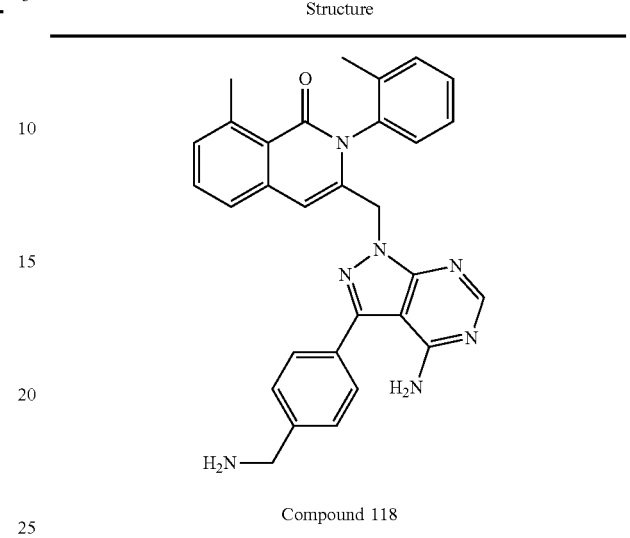
Compound 118
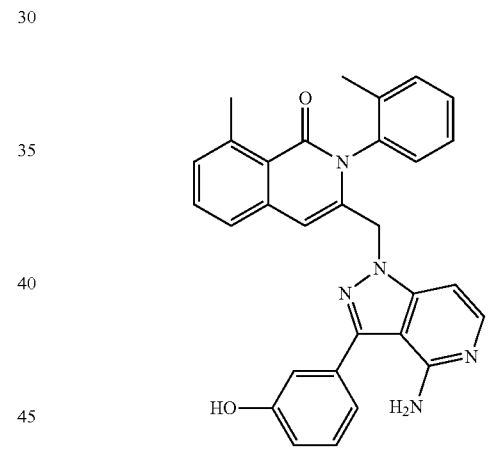
Compound 119
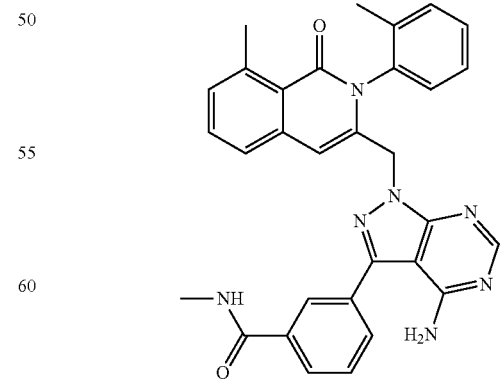
Compound 120

TABLE 4-continued
Structures of the Compounds for the IC50 results described in Table 3.
Structure
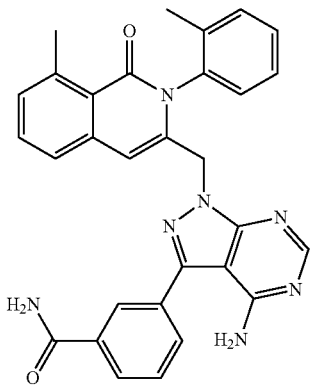 [SMILES: Cc1ccccc1-n1c(Cn2nc(-c3cccc(C(N)=O)c3)c3c(N)ncnc32)cc2cccc(C)c2c1=O]
Compound 121
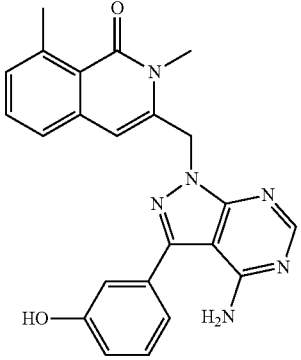
Compound 124
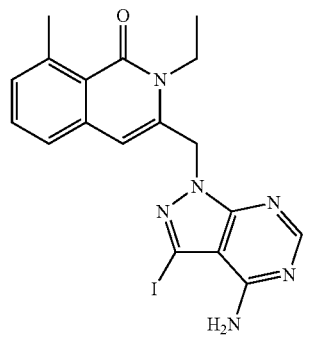 [SMILES: CCn1c(Cn2nc(I)c3c(N)ncnc32)cc2cccc(C)c2c1=O]
Compound 122
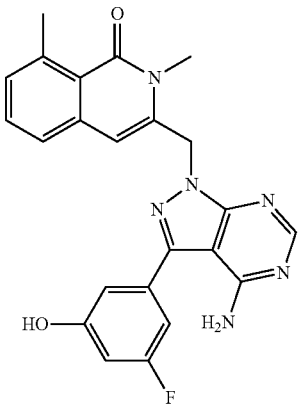
Compound 125
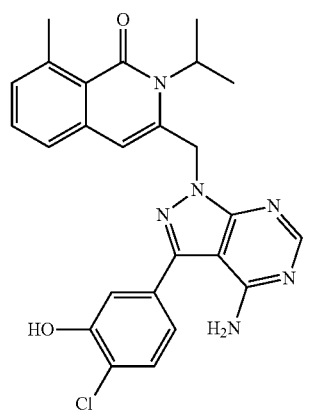 [SMILES: Cc1cccc2cc(Cn3nc(-c4ccc(Cl)c(O)c4)c4c(N)ncnc43)n(C(C)C)c(=O)c12]
Compound 123
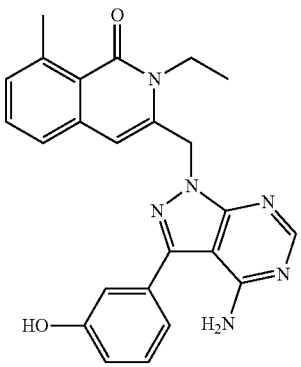 [SMILES: CCn1c(Cn2nc(-c3cccc(O)c3)c3c(N)ncnc32)cc2cccc(C)c2c1=O]
Compound 126

TABLE 4-continued
Structures of the Compounds for the IC50 results described in Table 3.
Structure
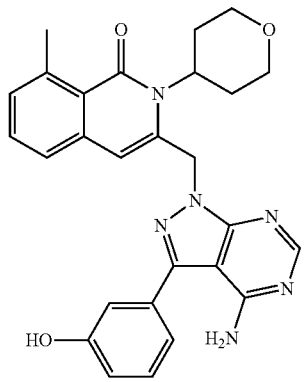 [SMILES: Cc1cccc2cc(Cn3nc(-c4cccc(O)c4)c4c(N)ncnc43)n(C3CCOCC3)c(=O)c12]
Compound 127
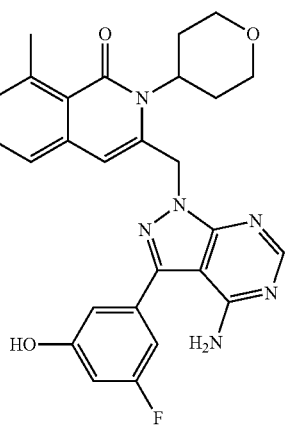
Compound 128
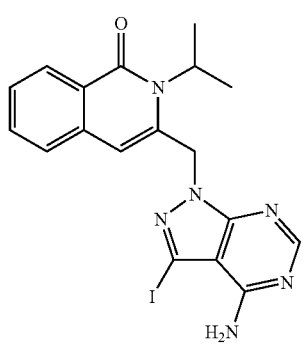 [SMILES: CC(C)n1c(Cn2nc(I)c3c(N)ncnc32)cc2ccccc2c1=O]
Compound 129
TABLE 4-continued
Structures of the Compounds for the IC50 results described in Table 3.
Structure
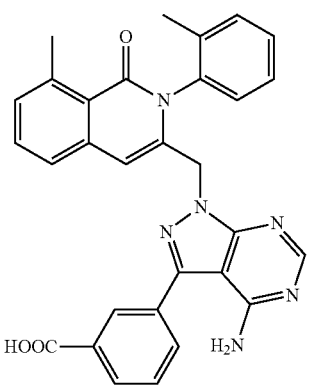 [SMILES: Cc1ccccc1-n1c(Cn2nc(-c3cccc(C(=O)O)c3)c3c(N)ncnc32)cc2cccc(C)c2c1=O]
Compound 130
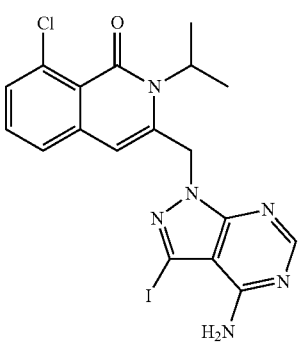 [SMILES: CC(C)n1c(Cn2nc(I)c3c(N)ncnc32)cc2cccc(Cl)c2c1=O]
Compound 131
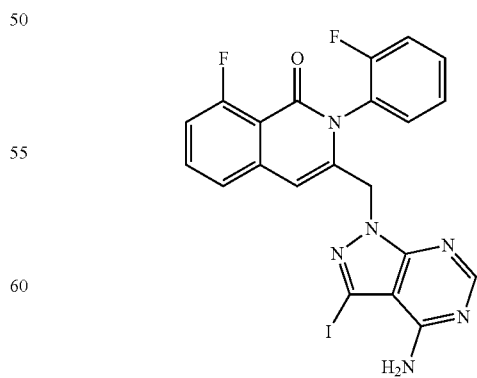
Compound 132

TABLE 4-continued
Structures of the Compounds for the IC50 results described in Table 3.
Structure
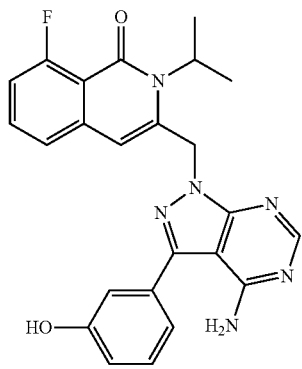 [SMILES: CC(C)n1c(Cn2nc(-c3cccc(O)c3)c3c(N)ncnc32)cc2cccc(F)c2c1=O]
Compound 133
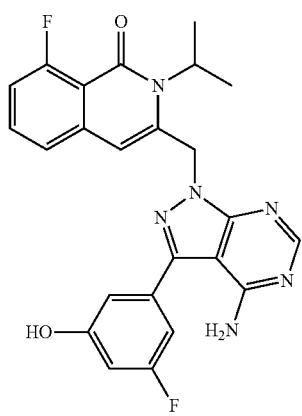
Compound 134
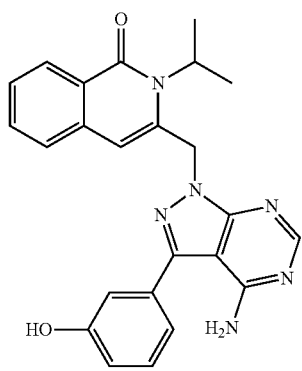 [SMILES: CC(C)n1c(Cn2nc(-c3cccc(O)c3)c3c(N)ncnc32)cc2ccccc2c1=O]
Compound 135
TABLE 4-continued
Structures of the Compounds for the IC50 results described in Table 3.
Structure
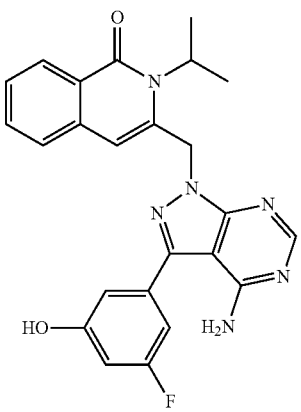 [SMILES: CC(C)n1c(Cn2nc(-c3cc(O)cc(F)c3)c3c(N)ncnc32)cc2ccccc2c1=O]
Compound 136
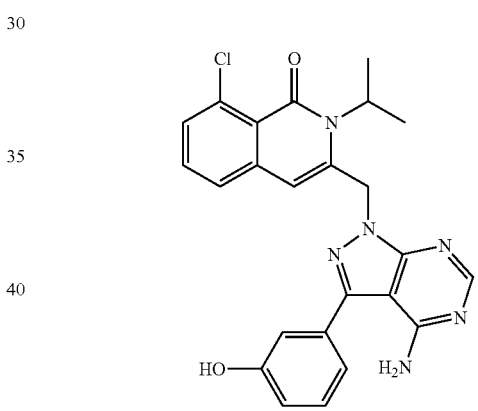
Compound 137
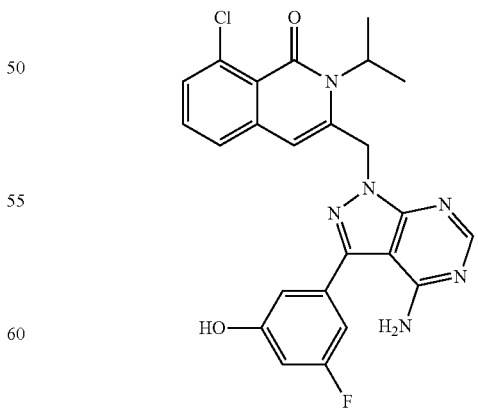
Compound 138

TABLE 4-continued
Structures of the Compounds for the IC50 results described in Table 3.
Structure
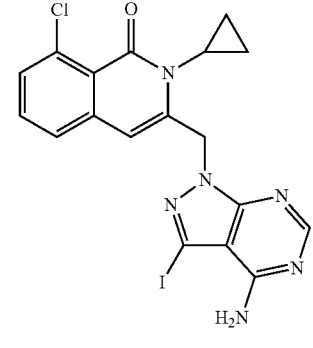 [SMILES: Nc1ncnc2c1c(I)nn2Cc1cc2cccc(Cl)c2c(=O)n1C1CC1]
Compound 139
Compound 141
Compound 142
Compound 143
Compound 144
Compound 145

TABLE 4-continued
Structures of the Compounds for the IC50 results described in Table 3.
Structure
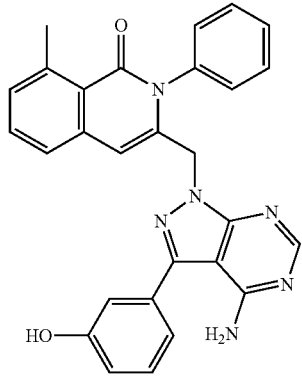 [SMILES: Cc1cccc2cc(Cn3nc(-c4cccc(O)c4)c4c(N)ncnc43)n(-c3ccccc3)c(=O)c12]
Compound 146
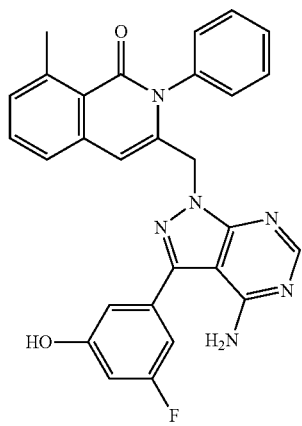 [SMILES: Cc1cccc2cc(Cn3nc(-c4cc(O)cc(F)c4)c4c(N)ncnc43)n(-c3ccccc3)c(=O)c12]
Compound 147
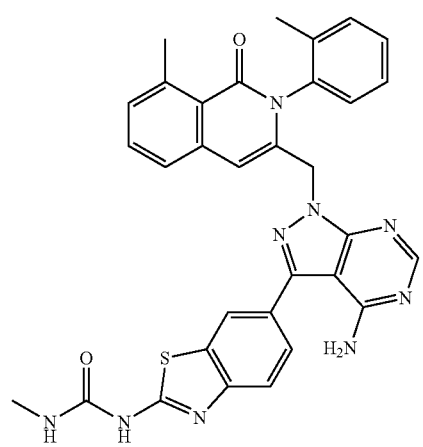 [SMILES: CNC(=O)Nc1nc2ccc(-c3nn(Cc4cc5cccc(C)c5c(=O)n4-c4ccccc4C)c4ncnc(N)c34)cc2s1]
Compound 148
TABLE 4-continued
Structures of the Compounds for the IC50 results described in Table 3.
Structure
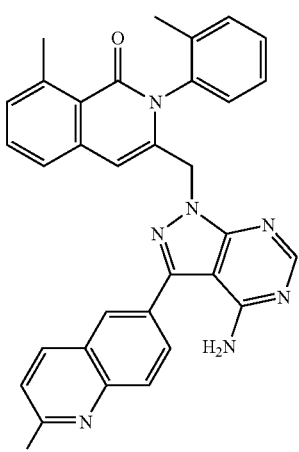
Compound 149
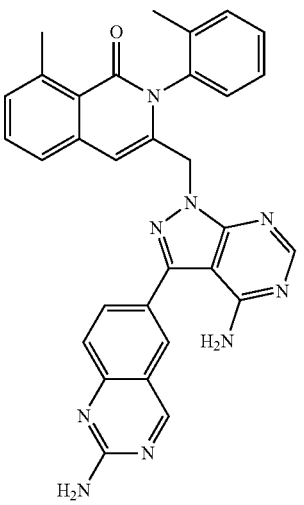 [SMILES: Cc1ccccc1-n1c(Cn2nc(-c3ccc4nc(N)ncc4c3)c3c(N)ncnc32)cc2cccc(C)c2c1=O]
Compound 150

TABLE 4-continued
Structures of the Compounds for the IC50 results described in Table 3.
Structure
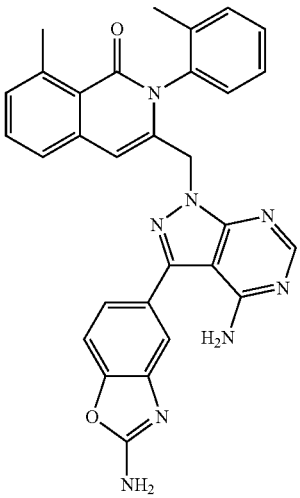 [SMILES: Cc1ccccc1-n1c(Cn2nc(-c3ccc4oc(N)nc4c3)c3c(N)ncnc32)cc2cccc(C)c2c1=O]
Compound 151
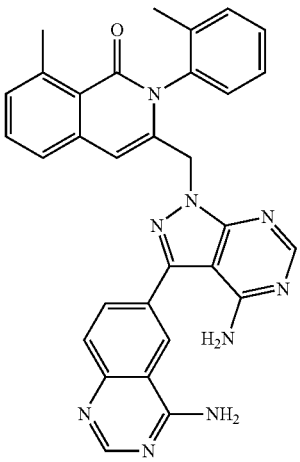 [SMILES: Cc1ccccc1-n1c(Cn2nc(-c3ccc4ncnc(N)c4c3)c3c(N)ncnc32)cc2cccc(C)c2c1=O]
Compound 152
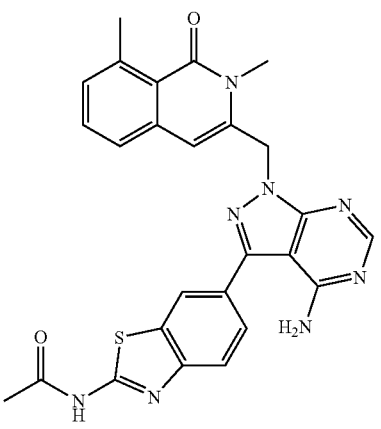 [SMILES: CC(=O)Nc1nc2ccc(-c3nn(Cc4cc5cccc(C)c5c(=O)n4C)c4ncnc(N)c34)cc2s1]
Compound 153
TABLE 4-continued
Structures of the Compounds for the IC50 results described in Table 3.
Structure
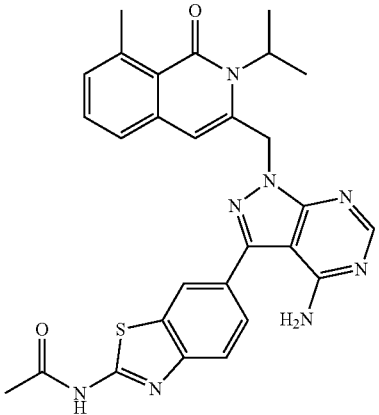 [SMILES: CC(=O)Nc1nc2ccc(-c3nn(Cc4cc5cccc(C)c5c(=O)n4C(C)C)c4ncnc(N)c34)cc2s1]
Compound 154
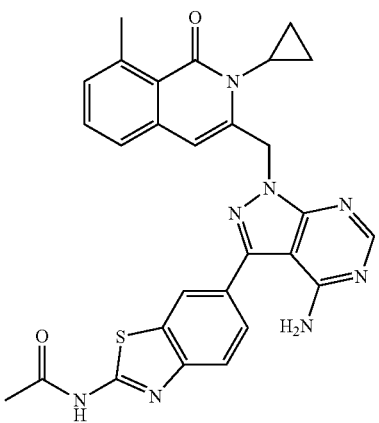 [SMILES: CC(=O)Nc1nc2ccc(-c3nn(Cc4cc5cccc(C)c5c(=O)n4C4CC4)c4ncnc(N)c34)cc2s1]
Compound 155
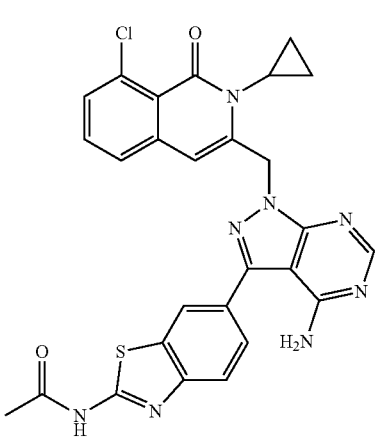 [SMILES: CC(=O)Nc1nc2ccc(-c3nn(Cc4cc5cccc(Cl)c5c(=O)n4C4CC4)c4ncnc(N)c34)cc2s1]
Compound 156

TABLE 4-continued

Structures of the Compounds for the IC50 results described in Table 3.

Structure

Compound 157

Compound 158

Compound 159

TABLE 4-continued

Structures of the Compounds for the IC50 results described in Table 3.

Structure

Compound 160

Compound 161

Compound 162

TABLE 4-continued
Structures of the Compounds for the IC50 results described in Table 3.
Structure
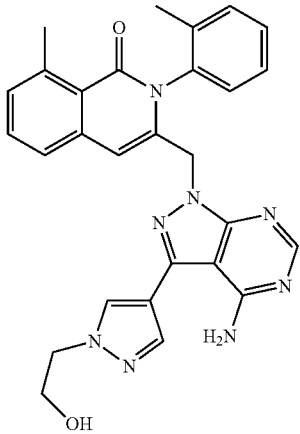 [SMILES: Cc1ccccc1-n1c(Cn2nc(-c3cnn(CCO)c3)c3c(N)ncnc32)cc2cccc(C)c2c1=O]
Compound 163
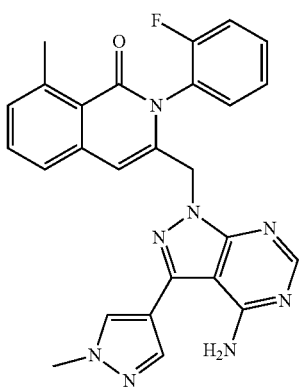 [SMILES: Cc1cccc2cc(Cn3nc(-c4cnn(C)c4)c4c(N)ncnc43)n(-c3ccccc3F)c(=O)c12]
Compound 164
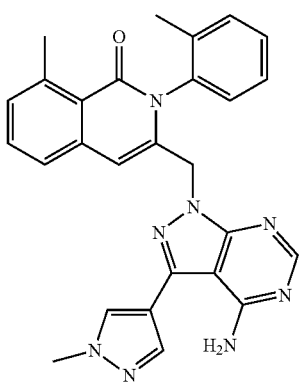 [SMILES: Cc1ccccc1-n1c(Cn2nc(-c3cnn(C)c3)c3c(N)ncnc32)cc2cccc(C)c2c1=O]
Compound 165
TABLE 4-continued
Structures of the Compounds for the IC50 results described in Table 3.
Structure
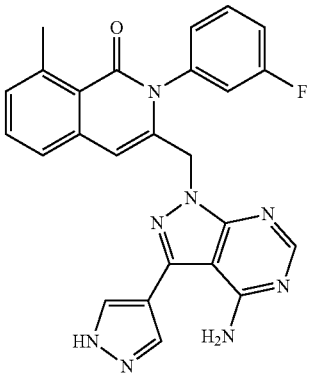 [SMILES: Cc1cccc2cc(Cn3nc(-c4cn[nH]c4)c4c(N)ncnc43)n(-c3cccc(F)c3)c(=O)c12]
Compound 166
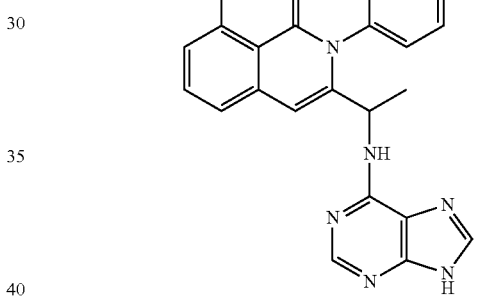
Compound 167
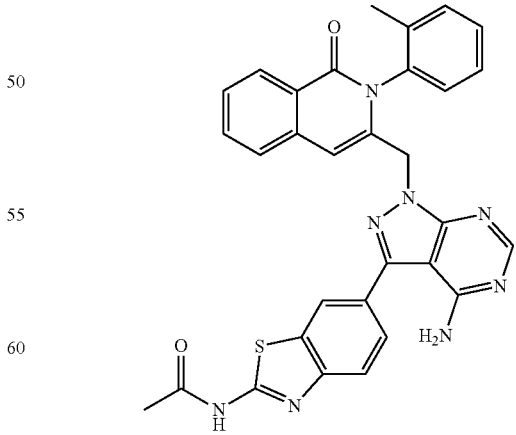
Compound 168

TABLE 4-continued
Structures of the Compounds for the IC50 results described in Table 3.
Structure
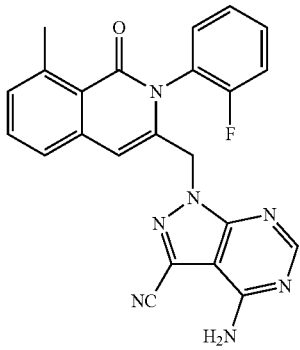 [SMILES: Cc1cccc2cc(Cn3nc(C#N)c4c(N)ncnc43)n(-c3ccccc3F)c(=O)c12]
Compound 169
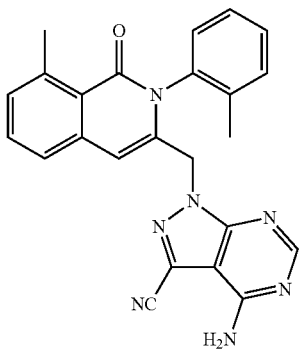 [SMILES: Cc1ccccc1-n1c(Cn2nc(C#N)c3c(N)ncnc32)cc2cccc(C)c2c1=O]
Compound 170
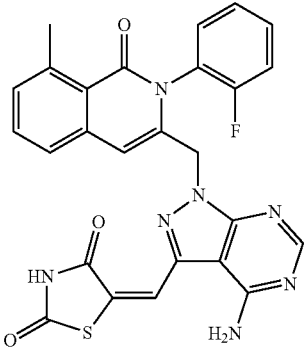 [SMILES: Cc1cccc2cc(Cn3nc(/C=C4/SC(=O)NC4=O)c4c(N)ncnc43)n(-c3ccccc3F)c(=O)c12]
Compound 171
TABLE 4-continued
Structures of the Compounds for the IC50 results described in Table 3.
Structure
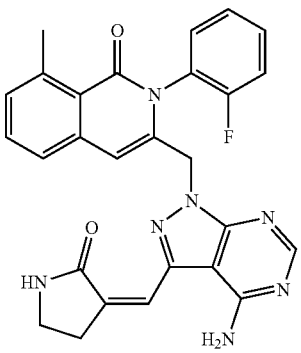 [SMILES: Cc1cccc2cc(Cn3nc(/C=C4/CCNC4=O)c4c(N)ncnc43)n(-c3ccccc3F)c(=O)c12]
Compound 172
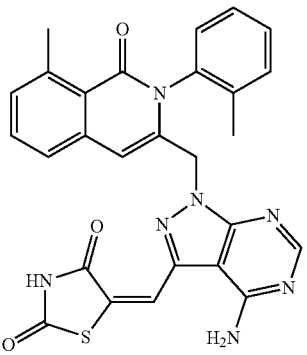 [SMILES: Cc1ccccc1-n1c(Cn2nc(/C=C3/SC(=O)NC3=O)c3c(N)ncnc32)cc2cccc(C)c2c1=O]
Compound 173
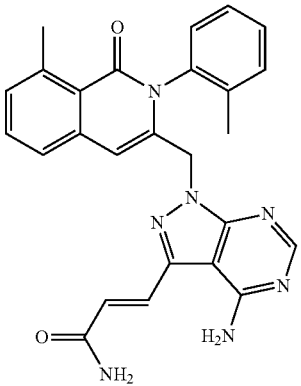 [SMILES: Cc1ccccc1-n1c(Cn2nc(/C=C/C(N)=O)c3c(N)ncnc32)cc2cccc(C)c2c1=O]
Compound 174

TABLE 4-continued
Structures of the Compounds for the IC50 results described in Table 3.
Structure
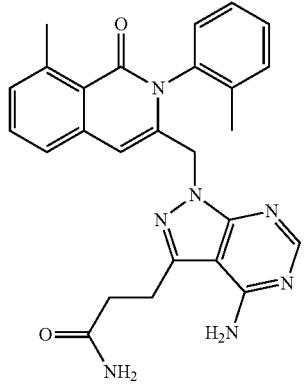 [SMILES: Cc1ccccc1-n1c(Cn2nc(CCC(N)=O)c3c(N)ncnc32)cc2cccc(C)c2c1=O]
Compound 175
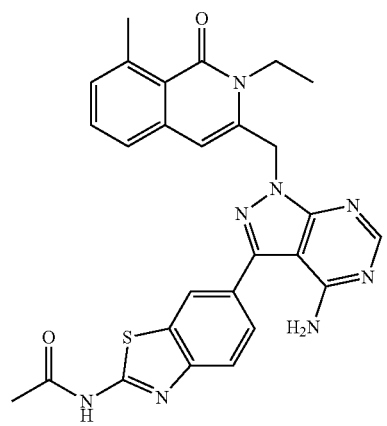 [SMILES: CCn1c(Cn2nc(-c3ccc4nc(NC(C)=O)sc4c3)c3c(N)ncnc32)cc2cccc(C)c2c1=O]
Compound 176
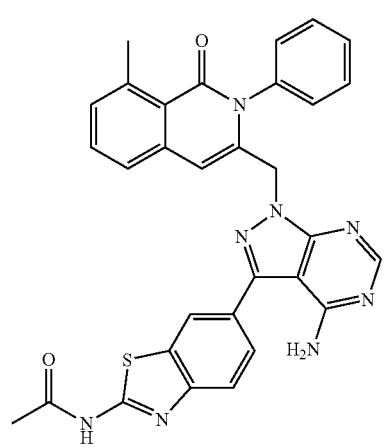 [SMILES: CC(=O)Nc1nc2ccc(-c3nn(Cc4cc5cccc(C)c5c(=O)n4-c4ccccc4)c4ncnc(N)c34)cc2s1]
Compound 177
TABLE 4-continued
Structures of the Compounds for the IC50 results described in Table 3.
Structure
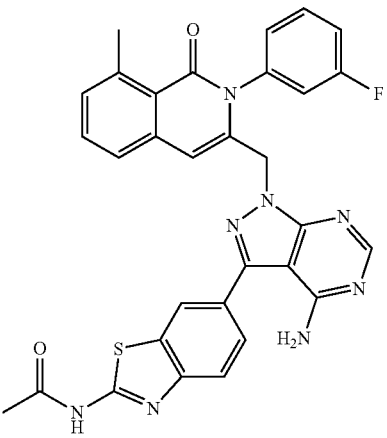 [SMILES: CC(=O)Nc1nc2ccc(-c3nn(Cc4cc5cccc(C)c5c(=O)n4-c4cccc(F)c4)c4ncnc(N)c34)cc2s1]
Compound 178
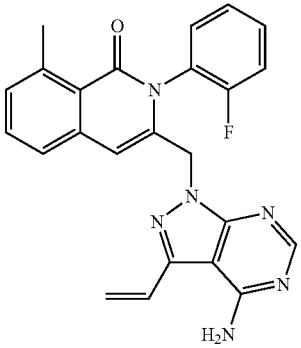
Compound 179
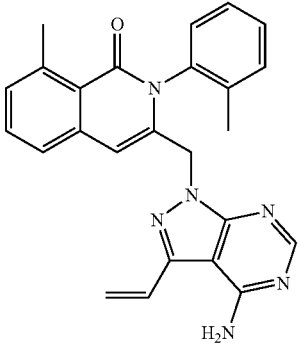 [SMILES: C=Cc1nn(Cc2cc3cccc(C)c3c(=O)n2-c2ccccc2C)c2ncnc(N)c12]
Compound 180

TABLE 4-continued
Structures of the Compounds for the IC50 results described in Table 3.
Structure
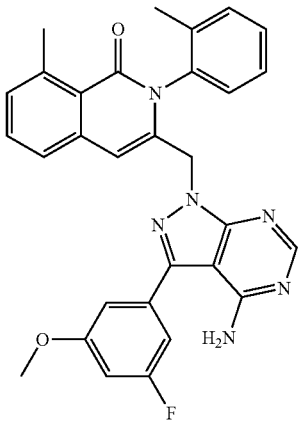 [SMILES: COc1cc(F)cc(-c2nn(Cc3cc4cccc(C)c4c(=O)n3-c3ccccc3C)c3ncnc(N)c23)c1]
Compound 181
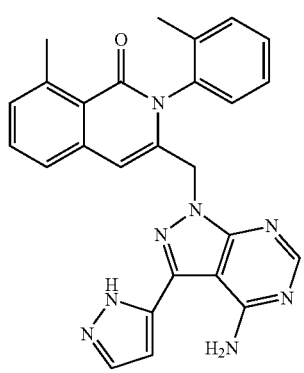 [SMILES: Cc1ccccc1-n1c(Cn2nc(-c3ccn[nH]3)c3c(N)ncnc32)cc2cccc(C)c2c1=O]
Compound 182
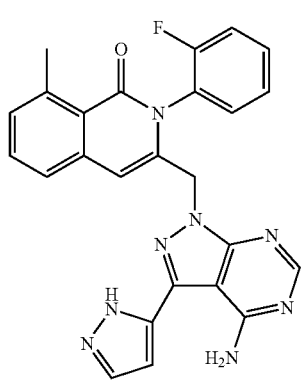 [SMILES: Cc1cccc2cc(Cn3nc(-c4ccn[nH]4)c4c(N)ncnc43)n(-c3ccccc3F)c(=O)c12]
Compound 183
TABLE 4-continued
Structures of the Compounds for the IC50 results described in Table 3.
Structure
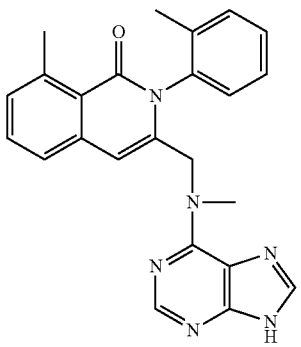 [SMILES: Cc1ccccc1-n1c(CN(C)c2ncnc3[nH]cnc23)cc2cccc(C)c2c1=O]
Compound 184
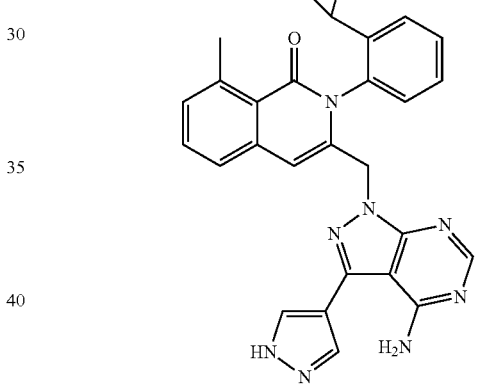
Compound 185
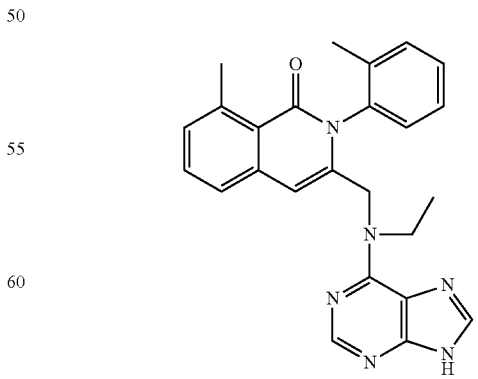
Compound 186

TABLE 4-continued
Structures of the Compounds for the IC50 results described in Table 3.
Structure
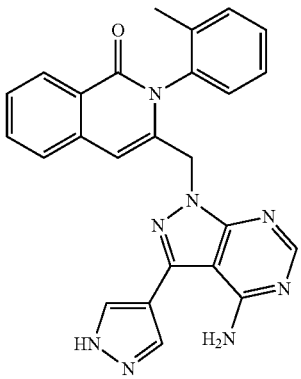 [SMILES: Cc1ccccc1-n1c(Cn2nc(-c3cn[nH]c3)c3c(N)ncnc32)cc2ccccc2c1=O]
Compound 187
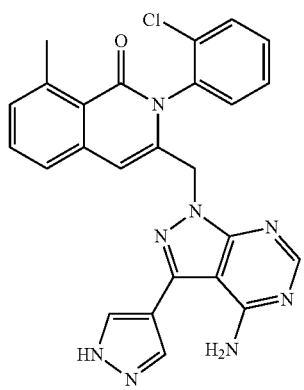
Compound 188
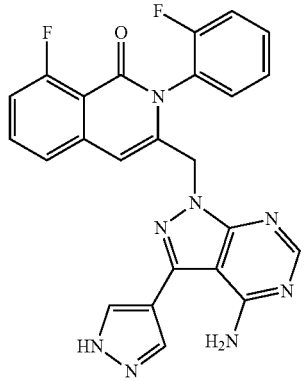 [SMILES: Nc1ncnc2c1c(-c1cn[nH]c1)nn2Cc1cc2cccc(F)c2c(=O)n1-c1ccccc1F]
Compound 189
TABLE 4-continued
Structures of the Compounds for the IC50 results described in Table 3.
Structure
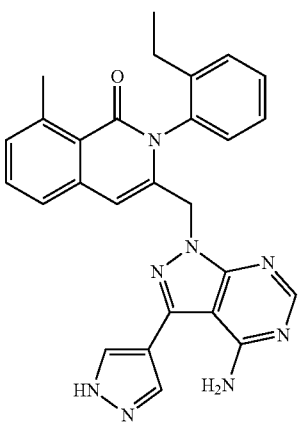 [SMILES: CCc1ccccc1-n1c(Cn2nc(-c3cn[nH]c3)c3c(N)ncnc32)cc2cccc(C)c2c1=O]
Compound 190
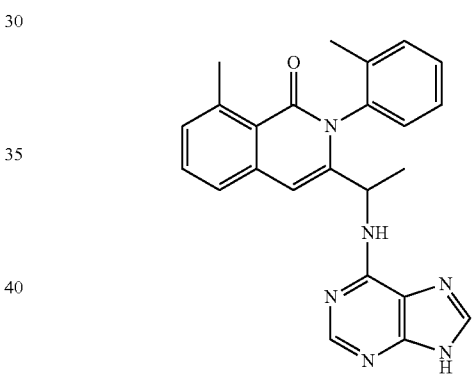
Compound 191
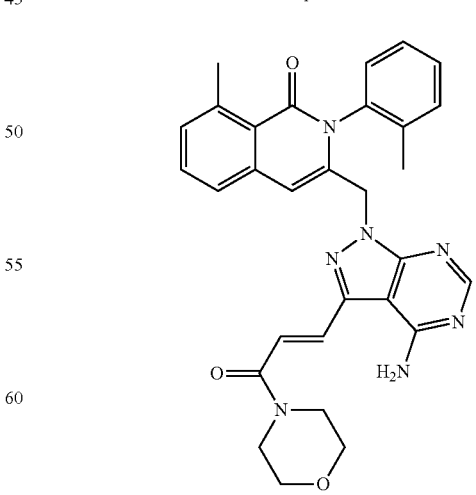
Compound 192

TABLE 4-continued
Structures of the Compounds for the IC50 results described in Table 3.
Structure
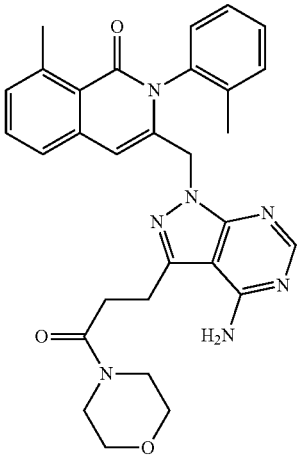 [SMILES: Cc1ccccc1-n1c(Cn2nc(CCC(=O)N3CCOCC3)c3c(N)ncnc32)cc2cccc(C)c2c1=O]
Compound 193
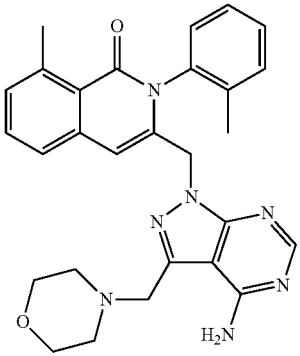 [SMILES: Cc1ccccc1-n1c(Cn2nc(CN3CCOCC3)c3c(N)ncnc32)cc2cccc(C)c2c1=O]
Compound 194
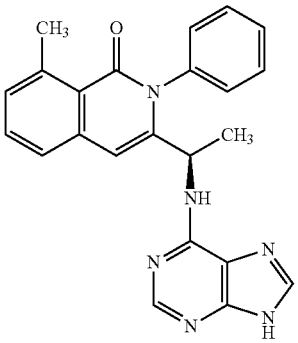 [SMILES: Cc1cccc2cc([C@@H](C)Nc3ncnc4[nH]cnc34)n(-c3ccccc3)c(=O)c12]
Compound 195
TABLE 4-continued
Structures of the Compounds for the IC50 results described in Table 3.
Structure
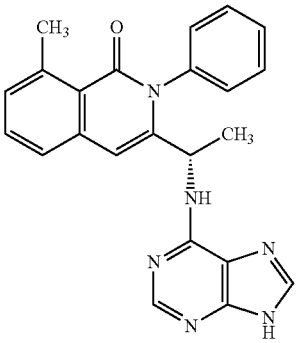 [SMILES: Cc1cccc2cc([C@H](C)Nc3ncnc4[nH]cnc34)n(-c3ccccc3)c(=O)c12]
Compound 196
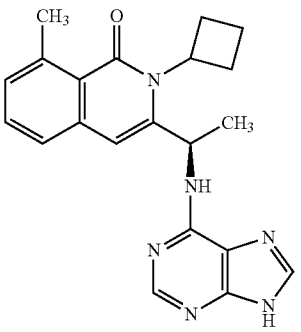 [SMILES: Cc1cccc2cc([C@@H](C)Nc3ncnc4[nH]cnc34)n(C3CCC3)c(=O)c12]
Compound 197
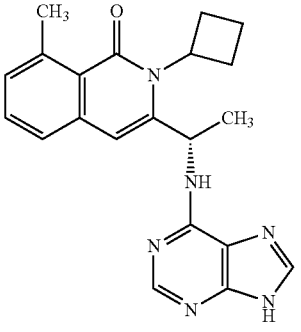 [SMILES: Cc1cccc2cc([C@H](C)Nc3ncnc4[nH]cnc34)n(C3CCC3)c(=O)c12]
Compound 198
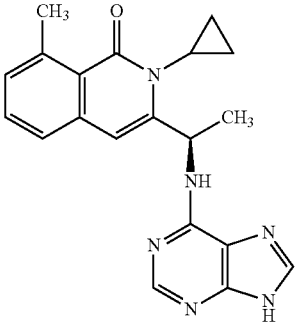 [SMILES: Cc1cccc2cc([C@@H](C)Nc3ncnc4[nH]cnc34)n(C3CC3)c(=O)c12]
Compound 199

TABLE 4-continued

Structures of the Compounds for the IC50 results described in Table 3.

Structure

Compound 200

Compound 201

Compound 202

Compound 203

TABLE 4-continued

Structures of the Compounds for the IC50 results described in Table 3.

Structure

Compound 204

Compound 205

Compound 206

TABLE 4-continued
Structures of the Compounds for the IC50 results described in Table 3.
Structure
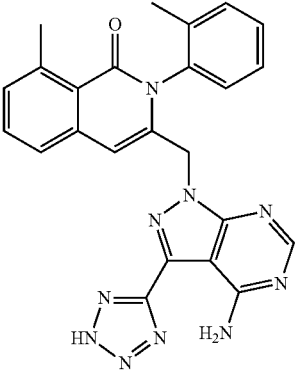 [SMILES: Cc1ccccc1-n1c(Cn2nc(-c3nn[nH]n3)c3c(N)ncnc32)cc2cccc(C)c2c1=O]
Compound 207
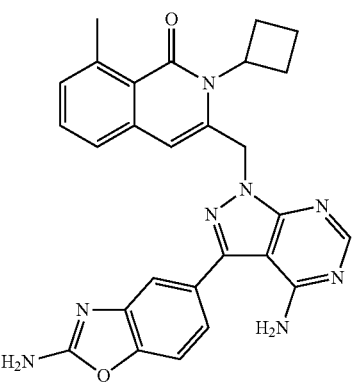 [SMILES: Cc1cccc2cc(Cn3nc(-c4ccc5oc(N)nc5c4)c4c(N)ncnc43)n(C3CCC3)c(=O)c12]
Compound 208
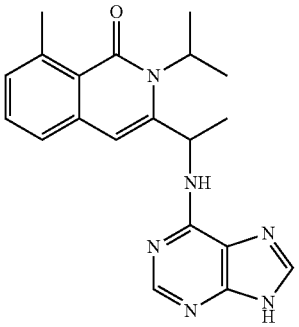 [SMILES: Cc1cccc2cc(C(C)Nc3ncnc4[nH]cnc34)n(C(C)C)c(=O)c12]
Compound 209
TABLE 4-continued
Structures of the Compounds for the IC50 results described in Table 3.
Structure
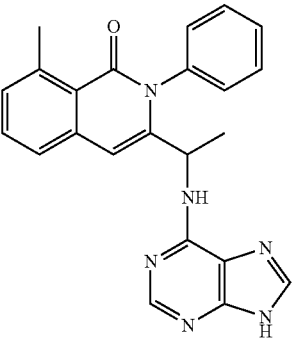 [SMILES: Cc1cccc2cc(C(C)Nc3ncnc4[nH]cnc34)n(-c3ccccc3)c(=O)c12]
Compound 210
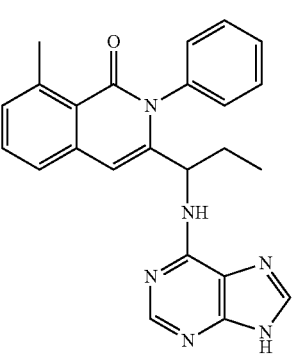 [SMILES: CCC(Nc1ncnc2[nH]cnc12)c1cc2cccc(C)c2c(=O)n1-c1ccccc1]
Compound 211
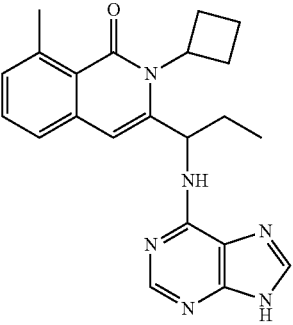 [SMILES: CCC(Nc1ncnc2[nH]cnc12)c1cc2cccc(C)c2c(=O)n1C1CCC1]
Compound 212
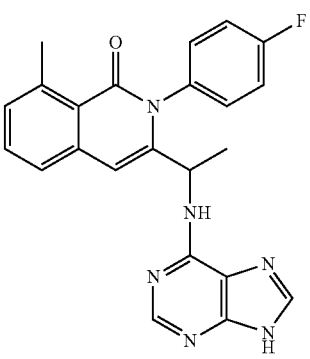 [SMILES: Cc1cccc2cc(C(C)Nc3ncnc4[nH]cnc34)n(-c3ccc(F)cc3)c(=O)c12]
Compound 213

TABLE 4-continued
Structures of the Compounds for the IC50 results described in Table 3.
Structure
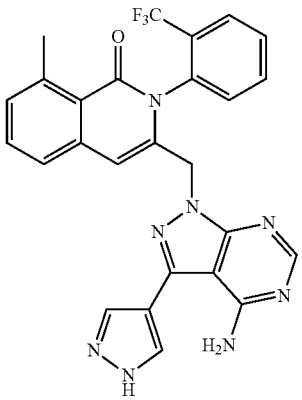 [SMILES: Cc1cccc2cc(Cn3nc(-c4cn[nH]c4)c4c(N)ncnc43)n(-c3ccccc3C(F)(F)F)c(=O)c12]
Compound 214
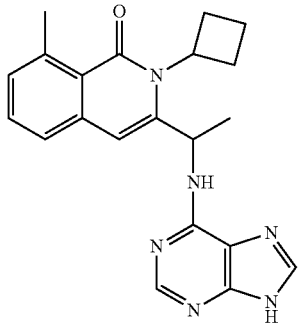 [SMILES: Cc1cccc2cc(C(C)Nc3ncnc4[nH]cnc34)n(C3CCC3)c(=O)c12]
Compound 215
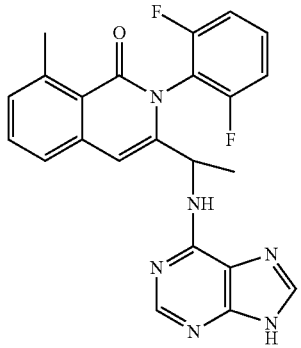 [SMILES: Cc1cccc2cc(C(C)Nc3ncnc4[nH]cnc34)n(-c3c(F)cccc3F)c(=O)c12]
Compound 216
TABLE 4-continued
Structures of the Compounds for the IC50 results described in Table 3.
Structure
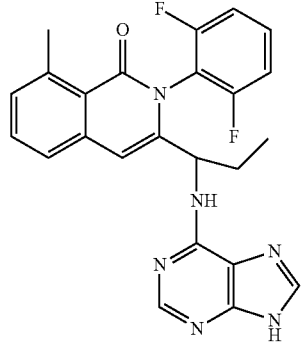 [SMILES: CCC(Nc1ncnc2[nH]cnc12)c1cc2cccc(C)c2c(=O)n1-c1c(F)cccc1F]
Compound 217
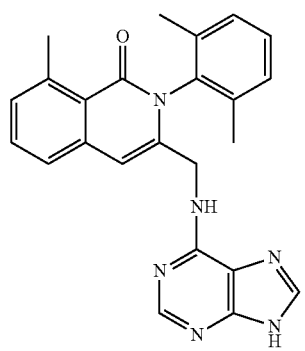 [SMILES: Cc1cccc(C)c1-n1c(CNc2ncnc3[nH]cnc23)cc2cccc(C)c2c1=O]
Compound 218
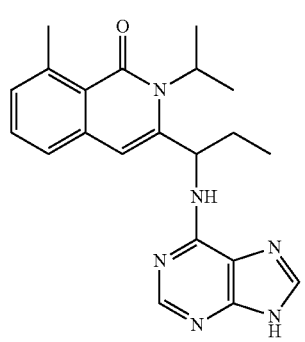 [SMILES: CCC(Nc1ncnc2[nH]cnc12)c1cc2cccc(C)c2c(=O)n1C(C)C]
Compound 219
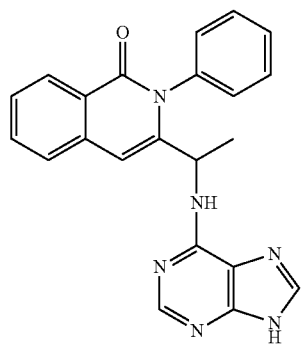 [SMILES: CC(Nc1ncnc2[nH]cnc12)c1cc2ccccc2c(=O)n1-c1ccccc1]
Compound 220

TABLE 4-continued
Structures of the Compounds for the IC50 results described in Table 3.
Structure
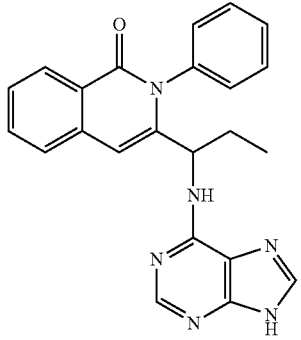 [SMILES: CCC(Nc1ncnc2[nH]cnc12)c1cc2ccccc2c(=O)n1-c1ccccc1]
Compound 221
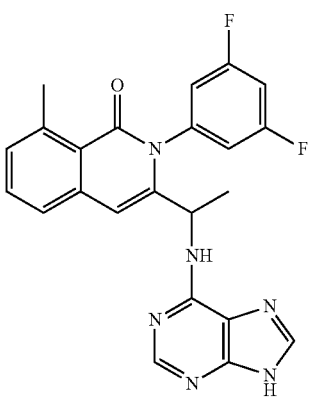
Compound 222
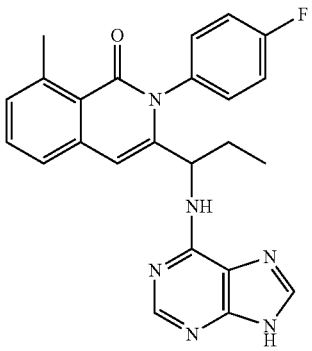
Compound 223
TABLE 4-continued
Structures of the Compounds for the IC50 results described in Table 3.
Structure
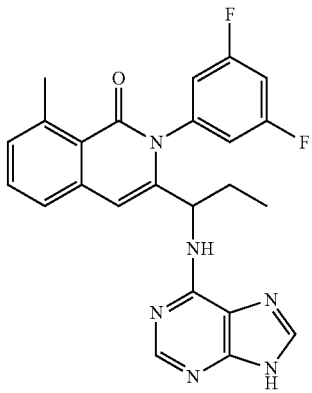 [SMILES: CCC(Nc1ncnc2[nH]cnc12)c1cc2cccc(C)c2c(=O)n1-c1cc(F)cc(F)c1]
Compound 224
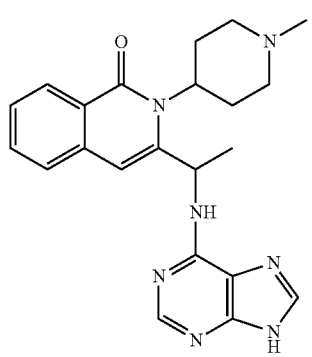 [SMILES: CC(Nc1ncnc2[nH]cnc12)c1cc2ccccc2c(=O)n1C1CCN(C)CC1]
Compound 225
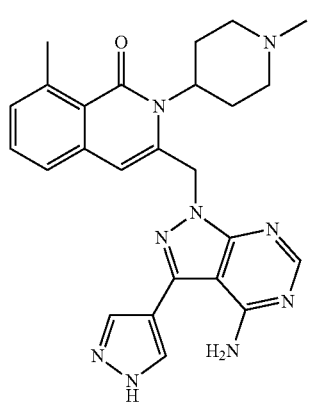 [SMILES: Cc1cccc2cc(Cn3nc(-c4cn[nH]c4)c4c(N)ncnc43)n(C3CCN(C)CC3)c(=O)c12]
Compound 226

TABLE 4-continued
Structures of the Compounds for the IC50 results described in Table 3.
Structure
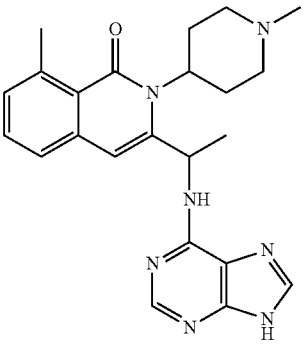 [SMILES: Cc1cccc2cc(C(C)Nc3ncnc4[nH]cnc34)n(C3CCN(C)CC3)c(=O)c12]
Compound 227
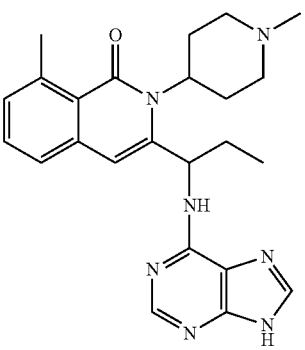 [SMILES: CCC(Nc1ncnc2[nH]cnc12)c1cc2cccc(C)c2c(=O)n1C1CCN(C)CC1]
Compound 228
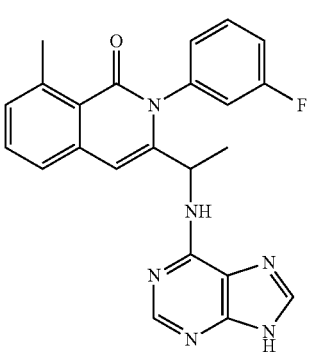 [SMILES: Cc1cccc2cc(C(C)Nc3ncnc4[nH]cnc34)n(-c3cccc(F)c3)c(=O)c12]
Compound 229
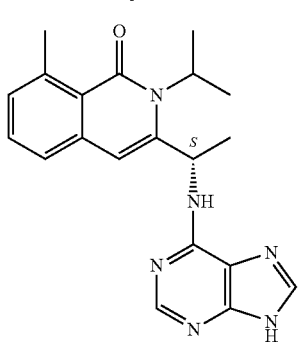
Compound 230
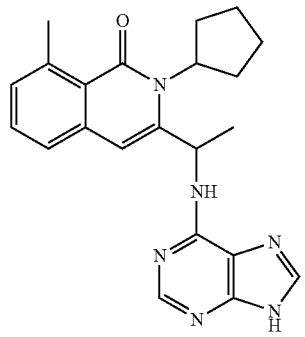 [SMILES: Cc1cccc2cc(C(C)Nc3ncnc4[nH]cnc34)n(C3CCCC3)c(=O)c12]
Compound 231
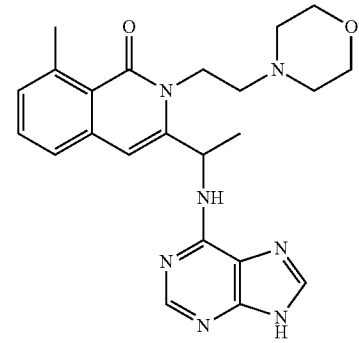 [SMILES: Cc1cccc2cc(C(C)Nc3ncnc4[nH]cnc34)n(CCN3CCOCC3)c(=O)c12]
Compound 232
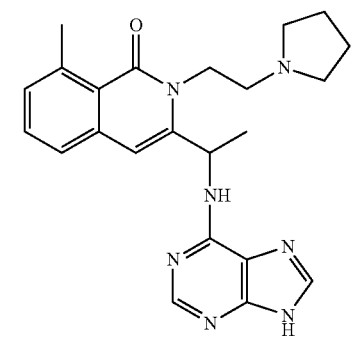 [SMILES: Cc1cccc2cc(C(C)Nc3ncnc4[nH]cnc34)n(CCN3CCCC3)c(=O)c12]
Compound 233
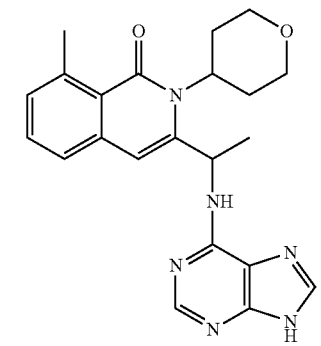 [SMILES: Cc1cccc2cc(C(C)Nc3ncnc4[nH]cnc34)n(C3CCOCC3)c(=O)c12]
Compound 234

TABLE 4-continued
Structures of the Compounds for the IC50 results described in Table 3.
Structure
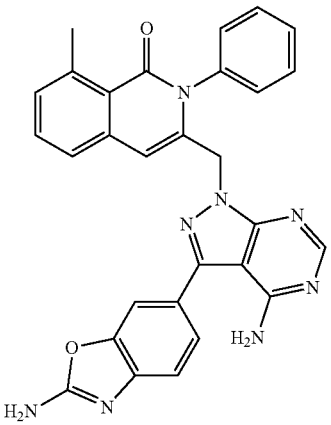 [SMILES: Cc1cccc2cc(Cn3nc(-c4ccc5nc(N)oc5c4)c4c(N)ncnc43)n(-c3ccccc3)c(=O)c12]
Compound 235
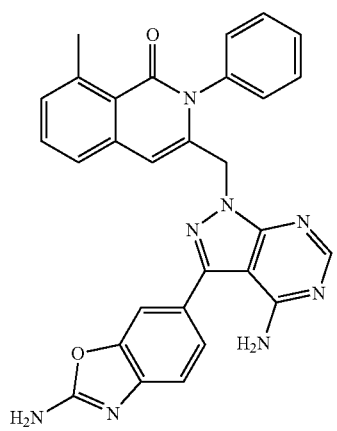 [SMILES: Cc1cccc2cc(Cn3nc(-c4ccc5nc(N)oc5c4)c4c(N)ncnc43)n(-c3ccccc3)c(=O)c12]
Compound 236
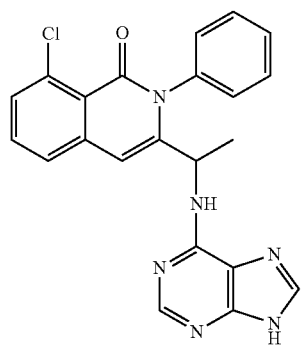 [SMILES: CC(Nc1ncnc2[nH]cnc12)c1cc2cccc(Cl)c2c(=O)n1-c1ccccc1]
Compound 237
TABLE 4-continued
Structures of the Compounds for the IC50 results described in Table 3.
Structure
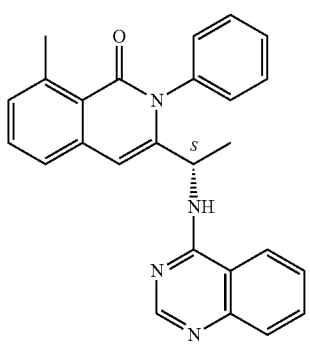
Compound 238
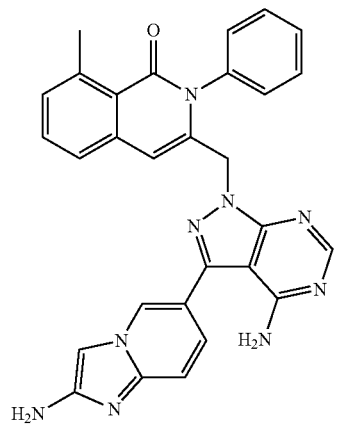 [SMILES: Cc1cccc2cc(Cn3nc(-c4ccc5nc(N)cn5c4)c4c(N)ncnc43)n(-c3ccccc3)c(=O)c12]
Compound 239
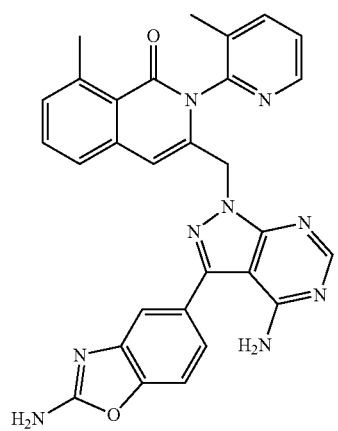
Compound 240

TABLE 4-continued
Structures of the Compounds for the IC50 results described in Table 3.
Structure
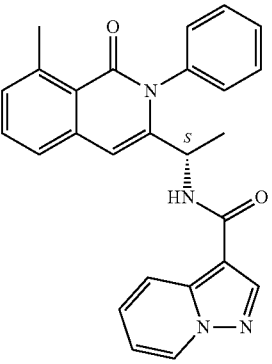
Compound 241
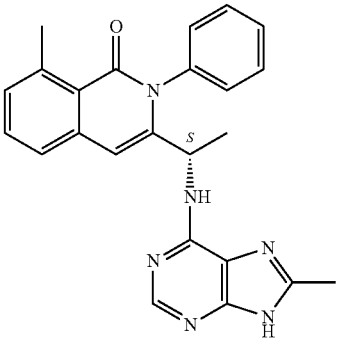
Compound 242
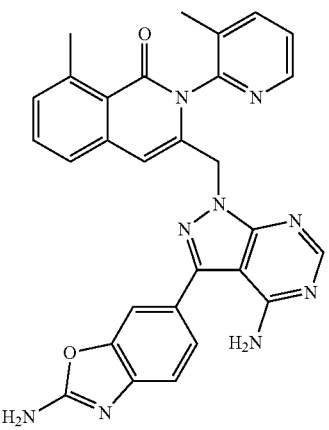 [SMILES: Cc1cccnc1-n1c(Cn2nc(-c3ccc4nc(N)oc4c3)c3c(N)ncnc32)cc2cccc(C)c2c1=O]
Compound 243
TABLE 4-continued
Structures of the Compounds for the IC50 results described in Table 3.
Structure
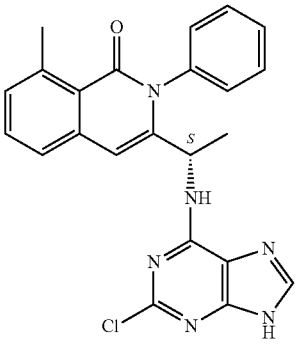
Compound 244
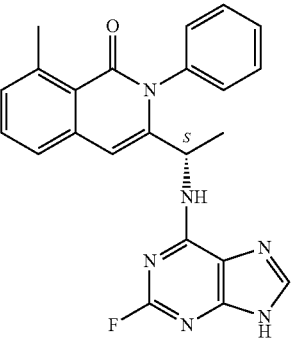
Compound 245
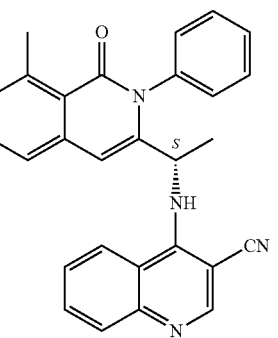
Compound 246
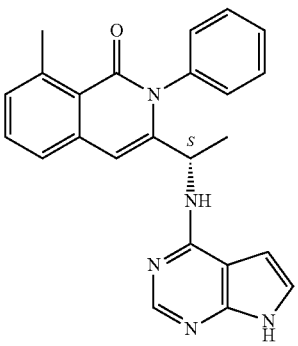
Compound 247

TABLE 4-continued
Structures of the Compounds for the IC50 results described in Table 3.
Structure
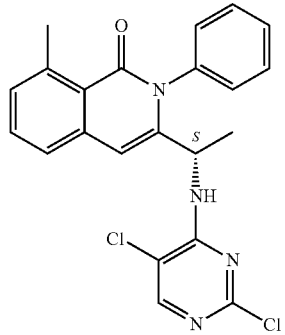
Compound 248
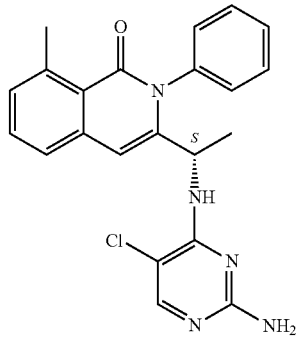
Compound 249
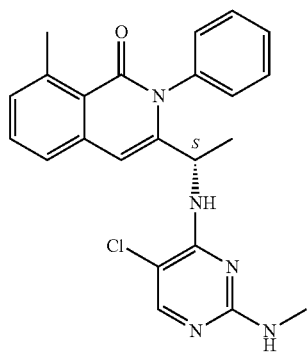
Compound 250
TABLE 4-continued
Structures of the Compounds for the IC50 results described in Table 3.
Structure
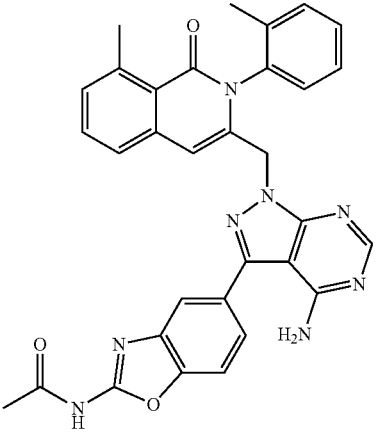
Compound 251
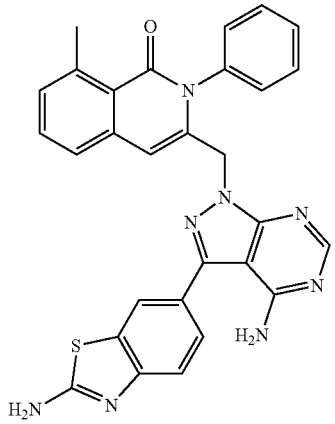 [SMILES: Cc1cccc2cc(Cn3nc(-c4ccc5nc(N)sc5c4)c4c(N)ncnc43)n(-c3ccccc3)c(=O)c12]
Compound 252
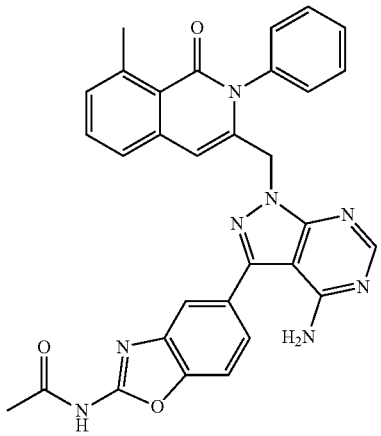 [SMILES: CC(=O)Nc1nc2cc(-c3nn(Cc4cc5cccc(C)c5c(=O)n4-c4ccccc4)c4ncnc(N)c34)ccc2o1]
Compound 253

TABLE 4-continued
Structures of the Compounds for the IC50 results described in Table 3.
Structure
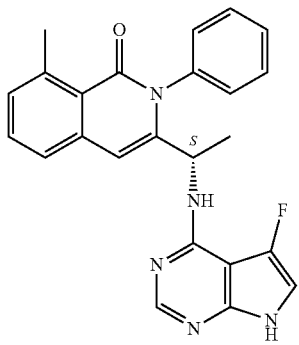
Compound 254
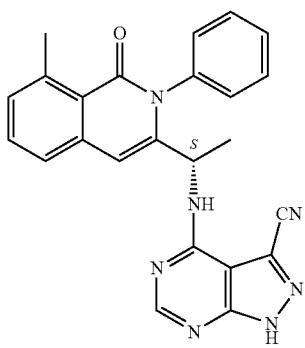
Compound 255
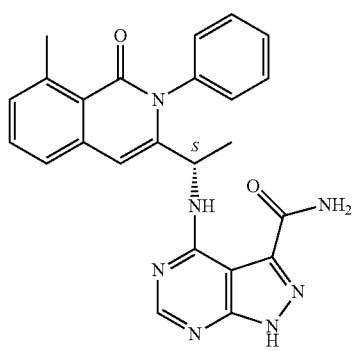
Compound 256
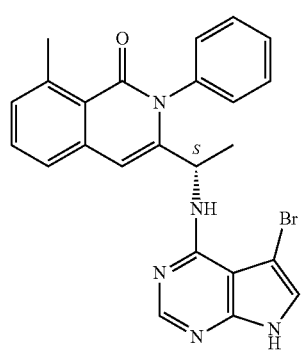
Compound 257
TABLE 4-continued
Structures of the Compounds for the IC50 results described in Table 3.
Structure
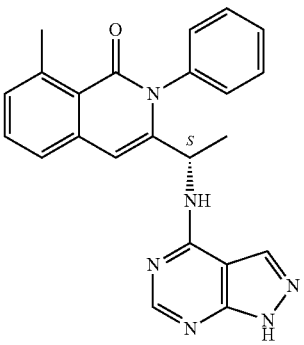
Compound 258
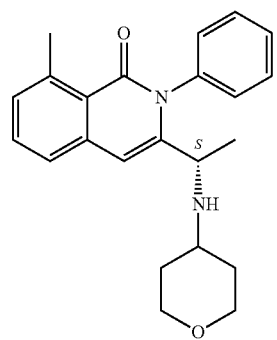
Compound 259
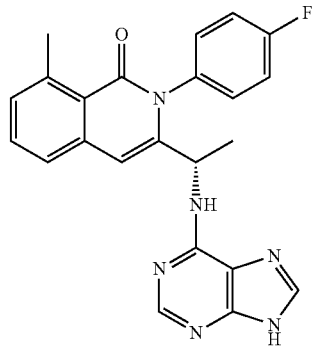 [SMILES: Cc1cccc2cc([C@H](C)Nc3ncnc4[nH]cnc34)n(-c3ccc(F)cc3)c(=O)c12]
Compound 260
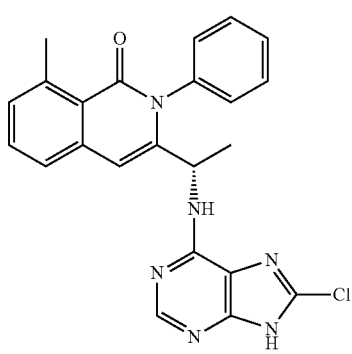 [SMILES: Cc1cccc2cc([C@H](C)Nc3ncnc4[nH]c(Cl)nc34)n(-c3ccccc3)c(=O)c12]
Compound 261

TABLE 4-continued
Structures of the Compounds for the IC50 results described in Table 3.
Structure
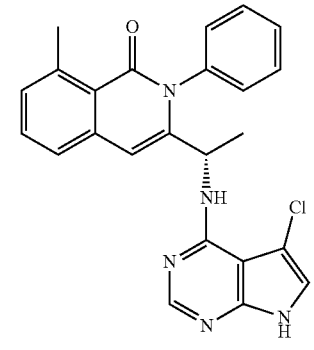 [SMILES: Cc1cccc2cc([C@H](C)Nc3ncnc4[nH]cc(Cl)c34)n(-c3ccccc3)c(=O)c12]
Compound 262
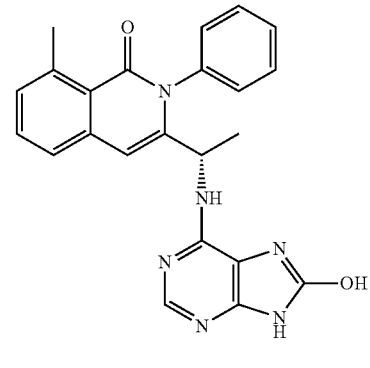 [SMILES: Cc1cccc2cc([C@H](C)Nc3ncnc4[nH]c(O)nc34)n(-c3ccccc3)c(=O)c12]
Compound 263
Compound 264
Compound 265
TABLE 4-continued
Structures of the Compounds for the IC50 results described in Table 3.
Structure
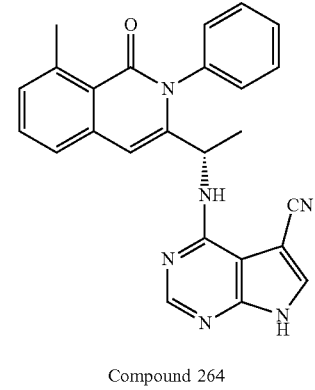
Compound 266
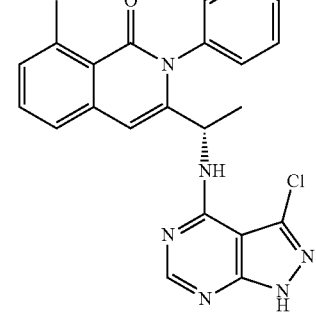
Compound 267
Compound 268

TABLE 4-continued

Structures of the Compounds for the IC50 results described in Table 3.

Structure

Compound 269

Compound 270

Compound 271

TABLE 4-continued

Structures of the Compounds for the IC50 results described in Table 3.

Structure

Compound 272

Compound 273

Compound 274

TABLE 4-continued
Structures of the Compounds for the IC50 results described in Table 3.
Structure
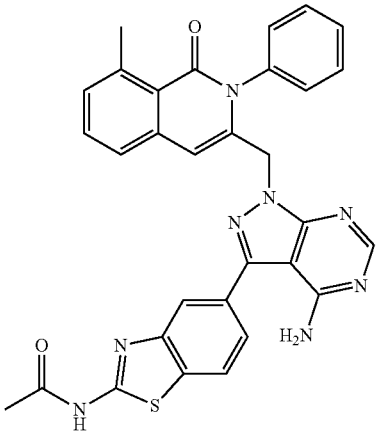
Compound 275
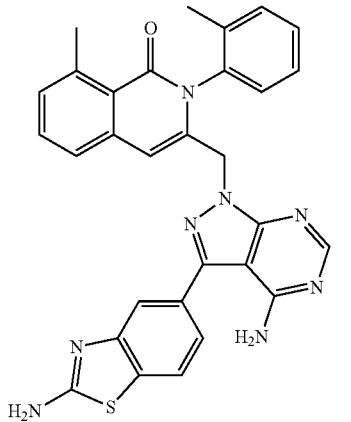 [SMILES: Cc1ccccc1-n1c(Cn2nc(-c3ccc4sc(N)nc4c3)c3c(N)ncnc32)cc2cccc(C)c2c1=O]
Compound 276
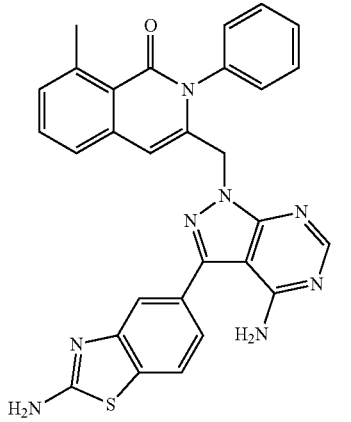 [SMILES: Cc1cccc2cc(Cn3nc(-c4ccc5sc(N)nc5c4)c4c(N)ncnc43)n(-c3ccccc3)c(=O)c12]
Compound 277
TABLE 4-continued
Structures of the Compounds for the IC50 results described in Table 3.
Structure
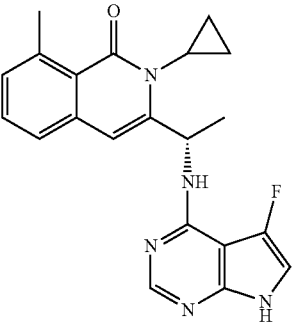 [SMILES: Cc1cccc2cc([C@H](C)Nc3ncnc4[nH]cc(F)c34)n(C3CC3)c(=O)c12]
Compound 278
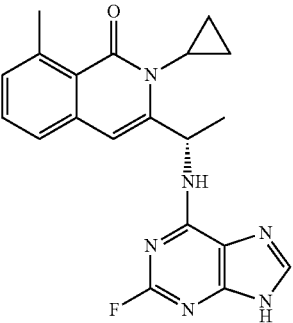 [SMILES: Cc1cccc2cc([C@H](C)Nc3nc(F)nc4[nH]cnc34)n(C3CC3)c(=O)c12]
Compound 279
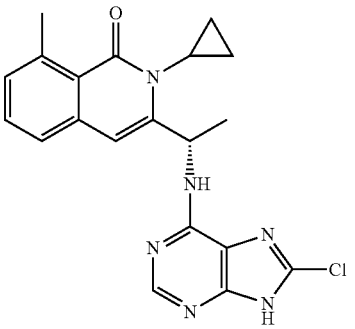 [SMILES: Cc1cccc2cc([C@H](C)Nc3ncnc4[nH]c(Cl)nc34)n(C3CC3)c(=O)c12]
Compound 280
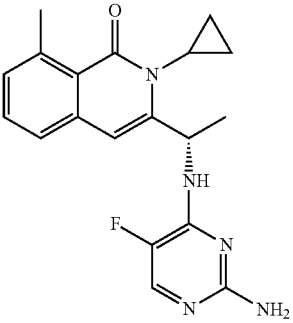 [SMILES: Cc1cccc2cc([C@H](C)Nc3nc(N)ncc3F)n(C3CC3)c(=O)c12]
Compound 281

TABLE 4-continued

Structures of the Compounds for the IC50 results described in Table 3.

Structure

Compound 282

Compound 283

Compound 284

Compound 285

Compound 286

Compound 287

Compound 288

Compound 289

TABLE 4-continued

Structures of the Compounds for the IC50 results described in Table 3.

Structure

Compound 290

Compound 291

Compound 292

Compound 293

TABLE 4-continued

Structures of the Compounds for the IC50 results described in Table 3.

Structure

Compound 294

Compound 295

Compound 296

TABLE 4-continued
Structures of the Compounds for the IC50 results described in Table 3.
Structure
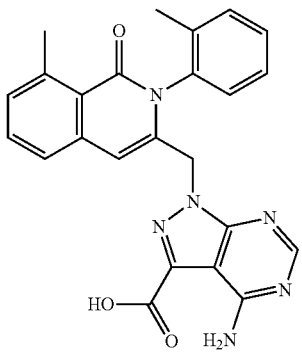 [SMILES: Cc1ccccc1-n1c(Cn2nc(C(=O)O)c3c(N)ncnc32)cc2cccc(C)c2c1=O]
Compound 297
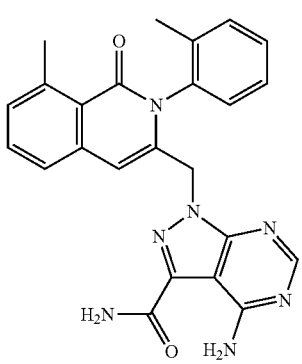 [SMILES: Cc1ccccc1-n1c(Cn2nc(C(N)=O)c3c(N)ncnc32)cc2cccc(C)c2c1=O]
Compound 298
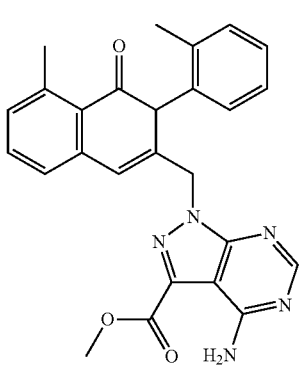 [SMILES: COC(=O)c1nn(CC2=Cc3cccc(C)c3C(=O)C2c2ccccc2C)c2ncnc(N)c12]
Compound 299
TABLE 4-continued
Structures of the Compounds for the IC50 results described in Table 3.
Structure
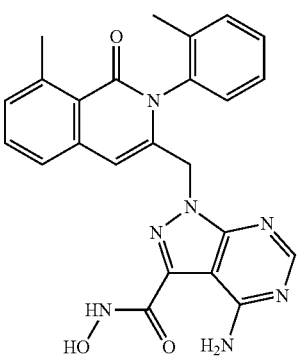 [SMILES: Cc1ccccc1-n1c(Cn2nc(C(=O)NO)c3c(N)ncnc32)cc2cccc(C)c2c1=O]
Compound 300
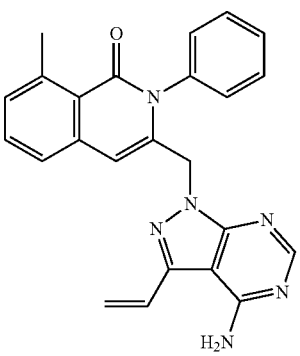 [SMILES: C=Cc1nn(Cc2cc3cccc(C)c3c(=O)n2-c2ccccc2)c2ncnc(N)c12]
Compound 301
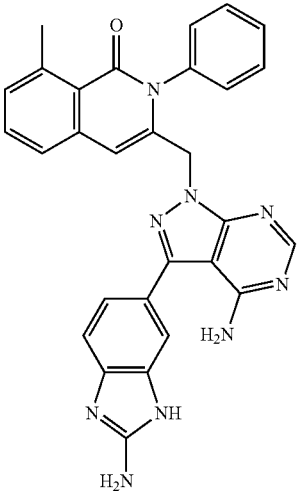 [SMILES: Cc1cccc2cc(Cn3nc(-c4ccc5nc(N)[nH]c5c4)c4c(N)ncnc43)n(-c3ccccc3)c(=O)c12]
Compound 302

TABLE 4-continued
Structures of the Compounds for the IC50 results described in Table 3.
Structure
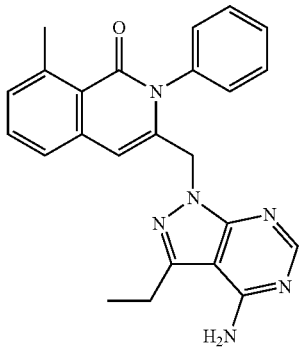 [SMILES: CCc1nn(Cc2cc3cccc(C)c3c(=O)n2-c2ccccc2)c2ncnc(N)c12]
Compound 303
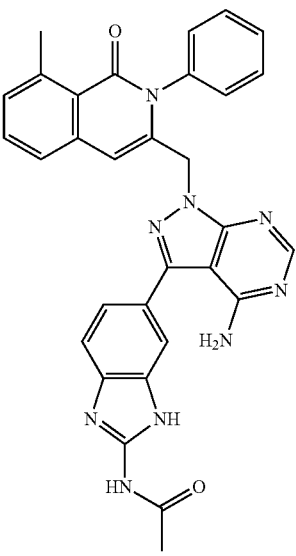 [SMILES: CC(=O)Nc1nc2ccc(-c3nn(Cc4cc5cccc(C)c5c(=O)n4-c4ccccc4)c4ncnc(N)c34)cc2[nH]1]
Compound 304
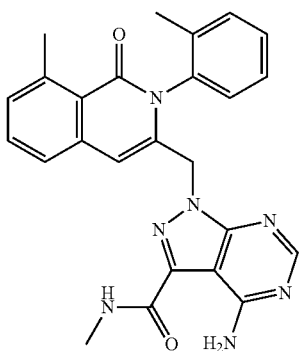
Compound 305
TABLE 4-continued
Structures of the Compounds for the IC50 results described in Table 3.
Structure
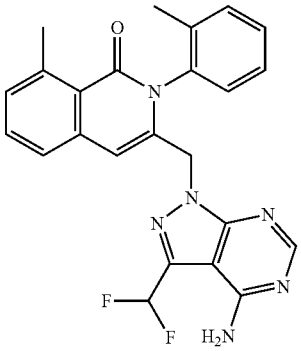 [SMILES: Cc1ccccc1-n1c(Cn2nc(C(F)F)c3c(N)ncnc32)cc2cccc(C)c2c1=O]
Compound 306
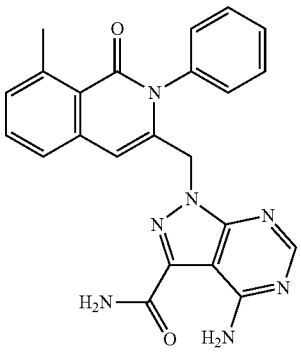 [SMILES: Cc1cccc2cc(Cn3nc(C(N)=O)c4c(N)ncnc43)n(-c3ccccc3)c(=O)c12]
Compound 307
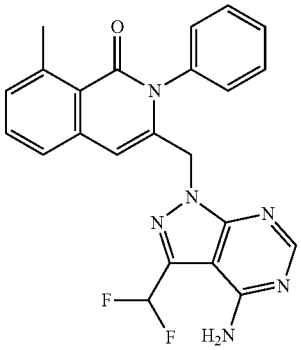 [SMILES: Cc1cccc2cc(Cn3nc(C(F)F)c4c(N)ncnc43)n(-c3ccccc3)c(=O)c12]
Compound 308

TABLE 4-continued
Structures of the Compounds for the IC50 results described in Table 3.
Structure
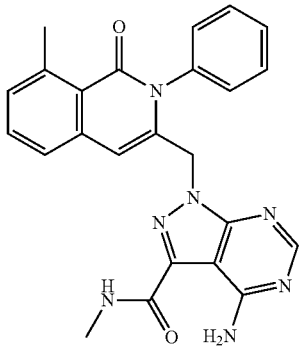 [SMILES: CNC(=O)c1nn(Cc2cc3cccc(C)c3c(=O)n2-c2ccccc2)c2ncnc(N)c12]
Compound 309
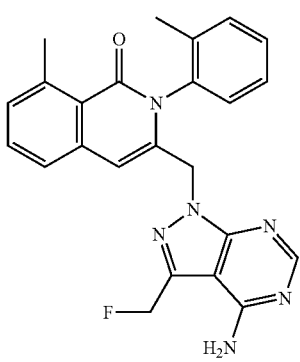 [SMILES: Cc1ccccc1-n1c(Cn2nc(CF)c3c(N)ncnc32)cc2cccc(C)c2c1=O]
Compound 310
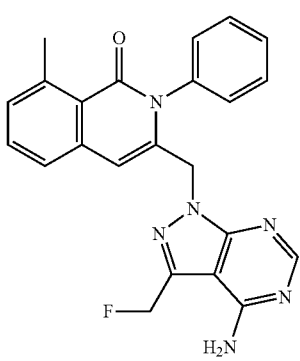 [SMILES: Cc1cccc2cc(Cn3nc(CF)c4c(N)ncnc43)n(-c3ccccc3)c(=O)c12]
Compound 311
TABLE 4-continued
Structures of the Compounds for the IC50 results described in Table 3.
Structure
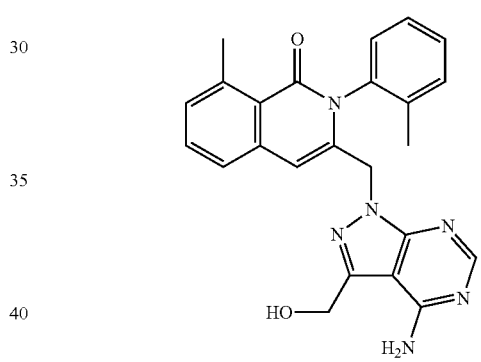
Compound 312
Compound 313
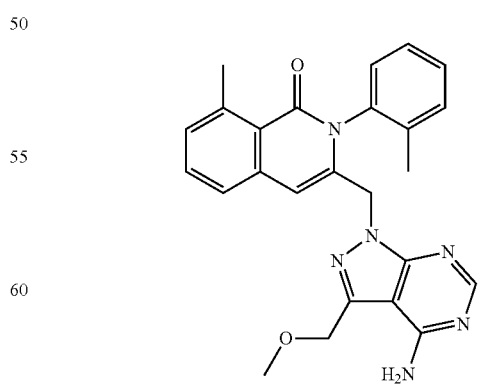
Compound 314

TABLE 4-continued
Structures of the Compounds for the IC50 results described in Table 3.
Structure
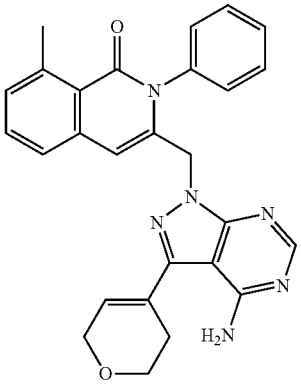 [SMILES: Cc1cccc2cc(Cn3nc(C4=CCOCC4)c4c(N)ncnc43)n(-c3ccccc3)c(=O)c12]
Compound 315
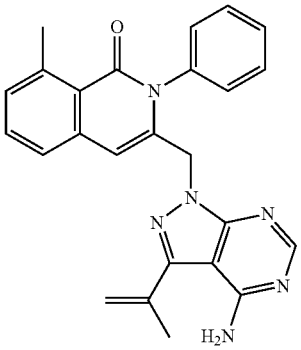 [SMILES: C=C(C)c1nn(Cc2cc3cccc(C)c3c(=O)n2-c2ccccc2)c2ncnc(N)c12]
Compound 316
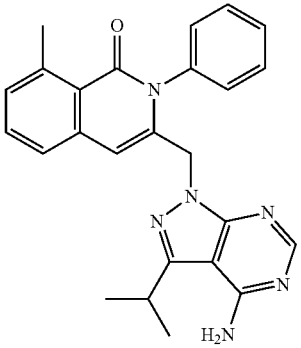 [SMILES: Cc1cccc2cc(Cn3nc(C(C)C)c4c(N)ncnc43)n(-c3ccccc3)c(=O)c12]
Compound 317
TABLE 4-continued
Structures of the Compounds for the IC50 results described in Table 3.
Structure
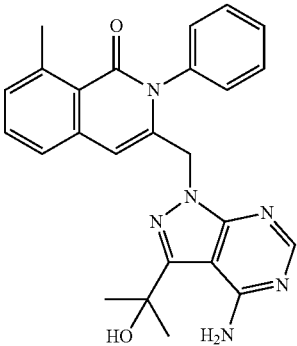 [SMILES: Cc1cccc2cc(Cn3nc(C(C)(C)O)c4c(N)ncnc43)n(-c3ccccc3)c(=O)c12]
Compound 318
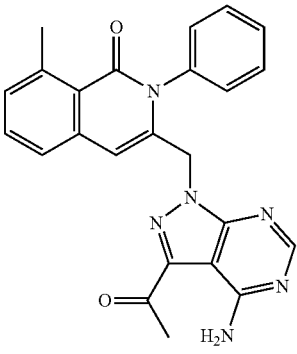 [SMILES: CC(=O)c1nn(Cc2cc3cccc(C)c3c(=O)n2-c2ccccc2)c2ncnc(N)c12]
Compound 319
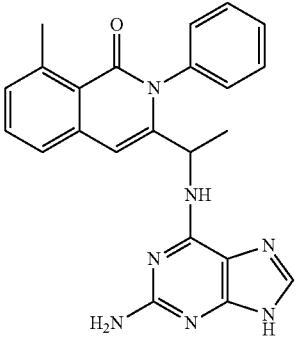 [SMILES: Cc1cccc2cc(C(C)Nc3nc(N)nc4[nH]cnc34)n(-c3ccccc3)c(=O)c12]
Compound 320
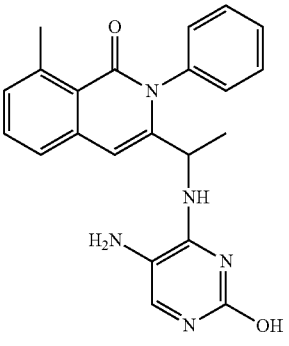 [SMILES: Cc1cccc2cc(C(C)Nc3nc(O)ncc3N)n(-c3ccccc3)c(=O)c12]
Compound 321

TABLE 4-continued

Structures of the Compounds for the IC50 results described in Table 3.

Structure

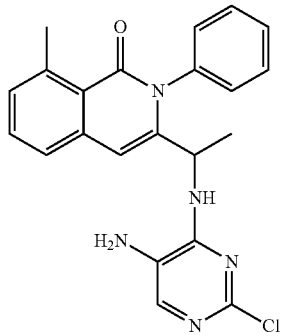 [SMILES: Cc1cccc2cc(C(C)Nc3nc(Cl)ncc3N)n(-c3ccccc3)c(=O)c12]

Compound 322

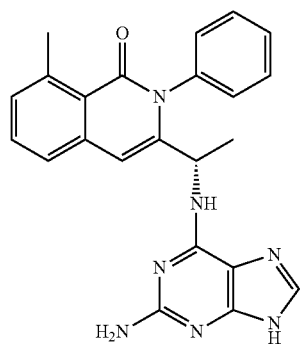 [SMILES: Cc1cccc2cc([C@H](C)Nc3nc(N)nc4[nH]cnc34)n(-c3ccccc3)c(=O)c12]

Compound 323

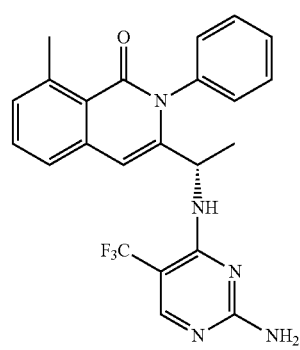 [SMILES: Cc1cccc2cc([C@H](C)Nc3nc(N)ncc3C(F)(F)F)n(-c3ccccc3)c(=O)c12]

Compound 324

TABLE 4-continued

Structures of the Compounds for the IC50 results described in Table 3.

Structure

Compound 325

Example 2

Expression and Inhibition Assays of p110α/p85α, p110β/p85α, p110δ/p85α, and p110γ

Class I PI3Ks can be either purchased (p110α/p85α, p110β/p85α, p110δ/p85α from Upstate, and p110γ from Sigma) or expressed as previously described (Knight et al., 2004). IC50 values are measured using either a standard TLC assay for lipid kinase activity (described below) or a high-throughput membrane capture assay. Kinase reactions are performed by preparing a reaction mixture containing kinase, a compound provided herein (2% DMSO final concentration), buffer (25 mM HEPES, pH 7.4, 10 mM $MgCl_2$), and freshly sonicated phosphatidylinositol (100 µg/ml). Reactions are initiated by the addition of ATP containing 10 µCi of γ-32P-ATP to a final concentration 10 or 100 µM and allowed to proceed for 5 minutes at room temperature. For TLC analysis, reactions are then terminated by the addition of 105 µL 1N HCl followed by 160 µl $CHCl_3$: MeOH (1:1). The biphasic mixture is vortexed, briefly centrifuged, and the organic phase is transferred to a new tube using a gel loading pipette tip precoated with $CHCl_3$. This extract is spotted on TLC plates and developed for 3-4 hours in a 65:35 solution of n-propanol:1M acetic acid. The TLC plates are then dried, exposed to a phosphorimager screen (Storm, Amersham), and quantitated. For each compound, kinase activity is measured at 10-12 compound concentrations representing two-fold dilutions from the highest concentration tested (typically, 200 µM). For compounds showing significant activity, IC50 determinations are repeated two to four times, and the reported value is the average of these independent measurements.

Other commercial kits or systems for assaying PI3K activities are available. The commercially available kits or systems can be used to screen for modulators, e.g., inhibitors and/or agonists, of PI3Ks including but not limited to PI 3-Kinase α, β, δ, and γ. An exemplary system is PI 3-Kinase (human) HTRF™ Assay from Upstate. The assay can be carried out according to the procedures suggested by the manufacturer. Briefly, the assay is a time resolved FRET assay that indirectly measures PIP3 product formed by the activity of a PI3K. The kinase reaction is performed in a microtitre plate (e.g., a 384 well microtitre plate). The total reaction volume is approximately 20 uL per well. In the first step, each well receives 2 uL of test compound in 20% dimethylsulphoxide resulting in a 2% DMSO final concentration. Next, approximately 14.5 uL of a kinase/PIP2 mixture (diluted in 1× reaction buffer) is added per well for a final concentration of 0.25-0.3 ug/mL kinase and 10 uM PIP2. The plate is sealed and incubated for 15 minutes at room temperature. To start the reaction, 3.5 uL of ATP (diluted in 1× reaction buffer) is added per well for a final concentration of 10 uM ATP. The plate is sealed and incubated for 1 hour at room temperature. The reaction is stopped by adding 5 uL of Stop Solution per well and then 5 uL of Detection Mix is added per well. The plate is sealed, incubated for 1 hour at room temperature, and then read on an appropriate plate reader. Data is analyzed and IC50s are generated using GraphPad Prism® 5.

Example 3

Compound 292 Inhibits PI3K-δ, PI3K-γ, PI3K-β, and PI3K-α

The PI3K inhibitory activity of Compound 292 was tested in several assays described herein. The results are shown in Table 5 below, indicating that Compound 292 is a potent inhibitor of PI3K-δ and PI3K-γ. In these assays, Compound 292 inhibits PI3K-δ activity at lower doses as compared to other PI3Ks (e.g., at least 10-fold lower dose compared to PI3K-γ, PI3K-β or PI3K-α).

TABLE 5

Biochemical and Cellular Activity Data for Compound 292

| Compound 292 | PI3K-α | PI3K-β | PI3K-δ | PI3K-γ |
|---|---|---|---|---|
| $K_i$ | >10,000 pM | 1,000-10,000 pM | <100 pM | 100-1,000 pM |
| TLC $IC_{50}$ | 1,000-10,000 nM | 10-1000 nM | <10 nM | 10-1,000 nM |
| Cellular $IC_{50}$ | 1,000-10,000 nM | 10-1000 nM | <10 nM | 10-1,000 nM |

Example 4

Functional Cellular Activity of Compound 292

The functional cellular activities of Compound 292 were assessed. The results are shown in Table 6 below. Compound 292 suppressed murine B-cell proliferation and human B-cell proliferation at subnanomolar concentrations, with an $EC_{50}$ of 0.5 nM. Compound 292 suppressed human T-cell proliferation at nanomolar concentrations, with an $EC_{50}$ of 9.5 nM.

To determine PI3K-δ,γ isoform activity in vitro, Compound 292 was assessed in PI3K-δ and PI3K-γ selective cell-based assays. To assess the ability to inhibit the PI3K-δ isoform, AKT phosphorylation (T308) was measured by enzyme-linked immunosorbent assay (ELISA) in anti-IgM antibody-stimulated RAJI cells, a human Burkitt lymphoma cell line, in the presence or absence of Compound 292. Compound 292 potently inhibited AKT phosphorylation with an $IC_{50}$ value of 2.0 nM. To assess the ability to inhibit the PI3K-γ isoform, the murine macrophage-like cell line, RAW 264.7, was stimulated with C5a, and the level of AKT phosphorylation (T308) was measured by ELISA. Compound 292 inhibited PI3K-γ in C5a activated RAW 264.7 cells with an $IC_{50}$ value of 44.0 nM. Compound 292 is a potent inhibitor of both PI3K-δ and PI3K-γ in isoform-selective cell-based assays.

TABLE 6

Compound 292 Functional Cellular Activity

| Functional Cellular Activity | $EC_{50}$ |
|---|---|
| Murine B-cell proliferation | <5 nM |
| Human B-cell proliferation | <5 nM |
| Human T-cell proliferation | 5-10 nM |
| PI3K-δ selective assay (RAJI cells, human lymphoma cell line) | <5 nM |
| PI3K-γ selective assay (RAW 264.7, murine macrophage-like cell line) | 10-100 nM |
| Anti-fCER1 BAT (delta) | 10-100 nM |

In one exemplary assay tested, Compound 292 potently inhibited PI3K-δ specific basophil activation in human whole blood with an $IC_{50}$ of 78 nM.

Example 5

Safety Pharmacology Studies of Compound 292

In Vitro hERG Assay

The in vitro effects of Compound 292 on the hERG channel current were examined as a surrogate for $I_{Kr}$, the rapidly activating, delayed rectifier cardiac potassium current. Compound 292 inhibited hERG current by 11.9% at 10 µM, 33.2% at 30 µM, 71.1% at 100 µM, and 92.8% at 300 µM compared to 0.9% in the vehicle control. The $IC_{50}$ value for the inhibitory effect of Compound 292 on hERG potassium current was 49.8 µM (Hill coefficient=1.3).

Compound 292 was highly bound in vitro to components of plasma of all species tested, including the rat, monkey, and human. In rat, monkey, and human plasma, Compound 292 was 85.8, 76.8, and 85.9% protein bound, respectively, at 100 µM (41700 ng/mL). The hERG assay was performed in a protein-free solution. Therefore, based on the free fractions, the $IC_{50}$ value of 49.8 µM (20800 ng/mL) for unbound Compound 292 would equate to total plasma concentrations of 351 µM (146200 ng/mL), 215 µM (89500 ng/mL), and 353 µM (147200 ng/mL) in rat, monkey, and human, respectively. These high concentrations suggest a very low potential for QT prolongation in humans.

Neurofunctional Study in Sprague-Dawley Rat

This study was conducted to evaluate the potential effects of Compound 292 on the central nervous system following a single oral administration in male rats. During this study, a Functional Observation Battery (FOB) test and motor activity evaluation were performed pre-dose and at 2, 6, and 24 h following Compound 292 administration.

Compound 292, administered to male rats as a single oral dose up to 350 mg/kg, caused no changes in qualitative or quantitative FOB parameters up to 24 h post-dose. Significant decreases in locomotor activity were observed in animals tested 2 h after a 350 mg/kg dose. However, given that no concurrent effects on locomotor activity or arousal were noted in the FOB arena at the same time period, a definitive effect of Compound 292 could not be confirmed at these assessment intervals. No effects on the central nervous system were observed at dose levels ≤50 mg/kg.

Respiratory Study in Sprague-Dawley Rat

This study was conducted to evaluate the potential effects of Compound 292 on the respiratory system following a single oral administration in the male rat. During this study, animals were placed in "head out" plethysmographs and respiratory parameters (tidal volume, respiratory rate, and derived minute volume) were measured for a period of approximately 30 minutes pre-dose, continuously from 1 to 3 h post-dose, and for 30-minute intervals at 6 and 24 h post-dose.

A single oral administration of Compound 292 at dose levels up to 350 mg/kg resulted in no Compound 292-related effects on respiratory parameters, including respiratory rate, tidal volume, and minute volume.

Cardiovascular Study in Instrumented Cynomolgus Monkey

This study was conducted to evaluate the potential effects of Compound 292 on the hemodynamic and electrocardiographic parameters following a single oral administration to cynomolgus monkeys via telemetry. Four non-naive, male monkeys implanted with radiotelemetry transmitters were utilized during the conduct of this study.

No Compound 292-related effects were observed on hemodynamic or electrocardiographic parameters (arterial blood pressures (systolic, diastolic, mean and pulse pressure), heart rate, and quantitative electrocardiographic intervals (PR, QRS, QT and QTc)) following a single oral dose of 5, 30, and 150 mg/kg in male cynomolgus monkeys. In addition, no waveform abnormalities or arrhythmias related to the administration of Compound 292 up to 150 mg/kg were noted.

Example 6

Pharmacokinetics of Compound 292 in Animals

The absorption and pharmacokinetics of Compound 292 were investigated in absolute bioavailability studies in mice, rats, dogs, and monkeys. The results of these bioavailability studies are summarized in Table 7. The data demonstrate that Compound 292 was readily absorbed in a majority of the nonclinical test species when administered as a suspension formulation with oral bioavailability values of 57%, 40%, 40% and 7% in rats, monkeys, dogs and mice, respectively. The half-life of Compound 292 was 5 hrs in monkeys, 2 hrs in the dog, and less than 2 hrs in the rat and mouse. Compound 292 achieved a high volume of distribution and showed low to moderate clearance in monkey and rat. Binding of Compound 292 to plasma proteins was concentration and species dependent. Percent Compound 292 free in rat and monkey plasma was consistently higher than in human plasma at all concentrations tested. Distribution of Compound 292 into rat tissues was rapid and extensive based on the blood to tissue ratio being greater than 1 for a majority of tissues. Elimination of radiolabelled Compound 292 from tissues was also rapid with a majority of tissues without quantifiable levels of radioactivity at 24 hr.

TABLE 7

Compound 292 Pharmacokinetic Parameters in BALB/c Mice, Sprague-Dawley Rats, Beagle Dogs and Cynomolgus Monkeys Following Intravenous and Oral Administration

| Species (Report Number) | # animals/ gender | Route | Dose (mg/kg) | $C_{max}$ (ng/mL) | $T_{max}$ (h) | $AUC_{0-last}$ (ng*h/mL) | $AUC_{0-inf}$ (ng*h/mL) | $T_{1/2}$ (h) | Cl (L/h/kg) | $V_{ss}$ (L/kg) | $F_{oral}$ (%) |
|---|---|---|---|---|---|---|---|---|---|---|---|
| Mouse | 27/M | IVc | 10 | 5563 | 0.083 | 1900 | 1903 | 0.22 | 5.25 | 1.14 | — |
|  | 27/M | POd | 10 | 390 | 0.083 | 136.8 | NC | NC | — | — | 7i |
| Rat | 3/M | IVc | 2 | 1519 | 0.083 | 1153 | 1157 | 0.73 | 1.83 | 1.66 | — |
|  | 3/M | POd | 10 | 785 | 1.2 | 2929 | 3298 | 2.4 | — | — | 57 |
| Dog | 3/M | IVe | 0.5 | 4413a | NC | 11738b | 11921 | 2 | 0.051 | 0.13 | — |
|  | 3/M | POf | 5 | 9597 | 3.00 | 105068b | 107062 | 3.9 | — | — | 97g, i |
| Dog | 3/M | IVe | 1 | 1804a | NC | 5875b | 6268 | 1.83 | 0.194 | 0.493 | — |
|  | 3/M | POf | 5 | 2367 | 1.33 | 10942b | 13805 | 3.15 | — | — | 40h, i |
| Monkey | 4/(2M, 2F) | IVc | 1 | 1545 | 0.083 | 2357 | 2379 | 5.0 | 0.43 | 1.27 | — |
|  | 4/(2M, 2F) | POd | 5 | 1327 | 1.5 | 4596 | 4685 | 5.4 | — | — | 40 |

— = not applicable
NC = not calculated
aReported value is $C_0$
b$AUC_{0-24}$
cIV formulation (mouse, rat, monkey) = 5% NMP, 10% Solutol ® HS 15, 30% PEG400, 55% water with 3% dextrose
dPO formulation (mouse, rat, monkey) = 0.5% (w/v) low viscosity CMC and 0.05% (v/v) TWEEN ® 80 in ultra pure water
eIV formulation (dog) = 5% 0.1N HCl, 5% PEG400 in 10% (2-hydroxypropyl)-β-cyclodextrin or 2.5% 1N HCl, 20% PEG400 in PBS
fPO formulation (dog) = 5% NMP, 60% PEG400 and 35% water solution ($_{ADME-11-008}$) or 5% NMP and 95% water suspension ($_{ADME-11-009}$)
g$F_{oral}$ was calculated using 0.5 mg/kg IV dose as reference
h$F_{oral}$ was calculated using 1 mg/kg IV dose as reference
i$F_{oral}$ was calculated using $AUC_{0-last}$ Membrane permeability and interaction of Compound 292 with human P-glycoprotein was assessed in vitro using Caco-2 cell monolayers. It was determined that Compound 292 has moderate cell membrane permeability, is a P-gp substrate and has the potential to inhibit the active transport of other P-gp substrates.

Example 7

Toxicology of Compound 292 in Animals

Single-dose toxicity study was conducted to determine the maximum tolerated dose (MTD) following a single oral dose and potential toxicity following 7-day repeat oral doses of Compound 292 in monkeys. It was determined that the MTD following a single oral administration of Compound 292 in monkeys was 500 mg/kg.

4- and 13-Week repeat-dose nonclinical safety studies were conducted in which rats and cynomolgus monkeys received daily Compound 292 doses by oral gavage. The no observed adverse effect level (NOAEL) in the 13-week rat study was 25 mg/kg/day (150 mg/m$^2$/day) and the NOAEL in the 13-week monkey study was 5 mg/kg/day (60 mg/m$^2$/day). On Day 91, the mean $AUC_{0-24}$ hr values for combined sexes at the NOAELs were 14150 ng*h/mL in the rat, and 4015 ng*h/mL in the monkey. Based on PK data from the clinical study in healthy subjects, exposure in humans following repeated oral doses of 5 mg BID Compound 292 (mean $AUC_{0-24}$ hr=2582 ng*h/mL following 14 days of oral dosing) is less than exposure at either the rat or monkey NOAEL.

There was no genetic toxicity associated with Compound 292 in the in vitro genetic toxicity studies, and Compound 292 had no direct adverse effect in the in vivo rat micronucleus assay. Reproductive toxicity of Compound 292 was assessed in embryo/fetal developmental toxicity studies in rats and rabbits. The maternal and fetal NOAELs of Compound 292 in the rat and rabbit were 35 mg/kg/day (210 mg/m$^2$/day) and 75 mg/kg/day (900 mg/m$^2$/day), respectively. On the last day of dosing, the mean $AUC_{0-24}$ hr values at the NOAELs were 62200 ng*h/mL and 66200 ng*h/mL for pregnant rats and rabbits, respectively.

Example 8

Clinical Studies in Human

A randomized, double-blind, placebo-controlled, clinical study in healthy adult subjects was conducted with Compound 292. One-hundred and six (106) subjects were enrolled overall, which included 36 subjects in the single ascending dose (SAD) portion (24 active treatment; 12 placebo), 48 subjects in the multiple ascending dose (MAD) portion (36 active treatment; 12 placebo), 6 subjects in the food effect (FE) effect portion (consisting of Compound 292 dosing with sequential fed and fasting portions), and 16 subjects in the DDI portion (consisting of Compound 292 dosing periods with and without ketoconazole). The total subject exposure to Compound 292 is summarized in Table 8.

TABLE 8

Subject Exposure of Compound 292 in Clinical Safety Studies

| PART | Treatment Exposure | Duration of Treatment | Total Exposure per Subject (mg) | Total No. of Subjects Exposed |
|---|---|---|---|---|
| SAD | Placebo SD | 1 day | 0 | 12 |
|  | 1 mg Compound 292 SD | 1 day | 1 | 4 |
|  | 2 mg Compound 292 SD | 1 day | 2 | 4 |
|  | 5 mg Compound 292 SD | 1 day | 5 | 4 |
|  | 10 mg Compound 292 SD | 1 day | 10 | 4 |
|  | 20 mg Compound 292 SD | 1 day | 20 | 4 |
|  | 30 mg Compound 292 SD | 1 day | 30 | 4 |
| MAD | Placebo Q12 h or Q24 h | 14 days | 0 | 12 |
|  | 1 mg Compound 292 Q12 h* | 14 days | 26 | 9 |
|  | 2 mg Compound 292 Q12 h* | 14 days | 52 | 9 |
|  | 5 mg Compound 292 Q12 h* | 14 days | 130 | 9 |
|  | 10 mg Compound 292 Q24 h | 14 days | 140 | 9 |
| FE | 25 mg Compound 292 Fasted-Fed | 2 days | 50 | 3 |
|  | 25 mg Compound 292 Fed-Fasted | 2 days | 50 | 3 |
| DDI | 10 mg Compound 292 SD | 2 days | 20 | 16 |

SD = single dose;
Q12 h = once every 12 hrs;
Q24 h = once every 24 hrs;
SAD = single ascending dose;
MAD = multiple ascending dose;
FE = food effect;
DDI = drug-drug interaction.
*includes QD dosing on Days 1 and 14.

Compound 292 was well tolerated at the doses evaluated. There were no deaths and no serious adverse events (SAEs). There did not appear to be a dose-related increase in AEs across the single dose range of 1 to 30 mg or the multiple dose range of 2 to 10 mg daily of Compound 292. No clinically significant safety laboratory or electrocardiogram (ECG) abnormalities were observed during any portion of the study.

Pharmacokinetic assessments demonstrated that Compound 292 was rapidly absorbed following single and multiple dose oral administration, with the maximum plasma concentration observed typically 1 hr after dosing. Across the dose ranges evaluated, Compound 292 exposure increased proportionally to dose. The mean elimination half-life ranged from 6.5 to 11.7 hrs after repeat dosing and did not depend on the dose level administered. Compound 292 accumulation was less than 2-fold following 14 days of Q12 h oral administration. A summary of Compound 292 PK parameters from the single dose portion is provided in Table 9 below. A summary of Compound 292 PK parameters from the multiple dose portion is provided in Table 10 below.

TABLE 9

Summary of Compound 292 PK Parameters Following Single Dose Administration (Mean, % CV)

| Compound 292 Dose | $C_{max}$ (ng/mL) | $T_{max}$ (hr)* | $AUC_{(0-t)}$ (ng*hr/mL) | $AUC_{(0-24)}$ (ng*hr/mL) | $AUC_{(0-inf)}$ (ng*hr/mL) | CL/F (L/h) | Vz/F (L) | $T_{1/2}$ (hr) |
|---|---|---|---|---|---|---|---|---|
| 1 mg | 43.4 (31) | 1.00 (1.00-1.00) | 148 (68) | 149 (67) | 151 (68) | 8.39 (42) | 38.8 (28) | 3.52 (29) |
| 2 mg | 78.8 (16) | 1.00 (0.50-2.00) | 291 (45) | 289 (43) | 296 (44) | 7.69 (37) | 57.9 (38) | 5.43 (25) |
| 5 mg | 246 (16) | 1.00 (0.50-1.50) | 735 (5) | 733 (5) | 743 (5) | 6.74 (5) | 53.0 (15) | 5.43 (10) |
| 10 mg | 454 (40) | 0.50 (0.50-1.50) | 905 (15) | 891 (14) | 914 (14) | 11.1 (15) | 147 (29) | 9.47 (38) |
| 20 mg | 997 (32) | 1.00 (1.00-1.00) | 2243 (16) | 2193 (16) | 2250 (16) | 9.09 (18) | 99.1 (46) | 7.79 (51) |
| 30 mg | 1140 (38) | 1.00 (0.50-1.00) | 3384 (38) | 3263 (38) | 3395 (38) | 9.73 (33) | 113 (31) | 8.12 (18) |

*median (range);
h = hours

TABLE 10

Summary of Compound 292 PK Parameters Following Multiple Dose Administration (Mean, % CV)

| Compound 292 Dose Regimen | Day | $C_{max}$ (ng/mL) | $T_{max}$ (h)* | $AUC_{(0-tau)}$ (ng*h/mL) | $T_{1/2}$ (h) | Racc |
|---|---|---|---|---|---|---|
| 1 mg Q12 h | 1 | 49.1 (26) | 0.52 (0.50-1.00) | 124 (40) | 3.46 (39) | — |
|  | 14 | 66.8 (36) | 1.00 (0.50-1.50) | 199 (39) | 6.46 (20) | 1.65 (19) |
| 2 mg Q12 h | 1 | 101 (31) | 1.00 (0.50-2.00) | 290 (49) | 6.34 (35) | — |
|  | 14 | 140 (36) | 1.00 (0.50-2.00) | 524 (47) | 9.75 (37) | 1.83 (22) |
| 5 mg Q12 h | 1 | 257 (38) | 1.00 (0.50-1.50) | 774 (41) | 5.76 (11) | — |
|  | 14 | 355 (37) | 1.00 (0.50-2.02) | 1291 (38) | 8.32 (35) | 1.71 (15) |
| 10 mg Q24 h | 1 | 553 (27) | 0.52 (0.50-1.52) | 1527 (37) | 6.00 (13) | — |
|  | 14 | 605 (16) | 1.00 (0.50-1.55) | 2232 (25) | 11.7 (82) | 1.54 (18) | h = hours,
CV = coefficient of variation,
Racc = accumulation ratio,
* Median (range)

Data from the food effect portion indicate that food does not significantly alter systemic exposure to Compound 292. When administered in the presence of a high fat meal, Compound 292 concentration decreased by approximately 10% and median $T_{max}$ was delayed from 1 hr (fasted) to 3 hrs (fed). Overall exposure, as assessed by $AUC_{(0-last)}$ and $AUC_{(0-inf)}$, increased by approximately 9% in the presence of a high fat meal.

Data from the DDI portion indicated that concomitant administration of 200 mg q12h ketoconazole increased exposure to Compound 292. On average, $C_{max}$, $AUC_{0-last}$ and $AUC_{0-inf}$ increased by approximately 66%, 285% and 295%, respectively, in the presence of ketoconazole compared to Compound 292 administered alone.

Figure 2:
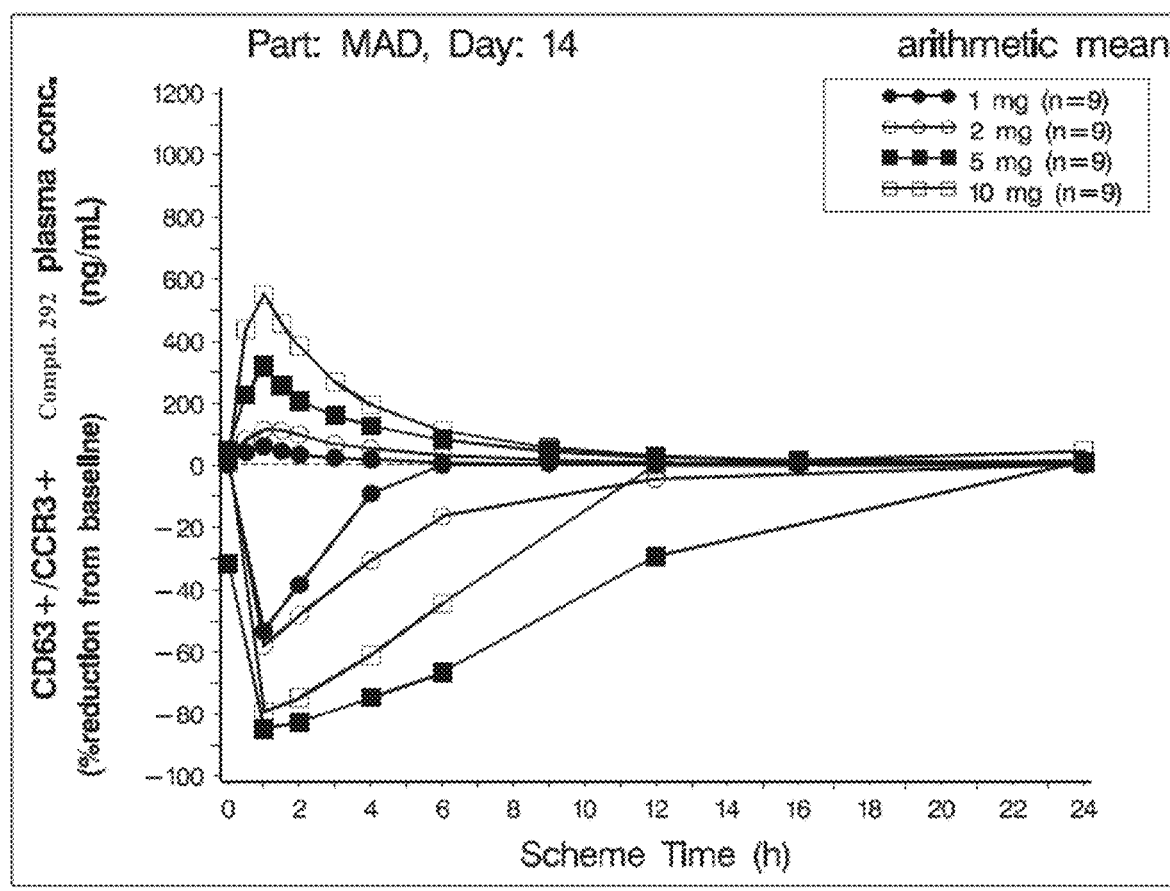
FIG. 2 depicts the PK/PD relationship of mean drug plasma concentration and mean % reduction from pre-dose for basophil activation over time, following multiple dose administration of Compound 292 in human.
Figure 3:
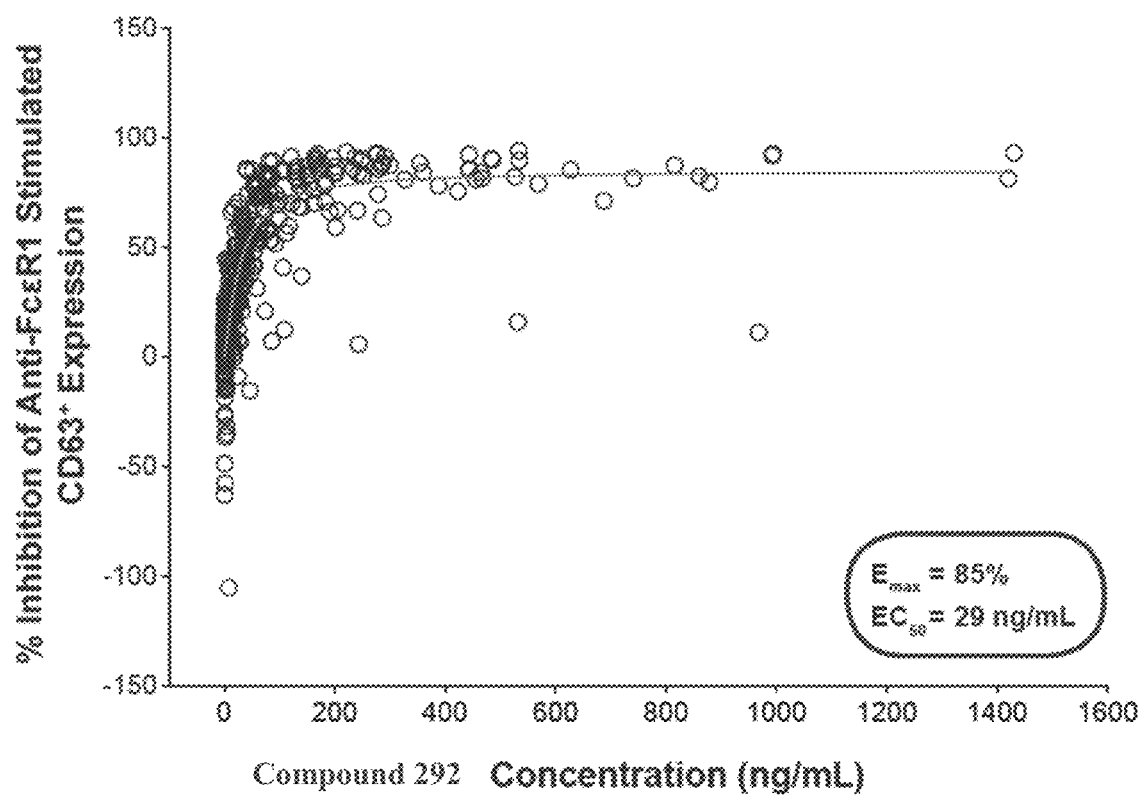
FIG. 3 depicts the pharmacodynamic response versus concentration of Compound 292 in human.

Following single and multiple Compound 292 doses, a dose-dependent reduction of basophil activation was observed at all dose levels, with a maximum reduction at 1 hr post dose; no notable change was observed following treatment with placebo. The PK/PD summary following single dose administration is shown in FIG. 1-3, which demonstrates that the PD response was rapid and that maximal response was achieved at 5 mg dosing. A relationship was apparent between reduction of basophil activation and Compound 292 plasma concentrations, with saturation of the effect at higher Compound 292 plasma concentrations.

Serial ECGs were performed at multiple time points after dosing in all study groups. No subject had a QTcF greater than 500 msec at any assessment, and the largest change from baseline in QTcF was 37 msec.

Overall, Compound 292 was well tolerated in healthy subjects at single doses up to 30 mg (highest dose tested) and up to 10 mg total daily dose (highest dose tested; 5 mg BID or 10 mg QD) for 14 days. In healthy subjects, the PK profile of Compound 292 is characterized by rapid absorption (peak plasma concentrations reached within 0.5-1 hour), moderately rapid elimination (half-life 3.5 to 9.5 hours following a single dose and 6.5 to 11.7 hours following repeat dosing) and dose proportional increases in systemic exposure ($C_{max}$ and AUC). Minimal accumulation was observed after multiple dose administration (accumulation ratio 1.65-1.83 for BID dosing and 1.54 for QD dosing). Following single oral dose administration, clearance ranged from 6.7 L/h to 11.1 L/h and the volume of distribution ranged from 38.8 L to 147 L. Excretion of unchanged Compound 292 in urine was <2% of the administered dose, indicating minimal renal elimination of parent drug. CD63 expression on the surface of activated CCR3+ basophils was reduced in a dose-dependent manner at all single and multiple dose levels, with a maximum reduction at 1 hour post dose, corresponding to the time of maximum Compound 292 plasma concentrations. Inhibition of basophil activation mirrored the Compound 292 concentration-time profile, with CD63 expression returning to baseline levels as plasma concentrations declined. Administration of 5 mg BID maintained PI3K-δ inhibition ($EC_{50}$=48 ng/mL) throughout the 12 hour dosing interval. Concomitant administration of a high-fat, high-calorie meal decreased $C_{max}$ approximately 10%, shifted median $T_{max}$ from 1 to 3 hours, and increased overall exposure (AUC) approximately 8-9%. These data suggest Compound 292 can be administered without regard to meals.

Thus, Compound 292 was rapidly absorbed after single and multiple doses. Mean systemic exposure ($C_{max}$ and AUC) increased dose proportionally, indicating linear PK. Mean apparent terminal elimination half-life ($t_{1/2}$) following 14 days of Compound 292 dosing ranged from 6.5 to 11.7 hours. Accumulation ratio (mean ratio of Day 14/Day 1 AUC) was 1.54 for QD dosing, 1.65 to 1.83 over BID dose range. Following administration with a high-fat, high calorie meal, $AUC_{0-inf}$ increased by 9%, $C_{max}$ decreased by 10%, and median $T_{max}$ shifted from 1 hr to 3 hr. Based on the magnitude of these changes, Compound 292 can be administered without regard to meals. In addition, a rapid response was observed, assessed as reduction in CD63+ expression on CCR3+ basophils in an ex vivo anti-FcεR1 activation assay (FIG. 1-3). Maximal response was observed at the time of maximal plasma concentrations, one hour after single- and multiple-dose administration. CD63+ expression returned to baseline as plasma drug concentrations declined. Moreover, Compound 292 was well-tolerated at all doses studied: single doses up to 30 mg, and multiple doses up to 10 mg daily for 14 days. In subjects who received multiple doses of Compound 292 (n=36) (PLB n=12) for 2 weeks, the most common adverse events (AEs) were related to blood draws and protocol-associated procedures. The most common non-procedural AEs occurring in ≥2 subjects were headache (8% vs. 25% PLB), myalgia (6% vs. 8% PLB), and nasopharyngitis (6% vs. 0% PLB). No dose-related trends in AEs were observed. No clinical significant findings in safety lab studies of ECGs were observed. No increases in IgE related to Compound 292 were observed.

Example 9

Clinical Studies in Advanced Hematologic Malignancies

A Phase 1 dose-escalation study was designed to evaluate the safety, pharmacokinetics (PK), and activity of orally administered Compound 292 in patients with advanced hematologic malignancies, including T-cell lymphomas/leukemias. Sequential cohorts of patients were enrolled at progressively higher dose levels with expansion cohorts of patients with select hematologic malignancies. Compound 292 was administered orally 2 times per day (BID) continuously in 28-day cycles. Tumor response was evaluated based on disease-specific standard criteria.

The study had enrolled 20 (or more) patients; 5 patients with chronic lymphocytic leukemia (CLL)/small lymphocytic lymphoma (SLL), 4 with indolent non-Hodgkin lymphoma (iNHL), 3 with aggressive B-cell NHL [including diffuse large B-cell lymphoma (DLBCL) n=2; and Richter's n=1], 3 with multiple myeloma (MM), 2 with Hodgkin lymphoma (HL), 2 with T-cell lymphoma [anaplastic large-cell lymphoma (ALCL) n=2] and 1 with mantle cell lymphoma (MCL). Of these patients, 11 were male and 9 female, with a median [range] age of 63 years [30-81], with 36%<6 month from most recent prior systemic therapy. The median [range] number of prior therapies was 3 [1-8].

Compound 292 doses administered include 8 mg BID (n=1), 15 mg BID (n=6), 25 mg BID (n=7), 35 mg BID (n=3), and 50 mg BID (n=3). The median [range] number of treatment cycles was 2 [1-8], with 12 (60%) patients continuing on treatment. Adverse events (AEs) had occurred in 13 (65%) patients, including 7 (35%) patients with AEs Grade >3. Treatment-related AEs occurred in 11 patients (55%) with Grade >3 occurring in 5 patients (25%). Grade 4 neutropenia was the one dose limiting toxicity observed to date (15 mg dose cohort). New Grade >3 hematological laboratory abnormalities included neutropenia [n=6 (30%)] and thrombocytopenia [n=1 (5%)]. Grade 3 ALT/AST elevations occurred in 1 (5%) MM patient with onset 6 weeks after initiation of dosing of Compound 292.

PK indicated dose-proportional increases in plasma $C_{max}$ and AUC over the dose range studied. Further, the PK and initial pharmacodynamic (PD) data from the first three cohorts (8 25 mg BID) predicted continuous suppression of the PI3K-δ pathway with increasing inhibition of the PI3K-γ pathway with a 25 mg BID dose or greater.

In the evaluable patients (n=11), responses were observed at the 8, 15, and 25 mg BID dose levels including 2/3 in CLL/SLL (0 CR/2 PR/1 SD), 1/2 in iNHL (1 CR/0 PR/1 SD), and 1/1 in MCL (1 PR). All patients with at least SD after 2 cycles (n=6) remained on treatment including the first patient dosed.

PK and PD markers were evaluated after the first dose (e.g., 8 mg BID) and at steady state. PD activity (PI3K inhibition) in whole blood was evaluated using a basophil activation assay which measured reduction in CD63 expression on the surface of basophils following ex vivo stimulation.

The data demonstrated rapid drug absorption and dose-proportional PK. As in healthy subjects, maximum inhibition of basophil activation was observed 1 hour post dose. Prior to dose administration at the beginning of Cycle 2 (i.e. after 28 days of BID dosing), CD63 expression was reduced 45% or more relative to the start of treatment. Mean steady-state trough concentrations were maintained above levels sufficient for PI3K-δ inhibition following doses ≥15 mg BID. Clinical response were observed.

Thus, in both studies (in healthy subjects and in advanced hematologic malignancies), Compound 292 drug absorption was rapid and exposure was proportional to dose. CD63 expression on the surface of activated basophils was reduced in the presence of Compound 292 in both healthy and oncology subjects, an observation consistent with PI3K-δ inhibition. An exposure-response relationship was evident, suggesting a concentration-dependent pharmacological response to Compound 292. PK/PD data from the oncology study demonstrated inhibition of PI3K-δ activity and suggested higher doses increasingly suppress PI3K-γ activity.

Based on the PK/PD and activity observed in patients with CLL (e.g., CLL/SLL), iNHL and MCL, an expansion cohort to further evaluate the safety and preliminary activity of Compound 292 was enrolling patients in these select hematologic diseases dosed at 25 mg BID. Dose escalation continued with a focus on patients with T-cell malignancies and DLBCL, where increasing suppression of the PI3K-γ isoform can improve the efficacy profile.

Additional expansion cohorts can be opened in T-cell lymphoma, DLBCL, myeloproliferative neoplasms, acute leukemias, T-cell/aggressive NHL, and the CLL/iNHL/MCL to further define disease specific activity.

Thus, Compound 292, an oral, potent PI3K-δ, γ inhibitor or modulator, is well tolerated at doses ranging from 8 mg BID to 50 mg BID, and has shown clinical activity in patients with iNHL, MCL, and CLL. A dose of 25 mg BID effectively inhibits PI3K-δ, providing a rationale for expansion in CLL/iNHL/MCL.

Example 10

Clinical Studies in Hematologic Malignancies: Additional Data

PI3K-δ and PI3K-γ are involved in leukocyte signaling and B-cell, T-cell, and myeloid cell function, including differentiation, activation, proliferation and migration. PI3K-δ and PI3K-γ support the growth and survival of certain B- and T-cell malignancies. As exemplified herein, Compound 292 is a potent oral inhibitor of PI3K-δ and PI3K-γ isoforms (e.g., Table 11).

TABLE 11

Summary of Compound 292 In Vitro Activities

| PI3K Isoforms* | PI3K-δ | PI3K-γ | PI3K-α | PI3K-β |
|---|---|---|---|---|
| Expression | Primarily Leukocytes | Primarily Leukocytes | Ubiquitous | Ubiquitous |
| Role | B-cell activation and function T-cell activation and function | Innate immune function Immune cell trafficking | Platelet activation Insulin signaling | Insulin signaling Angiogenesis |
| Isoform Specific Cellular Assay Inhibition of pAKT ($IC_{50}$) | 1 nM | 43 nM | 171 nM | 1547 nM |
| Biochemical Activity ($K_D$) | 23 pM | 243 pM | 1564 pM | 25900 pM |
| Whole Blood Assay (IC50) (Healthy Donors) | 69 nM Anti-FcεR1 | 1200 nM fMLP | 4700 nM Platelet | — |

*PI3K-α and PI3K-β (ubiquitous expression) not shown.

In a Phase I study in healthy subjects, single and multiple doses of Compound 292 were well tolerated with dose-proportional pharmacokinetics through 5 mg BID and a $t_{1/2}$ of 6.5 to 11.7 hr and pharmacodynamic response (anti-FcεR1) mirrored plasma concentrations, with maximal effects observed at the time of maximal plasma concentrations (e.g., FIGS. 1-3).

Study Design: One clinical study of Compound 292 is a Phase I, open-label study enrolling 1-6 adult patients per dose level with hematologic malignancies at progressively higher dose levels. Dosing was orally, twice daily (BID) on a 28-day cycle. The primary objectives were to determine safety and MTD for Compound 292. Endpoints included safety, efficacy, pharmacokinetics (PK), and pharmacodynamics (PD). Expansion cohorts of selected hematologic malignancies are allowed at ≤MTD based on PK/PD/clinical activity for PI3K-δ and PI3K-γ inhibition. Key inclusion criteria included: (1) progressed during, refractory to, intolerant of, or ineligible for established therapy, or has disease with no established therapy; (2) adequate hepatic and renal function (≤Grade 1); (3) adequate hematopoietic function (escalation phase only) with baseline ANC≥750 cells/4, platelets ≥75K/μL, and hemoglobin >8.0 g/dL; (4) no prior treatment with a PI3K inhibitor (escalation phase) or within 4 weeks of first dose of Compound 292 (expansion phase). Dose escalation study included the following doses: 8 mg BID, 15 mg BID, 25 mg BID, 35 mg BID, 50 mg BID, 60 mg BID, 75 mg BID, and 100 mg BID (enrolling). Cohort expansions at ≤MTD are carried out in hematologic malignancies such as diffuse large B-cell lymphoma, T-cell lymphomas, acute lymphocytic leukemia, myeloproliferative neoplasms, CLL/SLL, iNHL, and MCL (for example, 25 mg BID expansion was carried out in CLL/SLL, iNHL, and MCL). Dose-limiting toxicities (DLTs) during Cycle 1, used to determine MTD, include (1) death; (2) Grade ≥4 hematologic toxicity lasting >7 days, or Grade 3 febrile neutropenia, Grade 3 thrombocytopenia with Grade ≥2 hemorrhage, or Grade 4 thrombocytopenia of any duration requiring transfusion; (3) Grade 3 diarrhea or nausea lasting ≥24 hours, despite medical treatment, or any other Grade 3 non-hematologic toxicity of any duration.

The patient demographics and disposition are summarized in Tables 12 and 13. After dose escalation to 75 mg BID, MTD was not yet reached and dose escalation was continuing There were three discontinuations due to treatment related AEs: (1) Grade 3 pneumonitis (15 mg BID); (2) Grade 4 ALT elevation (25 mg BID); (3) AE grade and etiology not reported at data cut-off (25 mg BID).

TABLE 12

Patient Demographics

| | |
|---|---|
| Evaluable Patients (Safety), n | 55 (28 Escalation, 27 Expansion at 25 mg BID) |
| Evaluable Patients (Efficacy), n | 41 (24 Escalation, 17 Expansion at 25 mg BID) |
| Median Age, years (range) | 67 (30-86) |
| Females, n (%) | 19 (35%) |
| Diagnosis* | 17 iNHL    4 MCL<br>16 CLL/SLL    3 MM<br>7 T-cell Lymphoma    3 HL<br>5 Aggressive B-cell NHL (aNHL) |
| ECOG Score 0-1 (%) | 51 (93%) |
| Poor/High Risk Lymphoma (IPI/FLIPI/MIPI), n (%) | 13 of 24 (54%) |
| Prior Systemic Therapies, median (range) | 4 (1-13) |
| Patients with ≥3 Prior Systemic Therapies | 39 (72%) |
| Months Since Last Therapy to First Dose of Compound 292, n (%) | <6 months    ≥6 months<br>30 (58%)    22 (42%) |

*iNHL (indolent non-Hodgkin lymphoma),
MCL (mantle cell lymphoma),
CLL/SLL (chronic lymphocytic leukemia/small lymhocytic lymphoma),
MM (multiple myeloma),
HL (Hodgkin lymphoma)

TABLE 13

Patient Disposition

| Compound 292 Dose | Patients (n) | Disposition |
|---|---|---|
| 8 mg BID | 1 | 1 on study |
| 15 mg BID | 6 | 20 on study/4 off study (3 PD/1 AE) |
| 25 mg BID | 7 | 5 on study/2 off study (PD) |
| 25 mg BID (expansion) | 27 | 21 on study/6 off study (3 PD, 2 AE, 1 ineligible) |
| 35 mg BID | 3 | 3 off study (2 PD, 1 withdrew consent) |
| 50 mg BID | 3 | 1 on study/2 off study (1 PD/1 CR → auto-transplant) |
| 60 mg BID | 3 | 3 on study |
| 75 mg BID | 5 | 4 on study/1 off study (PD) |
| Total* | 55 | 37 on study/18 off study (12 PD) |

Figure 4:
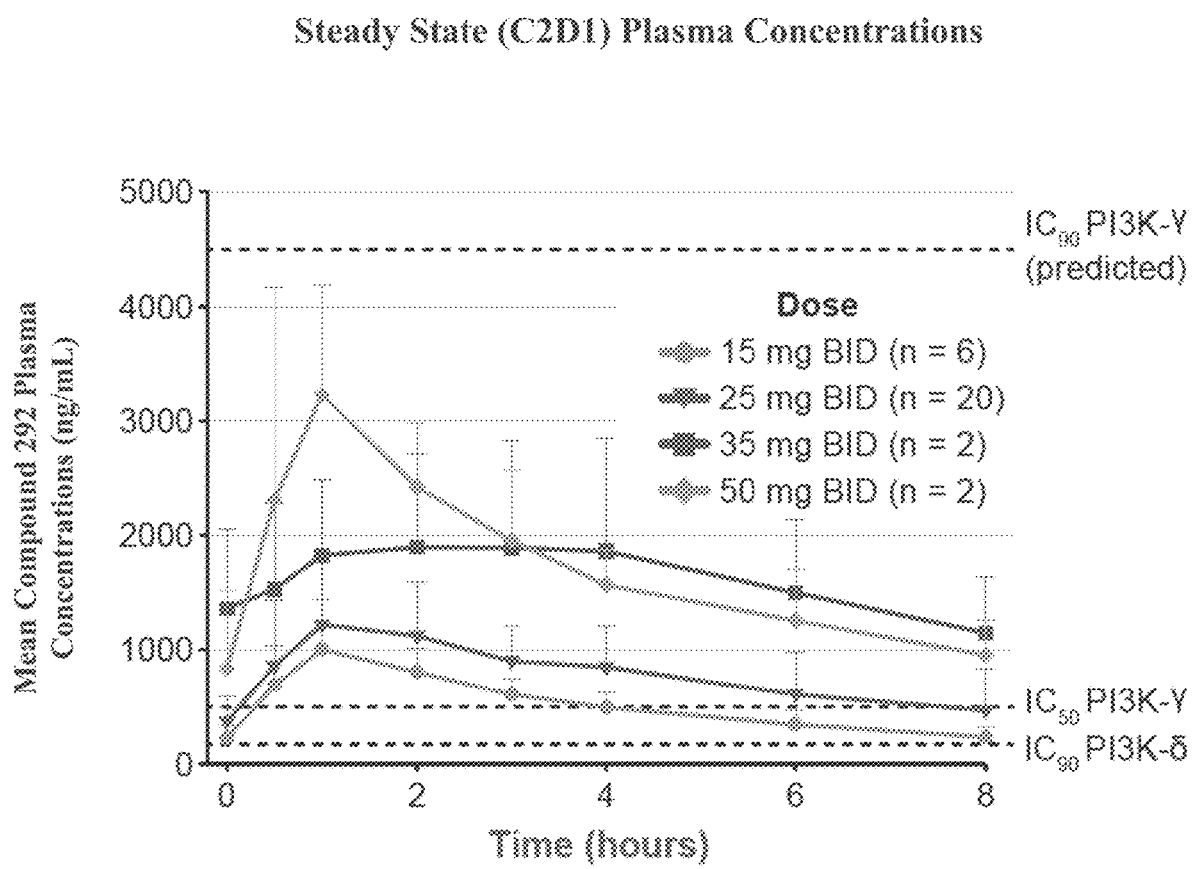
FIG. 4 depicts the steady state (C2D1) plasma concentrations over time after administration of Compound 292 in human.
Figure 5A:
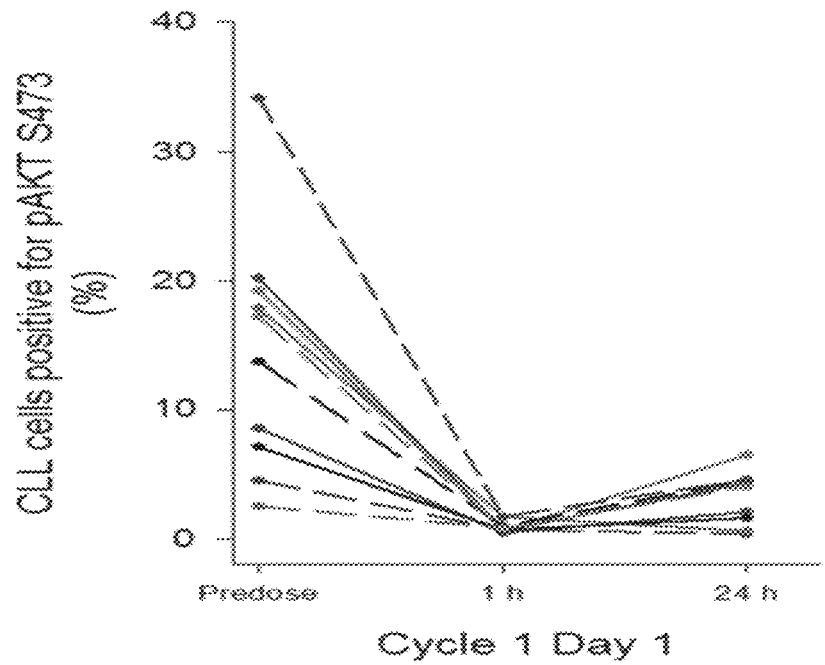
FIG. 5A depicts AKT phosphorylation in CLL/SLL cells of Compound 292 during Cycle 1 Day 1.
Figure 5B:
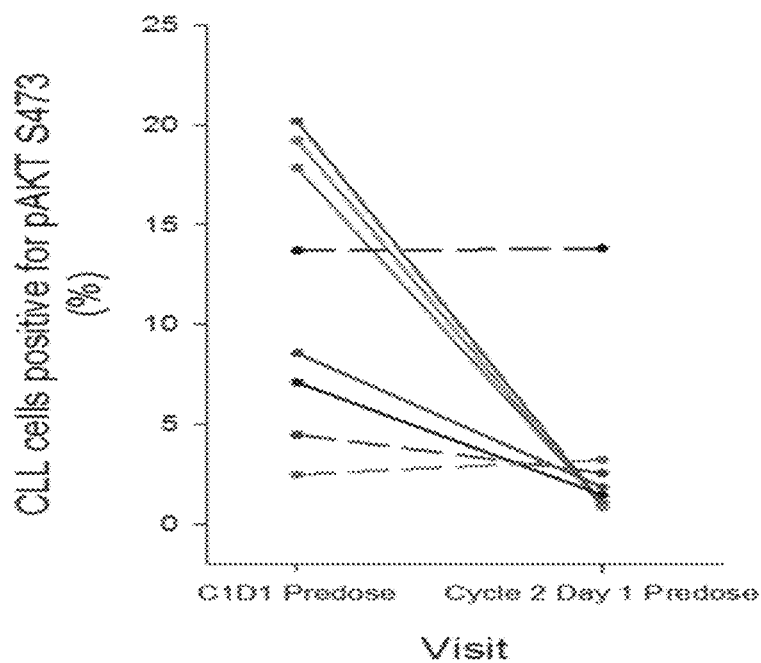
FIG. 5B depicts changes in AKT phosphorylation in CLL/SLL cells of Compound 292 between visits.

Pharmacokinetics and pharmacodynamics data are summarized in FIGS. 4 and 5. Compound 292 was rapidly absorbed with a linear PK profile through 50 mg BID (eliminating $t_{1/2}$ was 6 to 10 hours). The data showed that complete inhibition of PI3K-δ can be achieved at doses of 15 mg BID or greater; and doses of 25 mg BID or greater increasingly suppress PI3K-γ (FIG. 4). In addition, rapid and sustained inhibition of AKT phosphorylation by Compound 292 in CLL/SLL cells was observed by flow cytometry after one dose (25 mg) (FIG. 5). These PK/PD results supported an expansion cohort at 25 mg BID to evaluate the tolerability and activity of Compound 292 in selected hematologic malignancies.

Figure 6:
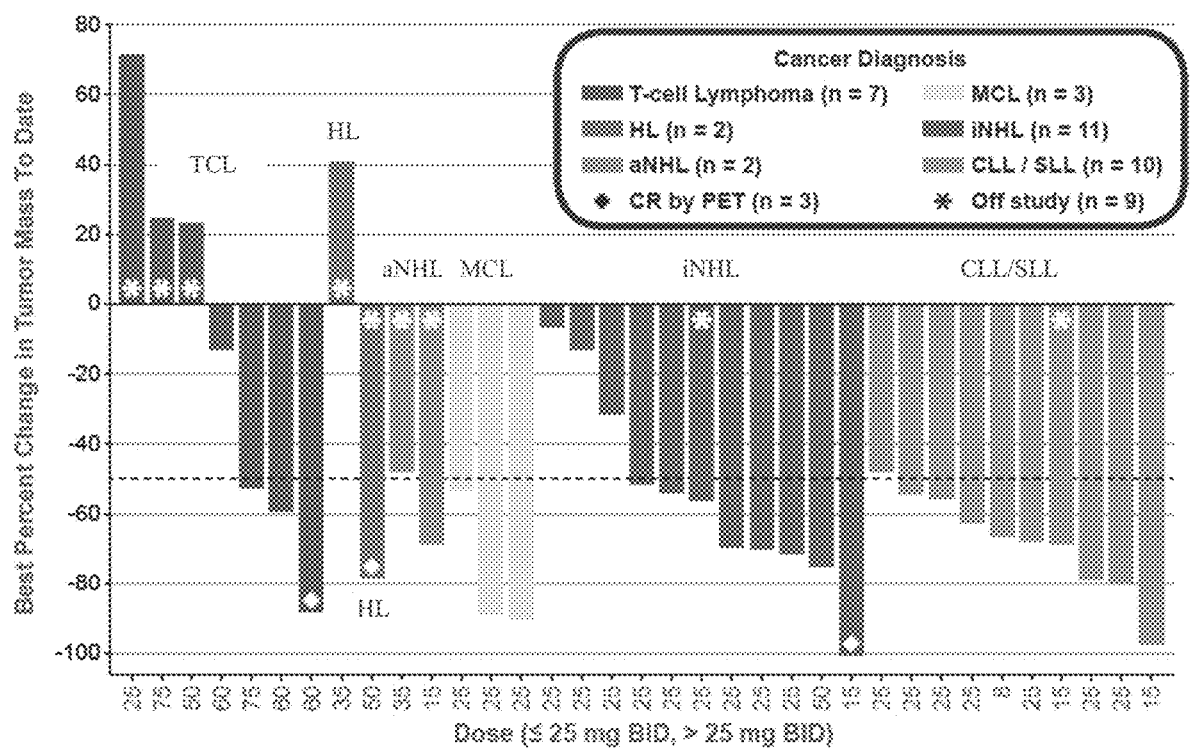
FIG. 6 depicts changes in tumor size after administration of Compound 292 in human.

Clinical efficacy data for Compound 292 in B-cell and T-cell malignancies are summarized in Tables 14 and maximum change in tumor size on treatment with Compound 292 are shown in FIG. 6. Reduction in tumor mass was observed in all indications and at all dose levels evaluated. Patients with measurable disease by CT scan and with ≥1 on-treatment CT assessment are shown in FIG. 6, including patients (n=2) who have not had a response assessment. Patients off study with PD before first CT assessment (n=2) or disease not assessed by CT (n=4) are not shown in the figure.

TABLE 14

Clinical Response in B-Cell and T-Cell Hematologic Malignancies.

| Population | Patients (n) Treated | Evaluable [b] | Best Observed Response (n) [a] CR | PR | SD | PD | Time to Response in Months Median (range) |
|---|---|---|---|---|---|---|---|
| iNHL | 17 | 13 | 1 | 7 | 4 | 1 | 1.8 (1.7, 2.8) |
| CLL/SLL | 16 | 11 | 0 | 6 | 4 [c] | 1 | 2.9 (1.8, 5.6) |
| T-Cell Lymphoma | 7 | 6 | 1 | 1 | 1 | 3 | 2.4 (1.8, 3.1) |
| aNHL | 5 | 3 | 0 | 0 | 1 | 2 | N/A |
| MCL | 4 | 3 | 0 | 2 | 0 | 1 | 1.9 (1.9, 1.9) |
| MM | 3 | 3 | 0 | 0 | 1 | 2 | N/A |
| HL | 3 | 2 | 1 | 0 | 0 | 1 | 1.7 (1.7, 1.7) |

[a] Responses: Complete Response (CR), Partial Response (PR), Stable Disease (SD), Progressive Disease (PD).
[b] At least one response assessment or progressive disease (PD).
[c] Four nodal responses.

Figure 7:
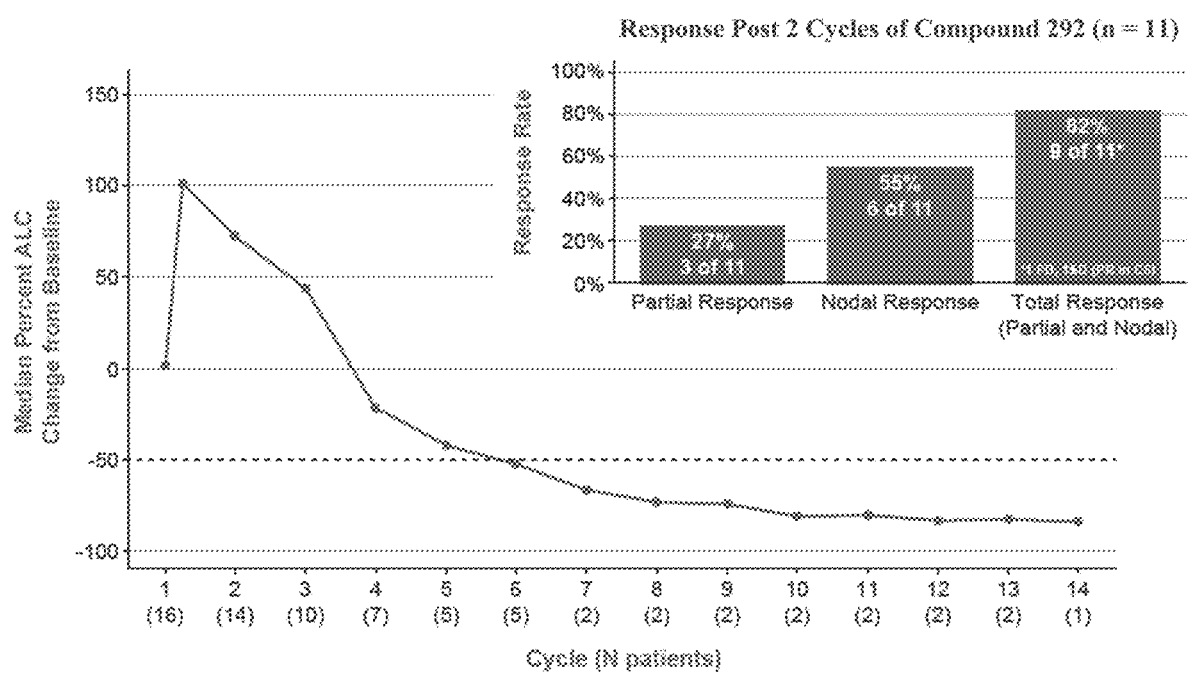
FIG. 7 depicts rapid onset of clinical activity of Compound 292 in CLL/SLL patients.
Figure 8:
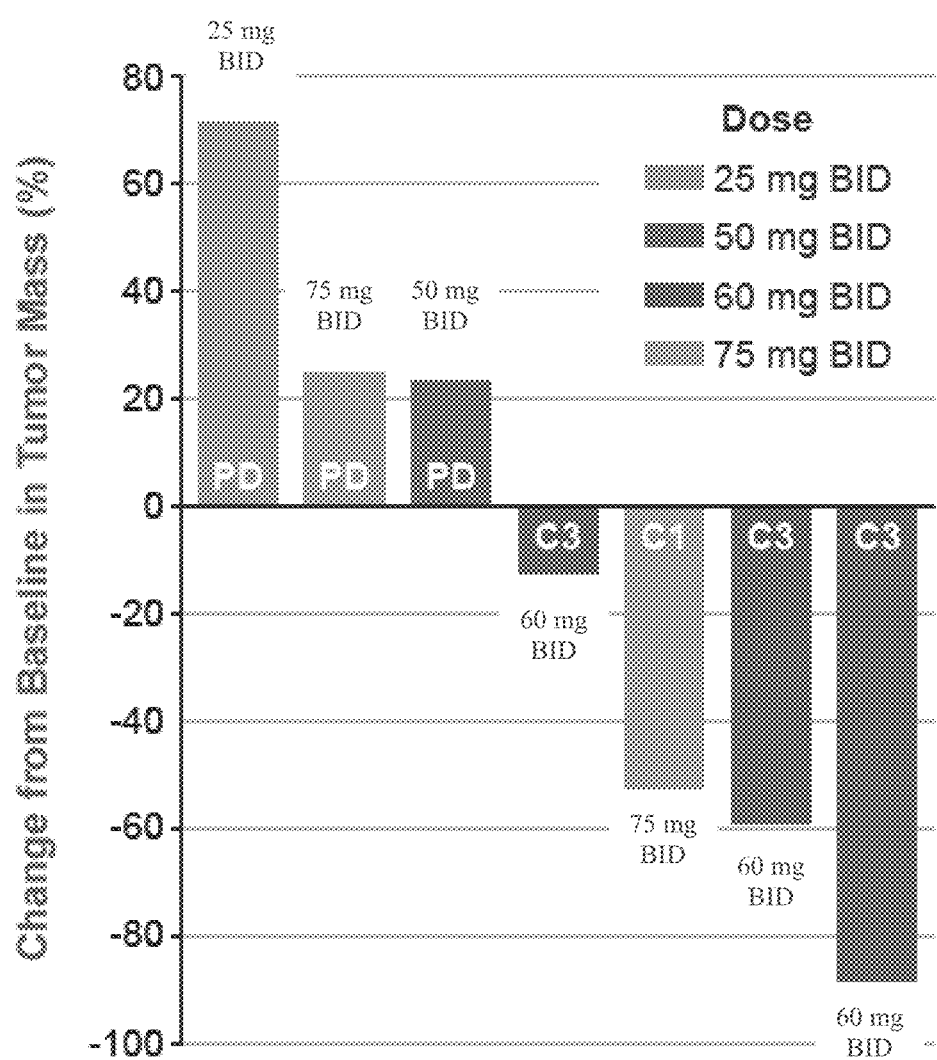
FIG. 8 depicts clinical activity of Compound 292 in T-cell lymphoma patients.

Rapid onset of clinical activity of Compound 292 was observed in CLL/SLL (FIG. 7). Clinical activity of Compound 292 in T-cell lymphoma was observed (FIG. 8), with first response assessment after 2 cycles of Compound 292 therapy: 1 complete response (CR), 1 partial response (PR), 1 stable disease (SD), 3 progressive disease (PD) (and 1 status unknown). Four patients remained on study. In addition, a 72-year-old patient with enteropathy-associated T-cell lymphoma demonstrated complete resolution of pulmonary metastases (white arrows), as shown by PET/CT, after 2 cycles of Compound 292 (60 mg BID) (FIG. 9).

Further, among subjects having T cell lymphoma, it was found that Compound 292 has efficacy in treating both peripheral T cell lymphoma (PTCL) and cutaneous T cell lymphoma (CTCL), as shown in Table 15 below:

TABLE 15

Clinical Responses in TCL

| Population | Patients (n) T/E* | Best Observed Response (n) CR | PR | SD | PD | Median Time to Response in Months (range) |
|---|---|---|---|---|---|---|
| TCL Total | 17/9 | 1 | 2 | 2 | 4 | 1.9 (1.7-2.7) |
| PTCL | 7/5 | 1 | 1 | 0 | 3 | 2.3 (1.9-2.7) |
| CTCL | 10/4 | 0 | 1 | 2 | 1 | 1.7 (—) |

Figure 10:
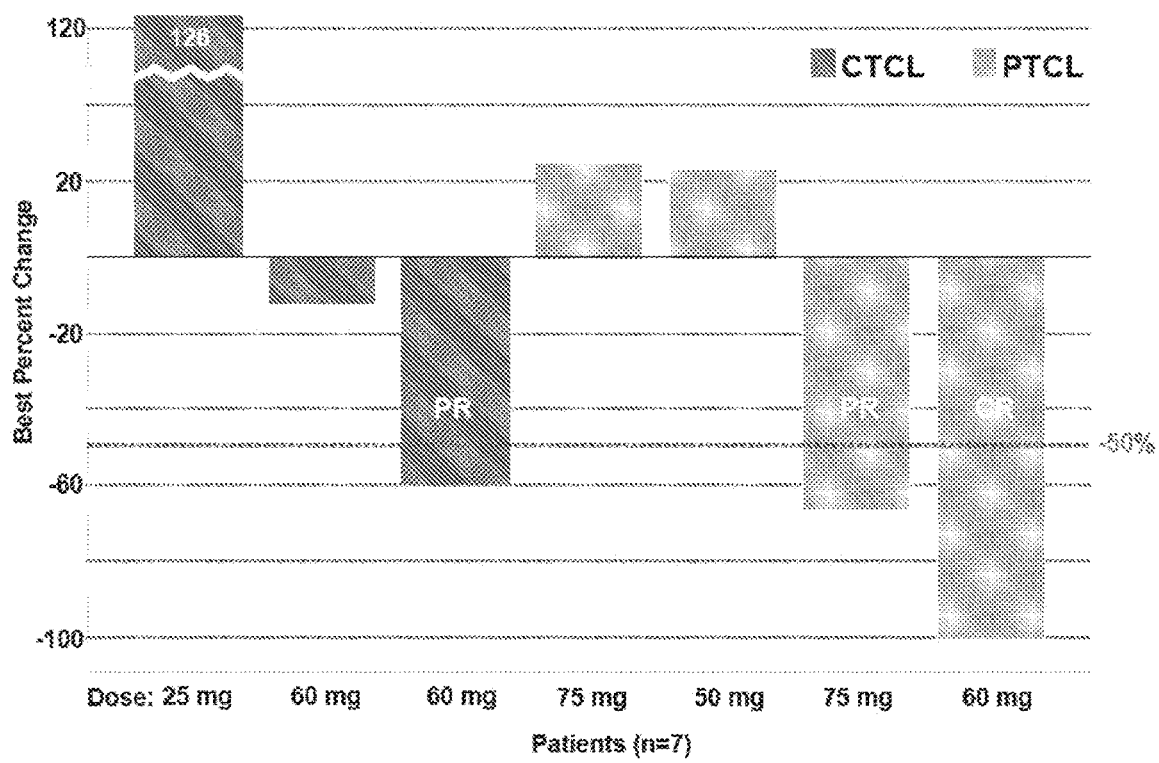
FIG. 10 depicts percent changes in measurable disease in patients with peripheral T-cell lymphoma (PTCL) and cutaneous T-cell lymphoma.

*Treated/Evaluable (Evaluable = at least 1 response assessment or PD prior to C3D1 response assessment)
CR = Complete Response;
PR = Partial Response;
SD = Stable Disease;
PD = Progressive Disease Percent changes in measurable disease as assessed by CT scans following the administration of Compound 292 at the specified doses (all BID) is illustrated in FIG. 10. As shown in the figure, 33% of the patients (2 PTCL and 1 CTCL) showed at least 50% tumor response.

Clinical responses observed in various B cell lymphoma patients are summarized in Table 16 below:

TABLE 16

Clinical Responses in BCL

| Population | Patients (n) T/E* | Best Observed Response, n (%) Overall | CR | PR | MR | SD | PD | Median Time to Rsp in Months (Range) |
|---|---|---|---|---|---|---|---|---|
| iNHL | 26/19 | 13 (68) | 3 (16) | 10 (53) | 1 (5) | 3 (16) | 2 (11) | 1.8 (1.7-4.1) |
| MCL | 9/6 | 4 (67) | 1 (17) | 3 (50) | N/A | 1 (17) | 1 (17) | 1.8 (1.6-1.9) |
| HL | 3/3 | 1 (33) | 1 (33) | 0 | N/A | 1 (33) | 1 (33) | 1.7 |
| aNHL | 13/10 | 0 | 0 | 0 | N/A | 4 (40) | 6 (60) | N/A |

Figure 11:
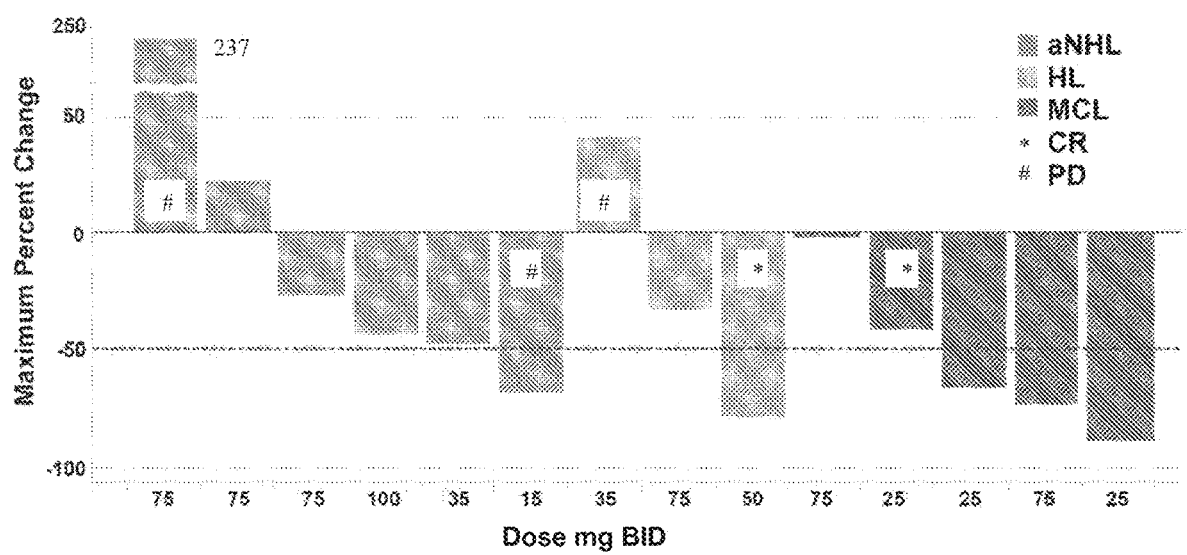
FIG. 11 depicts percent changes in measurable disease in patients with aggressive NHL (aNHL), Hodgkin's lymphoma and mantle cell lymphoma (MCL).
Figure 12:
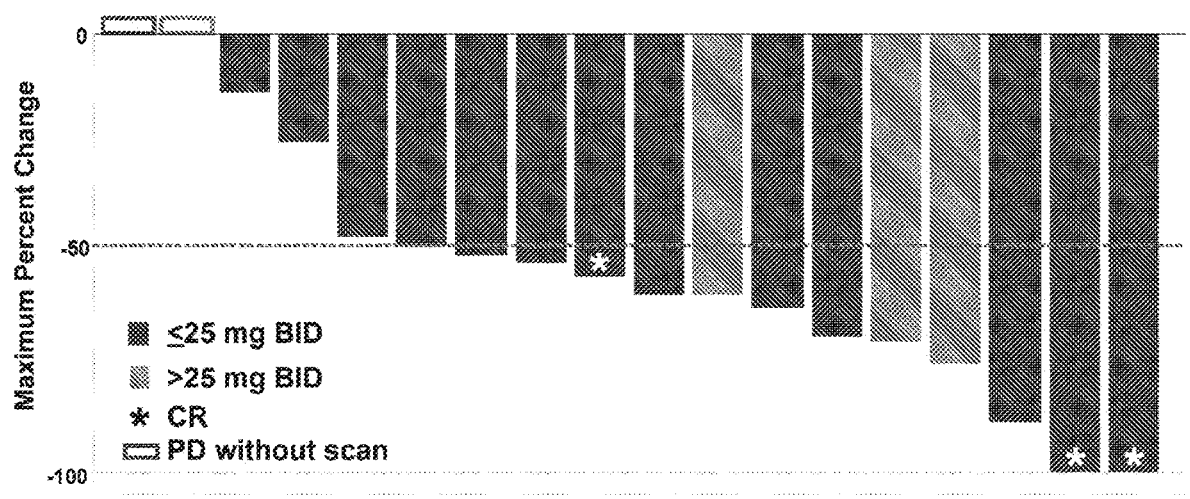
FIG. 12 depicts percent changes in measurable disease in patients with indolent NHL (iNHL). iNHL patients included patients with follicular lymphoma, Waldenstrom macroglobulinemia (lymphoplasmacytic lymphoma) and marginal zone lymphoma (MZL).

*Treated/Evaluable
CR = Complete Response;
PR = Partial Response;
MR = Minor Response for Waldenstrom's;
SD = Stable Disease;
PD = Progressive Disease
iNHL included 11 follicular lymphoma, 2 Waldenstrom's, 1 marginal zone lymphoma (MZL) and 12 iNHL As can be seen above, responses were observed (including CRs) in indolent, mantle and Hodgkin's lymphomas. Responses occurred early in 16 out of 18 responders (89%) by first assessment, within about 2 months. Percent changes in measurable disease assessed by CT scans for MCL, HL and a NHL patients are provided in FIG. 11, and those for iNHL (including follicular lymphoma, Waldenstrom's and MZL) are provided in FIG. 12.

Clinical safety data for Compound 292 are summarized in Tables 17 and 18. No dose-related trends were observed in related Grade 3 or Grade 4 AEs. DLTs included Grade 4 neutropenia (15 mg BID) and Grade 3 cellulitis (wound infection, 75 mg BID).

TABLE 17

Safety of Compound 292.

| Subject Safety Outcomes | 25 mg BID (n = 34) | Safety Population (n = 55) |
|---|---|---|
| Deaths on Study, n (%)* | 0 (0%) | 3 (5%) |
| AE Leading to Discontinuation, n (%) | 2 (6%) | 3 (5%) |
| SAE, n (%) | 4 (12%) | 11 (20%) |
| Related SAE, n (%) | 1 (3%) | 4 (7%) |
| All infectious SAEs, n (%) | 1 (3%) | 3 (5%) |
| Any AE | 27 (79%) | 46 (84%) |
| Grade 3/4 (%/%) | 7/5 (21%/15%) | 18/8 (33%/15%) |
| Related AE | 18 (53%) | 31 (56%) |
| Related Grade 3/4 (%/%) | 4/4 (12%/12%) | 14/6 (25%/11%) |
| New Grade 3/4 ANC (%/%) | 2/4 (6%/12%) | 10/5 (18%/9%) |
| Dose Reduced, n (%) | 2 (6%) | 5 (9%) |
| New Grade 3/4 ALT (%/%) | 3/1 (9%/3%) | 5/2 (9%/4%) |
| Dose Reduced, n (%) | 3 (9%) | 6 (11%) |

*Cause of death: all due to disease progression.

TABLE 18

Safety of Compound 292

| | Compound 292 BID Dose (n) | | | | | | |
|---|---|---|---|---|---|---|---|
| Grade 3 and 4 Related AEs | 8 mg (n = 1) | 15 mg (n = 6) | 25 mg (n = 34) | 35 mg (n = 3) | 50 mg (n = 3) | 60 mg (n = 3) | 75 mg (n = 5) |
| Neutropenia | 1 | 3 | 3 | 1 | 0 | 0 | 0 |
| Febrile Neutropenia | 1 | 0 | 0 | 0 | 0 | 0 | 0 |
| Anemia | 0 | 1 | 0 | 0 | 0 | 0 | 0 |
| Thrombocytopenia | 0 | 1 | 0 | 0 | 0 | 0 | 0 |
| ALT/AST Increased | 0 | 1 | 3 | 0 | 0 | 1 | 1 |
| Rash (general) | 0 | 0 | 0 | 0 | 1 | 0 | 1 |
| Cellulitis | 0 | 0 | 0 | 0 | 0 | 0 | 1 |
| Pneumonitis | 0 | 1 | 0 | 0 | 0 | 0 | 0 |
| Tumor Lysis/Hyperkalemia | 0 | 0 | 1 | 0 | 0 | 0 | 0 |
| Nausea | 0 | 1 | 0 | 0 | 0 | 0 | 0 |
| Dehydration | 0 | 0 | 1 | 0 | 0 | 0 | 0 |
| Mucosal Inflammation | 0 | 0 | 1 | 0 | 0 | 0 | 0 |
| Hypophosphatemia | 0 | 0 | 1 | 0 | 0 | 0 | 0 |

Figure 13:
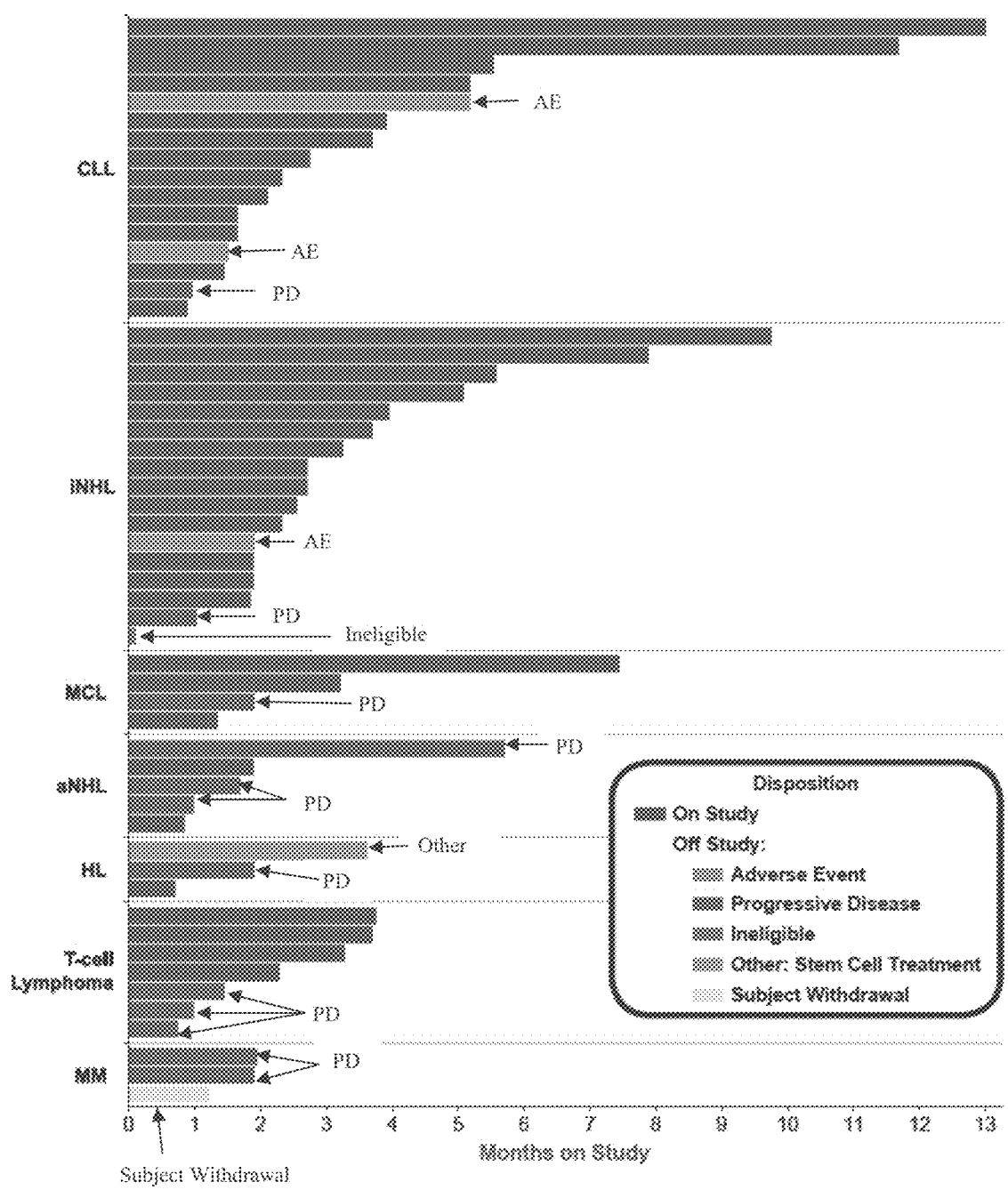
FIG. 13 depicts months on study by subject and diagnosis for patients treated with Compound 292.

FIG. 13 shows months on study by subject and diagnosis. An early analysis of time on study (median 2.2 months) showed that 67% of all patients remained on study. 90% (n=26) of patients with no PD (progressive disease) after 2 cycles of Compound 292 treatment remained on study.

In summary, Compound 292 is a potent oral inhibitor of PI3K-δ and PI3K-γ and is well-tolerated and clinically active in patients with advanced hematological malignancies. Doses up through 75 mg BID were examined; dose escalation of single agent Compound 292 was investigated. The PK profile indicated complete inhibition of PI3K-δ can be achieved at ≥15 mg BID for Compound 292 and doses ≥25 mg BID increasingly suppress PI3K-γ. Expansion cohorts in selected malignancies are carried out at or below the MTD. SAEs were consistent with co-morbidities seen in advanced hematologic oncology patients. The most common related Grade 3 or Grade 4 AEs were cytopenias and ALT/AST elevations. Overall, these AEs were not dose-related and were managed by dose interruption and dose reductions. The results indicated that clinical activity was observed at all doses. Responses were observed in iNHL, CLL/SLL, and MCL at ≤50 mg BID. Responses were observed in T-cell lymphoma and Hodgkin lymphoma at ≥50 mg BID, which illustrates that B-cell and T-cell malignancies are sensitive to PI3K-δ and PI3K-γ inhibition.

Example 11

Figure 14A:
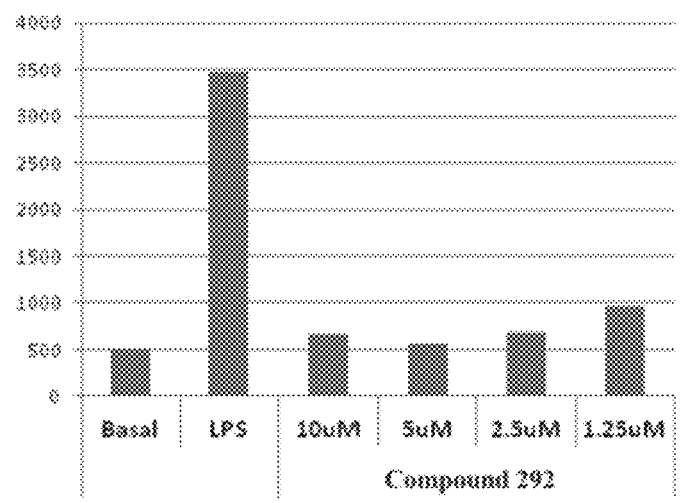
FIG. 14A depicts that Compound 292 inhibits TNF-α production from diluted whole blood stimulated with LPS.
Figure 14B:
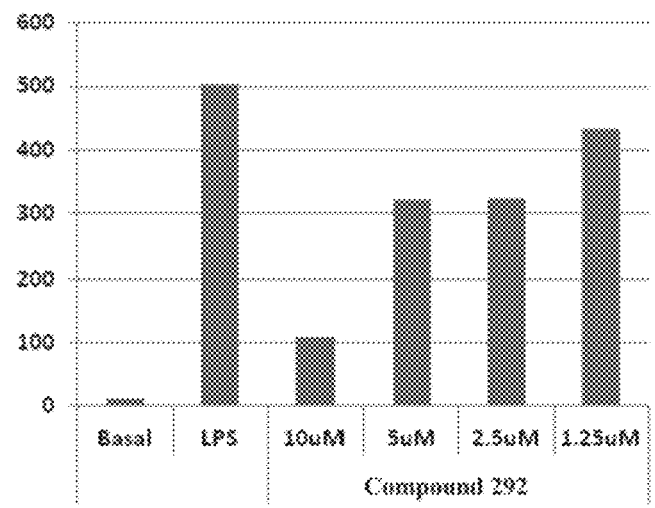
FIG. 14B depicts that Compound 292 inhibits IL-10 production from diluted whole blood stimulated with LPS.

Clinical Studies in Hematologic Malignancies: Serum Cytokines/Chemokines Production It had been observed that pre-treatment of diluted whole blood (1:1) with Compound 292 for 24 hours led to inhibition of cytokine (e.g., TNF-α and IL-10) production stimulated with 100 µg/mL of LPS (FIG. 14). To further investigate the effect of Compound 292 on cytokine/chemokine production, serum samples were collected from human subjects that participated in the clinical studies of Compound 292 for hematologic malignancies. Serum concentrations of a panel of human cytokines/chemokines were determined by Milliplex 96-well immuno-assay as described below.

Sample collection and storage: the blood was allowed to clot for at least 30 minutes before centrifugation for 10 minutes at 1000×g. Serum was removed and either assayed immediately or aliquoted and stored at ≤−20° C. When using frozen samples, it is recommended to thaw the samples completely, mix well by vortexing and centrifuge prior to use in the assay to remove particulates.

Preparation of serum matrix: 1.0 mL deionized water was added to the bottle containing lyophilized Serum Matrix (catalog number MX HSM from MILLIPLEX® Map), and was allowed to be mixed will for at least 10 minutes for complete reconstitution.

Assay procedure: 200 µL of wash buffer was added into each well of the plate. The plate was sealed and mixed on a plate shaker for 10 minutes at room temperature (20-25° C.).

The wash buffer was decanted and the residual amount was removed from all wells by inverting the plate and tapping it smartly onto absorbent towels several times. 25 µL of each standard or control was added into the appropriate wells. Assay buffer was used for 0 pg/mL standard (Background). 25 µL of assay buffer was added to the sample wells. 25 µL of appropriate matrix solution was added to the background, standards, and control wells. 25 µL of serum sample was added into the appropriate wells. 25 µL of the mixed or premixed Beads for the tested cytokines/chemokines was added to each well. The plate was sealed with a plate sealer, wrapped with foil and incubated with agitation on a plate shaker overnight at 4° C. or 2 hours at room temperature (20-25° C.). An overnight incubation (16-18 hr) may improve assay sensitivity for some analytes. Well contents were gently removed and the plate was washed twice. 25 µL of detection antibodies was added into each well. The plate was then sealed, covered with foil and incubated with agitation on a plate shaker for 1 hour at room temperature (20-25° C.). 25 µL Streptavidin-Phycoerythrin was added to each well containing the 25 µL of detection antibodies. The plate was then sealed, covered with foil and incubated with agitation on a plate shaker for 30 minutes at room temperature (20-25° C.). Well contents were gently removed and the plate was washed twice. 150 µL of Sheath Fluid (or Drive Fluid if using MAGPIX®) was added to all wells. The beads were resuspended on a plate shaker for 5 minutes.

Data analysis: The plate was run on Luminex 200™, HTS, FLEXMAP 3D™ or MAGPIX® with xPONENT software. The Median Fluorescent Intensity (MFI) data was saved and analyzed using a 5-parameter logistic or spline curve-fitting method for calculating cytokine/chemokines concentrations in samples.

Results: The serum analytes examined included: (1) human cytokines/chemokinds (EGF, CCL11, FGF-2, Flt-3 ligand, CX3CL1, G-CSF, GM-CSF, CXCL1, CXCL10, IFNα2, IFNγ, IL-α, IL-β, IL-1ra, IL-2, sIL-2Rα, IL-3, IL-4, IL-5, IL-6, IL-7, IL-8, IL-9, IL-10, IL-12 (p40), IL-12 (p70), IL-13, IL-15, IL-17, IL-1ra, IL-1α, IL-1β, IL- 2, IL-3, CCL2, CCL7, CCL22, CCL3, CCL4, PDGF-AA, PDGF-AB/BB, CCL5, sCD40L, sIL-2Rα, TGFα, TNFα, TNFβ, VEGF, CCL21, CXCL13, CCL27, CXCL5, CCL24, CCL26, CCL1, IL-16, IL-20, IL-21, IL-23, IL-28, IL-33, LIF, CCL8, CCL13, CCL15, SCF, CXCL12, CCL17, TPO, TRAIL, and TSLP); and (2) matrix metalloproteinases (MMP-1, MMP-2, MMP-3, MMP-7, MMP-9, MMP-10, MMP-12, MMP-13, TIMP-1, and TIMP-2). The change in serum concentration of an analyte was determined by comparing the pre- and post-treatment serum samples.

Figure 15A:
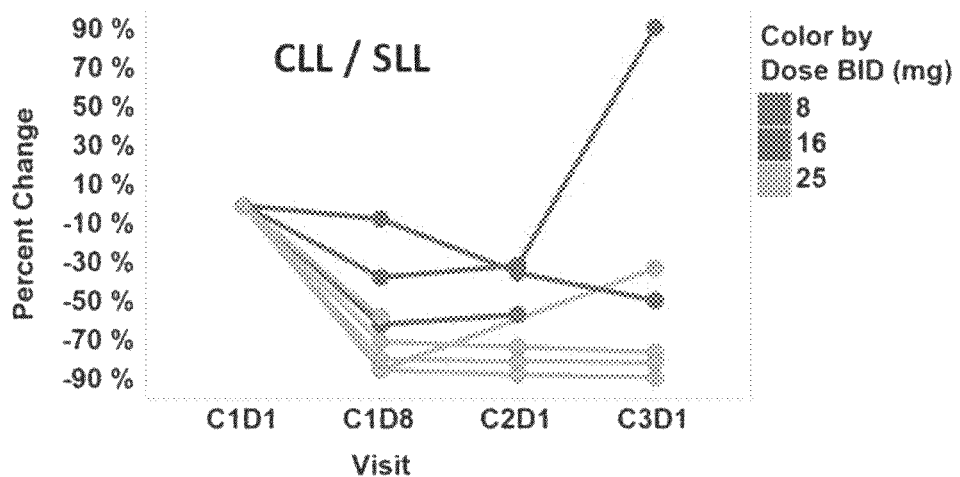
FIG. 15A depicts the effects of Compound 292 treatment on serum concentration of CXCL13 in CLL/SLL patients.
Figure 15B:
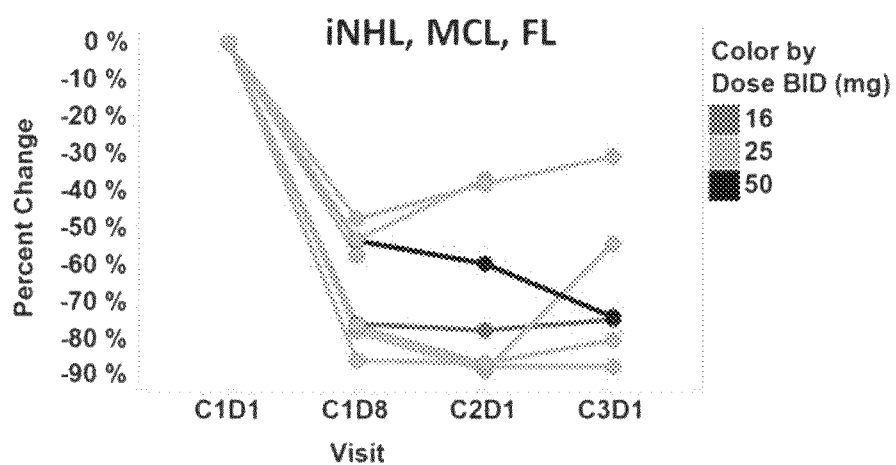
FIG. 15B depicts the effects of Compound 292 treatment on serum concentration of CXCL13 in iNHL/MCL/FL patients.
Figure 16A:
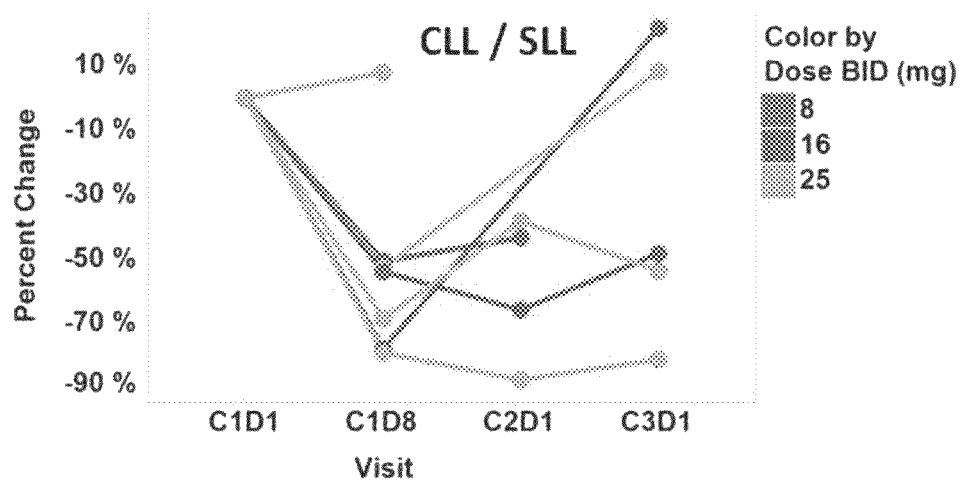
FIG. 16A depicts the effects of Compound 292 treatment on serum concentration of CCL4 in CLL/SLL patients.
Figure 16B:
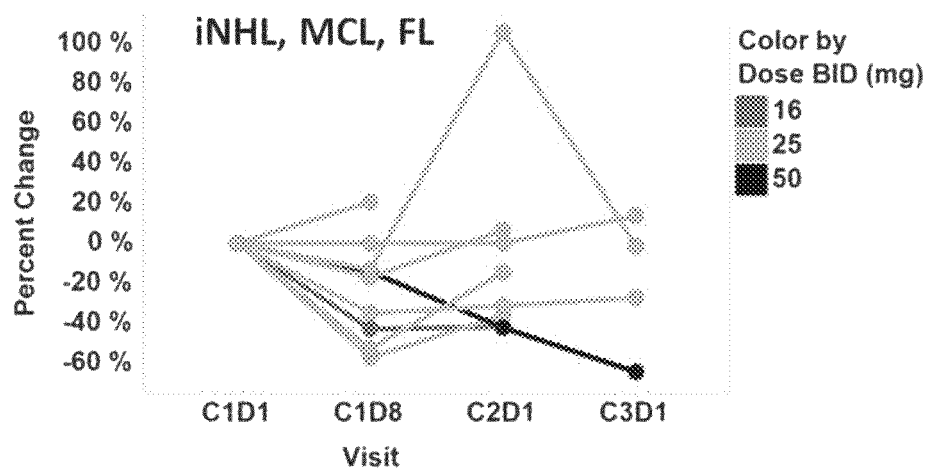
FIG. 16B depicts the effects of Compound 292 treatment on serum concentration of CCL4 in iNHL/MCL/FL patients.
Figure 17A:
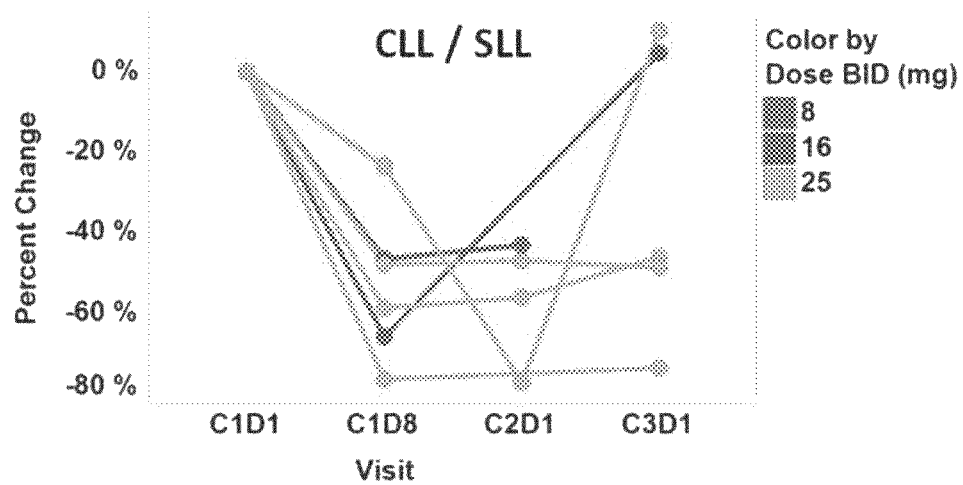
FIG. 17A depicts the effects of Compound 292 treatment on serum concentration of CCL17 in CLL/SLL patients.
Figure 17B:
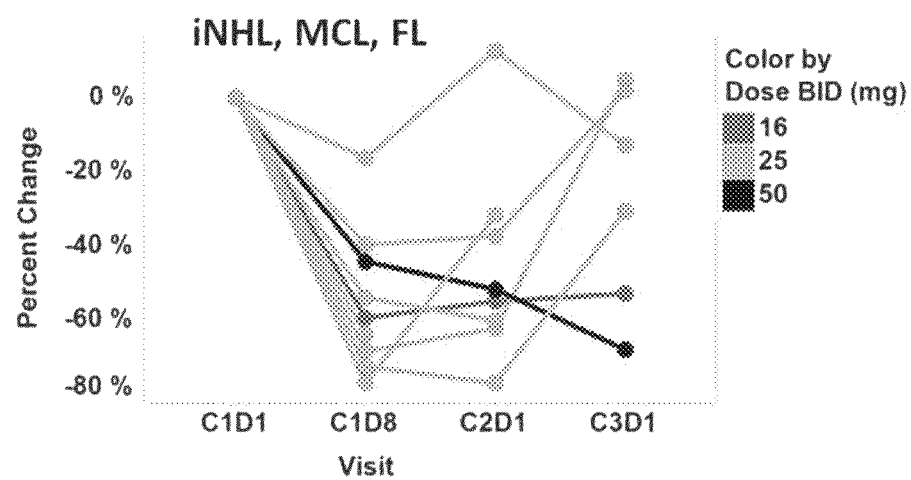
FIG. 17B depicts the effects of Compound 292 treatment on serum concentration of CCL17 in iNHL/MCL/FL patients.
Figure 18A:
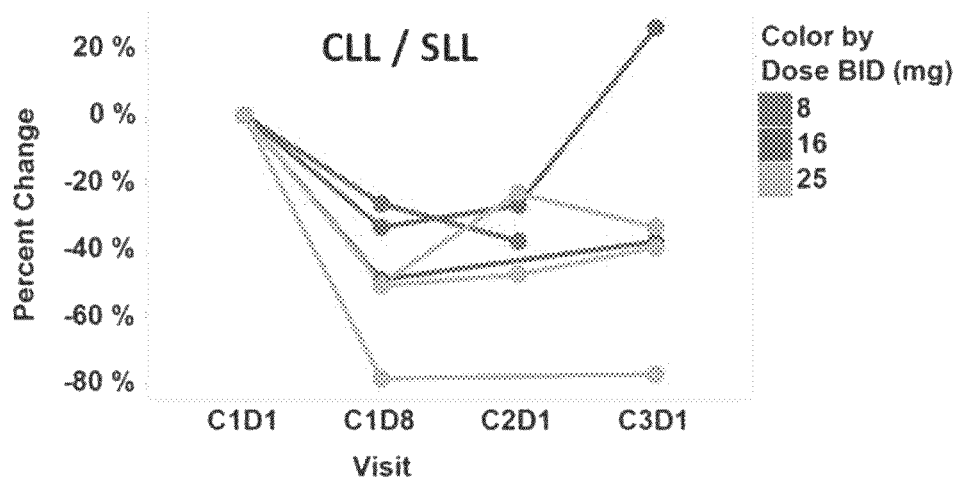
FIG. 18A depicts the effects of Compound 292 treatment on serum concentration of CCL22 in CLL/SLL patients.
Figure 18B:
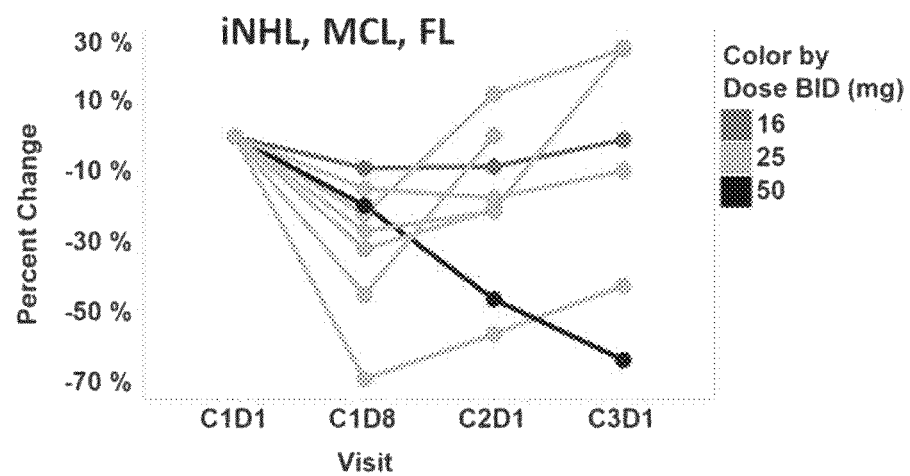
FIG. 18B depicts the effects of Compound 292 treatment on serum concentration of CCL22 in iNHL/MCL/FL patients.
Figure 19A:
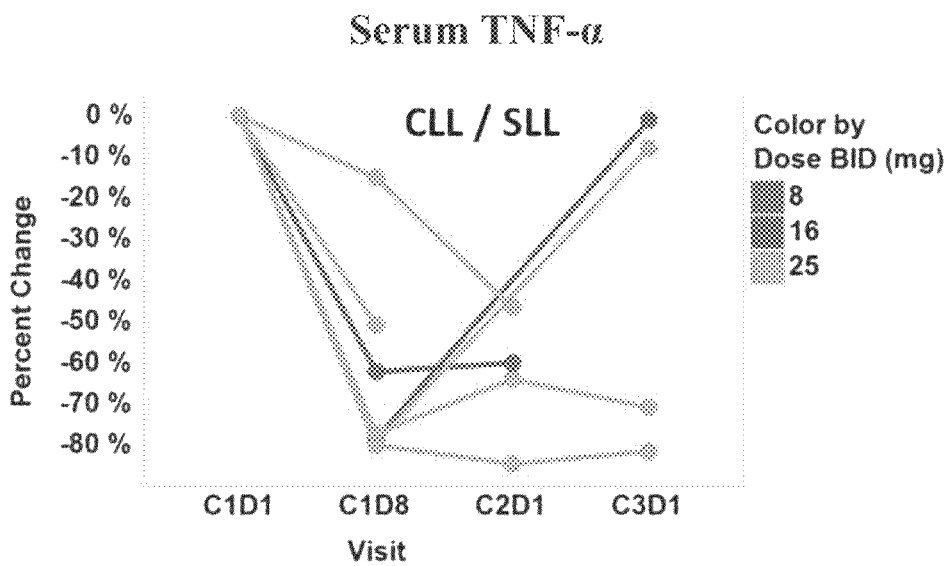
FIG. 19A depicts the effects of Compound 292 treatment on serum concentration of TNF-α in CLL/SLL patients.
Figure 19B:
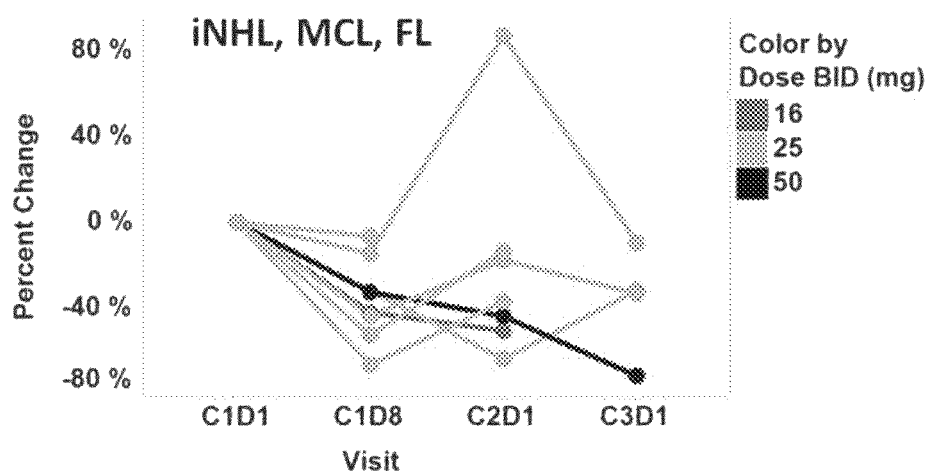
FIG. 19B depicts the effects of Compound 292 treatment on serum concentration of TNF-α in iNHL/MCL/FL patients.
Figure 21:
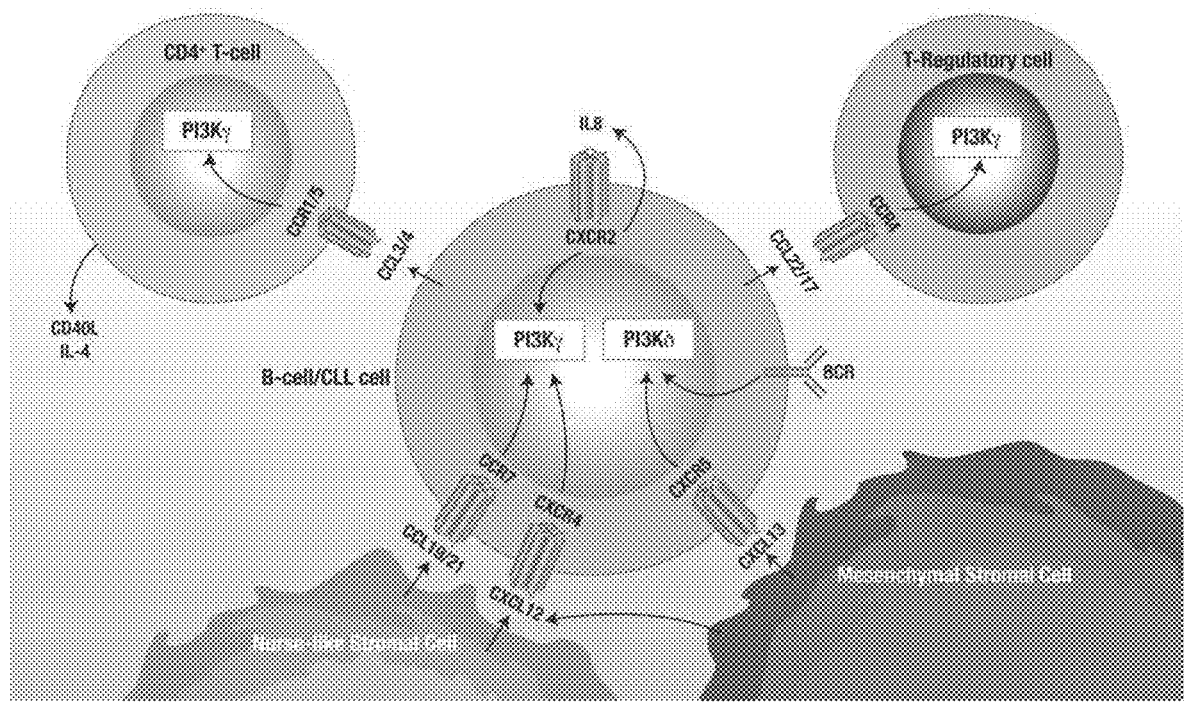
FIG. 21 depicts a possible mechanism of actions for certain chemokines in patients with hematologic malignancies.

In one exemplary study, serum samples were collected from patients with hematologic malignancies at Cycle 1 Day 1 (C1D1), Cycle 1 Day 8 (C1D8 or Day 8), Cycle 2 Day 1 (C2D1 or Day 28), and Cycle 3 Day 1 (C3D1). CXCL13 (FIG. 15), CCL4 (FIG. 16), CCL17 (FIG. 17), CCL22 (FIG. 18), and TNF-α (FIG. 19) all exhibited decreased serum concentrations with Compound 292 treatment in CLL/SLL and iNHL/MCL/FL patients. A trend toward decreasing serum MMP9 concentration was observed with Compound 292 treatment in some non-CLL/iNHL indications (FIG. 20). These data demonstrate that reduced serum concentration of CXCL13, CCL4, CCL17, CCL22, TNF-α, and/or MMP9 at Day 28 when compared to the baseline in patients indicates the effectiveness of the Compound 292 treatment of B-cell lymphomas, T-cell lymphomas, and leukemias. An increase of the serum concentration of CXCL13, CCL4, CCL17, CCL22, TNF-α, and/or MMP9 was observed at C3D1 for certain patients who withdrew from treatment by Compound 292 during Cycle 2, which further demonstrated that the serum concentration of CXCL13, CCL4, CCL17, CCL22, TNF-α, and/or MMP9 is indeed indicative of the pharmacodynamic effect of Compound 292. Without being limited by any particular theory, a possible mechanism of actions for these chemokines in patients with hematologic malignancies is depicted in FIG. 21.

Example 12

PI3K Isoform mRNA Expression in Hematologic Disorders mRNA expression of PI3K isoforms (PI3K-α, β, δ, and/or γ) in hematologic malignancies (e.g., cell lines, cell types, or tissue samples of hematologic malignancies) was analyzed.

RNA Isolation and Quantitative Real-Time PCR: RNA was isolated from cell pellets using the RNAqueous®-4PCR kit (Ambion) or FFPE material using the Rneasy FFPE kit (Qiagen). Fifty ng of RNA was added to each 25 µL reaction in One-step master mix (Life technologies #4392938) and run on the 7300RT cycler (Applied Biosystems) for 40 cycles. All primer and probe sets to assess isoform expression were purchased from Applied Biosystems: human PIK3CA (Hs00907957_m1), human PIK3CB (Hs00927728_m1), human PIK3CD (Hs00192399_m1), human PIK3CG (Hs00277090_ml) and human GAPDH (4310884E). All genes tested were normalized to GAPDH. The formula, $2^{-\Delta\Delta CT}$, where CT refers to threshold cycle, was applied to calculate the fold-change of gene expression.

PIK3CG and PIK3CD in Situ RNA Detection on Formalin-fixed, Paraffin-embedded Tissues: RNAscope™ FFPE Assay kits for PIK3CG and PIK3CD were developed and purchased from Advanced Cell Diagnostics, Inc (ACD). Each kit targets ~a 1 Kb region, and the RNA molecule is targeted by 20 probe pairs, each ~50 nucleotides (nt) in length. The PIK3CG and PIK3CD probe coverage of transcripts and regions are listed in Table 19. All tissues tested were fixed for 24 hours in 10% neutral buffered formalin (NBF), processed, paraffin-embedded and cut as 5 uM sections onto charged slides. Prior to staining, all slides were placed in a 60° C. oven and baked for 1 hour. Sections were deparaffinized in xylene (2×5 min) and rehydrated through a graded series of ethanols (100%, 95%,) for 3 minutes each. Slides were allowed to air dry for 5 minutes. The standard kit protocol recommended by ACD for steps Pretreatment 1-2 and Amplification 1-6 were followed as previously described (Fay Wang, et al., "RNAscope: A Novel in Situ RNA Analysis Platform for Formalin-Fixed, Paraffin-Embedded Tissues." *The Journal of Molecular Diagnostics*, 2012, 14(1): 22-29). Based on the sample-type tested, the following optimal dilutions were determined for Pretreatment #3: Lymphoid tissue 1:5, Lymphoma tissue 1:10 and cell pellets 1:15. To visualize the staining, slides were developed with DAB-chromogen substrate and counterstained with hematoxylin I. In parallel, slides were stained with the endogenous housekeeping gene, PPIB, to ensure good tissue quality.

TABLE 19

PIK3CG and PIK3CD Probe Coverage of Transcripts and Regions

| Probe | Covered transcript | Covered region | Region location |
|---|---|---|---|
| PIK3CG | NM_002649 | 2748-3708 | mRNA coding region |
| PIK3CD | NM_005026 | 3714-5303 | 3' UTR |

PI3K Isoform mRNA Expression in Hematologic Disorders

In one study, mRNA expression in cell lines of B-ALL, MCL, CLL, B-cell lymphoma, CTCL, AML, DLBCL, Burkitt lymphoma, T-ALL, CML (blast phase), Hodgkin lymphoma, CML, myeloma (e.g., multiple myeloma), and ALCL was analyzed. It was determined that CLL had relatively high delta expression and relatively low gamma expression. DLBCL and B-ALL had high gamma expression. Myeloma had low delta expression and a broad range of gamma expression. AML and CML had relatively high beta expression.

In another study, mRNA expression in human leukemia in pediatric B-ALL, adult B-ALL, CML, Burkitt lymphoma, infantile B-ALL, CLL, MDS, AML, and T-ALL, and non-leukemia/healthy bone marrow was analyzed. It was determined that there was not a lot of variability in delta expression among leukemia types (in contrast to cell lines). CLL and T-ALL had relatively low gamma expression. B-ALL had relatively high gamma expression. AML and CML had relatively high beta expression. MDS had relatively high beta expression.

In yet another study, mRNA expression in DLBCL, FL, and CTCL was analyzed, which included analysis of mRNA expression in memory B-cells, naive B-cells, GC centrocytes, GC centroblasts, lymphoblastoid cell lines, follicular lymphoma (FL), and DLBCL. It was determined that DLBCL and FL had broad gamma expression that extended to the higher end of the spectrum. CTCL had relatively low gamma expression, potentially due to factors such as tumor content.

Example 13

Steady State Plasma Concentrations of Compound 292

Figure 22:
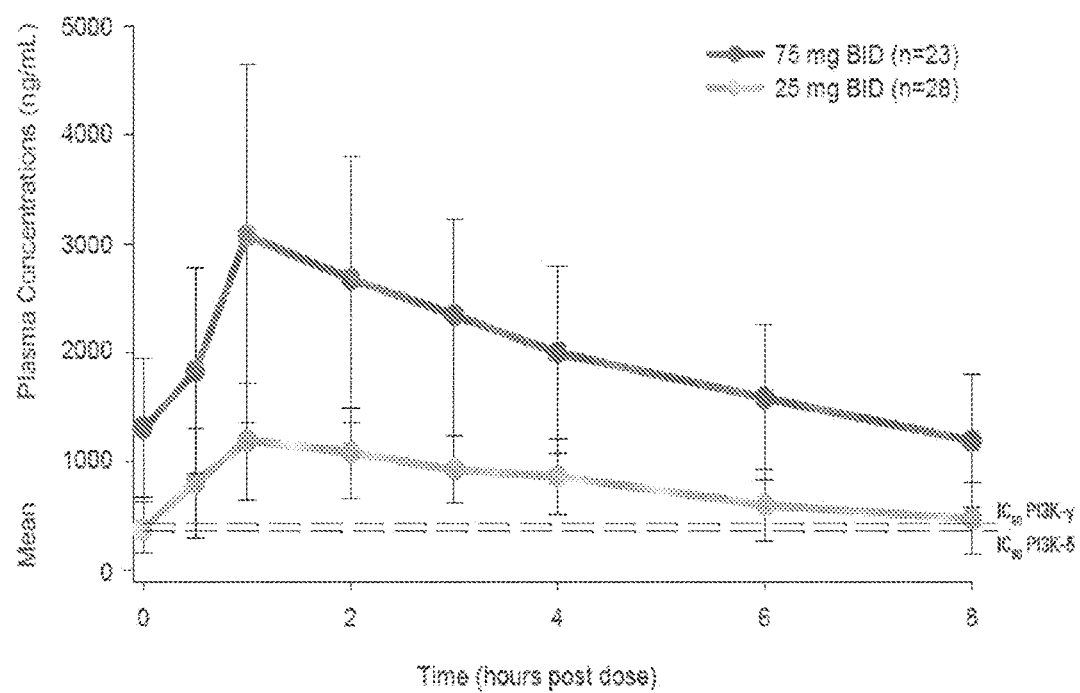
FIG. 22 depicts steady state plasma concentrations of Compound 292 on cycle 2, day 1 of 28 day cycles, 25 mg and 75 mg BID administration.

Following 28 days cycle, 25 mg or 75 mg BID administration of Compound 292, steady state concentrations of Compound 292 were determined on Cycle 2, Day 1 (C2D1) using procedures substantially similar to those described above in Example 8. As shown in FIG. 22, it was found that Compound 292 is rapidly absorbed, with maximum plasma concentration typically observed at about 1 hour post-dosing at both 25 mg and 75 mg regimens. It was also found that AUC increases proportionally with doses through 75 mg BID, but elimination half life is independent of dose. The mean predose steady state plasma concentration following 25 mg BID was determined to be 390 ng/ml, indicating complete suppression of PI3K-δ (IC90=361 ng/ml) with inhibition of PI3K-γ (IC50=429 ng/ml) throughout the dosing interval.

Example 14

Decreased Serum Biomarker Levels in CLL Patients

Figure 23:
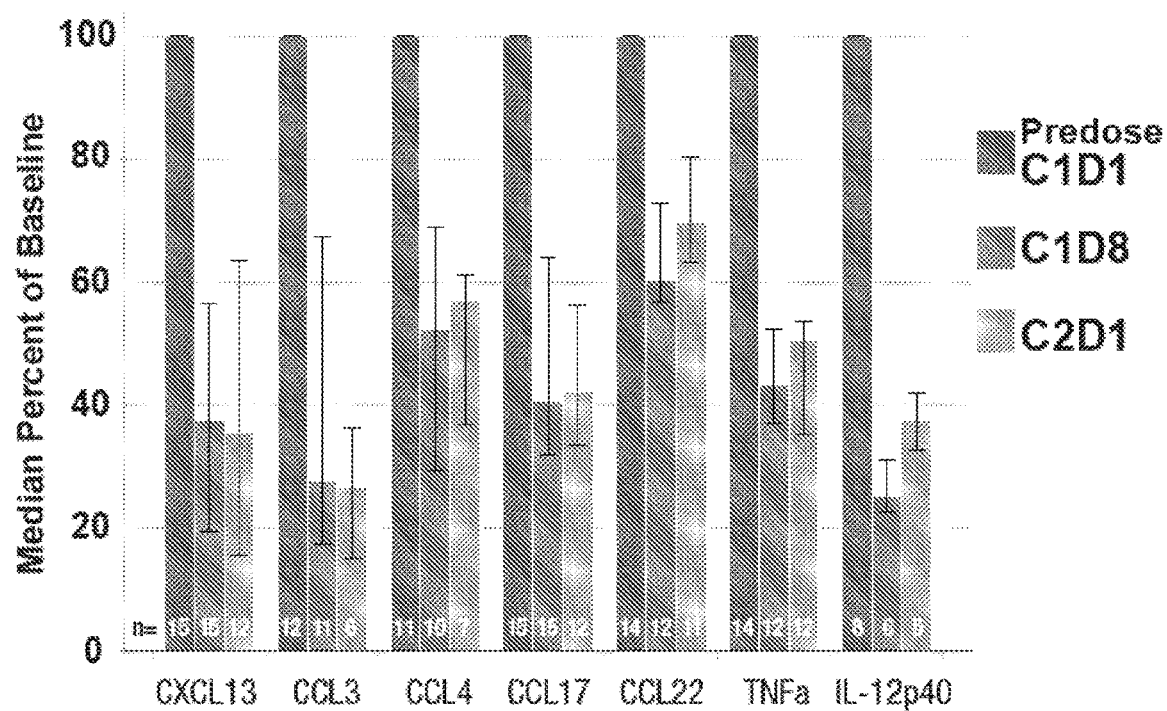
FIG. 23 depicts decrease in levels of CLL biomarkers in serum at various time points following 28 day cycles, 25 mg BID administration of Compound 292.

Following 28 days cycle, 25 mg BID administration of Compound 292 to patients with CLL, levels of various cytokines/chemokines in serum were determined using the Milliplex platform based on procedures substantially similar to those described above in Example 11. As shown in FIG. 23, at both cycle 1, day 8 (C1D8) and cycle 2, day 1 (C2D1), levels of CXCL13, CCL3, CCL4, CCL17, CCL22, TNFα and IL-12 (p40) were substantially reduced as compared to cycle 1, day 1 (C1D1) predosing levels. These cytokines/chemokines are known to be critical in lymphocyte trafficking and function presented. Furthermore, it was also found that CCL1 and IL-10 exhibited similar reduction following 28 days cycle, 25 mg or 75 mg BID administration of Compound 292.

Figure 24:
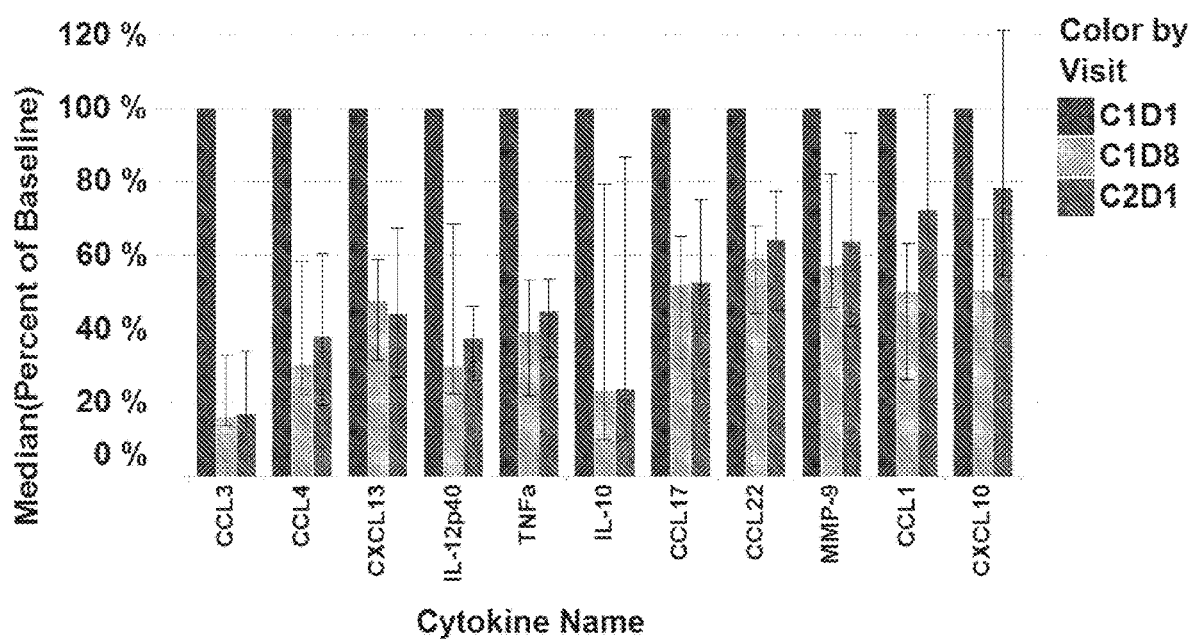
FIG. 24 depicts decrease in levels of CLL biomarkers in serum at various time points following 28 day cycles, 25 mg or 75 mg BID administration of Compound 292.

When analytes from various doses of Compound 292 to CLL patient is were pooled together (n=1 at 8 mg BID, 2 at 15 mg BID, 15 at 25 mg BID, and 13 at 75 mg BID) and evaluated for a consistent change (reduction or increase) in serum levels at C1D8 and/or C2D1 compared to baseline (predose level), 10 of 72 analytes decreased after compound 292 treatment compared to baseline, whereas none increased significantly. Analytes that decreased after Compound 292 treatment include CXCL13, CCL3, CCL4, IL-10, TNFα, IL-12p40, MMP-9, CCL17, CCL22, CCL1, and CXCL10 (FIG. 24). Median serum levels of these analytes decreased by C1D8, ranging from 16% to 59% of baseline. Interestingly, many of the analytes that decrease with Compound 292 treatment are involved in the communication between malignant B-cells and the microenvironment. CCL3, CCL4, CCL17 and CCL22 are expressed by malignant B-cells and can play a role in recruiting T-cells to interact with the malignant B-cells. CXCL13 is secreted by stromal cells and recruits malignant B-cells to the lymph nodes. In addition, IL-10 is produced by many normal immune cell types as well as by neoplastic B-cells. IL-10 is known to be an autocrine growth factor for B-cell lymphoma cell lines.

The results demonstrate that administration of Compound 292 causes reduction in levels of these cytokines/chemokines and support the use of these cytokines/chemokines as biomarkers for compounds provided herein in CLL patients.

Example 15

Lymphocytosis Response as Function of Baseline Absolute Lymphocyte Count

Figure 25:
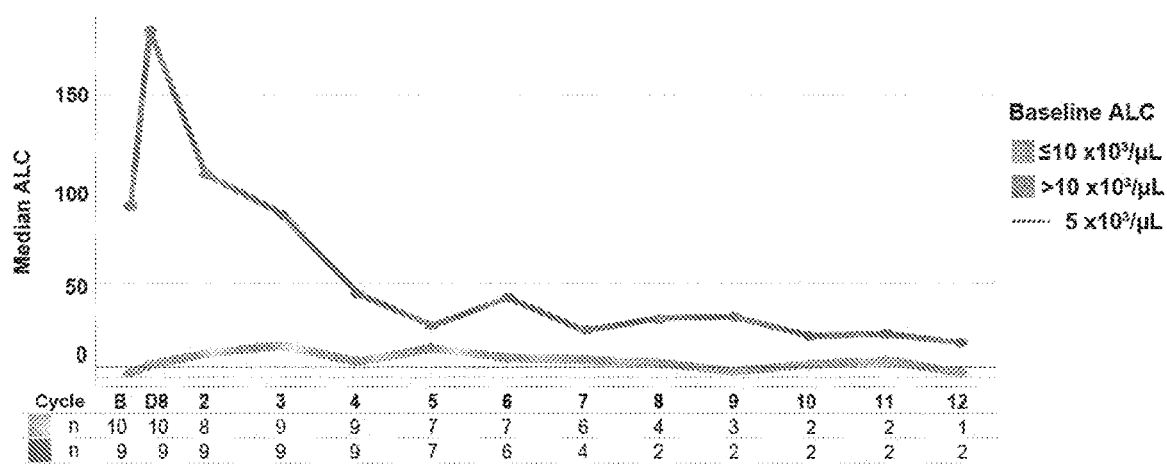
FIG. 25 depicts median Absolute Lymphocyte Count (ALC) at various time points following 28 day cycles, 25 mg BID administration in patients with higher than 10×103/µl baseline ALC (darker line) and lower than 10×103/µl baseline ALC (lighter line).
Figure 26:
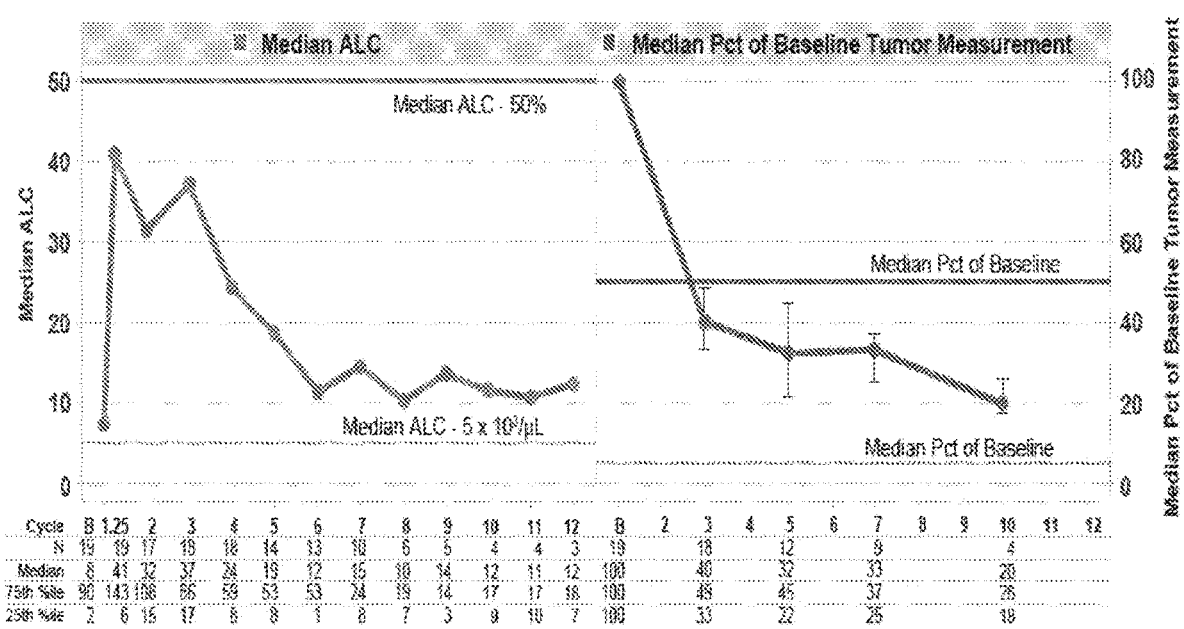
FIG. 26 depicts median ALC at various time points following 28 day cycles, 25 mg BID administration and changes in tumor measurement.

Predose baseline Absolute Lymphocyte Count (ALC) was determined in a pool of patients with CLL. Depending on the initial baseline ALC, the patients were grouped into two categories: (1) those with baseline ALC equal to, or higher than, $10 \times 10^3/\mu l$ and (2) those with baseline ALC lower than $10 \times 10^3/\mu l$. Upon initiation of administration of Compound 292 (28 days cycle, 25 mg BID), blood samples were drawn from the patients at cycles as indicated in FIG. 25, and median ALC from each of the two groups was determined separately from the other group. As shown in FIG. 25, patients with higher baseline ALC demonstrated a different trend in post-baseline ALC over time than those with lower baseline ALC. The data suggest that patients with higher baseline ALC are likely to have much more rapid onset following the administration of Compound 292, followed by stable decrease in median ALC, indicating that patients with higher baseline ALC are likely more responsive to the treatment by a compound provided herein than those with lower baseline ALC. As shown in FIG. 26, rapid lymphocytosis (i.e., rapid onset) similar to the profile exhibited by patients with higher baseline ALC corresponds well to rapid reduction in tumor measurement.

Example 16

Decreased Serum Biomarker Levels in Lymphoma Patients

Following 28 days cycle, 25 mg BID administration of Compound 292 to patients with lymphoma, levels of CXCL13, CCL17 and MMP-9 in serum were determined using the Milliplex platform based on procedures substantially similar to those described above in Example 11. As shown in FIG. 27A, at both cycle 1, day 8 (C1D8) and cycle 2, day 1 (C2D1), levels of CXCL13, CCL17 and MMP-9 were substantially reduced as compared to cycle 1, day 1 (C1D1) predosing levels.

Figure 28:
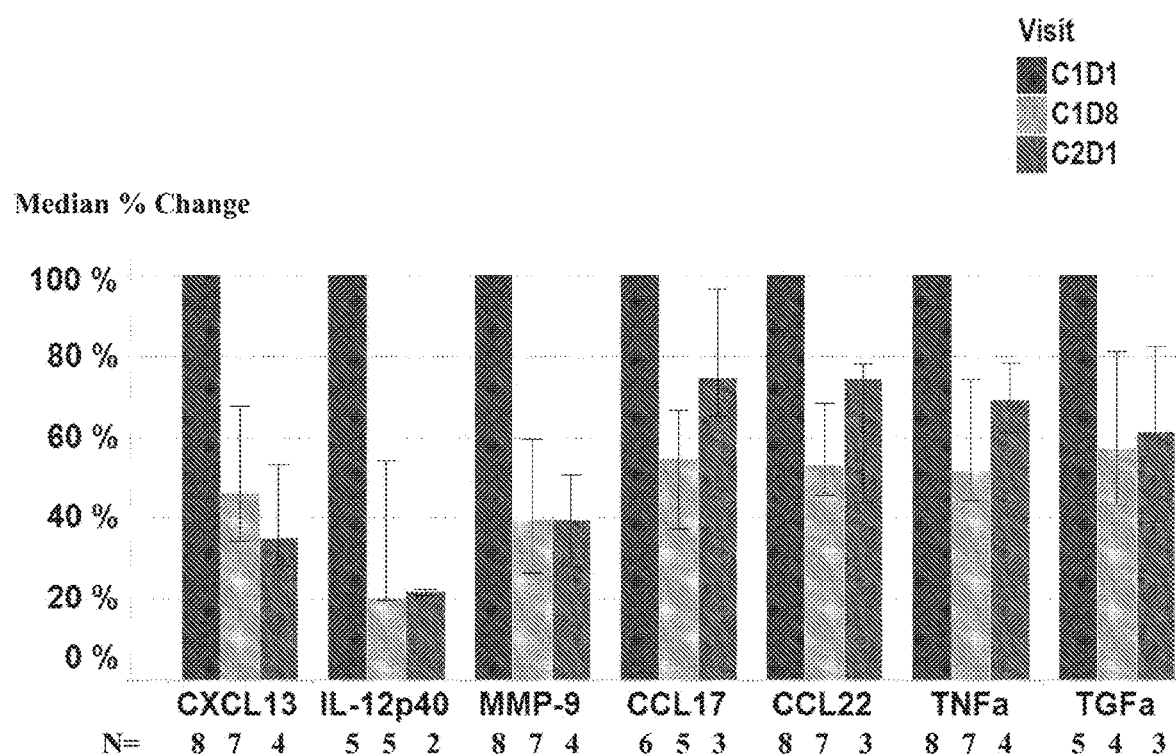
FIG. 28 depicts decrease in levels of T-cell lymphoma biomarkers in serum at various time points following 28 day cycles, 25 mg BID administration of Compound 292.

Further, as shown in FIG. 27B, CXCX13, CCL17, CCL22 and TNFα showed significant reduction in levels following 28 days cycle, 25 mg BID administration of Compound 292 in iNHL patients. It was also found that CCL1, CCL17, CXCL13, IL-12 (p40), MMP-12, MMP-9 and TNFα exhibited similar reduction following 28 days cycle, 25 mg or 75 mg BID administration of Compound 292 in iNHL patients. In addition, CCL17, CCL22, CXCL10, CXCL13 and MMP-9 exhibited similar reduction following 28 days cycle, 25 mg or 75 mg BID administration of Compound 292 in MCL patients, and CCL17, CCL22, CXCL10, CXCL13, MMP-9, CM-CSF and IL-12 (p40) exhibited similar reduction following 28 days cycle, 25 mg or 75 mg BID administration of Compound 292 in T-cell lymphoma patients. Moreover, also in T cell lymphoma patients, it was shown that CXCL13, IL-12 (p40), MMP-9, CCL17, CCL22, TNFα and TGFα exhibit similar trend following 28 days cycle. (FIG. 28).

Figure 29:
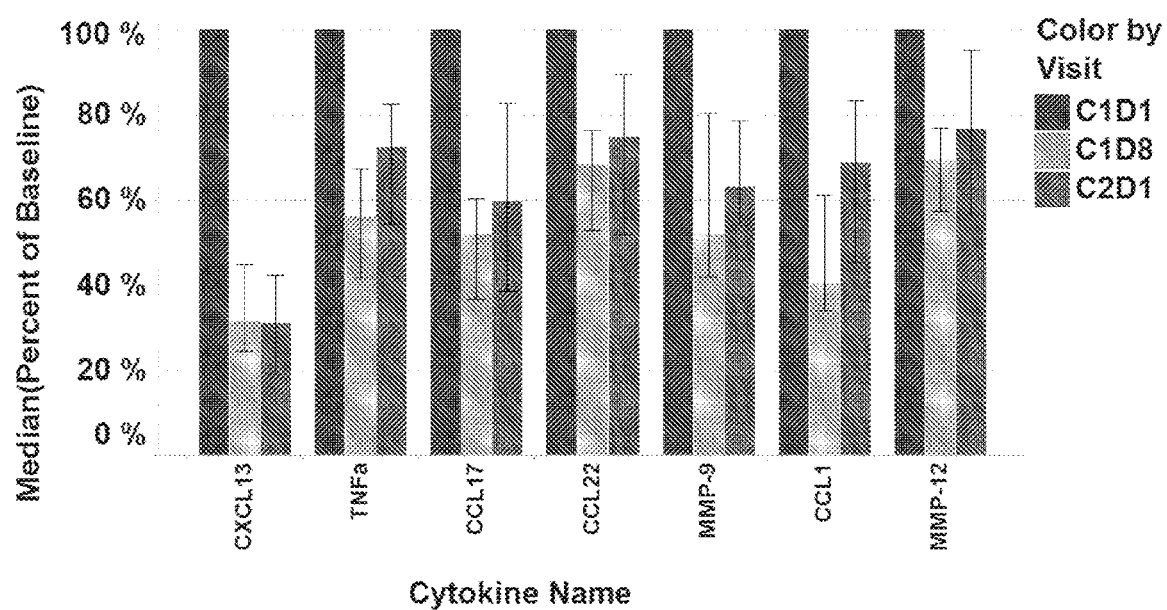
FIG. 29 depicts decrease in levels of iNHL biomarkers in serum at various time points following 28 day cycles, 25 mg or 75 mg BID administration of Compound 292.

When analytes from various doses of Compound 292 to iNHL patients were pooled together (n=1 at 15 mg BID, 12 at 25 mg BID, 1 at 50 mg BID, and 5 at 75 mg BID) and evaluated for a consistent change (reduction or increase) in serum levels at C1D8 and/or C2D1 compared to baseline (predose level), the median serum levels of 7 analytes decreased by C1D8 (ranging from 32% to 70% of baseline), whereas none increased significantly. The 7 analytes that decreased in iNHL subjects were CXCL13, MMP-9, TNFα, CCL22, CCL1, CCL17, and MMP-12 (FIG. 29).

The results demonstrate that administration of Compound 292 causes reduction in levels of the above-mentioned cytokines/chemokines, and support the use of these molecules as biomarkers for compounds provided herein in lymphoma patients.

Example 17

Clinical Activity of Compound 292 in Sézary Syndrome

Figure 30A:
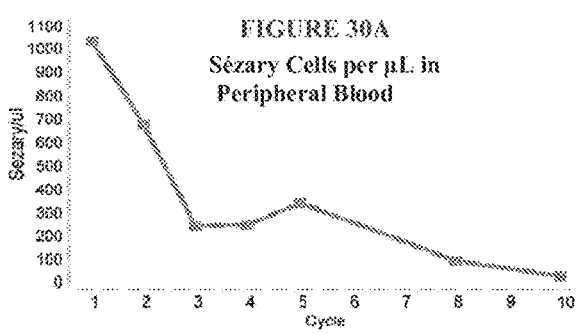
FIG. 30A depicts number of Sézary cells per microliter of peripheral blood at various time points following 28 day cycles, 25 mg BID administration of Compound 292.
Figure 30B:
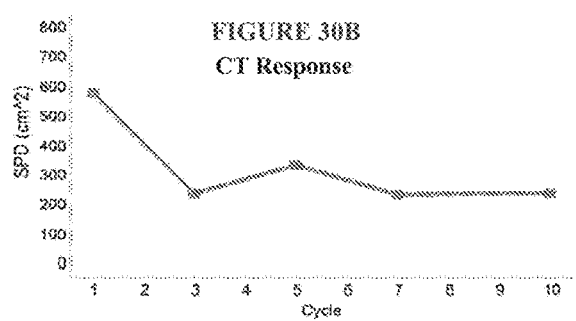
FIG. 30B depicts CT response shown in terms of Sum of Product Diameters (SPD) at various time points following 28 day cycles, 25 mg BID administration of Compound 292.
Figure 30C:
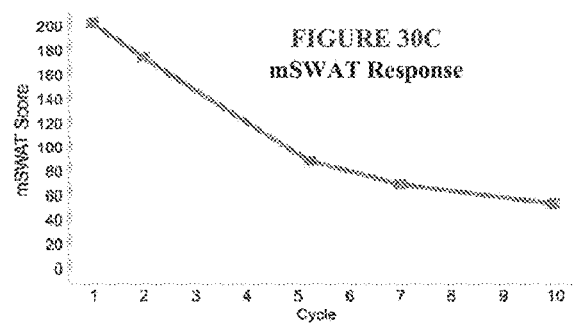
FIG. 30C depicts mSWAT score at various time points following 28 day cycles, 25 mg BID administration of Compound 292.

Following 28 days cycle, 60 mg BID administration of Compound 292 to patients with Sézary syndrome, the following criteria were investigated to evaluate clinical efficacy of Compound 292 in treating Sézary syndrome: (1) number of Sézary cells in peripheral blood; (2) CT response; and mSWAT scores. Number of Sézary cells were determined by following conventional procedures using flowcytometry. As shown in FIG. 30A, substantial reduction in number of Sézary cells was observed over the progress of administration cycles. CT response was assessed in terms of Sum of Product Diameters (SPD). As shown in FIG. 30B, reduction in SPD was also observed over the progress of administration cycles. Finally, mSWAT scores were determined using conventional procedures well-known in the art (see, e.g., Olsen et al., DOI: 10.1200/JCO.2010.32.0630, *Journal of Clinical Oncology* 29, no. 18 (2011) 2598-2607). As shown in FIG. 30C, spontaneous reduction in mSWAT scores was observed over the progress of administration cycles. These results clearly suggest that compounds provided herein can be efficacious in treating Sézary syndrome.

Example 18

Biomarker Studies for Treating CLL with PI3K Isoform Selective Compound

PI3Kδ is over-expressed in several B-cell malignancies including chronic lymphocytic leukemia (CLL), while PI3Kγ is expressed high in solid tumors and play roles for immune cell trafficking. CLL B-cells are regulated by PI3K pathways and in interaction with other immune cells, a compound such as Compound 292 can have impact on regulating the survival of CLL B cells. Manipulating potential targets associated with PI3K pathway plus chemokine secretion using a compound such as Compound 292 can enhance apoptosis in CLL-B cells.

Therapeutic response (dose and time response) of Compound 292 in CLL with recurrent genetic lesions and adverse prognosis: Freshly obtained CLL leukemia cells from patients with CLL are treated with a wide range of concentrations of Compound 292 and the sensitization of CLL cells to Compound 292 is measured by annexin/PI assay and MTS assay. Incubating the leukemia cells at various time periods can derive the optimal dose and optimal time at which Compound 292 induces cyto-toxicity in CLL primary cells. Apoptosis, mitochondrial outer membrane permeabilization, MTS assay and PARP protein cleavage are analyzed and quantitated using established methods, e.g., Balakrishnan et al., 2010, "Influence of bone marrow stromal microenvironment on forodesine-induced responses in CLL primary cells," *Blood* 116, 1083-91; Balakrishnan et al., 2009, "AT-101 induces apoptosis in CLL B cells and overcomes stromal cell-mediated Mcl-1 induction and drug resistance," *Blood* 113, 149-53. In order to derive the functional relationship between therapeutic response to Compound 292 and the clinical characteristics of CLL patients, subsets of patients with different prognostic factors such as Rai stages, β2-microglobulin as well as diverse cytogenetics including trisomy 12, del13q, 17p, and 11q mutations or deletions, ZAP-70 status, CD38 status, CD49d status, and IgHV gene mutations are included in the study. The same cohorts of samples are treated in parallel with other PI3K inhibitors in order to compare the selectivity and sensitivity of individual kinase inhibitors.

Stromal mediated CLL cell survival: PI3K and its downstream targets are activated in response to the tumor microenvironment. A compound such as Compound 292 can disrupt the leukemia-stromal interactions in CLL. CLL primary cells are co-cultured with or without stromal cells (bone marrow stromal cells; NKTert cells and lymph node microenvironment; nurse like cells) [Balakrishnan et al., 2010, "Influence of bone marrow stromal microenvironment on forodesine-induced responses in CLL primary cells," *Blood* 116, 1083-91; Burger et al., 2000, "Blood-derived nurse-like cells protect chronic lymphocytic leukemia B cells from spontaneous apoptosis through stromal cell-derived factor-1," *Blood* 96, 2655-63.] in presence or absence of PI3K inhibitor, and apoptosis, mitochondrial outer membrane permeabilization, MTS assay and PARP protein cleavage are measured [Balakrishnan et al., 2010, supra; Balakrishnan et al., 2009, supra]. To evaluate the role of microenvironment, the CLL-stromal co-culture model system are used [Balakrishnan et al., 2010, supra], that have been established and tested with CLL [Balakrishnan et al., 2009, supra]. These results are used to study the basis of survival advantage to CLL cells by diverse microenvironment and abrogation of this protection by PI3K inhibitor.

Molecular mechanism involved in the activity of Compound 292 in CLL primary cells: PI3K is downstream BCR signaling which is a major therapeutic target in CLL. Activation of PI3K can impact downstream targets such as Akt or Erk kinases and the target substrates. To evaluate the molecular events regulated during PI3K inhibitor treatment, the post-translational modifications of target proteins such as Akt and Erk are evaluated by probing with antibodies that can detect the phosphorylation of Akt at Ser473 and Erk at Thr202/Tyr204 along with downstream mediators such as phospho-PRAS and S6. In addition, expression levels of PI3K isoforms (e.g., gamma and delta) are profiled from each sample tested, and the relative levels correlated with cellular response to inhibitor. Compound 292 can manipulate the cells in association with immune system and thereby chemokine production. The levels of C—X and C—C chemokines such as CXCL12, CXCL13, CCL2 and CCL3 that are shown to play a role in CLL pathogenesis (Sivina et al., 2011, "CCL3 (MIP-1alpha) plasma levels and the risk for disease progression in chronic lymphocytic leukemia," *Blood* 117, 1662-69) are measured. Both lysate and conditioned media from these studies are also analyzed of other potential factors.

Example 19

Correlation Between Growth Inhibition and PD Responses in DLBCL Cell Lines

Figure 31:
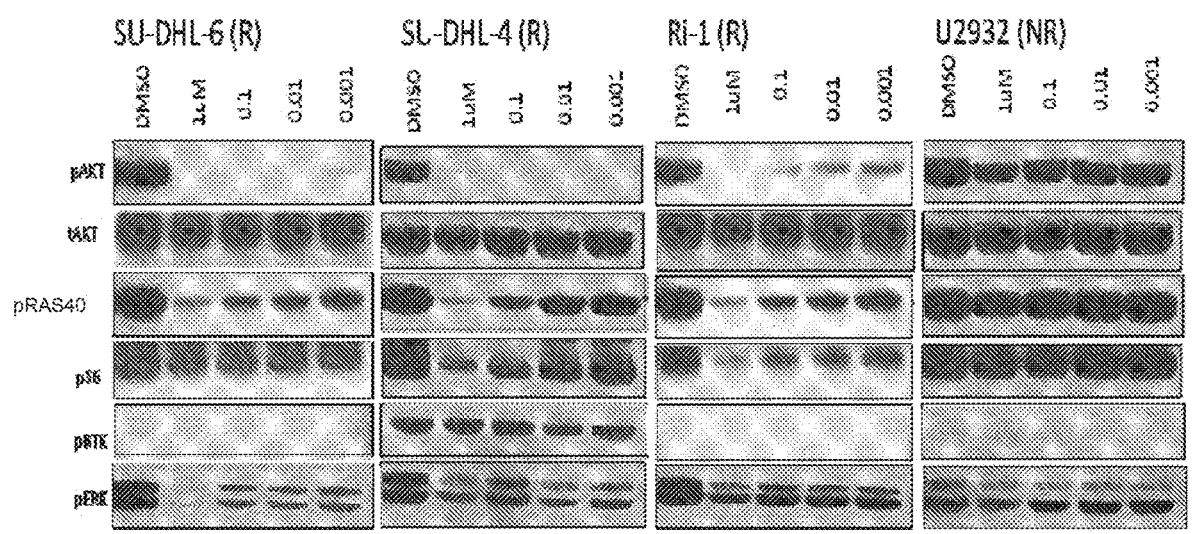
FIG. 31 depicts correlation between growth inhibition and pharmacodynamic response in DLBCL cell lines DHL-6, DHL-4, Ri-1 and U2932, as assessed by western blot of various proteins.

Various DLBCL cell lines were tested for the sensitivity to treatment by Compound 292 using 72 hour CTG assay. It was found that Ri-1 (ABD subtype) and DHL-4 and DHL-6 (both GCB subtype) cells were found to be more sensitive than other DLBCL cell lines (data not shown). These three responsive cell lines, and U2932 cell line (non responsive to Compound 292), were treated with DMSO (control) and Compound 292 at 0.001, 0.01, 0.1 and 1 µM concentrations. At 1 hour after the treatment, levels of various proteins were assessed by western blot, the results of which are shown in FIG. 31. As shown in FIG. 31, in all responsive cell lines (SU-DHL-6, SU-DHL-4 and Ri-1), levels of pAKT, pPRAS40 and pS6 were shown to decrease upon the treatment by Compound 292 in a dose dependent way, although the responses for pPRAS40 and pS6 were not as robust. Importantly, while DHA 4 cells had good baseline levels of pBTK, it was shown that the level of pBTK was not modulated by the administration of Compound 292. In addition, it was shown that pERK was somewhat modulated in the responsive cell lines, but the degree of modulation was shown to be somewhat less significant than other well-modulated proteins. These results suggest that Compound 292 may not work through BTK or MEK pathway, and thus, provides rationale for therapies using inhibitors of BTK or MEK in combination with a compound provided herein.

Example 20

Synergistic Effect of Combining Compound 292 and a BTK Inhibitor

Activation of the PI3K pathway is an important component of normal B-cell receptor (BCR) signaling and has been implicated in the pathogenesis of DLBCL. To further explore the role of PI3K signaling in DLBCL cell lines of varying molecular profiles, a panel of more than 10 DLBCL cell lines was treated with compound 292. PI3K-δ and PI3K-γ were found to be expressed at varying levels across the DLBCL cell line panel, without evidence of a correlation with molecular subtype. In a cellular growth inhibition assay, 3 cell lines including 2 GCB (SU-DHL-4, SU-DHL-6) and 1 ABC (Ri-1) subtype were sensitive to compound 292 treatment in the nanomolar (nM) range, and another 2 GCB cell lines (OCI-LY-8 and WSU-DLCL-2) were moderately sensitive with $IC_{50}$s in the low micromolar (µM) range. Several cell lines (OCI-LY3, Pfeiffer, Toledo and U2932) were insensitive to compound 292 (IC50>50 µM). There was no evidence of a correlation between compound 292 sensitivity and COO (cell of origin) or CC (consensus clustering) molecular profile in this panel. Compound 292 sensitivity did correlate with evidence of PI3K pathway inhibition as measured by reduction in phospho-AKT. To better characterize the kinetics of pathway modulation, phosphorylation of AKT, PRAS40, and S6 was examined following a time-course of Compound 292 treatment in selected cell lines. There was rapid modulation of phospho-AKT and phospho-PRAS40 by 30 minutes, whereas modulation of phospho-S6 was not detected until after 8 hours. Upon BCR stimulation via antibody-induced crosslinking, some cell lines exhibited enhanced AKT phosphorylation, which could be inhibited with Compound 292. The GCB cell line OCI-LY-8 was moderately sensitive to Compound 292 without BCR crosslinking (low µM range) and exhibited enhanced sensitivity to compound 292 with BCR crosslinking (nM range). These results suggest that intact BCR pathway signaling contributes to compound 292 sensitivity in DLBCL cell lines, regardless of COO or CC subtype.

Compound 292 activity was also explored in combination with ibrutinib, an irreversible inhibitor of Bruton agammaglobulinemia tyrosine kinase (BTK). Interestingly, in the setting of BCR crosslinking, OCI-LY-8 cells exhibited a robust increase in phospho-AKT which was completely inhibited by compound 292 but only partially inhibited by ibrutinib. In other cell lines, such as SU-DHL-4, robust inhibition of phospho-BTK was observed with ibrutinib treatment but not with compound 292. These biochemical findings indicate a mechanistic rationale for combination of PI3K-δ, γ and BTK inhibition. In addition, a significant combination effect was observed in a cellular growth inhibition assay with Compound 292 plus ibrutinib in the SU-DHL-4 cell line and in the OCI-LY-8 cell line with BCR crosslinking.

In another exemplary study, various DLBCL cell lines were plated into 96-well plates in triplicate, and testing compounds (combination of Compound 292 and ibrutinib) were added 4-6 hours after plating. After 72 hours of drug-treatment, cells were incubated with Cell Titer Glo reagent (Promega). To determine the Combination Index (CI), a fixed ratio of drugs was used and CI values were calculated using CalcuSyn. The results are listed in Table 20 below.

TABLE 20

Synergistic effects of Combination of Compound 292 and Ibrutinib

| Cell line | Fixed ratio (Compound 292/Ibrutinib) | Combination Index* |
|---|---|---|
| OCI-Ly8 | 1 | 0.06 |
| OCI-Ly7 | 1.3 | 0.15 |
| SU-DHL-4 | 1 | 0.34 |
| SU-DHL-10 | 0.2 | 0.46 |
| SU-DHL-6 | 0.5 | 0.76 |

*additive: 0.5 < CI < 1.0; synergistic CI ≤ 0.5.

Example 21

Sensitivity of PTEN Deletion Cell Lines to Compound 292

One hundred forty five (145) subsets of PTEN deletion cell lines were treated with Compound 292, and sensitivity to Compound 292 was determined for these subsets. It was found that the cell lines tested are differentially susceptible to the treatment by Compound 292. Importantly, it was found that PTEN wild type cells are not sensitive to Compound 292, implying that PTEN mutation may play a role in rendering the cells susceptible to the treatment by Compound 292.

Example 22

Sensitivity of T-ALL Cells to Different PI3K Inhibitors and Doxorubicin

Various human and marine ALL cell lines including PTEN deficient cell lines (Loucy, Molt-4 luc, CCRF-CEM, p12 Ichikawa, Karpas-45 and CEM/C2) and PTEN wildtype cell lines (Molt-13 and Molt-16) were treated with Compound 292, and inhibition of growth was assessed. The treatment resulted in variable degrees of growth inhibition, with the PTEN deficient Loucy cell line demonstrating the greatest sensitivity with an $IC_{50}$ of 245 nM. In the cell lines tested, growth inhibition by Compound 292 was only seen in PTEN deficient cell lines, while all PTEN wildtype cell lines were resistant to Compound 292 (data not shown). Additionally, it was found that murine cell lines derived from a PTEN deficient transgenic model of T-ALL (i.e., LPN049 and LPN236) are both sensitive to treatment by Compound 292 as measured by MTT assay.

Figure 32:
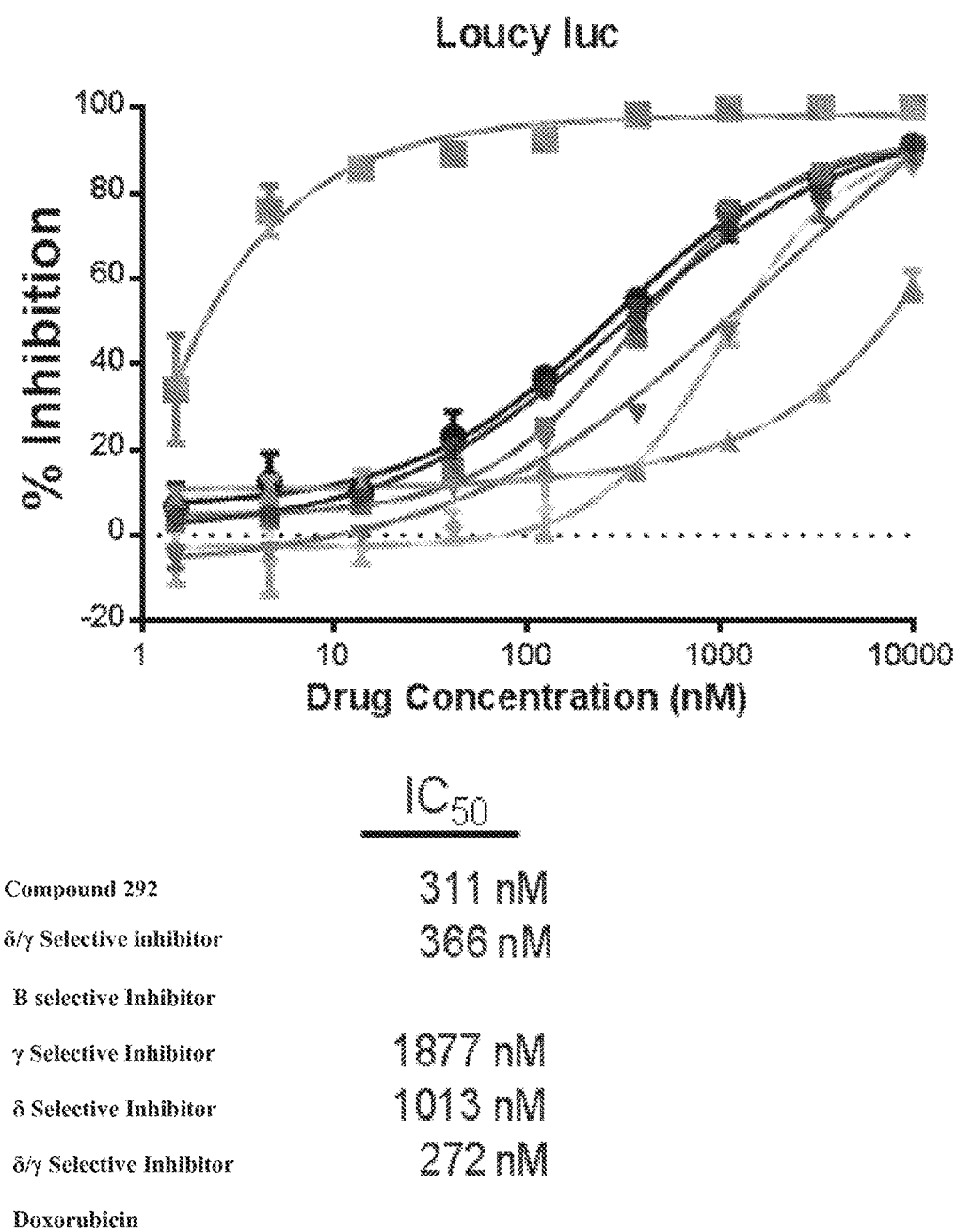
FIG. 32 depicts sensitivity of Loucy ALL cell line to different PI3K isoform inhibitors.

To further explore the individual contributions of the varying PI3K isoforms on T-ALL cell growth, Loucy ALL cells were treated with doxorubicin and various PI3K inhibitors as shown in FIG. 32 at various concentrations as denoted in the figure. As shown in FIG. 32, inhibitors of PI3K δ or γ isoform showed a gradual increase in percent inhibition of Loucy cells in as the doses increased. However, inhibitor of PI3K β was shown to be less effective in inhibiting Loucy cells than the inhibitors of other isoforms. The results suggest that the sensitivity to Compound 292 (and other inhibitors of PI3K δ and/or γ) is likely due to the inhibition of δ and/or γ isoforms of PI3K, but is not likely related to the β isoform.

Furthermore, FIG. 32 also shows that sensitivity of Loucy cells to doxorubicin shows a different pattern than that to PI3K inhibitors. Such differential sensitivity profiles can support the rationale for combining doxorubicin with a compound provided herein.

Example 23

Sensitivity of CTCL Cells to Compound 292

Sensitivity of CTCL cell lines to the treatment by Compound 292 was assessed using the following cell lines: Sézary Syndrome-derived cells HH; Sézary Syndrome-derived cells HuT78; and mycosis fungoides-derived cells MJ. MJ and HuT78 cells were grown in IMDM 20% FBS, and HH cells were grown in RPMI 10% FBS. For cytotoxicity, the cells were incubated with Compound 292 for 72 hours. After incubation with or without Compound 292 for 1 or 2 hours, the cells were subjected to protein analysis by western blotting based on the following general procedure.

Cells were washed with fresh media and lysed by adding 1×SDS sample buffer, followed by sonication. After heating the sample at 95-100° C. for 5 minutes and cooling on ice, the sample was microcentrifuged and run on SDS-PAGE. The resulting samples were electrotransfered to nitrocellulose or PVDF membrane. After washing, the membrane was incubated in blocking buffer for 1 hour at room temperature, followed by washing with TBS/T. The membrane and primary antibodies are then incubated overnight at 4° C. The membrane was again washed with TBS/T, and incubated with appropriate HRP-conjugated secondary antibodies. For biotinylated primary antibodies, the membrane was incubated with HRP-Streptavidin in milk. Upon completion of the incubation, the membrane was washed with TBS/T and was subjected to detection using LumiGLO®.

Figure 33:
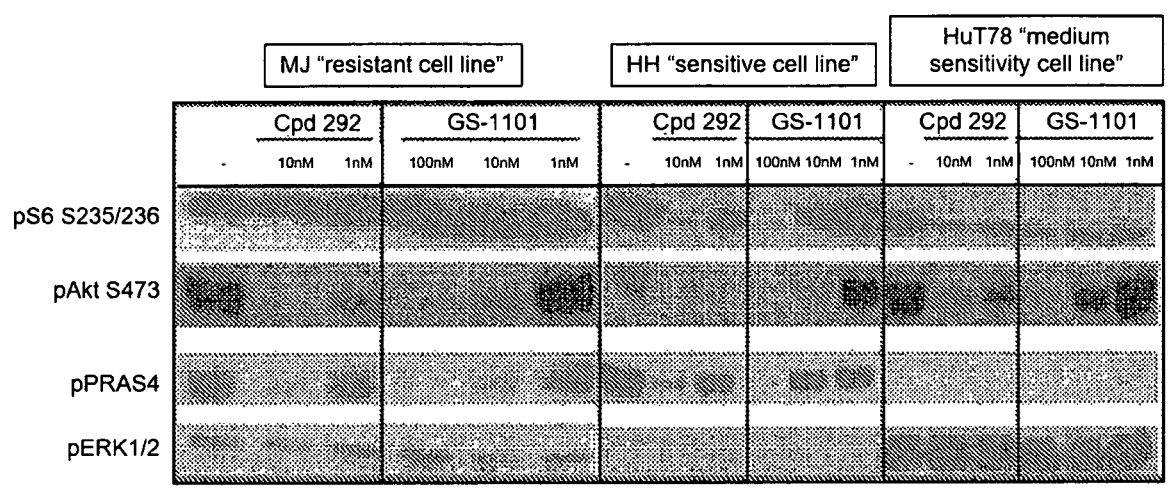
FIG. 33 depicts decrease in level of pPRAS40 upon treatment by Compound 292, as compared to the administration of GS-1101, and that the level of pERK1/2 is much lower in HH cells than MJ or HuT78 cells.

As shown in FIG. 33, it was observed that the level of pPRAS40 is dose dependently reduced by Compound 292 in the cells tested. In addition, the cytotoxicity study revealed that HH cells are the more sensitive to the treatment by Compound 292 than MJ or HuT78 cells. Indeed, MJ cells were resistant to the treatment by Compound 292 or GS-1101, and HuT78 cells showed medium sensitivity. It was observed that the level of pERK1/2 was shown to be the lowest in HH cells as compared to MJ or HuT78 cells, suggesting that high level of ERK can be marker of insensitivity to the treatment by Compound 292. Furthermore, it was found that pS6 is not modulated in resistant MJ cells, indicating that modulation of pS6 by the compound provided herein can be important in the efficacy to kill cancer cells. This results also suggests that modulation of pS6 can also be biomarker for predicting efficacy of the treatment by the compound provided herein.

Example 24

Compound 292 Inhibits Proliferation of CLL Cells in the Lymph Nodes

To mimic the proliferative effect of lymph node pseudofollicle, CLL cells were stimulated to proliferate with CD40L/IL-2/IL-10 and the effect of compound 292 was measured. Generally, CLL cells were seeded and incubated with proliferation cocktail (containing sCD40L, rH-IL 10 and rH-IL 2) in media. Then, four color FACS analysis was performed using antibodies to pAKT, Ki-67, CD19 and CD5.

Figure 34:
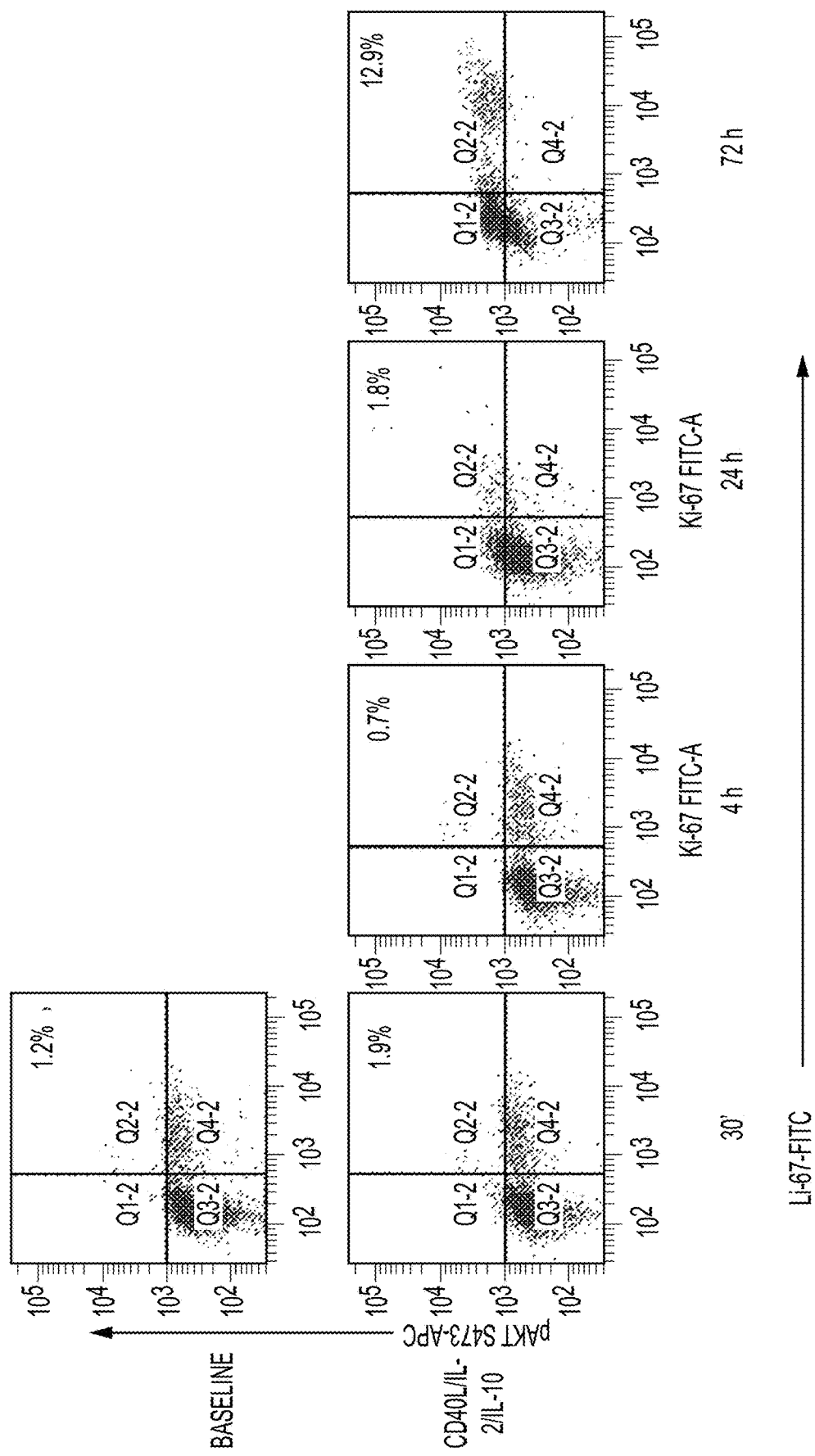
FIG. 34 depicts increase of Ki-67/pAKT positive CLL cells at 30 minutes, 4 hours, 24 hours and 72 hours after the treatment by a cytokine cocktail consisting of CD40L, IL-2 and Il-10.

As shown in FIG. 34, it was found that the cytokine cocktail of CD40L/IL-2/IL-10 significantly increases the percent number of pAKT/Ki 67 positive cell population. This indicates that the cytokine cocktail can mimic microenvironmental proliferative signals and induce PI3K signaling and proliferation in CLL cells.

Figure 35:
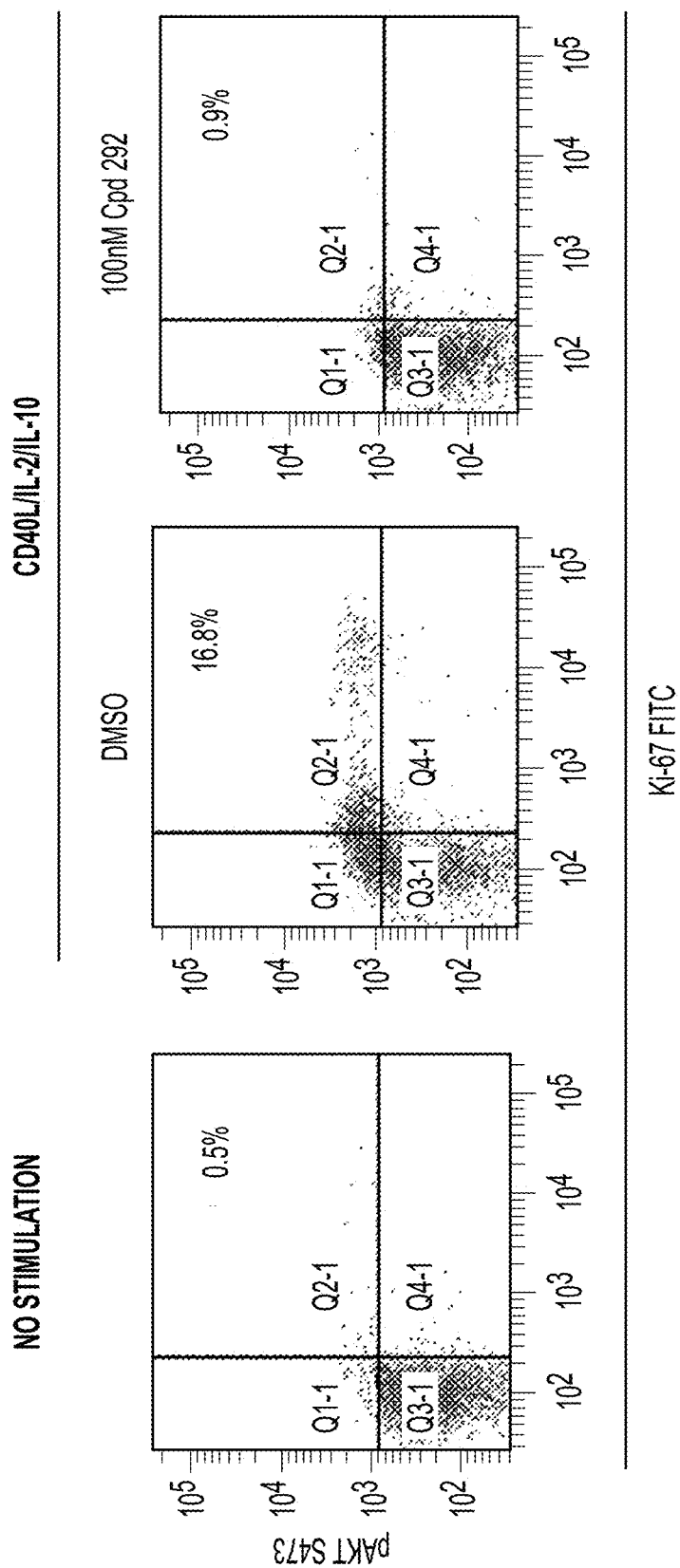
FIG. 35 depicts reduction in Ki-67/pAKT positive CLL cells treated by cytokine cocktail upon treatment by 100 nM Compound 292.
Figure 36:
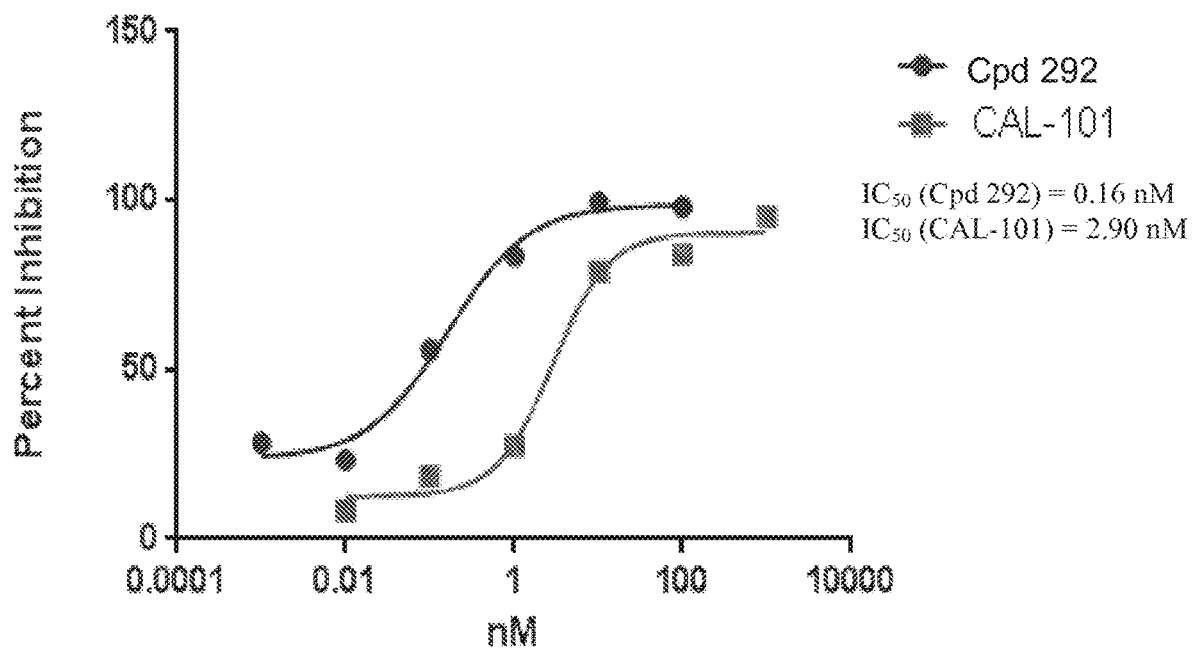
FIG. 36 depicts percent inhibition of CLL cell proliferation by Compound 292 in comparison with CAL-101.

Both pAKT and Ki-67 expression were markedly inhibited in primary CLL cells at concentrations of Compound 292 in the low nanomolar range ($EC_{50}$<10 nM; n=2), indicating a potent anti-proliferative effect of compound 292 on CLL cells in the nodal environment. (FIGS. 35 and 36). Consequently, the results indicate that compound 292 can inhibit proliferation of CLL cells in the lymph nodes. In addition, this direct inhibitory effect on CLL cells in the lymph nodes could lead to rapid and prolonged responses in cancer patients. Therefore, the results also indicate that compound 292 is capable of producing a rapid onset of response in CLL patients. Given the significant role of the chemo-attractant, SDF-1 (CXCL13) in the directed migration of B-cells, a chemotaxis assay demonstrated reduction in migration of CLL cells with compound 292 (% control reduction—median 23%; range 2-42%; n=8). Furthermore, compound 292 treatment enhanced the production of reactive oxygen species (n=6).

Example 25

Selective Reduction of CD38/CD69 Positive Cells by Compound 292 in CLL Patients

The effects of Compound 292 in number of CLL cells associated with high-risk disease (CD38/CD69 positive CLL cells) were assessed using phosphospecific flow cytometry. Briefly, eight (8) CLL patients were treated with Compound 292 25 mg BID, and samples were collected at 1, 2, 4 and 24 hours post treatment on Day 1 of Cycle 1, and at Day 1 of Cycle 2 (28 days after Cycle 1), Day 1 of Cycle 3 (56 days after Cycle 1), and Day 1 of Cycle 4 (84 days after Cycle 1). In order to characterize the surface phenotype of the cells present in CLL patients, antibodies against, among others, CD38 and CD69 were included in the panel, and the samples were subjected to phosphor-specific flow cytometry.

Figure 37A:
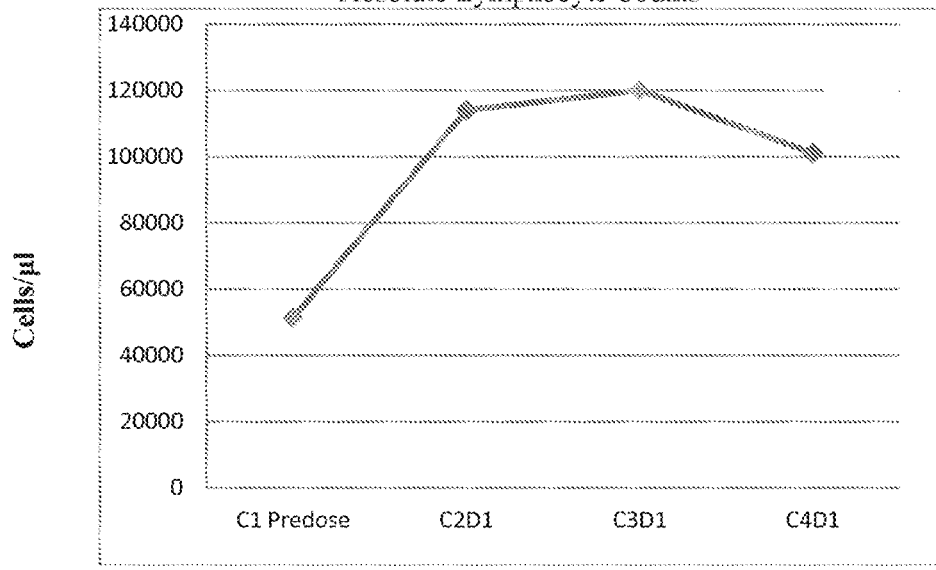
FIG. 37A depicts absolute lymphocyte counts in CLL patients treated by 25 mg BID Compound 292.
Figure 37B:
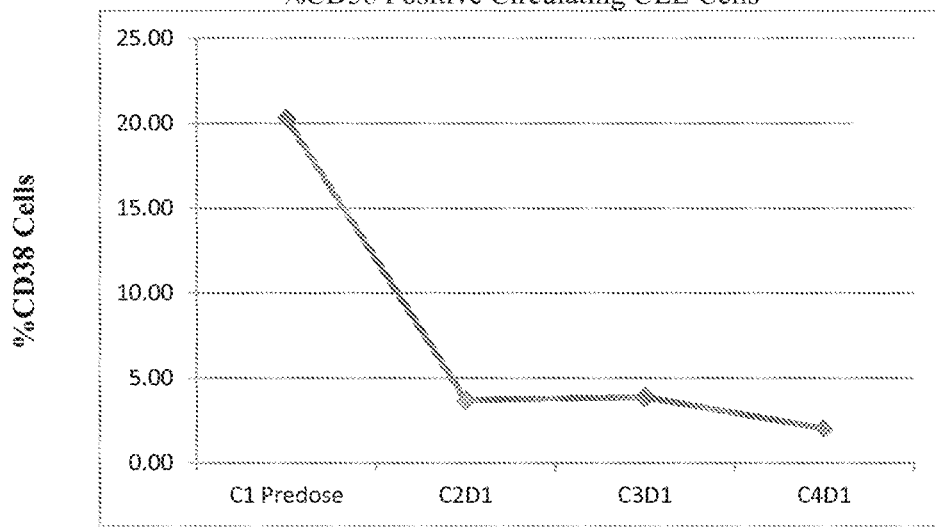
FIG. 37B depicts reduction in CD38 positive circulating CLL cells in CLL patients treated by 25 mg BID Compound 292.

The results from phosphor-specific flow cytometry were plotted and shown in FIG. 37. As shown in FIG. 37, it was found that there were significant reductions in CD38 positive circulating CLL cells, CD69 positive circulating CLL cells, CD38/CD69 double positive circulating CLL cells upon treatment by Compound 292. The result indicates that Compound 292 can selectively decrease CLL cells associated with high-risk disease.

Example 26

Effects of Compound 292 in Combination with Ibrutinib on DLBCL Cells

Figure 38:
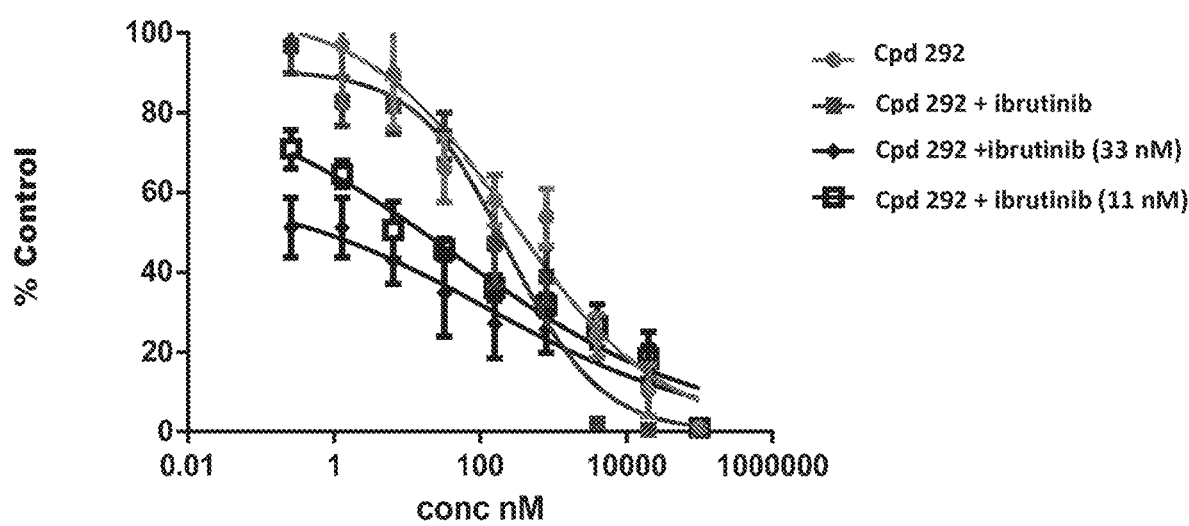
FIG. 38 depicts the effects of Compound 292/ibrutinib combination on viability of DLBCL cells as compared with the monotherapy.

SU-DHL-4 GCB DLBCL cell line was treated with varying amount of Compound 292 or ibrutinib alone, or with Compound 292 (varying amount) in combination with 11 nM or 33 nM ibrutinib. After 72 hours, cell viability was measured using CellTiter Glo®, and the results are shown in FIG. 38. As shown in the figure, both the monotherapy and combination therapy dose dependently inhibited viability of DLBCL cells. Furthermore, combination, in particular with 33 nM ibrutinib, showed increased efficacy as compared to monotherapies.

While exemplary embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments described herein can be employed in practicing the subject matter of the disclosure. It is intended that the following claims define the scope of the invention and that methods and structures within the scope of these claims and their equivalents be covered thereby.

What is claimed is:

1. A method of treating a hematologic malignancy in a human subject in need thereof, comprising orally administering to the subject twice daily about 25 mg to about 75 mg of a compound having the following structure or a pharmaceutically acceptable salt, solvate, hydrate, co-crystal, clathrate, or polymorph thereof:

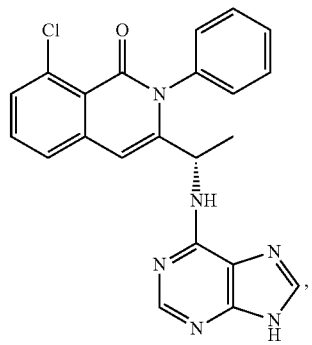 [SMILES: C[C@H](Nc1ncnc2[nH]cnc12)c1cc2cccc(Cl)c2c(=O)n1-c1ccccc1 ; ","]

wherein the hematologic malignancy is chronic lymphocytic leukemia (CLL), small lymphocytic lymphoma (SLL), CLL/SLL, indolent non-Hodgkin lymphoma (iNHL), peripheral T-cell lymphoma (PTCL), cutaneous T-cell lymphoma (CTCL), or follicular lymphoma (FL).

2. The method of claim 1, wherein the hematologic malignancy has a high expression level of PI3K-δ, or PI3K-γ, or both PI3K-δ and PI3K-γ.

3. The method of claim 1, wherein the compound or pharmaceutically acceptable salt, solvate, hydrate, co-crystal, clathrate, or polymorph thereof is administered in an amount sufficient to provide a plasma concentration of the compound at steady state at a level higher than the $IC_{90}$ for PI3K-δ and at a level higher than the $IC_{50}$ for PI3K-γ.

4. The method of claim 1, wherein the compound or pharmaceutically acceptable salt, solvate, hydrate, co-crystal, clathrate, or polymorph thereof is administered in an amount sufficient to provide a plasma concentration of the compound at steady state of 300 ng/ml to 500 ng/ml.

5. The method of claim 1, wherein the hematologic malignancy is relapsed or refractory.

6. The method of claim 1, wherein the hematologic malignancy is refractory to rituximab therapy, chemotherapy, and/or radioimmunotherapy.

7. The method of claim 1, wherein the subject is identified as having a change in the serum concentration over time or relative to a reference or control level of a biomarker chosen from MMP-9, CXCL13, CCL4, CCL17, CCL22, or TNF-a, or a combination thereof.

8. The method of claim 1, wherein the compound or pharmaceutically acceptable salt, solvate, hydrate, co-crystal, clathrate, or polymorph thereof is administered in combination with a BCL-2 inhibitor, a BTK inhibitor, an HDAC inhibitor, a MEK inhibitor, an EZH2 inhibitor, a PLK-1 inhibitor, an anti-CD37 antibody, an anti-CD20 antibody, or an anti-CD52 antibody.

9. The method of claim 1, comprising orally administering to the subject twice daily 25 mg, 30 mg, 35 mg, 40 mg, 45 mg, 50 mg, 55 mg, 60 mg, 65 mg, 70 mg, or 75 mg of the compound or pharmaceutically acceptable salt, solvate, hydrate, co-crystal, clathrate, or polymorph thereof.

10. The method of claim 1, wherein the hematologic malignancy is relapsed or refractory CLL.

11. The method of claim 1, wherein the hematologic malignancy is relapsed or refractory SLL.

12. The method of claim 1, wherein the hematologic malignancy is relapsed or refractory follicular lymphoma.

13. The method of claim 1, comprising orally administering to the subject twice daily about 25 mg or about 75 mg of the compound or pharmaceutically acceptable salt, solvate, hydrate, co-crystal, clathrate, or polymorph thereof.

14. The method of claim 1, wherein the compound or pharmaceutically acceptable salt, solvate, hydrate, co-crystal, clathrate, or polymorph thereof is administered in a solid oral dosage form.

15. The method of claim 14, wherein the solid dosage form is formulated with a pharmaceutically acceptable excipient or carrier.

16. The method of claim 14, wherein the solid dosage form is a capsule.

17. The method of claim 1, comprising administering the pharmaceutically acceptable hydrate of

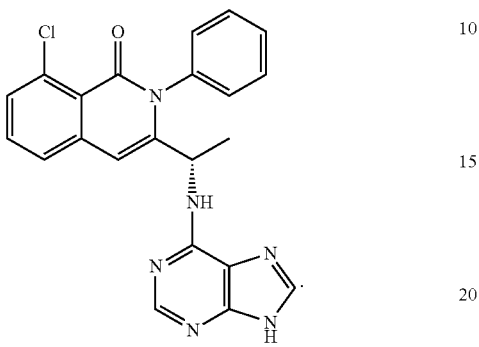

18. The method of claim 1, comprising orally administering to the subject twice daily about 25 mg of the compound or pharmaceutically acceptable salt, solvate, hydrate, co-crystal, clathrate, or polymorph thereof.

19. The method of claim 1, comprising orally administering to the subject twice daily about 75 mg of the compound or pharmaceutically acceptable salt, solvate, hydrate, co-crystal, clathrate, or polymorph thereof.

* * * * *

UNITED STATES PATENT AND TRADEMARK OFFICE
CERTIFICATE OF CORRECTION

| | | |
|---|---|---|
| PATENT NO. | : 12,213,983 B2 | Page 1 of 1 |
| APPLICATION NO. | : 16/848485 | |
| DATED | : February 4, 2025 | |
| INVENTOR(S) | : Stern et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 836 days.

Signed and Sealed this
Twelfth Day of August, 2025

Coke Morgan Stewart
*Acting Director of the United States Patent and Trademark Office*